US012760083B2

(12) United States Patent
Sabzevari et al.

(10) Patent No.: US 12,760,083 B2
(45) Date of Patent: Oct. 13, 2026

(54) CHIMERIC RECEPTOR THERAPY

(71) Applicant: PRECIGEN, INC., Germantown, MD (US)

(72) Inventors: Helen Sabzevari, Germantown, MD (US); Cheryl G. Bolinger, Germantown, MD (US); Rutul R. Shah, Germantown, MD (US); ChangHung Chen, Germantown, MD (US); Vinodhbabu Kurella, Germantown, MD (US); Amy Wesa, Germantown, MD (US)

( * ) Notice: Subject to any disclaimer, the term of this patent is extended or adjusted under 35 U.S.C. 154(b) by 36 days.

(21) Appl. No.: 17/572,618

(22) Filed: Jan. 10, 2022

(65) Prior Publication Data

US 2022/0220187 A1 Jul. 14, 2022

Related U.S. Application Data

(60) Provisional application No. 63/263,508, filed on Nov. 3, 2021, provisional application No. 63/263,001, filed on Oct. 25, 2021, provisional application No. 63/136,611, filed on Jan. 12, 2021, provisional application No. 63/136,074, filed on Jan. 11, 2021.

(51) Int. Cl.

| | |
|---|---|
| ***A61K 40/11*** | (2025.01) |
| ***A61K 40/31*** | (2025.01) |
| ***A61K 40/36*** | (2025.01) |
| ***A61K 40/42*** | (2025.01) |
| ***A61P 35/00*** | (2006.01) |
| ***C07K 14/705*** | (2006.01) |
| ***C07K 16/28*** | (2006.01) |
| *A61K 39/00* | (2006.01) |
| *A61K 40/50* | (2025.01) |

(52) U.S. Cl.

CPC .......... *C07K 14/7051* (2013.01); *A61K 40/11* (2025.01); *A61K 40/31* (2025.01); *A61K 40/36* (2025.01); *A61K 40/4202* (2025.01); *A61K 40/421* (2025.01); *A61K 40/4257* (2025.01); *A61P 35/00* (2018.01); *C07K 16/2803* (2013.01); *A61K 2039/505* (2013.01); *A61K 40/50* (2025.01); *A61K 2239/28* (2023.05); *A61K 2239/31* (2023.05); *A61K 2239/38* (2023.05); *A61K 2239/48* (2023.05); *A61K 2239/49* (2023.05); *A61K 2239/54* (2023.05); *A61K 2239/59* (2023.05); *C07K 2317/21* (2013.01); *C07K 2317/565* (2013.01); *C07K 2317/622* (2013.01); *C07K 2319/02* (2013.01); *C07K 2319/03* (2013.01); *C07K 2319/33* (2013.01)

(58) Field of Classification Search

None

See application file for complete search history.

(56) References Cited

U.S. PATENT DOCUMENTS

| | | | | |
|---|---|---|---|---|
| 5,283,173 | A | 2/1994 | Fields et al. | |
| 9,217,040 | B2 | 12/2015 | Kipps et al. | |
| 9,228,023 | B2 | 1/2016 | Rohlff et al. | |
| 9,637,547 | B2 | 5/2017 | Ab et al. | |
| 10,934,550 | B2 * | 3/2021 | Wolfson | C12N 15/1137 |
| 11,692,194 | B2 | 7/2023 | Shah et al. | |
| 11,787,848 | B2 | 10/2023 | Shah et al. | |
| 2013/0101607 | A1 | 4/2013 | Kipps et al. | |
| 2015/0225482 | A1 | 8/2015 | Song | |
| 2016/0158285 | A1 | 6/2016 | Cooper et al. | |
| 2016/0317678 | A1 | 11/2016 | Roeth et al. | |
| 2017/0226183 | A1 | 8/2017 | Schiffer-Mannioui | |
| 2017/0283497 | A1 | 10/2017 | Schiffer-Mannioui | |
| 2018/0014727 | A1 | 1/2018 | Bublitz et al. | |
| 2018/0147271 | A1 | 5/2018 | Morgan et al. | |
| 2018/0362940 | A1 * | 12/2018 | Shah | C07K 14/7051 |

(Continued)

FOREIGN PATENT DOCUMENTS

| | | | |
|---|---|---|---|
| CN | 113337544 | A | 9/2021 |
| WO | 9738117 | A1 | 10/1997 |

(Continued)

OTHER PUBLICATIONS

NCBI search results SEQ ID No. 467 (Year: 2023).*
NCBI search results SEQ ID No. 473. (Year: 2023).*
Wang, Qingshui, et al. "The roles of microRNAs in regulating the expression of PD-1/PD-L1 immune checkpoint." International journal of molecular sciences 18.12 (2017): 2540. (Year: 2017).*
Dotti et al., Immunological Reviews (2014), 257:107-126.
Hudecek et al., Clinical Cancer Research (2013), 19:3153-3164.
GenBank Accession No. AY866202.

(Continued)

*Primary Examiner* — Anoop K Singh
*Assistant Examiner* — Constantina E Stavrou
(74) *Attorney, Agent, or Firm* — Barnes & Thornburg LLP; Gene Yao

(57) ABSTRACT

A non-naturally occurring polynucleotide encoding a miRNA that inhibits the expression of an immune checkpoint protein. The polynucleotide may further encode a chimeric receptor, a cytokine, and/or a cell tag. A vector comprising the aforementioned polynucleotide. A modified immune effector cell comprising the aforementioned polynucleotide. Compositions and kits comprising the aforementioned polynucleotide and/or cell. A method for treating a subject suffering from a disease or disorder, comprising administering the aforementioned cell to a subject in need thereof. The use of the aforementioned cell in the manufacture of a medicament for the treatment of a disease or disorder. A method for the detection of a disease or disorder associated with the overexpression of an antigen in a subject. A method for the treatment of a disease or disorder comprising the serial administration of polynucleotides encoding a chimeric antigen receptor or a cell comprising the same.

13 Claims, 24 Drawing Sheets

Specification includes a Sequence Listing.

(56) References Cited

U.S. PATENT DOCUMENTS

| | | | |
|---|---|---|---|
| 2019/0048343 | A1 | 2/2019 | Gao et al. |
| 2019/0111080 | A1 | 4/2019 | Shah et al. |
| 2020/0181624 | A1 | 6/2020 | Jensen et al. |
| 2020/0283778 | A1 | 9/2020 | Shah et al. |
| 2021/0177902 | A1 | 6/2021 | Shah et al. |

FOREIGN PATENT DOCUMENTS

| | | | | |
|---|---|---|---|---|
| WO | 9902683 | A1 | 1/1999 | |
| WO | 9958155 | A1 | 11/1999 | |
| WO | 2013154760 | A1 | 10/2013 | |
| WO | 2014/144622 | A2 | 9/2014 | |
| WO | 2015095249 | A1 | 6/2015 | |
| WO | 2016048903 | A1 | 3/2016 | |
| WO | 2016115559 | A1 | 7/2016 | |
| WO | 2017062953 | A1 | 4/2017 | |
| WO | 2017172981 | A2 | 10/2017 | |
| WO | 2017214333 | A1 | 12/2017 | |
| WO | 2018102606 | A1 | 6/2018 | |
| WO | 2018/226897 | A1 | 10/2019 | |
| WO | 2019/186274 | A2 | 10/2019 | |
| WO | WO-2020014366 | A1 * | 1/2020 | ............. A61K 35/17 |
| WO | 2020221939 | A1 | 11/2020 | |

OTHER PUBLICATIONS

Hurton et al., "Tethered IL-15 augments antitumor activity and promotes a stem-cell memory subset in tumor-specific T cells," PNAS 2016, pp. 1-30.

Harris et al., Trends in Pharmacological Sciences (2016), 37:220-230.

Deniger et al., PLoS One (2015), 10:e0128151.

Sela-Culang et al., Frontiers in Immunology (2013), 4:302.

Wu et al., Expert Opinions on Biological Therapy (2016), 16:1469-1478.

International Search Report and Written Opinion for corresponding PCT Application No. PCT/US2019/041213 issued Nov. 8, 2019.

T.D. Lebedev, P.V. Spirin & V.S. Prassolov, Transfer and Expression of Small Interfering RNAs in Mammalian Cells Using Lentiviral Vectors, 5 Acta Naturae 7 (2013).

William R. Burns et al., A High Molecular Weight Melanoma-Associated Antigen-Specific Chimeric Antigen Receptor Redirects Lymphocytes to Target Human Melanomas, 70 Cancer Res. 3027 (2010).

Shivani Srivastava & Stanley R. Riddell, Engineering CAR-T Cells: Design Concepts, 36 Trends Immunol. 494 (2015).

Michael Hudecek et al., The Nonsignaling Extracellular Spacer Domain of Chimeric Antigen Receptors Is Decisive for In Vivo Antitumor Activity, 3 Cancer Immunol. Res. 125 (2015).

Shaun-Paul Cordoba et al., The Large Ectodomains of CD45 and CD148 Regulate Their Segregation from and Inhibition of Ligated T-Cell Receptor, 121 Blood 4295 (2013).

I.V. Kolyadina et al., Immunobiology of Breast Cancer: Theories and Prospects (Review), 17 J. Mod. Oncol. 12 (2015).

Eva-Maria Jahn & Christian K. Schneider, How to Systematically Evaluate Immunogenicity of Therapeutic Proteins—Regulatory Considerations, 25 New Biotechnol. 280 (2009).

Joana R. Viola et al., Non-Viral Nanovectors for Gene Delivery: Factors That Govern Successful Therapeutics, 7 Expert Opin. Drug Deliv. 721 (2010).

Kishwar Hayat Khan, Gene Expression in Mammalian Cells and Its Applications, 3 Adv. Pharm. Bull. 257 (2013).

A. Royt et al., Immunology 4-6 (Moscow, Mir, 2000).

Brunner, T., Mueller, C. Cytotoxic T cells: Double-barreled shot guns. Nat Med 5, 20 (1999).

Katharina Kriegsmann et al., NKT Cells—New Players in CAR Cell Immunotherapy?, 101 Eur. J. Haematol. 750 (2018).

Hao Zhang et al., New Strategies for the Treatment of Solid Tumors with CAR-T Cells, 12 Int'l J. Biol. Sci. 718 (2016).

Jian Li et al., Chimeric Antigen Receptor T Cell (CAR-T) Immunotherapy for Solid Tumors: Lessons Learned and Strategies for Moving Forward, 11 J. Hematol. Oncol. 22 (2018).

Chen et al., "Construction of a novel lentiviral vector knocking down PD-1 via microRNA and its application in CAR-T cells," Chinese Journal of Biotechnology (2020), 36(7):1395-1404.

Roussel-Gervais et al., "A novel bimodal construct for multiplex cell engineering and the development of allogeneic chimeric antigen receptor T cells", ASGCT Annual Meeting 2021, Retrieved from the Internet: URL:https://antionbio.com/public/posters/No1477_Roussel-Gervais_A_ASGCT_Poster.pdf [retrieved on Apr. 25, 2023].

Firoz Ahmed et al., Prediction of Guide Strand of MicroRNAs from Its Sequence and Secondary Structure, 10 BMC Bioinformatics 105 (2009).

Christine Roden et al., Novel Determinants of Mammalian Primary microRNA Processing Revealed by Systematic Evaluation of Hairpin-Containing Transcripts and Human Genetic Variation, 27 Genome Res. 374 (2017).

Jianzhi Zhang, Rates of Conservative and Radical Nonsynonymous Nucleotide Substitutions in Mammalian Nuclear Genes, 50 J. Mol. Evol. 56 (2000).

* cited by examiner

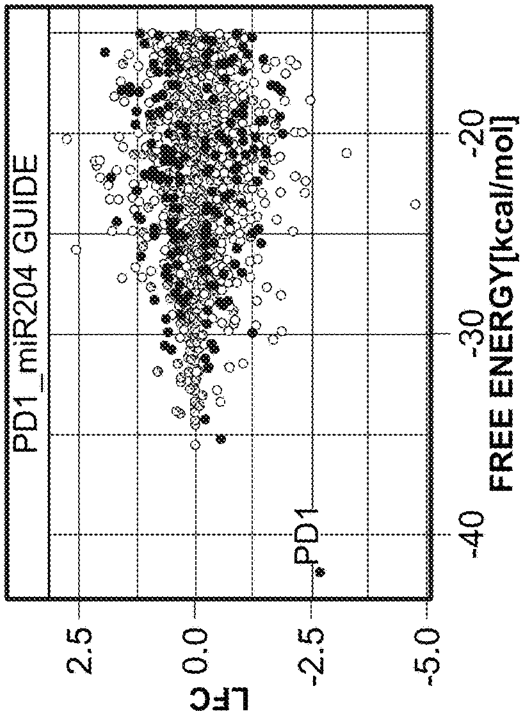
FIG. 15A
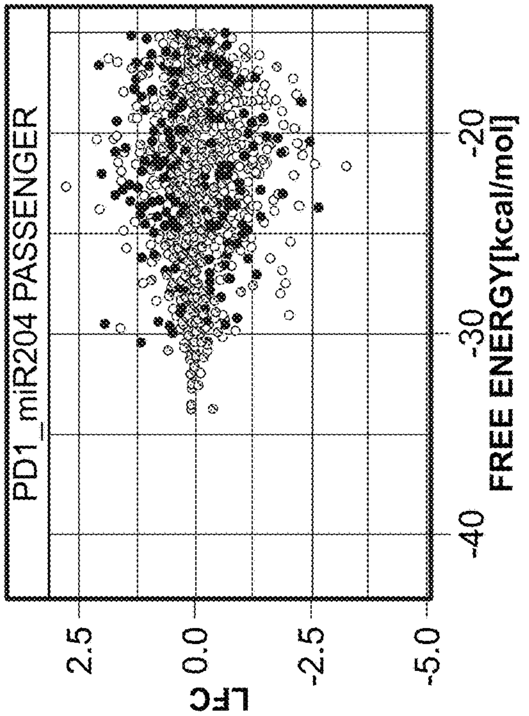
FIG. 15B
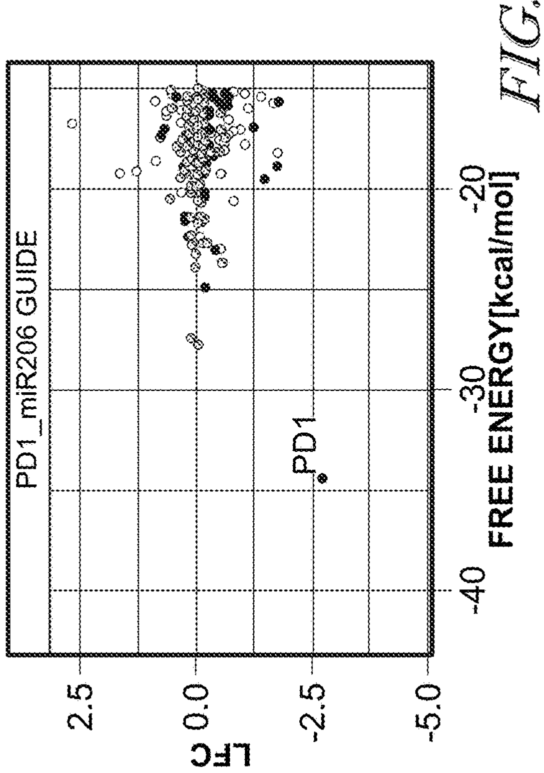
FIG. 15C
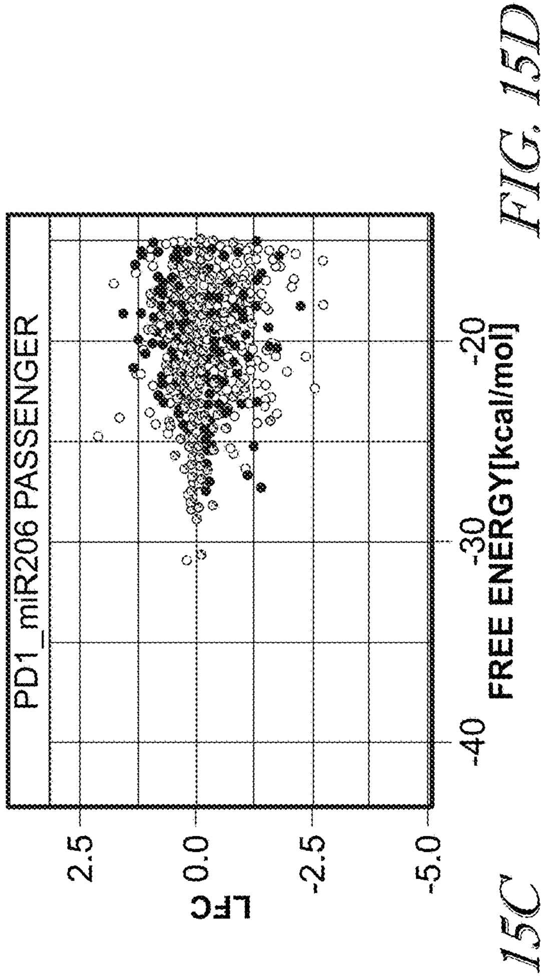
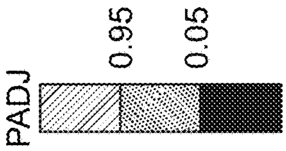
FIG. 15D

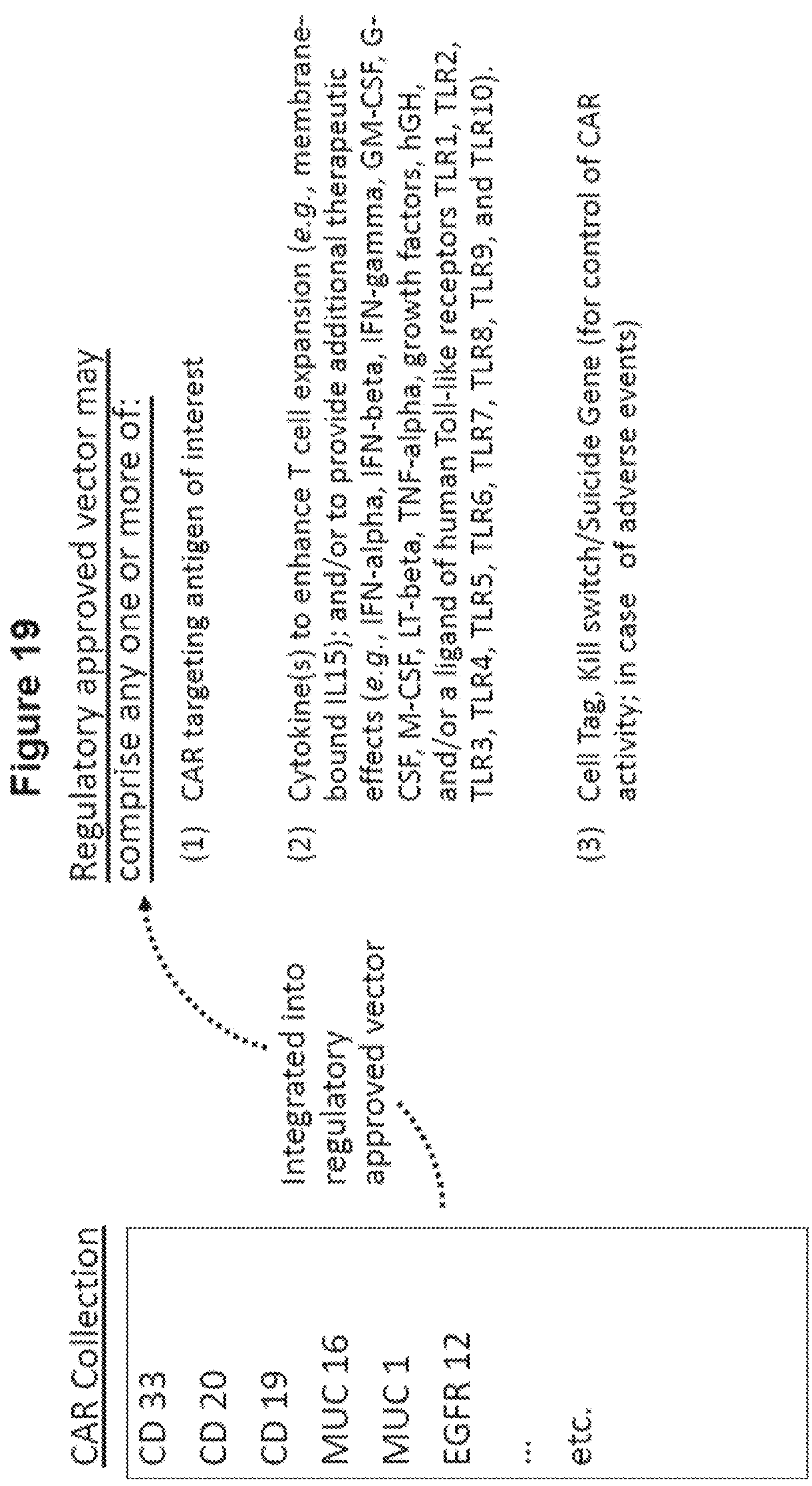
Figure 19
CAR Collection
CD 33
CD 20
CD 19
MUC 16
MUC 1
EGFR 12
...
etc.
Integrated into regulatory approved vector
Regulatory approved vector may comprise any one or more of:
(1) CAR targeting antigen of interest
(2) Cytokine(s) to enhance T cell expansion (e.g., membrane-bound IL15); and/or to provide additional therapeutic effects (e.g., IFN-alpha, IFN-beta, IFN-gamma, GM-CSF, G-CSF, M-CSF, LT-beta, TNF-alpha, growth factors, hGH, and/or a ligand of human Toll-like receptors TLR1, TLR2, TLR3, TLR4, TLR5, TLR6, TLR7, TLR8, TLR9, and TLR10).
(3) Cell Tag, Kill switch/Suicide Gene (for control of CAR activity; in case of adverse events)

CARs in collection may be further modified and differentiated by varying domains/regions

SEQUENCE LISTING

<160> NUMBER OF SEQ ID NOS: 729

<210> SEQ ID NO 1
<211> LENGTH: 82
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1
aggagggtgg gggtggaggc aagcagagga cttcctgatc gcgtacccat ggctacagtc 60
tttcttcatg tgactcgtgg ac 82

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 2
gagaatatat gaagg 15

<210> SEQ ID NO 3
<211> LENGTH: 70
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 3
gttcaattgt catcactggc atcttttttg atcattgcac catcatcaaa tgcattggga 60
taaccatgac 70

<210> SEQ ID NO 4
<211> LENGTH: 62
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 4
gatgctacaa gtggcccact tctgagatgc gggctgcttc tggatgacac tgcttcccga 60
gg 62

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 5
tatggattac tttgcta 17

<210> SEQ ID NO 6
<211> LENGTH: 62
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 6
tttcggcaag tgcctcctcg ctggccccag ggtaccaccc ggagcacagg tttggtgacc     60
tt                                                                    62

<210> SEQ ID NO 7
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ttagcaggaa aaaagagaac atcaccttgt aaaactgaag attgtgacca gtcagaataa     60
tgt                                                                   63

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tgatatgtgc at                                                         12

<210> SEQ ID NO 9
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gcattatggt gacagctgcc tcgggaagcc aagttgggct ttaaagtgca gggcctgctg     60
atgt                                                                  64

<210> SEQ ID NO 10
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
agggactggg cccacgggga ggcagcgtcc ccgaggcagc agcggcagcg gcggctcctc     60
tccccatggc cctg                                                       74

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctgggctcag                                                            10

```
<210> SEQ ID NO 12
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

cagggacctg gggaccccgg caccggcagg ccccaagggg tgaggtgagc gggcattggg     60

acctcccctc cctgtactc                                                  79


<210> SEQ ID NO 13
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

agggactggg cccacgggga ggcagcgtcc ccgaggcagc agcggcagcg gcggctcctc     60

tccccatggc c                                                          71


<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

tgctgggctc agacc                                                      15


<210> SEQ ID NO 15
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

ggacctgggg accccggcac cggcaggccc caaggggtga ggtgagcggg cattgggacc     60

tcccctccct gtactc                                                     76


<210> SEQ ID NO 16
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16

cttctgaaga aaatatattt ctttttattc atagctctta tgatagcaat gtcagcagtg     60

cct                                                                   63


<210> SEQ ID NO 17
<211> LENGTH: 20
<212> TYPE: DNA
<213> ORGANISM: Artificial Sequence
```

<220> FEATURE:
<223> OTHER INFORMATION: Description of Artificial Sequence: Synthetic
oligonucleotide

<400> SEQUENCE: 17
ttaagattct aaaattatct 20

<210> SEQ ID NO 18
<211> LENGTH: 63
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 18
aagtaaggtt gaccatactc tacagttgtg ttttaatgta tattaatgtt actaatgtgt 60
ttt 63

<210> SEQ ID NO 19
<211> LENGTH: 55
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
caggttaacc caacagaagg ctaaagaagg tatattgctg ttgacagtga gcgac 55

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
ctgtgaagcc acagatggg 19

<210> SEQ ID NO 21
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
tgcctactgc ctcggacttc aaggggctac tttaggagca attatcttgt tta 53

<210> SEQ ID NO 22
<211> LENGTH: 62
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
ccggggtcct gtctgcatcc agcgcagcat tctggaagac gccacgcctc cgctggcgac 60
gg 62

<210> SEQ ID NO 23

<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
ctgtgacact tcaaac 16

<210> SEQ ID NO 24
<211> LENGTH: 62
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 24
ccgtccacgg caccgcatcg aaaacgccgc tgagacctca gccttgacct ccctcagcgt 60
gg 62

<210> SEQ ID NO 25
<211> LENGTH: 64
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 25
caatggtgga atgtggaggt gaagttaaca ccttcgtggc tacagagttt ccttagcaga 60
gctg 64

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 26
tgtctaaact at 12

<210> SEQ ID NO 27
<211> LENGTH: 92
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 27
tagctactgc taggcaatcc ttccctcgat aaatgtcttg gcatcgtttg ctttgagcaa 60
gaaggttcat ctgatatcag tcttctcaat ct 92

<210> SEQ ID NO 28
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 28
acaggctgat tgtatctgtc tatgagcaaa ggaaacctga aggaaccaag ggcctggctg 60
gacagagttg tcatgtg 77

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 29
gcagaacatc cgctcacctg t 21

<210> SEQ ID NO 30
<211> LENGTH: 68
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 30
cacatgacaa cccagcctga atgacaacca gccattgaaa gaaagcagcc ctcacaccat 60
agcatcta 68

<210> SEQ ID NO 31
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 31
acaggctgat tgtatctgtc tatgagcaaa ggaaacctga aggaaccaag ggcctggctg 60
gacagagttg tcatgtgtc 79

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 32
agaacatccg ctcacct 17

<210> SEQ ID NO 33
<211> LENGTH: 68
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 33
cacatgacaa cccagcctga atgacaacca gccattgaaa gaaagcagcc ctcacaccat 60
agcatcta 68

<210> SEQ ID NO 34
<211> LENGTH: 57

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
gggtttattg taagagagca ttatgaagaa aaaaatagat cataaagctt cttcagg 57

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 35
gatttaaata gtgattgtc 19

<210> SEQ ID NO 36
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 36
cttgggggag accagctgcg ctgcactacc aacagcaaaa gaagtgaatg ggacagct 58

<210> SEQ ID NO 37
<211> LENGTH: 59
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 37
gggtttattg taagagagca ttatgaagaa aaaaatagat cataaagctt cttcaggaa 59

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 38
tttaaatagt gattg 15

<210> SEQ ID NO 39
<211> LENGTH: 61
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 39
gttcttgggg gagaccagct gcgctgcact accaacagca aaagaagtga atgggacagc 60
t 61

<210> SEQ ID NO 40

<211> LENGTH: 64
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 40
tttaccaatg aaaagcattt aactgttttg gattccaaac tagcagcact acaatgcttt 60
gcta 64

<210> SEQ ID NO 41
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 41
tcgcctcttc aatgga 16

<210> SEQ ID NO 42
<211> LENGTH: 64
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42
tagctatgca ttgattacta cgggacaacc aacgttttca tttgtgaata tcaattactt 60
gcca 64

<210> SEQ ID NO 43
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 43
tgaagccaca ggagccaaga gcaggaggac caaggccctg gcgaaggccg tggcctcg 58

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 44
gtgcaggtcc caatg 15

<210> SEQ ID NO 45
<211> LENGTH: 59
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 45
cggggacgcg ggcctggacg ccggcatccg ggctcaggac ccccctctct gccagaggc 59

<210> SEQ ID NO 46
<211> LENGTH: 68
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 46
gtcttggagg ctggggcacc tcggggaagg acgccggcat cagcaccatt ctggggtacg 60
gggatgga 68

<210> SEQ ID NO 47
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 47 gtttct 6

<210> SEQ ID NO 48
<211> LENGTH: 70
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 48
gccgtccgta tccgctgcag cctgtggggc ctgcgggccg gggagccgat cgcgcttcag 60
ctcagcgcct 70

<210> SEQ ID NO 49
<211> LENGTH: 61
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 49
ccaataattc aagccaagca agtatatagg tgttttaata gtttttgttt gcagtcctct 60
g 61

<210> SEQ ID NO 50
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 50
tacaagaaga atgtagt 17

<210> SEQ ID NO 51
<211> LENGTH: 61
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 51
tggtggcctg ctatttcctt caaatgaatg atttttacta attttgtgta cttttattgt 60
g 61

<210> SEQ ID NO 52
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 52
tgtctgcttg ttttgcctac catcgtgaca tctccatggc tgtaccacct tgtcggg 57

<210> SEQ ID NO 53
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 53
ctgttgaatc tcatgg 16

<210> SEQ ID NO 54
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 54
tctgacattt tggtatcttt catctgacca tccatatcca atgttctcat ttaaaca 57

<210> SEQ ID NO 55
<211> LENGTH: 65
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 55
ggagtcagga ggcctgggca gcctgaagag tacacgccga cggacagaca gacagtgcag 60
tcacc 65

<210> SEQ ID NO 56
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 56
aacagcactg gaggg 15

<210> SEQ ID NO 57
<211> LENGTH: 65
<212> TYPE: DNA

-continued

<213> ORGANISM: Artificial Sequence
<220> FEATURE:
<223> OTHER INFORMATION: Description of Artificial Sequence: Synthetic
      oligonucleotide

<400> SEQUENCE: 57
gatgagtgta ctgtgggctt cggagatcac gccactgctg ccgcccgctg cccgccacca     60
tcttc                                                                 65

<210> SEQ ID NO 58
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cagttctgtt ttgatttttt ttgtttgttt tttgatcagt gctaatcttc gatactcgaa     60
gga                                                                   63

<210> SEQ ID NO 59
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tctttattta tga                                                        13

<210> SEQ ID NO 60
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60 tttttagta tcaaatccca ccctggaggc acttcctgtt cctgatgcag ccttcaggga     60
gg                                                                    62

<210> SEQ ID NO 61
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cggaccacgg tgtccccttc tctccagctg ggggtctcgg gtcctggcgc tgagaggccg     60
c                                                                     61

<210> SEQ ID NO 62
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gtgcacccgt g 11

<210> SEQ ID NO 63
<211> LENGTH: 63
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 63
gcggccctag cgacctgcgg cggcgccggg aaagccctgc ctctgcagcg ggtcccaggg 60
gtc 63

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 64
aatatagtct tctccctcgc tt 22

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 65
aagcagggac aggactatat t 21

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 66
aatatagtct tctccctcgc tt 22

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 67
gagcgaggga taggactata ct 22

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 68
aatatagtct tctccctcgc tg 22

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 69
cagtgaggga agactatgtt 20

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 70
aatatagtct tctccctcgc tg 22

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 71
cagcgaggga gaagattacc att 23

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 72
ttcaggaatg ggttccaagg at 22

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 73
atcctggaag ctattcctga c 21

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 74
tataatataa tagaaccaca gg 22

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 75
cctgtggttc tgttatatcc ata 23

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 76
ttcaggaatg ggttccaagg ag 22

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 77
ctccttggac cattcctgaa 20

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 78
ttcaggaatg ggttccaagg aatt 24

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 79
aatgtcctga agccattcat gga 23

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 80

-continued ttcaggaatg ggttccaagg ag 22

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 81
ctccttggaa cacattccta ca 22

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 82
ttcaggaatg ggttccaagg aag 23

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
cttcttggta cacgttcctg ctca 24

<210> SEQ ID NO 84

<400> SEQUENCE: 84

000

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 85
acgtgtggtt tatcctgttg ta 22

<210> SEQ ID NO 86

<400> SEQUENCE: 86

000

<210> SEQ ID NO 87
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
ccagcttgtg gttctattat gttata 26

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 88
agatccacgt tactcaccct ag 22

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 89
ctagggtgtg tcatgtggat gaa 23

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
agatccacgt tactcacccg tg 22

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
acccgggtga taatatggat ct 22

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 92
agatccacgt tactcacccc ct 22

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93
aggggtgaga agcgtggatc c 21

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 94
agatccacgt tactcaccct ta 22

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 95
taggtgagtt acgtggatct gtt 23

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 96
agatccacgt tactcaccct gc 22

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 97
gtagggtgag actcgtggat ct 22

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 98
accacgatga ctgctgtgca ga 22

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 99
tctgcgtagc agtcatcgcc ggt 23

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 100
accacgatga ctgctgtgca ga 22

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 101
tctgatggcc gtcatcgtgg c 21

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 102
accacgatga ctgctgtgca ga 22

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 103
tctgtacagc agcatcgatg gt 22

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 104
accacgatga ctgctgtgca ga 22

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 105
tgcgcagctg ttcatcgtgg t 21

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 106
accacgatga ctgctgtgca ga 22

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 107
ctgcgaagca gcatcgtggc 20

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 108
accacgatga ctgctgtgca ga 22

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 109
tctgcaacgc agtctcgctg g 21

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 110
accacgatga ctgctgtgca ga 22

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 111
gatgcacagc aatcatcgtg gt 22

<210> SEQ ID NO 112

<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 112
accacgatga ctgctgtgca gat 23

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 113
atctgcacag cagttcgtgg 20

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 114
accacgatga ctgctgtgca ga 22

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 115
tctgccaata gctgtaatcg tgg 23

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 116
tatcgttcac ggtcagcgac tg 22

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 117
cagtcgttga ctgtggactt ata 23

<210> SEQ ID NO 118
<211> LENGTH: 22

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 118
tatcgttcac ggtcagcgac tg 22

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 119
cagtgctgaa cgtgaacgat c 21

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 120
tatcgttcac ggtcagcgac tg 22

<210> SEQ ID NO 121
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 121
tagtcgctga cttgaacaga ta 22

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 122
tatcgttcac ggtcagcgac t 21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 123
tgtcgctgac agtgaacgat a 21

<210> SEQ ID NO 124
<211> LENGTH: 22
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 124

tatcgttcac ggtcagcgac tg                                              22


<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125

gtcgctgagc gctgaacgat g                                               21


<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126

taactcagga cattgaagta gt                                              22


<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127

actacttcaa tgtcctgacc tta                                             23


<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128

taactcagga cattgaagta gt                                              22


<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129

actattcaga gtcctgagtt c                                               21


<210> SEQ ID NO 130
<211> LENGTH: 22
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 130
taactcagga cattgaagta gt 22

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ctactccaat gcctgagttg 20

<210> SEQ ID NO 132
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
taactcagga cattgaagta gt 22

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
actactgtaa tgtctgacgt t 21

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
taactcagga cattgaagta gtc 23

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gactacttca atgttgagtt 20

<210> SEQ ID NO 136
<211> LENGTH: 22
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 136
agatccacgt tactcaccct ag 22

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ctaggcagtg agcaaagtgg atc 23

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
agatccacgt tactcaccct ag 22

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ctaggtgaga aacgtggatc g 21

<210> SEQ ID NO 140
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
agatccacgt tactcaccct ag 22

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ctagggtgag taacgtggcc tct 23

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 142
agatccacgt tactcaccct ag 22

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 143
tagggcgagt acgtggatcg 20

<210> SEQ ID NO 144
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 144
agatccacgt tactcaccct ag 22

<210> SEQ ID NO 145
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 145
ctagggtgag tacgtggcat ct 22

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 146
cattatgcct gggatttgga tc 22

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 147
gatcagatcg caggcataat t 21

<210> SEQ ID NO 148
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 148
cattatgcct gggatttgga tc 22

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 149
gatccggatc ctaggtatcc atg 23

<210> SEQ ID NO 150
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 150
cattatgcct gggatttgga tcg 23

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 151
cggccagaac caaggcataa gta 23

<210> SEQ ID NO 152
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 152
cattatgcct gggatttgga tc 22

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 153
actccaaatc ccgtgcataa tcg 23

<210> SEQ ID NO 154
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 154
cattatgcct gggatttgga tc 22

<210> SEQ ID NO 155
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 155
gattcgaatc caaggcatat gg 22

<210> SEQ ID NO 156
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 156
taattcacat ccctttcatc ag 22

<210> SEQ ID NO 157
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 157
atgatgaaag gacagtgaat ta 22

<210> SEQ ID NO 158
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 158
tagtcgttgg gtaaagtcgc ca 22

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 159
tggtgacttc tcaacgatta 20

<210> SEQ ID NO 160
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 160
gttgctttcc gctaagtggt ga 22

<210> SEQ ID NO 161
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 161
tcaccactta gaggaaagcc tc 22

<210> SEQ ID NO 162
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 162
tttgcagtgg ccttcgtggc cc 22

<210> SEQ ID NO 163
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 163
gggctatgaa ggccattgag aaa 23

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 164
agcctcccgt cctaagaccc cac 23

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 165
gtgggtctta ggtcgggagc tgct 24

<210> SEQ ID NO 166
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 166
tgaacgacca gtgtttaacc gg 22

<210> SEQ ID NO 167
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 167
ccggttgaac attggttgcc tca 23

<210> SEQ ID NO 168
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 168
ttctccttgg agttcatccg cg 22

<210> SEQ ID NO 169
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 169
atgaacttag aggagacg 18

<210> SEQ ID NO 170
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 170
ttctccttgg agttcatccg cg 22

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 171
cgcggatgat ccaaggagga 20

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178
<211> LENGTH: 210
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 178
aggagggtgg gggtggaggc aagcagagga cttcctgatc gcgtacccat ggctacagtc 60
tttcttcatg tgactcgtgg acaatatagt cttctccctc gcttgagaat atatgaagga 120
agcagggaca ggactatatt gttcaattgt catcactggc atcttttttg atcattgcac 180
catcatcaaa tgcattggga taaccatgac 210

<210> SEQ ID NO 179
<211> LENGTH: 210
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 179
aggagggtgg gggtggaggc aagcagagga cttcctgatc gcgtacccat ggctacagtc 60
tttcttcatg tgactcgtgg acttcaggaa tgggttccaa ggatgagaat atatgaagga 120
tcctggaagc tattcctgac gttcaattgt catcactggc atcttttttg atcattgcac 180
catcatcaaa tgcattggga taaccatgac 210

<210> SEQ ID NO 180
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 180
gatgctacaa gtggcccact tctgagatgc gggctgcttc tggatgacac tgcttcccga 60
ggcctgtggt tctgttatat ccatatatgg attactttgc tatataatat aatagaacca 120
caggtttcgg caagtgcctc ctcgctggcc ccagggtacc acccggagca caggtttggt 180
gacctt 186

<210> SEQ ID NO 181
<211> LENGTH: 184
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 181
ttagcaggaa aaaagagaac atcaccttgt aaaactgaag attgtgacca gtcagaataa 60
tgtagatcca cgttactcac cctagtgata tgtgcatcta gggtgtgtca tgtggatgaa 120
gcattatggt gacagctgcc tcgggaagcc aagttgggct ttaaagtgca gggcctgctg 180
atgt 184

<210> SEQ ID NO 182
<211> LENGTH: 207
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 182
agggactggg cccacgggga ggcagcgtcc ccgaggcagc agcggcagcg gcggctcctc 60
tccccatggc cctgagatcc acgttactca cccgtgctgg gctcagaccc gggtgataat 120
atggatctca gggacctggg gaccccggca ccggcaggcc ccaaggggtg aggtgagcgg 180
gcattgggac ctcccctccc tgtactc 207

<210> SEQ ID NO 183
<211> LENGTH: 210
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 183
aggagggtgg gggtggaggc aagcagagga cttcctgatc gcgtacccat ggctacagtc 60
tttcttcatg tgactcgtgg acagatccac gttactcacc ccctgagaat atatgaagga 120
ggggtgagaa gcgtggatcc gttcaattgt catcactggc atctttttg atcattgcac 180 catcatcaaa tgcattggga taaccatgac 210

<210> SEQ ID NO 184
<211> LENGTH: 186
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 184
gatgctacaa gtggcccact tctgagatgc gggctgcttc tggatgacac tgcttcccga 60
ggtctgcgta gcagtcatcg ccggttatgg attactttgc taaccacgat gactgctgtg 120
cagatttcgg caagtgcctc ctcgctggcc ccagggtacc acccggagca caggtttggt 180
gacctt 186

<210> SEQ ID NO 185
<211> LENGTH: 210
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 185
aggagggtgg gggtggaggc aagcagagga cttcctgatc gcgtacccat ggctacagtc 60
tttcttcatg tgactcgtgg acaccacgat gactgctgtg cagagagaat atatgaaggt 120
ctgatggccg tcatcgtggc gttcaattgt catcactggc atctttttttg atcattgcac 180 catcatcaaa tgcattggga taaccatgac 210

<210> SEQ ID NO 186
<211> LENGTH: 185
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 186
cattttccct ccctttccct taggagcctg ttcctctcac gccctcacct ggctgagccg 60
catctgtaca gcagcatcga tggttatgtc ctgacccagc taaccacgat gactgctgtg 120
cagatgccct ctgcccctgg cttcgaggag gaggaggagc tgctttcccc atcatctgga 180
aggtg 185

<210> SEQ ID NO 187
<211> LENGTH: 188
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 187
cttctgaaga aaatatattt ctttttattc atagctctta tgatagcaat gtcagcagtg 60
cctaccacga tgactgctgt gcagattaag attctaaaat tatcttgcgc agctgttcat 120
cgtggtagta aggttgacca tactctacag ttgtgtttta atgtatatta atgttactaa 180
tgtgtttt 188

<210> SEQ ID NO 188
<211> LENGTH: 189
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 188
cttctgaaga aaatatattt ctttttattc atagctctta tgatagcaat gtcagcagtg 60
cctaccacga tgactgctgt gcagattaag attctaaaat tatcttgcgc agctgttcat 120
cgtggtaagt aaggttgacc atactctaca gttgtgtttt aatgtatatt aatgttacta 180
atgtgtttt 189

<210> SEQ ID NO 189
<211> LENGTH: 172
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 189
tgtctgcttg ttttgcctac catcgtgaca tctccatggc tgtaccacct tgtcgggacc 60
acgatgactg ctgtgcagac tgttgaatct catggctgcg aagcagcatc gtggctctga 120
cattttggta tctttcatct gaccatccat atccaatgtt ctcatttaaa ca 172

<210> SEQ ID NO 190
<211> LENGTH: 181
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 190
cagttctgtt ttgatttttt ttgtttgttt tttgatcagt gctaatcttc gatactcgaa 60
ggatctgcaa cgcagtctcg ctggtcttta tttatgaacc acgatgactg ctgtgcagat 120
tttttagtat caaatcccac cctggaggca cttcctgttc ctgatgcagc cttcagggag 180
g 181

<210> SEQ ID NO 191
<211> LENGTH: 187
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 191
ggagtcagga ggcctgggca gcctgaagag tacacgccga cggacagaca gacagtgcag 60
tcaccaccac gatgactgct gtgcagaaca gcactggagg gatgcacagc aatcatcgtg 120
gtgatgagtg tactgtgggc ttcggagatc acgccactgc tgccgcccgc tgcccgccac 180
catcttc 187

<210> SEQ ID NO 192
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 192
ccaataattc aagccaagca agtatatagg tgttttaata gtttttgttt gcagtcctct 60
gatctgcaca gcagttcgtg gtacaagaag aatgtagtac cacgatgact gctgtgcaga 120
ttggtggcct gctatttcct tcaaatgaat gatttttact aattttgtgt acttttattg 180
tg 182

<210> SEQ ID NO 193
<211> LENGTH: 180

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 193
cggaccacgg tgtccccttc tctccagctg ggggtctcgg gtcctggcgc tgagaggccg 60
caccacgatg actgctgtgc agagtgcacc cgtgtctgcc aatagctgta atcgtgggcg 120
gccctagcga cctgcggcgg cgccgggaaa gccctgcctc tgcagcgggt cccaggggtc 180

<210> SEQ ID NO 194
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 194
gatgctacaa gtggcccact tctgagatgc gggctgcttc tggatgacac tgcttcccga 60
ggcagtcgtt gactgtggac ttatatatgg attactttgc tatatcgttc acggtcagcg 120
actgtttcgg caagtgcctc ctcgctggcc ccagggtacc acccggagca caggtttggt 180
gacctt 186

<210> SEQ ID NO 195
<211> LENGTH: 210
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 195
aggagggtgg gggtggaggc aagcagagga cttcctgatc gcgtacccat ggctacagtc 60
tttcttcatg tgactcgtgg actatcgttc acggtcagcg actggagaat atatgaaggc 120
agtgctgaac gtgaacgatc gttcaattgt catcactggc atcttttttg atcattgcac 180
catcatcaaa tgcattggga taaccatgac 210

<210> SEQ ID NO 196
<211> LENGTH: 185
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 196
cattttccct ccctttccct taggagcctg ttcctctcac gccctcacct ggctgagccg 60
catagtcgct gacttgaaca gatatatgtc ctgacccagc tatatcgttc acggtcagcg 120
actgtgccct ctgcccctgg cttcgaggag gaggaggagc tgctttcccc atcatctgga 180
aggtg 185

<210> SEQ ID NO 197
<211> LENGTH: 187
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 197
ggagtcagga ggcctgggca gcctgaagag tacacgccga cggacagaca gacagtgcag 60
tcacctatcg ttcacggtca gcgactaaca gcactggagg gtgtcgctga cagtgaacga 120
tagatgagtg tactgtgggc ttcggagatc acgccactgc tgccgcccgc tgcccgccac 180
catcttc 187

<210> SEQ ID NO 198
<211> LENGTH: 189
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 198
cttctgaaga aaatatattt ctttttattc atagctctta tgatagcaat gtcagcagtg 60
ccttatcgtt cacggtcagc gactgttaag attctaaaat tatctgtcgc tgagcgctga 120
acgatgaagt aaggttgacc atactctaca gttgtgtttt aatgtatatt aatgttacta 180
atgtgtttt 189

<210> SEQ ID NO 199
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 199
gatgctacaa gtggcccact tctgagatgc gggctgcttc tggatgacac tgcttcccga 60
ggactacttc aatgtcctga ccttatatgg attactttgc tataactcag gacattgaag 120
tagttttcgg caagtgcctc ctcgctggcc ccagggtacc acccggagca caggtttggt 180
gacctt 186

<210> SEQ ID NO 200
<211> LENGTH: 210
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 200
aggagggtgg gggtggaggc aagcagagga cttcctgatc gcgtacccat ggctacagtc 60
tttcttcatg tgactcgtgg actaactcag gacattgaag tagtgagaat atatgaagga 120
ctattcagag tcctgagttc gttcaattgt catcactggc atcttttttg atcattgcac 180
catcatcaaa tgcattggga taaccatgac 210

<210> SEQ ID NO 201
<211> LENGTH: 172
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 201
tgtctgcttg ttttgcctac catcgtgaca tctccatggc tgtaccacct tgtcgggtaa 60
ctcaggacat tgaagtagtc tgttgaatct catggctact ccaatgcctg agttgtctga 120
cattttggta tctttcatct gaccatccat atccaatgtt ctcatttaaa ca 172

<210> SEQ ID NO 202
<211> LENGTH: 181
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 202
cagttctgtt ttgatttttt ttgtttgttt tttgatcagt gctaatcttc gatactcgaa 60
ggaactactg taatgtctga cgtttcttta tttatgataa ctcaggacat tgaagtagtt 120
tttttagtat caaatcccac cctggaggca cttcctgttc ctgatgcagc cttcagggag 180
g 181

<210> SEQ ID NO 203
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 203
ccaataattc aagccaagca agtatatagg tgttttaata gtttttgttt gcagtcctct 60
ggactacttc aatgttgagt ttacaagaag aatgtagtta actcaggaca ttgaagtagt 120
ctggtggcct gctatttcct tcaaatgaat gatttttact aattttgtgt acttttattg 180
tg 182

<210> SEQ ID NO 204
<211> LENGTH: 180
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 204
cggaccacgg tgtccccttc tctccagctg gggtctcgg gtcctggcgc tgagaggccg 60
cagatccacg ttactcaccc taggtgcacc cgtgctaggc agtgagcaaa gtggatcgcg 120
gccctagcga cctgcggcgg cgccgggaaa gccctgcctc tgcagcgggt cccaggggtc 180

<210> SEQ ID NO 205
<211> LENGTH: 210
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 205
aggagggtgg gggtggaggc aagcagagga cttcctgatc gcgtacccat ggctacagtc 60
tttcttcatg tgactcgtgg acagatccac gttactcacc ctaggagaat atatgaaggc 120
taggtgagaa acgtggatcg gttcaattgt catcactggc atcttttttg atcattgcac 180
catcatcaaa tgcattggga taaccatgac 210

<210> SEQ ID NO 206
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 206
gatgctacaa gtggcccact tctgagatgc gggctgcttc tggatgacac tgcttcccga 60
ggctagggtg agtaacgtgg cctcttatgg attactttgc taagatccac gttactcacc 120
ctagtttcgg caagtgcctc ctcgctggcc ccagggtacc acccggagca caggtttggt 180
gacctt 186

<210> SEQ ID NO 207
<211> LENGTH: 172
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 207
tgtctgcttg ttttgcctac catcgtgaca tctccatggc tgtaccacct tgtcgggaga 60
tccacgttac tcaccctagc tgttgaatct catggtaggg cgagtacgtg gatcgtctga 120
cattttggta tctttcatct gaccatccat atccaatgtt ctcatttaaa ca 172

<210> SEQ ID NO 208
<211> LENGTH: 185
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 208
cattttccct ccctttccct taggagcctg ttcctctcac gccctcacct ggctgagccg 60
cactagggtg agtacgtggc atcttatgtc ctgacccagc taagatccac gttactcacc 120
ctagtgccct ctgcccctgg cttcgaggag gaggaggagc tgctttcccc atcatctgga 180
aggtg 185

<210> SEQ ID NO 209
<211> LENGTH: 210
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 209
aggagggtgg gggtggaggc aagcagagga cttcctgatc gcgtacccat ggctacagtc 60
tttcttcatg tgactcgtgg accattatgc ctgggatttg gatcgagaat atatgaaggg 120
atcagatcgc aggcataatt gttcaattgt catcactggc atcttttttg atcattgcac 180
catcatcaaa tgcattggga taaccatgac 210

<210> SEQ ID NO 210
<211> LENGTH: 207
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 210
agggactggg cccacgggga ggcagcgtcc ccgaggcagc agcggcagcg gcggctcctc 60
tccccatggc cctgcattat gcctgggatt tggatcctgg gctcagacct ccaaatccac 120
acatagtgca gggacctggg gaccccggca ccggcaggcc ccaaggggtg aggtgagcgg 180
gcattgggac ctcccctccc tgtactc 207

<210> SEQ ID NO 211
<211> LENGTH: 171
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 211
caggttaacc caacagaagg ctaaagaagg tatattgctg ttgacagtga gcgaccatta 60
tgcctgggat ttggatcctg tgaagccaca gatggggatc cagatcaggc atagtggctg 120
cctactgcct cggacttcaa ggggctactt taggagcaat tatcttgttt a 171

<210> SEQ ID NO 212
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 212
gatgctacaa gtggcccact tctgagatgc gggctgcttc tggatgacac tgcttcccga 60
gggatccgga tcctaggtat ccatgtatgg attactttgc tacattatgc ctgggatttg 120
gatctttcgg caagtgcctc ctcgctggcc ccagggtacc acccggagca caggtttggt 180
gacctt 186

<210> SEQ ID NO 213
<211> LENGTH: 189
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 213
cttctgaaga aaatatattt ctttttattc atagctctta tgatagcaat gtcagcagtg 60
cctcattatg cctgggattt ggatcttaag attctaaaat tatcttccga atcacatggc 120
ataatgaagt aaggttgacc atactctaca gttgtgtttt aatgtatatt aatgttacta 180
atgtgtttt 189

<210> SEQ ID NO 214
<211> LENGTH: 185
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 214
ttagcaggaa aaaagagaac atcaccttgt aaaactgaag attgtgacca gtcagaataa 60
tgtcattatg cctgggattt ggatcgtgat atgtgcatcg gccagaacca aggcataagt 120
agcattatgg tgacagctgc ctcgggaagc caagttgggc tttaaagtgc agggcctgct 180
gatgt 185

<210> SEQ ID NO 215
<211> LENGTH: 185
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 215
ccggggtcct gtctgcatcc agcgcagcat tctggaagac gccacgcctc cgctggcgac 60
ggactccaaa tcccgtgcat aatcgctgtg acacttcaaa ccattatgcc tgggatttgg 120
atcccgtcca cggcaccgca tcgaaaacgc cgctgagacc tcagccttga cctccctcag 180
cgtgg 185

<210> SEQ ID NO 216
<211> LENGTH: 212
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 216
caatggtgga atgtggaggt gaagttaaca ccttcgtggc tacagagttt ccttagcaga 60
gctgcattat gcctgggatt tggatctgtc taaactatga ttcgaatcca aggcatatgg 120
tagctactgc taggcaatcc ttccctcgat aaatgtcttg gcatcgtttg ctttgagcaa 180
gaaggttcat ctgatatcag tcttctcaat ct 212

<210> SEQ ID NO 217
<211> LENGTH: 210
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 217
acaggctgat tgtatctgtc tatgagcaaa ggaaacctga aggaaccaag ggcctggctg 60
gacagagttg tcatgtgatg atgaaaggac agtgaattag cagaacatcc gctcacctgt 120
taattcacat ccctttcatc agcacatgac aacccagcct gaatgacaac cagccattga 180
aagaaagcag ccctcacacc atagcatcta 210

<210> SEQ ID NO 218
<211> LENGTH: 181
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 218
gggtttattg taagagagca ttatgaagaa aaaaatagat cataaagctt cttcaggacg 60
atggaagggt tgtgaacgtt agatttaaat agtgattgtc taattcacat ccctttcatc 120
agtcttgggg gagaccagct gcgctgcact accaacagca aaagaagtga atgggacagc 180
t 181

<210> SEQ ID NO 219
<211> LENGTH: 210
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 219
aggagggtgg gggtggaggc aagcagagga cttcctgatc gcgtacccat ggctacagtc 60
tttcttcatg tgactcgtgg actaattcac atccctttca tcaggagaat atatgaaggc 120
tgaggaagag gtgtgaattc gttcaattgt catcactggc atctttttg atcattgcac 180 catcatcaaa tgcattggga taaccatgac 210

<210> SEQ ID NO 220
<211> LENGTH: 188
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 220
tttaccaatg aaaagcattt aactgttttg gattccaaac tagcagcact acaatgcttt 60
gctagtgatg aataggctgc gaattatcgc ctcttcaatg gataattcac atccctttca 120
tcagtagcta tgcattgatt actacgggac aaccaacgtt ttcatttgtg aatatcaatt 180
acttgcca 188

<210> SEQ ID NO 221
<211> LENGTH: 171
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 221
caggttaacc caacagaagg ctaaagaagg tatattgctg ttgacagtga gcgactagtc 60
gttgggtaaa gtcgccactg tgaagccaca gatgggtggt gacttctcaa cgattagctg 120
cctactgcct cggacttcaa ggggctactt taggagcaat tatcttgttt a 171

<210> SEQ ID NO 222
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 222
gatgctacaa gtggcccact tctgagatgc gggctgcttc tggatgacac tgcttcccga 60
ggtggcgatt ttacccaatg ctctatatgg attactttgc tatagtcgtt gggtaaagtc 120
gccatttcgg caagtgcctc ctcgctggcc ccagggtacc acccggagca caggtttggt 180
gacctt 186

<210> SEQ ID NO 223
<211> LENGTH: 210
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 223
aggagggtgg gggtggaggc aagcagagga cttcctgatc gcgtacccat ggctacagtc 60
tttcttcatg tgactcgtgg actagtcgtt gggtaaagtc gccagagaat atatgaaggt 120
ggcactttcc tcaacgactc gttcaattgt catcactggc atctttttg atcattgcac 180 catcatcaaa tgcattggga taaccatgac 210

<210> SEQ ID NO 224
<211> LENGTH: 207
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 224
agggactggg cccacgggga ggcagcgtcc ccgaggcagc agcggcagcg gcggctcctc 60
tccccatggc cctgtagtcg ttgggtaaag tcgccactgg gctcagaccg cgacttacca 120
cacgactaca gggacctggg gaccccggca ccggcaggcc ccaaggggtg aggtgagcgg 180
gcattgggac ctcccctccc tgtactc 207

<210> SEQ ID NO 225
<211> LENGTH: 185
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 225
ttagcaggaa aaaagagaac atcaccttgt aaaactgaag attgtgacca gtcagaataa 60
tgtgttgctt tccgctaagt ggtgagtgat atgtgcatct cccactcaga ggaaagcact 120
agcattatgg tgacagctgc ctcgggaagc caagttgggc tttaaagtgc agggcctgct 180
gatgt 185

<210> SEQ ID NO 226
<211> LENGTH: 212
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 226
caatggtgga atgtggaggt gaagttaaca ccttcgtggc tacagagttt ccttagcaga 60
gctggttgct ttccgctaag tggtgatgtc taaactattc accacttaga ggaaagcctc 120
tagctactgc taggcaatcc ttccctcgat aaatgtcttg gcatcgtttg ctttgagcaa 180
gaaggttcat ctgatatcag tcttctcaat ct 212

<210> SEQ ID NO 227
<211> LENGTH: 185
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 227
ccggggtcct gtctgcatcc agcgcagcat tctggaagac gccacgcctc cgctggcgac 60
gggaaccact tagcgcgaag caaggctgtg acacttcaaa cgttgctttc cgctaagtgg 120
tgaccgtcca cggcaccgca tcgaaaacgc cgctgagacc tcagccttga cctccctcag 180
cgtgg 185

<210> SEQ ID NO 228
<211> LENGTH: 171
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 228
caggttaacc caacagaagg ctaaagaagg tatattgctg ttgacagtga gcgactttgc 60
agtggccttc gtggcccctg tgaagccaca gatggggggt cacgagccac tgcgaagctg 120
cctactgcct cggacttcaa ggggctactt taggagcaat tatcttgttt a 171

<210> SEQ ID NO 229
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 229
gatgctacaa gtggcccact tctgagatgc gggctgcttc tggatgacac tgcttcccga 60
gggggctatg aaggccattg agaaatatgg attactttgc tatttgcagt ggccttcgta 120
gccctttcgg caagtgcctc ctcgctggcc ccagggtacc acccggagca caggtttggt 180
gacctt 186

<210> SEQ ID NO 230
<211> LENGTH: 185
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 230
ttagcaggaa aaaagagaac atcaccttgt aaaactgaag attgtgacca gtcagaataa 60
tgttttgcag tggccttcgt ggcccgtgat atgtgcatcg gtcacgtaga ctactgcact 120
cgcattatgg tgacagctgc ctcgggaagc caagttgggc tttaaagtgc agggcctgct 180
gatgt 185

<210> SEQ ID NO 231
<211> LENGTH: 212
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 231
caatggtgga atgtggaggt gaagttaaca ccttcgtggc tacagagttt ccttagcaga 60
gctgtttgca gtggccttcg tggccctgtc taaactatgg gtcacgaaga ccactgccca 120
tagctactgc taggcaatcc ttccctcgat aaatgtcttg gcatcgtttg ctttgagcaa 180
gaaggttcat ctgatatcag tcttctcaat ct 212

<210> SEQ ID NO 232
<211> LENGTH: 207
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 232
agggactggg cccacgggga ggcagcgtcc ccgaggcagc agcggcagcg gcggctcctc 60
tccccatggc cctgagcctc ccgtcctaag accccactgg gctcagacag ggtcttggaa 120
aggaggctca gggacctggg gaccccggca ccggcaggcc ccaaggggtg aggtgagcgg 180
gcattgggac ctcccctccc tgtactc 207

<210> SEQ ID NO 233
<211> LENGTH: 181
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 233
gggtttattg taagagagca ttatgaagaa aaaaatagat cataaagctt cttcagggtg 60
ggtcttaggt cgggagctgc tgatttaaat agtgattgtc agcctcccgt cctaagaccc 120
caccttgggg gagaccagct gcgctgcact accaacagca aaagaagtga atgggacagc 180
t 181

<210> SEQ ID NO 234
<211> LENGTH: 209
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 234
tctcccatcc ccttcagata cttacagata ctgtaaagtg agtagaattc tgagttttga 60
ggttgcttca gtgagcctcc cgtcctaaga ccccacttgg aattaaaatc aagtgggtct 120
tgacgggtgg caccctatgg ctaaccatca tctactccat ggtgctcaga attcgctgaa 180
gacaggaaac caaaggtgga cacaccagg 209

<210> SEQ ID NO 235
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 235
gatgctacaa gtggcccact tctgagatgc gggctgcttc tggatgacac tgcttcccga 60
ggccagggtg agtaacgtgg cctcttatgg attactttgc taagatccac gttactcacc 120
ctggtttcgg caagtgcctc ctcgctggcc ccagggtacc acccggagca caggtttggt 180
gacctt 186

<210> SEQ ID NO 236
<211> LENGTH: 171
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 236
caggttaacc caacagaagg ctaaagaagg tatattgctg ttgacagtga gcgacagatc 60
cacgttactc acccaagctg tgaagccaca gatgggcttg ggtgagacgt ggatctgctg 120
cctactgcct cggacttcaa ggggctactt taggagcaat tatcttgttt a 171

<210> SEQ ID NO 237
<211> LENGTH: 188
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 237
tttaccaatg aaaagcattt aactgttttg gattccaaac tagcagcact acaatgcttt 60
gctagagggg tgtataccgc ggatcttcgc ctcttcaatg gaagatccac gttactcacc 120
cctgtagcta tgcattgatt actacgggac aaccaacgtt ttcatttgtg aatatcaatt 180
acttgcca 188

<210> SEQ ID NO 238
<211> LENGTH: 212
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 238
caatggtgga atgtggaggt gaagttaaca ccttcgtggc tacagagttt ccttagcaga 60
gctgagatcc acgttactca cccttgtgtc taaactatca agggtgagtc acgtggagat 120
tagctactgc taggcaatcc ttccctcgat aaatgtcttg gcatcgtttg ctttgagcaa 180
gaaggttcat ctgatatcag tcttctcaat ct 212

<210> SEQ ID NO 239
<211> LENGTH: 181
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 239
gggtttattg taagagagca ttatgaagaa aaaaatagat cataaagctt cttcaggaaa 60
gatccacgtt actcaccctt agatttaaat agtgattgtc taggtgagtt acgtggatct 120
gttcttgggg gagaccagct gcgctgcact accaacagca aaagaagtga atgggacagc 180
t 181

<210> SEQ ID NO 240
<211> LENGTH: 210
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 240
acaggctgat tgtatctgtc tatgagcaaa ggaaacctga aggaaccaag ggcctggctg 60
gacagagttg tcatgtgtca gatccacgtt actcaccctg cagaacatcc gctcacctgt 120
agggtgagac tcgtggatct gtcacatgac aacccagcct gaatgacaac cagccattga 180
aagaaagcag ccctcacacc atagcatcta 210

<210> SEQ ID NO 241
<211> LENGTH: 171
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 241
caggttaacc caacagaagg ctaaagaagg tatattgctg ttgacagtga gcgacttcag 60
gaatgggttc caaggagctg tgaagccaca gatgggctcc ttggaccatt cctgaagctg 120
cctactgcct cggacttcaa ggggctactt taggagcaat tatcttgttt a 171

<210> SEQ ID NO 242
<211> LENGTH: 191
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 242
gtcttggagg ctggggcacc tcggggaagg acgccggcat cagcaccatt ctggggtacg 60
gggatggatt caggaatggg ttccaaggaa ttgtttctaa tgtcctgaag ccattcatgg 120
agccgtccgt atccgctgca gcctgtgggg cctgcgggcc ggggagccga tcgcgcttca 180
gctcagcgcc t 191

<210> SEQ ID NO 243
<211> LENGTH: 185
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 243
ttagcaggaa aaaagagaac atcaccttgt aaaactgaag attgtgacca gtcagaataa 60
tgtttcagga atgggttcca aggaagtgat atgtgcatct tcttggtaca cgttcctgct 120
cacattatgg tgacagctgc ctcgggaagc caagttgggc tttaaagtgc agggcctgct 180
gatgt 185

<210> SEQ ID NO 244
<211> LENGTH: 212
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 244
caatggtgga atgtggaggt gaagttaaca ccttcgtggc tacagagttt ccttagcaga 60
gctgttcagg aatgggttcc aaggagtgtc taaactatct ccttggaaca cattcctaca 120
tagctactgc taggcaatcc ttccctcgat aaatgtcttg gcatcgtttg ctttgagcaa 180
gaaggttcat ctgatatcag tcttctcaat ct 212

<210> SEQ ID NO 245
<211> LENGTH: 207
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 245
agggactggg cccacgggga ggcagcgtcc ccgaggcagc agcggcagcg gcggctcctc 60
tccccatggc cctgtataat ataatagaac cacaggctgg gctcagacgt gtggtttatc 120
ctgttgtaca gggacctggg gaccccggca ccggcaggcc ccaaggggtg aggtgagcgg 180
gcattgggac ctcccctccc tgtactc 207

<210> SEQ ID NO 246
<211> LENGTH: 168
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 246
tgtggtgctg ggggcttcag cggccggctc tgatctccat cctccctggg gcatataata 60
taatagaacc acagggccct tcatgctgcc cagcttgtgg ttctattatg ttataactcg 120
gggtgggagt cagcaggagg tgagggggca tggtggcccc agtgcagc 168

<210> SEQ ID NO 247
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 247
gatgctacaa gtggcccact tctgagatgc gggctgcttc tggatgacac tgcttcccga 60
ggcgtgctga actggtatcg aaatgtatgg attactttgc tacatgcggt accagtttag 120
cacgtttcgg caagtgcctc ctcgctggcc ccagggtacc acccggagca caggtttggt 180
gacctt 186

<210> SEQ ID NO 248
<211> LENGTH: 212
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 248
caatggtgga atgtggaggt gaagttaaca ccttcgtggc tacagagttt ccttagcaga 60
gctgcatgcg gtaccagttt agcacgtgtc taaactatcg tgctagactt gtactgtcag 120
tagctactgc taggcaatcc ttccctcgat aaatgtcttg gcatcgtttg ctttgagcaa 180
gaaggttcat ctgatatcag tcttctcaat ct 212

<210> SEQ ID NO 249
<211> LENGTH: 171
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 249
caggttaacc caacagaagg ctaaagaagg tatattgctg ttgacagtga gcgaccatgc 60
ggtaccagtt tagcacgctg tgaagccaca gatgggcgtg ctagaggtgt cgcatggctg 120
cctactgcct cggacttcaa ggggctactt taggagcaat tatcttgttt a 171

<210> SEQ ID NO 250
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 250
gatgctacaa gtggcccact tctgagatgc gggctgcttc tggatgacac tgcttcccga 60
ggcagcgagg gagaagatta ccatttatgg attactttgc taaatatagt cttctccctc 120
gctgtttcgg caagtgcctc ctcgctggcc ccagggtacc acccggagca caggtttggt 180
gacctt 186

<210> SEQ ID NO 251
<211> LENGTH: 176
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 251
tgaagccaca ggagccaaga gcaggaggac caaggccctg gcgaaggccg tggcctcgaa 60
tatagtcttc tccctcgctt gtgcaggtcc caatggagcg agggatagga ctatactcgg 120
ggacgcgggc ctggacgccg gcatccgggc tcaggacccc cctctctgcc agaggc 176

<210> SEQ ID NO 252
<211> LENGTH: 171
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 252
caggttaacc caacagaagg ctaaagaagg tatattgctg ttgacagtga gcgacaatat 60
agtcttctcc ctcgctgctg tgaagccaca gatgggcagt gagggaagac tatgttgctg 120
cctactgcct cggacttcaa ggggctactt taggagcaat tatcttgttt a 171

<210> SEQ ID NO 253
<211> LENGTH: 186
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 253
gatgctacaa gtggcccact tctgagatgc gggctgcttc tggatgacac tgcttcccga 60
ggccggttga acattggttg cctcatatgg attactttgc tatgaacgac cagtgtttaa 120
ccggtttcgg caagtgcctc ctcgctggcc ccagggtacc acccggagca caggtttggt 180
gacctt 186

<210> SEQ ID NO 254
<211> LENGTH: 185
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 254
ccggggtcct gtctgcatcc agcgcagcat tctggaagac gccacgcctc cgctggcgac 60
gggacggatg aacttagagg agacgctgtg acacttcaaa cttctccttg gagttcatcc 120
gcgccgtcca cggcaccgca tcgaaaacgc cgctgagacc tcagccttga cctccctcag 180
cgtgg 185

<210> SEQ ID NO 255
<211> LENGTH: 171
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 255
caggttaacc caacagaagg ctaaagaagg tatattgctg ttgacagtga gcgacttctc 60
cttggagttc atccgcgctg tgaagccaca gatgggcgcg gatgatccaa ggaggagctg 120
cctactgcct cggacttcaa ggggctactt taggagcaat tatcttgttt a 171

<210> SEQ ID NO 256
<211> LENGTH: 207
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 256
agggactggg cccacgggga ggcagcgtcc ccgaggcagc agcggcagcg gcggctcctc 60
tccccatggc cctgatacac atcagaatcc ttactgctgg gctcagaccg taaggatctc 120
ctgtgtatca gggacctggg gaccccggca ccggcaggcc ccaaggggtg aggcgagcgg 180
gcattgggac ctcccctccc tgtactc 207

<210> SEQ ID NO 257
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 257
aggagggtgg gggtggaggc aagcagagga cttcctgatc gcgtacccat ggctacagtc     60
tttcttcatg tgactcgtgg acatacacat cagaatcctt acttgagaat atatgaagga    120
ggtaggatac tgatgtgtac gttcaattgt catcactggc atctttttttg atcattgcac    180 catcatcaaa tgcattggga taaccatgac                                      210

<210> SEQ ID NO 258
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 258
gatgctacaa gtggcccact tctgagatgc gggctgcttc tggatgacac tgcttcccga     60
ggcggtaagg attctgatgt aatattatgg attactttgc taatacacat cagaatcctt    120
actgtttcgg caagtgcctc ctcgctggcc ccagggtacc acccggagca caggtttggt    180
gacctt                                                                186

<210> SEQ ID NO 259
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 259
tgaagccaca ggagccaaga gcaggaggac caaggccctg gcgaaggccg tggcctcgat     60
acacatcaga atccttactt gtgcaggtcc caatggagta aggatcctga tgtgtctcgg    120
ggacgcgggc ctggacgccg gcatccgggc tcaggacccc cctctctgcc agaggc         176

<210> SEQ ID NO 260
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 260
agggactggg cccacgggga ggcagcgtcc ccgaggcagc agcggcagcg gcggctcctc     60
tccccatggc cctgttgttg aaggcgtttg cacatgctgg gctcagacct gtgcaatgcg    120
atcaatagca gggacctggg gaccccggca ccggcaggcc ccaaggggtg aggcgagcgg    180
gcattgggac ctcccctccc tgtactc                                         207

<210> SEQ ID NO 261
<211> LENGTH: 189
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 261
cttctgaaga aaatatattt ctttttattc atagctctta tgatagcaat gtcagcagtg 60
cctttgttga aggcgtttgc acatgttaag attctaaaat tatcttgtgc ggaagcactt 120
caataaaagt aaggttgacc atactctaca gttgtgtttt aatgtatatt aatgttacta 180
atgtgtttt 189

<210> SEQ ID NO 262
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 262
gatgctacaa gtggcccact tctgagatgc gggctgcttc tggatgacac tgcttcccga 60
ggcgtgtgtg aacgccttca cataatatgg attactttgc tattgttgaa ggcgtttgca 120
catgtttcgg caagtgcctc ctcgctggcc ccagggtacc acccggagca caggtttggt 180
gacctt 186

<210> SEQ ID NO 263
<211> LENGTH: 176
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 263
tgaagccaca ggagccaaga gcaggaggac caaggccctg gcgaaggccg tggcctcgtt 60
gttgaaggcg tttgcacatt gtgcaggtcc caatgggtgt gcaaaggtct tcaatcacgg 120
ggacgcgggc ctggacgccg gcatccgggc tcaggacccc cctctctgcc agaggc 176

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 267
aggagggtgg gggtggaggc aagcagagga cttcctgatc gcgtacccat ggctacagtc 60
tttcttcatg tgactcgtgg acttcaggaa tgggttccaa ggatgagaat atatgaagga 120
tcctggaagc tattcctgac gttcaattgt catcactggc atcttttttg atcattgcac 180
catcatcaaa tgcattggga taaccatgac gatgctacaa gtggcccact tctgagatgc 240
gggctgcttc tggatgacac tgcttcccga ggcctgtggt tctgttatat ccatatatgg 300
attactttgc tatataatat aatagaacca caggtttcgg caagtgcctc ctcgctggcc 360
ccagggtacc acccggagca caggtttggt gacctt 396

<210> SEQ ID NO 268
<211> LENGTH: 417
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 268
aggagggtgg gggtggaggc aagcagagga cttcctgatc gcgtacccat ggctacagtc 60
tttcttcatg tgactcgtgg acttcaggaa tgggttccaa ggatgagaat atatgaagga 120
tcctggaagc tattcctgac gttcaattgt catcactggc atcttttttg atcattgcac 180
catcatcaaa tgcattggga taaccatgac agggactggg cccacgggga ggcagcgtcc 240
ccgaggcagc agcggcagcg gcggctcctc tccccatggc cctgagatcc acgttactca 300
cccgtgctgg gctcagaccc gggtgataat atggatctca gggacctggg gaccccggca 360
ccggcaggcc ccaaggggtg aggtgagcgg gcattgggac ctcccctccc tgtactc 417

<210> SEQ ID NO 269
<211> LENGTH: 393
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 269
gatgctacaa gtggcccact tctgagatgc gggctgcttc tggatgacac tgcttcccga 60
ggcctgtggt tctgttatat ccatatatgg attactttgc tatataatat aatagaacca 120
caggtttcgg caagtgcctc ctcgctggcc ccagggtacc acccggagca caggtttggt 180
gaccttaggg actgggccca cggggaggca gcgtccccga ggcagcagcg gcagcggcgg 240
ctcctctccc catggccctg agatccacgt tactcacccg tgctgggctc agacccgggt 300
gataatatgg atctcaggga cctggggacc ccggcaccgg caggccccaa ggggtgaggt 360
gagcgggcat tgggacctcc cctccctgta ctc 393

<210> SEQ ID NO 270
<211> LENGTH: 394
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 270
ttagcaggaa aaaagagaac atcaccttgt aaaactgaag attgtgacca gtcagaataa 60
tgtagatcca cgttactcac cctagtgata tgtgcatcta gggtgtgtca tgtggatgaa 120
gcattatggt gacagctgcc tcgggaagcc aagttgggct ttaaagtgca gggcctgctg 180
atgtaggagg gtgggggtgg aggcaagcag aggacttcct gatcgcgtac ccatggctac 240
agtctttctt catgtgactc gtggacttca ggaatgggtt ccaaggatga gaatatatga 300
aggatcctgg aagctattcc tgacgttcaa ttgtcatcac tggcatcttt tttgatcatt 360
gcaccatcat caaatgcatt gggataacca tgac 394

<210> SEQ ID NO 271
<211> LENGTH: 370
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 271
ttagcaggaa aaaagagaac atcaccttgt aaaactgaag attgtgacca gtcagaataa 60
tgtagatcca cgttactcac cctagtgata tgtgcatcta gggtgtgtca tgtggatgaa 120
gcattatggt gacagctgcc tcgggaagcc aagttgggct ttaaagtgca gggcctgctg 180
atgtgatgct acaagtggcc cacttctgag atgcgggctg cttctggatg acactgcttc 240
ccgaggcctg tggttctgtt atatccatat atggattact ttgctatata atataataga 300
accacaggtt tcggcaagtg cctcctcgct ggccccaggg taccacccgg agcacaggtt 360
tggtgacctt 370

<210> SEQ ID NO 272
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 272
aggagggtgg gggtggaggc aagcagagga cttcctgatc gcgtacccat ggctacagtc 60
tttcttcatg tgactcgtgg acagatccac gttactcacc ccctgagaat atatgaagga 120
ggggtgagaa gcgtggatcc gttcaattgt catcactggc atcttttttg atcattgcac 180
catcatcaaa tgcattggga taaccatgac gatgctacaa gtggcccact tctgagatgc 240
gggctgcttc tggatgacac tgcttcccga ggcctgtggt tctgttatat ccatatatgg 300
attactttgc tatataatat aatagaacca caggtttcgg caagtgcctc ctcgctggcc 360
ccagggtacc acccggagca caggtttggt gacctt 396

<210> SEQ ID NO 273
<211> LENGTH: 417
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 273
agggactggg cccacgggga ggcagcgtcc ccgaggcagc agcggcagcg gcggctcctc 60
tccccatggc cctgagatcc acgttactca cccgtgctgg gctcagaccc gggtgataat 120
atggatctca gggacctggg gaccccggca ccggcaggcc ccaaggggtg aggtgagcgg 180
gcattgggac ctcccctccc tgtactcagg agggtggggg tggaggcaag cagaggactt 240
cctgatcgcg tacccatggc tacagtcttt cttcatgtga ctcgtggact tcaggaatgg 300
gttccaagga tgagaatata tgaaggatcc tggaagctat tcctgacgtt caattgtcat 360
cactggcatc tttttgatc attgcaccat catcaaatgc attgggataa ccatgac 417

<210> SEQ ID NO 274
<211> LENGTH: 393
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 274
agggactggg cccacgggga ggcagcgtcc ccgaggcagc agcggcagcg gcggctcctc 60
tccccatggc cctgagatcc acgttactca cccgtgctgg gctcagaccc gggtgataat 120
atggatctca gggacctggg gaccccggca ccggcaggcc ccaaggggtg aggtgagcgg 180
gcattgggac ctcccctccc tgtactcgat gctacaagtg gcccacttct gagatgcggg 240
ctgcttctgg atgacactgc ttcccgaggc ctgtggttct gttatatcca tatatggatt 300
actttgctat ataatataat agaaccacag gtttcggcaa gtgcctcctc gctggcccca 360
gggtaccacc cggagcacag gtttggtgac ctt 393

<210> SEQ ID NO 275
<211> LENGTH: 580
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 275
ttagcaggaa aaaagagaac atcaccttgt aaaactgaag attgtgacca gtcagaataa 60
tgtagatcca cgttactcac cctagtgata tgtgcatcta gggtgtgtca tgtggatgaa 120
gcattatggt gacagctgcc tcgggaagcc aagttgggct ttaaagtgca gggcctgctg 180
atgtaggagg gtgggggtgg aggcaagcag aggacttcct gatcgcgtac ccatggctac 240
agtctttctt catgtgactc gtggacttca ggaatgggtt ccaaggatga gaatatatga 300
aggatcctgg aagctattcc tgacgttcaa ttgtcatcac tggcatcttt tttgatcatt 360
gcaccatcat caaatgcatt gggataacca tgacgatgct acaagtggcc cacttctgag 420
atgcgggctg cttctggatg acactgcttc ccgaggcctg tggttctgtt atatccatat 480
atggattact ttgctatata atataataga accacaggtt tcggcaagtg cctcctcgct 540
ggccccaggg taccacccgg agcacaggtt tggtgacctt 580

<210> SEQ ID NO 276
<211> LENGTH: 748
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 276
ttaggatgag ttgagatccc agtgatcttc tcgctaagag tttcctgcct gggcaaggag 60
gaaattagca ggaaaaaaga gaacatcacc ttgtaaaact gaagattgtg accagtcaga 120

```
ataatgtaga tccacgttac tcaccctagt gatatgtgca tctagggtgt gtcatgtgga    180

tgaagcatta tggtgacagc tgcctcggga agccaagttg ggctttaaag tgcagggcct    240

gctgatgtag gagggtgggg gtggaggcaa gcagaggact tcctgatcgc gtacccatgg    300

ctacagtctt tcttcatgtg actcgtggac ttcaggaatg ggttccaagg atgagaatat    360

atgaaggatc ctggaagcta ttcctgacgt tcaattgtca tcactggcat ctttttttgat    420

cattgcacca tcatcaaatg cattgggata accatgacga tgctacaagt ggcccacttc    480

tgagatgcgg gctgcttctg gatgacactg cttcccgagg cctgtggttc tgttatatcc    540

atatatggat tactttgcta tataatataa tagaaccaca ggtttcggca agtgcctcct    600

cgctggcccc agggtaccac ccggagcaca ggtttggtga ccttcttcct catcagggct    660

ttgtgccagc aaatgactcc ctcaccaagg aagcaagagc ctctgaatcc catctgggct    720

cttcctgaac acccctatct ccccctct                                       748
```

<210> SEQ ID NO 277
<211> LENGTH: 761
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 277

```
ttagggatta tgctgaattt gtatggttta tagttgttag agtttgaggt gttaattcta     60

attatctatt tcaaatttta gcaggaaaaa agagaacatc accttgtaaa actgaagatt    120

gtgaccagtc agaataatgt agatccacgt tactcaccct agtgatatgt gcatctaggg    180

tgtgtcatgt ggatgaagca ttatggtgac agctgcctcg ggaagccaag ttgggcttta    240

aagtgcaggg cctgctgatg taggagggtg ggggtggagg caagcagagg acttcctgat    300

cgcgtaccca tggctacagt ctttcttcat gtgactcgtg gacttcagga atgggttcca    360

aggatgagaa tatatgaagg atcctggaag ctattcctga cgttcaattg tcatcactgg    420

catctttttt gatcattgca ccatcatcaa atgcattggg ataaccatga cgatgctaca    480

agtggcccac ttctgagatg cgggctgctt ctggatgaca ctgcttcccg aggcctgtgg    540

ttctgttata tccatatatg gattactttg ctatataata taatagaacc acaggtttcg    600

gcaagtgcct cctcgctggc cccagggtac cacccggagc acaggtttgg tgaccttctt    660

cctcatcagg gctttgtgcc agcaaatgac tccctcacca aggaagcaag agcctctgaa    720

tcccatctgg gctcttcctg aacaccccta tctccccctc t                        761
```

<210> SEQ ID NO 278
<211> LENGTH: 580
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 278

```
aggagggtgg gggtggaggc aagcagagga cttcctgatc gcgtacccat ggctacagtc     60

tttcttcatg tgactcgtgg acttcaggaa tgggttccaa ggatgagaat atatgaagga    120

tcctggaagc tattcctgac gttcaattgt catcactggc atcttttttg atcattgcac    180

catcatcaaa tgcattggga taaccatgac gatgctacaa gtggcccact tctgagatgc    240
```

```
gggctgcttc tggatgacac tgcttcccga ggcctgtggt tctgttatat ccatatatgg    300

attactttgc tatataatat aatagaacca caggtttcgg caagtgcctc ctcgctggcc    360

ccagggtacc acccggagca caggtttggt gaccttttag caggaaaaaa gagaacatca    420

ccttgtaaaa ctgaagattg tgaccagtca gaataatgta gatccacgtt actcacccta    480

gtgatatgtg catctagggt gtgtcatgtg gatgaagcat tatggtgaca gctgcctcgg    540

gaagccaagt tgggctttaa agtgcagggc ctgctgatgt                          580
```

<210> SEQ ID NO 279
<211> LENGTH: 748
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 279

```
ttaggatgag ttgagatccc agtgatcttc tcgctaagag tttcctgcct gggcaaggag     60

gaaaaggagg gtgggggtgg aggcaagcag aggacttcct gatcgcgtac ccatggctac    120

agtctttctt catgtgactc gtggacttca ggaatgggtt ccaaggatga gaatatatga    180

aggatcctgg aagctattcc tgacgttcaa ttgtcatcac tggcatcttt tttgatcatt    240

gcaccatcat caaatgcatt gggataacca tgacgatgct acaagtggcc cacttctgag    300

atgcgggctg cttctggatg acactgcttc ccgaggcctg tggttctgtt atatccatat    360

atggattact ttgctatata atataataga accacaggtt tcggcaagtg cctcctcgct    420

ggccccaggg taccacccgg agcacaggtt tggtgacctt ttagcaggaa aaaagagaac    480

atcaccttgt aaaactgaag attgtgacca gtcagaataa tgtagatcca cgttactcac    540

cctagtgata tgtgcatcta gggtgtgtca tgtggatgaa gcattatggt gacagctgcc    600

tcgggaagcc aagttgggct ttaaagtgca gggcctgctg atgtcttcct catcagggct    660

ttgtgccagc aaatgactcc ctcaccaagg aagcaagagc ctctgaatcc catctgggct    720

cttcctgaac acccctatct cccccctct                                      748
```

<210> SEQ ID NO 280
<211> LENGTH: 756
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 280

```
tggagaggag ggtgggggtg gaggcaagca gaggacctcc tgatcatgta cccataggac     60

agggtgatgg aaaggagggt gggggtggag gcaagcagag gacttcctga tcgcgtaccc    120

atggctacag tctttcttca tgtgactcgt ggacttcagg aatgggttcc aaggatgaga    180

atatatgaag gatcctggaa gctattcctg acgttcaatt gtcatcactg gcatcttttt    240

tgatcattgc accatcatca aatgcattgg gataaccatg acgatgctac aagtggccca    300

cttctgagat gcgggctgct tctggatgac actgcttccc gaggcctgtg gttctgttat    360

atccatatat ggattacttt gctatataat ataatagaac cacaggtttc ggcaagtgcc    420

tcctcgctgg ccccagggta ccacccggag cacaggtttg gtgacctttt agcaggaaaa    480

aagagaacat caccttgtaa aactgaagat tgtgaccagt cagaataatg tagatccacg    540

ttactcaccc tagtgatatg tgcatctagg gtgtgtcatg tggatgaagc attatggtga    600
```

cagctgcctc gggaagccaa gttgggcttt aaagtgcagg gcctgctgat gtcttcctca 660
tcagggcttt gtgccagcaa atgactccct caccaaggaa gcaagagcct ctgaatccca 720
tctgggctct tcctgaacac ccctatctcc ccctct 756

<210> SEQ ID NO 281
<211> LENGTH: 386
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 281
aggagggtgg gggtggaggc aagcagagga cttcctgatc gcgtacccat ggctacagtc 60
tttcttcatg tgactcgtgg acttcaggaa tgggttccaa ggatgagaat atatgaagga 120
tcctggaagc tattcctgac gttcaattgt catcactggc atcttttttg atcattgcac 180
catcatcaaa tgcattggga taaccatgac tgaagccaca ggagccaaga gcaggaggac 240
caaggccctg gcgaaggccg tggcctcgaa tatagtcttc tccctcgctt gtgcaggtcc 300
caatggagcg agggatagga ctatactcgg ggacgcgggc ctggacgccg gcatccgggc 360
tcaggacccc cctctctgcc agaggc 386

<210> SEQ ID NO 282
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 282
aggagggtgg gggtggaggc aagcagagga cttcctgatc gcgtacccat ggctacagtc 60
tttcttcatg tgactcgtgg acttcaggaa tgggttccaa ggatgagaat atatgaagga 120
tcctggaagc tattcctgac gttcaattgt catcactggc atcttttttg atcattgcac 180
catcatcaaa tgcattggga taaccatgac gatgctacaa gtggcccact tctgagatgc 240
gggctgcttc tggatgacac tgcttcccga ggcctgtggt tctgttatat ccatatatgg 300
attactttgc tatataatat aatagaacca caggtttcgg caagtgcctc ctcgctggcc 360
ccagggtacc acccggagca caggtttggt gacctt 396

<210> SEQ ID NO 283
<211> LENGTH: 362
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 283
gatgctacaa gtggcccact tctgagatgc gggctgcttc tggatgacac tgcttcccga 60
ggcctgtggt tctgttatat ccatatatgg attactttgc tatataatat aatagaacca 120
caggtttcgg caagtgcctc ctcgctggcc ccagggtacc acccggagca caggtttggt 180
gacctttgaa gccacaggag ccaagagcag gaggaccaag gccctggcga aggccgtggc 240
ctcgaatata gtcttctccc tcgcttgtgc aggtcccaat ggagcgaggg ataggactat 300
actcggggac gcgggcctgg acgccggcat ccgggctcag gacccccctc tctgccagag 360
gc 362

<210> SEQ ID NO 284
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 284
gatgctacaa gtggcccact tctgagatgc gggctgcttc tggatgacac tgcttcccga 60
ggcctgtggt tctgttatat ccatatatgg attactttgc tatataatat aatagaacca 120
caggtttcgg caagtgcctc ctcgctggcc ccagggtacc acccggagca caggtttggt 180
gaccttagga gggtgggggt ggaggcaagc agaggacttc ctgatcgcgt acccatggct 240
acagtctttc ttcatgtgac tcgtggacaa tatagtcttc tccctcgctt gagaatatat 300
gaaggaagca gggacaggac tatattgttc aattgtcatc actggcatct tttttgatca 360
ttgcaccatc atcaaatgca ttgggataac catgac 396

<210> SEQ ID NO 285
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 285
ttagcaggaa aaaagagaac atcaccttgt aaaactgaag attgtgacca gtcagaataa 60
tgtagatcca cgttactcac cctagtgata tgtgcatcta gggtgtgtca tgtggatgaa 120
gcattatggt gacagctgcc tcgggaagcc aagttgggct ttaaagtgca gggcctgctg 180
atgttgaagc cacaggagcc aagagcagga ggaccaaggc cctggcgaag gccgtggcct 240
cgaatatagt cttctccctc gcttgtgcag gtcccaatgg agcgagggat aggactatac 300
tcggggacgc gggcctggac gccggcatcc gggctcagga cccccctctc tgccagaggc 360

<210> SEQ ID NO 286
<211> LENGTH: 394
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 286
ttagcaggaa aaaagagaac atcaccttgt aaaactgaag attgtgacca gtcagaataa 60
tgtagatcca cgttactcac cctagtgata tgtgcatcta gggtgtgtca tgtggatgaa 120
gcattatggt gacagctgcc tcgggaagcc aagttgggct ttaaagtgca gggcctgctg 180
atgtaggagg gtgggggtgg aggcaagcag aggacttcct gatcgcgtac ccatggctac 240
agtctttctt catgtgactc gtggacaata tagtcttctc cctcgcttga gaatatatga 300
aggaagcagg gacaggacta tattgttcaa ttgtcatcac tggcatcttt tttgatcatt 360
gcaccatcat caaatgcatt gggataacca tgac 394

<210> SEQ ID NO 287
<211> LENGTH: 394

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 287
ttagcaggaa aaaagagaac atcaccttgt aaaactgaag attgtgacca gtcagaataa 60
tgtagatcca cgttactcac cctagtgata tgtgcatcta gggtgtgtca tgtggatgaa 120
gcattatggt gacagctgcc tcgggaagcc aagttgggct ttaaagtgca gggcctgctg 180
atgtaggagg gtgggggtgg aggcaagcag aggacttcct gatcgcgtac ccatggctac 240
agtctttctt catgtgactc gtggacttca ggaatgggtt ccaaggatga gaatatatga 300
aggatcctgg aagctattcc tgacgttcaa ttgtcatcac tggcatcttt tttgatcatt 360
gcaccatcat caaatgcatt gggataacca tgac 394

<210> SEQ ID NO 288
<211> LENGTH: 370
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 288
ttagcaggaa aaaagagaac atcaccttgt aaaactgaag attgtgacca gtcagaataa 60
tgtagatcca cgttactcac cctagtgata tgtgcatcta gggtgtgtca tgtggatgaa 120
gcattatggt gacagctgcc tcgggaagcc aagttgggct ttaaagtgca gggcctgctg 180
atgtgatgct acaagtggcc cacttctgag atgcgggctg cttctggatg acactgcttc 240
ccgaggcctg tggttctgtt atatccatat atggattact ttgctatata atataataga 300
accacaggtt tcggcaagtg cctcctcgct ggccccaggg taccacccgg agcacaggtt 360
tggtgacctt 370

<210> SEQ ID NO 289
<211> LENGTH: 386
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 289
aggagggtgg gggtggaggc aagcagagga cttcctgatc gcgtacccat ggctacagtc 60
tttcttcatg tgactcgtgg acagatccac gttactcacc ccctgagaat atatgaagga 120
ggggtgagaa gcgtggatcc gttcaattgt catcactggc atcttttttg atcattgcac 180
catcatcaaa tgcattggga taaccatgac tgaagccaca ggagccaaga gcaggaggac 240
caaggccctg gcgaaggccg tggcctcgaa tatagtcttc tccctcgctt gtgcaggtcc 300
caatggagcg agggatagga ctatactcgg ggacgcgggc ctggacgccg gcatccgggc 360
tcaggacccc cctctctgcc agaggc 386

<210> SEQ ID NO 290
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 290
aggagggtgg gggtggaggc aagcagagga cttcctgatc gcgtacccat ggctacagtc 60
tttcttcatg tgactcgtgg acagatccac gttactcacc ccctgagaat atatgaagga 120
ggggtgagaa gcgtggatcc gttcaattgt catcactggc atcttttttg atcattgcac 180
catcatcaaa tgcattggga taaccatgac gatgctacaa gtggcccact tctgagatgc 240
gggctgcttc tggatgacac tgcttcccga ggcctgtggt tctgttatat ccatatatgg 300
attactttgc tatataatat aatagaacca caggtttcgg caagtgcctc ctcgctggcc 360
ccagggtacc acccggagca caggtttggt gacctt 396

<210> SEQ ID NO 291
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 291
aggtaagagt cgatcg 16

<210> SEQ ID NO 292
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 292
acgcgttact aactggtacc tcttttttttt ttttgatatc ctgcaggc 48

<210> SEQ ID NO 293
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 293

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Asp Asp Phe Ala Thr Tyr Tyr Cys Gln Gln Ser Lys
                85                  90                  95

Glu Val Pro Trp Thr Phe Gly Gln Gly Thr Lys Val Glu Ile Lys
            100                 105                 110

<210> SEQ ID NO 294
<211> LENGTH: 116

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 294

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Ile
        35                  40                  45

Gly Tyr Ile Tyr Pro Tyr Asn Gly Gly Thr Gly Tyr Asn Gln Lys Phe
    50                  55                  60

Lys Ser Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
            100                 105                 110

Thr Val Ser Ser
        115

<210> SEQ ID NO 295
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 295

Gln Val Gln Leu Gln Gln Ser Gly Pro Glu Leu Val Arg Pro Gly Thr
1               5                   10                  15

Phe Val Lys Ile Ser Cys Lys Ala Ser Gly Tyr Thr Phe Thr Asn Tyr
            20                  25                  30

Asp Ile Asn Trp Val Asn Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Ala Lys Ala Thr Leu Thr Ala Asp Lys Ser Ser Ser Thr Ala Tyr
65                  70                  75                  80

Leu Gln Leu Asn Asn Leu Thr Ser Glu Asn Ser Ala Val Tyr Phe Cys
                85                  90                  95

Ala Ser Gly Tyr Glu Asp Ala Met Asp Tyr Trp Gly Gln Gly Thr Ser
            100                 105                 110

Val Thr Val Ser Ser
        115

<210> SEQ ID NO 296
<211> LENGTH: 108
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 296

Asp Ile Lys Met Thr Gln Ser Pro Ser Ser Met Tyr Ala Ser Leu Gly

-continued

```
1               5                   10                  15

Glu Arg Val Ile Ile Asn Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Leu
                85                  90                  95

Thr Phe Gly Ala Gly Thr Lys Leu Glu Leu Lys Arg
            100                 105
```

<210> SEQ ID NO 297
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 297

```
Glu Val Lys Leu Gln Glu Ser Gly Pro Glu Leu Val Lys Pro Gly Ala
1               5                   10                  15

Ser Val Lys Met Ser Cys Lys Ala Ser Gly Tyr Lys Phe Thr Asp Tyr
            20                  25                  30

Val Val His Trp Leu Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Val Ser Ser Leu Thr Ser Glu Asp Ser Ala Val Tyr Tyr Cys
                85                  90                  95

Ala Arg Asp Tyr Arg Tyr Glu Val Tyr Gly Met Asp Tyr Trp Gly Gln
            100                 105                 110

Gly Thr Ser Val Thr Val Ser Ser
        115                 120
```

<210> SEQ ID NO 298
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 298

```
Asp Ile Val Leu Thr Gln Ser Pro Thr Ile Met Ser Ala Ser Pro Gly
1               5                   10                  15

Glu Arg Val Thr Met Thr Cys Thr Ala Ser Ser Ser Val Asn Tyr Ile
            20                  25                  30

His Trp Tyr Gln Gln Lys Ser Gly Asp Ser Pro Leu Arg Trp Ile Phe
        35                  40                  45

Asp Thr Ser Lys Val Ala Ser Gly Val Pro Ala Arg Phe Ser Gly Ser
    50                  55                  60

Gly Ser Gly Thr Ser Tyr Ser Leu Thr Ile Ser Thr Met Glu Ala Glu
```

```
65                  70                  75                  80

Asp Ala Ala Thr Tyr Tyr Cys Gln Gln Trp Arg Ser Tyr Pro Leu Thr
                85                  90                  95

Phe Gly Asp Gly Thr Arg Leu Glu Leu Lys Arg Ala Asp Ala Ala Pro
            100                 105                 110

Thr Val Ser
        115


<210> SEQ ID NO 299
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Ala Gly Thr
            100                 105                 110

Thr Val Thr Val Ser Ser
        115


<210> SEQ ID NO 300
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Asn Ile Met Leu Thr Gln Ser Pro Ser Ser Leu Ala Val Ser Ala Gly
1               5                   10                  15

Glu Lys Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ser Glu Asp Leu Ala Ile Tyr Tyr Cys His Gln
                85                  90                  95

Tyr Leu Ser Ser Arg Thr Phe Gly Gly Gly Thr Lys Leu Glu Ile Lys
            100                 105                 110

Arg
```

<210> SEQ ID NO 301
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 301
gacattcaga tgacccagtc tccgagctct ctgtccgcat cagtaggaga cagggtcacc 60
atcacatgca gagccagcga aagtgtcgac aattatggca ttagctttat gaactggttc 120
caacagaaac ccgggaaggc tcctaagctt ctgatttacg ctgcatccaa ccaaggctcc 180
ggggtaccct ctcgcttctc aggcagtgga tctgggacag acttcactct caccatttca 240
tctctgcagc ctgatgactt cgcaacctat tactgtcagc aaagtaagga ggttccgtgg 300
acgttcggtc aagggaccaa ggtggagatc aaa 333

<210> SEQ ID NO 302
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 302
caggttcagc tggtgcagtc tggagctgag gtgaagaagc ctgggagctc agtgaaggtt 60
tcctgcaaag cttctggcta caccttcact gactacaaca tgcactgggt gaggcaggct 120
cctggccaag gcctggaatg gattggatat atttatcctt acaatggtgg taccggctac 180
aaccagaagt tcaagagcaa ggccacaatt acagcagacg agagtactaa cacagcctac 240
atggaactct ccagcctgag gtctgaggac actgcagtct attactgcgc aagagggcgc 300
cccgctatgg actactgggg ccaagggact ctggtcactg tctcttca 348

<210> SEQ ID NO 303
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 303

Asp Ile Gln Met Thr Gln Ser Pro Ser Ser Leu Ser Ala Ser Val Gly
1 5 10 15

Asp Arg Val Thr Ile Thr Cys Arg Ala Ser Glu Ser Val Asp Asn Tyr
20 25 30

Gly Ile Ser Phe Met Asn Trp Phe Gln Gln Lys Pro Gly Lys Ala Pro
35 40 45

Lys Leu Leu Ile Tyr Ala Ala Ser Asn Gln Gly Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Asp Asp Phe Ala Thr Tyr Tyr Cys Gln Gln Ser Lys
85 90 95

Glu Val Pro Trp Thr Phe Gly Gln Gly Thr Lys Val Glu Ile Lys Gly
100 105 110

```
Gly Gly Gly Ser Gly Gly Gly Gly Ser Gly Gly Gly Gly Ser Gln Val
        115                 120                 125

Gln Leu Val Gln Ser Gly Ala Glu Val Lys Lys Pro Gly Ser Ser Val
    130                 135                 140

Lys Val Ser Cys Lys Ala Ser Gly Tyr Thr Phe Thr Asp Tyr Asn Met
145                 150                 155                 160

His Trp Val Arg Gln Ala Pro Gly Gln Gly Leu Glu Trp Ile Gly Tyr
                165                 170                 175

Ile Tyr Pro Tyr Asn Gly Gly Thr Gly Tyr Asn Gln Lys Phe Lys Ser
            180                 185                 190

Lys Ala Thr Ile Thr Ala Asp Glu Ser Thr Asn Thr Ala Tyr Met Glu
        195                 200                 205

Leu Ser Ser Leu Arg Ser Glu Asp Thr Ala Val Tyr Tyr Cys Ala Arg
    210                 215                 220

Gly Arg Pro Ala Met Asp Tyr Trp Gly Gln Gly Thr Leu Val Thr Val
225                 230                 235                 240

Ser Ser
```

<210> SEQ ID NO 304
<211> LENGTH: 726
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 304

```
gacattcaga tgacccagtc tccgagctct ctgtccgcat cagtaggaga cagggtcacc     60

atcacatgca gagccagcga aagtgtcgac aattatggca ttagctttat gaactggttc    120

caacagaaac ccgggaaggc tcctaagctt ctgatttacg ctgcatccaa ccaaggctcc    180

ggggtaccct ctcgcttctc aggcagtgga tctgggacag acttcactct caccatttca    240

tctctgcagc ctgatgactt cgcaacctat tactgtcagc aaagtaagga ggttccgtgg    300

acgttcggtc aagggaccaa ggtggagatc aaaggtggcg gtggctcggg cggtggtggg    360

tcgggtggcg gcggatctca ggttcagctg gtgcagtctg gagctgaggt gaagaagcct    420

gggagctcag tgaaggtttc ctgcaaagct tctggctaca ccttcactga ctacaacatg    480

cactgggtga ggcaggctcc tggccaaggc ctggaatgga ttggatatat ttatccttac    540

aatggtggta ccggctacaa ccagaagttc aagagcaagg ccacaattac agcagacgag    600

agtactaaca cagcctacat ggaactctcc agcctgaggt ctgaggacac tgcagtctat    660

tactgcgcaa gagggcgccc cgctatggac tactggggcc aagggactct ggtcactgtc    720

tcttca                                                               726
```

<210> SEQ ID NO 305
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 305

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asn Phe
            20                  25                  30
```

Trp Met Asn Trp Val Arg Gln Ala Pro Gly Gln Gly Leu Glu Trp Met
35 40 45

Gly Gln Ile Tyr Pro Gly Asp Gly Asp Thr Asn Tyr Asn Gly Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Ser Tyr Tyr Arg Ser Ala Trp Phe Ala Tyr Trp Gly Gln Gly
100 105 110

Thr Leu Val Thr Val Ser Ser
115

<210> SEQ ID NO 306
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 306

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Ser Asn Phe
20 25 30

Trp Met Asn Trp Val Arg Gln Ala Pro Gly Gln Gly Leu Glu Trp Met
35 40 45

Gly Gln Ile Tyr Pro Gly Asp Gly Asp Thr Asn Tyr Asn Gly Lys Phe
50 55 60

Lys Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Ser Tyr Tyr Arg Ser Ala Trp Phe Ala Tyr Trp Gly Gln Gly
100 105 110

Thr Leu Val Thr Val Ser Ser
115

<210> SEQ ID NO 307
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 307

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Ser Asn Phe
20 25 30

Trp Met Asn Trp Val Arg Gln Ala Pro Gly Gln Gly Leu Glu Trp Met
35 40 45

Gly Gln Ile Tyr Pro Gly Asp Gly Asp Thr Asn Tyr Asn Gly Lys Phe
50 55 60

Lys Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Ser Tyr Tyr Arg Ser Ala Trp Phe Ala Tyr Trp Gly Gln Gly
100 105 110

Thr Leu Val Thr Val Ser Ser
115

<210> SEQ ID NO 308
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 308

Gln Val Gln Leu Val Gln Ser Gly Ala Glu Val Lys Lys Pro Gly Ala
1 5 10 15

Thr Val Lys Ile Ser Cys Lys Val Ser Gly Tyr Ala Phe Ser Asn Phe
20 25 30

Trp Met Asn Trp Val Gln Gln Ala Pro Gly Lys Gly Leu Glu Trp Met
35 40 45

Gly Gln Ile Tyr Pro Gly Asp Gly Asp Thr Asn Tyr Asn Gly Lys Phe
50 55 60

Lys Gly Arg Val Thr Ile Thr Ala Asp Thr Ser Thr Asp Thr Ala Tyr
65 70 75 80

Met Glu Leu Ser Ser Leu Arg Ser Glu Asp Thr Ala Val Tyr Tyr Cys
85 90 95

Ala Arg Ser Tyr Tyr Arg Ser Ala Trp Phe Ala Tyr Trp Gly Gln Gly
100 105 110

Thr Leu Val Thr Val Ser Arg
115

<210> SEQ ID NO 309
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 309

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ala Phe Ser Asn Phe
20 25 30

Trp Met Asn Trp Val Arg Gln Met Pro Gly Lys Gly Leu Glu Trp Met
35 40 45

Gly Gln Ile Tyr Pro Gly Asp Gly Asp Thr Asn Tyr Asn Gly Lys Phe
50 55 60

Lys Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Ser Tyr Tyr Arg Ser Ala Trp Phe Ala Tyr Trp Gly Gln Gly
100 105 110

Thr Leu Val Thr Val Ser Leu
115

<210> SEQ ID NO 310
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 310

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Asn Trp Pro Leu
                85                  90                  95

Thr Phe Gly Gln Gly Thr Lys Val Glu Ile Lys
            100                 105
```

<210> SEQ ID NO 311
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 311

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Ser
            20                  25                  30

Ile His Trp Tyr Gln Gln Lys Pro Gly Gln Ala Pro Arg Leu Leu Ile
        35                  40                  45

Tyr Tyr Ala Ser Glu Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Asn Trp Pro Leu
                85                  90                  95

Thr Phe Gly Gly Gly Thr Lys Val Glu Ile Lys
            100                 105
```

<210> SEQ ID NO 312
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 312

```
Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Gln Ser Ile Gly Thr Ser
            20                  25                  30

Ile His Trp Tyr Gln Gln Lys Pro Gly Gln Ala Pro Arg Leu Leu Ile
        35                  40                  45

Tyr Tyr Ala Ser Glu Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Asn Trp Pro Leu
                85                  90                  95

Thr Phe Gly Gly Gly Thr Lys Val Glu Ile Lys
            100                 105
```

<210> SEQ ID NO 313
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 313

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Thr Ser
            20                  25                  30

Ile His Trp Tyr Gln Gln Lys Pro Gly Lys Ala Pro Lys Leu Leu Ile
        35                  40                  45

Tyr Tyr Ala Ser Glu Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Asn Trp Pro Leu
                85                  90                  95

Thr Phe Gly Gly Gly Thr Lys Val Glu Ile Lys
            100                 105
```

<210> SEQ ID NO 314
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 314

```
Asp Ile Val Met Thr Gln Ser Pro Ser Leu Leu Ser Ala Ser Thr Gly
1               5                   10                  15

Asp Arg Val Thr Ile Ser Cys Arg Ala Ser Gln Ser Ile Gly Thr Ser
            20                  25                  30

Ile His Trp Tyr Gln Gln Lys Pro Gly Lys Ala Pro Glu Leu Leu Ile
        35                  40                  45

Tyr Tyr Ala Ser Glu Ser Ile Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Ser Asn Asn Trp Pro Leu
                85                  90                  95
```

```
Thr Phe Gly Gln Gly Thr Lys Val Glu Ile Lys
            100                 105


<210> SEQ ID NO 315
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Val Ser His
            20                  25                  30

Tyr Tyr Trp Ser Trp Ile Arg Gln His Pro Gly Lys Gly Leu Glu Trp
        35                  40                  45

Ile Gly Tyr Ile Ser Ser Asp Gly Ser Asn Tyr Tyr Asn Pro Ser Leu
    50                  55                  60

Lys Ser Leu Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Arg Gly Val Asp Tyr Trp Gly Gln Gly Thr Met Val Thr Val Ser
            100                 105                 110

Ser


<210> SEQ ID NO 316
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 316

caggtgcaac tgcaggaatc aggtccaggc ttggtcaagc catcgcagac tcttagtctg      60

acatgcaccg tgagtggcta tagcatcgtg tcgcactatt attggtcttg gatcaggcag     120

catccaggaa agggactgga gtggatcggg tacattagca gcgatgggag caactattac     180

aacccatctc tgaagtccct ggtaactatt agcgtggata caagcaaaaa tcagttttca     240

ttaaagctct cttcagtgac cgcagctgat accgccgtct attattgcgt gcggggggtg     300

gactactggg gtcagggcac catggttact gtgtcatca                            339


<210> SEQ ID NO 317
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Val Ser His
            20                  25                  30

Tyr Tyr Trp Gly Trp Ile Arg Gln Pro Pro Gly Lys Gly Leu Glu Trp
        35                  40                  45
```

```
Ile Gly Tyr Ile Ser Ser Asp Gly Ser Asn Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Val Arg Gly Val Asp Tyr Trp Gly Gln Gly Thr Met Val Thr Val Ser
            100                 105                 110

Ser


<210> SEQ ID NO 318
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 318

caggtacagc tgcaggagag tggccctggt ttagtaaagc catcagatac actttcactt      60

acctgcgccg tgtctggtta ttctatcgtg agccactatt actggggatg gatccgccag     120

ccccctggca aaggtcttga gtggattggc tatataagtt cggatggcag taactattac     180

aatccttctc tgaagagccg tgtcactatg agcgtggaca ctagcaaaaa ccagttcagc     240

ctgaagctgt cctccgtcac cgccgtagac accgctgtct actattgtgt tagggggtg     300

gactactggg gccaaggcac catggtcacg gtgagcagc                            339


<210> SEQ ID NO 319
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Val Ser His
            20                  25                  30

Tyr Tyr Met Ser Trp Val Arg Gln Ala Pro Gly Lys Gly Leu Glu Trp
        35                  40                  45

Val Ser Val Ile Ser Ser Asp Gly Ser Asn Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Gly Val Asp Tyr Trp Gly Gln Gly Thr Leu Val Thr Val Ser
            100                 105                 110

Ser


<210> SEQ ID NO 320

<400> SEQUENCE: 320

000
```

<210> SEQ ID NO 321
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 321

Glu Val Gln Leu Val Glu Ser Gly Gly Gly Leu Val Gln Pro Gly Arg
1               5                   10                  15

Ser Leu Arg Leu Ser Cys Ala Ala Ser Gly Tyr Ser Ile Val Ser His
            20                  25                  30

Tyr Tyr Met His Trp Val Arg Gln Ala Pro Gly Lys Gly Leu Glu Trp
        35                  40                  45

Val Ser Ala Ile Ser Ser Asp Gly Ser Asn Glu Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Gly Val Asp Tyr Trp Gly Gln Gly Thr Leu Val Thr Val Ser
            100                 105                 110

Ser

<210> SEQ ID NO 322
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 322
gaggtgcagc tcgtcgagtc cggaggcggt ctggtgcaac ccggccgttc tttgcggctg 60
agttgcgctg ccagtgggta tagcatcgtg agtcactatt acatgcattg ggttcgtcaa 120
gcccctggca agggactaga gtgggtgtcc gccatctcct cagacggtag taatgagtac 180
gcggacagcg tagagggtag attcaccatt tctcgggaca atgccaaaaa tagtctatac 240
ctccaaatga attcccttag ggccgaagac actgccgtgt actactgtgt tcggggcgtg 300
gactactggg ggcaggggac attggtgact gtgagctca 339

<210> SEQ ID NO 323
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 323

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Val Ser His
            20                  25                  30

Tyr Tyr Trp Ser Trp Ile Arg Gln His Pro Gly Lys Gly Leu Glu Trp
        35                  40                  45

Ile Gly Tyr Ile Ser Ser Asp Gly Ser Asn Glu Tyr Asn Pro Ser Leu
    50                  55                  60

Lys Ser Leu Val Thr Ile Ser Val Asp Thr Ser Lys Asn Gln Phe Ser
65 70 75 80

Leu Lys Leu Ser Ser Val Thr Ala Ala Asp Thr Ala Val Tyr Phe Cys
85 90 95

Val Arg Gly Val Asp Tyr Trp Gly Gln Gly Thr Met Val Thr Val Ser
100 105 110

Ser

<210> SEQ ID NO 324
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 324
caggtccaac tgcaggaatc tggccccgga ctggttaaac catctcagac actctccctg 60
acctgcaccg tgtctggata cagcatcgtt tctcattatt actggtcatg gattaggcag 120
catcccggaa aagggcttga atggattggc tacatctcct ccgacggctc caatgagtac 180
aacccatcac ttaaatctct ggtcacgata agcgtagaca catctaaaaa tcagttctca 240
ttaaagctca gctctgttac agctgccgac accgctgtgt acttctgtgt gcgaggggtt 300
gactactggg gcagggcac aatggtgaca gtgtcttcc 339

<210> SEQ ID NO 325
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 325

Gln Val Gln Leu Val Gln Ser Gly Ala Glu Val Lys Lys Pro Gly Ser
1 5 10 15

Ser Val Lys Val Ser Cys Lys Ala Ser Gly Tyr Ser Ile Val Ser His
20 25 30

Tyr Tyr Ile Ser Trp Val Arg Gln Ala Pro Gly Gln Gly Leu Glu Trp
35 40 45

Met Gly Gly Ile Ser Ser Asp Gly Ser Asn Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Val Arg Gly Val Asp Tyr Trp Gly Gln Gly Thr Leu Val Thr Val Ser
100 105 110

Ser

<210> SEQ ID NO 326
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 326
caggttcaac tggttcagtc cggagccgag gtcaaaaagc ctggatcctc tgtgaaggtg 60
tcatgtaagg cttctggcta cagcatcgtc tcacattatt acatatcttg ggtgcgacag 120
gcccccggcc aggggctcga gtggatggga ggtatttcct ccgacgggag taacaattac 180
gctcagaaat ttcagggccg ggtgaccatt accgccgacg aaagtacaag caccgcttat 240
atggaattaa gctctttaag atcagaggac acggctgtgt actactgtgt aaggggcgtg 300
gattactggg gtcaggggac gctcgtcacc gtctcgagc 339

<210> SEQ ID NO 327
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 327

Gln Val Gln Leu Gln Glu Ser Gly Pro Gly Leu Val Lys Pro Ser Glu
1 5 10 15

Thr Leu Ser Leu Thr Cys Thr Val Ser Gly Tyr Ser Ile Val Ser His
20 25 30

Tyr Tyr Trp Ser Trp Ile Arg Gln Pro Pro Gly Lys Gly Leu Glu Trp
35 40 45

Ile Gly Tyr Ile Ser Ser Asp Gly Ser Asn Asn Tyr Asn Pro Ser Leu
50 55 60

Lys Ser Arg Val Thr Ile Ser Val Asp Thr Ser Lys Asn Gln Phe Ser
65 70 75 80

Leu Lys Leu Ser Ser Val Thr Ala Ala Asp Thr Ala Val Tyr Tyr Cys
85 90 95

Val Arg Gly Val Asp Tyr Trp Gly Gln Gly Thr Thr Val Thr Val Ser
100 105 110

Ser

<210> SEQ ID NO 328
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 328
caggtccagc tccaggaatc cggcccaggg ttggtgaagc cttcggagac cctgtctctg 60
acatgcacag tcagcggcta tagtatcgtc tcccactatt attggtcttg gattcggcaa 120
cctccaggca aggggttaga atggattgga tacatctcaa gcgatgggtc caataactac 180
aacccaagtc tcaaaagtag agtgactatc tctgtggata ccagtaaaaa ccagttttca 240
ctcaagttga gttccgtcac cgccgccgac acagccgttt actactgtgt tcggggagtg 300
gactactggg gccaaggtac cacggttacc gtgagcagc 339

<210> SEQ ID NO 329
<211> LENGTH: 106
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 329

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Arg Asp Ile Asn Asn Phe
            20                  25                  30

Leu Asn Trp Tyr Gln Gln Lys Pro Gly Lys Ala Pro Lys Leu Leu Ile
        35                  40                  45

Tyr Arg Ala Asn Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Leu Gln Tyr Gly Asp Leu Tyr Thr
                85                  90                  95

Phe Gly Gly Gly Thr Lys Val Glu Ile Lys
            100                 105
```

<210> SEQ ID NO 330
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 330

```
gacatacaga tgactcagag cccctcctca ctctcggcat cagtcggcga cagggtcaca     60

attacctgtc aggcttctcg cgacattaat aacttcctga attggtatca gcaaaagccc    120

gggaaggccc ctaagctgtt gatttataga gcaaataatc tcgaaaccgg cgtgcccagt    180

aggtttagcg ggtccgggag cggaacagac ttcacattca ccatttctag tttgcagccc    240

gaagacattg ctacatattt ttgcctgcag tacggggatc tctacacttt cgggggcgga    300

acaaaggttg agataaaa                                                  318
```

<210> SEQ ID NO 331
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 331

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Arg Asp Ile Asn Asn Phe
            20                  25                  30

Leu Asn Trp Tyr Gln Gln Lys Pro Gly Lys Ala Pro Lys Leu Leu Ile
        35                  40                  45

Tyr Arg Ala Asn Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Gly Asp Leu Tyr Thr
                85                  90                  95

Phe Gly Gly Gly Thr Lys Val Glu Ile Lys
            100                 105
```

<210> SEQ ID NO 332
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 332
gatattcaaa tgacgcagtc accctcatcg ctctctgcgt cagtagggga tcgtgtcacg 60
ataacctgtc aagcatcaag ggacatcaac aacttcctca actggtacca acagaagcct 120
ggcaaggcac ctaaactcct gatctaccgg gctaacaacc tagaaaccgg ggttccgagc 180
cgattcagtg ggtctggaag cgggacagac tttacgttca ctattagttc gctacagccc 240
gaagacattg cgacatatta ctgtcttcag tatggggatt tgtatacctt tgggggaggc 300
accaaggtag agataaag 318

<210> SEQ ID NO 333
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 333

Asp Ile Gln Met Thr Gln Ser Pro Ser Ser Leu Ser Ala Ser Val Gly
1 5 10 15

Asp Arg Val Thr Ile Thr Cys Arg Ala Ser Arg Asp Ile Asn Asn Phe
20 25 30

Leu Gly Trp Tyr Gln Gln Lys Pro Gly Lys Ala Pro Lys Arg Leu Ile
35 40 45

Tyr Arg Ala Asn Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Leu Gln Tyr Gly Asp Leu Tyr Thr
85 90 95

Phe Gly Gln Gly Thr Lys Val Glu Ile Lys
100 105

<210> SEQ ID NO 334
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 334
gacatccaga tgactcagag cccgtcttct ctatccgcaa gtgtaggcga tcgtgtcacc 60
atcacatgcc gggcttcccg ggatatcaac aacttccttg ggtggtatca gcagaagccc 120
ggaaaagccc ccaaacggct catctacaga gcgaattccc tgcagtcagg tgtccccagt 180
aggttcagcg gatcaggctc ggggaccgaa ttcactctga ccattagctc actgcagcct 240
gaggatttcg ctacttacta ttgcctgcaa tacggcgatc tgtacacttt cgggcagggc 300
accaaggtgg aaataaaa 318

<210> SEQ ID NO 335

<211> LENGTH: 106
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 335

Glu Ile Val Leu Thr Gln Ser Pro Gly Thr Leu Ser Leu Ser Pro Gly
1 5 10 15

Glu Arg Ala Thr Leu Ser Cys Arg Ala Ser Arg Asp Ile Asn Asn Phe
20 25 30

Leu Ala Trp Tyr Gln Gln Lys Pro Gly Gln Ala Pro Arg Leu Leu Ile
35 40 45

Tyr Arg Ala Asn Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Leu Gln Tyr Gly Asp Leu Tyr Thr
85 90 95

Phe Gly Gln Gly Thr Lys Val Glu Ile Lys
100 105

<210> SEQ ID NO 336
<211> LENGTH: 318
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 336
gaaatcgtac tgacccagtc tcccggaacc ctgagtctct cacccggcga gcgcgcaaca 60
ctgtcgtgta gggccagtag ggacataaat aacttcctag cctggtacca acaaaaaccg 120
ggtcaggctc caagactgtt gatctataga gctaactcca gggccaccgg catcccagac 180
cgattctcag gctccggatc tggaaccgac ttcacgctca ccattagccg actagaacct 240
gaggactttg ctgtatacta ttgcctgcag tacggcgacc tgtatacctt tggacagggt 300
accaaggtcg agatcaag 318

<210> SEQ ID NO 337
<211> LENGTH: 106
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 337

Glu Ile Val Leu Thr Gln Ser Pro Ala Thr Leu Ser Leu Ser Pro Gly
1 5 10 15

Glu Arg Ala Thr Leu Ser Cys Arg Ala Ser Arg Asp Ile Asn Asn Phe
20 25 30

Leu Ala Trp Tyr Gln Gln Lys Pro Gly Gln Ala Pro Arg Leu Leu Ile
35 40 45

Tyr Arg Ala Asn Asn Arg Ala Thr Gly Ile Pro Ala Arg Phe Ser Gly
50 55 60

Ser Gly Pro Gly Thr Asp Phe Thr Leu Thr Ile Ser Ser Leu Glu Pro
65 70 75 80

```
Glu Asp Phe Ala Val Tyr Tyr Cys Leu Gln Tyr Gly Asp Leu Tyr Thr
                85                  90                  95

Phe Gly Gly Gly Thr Lys Val Glu Ile Lys
            100                 105


<210> SEQ ID NO 338
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 338

gagatcgtac ttacgcagag cccagcaact ctgtctctgt cccccggaga acgggccacc     60

ctgtcgtgcc gggccagccg tgatattaat aatttcctgg cctggtatca acaaaaaccg    120

gggcaggctc ctcgactgtt gatctaccgg gccaacaata gagcaactgg tatccctgct    180

cgcttctccg gcagtgggcc aggtacagac ttcaccctga ctatttcgtc actcgaacca    240

gaagactttg ccgtgtatta ttgcttacaa tacggggatc tgtacacttt cggaggagga    300

actaaggtcg aaattaag                                                  318


<210> SEQ ID NO 339
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Glu Ile Val Leu Thr Gln Ser Pro Asp Phe Gln Ser Val Thr Pro Lys
1               5                   10                  15

Glu Lys Val Thr Ile Thr Cys Arg Ala Ser Arg Asp Ile Asn Asn Phe
            20                  25                  30

Leu His Trp Tyr Gln Gln Lys Pro Asp Gln Ser Pro Lys Leu Leu Ile
        35                  40                  45

Lys Arg Ala Asn Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Leu Gln Tyr Gly Asp Leu Tyr Thr
                85                  90                  95

Phe Gly Gln Gly Thr Lys Val Glu Ile Lys
            100                 105


<210> SEQ ID NO 340
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 340

gagatcgtgc tgacccagag ccccgacttc cagagcgtga cccccaagga gaaggtgacc     60

atcacctgca gagccagcag agacatcaac aacttcctgc actggtacca gcagaagccc    120

gaccagagcc ccaagctgct gatcaagaga gccaaccaga gcttcagcgg cgtgcccagc    180

agattcagcg gcagcggcag cggcaccgac ttcaccctga ccatcaacag cctggaggcc    240
```

gaggacgccg ccacctacta ctgcctgcag tacggcgacc tgtacacctt cggccagggc 300
accaaggtgg agatcaag 318

<210> SEQ ID NO 341
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 341

Asp Ile Gln Met Thr Gln Ser Pro Ser Ser Leu Ser Ala Ser Val Gly
1 5 10 15

Asp Arg Val Thr Ile Thr Cys Arg Ala Ser Arg Asp Ile Asn Asn Phe
20 25 30

Leu Ala Trp Phe Gln Gln Lys Pro Gly Lys Ala Pro Lys Ser Leu Ile
35 40 45

Tyr Arg Ala Asn Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Gly Asp Leu Tyr Thr
85 90 95

Phe Gly Gly Gly Thr Lys Val Glu Ile Lys
100 105

<210> SEQ ID NO 342
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 342
gacatccaga tgacccagag ccccagcagc ctgagcgcca gcgtgggcga cagagtgacc 60
atcacctgca gagccagcag agacatcaac aacttcctgg cctggttcca gcagaagccc 120
ggcaaggccc ccaagagcct gatctacaga gccaacagcc tgcagagcgg cgtgcccagc 180
agattcagcg gcagcggcag cggcaccgac ttcaccctga ccatcagcag cctgcagccc 240
gaggacttcg ccacctacta ctgcctgcag tacggcgacc tgtacacctt cggcggcggc 300
accaaggtgg agatcaag 318

<210> SEQ ID NO 343
<211> LENGTH: 234
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 343

Asp Ile Lys Met Ala Gln Ser Pro Ser Ser Val Asn Ala Ser Leu Gly
1 5 10 15

Glu Arg Val Thr Ile Thr Cys Lys Ala Ser Arg Asp Ile Asn Asn Phe
20 25 30

Leu Ser Trp Phe His Gln Lys Pro Gly Lys Ser Pro Lys Thr Leu Ile
35 40 45

Tyr Arg Ala Asn Arg Leu Val Asp Gly Val Pro Ser Arg Phe Ser Gly
50 55 60

Ser Gly Ser Gly Gln Asp Tyr Ser Phe Thr Ile Ser Ser Leu Glu Tyr
65 70 75 80

Glu Asp Val Gly Ile Tyr Tyr Cys Leu Gln Tyr Gly Asp Leu Tyr Thr
85 90 95

Phe Gly Gly Gly Thr Lys Leu Glu Ile Lys Gly Gly Gly Gly Ser Gly
100 105 110

Gly Gly Gly Ser Gly Gly Gly Gly Ser Asp Val Gln Leu Leu Glu Ser
115 120 125

Gly Pro Gly Leu Val Arg Pro Ser Gln Ser Leu Ser Leu Thr Cys Ser
130 135 140

Val Thr Gly Tyr Ser Ile Val Ser His Tyr Tyr Trp Asn Trp Ile Arg
145 150 155 160

Gln Phe Pro Gly Asn Lys Leu Glu Trp Met Gly Tyr Ile Ser Ser Asp
165 170 175

Gly Ser Asn Glu Tyr Asn Pro Ser Leu Lys Asn Arg Ile Ser Ile Ser
180 185 190

Leu Asp Thr Ser Lys Asn Gln Phe Phe Leu Lys Phe Asp Phe Val Thr
195 200 205

Thr Ala Asp Thr Ala Thr Tyr Phe Cys Val Arg Gly Val Asp Tyr Trp
210 215 220

Gly Gln Gly Thr Thr Leu Thr Val Ser Ser
225 230

<210> SEQ ID NO 344
<211> LENGTH: 702
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 344
gacatcaaga tggctcagtc cccttctagc gtgaatgctt cgctagggga gcgtgtgacc 60
atcacatgta aagcatcacg cgacataaat aatttccttt cctggtttca tcagaaaccg 120
ggcaagtcgc ctaagacgct gatttacaga gcaaatcggt tggtagatgg agtgccaagc 180
agattcagcg ggagcggaag tggacaggat tatagcttca ctatttcatc cctggaatac 240
gaggacgtag gtatctatta ttgcctccag tatggcgatc tttacacatt tggtgggggg 300
actaagctgg agattaaggg cggaggcgga agcggaggcg gaggctccgg cggaggcgga 360
agcgacgtgc aacttctgga gagcgggcca gggctagtca ggccctccca gtcgctttca 420
ctgacttgca gtgtgaccgg ttactctatt gtgagtcact actattggaa ctggattcgg 480
cagttcccag gcaacaaact ggaatggatg ggtacatat cttccgatgg ctcgaatgaa 540
tataacccat cattgaaaaa tcgtatttcc atcagtctgg atacgagtaa aaaccagttt 600
ttcctcaaat tcgatttcgt gactacagca gatactgcca catacttctg tgtacgaggt 660
gtcgattatt ggggacaggg cacaacgctg accgtaagtt ct 702

<210> SEQ ID NO 345
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 345

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Arg Gly Gly Thr Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

Thr Leu Val Thr Val Ser Ser
115

<210> SEQ ID NO 346
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 346
gaggtgcagc tcgtggaatc cggcggtggc ctggtgcagc cgggcggcag tcttcgactc 60
tcctgtgcgg cgtcaggctt tacgttcagt tcttatgcca tgagctgggt gaggcaagct 120
cccggtaagg gactggagtg ggtctctgct atcagccggg gaggtacgac ctactacgct 180
gactccgtaa aaggaagatt taccataagt cgtgacaatt ccaaaaacac tctatactta 240
cagatgaact cgctcagggc cgaagatacc gcagtctact attgtgggag atacgattac 300
gacggctact atgctatgga ttattggggt cagggtacgc tcgtgacggt gtcctcc 357

<210> SEQ ID NO 347
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 347

Asp Ile Gln Met Thr Gln Ser Pro Ser Ser Leu Ser Ala Ser Val Gly
1 5 10 15

Asp Arg Val Thr Ile Thr Cys Gln Ala Ser Pro Asp Ile Asn Ser Tyr
20 25 30

Leu Asn Trp Tyr Gln Gln Lys Pro Gly Lys Ala Pro Lys Leu Leu Ile
35 40 45

Tyr Arg Ala Asn Asn Leu Glu Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Ile Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 348
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 348
gatattcaaa tgacgcaaag tcccagcagc ctctccgcct ccgttggaga cagggtgact 60
attacatgcc aagccagccc cgatattaat agctacttaa attggtatca gcagaaacct 120
gggaaggcac ctaaacttct catctaccgc gctaacaatc tggagaccgg cgtgccgtct 180
agattttccg gctctggatc agggaccgat tttactctga caattagttc cctgcaaccc 240
gaagacatcg ccacttatta ttgcctgcaa tatgatgagt ttccttacac atttggtcag 300
ggaactaaac tagagattaa g 321

<210> SEQ ID NO 349
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 349

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ser Ile Ser Arg Gly Gly Thr Thr Tyr Tyr Pro Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

Thr Leu Val Thr Val Ser Ser
115

<210> SEQ ID NO 350
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 350
gaagtgcaac tggtcgagtc tgggggcggc cttgtgcaac ctggaggcag ccttcgactc 60
agttgcgccg cgtctggttt taccttctcc tcttacgcga tgagctgggt tcgccaggcc 120
cccggcaagg gacttgagtg ggttagttcg atctcccgcg gaggcaccac atattatcct 180

-continued

```
gactcggtta agggacgctt cactatctct agggacaatt caaagaacac actgtatctc    240

caaatgaact ccttgcgggc cgaggacact gctgtgtatt attgcggacg atacgactac    300

gatgggtatt acgccatgga ttactggggg caaggtacac tggtcactgt gagttcg       357
```

<210> SEQ ID NO 351
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 351

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105
```

<210> SEQ ID NO 352
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 352

```
gatattcaga tgacccagtc accttcgagt ctgagcgcat ccgtgggcga cagagtgacc     60

attacctgta aggccagccc ggacattaac agctacctat cgtggtatca gcaaaagcct    120

ggtaaggccc ctaaactcct tatctacagg gctaataggt tggtagacgg ggtgcctagc    180

cggttctctg gttccggcag cggtacggac tttactctga ccataagctc tctgcaacca    240

gaagacatcg caacatacta ctgtttacaa tacgacgaat ttccttatac ctttggccag    300

gggaccaagt tagagatcaa g                                              321
```

<210> SEQ ID NO 353
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 353

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile Ile Trp Val Arg Gln Ala Pro Gly Lys Gly Leu Glu Trp Val
```

```
        35                  40                  45

Ala Arg Ile Ser Arg Gly Gly Thr Thr Arg Tyr Ala Asp Ser Val Lys
    50                  55                  60

Gly Arg Phe Thr Ile Ser Ala Asp Thr Ser Lys Glu Thr Ala Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115
```

<210> SEQ ID NO 354
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 354

```
gaggttcagc tggtcgagtc cgggggaggc ttagtgcagc caggaggcag tctgcggctc     60

tcttgcgctg caagtggctt cacattcagt tcatacgcaa tcatctgggt tcgacaggct    120

cctggtaagg gcctcgaatg ggtcgcaagg atatcacgag gtggaaccac tagatacgca    180

gactctgtta agggcaggtt cacaattagc gcggatacct ccaaggagac tgcttattta    240

cagatgaact ctctgagagc cgaggacact gctgtttact actgcggccg atacgattac    300

gacggatatt acgcaatgga ttactggggc cagggcacgc tggtgacagt ttcatcg       357
```

<210> SEQ ID NO 355
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 355

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105
```

<210> SEQ ID NO 356
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 356
gatatccaga tgactcagag tcccagtagc ctgtcggcaa gcgtcggaga tcgggtcaca 60
attacctgca aagctagtcc tgatattaat tcttacttgt cctggtatca gcagaagcct 120
ggtaaggccc ctaagttgct catctatcgg gctaaccggc tggtggacgg tgttccctct 180
agattctcag ggagtggaag cggcactgac ttcaccctga ctatatcgag ccttcagcca 240
gaggacattg ccacatacta ctgtctgcaa tatgatgaat ttccatatac attcggacaa 300
ggtacaaagt tagaaattaa g 321

<210> SEQ ID NO 357
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 357

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Ile Ile Trp Val Arg Gln Ala Pro Gly Lys Gly Leu Glu Trp Val
35 40 45

Ala Arg Ile Ser Arg Gly Gly Thr Thr Arg Tyr Ala Asp Ser Val Lys
50 55 60

Gly Arg Phe Thr Ile Ser Ala Asp Thr Ser Lys Glu Thr Ala Tyr Leu
65 70 75 80

Gln Met Asn Ser Leu Arg Ala Glu Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

Thr Leu Val Thr Val Ser Ser
115

<210> SEQ ID NO 358
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 358
gaagtccaac tggtggagtc tggcgggggc ttggtgcagc ccggtggctc ccttaggctg 60
tcttgcgctg ccagcgggtt cacattcagc tcctatgcga ttatatgggt ccgacaggca 120
cccggcaagg gattggagtg ggtggctcgc atcagcagag gcggcactac tcgttacgcc 180
gactccgtga aaggcagatt caccatcagt gcagacacat ccaaggaaac cgcatatctt 240
cagatgaata gcctgcgagc ggaggatacc gccgtctatt attgcggacg ctatgattac 300
gacggttatt atgctatgga ctactggggc cagggcacac ttgtgaccgt cagtagc 357

<210> SEQ ID NO 359
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 359

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Pro Asp Ile Asn Ser Tyr
            20                  25                  30

Val Ala Trp Tyr Gln Gln Lys Pro Gly Lys Ala Pro Lys Leu Leu Ile
        35                  40                  45

Tyr Arg Ala Asn Phe Leu Glu Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Val Glu Ile Lys
            100                 105
```

<210> SEQ ID NO 360
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 360

```
gacattcaaa tgacgcaaag ccctagtagc ttgtcagctt ctgtggggga ccgtgtcaca      60

atcacttgtc gggcctctcc agatataaac tcctacgttg cttggtatca gcagaagccc     120

ggaaaggctc cgaaattgtt gatttatcgc gctaatttct tagagtcagg agtgcccagc     180

cggttctcag ggtctcgctc tggaaccgac ttcacactca ctatttctag cctacagcct     240

gaggattttg caacttacta ctgtctacag tacgacgagt ttccgtacac tttcggacag     300

gggaccaagg tggagatcaa g                                               321
```

<210> SEQ ID NO 361
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 361

```
Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ile Pro Gly Lys Gly Leu Glu Trp Val
        35                  40                  45

Ser Ser Ile Ser Arg Gly Gly Thr Thr Tyr Tyr Pro Asp Ser Val Lys
    50                  55                  60

Gly Arg Phe Thr Ile Ser Arg Asp Asn Val Lys Asn Thr Leu Tyr Leu
65                  70                  75                  80

Gln Met Ser Ser Leu Arg Ala Glu Asp Thr Ala Val Tyr Tyr Cys Gly
                85                  90                  95
```

-continued

```
Arg Tyr Asp Tyr Asp Gly Tyr Tyr Ala Met Asp Tyr Trp Gly Gln Gly
            100                 105                 110

Thr Met Val Thr Val Ser Ser
        115
```

<210> SEQ ID NO 362
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 362

```
caagtacagc tcgtgcagag cggcggtggc ctggtgaagc caggaggtag tcttagactg     60

agctgtgcgg cttctggttt cacgttcagc agttatgcta tgtcctgggt taggcaaatc    120

cccggcaaag gattggagtg ggttagcagt atctcaaggg ggggaaccac atattatcct    180

gactctgtca aaggacggtt tacaatcagc cgcgataacg ttaaaaatac cctctacctc    240

cagatgtctt cgctccgcgc tgaagataca gcggtttact actgtggcag atacgactac    300

gacggttatt acgccatgga ctactgggga cagggaacta tggtcacagt tagctct       357
```

<210> SEQ ID NO 363
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 363

```
Asp Ile Lys Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Ser Trp Tyr Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Tyr
65                  70                  75                  80

Glu Asp Met Ala Ile Tyr Tyr Cys Leu Gln Tyr Asp Glu Phe Pro Tyr
                85                  90                  95

Thr Phe Gly Asp Gly Thr Lys Val Glu Ile Lys
            100                 105
```

<210> SEQ ID NO 364
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 364

```
gacatcaaaa tgacgcagtc acctagtagc ctctccgcct cggttggcga tcgggtaacc     60

attacctgca aagcatctcc agacataaat agttatctta gttggtatca acagaaacct    120

ggcaaagctc ctaagaccct catctaccgc gctaaccgcc tcgtggatgg tgttccaagt    180

cggttctcag gaagcggcag tggcacagac tttacactga caattagttc cctccagtat    240
```

gaggatatgg ccatatatta ctgccttcag tatgatgagt ttccatacac attcggagac 300
ggtacaaagg tggagatcaa g 321

<210> SEQ ID NO 365
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 365

Gln Val Ser Leu Arg Glu Ser Gly Gly Gly Leu Val Gln Pro Gly Arg
1 5 10 15

Ser Leu Arg Leu Ser Cys Thr Ala Ser Gly Phe Thr Phe Ser Ser Tyr
20 25 30

Ala Met Thr Trp Val Arg Gln Ala Pro Gly Lys Gly Leu Glu Trp Val
35 40 45

Ala Ser Ile Ser Arg Gly Gly Thr Thr His Phe Ala Asp Ser Val Lys
50 55 60

Gly Arg Phe Thr Ile Ser Arg Asp Asn Ser Asn Asn Thr Leu Tyr Leu
65 70 75 80

Gln Met Asp Asn Val Arg Asp Glu Asp Thr Ala Ile Tyr Tyr Cys Gly
85 90 95

Arg Tyr Asp Tyr Asp Gly Tyr Tyr Ala Met Asp Tyr Trp Gly Arg Gly
100 105 110

Thr Leu Val Thr Val Ser Ser
115

<210> SEQ ID NO 366
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 366
caagtgagcc tccgggagag tgggggcggt ctggtccaac caggacggtc actgcggctg 60
tcatgcactg ccagcggctt cacatttagc tcttacgcca tgacttgggt ccgccaagct 120
cccggtaagg gactggagtg ggtggccagc attagcaggg gtggtacaac ccacttcgcg 180
gattcagtta aggggagatt cactatctcc agggataatt ccaacaacac gctgtacctt 240
cagatggata acgtgagaga cgaggatacc gcgatatact actgtggccg ctatgactac 300
gatggttatt atgctatgga ttactggggg cggggcaccc tggtgactgt gtcctcg 357

<210> SEQ ID NO 367
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 367

Asp Ile Val Met Thr Gln Ser Pro Ser Ser Leu Ser Ala Ser Val Gly
1 5 10 15

Asp Arg Val Thr Ile Thr Cys Arg Ala Ser Pro Asp Ile Asn Ser Tyr
20 25 30

Leu Ala Trp Tyr Gln Gln Lys Pro Gly Lys Ala Pro Lys Leu Leu Ile
35 40 45

Tyr Arg Ala Asn Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Met Lys
100 105

<210> SEQ ID NO 368
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 368
gatatcgtga tgacacagtc acctagctcc ctgagcgcaa gcgtggggga tagggttacc 60
ataacttgca gggccagtcc cgacatcaat agttatttgg cctggtatca acagaagcct 120
gggaaggcac ctaagttgct tatttatagg gctaactcgt tacagagcgg tgtgccaagt 180
cggttctcag gctcagggtc cgggaccgag ttcaccctga ccatcagtag cttgcagcca 240
gaagattttg ccacctacta ctgtcttcaa tacgatgagt ttccttacac ttttggacag 300
ggcaccaaac tagagatgaa g 321

<210> SEQ ID NO 369
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 369

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met Asn Trp Val Arg Gln Ala Pro Ala Lys Gly Leu Glu Trp Val
35 40 45

Ala Ile Ile Ser Arg Gly Gly Thr Gln Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Gly Leu Arg Ala Glu Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

Thr Leu Val Thr Val Ser Ser
115

<210> SEQ ID NO 370
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 370
caggttcaac tggtagaatc cggcggaggt gtagtgcagc ctggaaggtc attacggtta 60
agttgcgccg cctccgggtt cacatttagc agctatgcta tgaactgggt gcgccaggcc 120
cctgcgaaag gactcgaatg ggttgccatc atcagccgag gaggcacaca gtattatgcc 180
gattctgtga agggtcgttt tactatttcc agagacaaca gtaaaaatac gctgtacctg 240
caaatgaacg gattgagggc tgaggatacc gccgtgtact actgtggacg ctacgactat 300
gatgggtact acgcgatgga ctattggggg caaggaaccc ttgtaaccgt tagttca 357

<210> SEQ ID NO 371
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 371

Glu Ile Val Leu Thr Gln Ser Pro Asp Phe Gln Ser Val Thr Pro Lys
1 5 10 15

Glu Lys Val Thr Ile Thr Cys Arg Ala Ser Pro Asp Ile Asn Ser Tyr
20 25 30

Leu Ser Trp Tyr Gln Gln Lys Pro Asp Gln Ser Pro Lys Leu Leu Ile
35 40 45

Lys Arg Ala Asn Gln Ser Phe Ser Gly Val Pro Ser Arg Phe Ser Gly
50 55 60

Ser Gly Ser Gly Thr Asp Phe Thr Leu Thr Ile Asn Ser Leu Glu Ala
65 70 75 80

Glu Asp Ala Ala Ala Tyr Tyr Cys Leu Gln Tyr Asp Glu Phe Pro Tyr
85 90 95

Thr Phe Gly Pro Gly Thr Lys Val Asp Ile Lys
100 105

<210> SEQ ID NO 372
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 372
gagatcgttt tgacacagag ccccgatttc cagagcgtca cgcccaagga gaaggtcacc 60
atcacctgcc gagccagccc cgacatcaac agttatcttt catggtatca acagaaacct 120
gatcagagcc ctaagctgct gattaagcgc gccaaccaga gcttctcagg ggttccttca 180
cggttttccg ggtcaggcag cgggactgac ttcacgttga ccattaactc tttggaggct 240
gaggatgctg ctgcctatta ctgccttcag tacgacgagt tcccctatac atttggtcct 300
ggaacaaaag tggatataaa g 321

<210> SEQ ID NO 373
<211> LENGTH: 119
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 373

Gln Val Gln Leu Val Gln Ser Gly Ala Glu Val Lys Lys Pro Gly Ala
1 5 10 15

Ser Val Lys Val Ser Cys Lys Ala Ser Gly Phe Thr Phe Ser Ser Tyr
20 25 30

Ala Met His Trp Val Arg Gln Ala Pro Gly Gln Gly Leu Glu Trp Met
35 40 45

Gly Asn Ile Ser Arg Gly Gly Thr Thr Asn Tyr Ala Glu Lys Phe Lys
50 55 60

Asn Arg Val Thr Met Thr Arg Asp Thr Ser Ile Ser Thr Ala Tyr Met
65 70 75 80

Glu Leu Ser Arg Leu Arg Ser Asp Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

Thr Leu Val Thr Val Ser Ser
115

<210> SEQ ID NO 374
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 374
caggtgcagc tcgtccagag cggagccgaa gtgaagaagc cgggagcatc agtgaaagtt 60
tcctgcaaag caagtggctt cactttcagc agttacgcga tgcactgggt gcggcaggca 120
ccaggtcagg gactggaatg gatggggaac atctctcgcg gcggaacaac caattacgca 180
gagaagttta agaatcgcgt tacgatgacc agagacactt ctattagtac agcctatatg 240
gagttgtcgc gtctgagaag cgacgatacc gctgtctact attgcggccg gtacgattat 300
gacggctact atgcaatgga ttactgggga cagggcacac ttgtgacagt gtctagt 357

<210> SEQ ID NO 375
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 375

Asp Ile Val Met Thr Gln Ser Pro Leu Ser Leu Pro Val Thr Pro Gly
1 5 10 15

Glu Pro Ala Ser Ile Ser Cys Arg Ser Ser Pro Asp Ile Asn Ser Tyr
20 25 30

Leu Glu Trp Tyr Leu Gln Lys Pro Gly Gln Ser Pro Gln Leu Leu Ile
35 40 45

Tyr Arg Ala Asn Asp Arg Phe Ser Gly Val Pro Asp Arg Phe Ser Gly
50 55 60

Ser Gly Ser Gly Thr Asp Phe Thr Leu Lys Ile Ser Arg Val Glu Ala
65 70 75 80

Glu Asp Val Gly Val Tyr Tyr Cys Leu Gln Tyr Asp Glu Phe Pro Tyr

```
                85                  90                  95

Thr Phe Gly Gln Gly Thr Lys Val Glu Ile Lys
            100                 105


<210> SEQ ID NO 376
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 376

gacattgtga tgactcagtc tccactcagc ctgcctgtca cgcccggcga acccgcttct      60

atctcttgta ggagtagccc tgatatcaac agctacctcg aatggtatct ccagaaacct     120

ggtcagagcc cccagctctt gatctataga gcaaacgaca ggttctctgg cgtgcctgat     180

aggttttccg gtagtggcag cggaaccgac ttcacactta agatttcaag ggtcgaggcc     240

gaggacgtgg gggtgtatta ctgcttacag tacgatgagt ttccgtatac attcgggcaa     300

ggcacaaagg tggaaattaa g                                               321


<210> SEQ ID NO 377
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 377

Glu Val Gln Leu Val Glu Ser Gly Gly Gly Leu Val Gln Pro Gly Gly
1               5                   10                  15

Ser Leu Arg Leu Ser Cys Thr Gly Ser Gly Phe Thr Phe Ser Ser Tyr
            20                  25                  30

Ala Met His Trp Leu Arg Gln Val Pro Gly Glu Gly Leu Glu Trp Val
        35                  40                  45

Ser Gly Ile Ser Arg Gly Gly Thr Ile Asp Tyr Ala Asp Ser Val Lys
    50                  55                  60

Gly Arg Phe Thr Ile Ser Arg Asp Asp Ala Lys Lys Thr Leu Ser Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Met Val Thr Val Ser Ser
        115


<210> SEQ ID NO 378
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 378

gaagtgcaac tggtcgaaag tggagggga ctagtgcagc ccggagggtc actgaggcta       60

tcatgcaccg gctctggttt tactttttcc agctatgcca tgcactggct cagacaggtt     120

ccgggggaag gactggagtg ggttagcgga atctccagag gcggaactat tgactacgca     180
```

gacagcgtga aaggtaggtt taccatcagc agggacgatg ctaaaaagac cctgtcactt 240
caaatgaata gcctgagagc tgaggatacg gccgtgtatt actgtggacg ctatgactac 300
gatggatatt acgcaatgga ctactggggc cagggaacaa tggtgaccgt ctcaagc 357

<210> SEQ ID NO 379
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 379

Glu Ile Val Leu Thr Gln Ser Pro Ala Thr Leu Ser Val Ser Pro Gly
1 5 10 15

Glu Arg Ala Thr Leu Ser Cys Arg Ala Ser Pro Asp Ile Asn Ser Tyr
20 25 30

Leu Ala Trp Tyr Gln Gln Lys Pro Gly Gln Ala Pro Arg Leu Leu Phe
35 40 45

Ser Arg Ala Asn Asn Arg Ala Thr Gly Ile Pro Ala Arg Phe Thr Gly
50 55 60

Ser Gly Ser Gly Thr Asp Phe Thr Leu Thr Ile Ser Ser Leu Glu Pro
65 70 75 80

Glu Asp Phe Ala Ile Tyr Tyr Cys Leu Gln Tyr Asp Glu Phe Pro Tyr
85 90 95

Thr Phe Gly Gln Gly Thr Lys Val Glu Ile Lys
100 105

<210> SEQ ID NO 380
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 380
gagatcgtcc tgacccagag cccagctact ttgtcagttt cgccaggcga gcgggccaca 60
ctgagctgta gggcttctcc tgatatcaat tcttacctgg cctggtatca acagaaaccg 120
ggacaggccc ctcgcctgct gttctcccgc gccaacaata gggcgactgg cataccagct 180
cggtttactg ggagtgggtc aggcactgat ttcacgctta caatcagtag cctggagccc 240
gaagacttcg ccatctacta ctgtttacaa tacgatgagt tcccctatac cttcggccaa 300
gggaccaagg tggagatcaa g 321

<210> SEQ ID NO 381
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 381

Glu Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

-continued

```
Ala Met Ser Trp Val Arg Gln Ala Pro Gly Lys Gly Leu Glu Trp Val
        35                  40                  45

Ala Ser Ile Ser Arg Gly Gly Thr Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Gly Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115
```

<210> SEQ ID NO 382
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 382

```
gaagtgcagc tagtagaaag tggtggtggg gtcgtgcagc caggccgctc gctcaggctg      60

tcttgcgctg cgagtggttt cacattctct tcatacgcca tgagctgggt gagacaggct     120

cccggcaagg gcctcgaatg ggtcgcatct ataagcagag gcggaaccca gtactacgct     180

gacagtgtga agggtcgctt tacaatctca cgggacaaca gtaaaaacac cctctatcta     240

cagatgaatg gcttgcgagc tgaagacacg gctgtgtatt attgcgggcg ctatgactat     300

gatggttact acgctatgga ttactggggc cagggcaccc tggttactgt ttcatca        357
```

<210> SEQ ID NO 383
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 383

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Pro Asp Ile Asn Ser Tyr
            20                  25                  30

Leu Pro Trp Tyr Gln Gln Lys Pro Asp Gln Ser Pro Lys Leu Leu Ile
        35                  40                  45

Lys Arg Ala Asn Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys Leu Gln Tyr Asp Glu Phe Pro Tyr
                85                  90                  95

Thr Phe Gly Pro Gly Thr Lys Val Asp Ile Lys
            100                 105
```

<210> SEQ ID NO 384
<211> LENGTH: 321
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 384
gaaatagtcc tgacccagag cccagacttc cagtccgtga cccctaagga gaaggttact 60
atcacttgca gggcaagccc tgacataaat tcatacctgc catggtatca gcagaagcca 120
gaccagtcgc cgaagctatt aatcaaacgc gccaaccagt cttttagcgg cgtaccatcc 180
cgattctcag gttcggggtc cgggaccgat ttcacactca cgataaactc ccttgaggca 240
gaggatgcag cggcttacta ctgtttacag tacgacgagt ttccatatac gttcggcccc 300
ggcacgaagg tagatatcaa g 321

<210> SEQ ID NO 385
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 385

Glu Val Gln Leu Val Glu Ser Gly Gly Gly Leu Val Gln Pro Gly Gly
1 5 10 15

Ser Leu Arg Leu Ser Cys Ala Thr Ser Gly Phe Thr Phe Ser Ser Tyr
20 25 30

Ala Met Ser Trp Met Arg Gln Ala Pro Gly Lys Gly Leu Glu Trp Val
35 40 45

Ala Ser Ile Ser Arg Gly Gly Thr Thr Tyr Tyr Ala Asp Ser Val Lys
50 55 60

Gly Arg Phe Thr Ile Ser Val Asp Lys Ser Lys Asn Thr Leu Tyr Leu
65 70 75 80

Gln Met Asn Ser Leu Arg Ala Glu Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

Thr Leu Val Thr Val Ser Ser
115

<210> SEQ ID NO 386
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 386
gaagtgcagc tggtggagtc tggcggcggt ctggtgcagc ccggcggctc tctgcgcctc 60
tcctgtgcca cctctggttt tacattctcc tcctacgcta tgtcctggat gcggcaagcc 120
cccggcaagg gcctagagtg ggtcgcctca atcagcaggg gcgggacgac ttattatgcc 180
gattcagtta aggggagatt cacaatttcc gtggataaat ccaagaatac cttatacctc 240
cagatgaact ctctgcgggc cgaagatacg gccgtatatt attgtgggag gtatgactac 300
gacggatatt acgccatgga ttattggggg caggggacac ttgttacagt gagttcc 357

<210> SEQ ID NO 387
<211> LENGTH: 107
<212> TYPE: PRT

<213> ORGANISM: Artificial Sequence
<220> FEATURE:
<223> OTHER INFORMATION: Description of Artificial Sequence: Synthetic
polypeptide

<400> SEQUENCE: 387

Asp Ile Gln Met Thr Gln Ser Pro Ser Ser Leu Ser Ala Ser Val Gly
1 5 10 15

Asp Arg Val Thr Ile Thr Cys Lys Ala Ser Pro Asp Ile Asn Ser Tyr
20 25 30

Leu Asn Trp Tyr Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Ala Gly Thr Lys Val Glu Ile Lys
100 105

<210> SEQ ID NO 388
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 388
gatatacaga tgacacagag cccttcaagt ttatctgcaa gcgtcggcga tcgtgttaca 60
ataacttgca aggcatctcc cgacatcaat tcctacctca actggtatca gcagaagcct 120
gggaaggctc ctaagctgct tatttacaga gcaaatcgcc tggtggacgg cgtgcccagt 180
cggttttccg ggtctgggag cggaacggat tacacactga ccatctcaag cctgcaaccc 240
gaagacttcg ctacatatta ctgccttcag tatgatgagt tcccatatac cttcggcgct 300
gggaccaagg tggagataaa g 321

<210> SEQ ID NO 389
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 389

Glu Val Gln Leu Val Glu Ser Gly Gly Gly Leu Val Gln Pro Gly Gly
1 5 10 15

Ser Leu Arg Leu Ser Cys Ala Ser Ser Gly Phe Thr Phe Ser Ser Tyr
20 25 30

Ala Met Ser Trp Arg Arg Gln Ala Pro Gly Lys Gly Leu Glu Trp Val
35 40 45

Ala Gly Ile Ser Arg Gly Gly Thr Thr Ser Tyr Ala Asp Ser Val Lys
50 55 60

Gly Arg Phe Thr Ile Ser Ser Asp Asp Ser Lys Asn Thr Leu Tyr Leu
65 70 75 80

Gln Met Asn Ser Leu Arg Ala Glu Asp Thr Ala Val Tyr Tyr Cys Gly
85 90 95

```
Arg Tyr Asp Tyr Asp Gly Tyr Tyr Ala Met Asp Tyr Trp Gly Gln Gly
            100                 105                 110

Thr Leu Val Thr Val Ser Ser
        115
```

<210> SEQ ID NO 390
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 390

```
gaggtccagc tcgtcgaatc tggcggaggt ttagtgcaac caggcgggtc gctccgatta     60

agttgtgcgt ccagtggctt caccttctcc agctacgcca tgtcgtggag gcgacaggct    120

cctggcaaag gcttggagtg ggttgctggt atctcccgag gaggcaccac tagttacgct    180

gacagtgtaa aaggacgttt cactatttcc tctgacgaca gcaagaacac actctatctg    240

caaatgaata gtctccgtgc tgaggacaca gccgtgtatt attgcgggcg gtatgattac    300

gacggctact acgctatgga ctactggggc cagggaactc tggtcactgt gagctct       357
```

<210> SEQ ID NO 391
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 391

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Pro Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Ile Glu Ile Lys
            100                 105
```

<210> SEQ ID NO 392
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 392

```
gatatacaga tgactcaaag tcctagctcc ttgagcgcct cagtgggaga tcgggtcact     60

ataacttgta gagcctcacc agatataaac tcctatctct cttggtatca gcagaagccc    120

ggcaaagcac caaagctctt gatctataga gctaatacgc tagagagcgg agtgccttca    180
```

-continued

```
cggttttctg gttccgggag cggaaccgac tttaccctta caatttctag cctccagcca    240

gaggacttcg caacttacta ttgtctccag tatgatgaat ttccttacac cttcggccaa    300

gggaccaaga tcgagataaa g                                              321


<210> SEQ ID NO 393
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 393

Glu Val Gln Leu Val Glu Ser Gly Gly Gly Leu Val Gln Pro Gly Gly
1               5                   10                  15

Ser Leu Arg Leu Ser Cys Ala Ser Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Gly Ile Ser Arg Gly Gly Thr Thr Ser Tyr Ala Asp Ser Val Lys
    50                  55                  60

Gly Arg Phe Thr Ile Ser Ala Asp Thr Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 394
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 394

gaggtgcagc tcgttgagtc cggtgggggg ctggtgcagc ctggcgggtc tctccgcctc     60

tcttgtgcct cctccggctt taccttcagc agctatgcta tgtcatgggt gcggcaggca    120

ccaggcaaag gtctggaatg ggtcgctggg atcagtagag gcggcacaac ctcctatgcc    180

gacagcgtta aggggaggtt cacaatctcg gctgatacaa gcaagaacac tctgtatctc    240

caaatgaaca gtctccgggc agaggacacc gcggtctatt actgcggccg gtacgactac    300

gacgggtact acgcaatgga ctattgggga cagggaactc tggttactgt cagctct      357


<210> SEQ ID NO 395
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 395

Asp Ile Gln Met Thr Gln Ser Pro Ser Ser Leu Ser Ala Ser Val Gly
1               5                   10                  15

Asp Arg Val Thr Ile Thr Cys Arg Ala Ser Pro Asp Ile Asn Ser Tyr
```

```
            20                  25                  30

Leu Ser Trp Tyr Gln Gln Lys Pro Gly Lys Ala Pro Lys Leu Leu Ile
        35                  40                  45

Tyr Arg Ala Asn Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Thr Gly Thr Lys Leu Glu Ile Lys
            100                 105


<210> SEQ ID NO 396
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 396

gatatccaga tgactcaaag cccatcttct ctcagcgcaa gcgtgggtga ccgagtgacc      60

atcacctgcc gggcgtctcc tgatatcaac tcatacctgt cctggtatca gcagaagccc     120

ggaaaggccc ctaagctgct gatctaccgc gcaaatacac tggagagcgg ggtcccaagc     180

agattcagtg ggtccggcag tggtacggac tttactctga ccatcagctc cctgcaaccg     240

gaggactttg ctacttatta ctgtctccag tacgacgagt tcccatacac tttcggaaca     300

ggcactaagc tggagatcaa a                                               321


<210> SEQ ID NO 397
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Arg Gly Gly Thr Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 398
<211> LENGTH: 357
<212> TYPE: DNA
```

<213> ORGANISM: Artificial Sequence
<220> FEATURE:
<223> OTHER INFORMATION: Description of Artificial Sequence: Synthetic
polynucleotide

<400> SEQUENCE: 398
gaggttcaac ttgtggaatc cggcggcggg ttagtccagc ccggcgggag cttgcggctg 60
tcctgcgccg cctctggatt cacttttagc tcctatgcta tgtcttgggt aaggcaggcc 120
cctggtaaag gactagagtg ggtggcctcg atctcccgtg gtggcactac atactacgcc 180
gactccgtta aaggccggtt taccatctcc cgtgacaact ctaaaaatac tttgtacctg 240
caaatgaact ccctgcgggc agaagacaca gccgtgtact attgcgggcg ttacgattac 300
gacggatatt acgcaatgga ctactggggc cagggcacac tggtcaccgt gagcagc 357

<210> SEQ ID NO 399
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 399

Asp Ile Gln Met Thr Gln Ser Pro Ser Ser Leu Ser Ala Ser Val Gly
1 5 10 15

Asp Arg Val Thr Ile Thr Cys Lys Ala Ser Pro Asp Ile Asn Ser Tyr
20 25 30

Leu Asn Trp Tyr Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Ile Ala Thr Tyr Tyr Cys Leu Gln Tyr Asp Glu Phe Pro Tyr
85 90 95

Thr Phe Gly Gly Gly Thr Lys Val Glu Ile Lys
100 105

<210> SEQ ID NO 400
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 400
gatatacaaa tgactcagtc ccctagtagc cttagtgcta gtgtgggaga cagagtgacc 60
atcacctgca aagcatctcc tgatatcaat tcctacctta actggtatca acagaagcct 120
ggcaaagctc caaagctcct gatttatcgc gcgaacagat tggtcgatgg ggtcccttcc 180
agattcagcg gctcagggtc agggaccgat ttcaccctca caattagttc acttcagccc 240
gaggacatcg ccacgtatta ttgccttcag tacgatgagt tcccttacac ctttggcggg 300
ggaactaaag tcgaaattaa g 321

<210> SEQ ID NO 401
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 401

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ala Ser Ile Ser Arg Gly Gly Thr Thr Tyr Tyr Pro Asp Ser Val Lys
50 55 60

Gly Arg Phe Thr Ile Ser Arg Asp Asn Val Arg Asn Ile Leu Tyr Leu
65 70 75 80

Gln Met Ser Ser Leu Arg Ser Glu Asp Thr Ala Met Tyr Tyr Cys Gly
85 90 95

Arg Tyr Asp Tyr Asp Gly Tyr Tyr Ala Met Asp Tyr Trp Gly Gln Gly
100 105 110

Thr Leu Val Thr Val Ser Ser
115

<210> SEQ ID NO 402
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 402
gaagtgcagc ttgtggagtc aggaggaggg ctagttcagc caggcggctc tctgagacta 60
tcttgtgctg cctccggctt cacatttagc tcttatgcaa tgtcctgggt ccgccaggcc 120
cctggtaaag gcctggaatg ggttgcttct atctctagag gcggaaccac ttactaccct 180
gattcagtga aggggagatt cacaattagt agggacaacg tgcggaacat cctctaccta 240
cagatgtcaa gtttacgcag tgaggacact gcgatgtatt actgcggtcg atacgattat 300
gatggatatt atgcaatgga ttattggggc cagggcactc tggtcacagt atcttcc 357

<210> SEQ ID NO 403
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 403

Asp Ile Gln Met Thr Gln Ser Pro Ser Ser Leu Ser Ala Ser Val Gly
1 5 10 15

Asp Arg Val Thr Ile Thr Cys Lys Ala Ser Pro Asp Ile Asn Ser Tyr
20 25 30

Leu Asn Trp Tyr Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Tyr Thr Leu Thr Ile Ser Ser Leu Gln Pro
65 70 75 80

-continued

```
Glu Asp Phe Ala Thr Tyr Tyr Cys Leu Gln Tyr Asp Glu Phe Pro Tyr
                85                  90                  95

Thr Phe Gly Ala Gly Thr Lys Val Glu Ile Lys
            100                 105


<210> SEQ ID NO 404
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 404

gacatccaga tgacccaatc accatcgagt cttagtgcat ccgttgggga tagagtgaca      60

atcacttgta aggcatcccc ggacatcaac tcatatctta attggtatca gcaaaagccg     120

ggcaaggccc ctaagctcct gatttatagg gccaaccgcc ttgtggatgg agtcccctcc     180

cgctttagtg gaagcggctc tggcacagac tacaccctga ctatcagctc cttgcagcct     240

gaggattttg ctacctacta ctgtcttcag tacgatgaat ttccatacac tttcggtgct     300

gggacaaaag tggagatcaa a                                               321


<210> SEQ ID NO 405
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 405

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Ser Tyr
            20                  25                  30

Ala Met Ser Trp Met Arg Lys Ala Pro Gly Lys Gly Leu Glu Tyr Val
        35                  40                  45

Ala Ser Ile Ser Arg Gly Gly Thr Thr Tyr Tyr Ala Asp Ser Val Lys
    50                  55                  60

Gly Arg Phe Thr Ile Ser Val Asp Lys Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 406
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 406

gaagtccagc tggttgagtc tggcggaggc ctcgtgcagc ccggtggttc cttgcgactg      60

tcatgcgcta ccagcgggtt cacattcagc tcttatgcaa tgtcctggat gcggaaggca     120
```

```
ccgggtaagg gcctggagta tgtggcctca atctcccgag gaggcaccac atactatgcc    180

gattctgtga aaggccgatt caccatttct gtggataagt ctaaaaacac tctctacctc    240

cagatgaact ccctacgtgc cgaagacaca gccgtgtatt attgcgggcg atacgattat    300

gacggttatt atgcgatgga ttactggggt caaggcacac tggtaacagt gtcttcc       357


<210> SEQ ID NO 407
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 407

Asp Ile Gln Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Asn Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Ala Gly Thr Lys Val Glu Ile Lys
            100                 105


<210> SEQ ID NO 408
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 408

gatattcaga tgacacaatc acctagctca ctgtcagcga gcgtcggtga ccgggttact     60

atcacatgca aagcctcacc cgatatcaat tcatacctta actggtatca acaaaaacca    120

ggaaaggctc caaagctgct aatttatcgg gccaatcggt tggtggatgg cgtcccgtcg    180

aggtttagtg gctccgggag cgggacagac tacactctta caatttcttc tctccagcca    240

gaggacttcg caacctacta ctgcttgcag tacgatgaat ttccatatac cttcggcgca    300

gggacaaaag tggaaatcaa a                                              321


<210> SEQ ID NO 409
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 409

Glu Val Gln Leu Val Glu Ser Gly Gly Gly Leu Val Gln Pro Gly Gly
1               5                   10                  15

Ser Leu Arg Leu Ser Cys Val Thr Ser Gly Phe Thr Phe Ser Ser Tyr
            20                  25                  30
```

```
Ala Met Ser Trp Val Arg Gln Ala Pro Gly Lys Gly Leu Glu Trp Val
        35                  40                  45

Ala Ser Ile Ser Arg Gly Gly Thr Thr Tyr Tyr Ser Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115
```

<210> SEQ ID NO 410
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 410

```
gaggtgcagc ttgtagaaag cggggggggc ctggtgcaac ctggcgggtc cctgcggctt      60

agttgcgtta cgagcggatt tacattttcc agttatgcca tgtcttgggt gagacaagcc     120

cccggtaagg gtctggagtg ggtggcaagc attagccgag gcggcactac atactacagt     180

gatagtgtga aaggccgttt cacaatcagt agagataatt ctaaaaacac cctgtacttg     240

cagatgaaca gcctgcgcgc cgaggataca gccgtgtact actgtggaag atacgactac     300

gatggatatt atgcgatgga ttactgggga cagggaaccc ttgtcaccgt ttcctct       357
```

<210> SEQ ID NO 411
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 411

```
Asp Ile Val Leu Thr Gln Ser Pro Ala Thr Leu Ser Leu Ser Pro Gly
1               5                   10                  15

Glu Arg Ala Thr Leu Ser Cys Lys Ala Ser Pro Asp Ile Asn Ser Tyr
            20                  25                  30

Met Asn Trp Tyr Gln Gln Lys Pro Gly Gln Ala Pro Arg Leu Leu Ile
        35                  40                  45

Ser Arg Ala Asn Arg Leu Val Asp Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Leu Gln Tyr Asp Glu Phe Pro Tyr
                85                  90                  95

Thr Phe Gly Gln Gly Thr Lys Val Glu Ile Lys
            100                 105
```

<210> SEQ ID NO 412
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 412
gacatagtgt tgacgcagtc ccctgccacc ctgagcctga gccccggaga gcgagcaacg     60
ttaagttgca aggccagtcc agatattaac tcatacatga attggtatca acagaaacca    120
ggccaggctc ctagacttct catatctcgg gcaaatcgac tggtggatgg agtacccgca    180
agattcagcg gcagcggcag cggaacggat ttcacgctca ccatctcttc ccttgagcct    240
gaggactttg cagtctatta ttgcttgcag tatgatgagt tcccctacac attcgggcaa    300
ggcacaaaag tggaaattaa g                                              321

<210> SEQ ID NO 413
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 413

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Arg Gly Gly Thr Thr Tyr Tyr Asp Pro Lys Phe Gln
    50                  55                  60

Asp Arg Ala Thr Ile Ser Ala Asp Asn Ser Lys Asn Thr Ala Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115

<210> SEQ ID NO 414
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 414
gaggtgcagc tggtggagag cggagggggc cttgtccaac caggaggtag cctcaggctg     60
tcttgcgctg cctcaggatt tacttttttca tcctacgcaa tgagctgggt gcggcaagcc    120
ccagggaagg gattagaatg ggttgccagc atttctaggg gggggacgac ctactacgat    180
ccgaagtttc aggatcgcgc cactatctca gccgataact ccaagaatac tgcctactta    240
cagatgaaca gcctgcgggc cgaagacacg gccgtctact attgcggccg atatgattac    300
gacggctatt acgccatgga ttactggggg caagggactc tggtcacagt gagctct       357

<210> SEQ ID NO 415
<211> LENGTH: 107

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 415

Asp Ile Gln Met Thr Gln Ser Pro Ser Ser Leu Ser Ala Ser Val Gly
1 5 10 15

Asp Arg Val Thr Ile Thr Cys Lys Ala Ser Pro Asp Ile Asn Ser Tyr
20 25 30

Leu Asn Trp Tyr Gln Gln Lys Pro Gly Lys Ala Pro Lys Val Leu Ile
35 40 45

Tyr Arg Ala Asn Arg Leu Val Asp Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Val Glu Ile Lys
100 105

<210> SEQ ID NO 416
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 416
gatattcaga tgacccagtc gcccagcagt ctctcggcct cagtgggcga ccgggtcact 60
atcacttgca aagcaagtcc tgatataaac tcctatctta attggtatca gcagaagccc 120
ggcaaggcac ctaaggttct gatatatcgc gcaaatcggc tcgtggatgg agtacccagc 180
cgattttccg gcagcggctc aggcactgac tacacactga caatcagcag cttgcagcct 240
gaagatttcg ccacatacta ttgtctacag tacgacgagt tcccttatac attcggccag 300
gggaccaagg tcgagatcaa g 321

<210> SEQ ID NO 417
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 417

Glu Val Gln Leu Val Glu Ser Gly Gly Gly Leu Val Gln Pro Gly Gly
1 5 10 15

Ser Leu Arg Leu Ser Cys Thr Gly Ser Gly Phe Thr Phe Ser Ser Tyr
20 25 30

Ala Met Ser Trp Leu Arg Gln Val Pro Gly Glu Gly Leu Glu Trp Val
35 40 45

Ser Ser Ile Ser Arg Gly Gly Thr Thr Asp Tyr Ala Asp Ser Val Lys
50 55 60

Gly Arg Phe Thr Ile Ser Arg Asp Asp Ala Lys Lys Thr Leu Ser Leu
65 70 75 80

Gln Met Asn Ser Leu Arg Ala Glu Asp Thr Ala Val Tyr Tyr Cys Gly

```
                85                  90                  95

Arg Tyr Asp Tyr Asp Gly Tyr Tyr Ala Met Asp Tyr Trp Gly Gln Gly
            100                 105                 110

Thr Met Val Thr Val Ser Ser
        115
```

<210> SEQ ID NO 418
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 418

```
gaggtccaac tcgtggagag cggagggggg ctagtgcaac caggtggctc cctccgcttg     60

tcctgtacgg gctcggggtt cacattttca tcctatgcca tgagctggct gagacaggtg    120

cctggcgagg gcctggaatg ggtgtctagt atcagcagag ggggtacaac tgattacgca    180

gattccgtca agggacgttt taccatctca agagacgatg ccaagaagac attatcactc    240

caaatgaact cactgagggc cgaggacacc gctgtgtact attgtgggag atacgactac    300

gacggatact atgccatgga ctattgggga caaggcacga tggtgacggt atctagc       357
```

<210> SEQ ID NO 419
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 419

```
Glu Ile Val Leu Thr Gln Ser Pro Ala Thr Leu Ser Val Ser Pro Gly
1               5                   10                  15

Glu Arg Ala Thr Leu Ser Cys Lys Ala Ser Pro Asp Ile Asn Ser Tyr
            20                  25                  30

Leu Ala Trp Tyr Gln Gln Lys Pro Gly Gln Ala Pro Arg Leu Leu Phe
        35                  40                  45

Ser Arg Ala Asn Arg Leu Val Asp Gly Ile Pro Ala Arg Phe Thr Gly
    50                  55                  60

Ser Gly Ser Gly Thr Asp Phe Thr Leu Thr Ile Ser Ser Leu Glu Pro
65                  70                  75                  80

Glu Asp Phe Ala Ile Tyr Tyr Cys Leu Gln Tyr Asp Glu Phe Pro Tyr
                85                  90                  95

Thr Phe Gly Gln Gly Thr Lys Val Glu Ile Lys
            100                 105
```

<210> SEQ ID NO 420
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 420

```
gagatagtgc taacccagtc tcccgcaacc ctgtctgtgt cccccggaga gcgcgctact     60

ctgagctgca aagccagccc ggacattaat tcctaccttg cctggtatca gcagaagcct    120

ggacaggccc caagattgct cttttcacgc gccaaccgcc tggtagatgg tattccagct    180
```

```
aggtttacgg gctcaggcag cggaacagac ttcactctca ctattagctc attggagcct    240

gaggactttg caatttacta ttgtcttcag tacgacgagt tcccatatac tttcggccag    300

ggcacaaaag tagagatcaa g                                              321


<210> SEQ ID NO 421
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 421

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met Ser Trp Val Arg Gln Val Pro Gly Lys Gly Leu Val Trp Ile
        35                  40                  45

Ser Ser Ile Ser Arg Gly Gly Thr Thr Tyr Tyr Ala Asp Ser Val Arg
    50                  55                  60

Gly Arg Phe Ile Ile Ser Arg Asp Asn Ala Lys Asn Thr Leu Tyr Leu
65                  70                  75                  80

Glu Met Asn Asn Leu Arg Gly Glu Asp Thr Ala Val Tyr Tyr Cys Ala
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 422
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 422

gaggttcaac tcgtggagtc tggaggcggg ctagtgcagc ctggcggctc cctgcgactg     60

tcttgcagcg catcaggctt tacattcagt tcttatgcca tgagctgggt gaggcaggtg    120

cccggcaagg gtctggtgtg gatcagctca atctccaggg gcgggactac atattacgcc    180

gattcggtca ggggtcgttt tatcattagc agggataatg ccaagaacac cttgtatttg    240

gagatgaaca acctaagagg cgaagacacc gctgtgtact attgtgcccg ttacgactac    300

gatgggtact acgccatgga ctattggggc cagggaacct tggtgactgt gtcaagt       357


<210> SEQ ID NO 423
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Asp Ile Gln Leu Thr Gln Ser Pro Asp Ser Leu Ala Val Ser Leu Gly
1               5                   10                  15
```

-continued

```
Glu Arg Ala Thr Ile Asn Cys Lys Ala Ser Pro Asp Ile Asn Ser Tyr
            20                  25                  30

Leu Ser Trp Tyr Gln Gln Arg Pro Gly Gln Pro Pro Arg Leu Leu Ile
        35                  40                  45

His Arg Ala Asn Arg Leu Val Asp Gly Val Pro Asp Arg Phe Ser Gly
    50                  55                  60

Ser Gly Phe Gly Thr Asp Phe Thr Leu Thr Ile Thr Ser Leu Gln Ala
65                  70                  75                  80

Glu Asp Val Ala Ile Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 424
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 424

gacatacagt tgactcagtc accggattcg ctggcagttt cgctgggtga gagagcaacc      60

atcaactgca aagcatctcc cgatatcaac tcttatctgt cttggtatca gcagcgtccg     120

ggacaacccc ctaggctgct tattcaccga gccaacaggc tggtggacgg ggtgccagac     180

cgcttctcgg gatcaggatt tggaaccgat tttaccctaa caattactag tctccaagcg     240

gaagacgtgg cgatctatta ttgtctacaa tatgacgagt tcccctacac cttcggccag     300

ggcacgaagt tggagatcaa g                                               321


<210> SEQ ID NO 425
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 425

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Arg Gly Gly Thr Thr Tyr Tyr Ala Asp Ser Val Lys
    50                  55                  60

Gly Arg Phe Thr Ile Ser Ala Asp Thr Ser Lys Asn Thr Ala Tyr Leu
65                  70                  75                  80

Gln Met Asn Ser Leu Arg Ala Glu Asp Thr Ala Val Tyr Tyr Cys Ala
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 426
<211> LENGTH: 357
```

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 426
gaggtccagc tcgtcgaatc cggtggaggg ctagttcagc caggcggctc attgcgtttg 60
tcttgtgccg cctccggttt cacattctct tcttacgcta tgtcctgggt ccgacaagcc 120
ccaggaaaag gcttggaatg ggtggccagt atcagtagag gtgggactac atattatgcc 180
gactccgtga agggcagatt caccatctca gctgacacca gtaagaacac tgcctaccta 240
cagatgaaca gccttcgggc cgaggacacc gctgtgtatt actgtgcccg gtacgattat 300
gatggatatt atgctatgga ctattggggt caggggacct tggtgaccgt ctctagc 357

<210> SEQ ID NO 427
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 427

Asp Ile Gln Met Thr Gln Ser Pro Ser Ser Leu Ser Ala Ser Val Gly
1 5 10 15

Asp Arg Val Thr Ile Thr Cys Lys Ala Ser Pro Asp Ile Asn Ser Tyr
20 25 30

Leu Ser Trp Tyr Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Val Glu Ile Lys
100 105

<210> SEQ ID NO 428
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 428
gacattcaga tgactcaatc gccgagttct cttagcgctt ctgttgggga ccgggtgaca 60
atcacatgca aggcctctcc cgatataaac tcctatctaa gctggtatca gcagaagcca 120
gggaaggccc ccaagttgtt aatctatcgc gccaacagac tggtggatgg ggtgccctct 180
cgattctccg ggagtggcag tgggactgat tttacactga ccatttcctc attgcagccc 240
gaagacttcg ctacctatta ctgcttgcag tacgatgagt tcccatatac attcggtcag 300
gggactaaag tggagataaa a 321

<210> SEQ ID NO 429
<211> LENGTH: 119
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 429

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Gly Gly Thr Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115

<210> SEQ ID NO 430
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 430
gaggtacagc tgctggaatc tggtgggggg ctggtccagc caggggggtc actacgactg     60
agctgcgctg cctccggttt tacattcagc agctatgcaa tgtcatgggt cagacaggca    120
ccaggtaaag gcctcgaatg ggtatcctcc atctcacgtg gtgggaccac ttactatgcc    180
gatagtgtga agggcaggtt cacgatctca agagataatt caaagaatac actctatcta    240
caaatgaaca gtttaagggc cgaggacacc gctgtttact attgtgccag atatgactac    300
gacggttatt atgctatgga ttactgggga caaggaacgc tggtaactgt tagctct       357

<210> SEQ ID NO 431
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 431

Asp Ile Gln Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Ser Trp Tyr Gln Gln Lys Pro Gly Glu Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

-continued

```
Glu Asp Phe Ala Thr Tyr Tyr Cys Leu Gln Tyr Asp Glu Phe Pro Tyr
                85                  90                  95

Thr Phe Gly Gln Gly Thr Lys Val Glu Ile Lys
            100                 105
```

<210> SEQ ID NO 432
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 432

```
gacatccaaa tgacccagtc gccttcctcc ttgtctgcat ctgtcggaga tcgggtgacg     60

atcacttgca aagcgagtcc agacatcaac tcatatctgt cctggtatca gcagaagccg    120

ggagaggcac ctaagctcct gatctacaga gcaaacagat tagtggatgg tgtgccctca    180

cggttttctg gctccgggtc cggcaccgat ttcaccttga ccatctcatc cctacagccc    240

gaggatttcg ctacttacta ttgcttacag tatgatgagt ttccatacac cttcggtcaa    300

ggcaccaagg ttgagattaa g                                              321
```

<210> SEQ ID NO 433
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 433

```
Glu Val Gln Leu Leu Glu Thr Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Val
        35                  40                  45

Ala Ser Ile Ser Arg Gly Gly Thr Thr Tyr Tyr Gly Asp Ser Val Lys
    50                  55                  60

Gly Arg Phe Thr Ile Ser Arg Asp His Ala Lys Asn Ser Leu Tyr Leu
65                  70                  75                  80

Gln Met Asn Ser Leu Arg Val Glu Asp Thr Ala Val Tyr Tyr Cys Val
                85                  90                  95

Arg Tyr Asp Tyr Asp Gly Tyr Tyr Ala Met Asp Tyr Trp Gly Leu Gly
            100                 105                 110

Thr Leu Val Thr Val Ser Ser
        115
```

<210> SEQ ID NO 434
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 434

```
gaagttcaac tgcttgagac cggaggcggc ctggtaaaac ctgggggctc actgaggctg     60

agttgtgccg cttctgggtt caccttttca tcctatgcga tgtcatggat acggcaggct    120
```

cctgggaagg ggcttgagtg ggttgcatca atttcacgag gtgggacaac ttattatggg 180
gattccgtta aaggtagatt tacgatctct agagaccatg ccaaaaattc tctctatctc 240
cagatgaata gtcttagggt ggaggacacc gctgtgtact actgtgtccg gtacgactat 300
gatgggtact atgctatgga ctattggggg ctcggcactc tggtcactgt tagctct 357

<210> SEQ ID NO 435
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 435

Ala Ile Arg Met Thr Gln Ser Pro Ser Phe Leu Ser Ala Ser Val Gly
1 5 10 15

Asp Arg Val Thr Ile Thr Cys Lys Ala Ser Pro Asp Ile Asn Ser Tyr
20 25 30

Leu Ser Trp Tyr Gln Gln Arg Pro Gly Lys Ala Pro Lys Leu Leu Ile
35 40 45

Tyr Arg Ala Asn Arg Leu Val Asp Gly Val Pro Ser Arg Phe Ser Gly
50 55 60

Gly Gly Ser Gly Thr Asp Phe Thr Leu Thr Ile Ser Ser Leu Gln Pro
65 70 75 80

Glu Asp Ile Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 436
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 436
gccatccgca tgacacaatc tccctccttc ctttctgcca gtgtcgggga cagagtgact 60
atcacatgca aagccagccc agatattaat tcgtacctgt cttggtatca gcagaggccc 120
ggcaaggcac caaagctgtt gatatatcgg gccaaccgct tagtggacgg tgtcccctct 180
cgattcagcg gaggcggtag cgggacggac tttacactga ccatctccag tctccaaccc 240
gaggatattg ccacttacta ttgtcttcag tatgacgagt tcccctacac atttggacag 300
ggcaccaagc tagaaattaa g 321

<210> SEQ ID NO 437
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 437

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr

```
            20                  25                  30

Ala Met Ser Trp Val Arg Gln Ala Pro Gly Lys Gly Leu Glu Trp Val
        35                  40                  45

Ala Ser Ile Ser Arg Gly Gly Thr Thr Tyr Tyr Ala Glu Ser Leu Glu
    50                  55                  60

Gly Arg Phe Thr Ile Ser Arg Asp Asp Ser Lys Asn Ser Leu Tyr Leu
65                  70                  75                  80

Gln Met Asn Ser Leu Lys Thr Glu Asp Thr Ala Val Tyr Tyr Cys Ala
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115
```

<210> SEQ ID NO 438
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 438

```
gaggttcagc tggtggagtc tggtgggggg ctcgtacagc cgggtggctc cctaaggctg      60

agttgcgctg cctcaggctt taccttctca agctacgcga tgtcctgggt gagacaggcc     120

cctggcaaag gactggagtg ggtggcaagc attagccggg gcggaactac ctattacgct     180

gagtcgttag aggggcggtt tactatctcc agagacgatt caaagaactc gttatacttg     240

cagatgaaca gcctcaagac cgaggacacc gccgtgtact actgcgcccg gtacgactat     300

gacgggtact atgctatgga ttattgggga caaggcaccc tcgtgaccgt ctctagc        357
```

<210> SEQ ID NO 439
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 439

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Ser Trp Tyr Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105
```

<210> SEQ ID NO 440
<211> LENGTH: 321
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 440
gacatccaga tgacacagtc cccttcttca ctttccgctt ctgtgggcga cagggtgacg 60
atcacgtgta aggcctcgcc agacattaat tcgtacttat cgtggtatca gcagaaaccg 120
ggtaaagctc cgaagactct gatctataga gcaaataggc tcgtagacgg tgtcccatct 180
agatttagtg ggagcggcag cggaaccgac ttcactctca ccatctcatc cctgcaaccg 240
gaggatttcg ctacttacta ttgcttgcag tatgacgagt ttccatatac gtttggtcag 300
ggaaccaaat tagagatcaa a 321

<210> SEQ ID NO 441
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 441

Gln Val Thr Leu Arg Glu Ser Gly Pro Ala Leu Val Lys Pro Thr Gln
1 5 10 15

Thr Leu Thr Leu Thr Cys Ala Ala Ser Gly Phe Thr Phe Ser Ser Tyr
20 25 30

Ala Met Ser Trp Ile Arg Gln Pro Pro Gly Lys Ala Leu Glu Trp Leu
35 40 45

Ala Ser Ile Ser Arg Gly Gly Thr Thr Tyr Tyr Asn Pro Ser Leu Lys
50 55 60

Asp Arg Leu Thr Ile Ser Lys Asp Thr Ser Ala Asn Gln Val Val Leu
65 70 75 80

Lys Val Thr Asn Met Asp Pro Ala Asp Thr Ala Thr Tyr Tyr Cys Ala
85 90 95

Arg Tyr Asp Tyr Asp Gly Tyr Tyr Ala Met Asp Tyr Trp Gly Gln Gly
100 105 110

Thr Thr Val Thr Val Ser Ser
115

<210> SEQ ID NO 442
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 442
caggtaacac tccgagagag tgggccagct ctcgtgaagc ccacgcagac tttaacacta 60
acgtgtgcgg caagcggctt tacattttcg agctacgcga tgagctggat aaggcaacct 120
cctgggaagg cgttggagtg gttggcctca attagccggg gtggcaccac ttactacaat 180
cctagtctta aggacagact tactatttca aaagatacgt ccgccaacca ggtggtactg 240
aaggtcacaa atatggaccc agctgacact gctacttact actgcgcccg gtacgattac 300
gatggttact acgctatgga ttactggggt caaggaacca cagtgaccgt cagttca 357

<210> SEQ ID NO 443

<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 443

Asp Ile Gln Met Thr Gln Ser Pro Ser Thr Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Ala Phe Thr Leu Thr Ile Ser Ser Leu Gln Pro
65                  70                  75                  80

Asp Asp Phe Ala Thr Tyr Tyr Cys Leu Gln Tyr Asp Glu Phe Pro Tyr
            85                  90                  95

Thr Phe Gly Gly Gly Thr Lys Val Glu Ile Lys
            100                 105

<210> SEQ ID NO 444
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 444
gatatccaga tgacgcagtc cccttcaacc ctcagtgcca gcgttggtga ccgggttact     60
atcacctgta aggctagtcc cgatataaat tcctatttgt cttggtatca gcagaagcca    120
ggcaaggctc ctaagctgct catctaccgg gctaacaggt tagttgacgg tgtgccctcc    180
cgattttccg gcagtggcag cgggaccgct ttcactctta caatctcatc tcttcaaccg    240
gacgacttcg ctacgtacta ctgcctccaa tatgatgagt ttccatacac attcggagga    300
ggcacaaaag tcgaaatcaa g                                              321

<210> SEQ ID NO 445
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 445

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Arg Gly Gly Thr Thr Tyr Tyr Ala Asp Ser Val Lys
    50                  55                  60

Gly Arg Phe Thr Ile Ser Ala Asp Thr Ser Lys Glu Thr Ala Tyr Leu
65                  70                  75                  80

```
Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 446
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 446

gaagtccagc tggtggagtc cggcggaggc ttggttcagc ccggaggatc tttgcgactg     60

tcttgcgccg ccagcggttt cactttcagc agctatgcca tgagttgggt tagacaagct    120

cccggcaagg ggctggaatg ggttagtgct attagccggg gagggacaac atattacgct    180

gactctgtca aaggccgatt caccatctct gctgacacga gcaaagaaac cgcctacctc    240

caaatgaaca gcctgcgagc tgaggacact gccgtctact attgtggtcg atatgattat    300

gatgggtact atgcaatgga ctattggggg cagggcacac tggtgaccgt gagctct       357


<210> SEQ ID NO 447
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 447

Asp Ile Gln Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 448
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 448

gatattcaga tgacgcagag tccctcctcc ctatctgcct ctgttggaga tcgagtcacc     60

attacgtgta aagcgtctcc cgatatcaac agctacctct cttggtatca gcagaaacca    120
```

gggaaggccc ccaagctgct gatctataga gctaatcgct tagtggatgg agtgccaagc 180
aggttctccg ggtccggcag tggaaccgat ttcaccttga caataagtag cttgcaacct 240
gaggatattg caacatacta ctgtctacag tacgacgagt tcccctacac cttcggccaa 300
gggacaaagc tggagattaa g 321

<210> SEQ ID NO 449
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 449

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Arg Gly Gly Thr Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

Thr Leu Val Thr Val Ser Ser
115

<210> SEQ ID NO 450
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 450
gaagtgcagc tcgtggagag cggcggcggt ctggtacagc caggggggtc actgcgtctc 60
tcatgtgctg cgagtggctt tacgttctct tcctacgcta tgtcctgggt caggcaggca 120
ccggggaagg gcttagagtg ggttagtgca atctctaggg gcggtacaac ctactatgcc 180
gactctgtca agggcaggtt tacaatttca agagataatt ctaagaatac tctttaccta 240
cagatgaata gcttgcgggc ggaagacaca gcagtctatt attgtggccg ctatgactac 300
gacggatact atgccatgga ctactggggc caaggcactt tggtcacggt gagctct 357

<210> SEQ ID NO 451
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 451

Asp Ile Gln Met Thr Gln Ser Pro Ser Ser Leu Ser Ala Ser Val Gly
1 5 10 15

```
Asp Arg Val Thr Ile Thr Cys Lys Ala Ser Pro Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 452
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 452

gacatccaga tgacccagag ccctagttca ttgtctgcca gtgtggggga tagggtcact     60

atcacgtgta aggcttcccc tgacatcaat tcatacctgt catggtatca gcagaagcct    120

ggaaaagccc ctaaactgct gatctaccgc gcgaataggc ttgtggacgg cgttccaagc    180

cgcttctctg gctctggatc agggaccgac ttcaccctca cgatctccag cctccaaccc    240

gaggatatcg ccacctatta ttgccttcag tacgatgagt tcccctatac attcggccag    300

gggacaaagc tggaaatcaa a                                              321


<210> SEQ ID NO 453
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 453

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Arg Gly Gly Thr Thr Tyr Tyr Ala Asp Ser Val Lys
    50                  55                  60

Gly Arg Phe Thr Ile Ser Ala Asp Thr Ser Lys Glu Thr Ala Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 454
```

<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 454

```
gaggtccagc tcgtcgagtc gggtgggggc ttggtgcaac ccggtggcag tttgcgcctg     60

agctgcgccg cgagcgggtt cactttcagt tcgtatgcca tgagttgggt gcgacaagcg    120

cccggcaaag gactggagtg ggtgtcagcc attagccggg gcggtactac ctactatgcg    180

gactcggtca agggaagatt caccatcagc gctgatacca gtaaggaaac cgcttatctt    240

cagatgaact ccctgcgtgc cgaggataca gcagtctact attgcgggcg ctacgattat    300

gacggatatt atgccatgga ttactggggg cagggcactc tggtcacagt cagctct       357
```

<210> SEQ ID NO 455
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 455

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Pro Asp Ile Asn Ser Tyr
            20                  25                  30

Leu Asn Trp Tyr Gln Gln Lys Pro Gly Lys Ala Pro Lys Leu Leu Ile
        35                  40                  45

Tyr Arg Ala Asn Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105
```

<210> SEQ ID NO 456
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 456

```
gatattcaga tgacgcagtc tccctcttcc ctgagcgcct ccgtcggcga tagagttacg     60

atcacctgtc aggccagccc agatatcaac tcctatctga attggtatca gcaaaagcct    120

gggaaggctc ccaagttgct gatctacaga gccaataact tagagactgg cgtgccgtct    180

cggttcagcg ggtccggcag tggaaccgac tttacactga ccatttccag cctccaacct    240

gaggatatcg ccacatatta ttgtctccag tatgacgagt tcccttacac atttggtcaa    300

ggaactaaac tggaaatcaa a                                              321
```

<210> SEQ ID NO 457
<211> LENGTH: 119

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 457

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Arg Gly Gly Thr Thr Tyr Tyr Ala Asp Ser Val Lys
    50                  55                  60

Gly Arg Phe Thr Ile Ser Ala Asp Thr Ser Lys Glu Thr Ala Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115
```

<210> SEQ ID NO 458
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 458

```
gaggtgcagc tggtcgaaag tggaggcgga ctcgtgcagc ccggcggtag tctgcgattg      60

agctgtgccg cgtccggctt tactttctca tcttacgcta tgagttgggt ccgccaggcc     120

ccaggcaaag gactggagtg ggtatcagcc atcagtaggg ggggaactac ctattacgca     180

gattctgtga agggacgctt caccatcagc gcggacacta gcaaggagac tgcctacctg     240

caaatgaata gtctgagagc cgaggatacc gccgtgtact attgtggcag gtatgactac     300

gatggctatt atgctatgga ttactggggc caggggacgt tagtgacagt aagctct        357
```

<210> SEQ ID NO 459
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 459

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Pro Asp Ile Asn Ser Tyr
            20                  25                  30

Val Ala Trp Tyr Gln Gln Lys Pro Gly Lys Ala Pro Lys Leu Leu Ile
        35                  40                  45

Tyr Arg Ala Asn Phe Leu Glu Ser Gly Val Pro Ser Arg Phe Ser Gly
    50                  55                  60

Ser Arg Ser Gly Thr Asp Phe Thr Leu Thr Ile Ser Ser Leu Gln Pro
```

-continued

```
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Val Glu Ile Lys
            100                 105


<210> SEQ ID NO 460
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 460

gatattcaga tgacccaatc cccttcttct ctgagcgctt ctgtgggcga tagagttaca     60

ataacctgtc gggcgtcccc agacattaac tcttatgtag catggtatca gcaaaagcct    120

ggaaaggcac caaagttact gatctaccgg gccaattttc tggagtcggg cgtgccctca    180

cgatttagcg gtagcagatc aggcacagac tttactctga ccattagctc tctgcaaccc    240

gaggacttcg ccacctacta ctgtttgcag tatgacgagt ttccatacac ttttggtcaa    300

ggaaccaaag tcgaaatcaa a                                              321


<210> SEQ ID NO 461
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 461

Gln Ile Gln Leu Val Gln Ser Gly Ala Glu Val Lys Lys Pro Gly Ala
1               5                   10                  15

Ser Val Lys Val Ser Cys Ala Ala Ser Gly Phe Thr Phe Ser Ser Tyr
            20                  25                  30

Ala Met Ser Trp Val Arg Gln Ala Pro Gly Lys Ser Phe Lys Trp Met
        35                  40                  45

Gly Ser Ile Ser Arg Gly Gly Thr Thr Tyr Tyr Ser Ala Asp Phe Lys
    50                  55                  60

Gly Arg Phe Ala Ile Thr Lys Asp Thr Ser Ala Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser
        115


<210> SEQ ID NO 462
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 462

cagatacagc tggtgcagtc tggtgccgag gttaaaaagc ccggagcctc ggttaaagtg     60
```

agttgtgcgg caagcggatt cacgttcagt tcctacgcta tgtcctgggt gcggcaggct 120
cctggcaagt catttaagtg gatggggtcg atctcacggg gtggaaccac ctattactct 180
gccgacttca aggggagatt tgcgattaca aaagatacaa gcgcctctac ggcctacatg 240
gagttaagta gccttagaag cgaagacacg gcggtgtact actgcgccag atatgactat 300
gacggctact acgccatgga ctactggggc cagggcacac tggttacagt cagctct 357

<210> SEQ ID NO 463
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 463

Asp Ile Val Met Thr Gln Ser Pro Asp Ser Leu Ala Val Ser Leu Gly
1 5 10 15

Glu Arg Ala Thr Ile Ser Cys Lys Ala Ser Pro Asp Ile Asn Ser Tyr
20 25 30

Leu Ser Trp Tyr Gln Gln Lys Pro Gly Gln Pro Pro Lys Leu Leu Ile
35 40 45

Tyr Arg Ala Asn Arg Leu Val Asp Gly Val Pro Asp Arg Phe Ser Gly
50 55 60

Ser Gly Ser Arg Thr Asp Phe Thr Leu Thr Ile Ser Ser Leu Gln Ala
65 70 75 80

Glu Asp Val Ala Val Tyr Tyr Cys Leu Gln Tyr Asp Glu Phe Pro Tyr
85 90 95

Thr Phe Gly Gln Gly Thr Lys Val Glu Ile Lys
100 105

<210> SEQ ID NO 464
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 464
gatatcgtga tgacacaaag cccagacagt ctggcagtgt ccctcggcga gcgcgctacc 60
atctcatgca aagctagtcc cgacatcaat tcctatctgt cctggtatca gcaaaaacca 120
ggccaacccc ccaagctgct tatctatcgg gctaaccgat tagtcgatgg ggtgccagat 180
agattttcag gctctggttc ccggacagat tttactctca cgatctcctc actacaggca 240
gaagatgttg cagtgtatta ctgcctgcaa tacgacgagt tcccctacac cttcggccaa 300
ggcacgaaag tggagatcaa g 321

<210> SEQ ID NO 465
<211> LENGTH: 241
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 465

Glu Val Gln Leu Val Glu Ser Gly Gly Gly Leu Val Gln Pro Gly Gly
1 5 10 15

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Gly Gly Thr Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Pro Asp Ile Asn Ser Tyr Leu Asn Trp Tyr Gln Gln Lys Pro Gly Lys
                165                 170                 175

Ala Pro Lys Leu Leu Ile Tyr Arg Ala Asn Arg Leu Val Asp Gly Val
            180                 185                 190

Pro Ser Arg Phe Ser Gly Ser Gly Ser Gly Thr Asp Tyr Thr Leu Thr
        195                 200                 205

Ile Ser Ser Leu Gln Pro Glu Asp Phe Ala Thr Tyr Tyr Cys Leu Gln
    210                 215                 220

Tyr Asp Glu Phe Pro Tyr Thr Phe Gly Ala Gly Thr Lys Val Glu Ile
225                 230                 235                 240

Lys
```

<210> SEQ ID NO 466
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 466

```
gaagtgcaac tggtcgagtc tgggggcggc cttgtgcaac ctggaggcag ccttcgactc     60

agttgcgccg cgtctggttt taccttctcc tcttacgcga tgagctgggt tcgccaggcc    120

cccggcaagg gacttgagtg ggttagttcg atctcccgcg gaggcaccac atattatcct    180

gactcggtta agggacgctt cactatctct agggacaatt caaagaacac actgtatctc    240

caaatgaact ccttgcgggc cgaggacact gctgtgtatt attgcggacg atacgactac    300

gatgggtatt acgccatgga ttactggggg caaggtacac tggtcactgt gagttcgggg    360

ggcggcggaa gtggtggagg gggaagtggt ggaggaggaa gcgatataca gatgacacag    420

agcccttcaa gtttatctgc aagcgtcggc gatcgtgtta caataacttg caaggcatct    480

cccgacatca attcctacct caactggtat cagcagaagc ctgggaaggc tcctaagctg    540

cttatttaca gagcaaatcg cctggtggac ggcgtgccca gtcggttttc cgggtctggg    600

agcggaacgg attacacact gaccatctca agcctgcaac ccgaagactt cgctacatat    660

tactgccttc agtatgatga gttcccatat accttcggcg ctgggaccaa ggtggagata    720
```

aag 723

<210> SEQ ID NO 467
<211> LENGTH: 47
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 467

Lys Pro Thr Thr Thr Pro Ala Pro Arg Pro Pro Thr Pro Ala Pro Thr
1 5 10 15

Ile Ala Ser Gln Pro Leu Ser Leu Arg Pro Glu Ala Cys Arg Pro Ala
20 25 30

Ala Gly Gly Ala Val His Thr Arg Gly Leu Asp Phe Ala Cys Asp
35 40 45

<210> SEQ ID NO 468
<211> LENGTH: 141
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 468
aagcccacca ccacccctgc ccctagacct ccaaccccag cccctacaat cgccagccag 60
cccctgagcc tgaggcccga agcctgtaga cctgccgctg gcggagccgt gcacaccaga 120
ggcctggatt tcgcctgcga c 141

<210> SEQ ID NO 469
<211> LENGTH: 47
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 469

Lys Pro Thr Thr Thr Pro Ala Pro Arg Pro Pro Thr Pro Ala Pro Thr
1 5 10 15

Ile Ala Ser Gln Pro Leu Ser Leu Arg Pro Glu Ala Ser Arg Pro Ala
20 25 30

Ala Gly Gly Ala Val His Thr Arg Gly Leu Asp Phe Ala Ser Asp
35 40 45

<210> SEQ ID NO 470
<211> LENGTH: 141
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 470
aagcctacca ccacccccgc acctcgtcct ccaacccctg cacctacgat tgccagtcag 60
cctctttcac tgcggcctga ggccagcaga ccagctgccg gcggtgccgt ccatacaaga 120
ggactggact tcgcgtccga t 141

<210> SEQ ID NO 471
<211> LENGTH: 141

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 471
aaacctacta ccactccagc cccaaggccc ccaaccccag caccgactat cgcatcacag 60
cctttgtcac tgcgtcctga agccagccgg ccagctgcag ggggggccgt ccacacaagg 120
ggactcgact ttgcgagtga t 141

<210> SEQ ID NO 472
<211> LENGTH: 141
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 472
aaacctacta caactcctgc cccccggcct cctacaccag ctcctactat cgcctcccag 60
ccactcagtc tcagacccga ggcttctagg ccagcggccg gaggcgcggt ccacacccgc 120
gggctggact ttgcatccga t 141

<210> SEQ ID NO 473
<211> LENGTH: 141
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 473

Lys Pro Thr Thr Thr Pro Ala Pro Arg Pro Pro Thr Pro Ala Pro Thr
1 5 10 15

Ile Ala Ser Gln Pro Leu Ser Leu Arg Pro Glu Ala Ser Arg Pro Ala
20 25 30

Ala Gly Gly Ala Val His Thr Arg Gly Leu Asp Phe Ala Ser Asp Lys
35 40 45

Pro Thr Thr Thr Pro Ala Pro Arg Pro Pro Thr Pro Ala Pro Thr Ile
50 55 60

Ala Ser Gln Pro Leu Ser Leu Arg Pro Glu Ala Ser Arg Pro Ala Ala
65 70 75 80

Gly Gly Ala Val His Thr Arg Gly Leu Asp Phe Ala Ser Asp Lys Pro
85 90 95

Thr Thr Thr Pro Ala Pro Arg Pro Pro Thr Pro Ala Pro Thr Ile Ala
100 105 110

Ser Gln Pro Leu Ser Leu Arg Pro Glu Ala Cys Arg Pro Ala Ala Gly
115 120 125

Gly Ala Val His Thr Arg Gly Leu Asp Phe Ala Cys Asp
130 135 140

<210> SEQ ID NO 474
<211> LENGTH: 423
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 474
aagcctacca ccacccccgc acctcgtcct ccaacccctg cacctacgat tgccagtcag 60
cctctttcac tgcggcctga ggccagcaga ccagctgccg gcggtgccgt ccatacaaga 120
ggactggact tcgcgtccga taaacctact accactccag ccccaaggcc cccaacccca 180
gcaccgacta tcgcatcaca gcctttgtca ctgcgtcctg aagccagccg gccagctgca 240
gggggggccg tccacacaag ggactcgac tttgcgagtg ataagcccac caccacccct 300
gcccctagac ctccaacccc agcccctaca atcgccagcc agcccctgag cctgaggccc 360
gaagcctgta gacctgccgc tggcggagcc gtgcacacca gaggcctgga tttcgcctgc 420
gac 423

<210> SEQ ID NO 475
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 475

Ile Tyr Ile Trp Ala Pro Leu Ala Gly Thr Cys Gly Val Leu Leu Leu
1 5 10 15

Ser Leu Val Ile Thr Leu Tyr Cys Asn His Arg Asn
20 25

<210> SEQ ID NO 476
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 476
atctacatct gggcccctct ggccggcacc tgtggcgtgc tgctgctgag cctggtcatc 60
accctgtact gcaaccaccg gaat 84

<210> SEQ ID NO 477
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 477

Phe Trp Val Leu Val Val Val Gly Gly Val Leu Ala Cys Tyr Ser Leu
1 5 10 15

Leu Val Thr Val Ala Phe Ile Ile Phe Trp Val Arg Ser Lys Arg Ser
20 25 30

<210> SEQ ID NO 478
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 478
ttttgggtgc tggtggtggt tggtggagtc ctggcttgct atagcttgct agtaacagtg 60

-continued gcctttatta ttttctgggt gaggagtaag aggagc 96

<210> SEQ ID NO 479
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 479

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 480
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 480
cgggtgaagt tcagccggag cgccgacgcc cctgcctacc agcagggcca gaaccagctg 60
tacaacgagc tgaacctggg ccggagggag gagtacgacg tgctggacaa gcggagaggc 120
cgggaccctg agatgggcgg caagccccgg agaaagaacc ctcaggaggg cctgtataac 180
gaactgcaga aagacaagat ggccgaggcc tacagcgaga tcggcatgaa gggcgagcgg 240
cggaggggca agggccacga cggcctgtac cagggcctga gcaccgccac caaggatacc 300
tacgacgccc tgcacatgca ggccctgccc cccaga 336

<210> SEQ ID NO 481
<211> LENGTH: 41
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 481

Arg Ser Lys Arg Ser Arg Gly Gly His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 482

<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 482
aggagcaagc ggagcagagg cggccacagc gactacatga acatgacccc ccggaggcct     60
ggccccaccc ggaagcacta ccagccctac gcccctccca gggacttcgc cgcctaccgg    120
agc                                                                  123

<210> SEQ ID NO 483
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 483

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 484
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 484
aagagaggcc ggaagaaact gctgtacatc ttcaagcagc ccttcatgcg gcccgtgcag     60
accacccagg aagaggacgg ctgcagctgc cggttccccg aggaagagga aggcggctgc    120
gaactg                                                               126

<210> SEQ ID NO 485
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Leu Cys Ala Arg Pro Arg Arg Ser Pro Ala Gln Glu Asp Gly Lys Val
1               5                   10                  15

Tyr Ile Asn Met Pro Gly Arg Gly
            20

<210> SEQ ID NO 486
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
ctgtgcgcac gcccacgccg cagccccgcc caagaagatg gcaaagtcta catcaacatg 60
ccaggcaggg gc 72

<210> SEQ ID NO 487
<211> LENGTH: 52
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 487

Tyr Phe Leu Gly Arg Leu Val Pro Arg Gly Arg Gly Ala Ala Glu Ala
1 5 10 15

Ala Thr Arg Lys Gln Arg Ile Thr Glu Thr Glu Ser Pro Tyr Gln Glu
20 25 30

Leu Gln Gly Gln Arg Ser Asp Val Tyr Ser Asp Leu Asn Thr Gln Arg
35 40 45

Pro Tyr Tyr Lys
50

<210> SEQ ID NO 488
<211> LENGTH: 156
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 488
tacttcctgg gccggctggt ccctcggggg cgaggggctg cggaggcagc gacccggaaa 60
cagcgtatca ctgagaccga gtcgccttat caggagctcc agggtcagag gtcggatgtc 120
tacagcgacc tcaacacaca gaggccgtat tacaaa 156

<210> SEQ ID NO 489
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 489

Met Leu Leu Leu Val Thr Ser Leu Leu Leu Cys Glu Leu Pro His Pro
1 5 10 15

Ala Phe Leu Leu Ile Pro
20

<210> SEQ ID NO 490
<211> LENGTH: 66
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 490
atgctgctgc tggtgaccag cctgctgctg tgtgagctgc cccaccccgc ctttctgctg 60
atcccc 66

<210> SEQ ID NO 491

<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 491

```
Met Arg Leu Pro Ala Gln Leu Leu Gly Leu Leu Met Leu Trp Val Pro
1               5                   10                  15

Gly Ser Ser Gly
            20
```

<210> SEQ ID NO 492
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 492

```
atgaggctcc ctgctcagct cctggggctg ctaatgctct gggtcccagg atccagtggg     60
```

<210> SEQ ID NO 493
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 493

```
Met Asp Trp Thr Trp Ile Leu Phe Leu Val Ala Ala Ala Thr Arg Val
1               5                   10                  15

His Ser
```

<210> SEQ ID NO 494
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 494

```
atggattgga cctggattct gtttctggtg gccgctgcca caagagtgca cagc           54
```

<210> SEQ ID NO 495
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 495

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 496
<211> LENGTH: 63
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 496
atggcgctgc ccgtgaccgc cttgctcctg ccgctggcct tgctgctcca cgccgccagg 60
ccg 63

<210> SEQ ID NO 497
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 497

Met Gly Trp Ser Cys Ile Ile Leu Phe Leu Val Ala Thr Ala Thr Gly
1 5 10 15

Val His Ser

<210> SEQ ID NO 498
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 498
atgggctggt cctgcatcat cctgtttctg gtggctaccg ccaccggcgt gcacagc 57

<210> SEQ ID NO 499
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 499

Met Ser Arg Ser Val Ala Leu Ala Val Leu Ala Leu Leu Ser Leu Ser
1 5 10 15

Gly Leu Glu Ala
20

<210> SEQ ID NO 500
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 500
atgtctcgct ccgtggcctt agctgtgctc gcgctactct ctctttctgg cctggaggct 60

<210> SEQ ID NO 501
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 501

Met Thr Arg Leu Thr Val Leu Ala Leu Leu Ala Gly Leu Leu Ala Ser
1 5 10 15

Ser Arg Ala

<210> SEQ ID NO 502
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 502
atgacccggc tgacagtcct ggccctgctg gctggtctgc tggcgtcctc gagggcc 57

<210> SEQ ID NO 503
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 503

Met Lys Trp Val Thr Phe Ile Ser Leu Leu Phe Leu Phe Ser Ser Ala
1 5 10 15

Tyr Ser

<210> SEQ ID NO 504
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 504
atgaagtggg taacctttat ttcccttctt tttctcttta gctcggctta ttcc 54

<210> SEQ ID NO 505
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 505

Met Gly Lys Asn Lys Leu Leu His Pro Ser Leu Val Leu Leu Leu Leu
1 5 10 15

Val Leu Leu Pro Thr Asp Ala
20

<210> SEQ ID NO 506
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 506
atggggaaga acaaactcct tcatccaagt ctggttcttc tcctcttggt cctcctgccc 60
acagacgcc 69

<210> SEQ ID NO 507
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 507

Met Glu Phe Gly Leu Ser Trp Leu Phe Leu Val Ala Ile Leu Lys Gly
1 5 10 15

Val Gln Cys

<210> SEQ ID NO 508
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 508
atggagtttg ggctgagctg gctttttctt gtggctattt taaaaggtgt ccagtgt 57

<210> SEQ ID NO 509
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 509

Met Asp Met Arg Val Pro Ala Gln Leu Leu Gly Leu Leu Leu Leu Trp
1 5 10 15

Leu Ser Gly Ala Arg Cys
20

<210> SEQ ID NO 510
<211> LENGTH: 66
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 510
atggacatga gggtccctgc tcagctcctg gggctcctgc tgctctggct ctcaggtgcc 60
agatgt 66

<210> SEQ ID NO 511
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 511

Met Glu Phe Gly Leu Ser Trp Val Phe Leu Val Ala Leu Phe Arg Gly
1 5 10 15

Val Gln Cys

<210> SEQ ID NO 512
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 512
atggagtttg ggctgagctg ggttttcctc gttgctcttt ttagaggtgt ccagtgt 57

<210> SEQ ID NO 513
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 513

Met Gly Thr Ser Leu Leu Cys Trp Met Ala Leu Cys Leu Leu Gly Ala
1 5 10 15

Asp His Ala Asp Ala
20

<210> SEQ ID NO 514
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 514
atgggcacca gcctcctctg ctggatggcc ctgtgtctcc tgggggcaga tcacgcagat 60
gct 63

<210> SEQ ID NO 515
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 515

Met Lys Arg Phe Leu Phe Leu Leu Leu Thr Ile Ser Leu Leu Val Met
1 5 10 15

Val Gln Ile Gln Thr Gly Leu Ser
20

<210> SEQ ID NO 516
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 516
atgaagcgct tcctcttcct cctactcacc atcagcctcc tggttatggt acagatacaa 60
actggactct ca 72

<210> SEQ ID NO 517
<211> LENGTH: 28

<212> TYPE: PRT
<213> ORGANISM: Artificial Sequence
<220> FEATURE:
<223> OTHER INFORMATION: Description of Artificial Sequence: Synthetic peptide

<400> SEQUENCE: 517

Met Gly Ala Gly Ala Thr Gly Arg Ala Met Asp Gly Pro Arg Leu Leu
1 5 10 15

Leu Leu Leu Leu Leu Gly Val Ser Leu Gly Gly Ala
20 25

<210> SEQ ID NO 518
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 518
atgggggcag gtgccaccgg ccgcgccatg gacgggccgc gcctgctgct gttgctgctt 60
ctgggggtgt cccttggagg tgcc 84

<210> SEQ ID NO 519
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 519

Asn Trp Val Asn Val Ile Ser Asp Leu Lys Lys Ile Glu Asp Leu Ile
1 5 10 15

Gln Ser Met His Ile Asp Ala Thr Leu Tyr Thr Glu Ser Asp Val His
20 25 30

Pro Ser Cys Lys Val Thr Ala Met Lys Cys Phe Leu Leu Glu Leu Gln
35 40 45

Val Ile Ser Leu Glu Ser Gly Asp Ala Ser Ile His Asp Thr Val Glu
50 55 60

Asn Leu Ile Ile Leu Ala Asn Asn Ser Leu Ser Ser Asn Gly Asn Val
65 70 75 80

Thr Glu Ser Gly Cys Lys Glu Cys Glu Glu Leu Glu Glu Lys Asn Ile
85 90 95

Lys Glu Phe Leu Gln Ser Phe Val His Ile Val Gln Met Phe Ile Asn
100 105 110

Thr Ser

<210> SEQ ID NO 520
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 520
aactgggtga atgtgatcag cgacctgaag aagatcgagg atctgatcca gagcatgcac 60
attgatgcca ccctgtacac agaatctgat gtgcacccta gctgtaaagt gaccgccatg 120 aagtgtttc tgctggagct gcaggtgatt tctctggaaa gcggagatgc ctctatccac 180

```
gacacagtgg agaatctgat catcctggcc aacaatagcc tgagcagcaa tggcaatgtg    240

acagagtctg gctgtaagga gtgtgaggag ctggaggaga agaacatcaa ggagtttctg    300

cagagctttg tgcacatcgt gcagatgttc atcaatacaa gc                       342


<210> SEQ ID NO 521
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 521

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr Val
                165                 170                 175

Ala Ile Ser Thr Ser Thr Val Leu Leu Cys Gly Leu Ser Ala Val Ser
            180                 185                 190

Leu Leu Ala Cys Tyr Leu Lys Ser Arg Gln Thr Pro Pro Leu Ala Ser
        195                 200                 205

Val Glu Met Glu Ala Met Glu Ala Leu Pro Val Thr Trp Gly Thr Ser
    210                 215                 220

Ser Arg Asp Glu Asp Leu Glu Asn Cys Ser His His Leu
225                 230                 235


<210> SEQ ID NO 522
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 522

attacatgcc ctcctccaat gtctgtggag cacgccgata tttgggtgaa gtcctacagc     60

ctgtacagca gagagagata catctgcaac agcggcttta agagaaaggc cggcacctct    120

tctctgacag agtgcgtgct gaataaggcc acaaatgtgg cccactggac aacacctagc    180
```

ctgaagtgca ttagagatcc tgccctggtc caccagaggc ctgcccctcc atctacagtg 240
acaacagccg gagtgacacc tcagcctgaa tctctgagcc cttctggaaa agaacctgcc 300
gccagctctc ctagctctaa taataccgcc gccacaacag ccgccattgt gcctggatct 360
cagctgatgc ctagcaagtc tcctagcaca ggcacaacag agatcagcag ccacgaatct 420
tctcacggaa caccttctca gaccaccgcc aagaattggg agctgacagc ctctgcctct 480
caccagcctc caggagtgta tcctcagggc cactctgata caacagtggc catcagcaca 540
tctacagtgc tgctgtgtgg actgtctgcc gtgtctctgc tggcctgtta cctgaagtct 600
agacagacac ctcctctggc ctctgtggag atggaggcca tggaagccct gcctgtgaca 660
tggggaacaa gcagcagaga tgaggacctg gagaattgtt ctcaccacct g 711

<210> SEQ ID NO 523
<211> LENGTH: 377
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 523

Asn Trp Val Asn Val Ile Ser Asp Leu Lys Lys Ile Glu Asp Leu Ile
1 5 10 15

Gln Ser Met His Ile Asp Ala Thr Leu Tyr Thr Glu Ser Asp Val His
20 25 30

Pro Ser Cys Lys Val Thr Ala Met Lys Cys Phe Leu Leu Glu Leu Gln
35 40 45

Val Ile Ser Leu Glu Ser Gly Asp Ala Ser Ile His Asp Thr Val Glu
50 55 60

Asn Leu Ile Ile Leu Ala Asn Asn Ser Leu Ser Ser Asn Gly Asn Val
65 70 75 80

Thr Glu Ser Gly Cys Lys Glu Cys Glu Glu Leu Glu Glu Lys Asn Ile
85 90 95

Lys Glu Phe Leu Gln Ser Phe Val His Ile Val Gln Met Phe Ile Asn
100 105 110

Thr Ser Ser Gly Gly Gly Ser Gly Gly Gly Gly Ser Gly Gly Gly Gly
115 120 125

Ser Gly Gly Gly Gly Ser Gly Gly Gly Ser Leu Gln Ile Thr Cys Pro
130 135 140

Pro Pro Met Ser Val Glu His Ala Asp Ile Trp Val Lys Ser Tyr Ser
145 150 155 160

Leu Tyr Ser Arg Glu Arg Tyr Ile Cys Asn Ser Gly Phe Lys Arg Lys
165 170 175

Ala Gly Thr Ser Ser Leu Thr Glu Cys Val Leu Asn Lys Ala Thr Asn
180 185 190

Val Ala His Trp Thr Thr Pro Ser Leu Lys Cys Ile Arg Asp Pro Ala
195 200 205

Leu Val His Gln Arg Pro Ala Pro Pro Ser Thr Val Thr Thr Ala Gly
210 215 220

Val Thr Pro Gln Pro Glu Ser Leu Ser Pro Ser Gly Lys Glu Pro Ala
225 230 235 240

Ala Ser Ser Pro Ser Ser Asn Asn Thr Ala Ala Thr Thr Ala Ala Ile
245 250 255

Val Pro Gly Ser Gln Leu Met Pro Ser Lys Ser Pro Ser Thr Gly Thr

```
            260                 265                 270

Thr Glu Ile Ser Ser His Glu Ser Ser His Gly Thr Pro Ser Gln Thr
        275                 280                 285

Thr Ala Lys Asn Trp Glu Leu Thr Ala Ser Ala Ser His Gln Pro Pro
    290                 295                 300

Gly Val Tyr Pro Gln Gly His Ser Asp Thr Thr Val Ala Ile Ser Thr
305                 310                 315                 320

Ser Thr Val Leu Leu Cys Gly Leu Ser Ala Val Ser Leu Leu Ala Cys
                325                 330                 335

Tyr Leu Lys Ser Arg Gln Thr Pro Pro Leu Ala Ser Val Glu Met Glu
            340                 345                 350

Ala Met Glu Ala Leu Pro Val Thr Trp Gly Thr Ser Ser Arg Asp Glu
        355                 360                 365

Asp Leu Glu Asn Cys Ser His His Leu
    370                 375


<210> SEQ ID NO 524
<211> LENGTH: 1131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 524

aactgggtga atgtgatcag cgacctgaag aagatcgagg atctgatcca gagcatgcac     60

attgatgcca ccctgtacac agaatctgat gtgcacccta gctgtaaagt gaccgccatg    120

aagtgttttc tgctggagct gcaggtgatt tctctggaaa gcggagatgc ctctatccac    180

gacacagtgg agaatctgat catcctggcc aacaatagcc tgagcagcaa tggcaatgtg    240

acagagtctg gctgtaagga gtgtgaggag ctggaggaga agaacatcaa ggagtttctg    300

cagagctttg tgcacatcgt gcagatgttc atcaatacaa gctctggcgg aggatctgga    360

ggaggcggat ctggaggagg aggcagtgga ggcggaggat ctggcggagg atctctgcag    420

attacatgcc ctcctccaat gtctgtggag cacgccgata tttgggtgaa gtcctacagc    480

ctgtacagca gagagagata catctgcaac agcggcttta agagaaaggc cggcacctct    540

tctctgacag agtgcgtgct gaataaggcc acaaatgtgg cccactggac aacacctagc    600

ctgaagtgca ttagagatcc tgccctggtc caccagaggc ctgcccctcc atctacagtg    660

acaacagccg gagtgacacc tcagcctgaa tctctgagcc cttctggaaa agaacctgcc    720

gccagctctc ctagctctaa taataccgcc gccacaacag ccgccattgt gcctggatct    780

cagctgatgc ctagcaagtc tcctagcaca ggcacaacag agatcagcag ccacgaatct    840

tctcacggaa caccttctca gaccaccgcc aagaattggg agctgacagc ctctgcctct    900

caccagcctc caggagtgta tcctcagggc cactctgata caacagtggc catcagcaca    960

tctacagtgc tgctgtgtgg actgtctgcc gtgtctctgc tggcctgtta cctgaagtct   1020

agacagacac ctcctctggc ctctgtggag atggaggcca tggaagccct gcctgtgaca   1080

tggggaacaa gcagcagaga tgaggacctg gagaattgtt ctcaccacct g            1131


<210> SEQ ID NO 525
<211> LENGTH: 395
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 525

```
Met Asp Trp Thr Trp Ile Leu Phe Leu Val Ala Ala Ala Thr Arg Val
1               5                   10                  15

His Ser Asn Trp Val Asn Val Ile Ser Asp Leu Lys Lys Ile Glu Asp
            20                  25                  30

Leu Ile Gln Ser Met His Ile Asp Ala Thr Leu Tyr Thr Glu Ser Asp
        35                  40                  45

Val His Pro Ser Cys Lys Val Thr Ala Met Lys Cys Phe Leu Leu Glu
    50                  55                  60

Leu Gln Val Ile Ser Leu Glu Ser Gly Asp Ala Ser Ile His Asp Thr
65                  70                  75                  80

Val Glu Asn Leu Ile Ile Leu Ala Asn Asn Ser Leu Ser Ser Asn Gly
                85                  90                  95

Asn Val Thr Glu Ser Gly Cys Lys Glu Cys Glu Glu Leu Glu Glu Lys
            100                 105                 110

Asn Ile Lys Glu Phe Leu Gln Ser Phe Val His Ile Val Gln Met Phe
        115                 120                 125

Ile Asn Thr Ser Ser Gly Gly Gly Ser Gly Gly Gly Gly Ser Gly Gly
    130                 135                 140

Gly Gly Ser Gly Gly Gly Gly Ser Gly Gly Gly Ser Leu Gln Ile Thr
145                 150                 155                 160

Cys Pro Pro Pro Met Ser Val Glu His Ala Asp Ile Trp Val Lys Ser
                165                 170                 175

Tyr Ser Leu Tyr Ser Arg Glu Arg Tyr Ile Cys Asn Ser Gly Phe Lys
            180                 185                 190

Arg Lys Ala Gly Thr Ser Ser Leu Thr Glu Cys Val Leu Asn Lys Ala
        195                 200                 205

Thr Asn Val Ala His Trp Thr Thr Pro Ser Leu Lys Cys Ile Arg Asp
    210                 215                 220

Pro Ala Leu Val His Gln Arg Pro Ala Pro Pro Ser Thr Val Thr Thr
225                 230                 235                 240

Ala Gly Val Thr Pro Gln Pro Glu Ser Leu Ser Pro Ser Gly Lys Glu
                245                 250                 255

Pro Ala Ala Ser Ser Pro Ser Ser Asn Asn Thr Ala Ala Thr Thr Ala
            260                 265                 270

Ala Ile Val Pro Gly Ser Gln Leu Met Pro Ser Lys Ser Pro Ser Thr
        275                 280                 285

Gly Thr Thr Glu Ile Ser Ser His Glu Ser Ser His Gly Thr Pro Ser
    290                 295                 300

Gln Thr Thr Ala Lys Asn Trp Glu Leu Thr Ala Ser Ala Ser His Gln
305                 310                 315                 320

Pro Pro Gly Val Tyr Pro Gln Gly His Ser Asp Thr Thr Val Ala Ile
                325                 330                 335

Ser Thr Ser Thr Val Leu Leu Cys Gly Leu Ser Ala Val Ser Leu Leu
            340                 345                 350

Ala Cys Tyr Leu Lys Ser Arg Gln Thr Pro Pro Leu Ala Ser Val Glu
        355                 360                 365

Met Glu Ala Met Glu Ala Leu Pro Val Thr Trp Gly Thr Ser Ser Arg
    370                 375                 380

Asp Glu Asp Leu Glu Asn Cys Ser His His Leu
385                 390                 395
```

<210> SEQ ID NO 526
<211> LENGTH: 1185
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 526
atggattgga cctggattct gtttctggtg gccgctgcca caagagtgca cagcaactgg 60
gtgaatgtga tcagcgacct gaagaagatc gaggatctga tccagagcat gcacattgat 120
gccaccctgt acacagaatc tgatgtgcac cctagctgta aagtgaccgc catgaagtgt 180
tttctgctgg agctgcaggt gatttctctg gaaagcggag atgcctctat ccacgacaca 240
gtggagaatc tgatcatcct ggccaacaat agcctgagca gcaatggcaa tgtgacagag 300
tctggctgta aggagtgtga ggagctggag gagaagaaca tcaaggagtt tctgcagagc 360
tttgtgcaca tcgtgcagat gttcatcaat acaagctctg gcggaggatc tggaggaggc 420
ggatctggag gaggaggcag tggaggcgga ggatctggcg gaggatctct gcagattaca 480
tgccctcctc caatgtctgt ggagcacgcc gatatttggg tgaagtccta cagcctgtac 540
agcagagaga gatacatctg caacagcggc tttaagagaa aggccggcac ctcttctctg 600
acagagtgcg tgctgaataa ggccacaaat gtggcccact ggacaacacc tagcctgaag 660
tgcattagag atcctgccct ggtccaccag aggcctgccc ctccatctac agtgacaaca 720
gccggagtga cacctcagcc tgaatctctg agcccttctg gaaaagaacc tgccgccagc 780
tctcctagct ctaataatac cgccgccaca acagccgcca ttgtgcctgg atctcagctg 840
atgcctagca agtctcctag cacaggcaca acagagatca gcagccacga atcttctcac 900
ggaacacctt ctcagaccac cgccaagaat tgggagctga cagcctctgc ctctcaccag 960
cctccaggag tgtatcctca gggccactct gatacaacag tggccatcag cacatctaca 1020
gtgctgctgt gtggactgtc tgccgtgtct ctgctggcct gttacctgaa gtctagacag 1080
acacctcctc tggcctctgt ggagatggag gccatggaag ccctgcctgt gacatgggga 1140
acaagcagca gagatgagga cctggagaat tgttctcacc acctg 1185

<210> SEQ ID NO 527
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 527

Gly Ser Thr Ser Gly Ser Gly Lys Pro Gly Ser Gly Glu Gly Ser Thr
1 5 10 15

Lys Gly

<210> SEQ ID NO 528
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 528
ggcagcacct ccggcagcgg caagcctggc agcggcgagg gcagcaccaa gggc 54

<210> SEQ ID NO 529
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 529

Ser Gly Gly Gly Ser Gly Gly Gly Gly Ser Gly Gly Gly Gly Ser Gly
1 5 10 15

Gly Gly Gly Ser Gly Gly Gly Ser Leu Gln
20 25

<210> SEQ ID NO 530
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 530
tctggcggag gatctggagg aggcggatct ggaggaggag gcagtggagg cggaggatct 60
ggcggaggat ctctgcag 78

<210> SEQ ID NO 531
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 531

Gly Ser Gly
1

<210> SEQ ID NO 532
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 532 ggaagcgga 9

<210> SEQ ID NO 533
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 533

Ser Gly Ser Gly
1

<210> SEQ ID NO 534
<211> LENGTH: 12
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 534
agtggcagcg gc 12

<210> SEQ ID NO 535
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 535

Gly Gly Gly Gly Ser Gly Gly Gly Gly Ser Gly Gly Gly Gly Ser
1 5 10 15

<210> SEQ ID NO 536
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 536
ggtggcggtg gctcgggcgg tggtgggtcg ggtggcggcg gatct 45

<210> SEQ ID NO 537
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 537

Arg Ala Lys Arg
1

<210> SEQ ID NO 538
<211> LENGTH: 12
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 538
cgtgcaaagc gt 12

<210> SEQ ID NO 539
<211> LENGTH: 28
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 539

Arg Ala Lys Arg Ala Pro Val Lys Gln Thr Leu Asn Phe Asp Leu Leu
1 5 10 15

Lys Leu Ala Gly Asp Val Glu Ser Asn Pro Gly Pro
20 25

<210> SEQ ID NO 540
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 540
agagccaaga gggcaccggt gaaacagact ttgaattttg accttctgaa gttggcagga 60
gacgttgagt ccaaccctgg gccc 84

<210> SEQ ID NO 541
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 541

Glu Gly Arg Gly Ser Leu Leu Thr Cys Gly Asp Val Glu Glu Asn Pro
1 5 10 15

Gly Pro

<210> SEQ ID NO 542
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 542
gagggcagag gaagtctgct aacatgcggt gacgtcgagg agaatcctgg acct 54

<210> SEQ ID NO 543
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 543

Arg Ala Lys Arg Gly Ser Gly Glu Gly Arg Gly Ser Leu Leu Thr Cys
1 5 10 15

Gly Asp Val Glu Glu Asn Pro Gly Pro
20 25

<210> SEQ ID NO 544
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 544
agagctaaga ggggaagcgg agagggcaga ggaagtctgc taacatgcgg tgacgtcgag 60
gagaatcctg gacct 75

<210> SEQ ID NO 545
<211> LENGTH: 26

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545

Arg Ala Lys Arg Ser Gly Ser Gly Glu Gly Arg Gly Ser Leu Leu Thr
1               5                   10                  15

Cys Gly Asp Val Glu Glu Asn Pro Gly Pro
            20                  25

<210> SEQ ID NO 546
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
agggccaaga ggagtggcag cggcgagggc agaggaagtc ttctaacatg cggtgacgtg     60
gaggagaatc ccggccct                                                   78

<210> SEQ ID NO 547
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 547

Ala Thr Asn Phe Ser Leu Leu Lys Gln Ala Gly Asp Val Glu Glu Asn
1               5                   10                  15

Pro Gly Pro

<210> SEQ ID NO 548
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
gcaacgaact tctctctcct aaaacaggct ggtgatgtgg aggagaatcc tggtcca        57

<210> SEQ ID NO 549
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 550
<211> LENGTH: 66
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 550
ggaagcggag ctactaactt cagcctgctg aagcaggctg gagacgtgga ggagaaccct 60
ggacct 66

<210> SEQ ID NO 551
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 551

Gln Cys Thr Asn Tyr Ala Leu Leu Lys Leu Ala Gly Asp Val Glu Ser
1 5 10 15

Asn Pro Gly Pro
20

<210> SEQ ID NO 552
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 552
cagtgtacta attatgctct cttgaaattg gctggagatg ttgagagcaa ccctggacct 60

<210> SEQ ID NO 553
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 553

Val Lys Gln Thr Leu Asn Phe Asp Leu Leu Lys Leu Ala Gly Asp Val
1 5 10 15

Glu Ser Asn Pro Gly Pro
20

<210> SEQ ID NO 554
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 554
gtcaaacaga ccctaaactt tgatctgcta aaactggccg gggatgtgga aagtaatccc 60
ggcccc 66

<210> SEQ ID NO 555
<211> LENGTH: 31
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 555

Arg Ala Lys Arg Ala Pro Val Lys Gln Gly Ser Gly Ala Thr Asn Phe
1 5 10 15

Ser Leu Leu Lys Gln Ala Gly Asp Val Glu Glu Asn Pro Gly Pro
20 25 30

<210> SEQ ID NO 556
<211> LENGTH: 93
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 556
cgtgcaaagc gtgcaccggt gaaacaggga agcggagcta ctaacttcag cctgctgaag 60
caggctggag acgtggagga gaaccctgga cct 93

<210> SEQ ID NO 557
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 557

Ala Pro Val Lys Gln Gly Ser Gly
1 5

<210> SEQ ID NO 558
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 558
gcaccggtga aacagggaag cgga 24

<210> SEQ ID NO 559
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 559

Gly Gly Gly Gly Ser Gly Gly Gly Ser Gly Gly Gly Gly Ser Gly Gly
1 5 10 15

Gly Gly Ser

<210> SEQ ID NO 560
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 560
ggtggcggtg gctcgggcgg tggtgggtcg ggtggcggcg gatctggtgg cggtggctcg 60

<210> SEQ ID NO 561
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 561

Ala Pro Val Lys Gln
1 5

<210> SEQ ID NO 562
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 562
gcaccggtga aacag 15

<210> SEQ ID NO 563
<211> LENGTH: 27
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: SITE
<222> LOCATION: (2)..(26)
<223> OTHER INFORMATION: This region may encompass 2-5 "Glu Ala Ala Ala
Lys" repeating units

<400> SEQUENCE: 563

Ala Glu Ala Ala Ala Lys Glu Ala Ala Ala Lys Glu Ala Ala Ala Lys
1 5 10 15

Glu Ala Ala Ala Lys Glu Ala Ala Ala Lys Ala
20 25

<210> SEQ ID NO 564

<400> SEQUENCE: 564

000

<210> SEQ ID NO 565
<211> LENGTH: 171
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 565

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

```
Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln
                165                 170
```

<210> SEQ ID NO 566
<211> LENGTH: 513
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 566

```
cgcaaagtgt gtaacggaat aggtattggt gaatttaaag actcactctc cataaatgct      60

acgaatatta aacacttcaa aaactgcacc tccatcagtg gcgatctcca catcctgccg     120

gtggcattta ggggtgactc cttcacacat actcctcctc tggatccaca ggaactggat     180

attctgaaaa ccgtaaagga aatcacaggg tttttgctga ttcaggcttg gcctgaaaac     240

aggacggacc tccatgcctt tgagaaccta gaaatcatac gcggcaggac caagcaacat     300

ggtcagtttt ctcttgcagt cgtcagcctg aacataacat ccttgggatt acgctccctc     360

aaggagataa gtgatggaga tgtgataatt tcaggaaaca aaaatttgtg ctatgcaaat     420

acaataaact ggaaaaaact gtttgggacc tccggtcaga aaaccaaaat tataagcaac     480

agaggtgaaa acagctgcaa ggccacaggc cag                                  513
```

<210> SEQ ID NO 567
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 567

```
Val Cys His Ala Leu Cys Ser Pro Glu Gly Cys Trp Gly Pro Glu Pro
1               5                   10                  15

Arg Asp Cys Val Ser
            20
```

<210> SEQ ID NO 568
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 568
gtctgccatg ccttgtgctc ccccgagggc tgctggggcc cggagcccag ggactgcgtc 60
tct 63

<210> SEQ ID NO 569
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 569

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 570
<211> LENGTH: 1005
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 570
cgcaaagtgt gtaacggaat aggtattggt gaatttaaag actcactctc cataaatgct 60
acgaatatta aacacttcaa aaactgcacc tccatcagtg gcgatctcca catcctgccg 120
gtggcattta ggggtgactc cttcacacat actcctcctc tggatccaca ggaactggat 180
attctgaaaa ccgtaaagga aatcacaggg tttttgctga ttcaggcttg gcctgaaaac 240
aggacggacc tccatgcctt tgagaaccta gaaatcatac gcggcaggac caagcaacat 300
ggtcagtttt ctcttgcagt cgtcagcctg aacataacat ccttgggatt acgctccctc 360
aaggagataa gtgatggaga tgtgataatt tcaggaaaca aaaatttgtg ctatgcaaat 420
acaataaact ggaaaaaact gtttgggacc tccggtcaga aaaccaaaat tataagcaac 480
agaggtgaaa acagctgcaa ggccacaggc caggtctgcc atgccttgtg ctcccccgag 540
ggctgctggg gcccggagcc cagggactgc gtctcttgcc ggaatgtcag ccgaggcagg 600
gaatgcgtgg acaagtgcaa ccttctggag ggtgagccaa gggagtttgt ggagaactct 660
gagtgcatac agtgccaccc agagtgcctg cctcaggcca tgaacatcac ctgcacagga 720
cggggaccag acaactgtat ccagtgtgcc cactacattg acggccccca ctgcgtcaag 780
acctgcccgg caggagtcat gggagaaaac aacaccctgg tctggaagta cgcagacgcc 840
ggccatgtgt gccacctgtg ccatccaaac tgcacctacg gatgcactgg gccaggtctt 900
gaaggctgtc caacgaatgg gcctaagatc ccgtccatcg ccactgggat ggtgggggcc 960
ctcctcttgc tgctggtggt ggccctgggg atcggcctct tcatg 1005

<210> SEQ ID NO 571
<211> LENGTH: 243
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 571

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val

```
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Gly Gly Gly Gly Ser Gly Gly Gly Ser Gly Gly Gly Gly Ser Gly Gly
        195                 200                 205

Gly Gly Ser Phe Trp Val Leu Val Val Val Gly Gly Val Leu Ala Cys
    210                 215                 220

Tyr Ser Leu Leu Val Thr Val Ala Phe Ile Ile Phe Trp Val Arg Ser
225                 230                 235                 240

Lys Arg Ser


<210> SEQ ID NO 572
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 572

cgcaaagtgt gtaacggaat aggtattggt gaatttaaag actcactctc cataaatgct      60

acgaatatta aacacttcaa aaactgcacc tccatcagtg gcgatctcca catcctgccg     120

gtggcattta ggggtgactc cttcacacat actcctcctc tggatccaca ggaactggat     180

attctgaaaa ccgtaaagga aatcacaggg tttttgctga ttcaggcttg gcctgaaaac     240

aggacggacc tccatgcctt tgagaaccta gaaatcatac gcggcaggac caagcaacat     300

ggtcagtttt ctcttgcagt cgtcagcctg aacataacat ccttgggatt acgctccctc     360

aaggagataa gtgatggaga tgtgataatt tcaggaaaca aaaatttgtg ctatgcaaat     420

acaataaact ggaaaaaact gtttgggacc tccggtcaga aaaccaaaat tataagcaac     480

agaggtgaaa acagctgcaa ggccacaggc caggtctgcc atgccttgtg ctcccccgag     540

ggctgctggg gcccggagcc cagggactgc gtctctggtg gcggtggctc gggcggtggt     600

gggtcgggtg gcggcggatc tggtggcggt ggctcgtttt gggtgctggt ggtggttggt     660

ggagtcctgg cttgctatag cttgctagta acagtggcct ttattatttt ctgggtgagg     720

agtaagagga gctaa                                                      735


<210> SEQ ID NO 573
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 573

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30
```

-continued

```
Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295


<210> SEQ ID NO 574
<211> LENGTH: 891
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 574

atgacaacac ccagaaattc agtaaatggg actttcccgg cagagccaat gaaaggccct     60

attgctatgc aatctggtcc aaaaccactc ttcaggagga tgtcttcact ggtgggcccc    120

acgcaaagct tcttcatgag ggaatctaag actttggggg ctgtccagat tatgaatggg    180

ctcttccaca ttgccctggg gggtcttctg atgatcccag cagggatcta tgcacccatc    240

tgtgtgactg tgtggtaccc tctctgggga ggcattatgt atattatttc cggatcactc    300

ctggcagcaa cggagaaaaa ctccaggaag tgtttggtca aaggaaaaat gataatgaat    360

tcattgagcc tctttgctgc catttctgga atgattcttt caatcatgga catacttaat    420

attaaaattt cccatttttt aaaaatggag agtctgaatt ttattagagc tcacacacca    480

tatattaaca tatacaactg tgaaccagct aatccctctg agaaaaactc cccatctacc    540
```

caatactgtt acagcataca atctctgttc ttgggcattt tgtcagtgat gctgatcttt 600
gccttcttcc aggaacttgt aatagctggc atcgttgaga atgaatggaa aagaacgtgc 660
tccagaccca aatctaacat agttctcctg tcagcagaag aaaaaaaaga acagactatt 720
gaaataaaag aagaagtggt tgggctaact gaaacatctt cccaaccaaa gaatgaagaa 780
gacattgaaa ttattccaat ccaagaagag gaagaagaag aaacagagac gaactttcca 840
gaacctcccc aagatcagga atcctcacca atagaaaatg acagctctcc t 891

<210> SEQ ID NO 575
<211> LENGTH: 263
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 575

Met Thr Thr Pro Arg Asn Ser Val Asn Gly Thr Phe Pro Ala Glu Pro
1 5 10 15

Met Lys Gly Pro Ile Ala Met Gln Ser Gly Pro Lys Pro Leu Phe Arg
20 25 30

Arg Met Ser Ser Leu Val Gly Pro Thr Gln Ser Phe Phe Met Arg Glu
35 40 45

Ser Lys Thr Leu Gly Ala Val Gln Ile Met Asn Gly Leu Phe His Ile
50 55 60

Ala Leu Gly Gly Leu Leu Met Ile Pro Ala Gly Ile Tyr Ala Pro Ile
65 70 75 80

Cys Val Thr Val Trp Tyr Pro Leu Trp Gly Gly Ile Met Tyr Ile Ile
85 90 95

Ser Gly Ser Leu Leu Ala Ala Thr Glu Lys Asn Ser Arg Lys Cys Leu
100 105 110

Val Lys Gly Lys Met Ile Met Asn Ser Leu Ser Leu Phe Ala Ala Ile
115 120 125

Ser Gly Met Ile Leu Ser Ile Met Asp Ile Leu Asn Ile Lys Ile Ser
130 135 140

His Phe Leu Lys Met Glu Ser Leu Asn Phe Ile Arg Ala His Thr Pro
145 150 155 160

Tyr Ile Asn Ile Tyr Asn Cys Glu Pro Ala Asn Pro Ser Glu Lys Asn
165 170 175

Ser Pro Ser Thr Gln Tyr Cys Tyr Ser Ile Gln Ser Leu Phe Leu Gly
180 185 190

Ile Leu Ser Val Met Leu Ile Phe Ala Phe Phe Gln Glu Leu Val Ile
195 200 205

Ala Gly Ile Val Glu Asn Glu Trp Lys Arg Thr Cys Ser Arg Pro Lys
210 215 220

Ser Asn Ile Val Leu Leu Ser Ala Glu Glu Lys Lys Glu Gln Thr Ile
225 230 235 240

Glu Ile Lys Glu Glu Val Val Gly Leu Thr Glu Thr Ser Ser Gln Pro
245 250 255

Lys Asn Glu Glu Asp Ile Glu
260

<210> SEQ ID NO 576
<211> LENGTH: 789
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 576
atgaccacac cacggaactc tgtgaatggc accttcccag cagagccaat gaagggacca 60
atcgcaatgc agagcggacc caagcctctg tttcggagaa tgagctccct ggtgggccca 120
acccagtcct tctttatgag agagtctaag acactgggcg ccgtgcagat catgaacgga 180
ctgttccaca tcgccctggg aggactgctg atgatcccag ccggcatcta cgcccctatc 240
tgcgtgaccg tgtggtaccc tctgtggggc ggcatcatgt atatcatctc cggctctctg 300
ctggccgcca cagagaagaa cagcaggaag tgtctggtga agggcaagat gatcatgaat 360
agcctgtccc tgtttgccgc catctctggc atgatcctga gcatcatgga catcctgaac 420
atcaagatca gccacttcct gaagatggag agcctgaact tcatcagagc ccacacccct 480
tacatcaaca tctataattg cgagcctgcc aacccatccg agaagaattc tccaagcaca 540
cagtactgtt attccatcca gtctctgttc ctgggcatcc tgtctgtgat gctgatcttt 600
gccttctttc aggagctggt catcgccggc atcgtggaga acgagtggaa gaggacctgc 660
agccgcccca agtccaatat cgtgctgctg tccgccgagg agaagaagga gcagacaatc 720
gagatcaagg aggaggtggt gggcctgacc gagacatcta gccagcctaa gaatgaggag 780
gatatcgag 789

<210> SEQ ID NO 577
<211> LENGTH: 404
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 577
gccgcaataa aatatcttta ttttcattac atctgtgtgt tggttttttg tgtgaatcgt 60
aactaacata cgctctccat caaaacaaaa cgaaacaaaa caaactagca aaataggctg 120
tccccagtgc aagtgcaggt gccagaacat ttctctatcg aaggatctgc gatcgctccg 180
gtgcccgtca gtgggcagag cgcacatcgc ccacagtccc cgagaagttg gggggagggg 240
tcggcaattg aaccggtgcc tagagaaggt ggcgcggggt aaactgggaa agtgatgtcg 300
tgtactggct ccgccttttt cccgagggtg ggggagaacc gtatataagt gcagtagtcg 360
ccgtgaacgt tctttttcgc aacgggtttg ccgccagaac acag 404

<210> SEQ ID NO 578
<211> LENGTH: 205
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 578
gtgatgcggt tttggcagta catcaatggg cgtggatagc ggtttgactc acggggattt 60
ccaagtctcc accccattga cgtcaatggg agtttgtttt ggcaccaaaa tcaacgggac 120
tttccaaaat gtcgtaacaa ctccgcccca ttgacgcaaa tgggcggtag gcgtgtacgg 180
tgggaggtct atataagcag agctc 205

<210> SEQ ID NO 579
<211> LENGTH: 674
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 579
tgtgagcaaa aggccagcaa aaggccagga accgtaaaaa ggccgcgttg ctggcgtttt 60
tccataggct ccgcccccct gacgagcatc acaaaaatcg acgctcaagt cagaggtggc 120
gaaacccgac aggactataa agataccagg cgtttccccc tggaagctcc ctcgtgcgct 180
ctcctgttcc gaccctgccg cttaccggat acctgtccgc ctttctccct tcgggaagcg 240
tggcgctttc tcatagctca cgctgtaggt atctcagttc ggtgtaggtc gttcgctcca 300
agctgggctg tgtgcacgaa ccccccgttc agcccgaccg ctgcgcctta tccggtaact 360
atcgtcttga gtccaacccg gtaagacacg acttatcgcc actggcagca gccactggta 420
acaggattag cagagcgagg tatgtaggcg gtgctacaga gttcttgaag tggtggccta 480
actacggcta cactagaaga acagtatttg gtatctgcgc tctgctgaag ccagttacct 540
tcggaaaaag agttggtagc tcttgatccg gcaaacaaac caccgctggt agcggtggtt 600
tttttgtttg caagcagcag attacgcgca gaaaaaaagg atctcaagaa gatcctttga 660
tcttttctac gggg 674

<210> SEQ ID NO 580
<211> LENGTH: 287
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 580
ctacagttga agtcggaagt ttacatacac ttaagttgga gtcattaaaa ctcgtttttc 60
aactactcca caaatttctt gttaacaaac aatagttttg gcaagtcagt taggacatct 120
actttgtgca tgacacaagt catttttcca acaattgttt acagacagat tatttcactt 180
ataattcact gtatcacaat tccagtgggt cagaagttta catacactaa gttgactgtg 240
cctttaaaca gcttggaaaa ttccagaaaa tgatgtcatg gctttag 287

<210> SEQ ID NO 581
<211> LENGTH: 299
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 581
gtggaaggct actcgaaatg tttgacccaa gttaaacaat ttaaaggcaa tgctaccaaa 60
tactaattga gtgtatgtta acttctgacc cactgggaat gtgatgaaag aaataaaagc 120
tgaaatgaat cattctctct actattattc tgatatttca cattcttaaa ataaagtggt 180
gatcctaact gaccttaaga cagggaatct ttactcggat taaatgtcag gaattgtgaa 240
aaagtgagtt taaatgtatt tggctaaggt gtatgtaaac ttccgacttc aactgtagg 299

<210> SEQ ID NO 582

<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 582
gatgctacaa gtggcccact tctgagatgc gggctgcttc tggatgacac tgcttcccga 60
ggcatttcgc cctatctgca agtactatgg attactttgc tagtggtgta gatagggtga 120
aatgtttcgg caagtgcctc ctcgctggcc ccagggtacc acccggagca caggtttggt 180
gacctt 186

<210> SEQ ID NO 583
<211> LENGTH: 207
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 583
agggactggg cccacgggga ggcagcgtcc ccgaggcagc agcggcagcg gcggctcctc 60
tccccatggc cctgtcacaa cctcctagaa agagtactgg gctcagaccc tctttcaggc 120
cgttgtgaca gggacctggg gaccccggca ccggcaggcc ccaaggggtg aggtgagcgg 180
gcattgggac ctcccctccc tgtactc 207

<210> SEQ ID NO 584
<211> LENGTH: 210
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 584
aggagggtgg gggtggaggc aagcagagga cttcctgatc gcgtacccat ggctacagtc 60
tttcttcatg tgactcgtgg acttgtacta cacaaaagta ctgtgagaat atatgaagga 120
caggctttag tgtagtatgc gttcaattgt catcactggc atcttttttg atcattgcac 180
catcatcaaa tgcattggga taaccatgac 210

<210> SEQ ID NO 585
<211> LENGTH: 210
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 585
ggtaagtcat gactccctac aatggacatg atcatagtag gtactataag gcacctagct 60
ataccctcct atagagagtt tgagtctatt gtagcaagtc tttcttttag ggcctaggac 120
tcttcccact ctcttccatc gcctaagctc taactcttcc ttgtagtaga aataagtcac 180
ttctaaggct gggaccctcc tagaccctaa 210

<210> SEQ ID NO 586
<211> LENGTH: 354
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 586
ttaggatgag ttgagatccc agtgatcttc tcgctaagag tttcctgcct gggcaaggag 60
gaaagatgct acaagtggcc cacttctgag atgcgggctg cttctggatg acactgcttc 120
ccgaggcatt tcgccctatc tgcaagtact atggattact ttgctagtgg tgtagatagg 180
gtgaaatgtt tcggcaagtg cctcctcgct ggccccaggg taccacccgg agcacaggtt 240
tggtgacctt cttcctcatc agggctttgt gccagcaaat gactccctca ccaaggaagc 300
aagagcctct gaatcccatc tgggctcttc ctgaacaccc ctatctcccc ctct 354

<210> SEQ ID NO 587
<211> LENGTH: 926
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 587

Pro Leu Leu Ala Leu Leu Ala Ala Leu Leu Leu Ala Ala Arg Gly Ala
1 5 10 15

Ala Ala Gln Glu Thr Glu Leu Ser Val Ser Ala Glu Leu Val Pro Thr
20 25 30

Ser Ser Trp Asn Ile Ser Ser Glu Leu Asn Lys Asp Ser Tyr Leu Thr
35 40 45

Leu Asp Glu Pro Met Asn Asn Ile Thr Thr Ser Leu Gly Gln Thr Ala
50 55 60

Glu Leu His Cys Lys Val Ser Gly Asn Pro Pro Pro Thr Ile Arg Trp
65 70 75 80

Phe Lys Asn Asp Ala Pro Val Val Gln Glu Pro Arg Arg Leu Ser Phe
85 90 95

Arg Ser Thr Ile Tyr Gly Ser Arg Leu Arg Ile Arg Asn Leu Asp Thr
100 105 110

Thr Asp Thr Gly Tyr Phe Gln Cys Val Ala Thr Asn Gly Lys Glu Val
115 120 125

Val Ser Ser Thr Gly Val Leu Phe Val Lys Phe Gly Pro Pro Pro Thr
130 135 140

Ala Ser Pro Gly Tyr Ser Asp Glu Tyr Glu Glu Asp Gly Phe Cys Gln
145 150 155 160

Pro Tyr Arg Gly Ile Ala Cys Ala Arg Phe Ile Gly Asn Arg Thr Val
165 170 175

Tyr Met Glu Ser Leu His Met Gln Gly Glu Ile Glu Asn Gln Ile Thr
180 185 190

Ala Ala Phe Thr Met Ile Gly Thr Ser Ser His Leu Ser Asp Lys Cys
195 200 205

Ser Gln Phe Ala Ile Pro Ser Leu Cys His Tyr Ala Phe Pro Tyr Cys
210 215 220

Asp Glu Thr Ser Ser Val Pro Lys Pro Arg Asp Leu Cys Arg Asp Glu
225 230 235 240

Cys Glu Ile Leu Glu Asn Val Leu Cys Gln Thr Glu Tyr Ile Phe Ala
245 250 255

Arg Ser Asn Pro Met Ile Leu Met Arg Leu Lys Leu Pro Asn Cys Glu
260 265 270

-continued

```
Asp Leu Pro Gln Pro Glu Ser Pro Glu Ala Ala Asn Cys Ile Arg Ile
        275                 280                 285

Gly Ile Pro Met Ala Asp Pro Ile Asn Lys Asn His Lys Cys Tyr Asn
    290                 295                 300

Ser Thr Gly Val Asp Tyr Arg Gly Thr Val Ser Val Thr Lys Ser Gly
305                 310                 315                 320

Arg Gln Cys Gln Pro Trp Asn Ser Gln Tyr Pro His Thr His Thr Phe
                325                 330                 335

Thr Ala Leu Arg Phe Pro Glu Leu Asn Gly Gly His Ser Tyr Cys Arg
            340                 345                 350

Asn Pro Gly Asn Gln Lys Glu Ala Pro Trp Cys Phe Thr Leu Asp Glu
        355                 360                 365

Asn Phe Lys Ser Asp Leu Cys Asp Ile Pro Ala Cys Asp Ser Lys Asp
    370                 375                 380

Ser Lys Glu Lys Asn Lys Met Glu Ile Leu Tyr Ile Leu Val Pro Ser
385                 390                 395                 400

Val Ala Ile Pro Leu Ala Ile Ala Leu Leu Phe Phe Phe Ile Cys Val
                405                 410                 415

Cys Arg Asn Asn Gln Lys Ser Ser Ser Ala Pro Val Gln Arg Gln Pro
            420                 425                 430

Lys His Val Arg Gly Gln Asn Val Glu Met Ser Met Leu Asn Ala Tyr
        435                 440                 445

Lys Pro Lys Ser Lys Ala Lys Glu Leu Pro Leu Ser Ala Val Arg Phe
    450                 455                 460

Met Glu Glu Leu Gly Glu Cys Ala Phe Gly Lys Ile Tyr Lys Gly His
465                 470                 475                 480

Leu Tyr Leu Pro Gly Met Asp His Ala Gln Leu Val Ala Ile Lys Thr
                485                 490                 495

Leu Lys Asp Tyr Asn Asn Pro Gln Gln Trp Thr Glu Phe Gln Gln Glu
            500                 505                 510

Ala Ser Leu Met Ala Glu Leu His His Pro Asn Ile Val Cys Leu Leu
        515                 520                 525

Gly Ala Val Thr Gln Glu Gln Pro Val Cys Met Leu Phe Glu Tyr Ile
    530                 535                 540

Asn Gln Gly Asp Leu His Glu Phe Leu Ile Met Arg Ser Pro His Ser
545                 550                 555                 560

Asp Val Gly Cys Ser Ser Asp Glu Asp Gly Thr Val Lys Ser Ser Leu
                565                 570                 575

Asp His Gly Asp Phe Leu His Ile Ala Ile Gln Ile Ala Ala Gly Met
            580                 585                 590

Glu Tyr Leu Ser Ser His Phe Phe Val His Lys Asp Leu Ala Ala Arg
        595                 600                 605

Asn Ile Leu Ile Gly Glu Gln Leu His Val Lys Ile Ser Asp Leu Gly
    610                 615                 620

Leu Ser Arg Glu Ile Tyr Ser Ala Asp Tyr Tyr Arg Val Gln Ser Lys
625                 630                 635                 640

Ser Leu Leu Pro Ile Arg Trp Met Pro Pro Glu Ala Ile Met Tyr Gly
                645                 650                 655

Lys Phe Ser Ser Asp Ser Asp Ile Trp Ser Phe Gly Val Val Leu Trp
            660                 665                 670

Glu Ile Phe Ser Phe Gly Leu Gln Pro Tyr Tyr Gly Phe Ser Asn Gln
        675                 680                 685
```

```
Glu Val Ile Glu Met Val Arg Lys Arg Gln Leu Leu Pro Cys Ser Glu
    690                 695                 700

Asp Cys Pro Pro Arg Met Tyr Ser Leu Met Thr Glu Cys Trp Asn Glu
705                 710                 715                 720

Ile Pro Ser Arg Arg Pro Arg Phe Lys Asp Ile His Val Arg Leu Arg
                725                 730                 735

Ser Trp Glu Gly Leu Ser Ser His Thr Ser Ser Thr Thr Pro Ser Gly
            740                 745                 750

Gly Asn Ala Thr Thr Gln Thr Thr Ser Leu Ser Ala Ser Pro Val Ser
        755                 760                 765

Asn Leu Ser Asn Pro Arg Tyr Pro Asn Tyr Met Phe Pro Ser Gln Gly
    770                 775                 780

Ile Thr Pro Gln Gly Gln Ile Ala Gly Phe Ile Gly Pro Pro Ile Pro
785                 790                 795                 800

Gln Asn Gln Arg Phe Ile Pro Ile Asn Gly Tyr Pro Ile Pro Pro Gly
                805                 810                 815

Tyr Ala Ala Phe Pro Ala Ala His Tyr Gln Pro Thr Gly Pro Pro Arg
            820                 825                 830

Val Ile Gln His Cys Pro Pro Pro Lys Ser Arg Ser Pro Ser Ser Ala
        835                 840                 845

Ser Gly Ser Thr Ser Thr Gly His Val Thr Ser Leu Pro Ser Ser Gly
    850                 855                 860

Ser Asn Gln Glu Ala Asn Ile Pro Leu Leu Pro His Met Ser Ile Pro
865                 870                 875                 880

Asn His Pro Gly Gly Met Gly Ile Thr Val Phe Gly Asn Lys Ser Gln
                885                 890                 895

Lys Pro Tyr Lys Ile Asp Ser Lys Gln Ala Ser Leu Leu Gly Asp Ala
            900                 905                 910

Asn Ile His Gly His Thr Glu Ser Met Ile Ser Ala Glu Leu
        915                 920                 925
```

<210> SEQ ID NO 588
<211> LENGTH: 2811
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 588

```
atgcaccggc cgcgccgccg cgggacgcgc ccgccgctcc tggcgctgct ggccgcgctg     60

ctgctggccg cacgcggggc tgctgcccaa gaaacagagc tgtcagtcag tgctgaatta    120

gtgcctacct catcatggaa catctcaagt gaactcaaca aagattctta cctgaccctc    180

gatgaaccaa tgaataacat caccacgtct ctgggccaga cagcagaact gcactgcaaa    240

gtctctggga atccacctcc caccatccgc tggttcaaaa atgatgctcc tgtggtccag    300

gagccccgga ggctctcctt tcggtccacc atctatggct ctcggctgcg gattagaaac    360

ctcgacacca cagacacagg ctacttccag tgcgtggcaa caaacggcaa ggaggtggtt    420

tcttccactg gagtcttgtt tgtcaagttt ggcccccctc ccactgcaag tccaggatac    480

tcagatgagt atgaagaaga tggattctgt cagccataca gagggattgc atgtgcaaga    540

tttattggca accgcaccgt ctatatggag tctttgcaca tgcaagggga aatagaaaat    600

cagatcacag ctgccttcac tatgattggc acttccagtc acttatctga taagtgttct    660

cagttcgcca ttccttccct gtgccactat gccttcccgt actgcgatga aacttcatcc    720
```

```
gtcccaaagc cccgtgactt gtgtcgcgat gaatgtgaaa tcctggagaa tgtcctgtgt    780
caaacagagt acatttttgc aagatcaaat cccatgattc tgatgaggct gaaactgcca    840
aactgtgaag atctccccca gccagagagc ccagaagctg cgaactgtat ccggattgga    900
attcccatgg cagatcctat aaataaaaat cacaagtgtt ataacagcac aggtgtggac    960
taccggggga ccgtcagtgt gaccaaatca gggcgccagt gccagccatg gaattcccag   1020
tatccccaca cacacacttt caccgccctt cgtttcccag agctgaatgg aggccattcc   1080
tactgccgca acccagggaa tcaaaaggaa gctccctggt gcttcacctt ggatgaaaac   1140
tttaagtctg atctgtgtga catcccagcg tgcgattcaa aggattccaa ggagaagaat   1200
aaaatggaaa tcctgtacat actagtgcca agtgtggcca ttcccctggc cattgcttta   1260
ctcttcttct tcatttgcgt ctgtcggaat aaccagaagt catcgtcggc accagtccag   1320
aggcaaccaa aacacgtcag aggtcaaaat gtagagatgt caatgctgaa tgcatataaa   1380
cccaagagca aggctaaaga gctacctctt tctgctgtac gctttatgga agaattgggt   1440
gagtgtgcct ttggaaaaat ctataaaggc catctctatc tcccaggcat ggaccatgct   1500
cagctggttg ctatcaagac cttgaaagac tataacaacc cccagcaatg gacggaattt   1560
caacaagaag cctccctaat ggcagaactg caccacccca atattgtctg ccttctaggt   1620
gccgtcactc aggaacaacc tgtgtgcatg ctttttgagt atattaatca gggggatctc   1680
catgagttcc tcatcatgag atccccacac tctgatgttg gctgcagcag tgatgaagat   1740
gggactgtga aatccagcct ggaccacgga gattttctgc acattgcaat tcagattgca   1800
gctggcatgg aatacctgtc tagtcacttc tttgtccaca aggaccttgc agctcgcaat   1860
attttaatcg gagagcaact tcatgtaaag atttcagact tggggctttc cagagaaatt   1920
tactccgctg attactacag ggtccagagt aagtccttgc tgcccattcg ctggatgccc   1980
cctgaagcca tcatgtatgg caaattctct tctgattcag atatctggtc ctttggggtt   2040
gtcttgtggg agattttcag ttttggactc cagccatatt atggattcag taaccaggaa   2100
gtgattgaga tggtgagaaa acggcagctc ttaccatgct ctgaagactg cccacccaga   2160
atgtacagcc tcatgacaga gtgctggaat gagattcctt ctaggagacc aagatttaaa   2220
gatattcacg tccggcttcg gtcctgggag ggactctcaa gtcacacaag ctctactact   2280
ccttcagggg gaaatgccac cacacagaca acctccctca gtgccagccc agtgagtaat   2340
ctcagtaacc ccagatatcc taattacatg ttcccgagcc agggtattac accacagggc   2400
cagattgctg gtttcattgg cccgccaata cctcagaacc agcgattcat tcccatcaat   2460
ggatacccaa tacctcctgg atatgcagcg tttccagctg cccactacca gccaacaggt   2520
cctcccagag tgattcagca ctgcccacct cccaagagtc ggtccccaag cagtgccagt   2580
gggtcgacta gcactggcca tgtgactagc ttgccctcat caggatccaa tcaggaagca   2640
aatattcctt tactaccaca catgtcaatt ccaaatcatc ctggtggaat gggtatcacc   2700
gtttttggca acaaatctca aaaaccctac aaaattgact caaagcaagc atctttacta   2760
ggagacgcca atattcatgg acacaccgaa tctatgattt ctgcagaact g            2811
```

<210> SEQ ID NO 589
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 589

Met His Arg Pro Arg Arg Arg Gly Thr Arg Pro Pro Leu Leu Ala Leu
1 5 10 15

Leu Ala Ala Leu Leu Leu Ala Ala Arg Gly Ala Ala Ala Gln Glu Thr
20 25 30

Glu Leu Ser Val Ser Ala Glu Leu Val Pro Thr Ser Ser Trp Asn Ile
35 40 45

Ser Ser Glu Leu Asn Lys Asp Ser Tyr Leu Thr Leu Asp Glu Pro Met
50 55 60

Asn Asn Ile Thr Thr Ser Leu Gly Gln Thr Ala Glu Leu His Cys Lys
65 70 75 80

Val Ser Gly Asn Pro Pro Pro Thr Ile Arg Trp Phe Lys Asn Asp Ala
85 90 95

Pro Val Val Gln Glu Pro Arg Arg Leu Ser Phe Arg Ser Thr Ile Tyr
100 105 110

Gly Ser Arg Leu Arg Ile Arg Asn Leu Asp Thr Thr Asp Thr Gly Tyr
115 120 125

Phe Gln Cys Val Ala Thr Asn Gly Lys Glu Val Val Ser Ser Thr Gly
130 135 140

Val Leu Phe Val Lys Phe Gly Pro Pro Pro Thr Ala Ser Pro Gly Tyr
145 150 155 160

Ser Asp Glu Tyr Glu Glu Asp Gly Phe Cys Gln Pro Tyr Arg Gly Ile
165 170 175

Ala Cys Ala Arg Phe Ile Gly Asn Arg Thr Val Tyr Met Glu Ser Leu
180 185 190

His Met Gln Gly Glu Ile Glu Asn Gln Ile Thr Ala Ala Phe Thr Met
195 200 205

Ile Gly Thr Ser Ser His Leu Ser Asp Lys Cys Ser Gln Phe Ala Ile
210 215 220

Pro Ser Leu Cys His Tyr Ala Phe Pro Tyr Cys Asp Glu Thr Ser Ser
225 230 235 240

Val Pro Lys Pro Arg Asp Leu Cys Arg Asp Glu Cys Glu Ile Leu Glu
245 250 255

Asn Val Leu Cys Gln Thr Glu Tyr Ile Phe Ala Arg Ser Asn Pro Met
260 265 270

Ile Leu Met Arg Leu Lys Leu Pro Asn Cys Glu Asp Leu Pro Gln Pro
275 280 285

Glu Ser Pro Glu Ala Ala Asn Cys Ile Arg Ile Gly Ile Pro Met Ala
290 295 300

Asp Pro Ile Asn Lys Asn His Lys Cys Tyr Asn Ser Thr Gly Val Asp
305 310 315 320

Tyr Arg Gly Thr Val Ser Val Thr Lys Ser Gly Arg Gln Cys Gln Pro
325 330 335

Trp Asn Ser Gln Tyr Pro His Thr His Thr Phe Thr Ala Leu Arg Phe
340 345 350

Pro Glu Leu Asn Gly Gly His Ser Tyr Cys Arg Asn Pro Gly Asn Gln
355 360 365

Lys Glu Ala Pro Trp Cys Phe Thr Leu Asp Glu Asn Phe Lys Ser Asp
370 375 380

Leu Cys Asp Ile Pro Ala Cys Asp Ser Lys Asp Ser Lys Glu Lys Asn
385 390 395 400

Lys Met Glu Ile Leu Tyr Ile Leu Val Pro Ser Val Ala Ile Pro Leu

```
                405                 410                 415

Ala Ile Ala Leu Leu Phe Phe Phe Ile Cys Val Cys Arg Asn Asn Gln
            420                 425                 430

Lys Ser Ser Ser Ala
        435
```

<210> SEQ ID NO 590
<211> LENGTH: 1311
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 590

```
atgcaccggc cgcgccgccg cgggacgcgc ccgccgctcc tggcgctgct ggccgcgctg     60

ctgctggccg cacgcggggc tgctgcccaa gaaacagagc tgtcagtcag tgctgaatta    120

gtgcctacct catcatggaa catctcaagt gaactcaaca aagattctta cctgaccctc    180

gatgaaccaa tgaataacat caccacgtct ctgggccaga cagcagaact gcactgcaaa    240

gtctctggga atccacctcc caccatccgc tggttcaaaa atgatgctcc tgtggtccag    300

gagccccgga ggctctcctt tcggtccacc atctatggct ctcggctgcg gattagaaac    360

ctcgacacca cagacacagg ctacttccag tgcgtggcaa caaacggcaa ggaggtggtt    420

tcttccactg gagtcttgtt tgtcaagttt ggccccccctc ccactgcaag tccaggatac    480

tcagatgagt atgaagaaga tggattctgt cagccataca gagggattgc atgtgcaaga    540

tttattggca accgcaccgt ctatatggag tctttgcaca tgcaagggga aatagaaaat    600

cagatcacag ctgccttcac tatgattggc acttccagtc acttatctga taagtgttct    660

cagttcgcca ttccttccct gtgccactat gccttcccgt actgcgatga aacttcatcc    720

gtcccaaagc ccgtgactt gtgtcgcgat gaatgtgaaa tcctggagaa tgtcctgtgt    780

caaacagagt acatttttgc aagatcaaat cccatgattc tgatgaggct gaaactgcca    840

aactgtgaag atctccccca gccagagagc ccagaagctg cgaactgtat ccggattgga    900

attcccatgg cagatcctat aaataaaaat cacaagtgtt ataacagcac aggtgtggac    960

taccggggga ccgtcagtgt gaccaaatca gggcgccagt gccagccatg gaattcccag   1020

tatccccaca cacacacttt caccgccctt cgtttcccag agctgaatgg aggccattcc   1080

tactgccgca acccagggaa tcaaaaggaa gctccctggt gcttcacctt ggatgaaaac   1140

tttaagtctg atctgtgtga catcccagcg tgcgattcaa aggattccaa ggagaagaat   1200

aaaatggaaa tcctgtacat actagtgcca agtgtggcca ttcccctggc cattgcttta   1260

ctcttcttct tcatttgcgt ctgtcggaat aaccagaagt catcgtcggc a             1311
```

<210> SEQ ID NO 591
<211> LENGTH: 654
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 591

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30
```

-continued

```
Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys Gly Ser Thr Ser Gly
            100                 105                 110

Ser Gly Lys Pro Gly Ser Gly Glu Gly Ser Thr Lys Gly Glu Val Lys
        115                 120                 125

Leu Val Glu Ser Gly Gly Gly Leu Val Lys Pro Gly Gly Ser Leu Lys
    130                 135                 140

Leu Ser Cys Ala Ala Ser Gly Phe Thr Phe Ser Ser Tyr Ala Met Ser
145                 150                 155                 160

Trp Val Arg Gln Ile Pro Glu Lys Arg Leu Glu Trp Val Ala Ser Ile
                165                 170                 175

Ser Arg Gly Gly Thr Thr Tyr Tyr Pro Asp Ser Val Lys Gly Arg Phe
            180                 185                 190

Thr Ile Ser Arg Asp Asn Val Arg Asn Ile Leu Tyr Leu Gln Met Ser
        195                 200                 205

Ser Leu Arg Ser Glu Asp Thr Ala Met Tyr Tyr Cys Gly Arg Tyr Asp
    210                 215                 220

Tyr Asp Gly Tyr Tyr Ala Met Asp Tyr Trp Gly Gln Gly Thr Ser Val
225                 230                 235                 240

Thr Val Ser Ser Glu Ser Lys Tyr Gly Pro Pro Cys Pro Pro Cys Pro
                245                 250                 255

Ala Pro Glu Phe Glu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser Gln Glu Asp Pro Glu Val Gln Phe Asn Trp Tyr
    290                 295                 300

Val Asp Gly Val Glu Val His Asn Ala Lys Thr Lys Pro Arg Glu Glu
305                 310                 315                 320

Gln Phe Gln Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Gly Leu Pro Ser Ser Ile Glu Lys Thr Ile Ser Lys Ala Lys Gly Gln
        355                 360                 365

Pro Arg Glu Pro Gln Val Tyr Thr Leu Pro Pro Ser Gln Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Arg Leu Thr Val Asp Lys Ser Arg Trp Gln Glu Gly Asn Val
        435                 440                 445
```

```
Phe Ser Cys Ser Val Met His Glu Ala Leu His Asn His Tyr Thr Gln
    450                 455                 460

Lys Ser Leu Ser Leu Ser Leu Gly Lys Met Phe Trp Val Leu Val Val
465                 470                 475                 480

Val Gly Gly Val Leu Ala Cys Tyr Ser Leu Leu Val Thr Val Ala Phe
                485                 490                 495

Ile Ile Phe Trp Val Arg Ser Lys Arg Ser Arg Gly Gly His Ser Asp
            500                 505                 510

Tyr Met Asn Met Thr Pro Arg Arg Pro Gly Pro Thr Arg Lys His Tyr
        515                 520                 525

Gln Pro Tyr Ala Pro Pro Arg Asp Phe Ala Ala Tyr Arg Ser Arg Val
    530                 535                 540

Lys Phe Ser Arg Ser Ala Asp Ala Pro Ala Tyr Gln Gln Gly Gln Asn
545                 550                 555                 560

Gln Leu Tyr Asn Glu Leu Asn Leu Gly Arg Arg Glu Glu Tyr Asp Val
                565                 570                 575

Leu Asp Lys Arg Arg Gly Arg Asp Pro Glu Met Gly Gly Lys Pro Arg
            580                 585                 590

Arg Lys Asn Pro Gln Glu Gly Leu Tyr Asn Glu Leu Gln Lys Asp Lys
        595                 600                 605

Met Ala Glu Ala Tyr Ser Glu Ile Gly Met Lys Gly Glu Arg Arg Arg
    610                 615                 620

Gly Lys Gly His Asp Gly Leu Tyr Gln Gly Leu Ser Thr Ala Thr Lys
625                 630                 635                 640

Asp Thr Tyr Asp Ala Leu His Met Gln Ala Leu Pro Pro Arg
                645                 650
```

```
<210> SEQ ID NO 592
<211> LENGTH: 1962
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 592

gacatcaaga tgacccagag ccccagctct atgtacgcca gcctgggcga gcgcgtgacc     60

atcacatgca aggccagccc cgacatcaac agctacctgt cctggttcca gcagaagccc    120

ggcaagagcc ccaagaccct gatctaccgg gccaaccggc tggtggacgg cgtgccaagc    180

agattttccg gcggaggcag cggccaggac tacagcctga ccatcaacag cctggaatac    240

gaggacatgg gcatctacta ctgcctgcag tacgacgagt tcccctacac cttcggaggc    300

ggcaccaagc tggaaatgaa gggcagcacc tccggcagcg gcaagcctgg cagcggcgag    360

ggcagcacca agggcgaagt gaagctggtg gaaagcggcg gaggcctggt gaaacctggc    420

ggcagcctga agctgagctg cgccgccagc ggcttcacct tcagcagcta cgccatgagc    480

tgggtccgac agatccccga gaagcggctg gaatgggtgg ccagcatcag caggggcggc    540

accacctact accccgacag cgtgaagggc cggttcacca tcagccggga caacgtgcgg    600

aacatcctgt acctgcagat gagcagcctg cggagcgagg acaccgccat gtactactgc    660

ggcagatacg actacgacgg ctactacgcc atggattact ggggccaggg caccagcgtg    720

accgtgtcta gcgagagcaa gtacggccct ccctgccccc cttgccctgc ccccgagttc    780

gagggcggac ccagcgtgtt cctgttcccc cccaagccca aggacaccct gatgatcagc    840

cggacccccg aggtgacctg tgtggtggtg gacgtgtccc aggaggaccc cgaggtccag    900
```

```
ttcaactggt acgtggacgg cgtggaggtg cacaacgcca agaccaagcc ccgggaggag    960

cagttccaga gcacctaccg ggtggtgtcc gtgctgaccg tgctgcacca ggactggctg   1020

aacggcaagg aatacaagtg taaggtgtcc aacaagggcc tgcccagcag catcgagaaa   1080

accatcagca aggccaaggg ccagcctcgg gagccccagg tgtacaccct gcccccctagc   1140

caagaggaga tgaccaagaa tcaggtgtcc ctgacctgcc tggtgaaggg cttctacccc   1200

agcgacatcg ccgtggagtg ggagagcaac ggccagcccg agaacaacta caagaccacc   1260

ccccctgtgc tggacagcga cggcagcttc ttcctgtaca gcaggctgac cgtggacaag   1320

agccggtggc aggagggcaa cgtctttagc tgctccgtga tgcacgaggc cctgcacaac   1380

cactacaccc agaagagcct gtccctgagc ctgggcaaga tgttctgggt gctggtcgtg   1440

gtgggtggcg tgctggcctg ctacagcctg ctggtgacag tggccttcat catcttttgg   1500

gtgaggagca agcggagcag aggcggccac agcgactaca tgaacatgac cccccggagg   1560

cctggcccca cccggaagca ctaccagccc tacgcccctc ccagggactt cgccgcctac   1620

cggagccggg tgaagttcag ccggagcgcc gacgcccctg cctaccagca gggccagaac   1680

cagctgtaca acgagctgaa cctgggccgg agggaggagt acgacgtgct ggacaagcgg   1740

agaggccggg accctgagat gggcggcaag ccccggagaa agaaccctca ggagggcctg   1800

tataacgaac tgcagaaaga caagatggcc gaggcctaca gcgagatcgg catgaagggc   1860

gagcggcgga ggggcaaggg ccacgacggc ctgtaccagg gcctgagcac cgccaccaag   1920

gatacctacg acgccctgca catgcaggcc ctgcccccca ga                      1962
```

<210> SEQ ID NO 593
<211> LENGTH: 663
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 593

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys Gly Ser Thr Ser Gly
            100                 105                 110

Ser Gly Lys Pro Gly Ser Gly Glu Gly Ser Thr Lys Gly Glu Val Lys
        115                 120                 125

Leu Val Glu Ser Gly Gly Gly Leu Val Lys Pro Gly Gly Ser Leu Lys
    130                 135                 140

Leu Ser Cys Ala Ala Ser Gly Phe Thr Phe Ser Ser Tyr Ala Met Ser
145                 150                 155                 160

Trp Val Arg Gln Ile Pro Glu Lys Arg Leu Glu Trp Val Ala Ser Ile
```

-continued

```
                165                 170                 175

Ser Arg Gly Gly Thr Thr Tyr Tyr Pro Asp Ser Val Lys Gly Arg Phe
            180                 185                 190

Thr Ile Ser Arg Asp Asn Val Arg Asn Ile Leu Tyr Leu Gln Met Ser
        195                 200                 205

Ser Leu Arg Ser Glu Asp Thr Ala Met Tyr Tyr Cys Gly Arg Tyr Asp
    210                 215                 220

Tyr Asp Gly Tyr Tyr Ala Met Asp Tyr Trp Gly Gln Gly Thr Ser Val
225                 230                 235                 240

Thr Val Ser Ser Gln Gly Thr Ser Val Thr Val Ser Ser Glu Ser Lys
                245                 250                 255

Tyr Gly Pro Pro Cys Pro Pro Cys Pro Ala Pro Glu Phe Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser Gln Glu
    290                 295                 300

Asp Pro Glu Val Gln Phe Asn Trp Tyr Val Asp Gly Val Glu Val His
305                 310                 315                 320

Asn Ala Lys Thr Lys Pro Arg Glu Glu Gln Phe Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Gly Leu Pro Ser Ser Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Gln Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Arg Leu Thr Val Asp
        435                 440                 445

Lys Ser Arg Trp Gln Glu Gly Asn Val Phe Ser Cys Ser Val Met His
    450                 455                 460

Glu Ala Leu His Asn His Tyr Thr Gln Lys Ser Leu Ser Leu Ser Leu
465                 470                 475                 480

Gly Lys Met Phe Trp Val Leu Val Val Val Gly Gly Val Leu Ala Cys
                485                 490                 495

Tyr Ser Leu Leu Val Thr Val Ala Phe Ile Ile Phe Trp Val Arg Ser
            500                 505                 510

Lys Arg Ser Arg Gly Gly His Ser Asp Tyr Met Asn Met Thr Pro Arg
        515                 520                 525

Arg Pro Gly Pro Thr Arg Lys His Tyr Gln Pro Tyr Ala Pro Pro Arg
    530                 535                 540

Asp Phe Ala Ala Tyr Arg Ser Arg Val Lys Phe Ser Arg Ser Ala Asp
545                 550                 555                 560

Ala Pro Ala Tyr Gln Gln Gly Gln Asn Gln Leu Tyr Asn Glu Leu Asn
                565                 570                 575

Leu Gly Arg Arg Glu Glu Tyr Asp Val Leu Asp Lys Arg Arg Gly Arg
            580                 585                 590
```

Asp Pro Glu Met Gly Gly Lys Pro Arg Arg Lys Asn Pro Gln Glu Gly
595 600 605

Leu Tyr Asn Glu Leu Gln Lys Asp Lys Met Ala Glu Ala Tyr Ser Glu
610 615 620

Ile Gly Met Lys Gly Glu Arg Arg Arg Gly Lys Gly His Asp Gly Leu
625 630 635 640

Tyr Gln Gly Leu Ser Thr Ala Thr Lys Asp Thr Tyr Asp Ala Leu His
645 650 655

Met Gln Ala Leu Pro Pro Arg
660

<210> SEQ ID NO 594
<211> LENGTH: 1989
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 594
gacatcaaga tgacccagag ccccagctct atgtacgcca gcctgggcga gcgcgtgacc 60
atcacatgca aggccagccc cgacatcaac agctacctgt cctggttcca gcagaagccc 120
ggcaagagcc ccaagaccct gatctaccgg gccaaccggc tggtggacgg cgtgccaagc 180
agattttccg gcggaggcag cggccaggac tacagcctga ccatcaacag cctggaatac 240
gaggacatgg gcatctacta ctgcctgcag tacgacgagt tcccctacac cttcggaggc 300
ggcaccaagc tggaaatgaa gggcagcacc agcggcagcg gcaagcctgg aagcggcgag 360
ggctccacca agggcgaagt gaagctggtg gaaagcggcg gaggcctggt gaaacctggc 420
ggcagcctga agctgagctg cgccgccagc ggcttcacct tcagcagcta cgccatgagc 480
tgggtccgac agatccccga gaagcggctg gaatgggtgg ccagcatcag caggggcggc 540
accacctact accccgacag cgtgaagggc cggttcacca tcagccggga caacgtgcgg 600
aacatcctgt acctgcagat gagcagcctg cggagcgagg acaccgccat gtactactgc 660
ggcagatacg actacgacgg ctactacgcc atggattact ggggccaggg caccagcgtg 720
accgtgtcta gccagggaac ctccgtgaca gtgtccagcg agtccaaata tggtccccca 780
tgcccaccat gcccagcacc tgagttcctg gggggaccat cagtcttcct gttcccccca 840
aaacccaagg acactctcat gatctcccgg acccctgagg tcacgtgcgt ggtggtggac 900
gtgagccagg aagaccccga ggtccagttc aactggtacg tggatggcgt ggaggtgcat 960
aatgccaaga caaagccccg ggaggagcag ttcaatagca cctaccgggt ggtgtccgtg 1020
ctgaccgtgc tgcaccagga ctggctgaac ggcaaggaat acaagtgtaa ggtgtccaac 1080
aagggcctgc ccagcagcat cgagaaaacc atcagcaagg ccaagggcca gcctcgggag 1140
ccccaggtgt acaccctgcc ccctagccaa gaggagatga ccaagaatca ggtgtccctg 1200
acctgcctgg tgaagggctt ctaccccagc gacatcgccg tggagtggga gagcaacggc 1260
cagcccgaga acaactacaa gaccaccccc cctgtgctgg acagcgacgg cagcttcttc 1320
ctgtacagca ggctgaccgt ggacaagagc cggtggcagg agggcaacgt ctttagctgc 1380
tccgtgatgc acgaggccct gcacaaccac tacacccaga agagcctgtc cctgagcctg 1440
ggcaagatgt tctgggtgct ggtcgtggtg ggtggcgtgc tggcctgcta cagcctgctg 1500
gtgacagtgg ccttcatcat cttttgggtg aggagcaagc ggagcagagg cggccacagc 1560

```
gactacatga acatgacccc ccggaggcct ggccccaccc ggaagcacta ccagccctac   1620

gcccctccca gggacttcgc cgcctaccgg agccgggtga agttcagccg gagcgccgac   1680

gcccctgcct accagcaggg ccagaaccag ctgtacaacg agctgaacct gggccggagg   1740

gaggagtacg acgtgctgga caagcggaga ggccgggacc ctgagatggg cggcaagccc   1800

cggagaaaga accctcagga gggcctgtat aacgaactgc agaaagacaa gatggccgag   1860

gcctacagcg agatcggcat gaagggcgag cggcggaggg gcaagggcca cgacggcctg   1920

taccagggcc tgagcaccgc caccaaggat acctacgacg ccctgcacat gcaggccctg   1980

ccccccaga                                                           1989


<210> SEQ ID NO 595
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 595

Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys Gly Ser Thr Ser Gly
            100                 105                 110

Ser Gly Lys Pro Gly Ser Gly Glu Gly Ser Thr Lys Gly Glu Val Lys
        115                 120                 125

Leu Val Glu Ser Gly Gly Gly Leu Val Lys Pro Gly Gly Ser Leu Lys
    130                 135                 140

Leu Ser Cys Ala Ala Ser Gly Phe Thr Phe Ser Ser Tyr Ala Met Ser
145                 150                 155                 160

Trp Val Arg Gln Ile Pro Glu Lys Arg Leu Glu Trp Val Ala Ser Ile
                165                 170                 175

Ser Arg Gly Gly Thr Thr Tyr Tyr Pro Asp Ser Val Lys Gly Arg Phe
            180                 185                 190

Thr Ile Ser Arg Asp Asn Val Arg Asn Ile Leu Tyr Leu Gln Met Ser
        195                 200                 205

Ser Leu Arg Ser Glu Asp Thr Ala Met Tyr Tyr Cys Gly Arg Tyr Asp
    210                 215                 220

Tyr Asp Gly Tyr Tyr Ala Met Asp Tyr Trp Gly Gln Gly Thr Ser Val
225                 230                 235                 240

Thr Val Ser Ser Lys Pro Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
```

```
        275                 280                 285

Ala Cys Asp Ile Tyr Ile Trp Ala Pro Leu Ala Gly Thr Cys Gly Val
    290                 295                 300

Leu Leu Leu Ser Leu Val Ile Thr Leu Tyr Cys Asn His Arg Asn Arg
305                 310                 315                 320

Ser Lys Arg Ser Arg Gly Gly His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470


<210> SEQ ID NO 596
<211> LENGTH: 1416
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 596

gacatcaaga tgacccagag ccccagctct atgtacgcca gcctgggcga gcgcgtgacc     60

atcacatgca aggccagccc cgacatcaac agctacctgt cctggttcca gcagaagccc    120

ggcaagagcc ccaagaccct gatctaccgg gccaaccggc tggtggacgg cgtgccaagc    180

agattttccg gcggaggcag cggccaggac tacagcctga ccatcaacag cctggaatac    240

gaggacatgg gcatctacta ctgcctgcag tacgacgagt tcccctacac cttcggaggc    300

ggcaccaagc tggaaatgaa gggcagcacc tccggcagcg gcaagcctgg cagcggcgag    360

ggcagcacca agggcgaagt gaagctggtg gaaagcggcg gaggcctggt gaaacctggc    420

ggcagcctga agctgagctg cgccgccagc ggcttcacct tcagcagcta cgccatgagc    480

tgggtccgac agatccccga gaagcggctg gaatgggtgg ccagcatcag caggggcggc    540

accacctact accccgacag cgtgaagggc cggttcacca tcagccggga caacgtgcgg    600

aacatcctgt acctgcagat gagcagcctg cggagcgagg acaccgccat gtactactgc    660

ggcagatacg actacgacgg ctactacgcc atggattact ggggccaggg caccagcgtg    720

accgtgtcta gcaagcccac caccacccct gcccctagac ctccaacccc agcccctaca    780

atcgccagcc agcccctgag cctgaggccc gaagcctgta gacctgccgc tggcggagcc    840

gtgcacacca gaggcctgga tttcgcctgc gacatctaca tctgggcccc tctggccggc    900
```

-continued

```
acctgtggcg tgctgctgct gagcctggtc atcaccctgt actgcaacca ccggaatagg    960

agcaagcgga gcagaggcgg ccacagcgac tacatgaaca tgaccccccg gaggcctggc   1020

cccacccgga agcactacca gccctacgcc cctcccaggg acttcgccgc ctaccggagc   1080

cgggtgaagt tcagccggag cgccgacgcc cctgcctacc agcagggcca gaaccagctg   1140

tacaacgagc tgaacctggg ccggagggag gagtacgacg tgctggacaa gcggagaggc   1200

cgggaccctg agatgggcgg caagccccgg agaaagaacc ctcaggaggg cctgtataac   1260

gaactgcaga aagacaagat ggccgaggcc tacagcgaga tcggcatgaa gggcgagcgg   1320

cggaggggca agggccacga cggcctgtac cagggcctga gcaccgccac caaggatacc   1380

tacgacgccc tgcacatgca ggccctgccc cccaga                             1416
```

<210> SEQ ID NO 597
<211> LENGTH: 519
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 597

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys Gly Ser Thr Ser Gly
            100                 105                 110

Ser Gly Lys Pro Gly Ser Gly Glu Gly Ser Thr Lys Gly Glu Val Lys
        115                 120                 125

Leu Val Glu Ser Gly Gly Gly Leu Val Lys Pro Gly Gly Ser Leu Lys
    130                 135                 140

Leu Ser Cys Ala Ala Ser Gly Phe Thr Phe Ser Ser Tyr Ala Met Ser
145                 150                 155                 160

Trp Val Arg Gln Ile Pro Glu Lys Arg Leu Glu Trp Val Ala Ser Ile
                165                 170                 175

Ser Arg Gly Gly Thr Thr Tyr Tyr Pro Asp Ser Val Lys Gly Arg Phe
            180                 185                 190

Thr Ile Ser Arg Asp Asn Val Arg Asn Ile Leu Tyr Leu Gln Met Ser
        195                 200                 205

Ser Leu Arg Ser Glu Asp Thr Ala Met Tyr Tyr Cys Gly Arg Tyr Asp
    210                 215                 220

Tyr Asp Gly Tyr Tyr Ala Met Asp Tyr Trp Gly Gln Gly Thr Ser Val
225                 230                 235                 240

Thr Val Ser Ser Lys Pro Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270
```

```
Ser Arg Pro Ala Ala Gly Gly Ala Val His Thr Arg Gly Leu Asp Phe
        275                 280                 285

Ala Ser Asp Lys Pro Thr Thr Thr Pro Ala Pro Arg Pro Pro Thr Pro
    290                 295                 300

Ala Pro Thr Ile Ala Ser Gln Pro Leu Ser Leu Arg Pro Glu Ala Cys
305                 310                 315                 320

Arg Pro Ala Ala Gly Gly Ala Val His Thr Arg Gly Leu Asp Phe Ala
                325                 330                 335

Cys Asp Ile Tyr Ile Trp Ala Pro Leu Ala Gly Thr Cys Gly Val Leu
            340                 345                 350

Leu Leu Ser Leu Val Ile Thr Leu Tyr Cys Asn His Arg Asn Arg Ser
        355                 360                 365

Lys Arg Ser Arg Gly Gly His Ser Asp Tyr Met Asn Met Thr Pro Arg
    370                 375                 380

Arg Pro Gly Pro Thr Arg Lys His Tyr Gln Pro Tyr Ala Pro Pro Arg
385                 390                 395                 400

Asp Phe Ala Ala Tyr Arg Ser Arg Val Lys Phe Ser Arg Ser Ala Asp
                405                 410                 415

Ala Pro Ala Tyr Gln Gln Gly Gln Asn Gln Leu Tyr Asn Glu Leu Asn
            420                 425                 430

Leu Gly Arg Arg Glu Glu Tyr Asp Val Leu Asp Lys Arg Arg Gly Arg
        435                 440                 445

Asp Pro Glu Met Gly Gly Lys Pro Arg Arg Lys Asn Pro Gln Glu Gly
    450                 455                 460

Leu Tyr Asn Glu Leu Gln Lys Asp Lys Met Ala Glu Ala Tyr Ser Glu
465                 470                 475                 480

Ile Gly Met Lys Gly Glu Arg Arg Arg Gly Lys Gly His Asp Gly Leu
                485                 490                 495

Tyr Gln Gly Leu Ser Thr Ala Thr Lys Asp Thr Tyr Asp Ala Leu His
            500                 505                 510

Met Gln Ala Leu Pro Pro Arg
        515
```

<210> SEQ ID NO 598
<211> LENGTH: 1557
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 598

```
gacatcaaga tgacccagag ccccagctct atgtacgcca gcctgggcga gcgcgtgacc     60

atcacatgca aggccagccc cgacatcaac agctacctgt cctggttcca gcagaagccc    120

ggcaagagcc ccaagaccct gatctaccgg gccaaccggc tggtggacgg cgtgccaagc    180

agattttccg gcggaggcag cggccaggac tacagcctga ccatcaacag cctggaatac    240

gaggacatgg gcatctacta ctgcctgcag tacgacgagt tcccctacac cttcggaggc    300

ggcaccaagc tggaaatgaa gggcagcacc tccggcagcg gcaagcctgg cagcggcgag    360

ggcagcacca agggcgaagt gaagctggtg gaaagcggcg gaggcctggt gaaacctggc    420

ggcagcctga agctgagctg cgccgccagc ggcttcacct tcagcagcta cgccatgagc    480

tgggtccgac agatccccga gaagcggctg gaatgggtgg ccagcatcag caggggcggc    540

accacctact accccgacag cgtgaagggc cggttcacca tcagccggga caacgtgcgg    600
```

-continued

```
aacatcctgt acctgcagat gagcagcctg cggagcgagg acaccgccat gtactactgc    660

ggcagatacg actacgacgg ctactacgcc atggattact ggggccaggg caccagcgtg    720

accgtgtcta gcaaacctac tacaactcct gcccccggc ctcctacacc agctcctact    780

atcgcctccc agccactcag tctcagaccc gaggcttcta ggccagcggc cggaggcgcg    840

gtccacaccc gcgggctgga ctttgcatcc gataagccca ccaccacccc tgcccctaga    900

cctccaaccc cagcccctac aatcgccagc cagcccctga gcctgaggcc cgaagcctgt    960

agacctgccg ctggcggagc cgtgcacacc agaggcctgg atttcgcctg cgacatctac   1020

atctgggccc ctctggccgg cacctgtggc gtgctgctgc tgagcctggt catcaccctg   1080

tactgcaacc accggaatag gagcaagcgg agcagaggcg gccacagcga ctacatgaac   1140

atgacccccc ggaggcctgg ccccacccgg aagcactacc agccctacgc ccctcccagg   1200

gacttcgccg cctaccggag ccgggtgaag ttcagccgga gcgccgacgc ccctgcctac   1260

cagcagggcc agaaccagct gtacaacgag ctgaacctgg gccggaggga ggagtacgac   1320

gtgctggaca agcggagagg ccgggaccct gagatgggcg gcaagccccg gagaaagaac   1380

cctcaggagg gcctgtataa cgaactgcag aaagacaaga tggccgaggc ctacagcgag   1440

atcggcatga agggcgagcg gcggaggggc aagggccacg acggcctgta ccagggcctg   1500

agcaccgcca ccaaggatac ctacgacgcc ctgcacatgc aggccctgcc ccccaga      1557
```

<210> SEQ ID NO 599
<211> LENGTH: 566
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 599

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys Gly Ser Thr Ser Gly
            100                 105                 110

Ser Gly Lys Pro Gly Ser Gly Glu Gly Ser Thr Lys Gly Glu Val Lys
        115                 120                 125

Leu Val Glu Ser Gly Gly Gly Leu Val Lys Pro Gly Gly Ser Leu Lys
    130                 135                 140

Leu Ser Cys Ala Ala Ser Gly Phe Thr Phe Ser Ser Tyr Ala Met Ser
145                 150                 155                 160

Trp Val Arg Gln Ile Pro Glu Lys Arg Leu Glu Trp Val Ala Ser Ile
                165                 170                 175

Ser Arg Gly Gly Thr Thr Tyr Tyr Pro Asp Ser Val Lys Gly Arg Phe
            180                 185                 190
```

```
Thr Ile Ser Arg Asp Asn Val Arg Asn Ile Leu Tyr Leu Gln Met Ser
        195                 200                 205

Ser Leu Arg Ser Glu Asp Thr Ala Met Tyr Tyr Cys Gly Arg Tyr Asp
    210                 215                 220

Tyr Asp Gly Tyr Tyr Ala Met Asp Tyr Trp Gly Gln Gly Thr Ser Val
225                 230                 235                 240

Thr Val Ser Ser Lys Pro Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Ser Arg Pro Ala Ala Gly Gly Ala Val His Thr Arg Gly Leu Asp Phe
        275                 280                 285

Ala Ser Asp Lys Pro Thr Thr Thr Pro Ala Pro Arg Pro Pro Thr Pro
    290                 295                 300

Ala Pro Thr Ile Ala Ser Gln Pro Leu Ser Leu Arg Pro Glu Ala Ser
305                 310                 315                 320

Arg Pro Ala Ala Gly Gly Ala Val His Thr Arg Gly Leu Asp Phe Ala
                325                 330                 335

Ser Asp Lys Pro Thr Thr Thr Pro Ala Pro Arg Pro Pro Thr Pro Ala
            340                 345                 350

Pro Thr Ile Ala Ser Gln Pro Leu Ser Leu Arg Pro Glu Ala Cys Arg
        355                 360                 365

Pro Ala Ala Gly Gly Ala Val His Thr Arg Gly Leu Asp Phe Ala Cys
    370                 375                 380

Asp Ile Tyr Ile Trp Ala Pro Leu Ala Gly Thr Cys Gly Val Leu Leu
385                 390                 395                 400

Leu Ser Leu Val Ile Thr Leu Tyr Cys Asn His Arg Asn Arg Ser Lys
                405                 410                 415

Arg Ser Arg Gly Gly His Ser Asp Tyr Met Asn Met Thr Pro Arg Arg
            420                 425                 430

Pro Gly Pro Thr Arg Lys His Tyr Gln Pro Tyr Ala Pro Pro Arg Asp
        435                 440                 445

Phe Ala Ala Tyr Arg Ser Arg Val Lys Phe Ser Arg Ser Ala Asp Ala
    450                 455                 460

Pro Ala Tyr Gln Gln Gly Gln Asn Gln Leu Tyr Asn Glu Leu Asn Leu
465                 470                 475                 480

Gly Arg Arg Glu Glu Tyr Asp Val Leu Asp Lys Arg Arg Gly Arg Asp
                485                 490                 495

Pro Glu Met Gly Gly Lys Pro Arg Arg Lys Asn Pro Gln Glu Gly Leu
            500                 505                 510

Tyr Asn Glu Leu Gln Lys Asp Lys Met Ala Glu Ala Tyr Ser Glu Ile
        515                 520                 525

Gly Met Lys Gly Glu Arg Arg Arg Gly Lys Gly His Asp Gly Leu Tyr
    530                 535                 540

Gln Gly Leu Ser Thr Ala Thr Lys Asp Thr Tyr Asp Ala Leu His Met
545                 550                 555                 560

Gln Ala Leu Pro Pro Arg
                565
```

<210> SEQ ID NO 600
<211> LENGTH: 1698
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 600

```
gacatcaaga tgacccagag ccccagctct atgtacgcca gcctgggcga gcgcgtgacc      60
atcacatgca aggccagccc cgacatcaac agctacctgt cctggttcca gcagaagccc     120
ggcaagagcc ccaagaccct gatctaccgg gccaaccggc tggtggacgg cgtgccaagc     180
agattttccg gcggaggcag cggccaggac tacagcctga ccatcaacag cctggaatac     240
gaggacatgg gcatctacta ctgcctgcag tacgacgagt tcccctacac cttcggaggc     300
ggcaccaagc tggaaatgaa gggcagcacc tccggcagcg gcaagcctgg cagcggcgag     360
ggcagcacca agggcgaagt gaagctggtg gaaagcggcg gaggcctggt gaaacctggc     420
ggcagcctga agctgagctg cgccgccagc ggcttcacct tcagcagcta cgccatgagc     480
tgggtccgac agatccccga gaagcggctg gaatgggtgg ccagcatcag caggggcggc     540
accacctact accccgacag cgtgaagggc cggttcacca tcagccggga caacgtgcgg     600
aacatcctgt acctgcagat gagcagcctg cggagcgagg acaccgccat gtactactgc     660
ggcagatacg actacgacgg ctactacgcc atggattact ggggccaggg caccagcgtg     720
accgtgtcta gcaagcctac caccaccccc gcacctcgtc ctccaacccc tgcacctacg     780
attgccagtc agcctctttc actgcggcct gaggccagca gaccagctgc cggcggtgcc     840
gtccatacaa gaggactgga cttcgcgtcc gataaaccta ctaccactcc agccccaagg     900
cccccaaccc cagcaccgac tatcgcatca cagcctttgt cactgcgtcc tgaagccagc     960
cggccagctg caggggggc cgtccacaca aggggactcg actttgcgag tgataagccc    1020
accaccaccc ctgcccctag acctccaacc ccagccccta caatcgccag ccagcccctg    1080
agcctgaggc ccgaagcctg tagacctgcc gctggcggag ccgtgcacac cagaggcctg    1140
gatttcgcct gcgacatcta catctgggcc cctctggccg gcacctgtgg cgtgctgctg    1200
ctgagcctgg tcatcaccct gtactgcaac caccggaata ggagcaagcg gagcagaggc    1260
ggccacagcg actacatgaa catgaccccc cggaggcctg gccccacccg gaagcactac    1320
cagccctacg cccctcccag ggacttcgcc gcctaccgga gccgggtgaa gttcagccgg    1380
agcgccgacg cccctgccta ccagcagggc cagaaccagc tgtacaacga gctgaacctg    1440
ggccggaggg aggagtacga cgtgctggac aagcggagag gccgggaccc tgagatgggc    1500
ggcaagcccc ggagaaagaa ccctcaggag ggcctgtata acgaactgca gaaagacaag    1560
atggccgagg cctacagcga gatcggcatg aagggcgagc ggcggagggg caagggccac    1620
gacggcctgt accagggcct gagcaccgcc accaaggata cctacgacgc cctgcacatg    1680
caggccctgc cccccaga                                                 1698
```

<210> SEQ ID NO 601
<211> LENGTH: 613
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 601

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30
```

-continued

```
Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys Gly Ser Thr Ser Gly
            100                 105                 110

Ser Gly Lys Pro Gly Ser Gly Glu Gly Ser Thr Lys Gly Glu Val Lys
        115                 120                 125

Leu Val Glu Ser Gly Gly Gly Leu Val Lys Pro Gly Gly Ser Leu Lys
    130                 135                 140

Leu Ser Cys Ala Ala Ser Gly Phe Thr Phe Ser Ser Tyr Ala Met Ser
145                 150                 155                 160

Trp Val Arg Gln Ile Pro Glu Lys Arg Leu Glu Trp Val Ala Ser Ile
                165                 170                 175

Ser Arg Gly Gly Thr Thr Tyr Tyr Pro Asp Ser Val Lys Gly Arg Phe
            180                 185                 190

Thr Ile Ser Arg Asp Asn Val Arg Asn Ile Leu Tyr Leu Gln Met Ser
        195                 200                 205

Ser Leu Arg Ser Glu Asp Thr Ala Met Tyr Tyr Cys Gly Arg Tyr Asp
    210                 215                 220

Tyr Asp Gly Tyr Tyr Ala Met Asp Tyr Trp Gly Gln Gly Thr Ser Val
225                 230                 235                 240

Thr Val Ser Ser Lys Pro Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Ser Arg Pro Ala Ala Gly Gly Ala Val His Thr Arg Gly Leu Asp Phe
        275                 280                 285

Ala Ser Asp Lys Pro Thr Thr Thr Pro Ala Pro Arg Pro Pro Thr Pro
    290                 295                 300

Ala Pro Thr Ile Ala Ser Gln Pro Leu Ser Leu Arg Pro Glu Ala Ser
305                 310                 315                 320

Arg Pro Ala Ala Gly Gly Ala Val His Thr Arg Gly Leu Asp Phe Ala
                325                 330                 335

Ser Asp Lys Pro Thr Thr Thr Pro Ala Pro Arg Pro Pro Thr Pro Ala
            340                 345                 350

Pro Thr Ile Ala Ser Gln Pro Leu Ser Leu Arg Pro Glu Ala Ser Arg
        355                 360                 365

Pro Ala Ala Gly Gly Ala Val His Thr Arg Gly Leu Asp Phe Ala Ser
    370                 375                 380

Asp Lys Pro Thr Thr Thr Pro Ala Pro Arg Pro Pro Thr Pro Ala Pro
385                 390                 395                 400

Thr Ile Ala Ser Gln Pro Leu Ser Leu Arg Pro Glu Ala Cys Arg Pro
                405                 410                 415

Ala Ala Gly Gly Ala Val His Thr Arg Gly Leu Asp Phe Ala Cys Asp
            420                 425                 430

Ile Tyr Ile Trp Ala Pro Leu Ala Gly Thr Cys Gly Val Leu Leu Leu
        435                 440                 445
```

-continued

```
Ser Leu Val Ile Thr Leu Tyr Cys Asn His Arg Asn Arg Ser Lys Arg
    450                 455                 460

Ser Arg Gly Gly His Ser Asp Tyr Met Asn Met Thr Pro Arg Arg Pro
465                 470                 475                 480

Gly Pro Thr Arg Lys His Tyr Gln Pro Tyr Ala Pro Pro Arg Asp Phe
                485                 490                 495

Ala Ala Tyr Arg Ser Arg Val Lys Phe Ser Arg Ser Ala Asp Ala Pro
            500                 505                 510

Ala Tyr Gln Gln Gly Gln Asn Gln Leu Tyr Asn Glu Leu Asn Leu Gly
        515                 520                 525

Arg Arg Glu Glu Tyr Asp Val Leu Asp Lys Arg Arg Gly Arg Asp Pro
    530                 535                 540

Glu Met Gly Gly Lys Pro Arg Arg Lys Asn Pro Gln Glu Gly Leu Tyr
545                 550                 555                 560

Asn Glu Leu Gln Lys Asp Lys Met Ala Glu Ala Tyr Ser Glu Ile Gly
                565                 570                 575

Met Lys Gly Glu Arg Arg Arg Gly Lys Gly His Asp Gly Leu Tyr Gln
            580                 585                 590

Gly Leu Ser Thr Ala Thr Lys Asp Thr Tyr Asp Ala Leu His Met Gln
        595                 600                 605

Ala Leu Pro Pro Arg
    610


<210> SEQ ID NO 602
<211> LENGTH: 1839
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 602

gacatcaaga tgacccagag ccccagctct atgtacgcca gcctgggcga gcgcgtgacc     60

atcacatgca aggccagccc cgacatcaac agctacctgt cctggttcca gcagaagccc    120

ggcaagagcc ccaagaccct gatctaccgg gccaaccggc tggtggacgg cgtgccaagc    180

agattttccg gcggaggcag cggccaggac tacagcctga ccatcaacag cctggaatac    240

gaggacatgg gcatctacta ctgcctgcag tacgacgagt tcccctacac cttcggaggc    300

ggcaccaagc tggaaatgaa gggcagcacc tccggcagcg gcaagcctgg cagcggcgag    360

ggcagcacca agggcgaagt gaagctggtg gaaagcggcg gaggcctggt gaaacctggc    420

ggcagcctga agctgagctg cgccgccagc ggcttcacct tcagcagcta cgccatgagc    480

tgggtccgac agatccccga gaagcggctg gaatgggtgg ccagcatcag caggggcggc    540

accacctact accccgacag cgtgaagggc cggttcacca tcagccggga caacgtgcgg    600

aacatcctgt acctgcagat gagcagcctg cggagcgagg acaccgccat gtactactgc    660

ggcagatacg actacgacgg ctactacgcc atggattact ggggccaggg caccagcgtg    720

accgtgtcta gcaagcctac caccaccccc gcacctcgtc ctccaacccc tgcacctacg    780

attgccagtc agcctctttc actgcggcct gaggccagca gaccagctgc cggcggtgcc    840

gtccatacaa gaggactgga cttcgcgtcc gataaaccta ctaccactcc agccccaagg    900

cccccaaccc cagcaccgac tatcgcatca cagcctttgt cactgcgtcc tgaagccagc    960

cggccagctg caggggggggc cgtccacaca aggggactcg actttgcgag tgataaacct   1020

actacaactc ctgcccccccg gcctcctaca ccagctccta ctatcgcctc ccagccactc   1080
```

```
agtctcagac ccgaggcttc taggccagcg gccggaggcg cggtccacac ccgcgggctg   1140

gactttgcat ccgataagcc caccaccacc cctgccccta gacctccaac cccagcccct   1200

acaatcgcca gccagcccct gagcctgagg cccgaagcct gtagacctgc cgctggcgga   1260

gccgtgcaca ccagaggcct ggatttcgcc tgcgacatct acatctgggc ccctctggcc   1320

ggcacctgtg gcgtgctgct gctgagcctg gtcatcaccc tgtactgcaa ccaccggaat   1380

aggagcaagc ggagcagagg cggccacagc gactacatga acatgacccc ccggaggcct   1440

ggccccaccc ggaagcacta ccagccctac gcccctccca gggacttcgc cgcctaccgg   1500

agccgggtga agttcagccg gagcgccgac gcccctgcct accagcaggg ccagaaccag   1560

ctgtacaacg agctgaacct gggccggagg gaggagtacg acgtgctgga caagcggaga   1620

ggccgggacc ctgagatggg cggcaagccc cggagaaaga accctcagga gggcctgtat   1680

aacgaactgc agaaagacaa gatggccgag gcctacagcg agatcggcat gaagggcgag   1740

cggcggaggg gcaagggcca cgacggcctg taccagggcc tgagcaccgc caccaaggat   1800

acctacgacg ccctgcacat gcaggccctg ccccccaga                          1839
```

```
<210> SEQ ID NO 603
<211> LENGTH: 647
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 603

Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys Gly Ser Thr Ser Gly
            100                 105                 110

Ser Gly Lys Pro Gly Ser Gly Glu Gly Ser Thr Lys Gly Glu Val Lys
        115                 120                 125

Leu Val Glu Ser Gly Gly Gly Leu Val Lys Pro Gly Gly Ser Leu Lys
    130                 135                 140

Leu Ser Cys Ala Ala Ser Gly Phe Thr Phe Ser Ser Tyr Ala Met Ser
145                 150                 155                 160

Trp Val Arg Gln Ile Pro Glu Lys Arg Leu Glu Trp Val Ala Ser Ile
                165                 170                 175

Ser Arg Gly Gly Thr Thr Tyr Tyr Pro Asp Ser Val Lys Gly Arg Phe
            180                 185                 190

Thr Ile Ser Arg Asp Asn Val Arg Asn Ile Leu Tyr Leu Gln Met Ser
        195                 200                 205

Ser Leu Arg Ser Glu Asp Thr Ala Met Tyr Tyr Cys Gly Arg Tyr Asp
    210                 215                 220
```

-continued

```
Tyr Asp Gly Tyr Tyr Ala Met Asp Tyr Trp Gly Gln Gly Thr Ser Val
225                 230                 235                 240

Thr Val Ser Ser Lys Glu Ala Cys Pro Thr Gly Leu Tyr Thr His Ser
                245                 250                 255

Gly Glu Cys Cys Lys Ala Cys Asn Leu Gly Glu Gly Val Ala Gln Pro
            260                 265                 270

Cys Gly Ala Asn Gln Thr Val Cys Glu Pro Cys Leu Asp Ser Val Thr
        275                 280                 285

Phe Ser Asp Val Val Ser Ala Thr Glu Pro Cys Lys Pro Cys Thr Glu
    290                 295                 300

Cys Val Gly Leu Gln Ser Met Ser Ala Pro Cys Val Glu Ala Asp Asp
305                 310                 315                 320

Ala Val Cys Arg Cys Ala Tyr Gly Tyr Tyr Gln Asp Glu Thr Thr Gly
                325                 330                 335

Arg Cys Glu Ala Cys Arg Val Cys Glu Ala Gly Ser Gly Leu Val Phe
            340                 345                 350

Ser Cys Gln Asp Lys Gln Asn Thr Val Cys Glu Glu Cys Pro Asp Gly
        355                 360                 365

Thr Tyr Ser Asp Glu Ala Asn His Val Asp Pro Cys Leu Pro Cys Thr
    370                 375                 380

Val Cys Glu Asp Thr Glu Arg Gln Leu Arg Glu Cys Thr Arg Trp Ala
385                 390                 395                 400

Asp Ala Glu Cys Glu Glu Ile Pro Gly Arg Trp Ile Thr Arg Ser Thr
                405                 410                 415

Pro Pro Glu Gly Ser Asp Ser Thr Ala Pro Ser Thr Gln Glu Pro Glu
            420                 425                 430

Ala Pro Pro Glu Gln Asp Leu Ile Ala Ser Thr Val Ala Gly Val Val
        435                 440                 445

Thr Thr Val Met Gly Ser Ser Gln Pro Val Val Thr Arg Gly Thr Thr
    450                 455                 460

Asp Asn Ile Tyr Ile Trp Ala Pro Leu Ala Gly Thr Cys Gly Val Leu
465                 470                 475                 480

Leu Leu Ser Leu Val Ile Thr Leu Tyr Cys Asn His Arg Asn Arg Ser
                485                 490                 495

Lys Arg Ser Arg Gly Gly His Ser Asp Tyr Met Asn Met Thr Pro Arg
            500                 505                 510

Arg Pro Gly Pro Thr Arg Lys His Tyr Gln Pro Tyr Ala Pro Pro Arg
        515                 520                 525

Asp Phe Ala Ala Tyr Arg Ser Arg Val Lys Phe Ser Arg Ser Ala Asp
    530                 535                 540

Ala Pro Ala Tyr Gln Gln Gly Gln Asn Gln Leu Tyr Asn Glu Leu Asn
545                 550                 555                 560

Leu Gly Arg Arg Glu Glu Tyr Asp Val Leu Asp Lys Arg Arg Gly Arg
                565                 570                 575

Asp Pro Glu Met Gly Gly Lys Pro Arg Arg Lys Asn Pro Gln Glu Gly
            580                 585                 590

Leu Tyr Asn Glu Leu Gln Lys Asp Lys Met Ala Glu Ala Tyr Ser Glu
        595                 600                 605

Ile Gly Met Lys Gly Glu Arg Arg Arg Gly Lys Gly His Asp Gly Leu
    610                 615                 620

Tyr Gln Gly Leu Ser Thr Ala Thr Lys Asp Thr Tyr Asp Ala Leu His
625                 630                 635                 640
```

Met Gln Ala Leu Pro Pro Arg
645

<210> SEQ ID NO 604
<211> LENGTH: 1941
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 604
gacatcaaga tgacccagag ccccagctct atgtacgcca gcctgggcga gcgcgtgacc 60
atcacatgca aggccagccc cgacatcaac agctacctgt cctggttcca gcagaagccc 120
ggcaagagcc ccaagaccct gatctaccgg gccaaccggc tggtggacgg cgtgccaagc 180
agattttccg gcggaggcag cggccaggac tacagcctga ccatcaacag cctggaatac 240
gaggacatgg gcatctacta ctgcctgcag tacgacgagt tcccctacac cttcggaggc 300
ggcaccaagc tggaaatgaa gggcagcacc tccggcagcg gcaagcctgg cagcggcgag 360
ggcagcacca agggcgaagt gaagctggtg gaaagcggcg gaggcctggt gaaacctggc 420
ggcagcctga agctgagctg cgccgccagc ggcttcacct tcagcagcta cgccatgagc 480
tgggtccgac agatccccga gaagcggctg gaatgggtgg ccagcatcag caggggcggc 540
accacctact accccgacag cgtgaagggc cggttcacca tcagccggga caacgtgcgg 600
aacatcctgt acctgcagat gagcagcctg cggagcgagg acaccgccat gtactactgc 660
ggcagatacg actacgacgg ctactacgcc atggattact ggggccaggg caccagcgtg 720
accgtgtcta gcaaggaggc atgccccaca ggcctgtaca cacacagcgg tgagtgctgc 780
aaagcctgca acctgggcga gggtgtggcc cagccttgtg gagccaacca gaccgtgtgt 840
gagccctgcc tggacagcgt gacgttctcc gacgtggtga gcgcgaccga gccgtgcaag 900
ccgtgcaccg agtgcgtggg gctccagagc atgtcggcgc cgtgcgtgga ggccgacgac 960
gccgtgtgcc gctgcgccta cggctactac caggatgaga cgactgggcg ctgcgaggcg 1020
tgccgcgtgt gcgaggcggg ctcgggcctc gtgttctcct gccaggacaa gcagaacacc 1080
gtgtgcgagg agtgccccga cggcacgtat tccgacgagg ccaaccacgt ggacccgtgc 1140
ctgccctgca ccgtgtgcga ggacaccgag cgccagctcc gcgagtgcac acgctgggcc 1200
gacgccgagt gcgaggagat ccctggccgt tggattacac ggtccacacc cccagagggc 1260
tcggacagca cagcccccag cacccaggag cctgaggcac ctccagaaca agacctcata 1320
gccagcacgg tggcaggtgt ggtgaccaca gtgatgggca gctcccagcc cgtggtgacc 1380
cgaggcacca ccgacaacat ctacatctgg gcccctctgg ccggcacctg tggcgtgctg 1440
ctgctgagcc tggtcatcac cctgtactgc aaccaccgga ataggagcaa gcggagcaga 1500
ggcggccaca gcgactacat gaacatgacc ccccggaggc ctggccccac ccggaagcac 1560
taccagccct acgcccctcc cagggacttc gccgcctacc ggagccgggt gaagttcagc 1620
cggagcgccg acgcccctgc ctaccagcag ggccagaacc agctgtacaa cgagctgaac 1680
ctgggccgga gggaggagta cgacgtgctg gacaagcgga gaggccggga ccctgagatg 1740
ggcggcaagc cccggagaaa gaaccctcag gagggcctgt ataacgaact gcagaaagac 1800
aagatggccg aggcctacag cgagatcggc atgaagggcg agcggcggag gggcaagggc 1860
cacgacggcc tgtaccaggg cctgagcacc gccaccaagg atacctacga cgccctgcac 1920
atgcaggccc tgccccccag a 1941

<210> SEQ ID NO 605
<211> LENGTH: 567
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 605

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ile Pro Glu Lys Arg Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Ser Val Thr Val Ser Ser Gly Ser Thr Ser Gly Ser Gly Lys Pro
        115                 120                 125

Gly Ser Gly Glu Gly Ser Thr Lys Gly Asp Ile Lys Met Thr Gln Ser
    130                 135                 140

Pro Ser Ser Met Tyr Ala Ser Leu Gly Glu Arg Val Thr Ile Thr Cys
145                 150                 155                 160

Lys Ala Ser Pro Asp Ile Asn Ser Tyr Leu Ser Trp Phe Gln Gln Lys
                165                 170                 175

Pro Gly Lys Ser Pro Lys Thr Leu Ile Tyr Arg Ala Asn Arg Leu Val
            180                 185                 190

Asp Gly Val Pro Ser Arg Phe Ser Gly Gly Gly Ser Gly Gln Asp Tyr
        195                 200                 205

Ser Leu Thr Ile Asn Ser Leu Glu Tyr Glu Asp Met Gly Ile Tyr Tyr
    210                 215                 220

Cys Leu Gln Tyr Asp Glu Phe Pro Tyr Thr Phe Gly Gly Gly Thr Lys
225                 230                 235                 240

Leu Glu Met Lys Lys Pro Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Ser Arg Pro Ala Ala Gly Gly Ala Val His Thr Arg Gly Leu Asp Phe
        275                 280                 285

Ala Ser Asp Lys Pro Thr Thr Thr Pro Ala Pro Arg Pro Pro Thr Pro
    290                 295                 300

Ala Pro Thr Ile Ala Ser Gln Pro Leu Ser Leu Arg Pro Glu Ala Ser
305                 310                 315                 320

Arg Pro Ala Ala Gly Gly Ala Val His Thr Arg Gly Leu Asp Phe Ala
                325                 330                 335

Ser Asp Lys Pro Thr Thr Thr Pro Ala Pro Arg Pro Pro Thr Pro Ala
            340                 345                 350

Pro Thr Ile Ala Ser Gln Pro Leu Ser Leu Arg Pro Glu Ala Cys Arg
```

```
        355                 360                 365

Pro Ala Ala Gly Gly Ala Val His Thr Arg Gly Leu Asp Phe Ala Cys
    370                 375                 380

Asp Ile Tyr Ile Trp Ala Pro Leu Ala Gly Thr Cys Gly Val Leu Leu
385                 390                 395                 400

Leu Ser Leu Val Ile Thr Leu Tyr Cys Asn His Arg Asn Lys Arg Gly
                405                 410                 415

Arg Lys Lys Leu Leu Tyr Ile Phe Lys Gln Pro Phe Met Arg Pro Val
            420                 425                 430

Gln Thr Thr Gln Glu Glu Asp Gly Cys Ser Cys Arg Phe Pro Glu Glu
        435                 440                 445

Glu Glu Gly Gly Cys Glu Leu Arg Val Lys Phe Ser Arg Ser Ala Asp
    450                 455                 460

Ala Pro Ala Tyr Gln Gln Gly Gln Asn Gln Leu Tyr Asn Glu Leu Asn
465                 470                 475                 480

Leu Gly Arg Arg Glu Glu Tyr Asp Val Leu Asp Lys Arg Arg Gly Arg
                485                 490                 495

Asp Pro Glu Met Gly Gly Lys Pro Arg Arg Lys Asn Pro Gln Glu Gly
            500                 505                 510

Leu Tyr Asn Glu Leu Gln Lys Asp Lys Met Ala Glu Ala Tyr Ser Glu
        515                 520                 525

Ile Gly Met Lys Gly Glu Arg Arg Arg Gly Lys Gly His Asp Gly Leu
    530                 535                 540

Tyr Gln Gly Leu Ser Thr Ala Thr Lys Asp Thr Tyr Asp Ala Leu His
545                 550                 555                 560

Met Gln Ala Leu Pro Pro Arg
                565
```

<210> SEQ ID NO 606
<211> LENGTH: 1701
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 606

```
gaagtgaagc tggtggaaag cggcggaggc ctggtgaaac ctggcggcag cctgaagctg     60

agctgcgccg ccagcggctt caccttcagc agctacgcca tgagctgggt ccgacagatc    120

cccgagaagc ggctggaatg ggtggccagc atcagcaggg gcggcaccac ctactacccc    180

gacagcgtga agggccggtt caccatcagc cgggacaacg tgcggaacat cctgtacctg    240

cagatgagca gcctgcggag cgaggacacc gccatgtact actgcggcag atacgactac    300

gacggctact acgccatgga ttactggggc cagggcacca gcgtgaccgt gtctagcggc    360

agcacctccg gcagcggcaa gcctggcagc ggcgagggca gcaccaaggg cgacatcaag    420

atgacccaga gccccagctc tatgtacgcc agcctgggcg agcgcgtgac catcacatgc    480

aaggccagcc ccgacatcaa cagctacctg tcctggttcc agcagaagcc cggcaagagc    540

cccaagaccc tgatctaccg ggccaaccgg ctggtggacg gcgtgccaag cagattttcc    600

ggcggaggca gcggccagga ctacagcctg accatcaaca gcctggaata cgaggacatg    660

ggcatctact actgcctgca gtacgacgag ttcccctaca ccttcggagg cggcaccaag    720

ctggaaatga agaagcctac caccaccccc gcacctcgtc ctccaacccc tgcacctacg    780

attgccagtc agcctctttc actgcggcct gaggccagca gaccagctgc cggcggtgcc    840
```

gtccatacaa gaggactgga cttcgcgtcc gataaaccta ctaccactcc agccccaagg 900
cccccaaccc cagcaccgac tatcgcatca cagcctttgt cactgcgtcc tgaagccagc 960
cggccagctg caggggggc cgtccacaca aggggactcg actttgcgag tgataagccc 1020
accaccaccc ctgcccctag acctccaacc ccagccccta caatcgccag ccagcccctg 1080
agcctgaggc ccgaagcctg tagacctgcc gctggcggag ccgtgcacac cagaggcctg 1140
gatttcgcct gcgacatcta catctgggcc cctctggccg gcacctgtgg cgtgctgctg 1200
ctgagcctgg tcatcaccct gtactgcaac caccggaata agagaggccg gaagaaactg 1260
ctgtacatct tcaagcagcc cttcatgcgg cccgtgcaga ccacccagga agaggacggc 1320
tgcagctgcc ggttccccga ggaagaggaa ggcggctgcg aactgcgggt gaagttcagc 1380
cggagcgccg acgcccctgc ctaccagcag ggccagaacc agctgtacaa cgagctgaac 1440
ctgggccgga gggaggagta cgacgtgctg gacaagcgga gaggccggga ccctgagatg 1500
ggcggcaagc cccggagaaa gaaccctcag gagggcctgt ataacgaact gcagaaagac 1560
aagatggccg aggcctacag cgagatcggc atgaagggcg agcggcggag gggcaagggc 1620
cacgacggcc tgtaccaggg cctgagcacc gccaccaagg atacctacga cgccctgcac 1680
atgcaggccc tgccccccag a 1701

<210> SEQ ID NO 607
<211> LENGTH: 656
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 607

Glu Val Lys Leu Val Glu Ser Gly Gly Gly Leu Val Lys Pro Gly Gly
1 5 10 15

Ser Leu Lys Leu Ser Cys Ala Ala Ser Gly Phe Thr Phe Ser Ser Tyr
20 25 30

Ala Met Ser Trp Val Arg Gln Ile Pro Glu Lys Arg Leu Glu Trp Val
35 40 45

Ala Ser Ile Ser Arg Gly Gly Thr Thr Tyr Tyr Pro Asp Ser Val Lys
50 55 60

Gly Arg Phe Thr Ile Ser Arg Asp Asn Val Arg Asn Ile Leu Tyr Leu
65 70 75 80

Gln Met Ser Ser Leu Arg Ser Glu Asp Thr Ala Met Tyr Tyr Cys Gly
85 90 95

Arg Tyr Asp Tyr Asp Gly Tyr Tyr Ala Met Asp Tyr Trp Gly Gln Gly
100 105 110

Thr Ser Val Thr Val Ser Ser Gly Ser Thr Ser Gly Ser Gly Lys Pro
115 120 125

Gly Ser Gly Glu Gly Ser Thr Lys Gly Asp Ile Lys Met Thr Gln Ser
130 135 140

Pro Ser Ser Met Tyr Ala Ser Leu Gly Glu Arg Val Thr Ile Thr Cys
145 150 155 160

Lys Ala Ser Pro Asp Ile Asn Ser Tyr Leu Ser Trp Phe Gln Gln Lys
165 170 175

Pro Gly Lys Ser Pro Lys Thr Leu Ile Tyr Arg Ala Asn Arg Leu Val
180 185 190

Asp Gly Val Pro Ser Arg Phe Ser Gly Gly Gly Ser Gly Gln Asp Tyr

-continued

```
        195                 200                 205

Ser Leu Thr Ile Asn Ser Leu Glu Tyr Glu Asp Met Gly Ile Tyr Tyr
    210                 215                 220

Cys Leu Gln Tyr Asp Glu Phe Pro Tyr Thr Phe Gly Gly Gly Thr Lys
225                 230                 235                 240

Leu Glu Met Lys Glu Ser Lys Tyr Gly Pro Pro Cys Pro Pro Cys Pro
                245                 250                 255

Ala Pro Glu Phe Glu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser Gln Glu Asp Pro Glu Val Gln Phe Asn Trp Tyr
    290                 295                 300

Val Asp Gly Val Glu Val His Asn Ala Lys Thr Lys Pro Arg Glu Glu
305                 310                 315                 320

Gln Phe Gln Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Gly Leu Pro Ser Ser Ile Glu Lys Thr Ile Ser Lys Ala Lys Gly Gln
        355                 360                 365

Pro Arg Glu Pro Gln Val Tyr Thr Leu Pro Pro Ser Gln Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Arg Leu Thr Val Asp Lys Ser Arg Trp Gln Glu Gly Asn Val
        435                 440                 445

Phe Ser Cys Ser Val Met His Glu Ala Leu His Asn His Tyr Thr Gln
    450                 455                 460

Lys Ser Leu Ser Leu Ser Leu Gly Lys Met Ile Tyr Ile Trp Ala Pro
465                 470                 475                 480

Leu Ala Gly Thr Cys Gly Val Leu Leu Leu Ser Leu Val Ile Thr Leu
                485                 490                 495

Tyr Cys Asn His Arg Asn Lys Arg Gly Arg Lys Lys Leu Leu Tyr Ile
            500                 505                 510

Phe Lys Gln Pro Phe Met Arg Pro Val Gln Thr Thr Gln Glu Glu Asp
        515                 520                 525

Gly Cys Ser Cys Arg Phe Pro Glu Glu Glu Glu Gly Gly Cys Glu Leu
    530                 535                 540

Arg Val Lys Phe Ser Arg Ser Ala Asp Ala Pro Ala Tyr Gln Gln Gly
545                 550                 555                 560

Gln Asn Gln Leu Tyr Asn Glu Leu Asn Leu Gly Arg Arg Glu Glu Tyr
                565                 570                 575

Asp Val Leu Asp Lys Arg Arg Gly Arg Asp Pro Glu Met Gly Gly Lys
            580                 585                 590

Pro Arg Arg Lys Asn Pro Gln Glu Gly Leu Tyr Asn Glu Leu Gln Lys
        595                 600                 605

Asp Lys Met Ala Glu Ala Tyr Ser Glu Ile Gly Met Lys Gly Glu Arg
    610                 615                 620
```

Arg Arg Gly Lys Gly His Asp Gly Leu Tyr Gln Gly Leu Ser Thr Ala
625 630 635 640

Thr Lys Asp Thr Tyr Asp Ala Leu His Met Gln Ala Leu Pro Pro Arg
645 650 655

<210> SEQ ID NO 608
<211> LENGTH: 1968
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 608
gaagtgaagc tggtggaaag cggcggaggc ctggtgaaac ctggcggcag cctgaagctg 60
agctgcgccg ccagcggctt caccttcagc agctacgcca tgagctgggt ccgacagatc 120
cccgagaagc ggctggaatg ggtggccagc atcagcaggg gcggcaccac ctactacccc 180
gacagcgtga agggccggtt caccatcagc cgggacaacg tgcggaacat cctgtacctg 240
cagatgagca gcctgcggag cgaggacacc gccatgtact actgcggcag atacgactac 300
gacggctact acgccatgga ttactggggc cagggcacca gcgtgaccgt gtctagcggc 360
agcacctccg gcagcggcaa gcctggcagc ggcgagggca gcaccaaggg cgacatcaag 420
atgacccaga gccccagctc tatgtacgcc agcctgggcg agcgcgtgac catcacatgc 480
aaggccagcc ccgacatcaa cagctacctg tcctggttcc agcagaagcc cggcaagagc 540
cccaagaccc tgatctaccg ggccaaccgg ctggtggacg gcgtgccaag cagattttcc 600
ggcggaggca gcggccagga ctacagcctg accatcaaca gcctggaata cgaggacatg 660
ggcatctact actgcctgca gtacgacgag ttccccctaca ccttcggagg cggcaccaag 720
ctggaaatga aggagagcaa gtacggccct ccctgccccc cttgccctgc ccccgagttc 780
gagggcggac ccagcgtgtt cctgttcccc cccaagccca aggacaccct gatgatcagc 840
cggacccccg aggtgacctg tgtggtggtg gacgtgtccc aggaggaccc cgaggtccag 900
ttcaactggt acgtggacgg cgtggaggtg cacaacgcca agaccaagcc ccgggaggag 960
cagttccaga gcacctaccg ggtggtgtcc gtgctgaccg tgctgcacca ggactggctg 1020
aacggcaagg aatacaagtg taaggtgtcc aacaagggcc tgcccagcag catcgagaaa 1080
accatcagca aggccaaggg ccagcctcgg gagccccagg tgtacaccct gcccccctagc 1140 caagaggaga tgaccaagaa tcaggtgtcc ctgacctgcc tggtgaaggg cttctacccc 1200
agcgacatcg ccgtggagtg ggagagcaac ggccagcccg agaacaacta caagaccacc 1260
ccccctgtgc tggacagcga cggcagcttc ttcctgtaca gcaggctgac cgtggacaag 1320
agccggtggc aggagggcaa cgtctttagc tgctccgtga tgcacgaggc cctgcacaac 1380
cactacaccc agaagagcct gtccctgagc ctgggcaaga tgatctacat ctgggcccct 1440
ctggccggca cctgtggcgt gctgctgctg agcctggtca tcaccctgta ctgcaaccac 1500
cggaataaga gaggccggaa gaaactgctg tacatcttca agcagccctt catgcggccc 1560
gtgcagacca cccaggaaga ggacggctgc agctgccggt tccccgagga agaggaaggc 1620
ggctgcgaac tgcgggtgaa gttcagccgg agcgccgacg cccctgccta ccagcagggc 1680
cagaaccagc tgtacaacga gctgaacctg ggccggaggg aggagtacga cgtgctggac 1740
aagcggagag gccgggaccc tgagatgggc ggcaagcccc ggagaaagaa ccctcaggag 1800
ggcctgtata acgaactgca gaaagacaag atggccgagg cctacagcga gatcggcatg 1860
aagggcgagc ggcggagggg caagggccac gacggcctgt accagggcct gagcaccgcc 1920
accaaggata cctacgacgc cctgcacatg caggccctgc cccccaga 1968

<210> SEQ ID NO 609
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 609

Asp Val Gln Ile Thr Gln Ser Pro Ser Ser Leu Tyr Ala Ser Leu Gly
1 5 10 15

Glu Arg Val Thr Ile Thr Cys Lys Ala Ser Pro Asp Ile Asn Ser Tyr
20 25 30

Leu Ser Trp Phe Gln Gln Lys Pro Gly Lys Ser Pro Lys Thr Leu Ile
35 40 45

Tyr Arg Ala Asn Arg Leu Val Asp Gly Val Pro Ser Arg Phe Ser Gly
50 55 60

Gly Gly Ser Gly Gln Asp Tyr Ser Leu Thr Ile Asn Ser Leu Glu Tyr
65 70 75 80

Glu Asp Met Gly Ile Tyr Tyr Cys Leu Gln Tyr Asp Glu Phe Pro Tyr
85 90 95

Thr Phe Gly Gly Gly Thr Lys Leu Glu Met Lys
100 105

<210> SEQ ID NO 610
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 610
gacgtgcaga tcacccagag ccccagcagc ctgtatgcca gcctgggcga gagagtgacc 60
attacctgca aggccagccc cgacatcaac agctacctga gctggttcca gcagaagccc 120
ggcaagagcc ccaagaccct gatctaccgg gccaacagac tggtggatgg cgtgcccagc 180
agattcagcg gcggaggctc tggccaggac tacagcctga ccatcaactc cctggaatac 240
gaggacatgg gcatctacta ctgcctgcag tacgacgagt tcccctacac cttcggaggc 300
ggcaccaagc tggaaatgaa g 321

<210> SEQ ID NO 611
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 611

Glu Val Lys Leu Val Glu Ser Gly Gly Gly Leu Val Lys Pro Gly Gly
1 5 10 15

Ser Leu Lys Leu Ser Cys Ala Ala Ser Gly Phe Thr Phe Ser Ser Tyr
20 25 30

Ala Met Ser Trp Val Arg Gln Ile Pro Glu Lys Arg Leu Glu Trp Val
35 40 45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Ser Val Thr Val Ser Ser
        115

<210> SEQ ID NO 612
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 612
gaagtgaagc tggtggaatc tggcggcgga ctcgtgaagc ctggcggctc tctgaagctg      60
tcttgtgccg ccagcggctt caccttcagc agctacgcca tgagctgggt gcggcagatc     120
cccgagaagc ggctggaatg ggtggccagc atcagcagag gcggaaccac ctactacccc     180
gactctgtga agggccggtt caccatcagc cgggacaacg tgcggaacat cctgtacctg     240
cagatgagca gcctgcggag cgaggacacc gccatgtact actgtggcag atacgactac     300
gacggctact atgccatgga ttactggggc cagggcacca gcgtgaccgt gtcatct        357

<210> SEQ ID NO 613
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 613

Asp Val Gln Ile Thr Gln Ser Pro Ser Ser Leu Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys Gly Ser Thr Ser Gly
            100                 105                 110

Ser Gly Lys Pro Gly Ser Gly Glu Gly Ser Thr Lys Gly Glu Val Lys
        115                 120                 125

Leu Val Glu Ser Gly Gly Gly Leu Val Lys Pro Gly Gly Ser Leu Lys
    130                 135                 140

Leu Ser Cys Ala Ala Ser Gly Phe Thr Phe Ser Ser Tyr Ala Met Ser
145                 150                 155                 160

-continued

```
Trp Val Arg Gln Ile Pro Glu Lys Arg Leu Glu Trp Val Ala Ser Ile
                165                 170                 175

Ser Arg Gly Gly Thr Thr Tyr Tyr Pro Asp Ser Val Lys Gly Arg Phe
            180                 185                 190

Thr Ile Ser Arg Asp Asn Val Arg Asn Ile Leu Tyr Leu Gln Met Ser
        195                 200                 205

Ser Leu Arg Ser Glu Asp Thr Ala Met Tyr Tyr Cys Gly Arg Tyr Asp
    210                 215                 220

Tyr Asp Gly Tyr Tyr Ala Met Asp Tyr Trp Gly Gln Gly Thr Ser Val
225                 230                 235                 240

Thr Val Ser Ser Lys Pro Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Ser Arg Pro Ala Ala Gly Gly Ala Val His Thr Arg Gly Leu Asp Phe
        275                 280                 285

Ala Ser Asp Lys Pro Thr Thr Thr Pro Ala Pro Arg Pro Pro Thr Pro
    290                 295                 300

Ala Pro Thr Ile Ala Ser Gln Pro Leu Ser Leu Arg Pro Glu Ala Ser
305                 310                 315                 320

Arg Pro Ala Ala Gly Gly Ala Val His Thr Arg Gly Leu Asp Phe Ala
                325                 330                 335

Ser Asp Lys Pro Thr Thr Thr Pro Ala Pro Arg Pro Pro Thr Pro Ala
            340                 345                 350

Pro Thr Ile Ala Ser Gln Pro Leu Ser Leu Arg Pro Glu Ala Cys Arg
        355                 360                 365

Pro Ala Ala Gly Gly Ala Val His Thr Arg Gly Leu Asp Phe Ala Cys
    370                 375                 380

Asp Ile Tyr Ile Trp Ala Pro Leu Ala Gly Thr Cys Gly Val Leu Leu
385                 390                 395                 400

Leu Ser Leu Val Ile Thr Leu Tyr Cys Asn His Arg Asn Arg Ser Lys
                405                 410                 415

Arg Ser Arg Gly Gly His Ser Asp Tyr Met Asn Met Thr Pro Arg Arg
            420                 425                 430

Pro Gly Pro Thr Arg Lys His Tyr Gln Pro Tyr Ala Pro Pro Arg Asp
        435                 440                 445

Phe Ala Ala Tyr Arg Ser Arg Val Lys Phe Ser Arg Ser Ala Asp Ala
    450                 455                 460

Pro Ala Tyr Gln Gln Gly Gln Asn Gln Leu Tyr Asn Glu Leu Asn Leu
465                 470                 475                 480

Gly Arg Arg Glu Glu Tyr Asp Val Leu Asp Lys Arg Arg Gly Arg Asp
                485                 490                 495

Pro Glu Met Gly Gly Lys Pro Arg Arg Lys Asn Pro Gln Glu Gly Leu
            500                 505                 510

Tyr Asn Glu Leu Gln Lys Asp Lys Met Ala Glu Ala Tyr Ser Glu Ile
        515                 520                 525

Gly Met Lys Gly Glu Arg Arg Arg Gly Lys Gly His Asp Gly Leu Tyr
    530                 535                 540

Gln Gly Leu Ser Thr Ala Thr Lys Asp Thr Tyr Asp Ala Leu His Met
545                 550                 555                 560

Gln Ala Leu Pro Pro Arg
                565
```

<210> SEQ ID NO 614
<211> LENGTH: 1698
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 614
gacgtgcaga tcacccagag ccccagcagc ctgtatgcca gcctgggcga gagagtgacc 60
attacctgca aggccagccc cgacatcaac agctacctga gctggttcca gcagaagccc 120
ggcaagagcc ccaagaccct gatctaccgg gccaacagac tggtggatgg cgtgcccagc 180
agattcagcg gcggaggctc tggccaggac tacagcctga ccatcaactc cctggaatac 240
gaggacatgg gcatctacta ctgcctgcag tacgacgagt tcccctacac cttcggaggc 300
ggcaccaagc tggaaatgaa gggcagcaca agcggcagcg gcaagcctgg atctggcgag 360
ggaagcacca agggcgaagt gaagctggtg gaatctggcg gcggactcgt gaagcctggc 420
ggctctctga agctgtcttg tgccgccagc ggcttcacct tcagcagcta cgccatgagc 480
tgggtgcggc agatccccga gaagcggctg gaatgggtgg ccagcatcag cagaggcgga 540
accacctact accccgactc tgtgaagggc cggttcacca tcagccggga caacgtgcgg 600
aacatcctgt acctgcagat gagcagcctg cggagcgagg acaccgccat gtactactgt 660
ggcagatacg actacgacgg ctactatgcc atggattact ggggccaggg caccagcgtg 720
accgtgtcat ctaagcctac caccaccccc gcacctcgtc ctccaacccc tgcacctacg 780
attgccagtc agcctctttc actgcggcct gaggccagca gaccagctgc cggcggtgcc 840
gtccatacaa gaggactgga cttcgcgtcc gataaaccta ctaccactcc agccccaagg 900
cccccaaccc cagcaccgac tatcgcatca cagcctttgt cactgcgtcc tgaagccagc 960
cggccagctg cagggggggc cgtccacaca aggggactcg actttgcgag tgataagccc 1020
accaccaccc ctgcccctag acctccaacc ccagccccta caatcgccag ccagcccctg 1080
agcctgaggc ccgaagcctg tagacctgcc gctggcggag ccgtgcacac cagaggcctg 1140
gatttcgcct gcgacatcta catctgggcc cctctggccg gcacctgtgg cgtgctgctg 1200
ctgagcctgg tcatcaccct gtactgcaac caccggaata ggagcaagcg gagcagaggc 1260
ggccacagcg actacatgaa catgaccccc cggaggcctg gccccacccg gaagcactac 1320
cagccctacg cccctcccag ggacttcgcc gcctaccgga gccgggtgaa gttcagccgg 1380
agcgccgacg cccctgccta ccagcagggc cagaaccagc tgtacaacga gctgaacctg 1440
ggccggaggg aggagtacga cgtgctggac aagcggagag gccgggaccc tgagatgggc 1500
ggcaagcccc ggagaaagaa ccctcaggag ggcctgtata acgaactgca gaaagacaag 1560
atggccgagg cctacagcga gatcggcatg aagggcgagc ggcggagggg caagggccac 1620
gacggcctgt accagggcct gagcaccgcc accaaggata cctacgacgc cctgcacatg 1680
caggccctgc cccccaga 1698

<210> SEQ ID NO 615
<211> LENGTH: 563
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 615

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Ser Tyr
            20                  25                  30

Ala Met Ser Trp Met Arg Gln Ala Pro Gly Lys Gly Leu Glu Trp Val
        35                  40                  45

Ala Ser Ile Ser Arg Gly Gly Thr Thr Tyr Tyr Ala Asp Ser Val Lys
    50                  55                  60

Gly Arg Phe Thr Ile Ser Val Asp Lys Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Pro Asp Ile Asn Ser Tyr Leu Asn Trp Tyr Gln Gln Lys Pro Gly Lys
                165                 170                 175

Ala Pro Lys Leu Leu Ile Tyr Arg Ala Asn Arg Leu Val Asp Gly Val
            180                 185                 190

Pro Ser Arg Phe Ser Gly Ser Gly Ser Gly Thr Asp Tyr Thr Leu Thr
        195                 200                 205

Ile Ser Ser Leu Gln Pro Glu Asp Phe Ala Thr Tyr Tyr Cys Leu Gln
    210                 215                 220

Tyr Asp Glu Phe Pro Tyr Thr Phe Gly Ala Gly Thr Lys Val Glu Ile
225                 230                 235                 240

Lys Lys Pro Thr Thr Thr Pro Ala Pro Arg Pro Pro Thr Pro Ala Pro
                245                 250                 255

Thr Ile Ala Ser Gln Pro Leu Ser Leu Arg Pro Glu Ala Ser Arg Pro
            260                 265                 270

Ala Ala Gly Gly Ala Val His Thr Arg Gly Leu Asp Phe Ala Ser Asp
        275                 280                 285

Lys Pro Thr Thr Thr Pro Ala Pro Arg Pro Pro Thr Pro Ala Pro Thr
    290                 295                 300

Ile Ala Ser Gln Pro Leu Ser Leu Arg Pro Glu Ala Ser Arg Pro Ala
305                 310                 315                 320

Ala Gly Gly Ala Val His Thr Arg Gly Leu Asp Phe Ala Ser Asp Lys
                325                 330                 335

Pro Thr Thr Thr Pro Ala Pro Arg Pro Pro Thr Pro Ala Pro Thr Ile
            340                 345                 350

Ala Ser Gln Pro Leu Ser Leu Arg Pro Glu Ala Cys Arg Pro Ala Ala
        355                 360                 365

Gly Gly Ala Val His Thr Arg Gly Leu Asp Phe Ala Cys Asp Ile Tyr
    370                 375                 380

Ile Trp Ala Pro Leu Ala Gly Thr Cys Gly Val Leu Leu Leu Ser Leu
385                 390                 395                 400

Val Ile Thr Leu Tyr Cys Asn His Arg Asn Arg Ser Lys Arg Ser Arg
                405                 410                 415
```

-continued

```
Gly Gly His Ser Asp Tyr Met Asn Met Thr Pro Arg Arg Pro Gly Pro
            420                 425                 430

Thr Arg Lys His Tyr Gln Pro Tyr Ala Pro Pro Arg Asp Phe Ala Ala
        435                 440                 445

Tyr Arg Ser Arg Val Lys Phe Ser Arg Ser Ala Asp Ala Pro Ala Tyr
    450                 455                 460

Gln Gln Gly Gln Asn Gln Leu Tyr Asn Glu Leu Asn Leu Gly Arg Arg
465                 470                 475                 480

Glu Glu Tyr Asp Val Leu Asp Lys Arg Arg Gly Arg Asp Pro Glu Met
                485                 490                 495

Gly Gly Lys Pro Arg Arg Lys Asn Pro Gln Glu Gly Leu Tyr Asn Glu
            500                 505                 510

Leu Gln Lys Asp Lys Met Ala Glu Ala Tyr Ser Glu Ile Gly Met Lys
        515                 520                 525

Gly Glu Arg Arg Arg Gly Lys Gly His Asp Gly Leu Tyr Gln Gly Leu
    530                 535                 540

Ser Thr Ala Thr Lys Asp Thr Tyr Asp Ala Leu His Met Gln Ala Leu
545                 550                 555                 560

Pro Pro Arg


<210> SEQ ID NO 616
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 616

gaagtgcagc tggtggagtc tggcggcggt ctggtgcagc ccggcggctc tctgcgcctc     60

tcctgtgcca cctctggttt tacattctcc tcctacgcta tgtcctggat gcggcaagcc    120

cccggcaagg gcctagagtg ggtcgcctca atcagcaggg gcgggacgac ttattatgcc    180

gattcagtta aggggagatt cacaatttcc gtggataaat ccaagaatac cttatacctc    240

cagatgaact ctctgcgggc cgaagatacg gccgtatatt attgtgggag gtatgactac    300

gacggatatt acgccatgga ttattggggg caggggacac ttgttacagt gagttccggt    360

ggtggggggt ctggaggcgg gggcagtgga ggcggagggt ctgatataca gatgacacag    420

agcccttcaa gtttatctgc aagcgtcggc gatcgtgtta caataacttg caaggcatct    480

cccgacatca attcctacct caactggtat cagcagaagc ctgggaaggc tcctaagctg    540

cttatttaca gagcaaatcg cctggtggac ggcgtgccca gtcggttttc cgggtctggg    600

agcggaacgg attacacact gaccatctca agcctgcaac ccgaagactt cgctacatat    660

tactgccttc agtatgatga gttcccatat accttcggcg ctgggaccaa ggtggagata    720

aagaagccta ccaccacccc cgcacctcgt cctccaaccc ctgcacctac gattgccagt    780

cagcctcttt cactgcggcc tgaggccagc agaccagctg ccggcggtgc cgtccataca    840

agaggactgg acttcgcgtc cgataaacct actaccactc cagccccaag gcccccaacc    900

ccagcaccga ctatcgcatc acagcctttg tcactgcgtc ctgaagccag ccggccagct    960

gcaggggggg ccgtccacac aaggggactc gactttgcga gtgataagcc caccaccacc   1020

cctgccccta gacctccaac cccagcccct acaatcgcca gccagcccct gagcctgagg   1080

cccgaagcct gtagacctgc cgctggcgga gccgtgcaca ccagaggcct ggatttcgcc   1140

tgcgacatct acatctgggc ccctctggcc ggcacctgtg gcgtgctgct gctgagcctg   1200
```

```
gtcatcaccc tgtactgcaa ccaccggaat aggagcaagc ggagcagagg cggccacagc   1260

gactacatga acatgacccc ccggaggcct ggccccaccc ggaagcacta ccagccctac   1320

gcccctccca gggacttcgc cgcctaccgg agccgggtga agttcagccg gagcgccgac   1380

gcccctgcct accagcaggg ccagaaccag ctgtacaacg agctgaacct gggccggagg   1440

gaggagtacg acgtgctgga caagcggaga ggccgggacc ctgagatggg cggcaagccc   1500

cggagaaaga accctcagga gggcctgtat aacgaactgc agaaagacaa gatggccgag   1560

gcctacagcg agatcggcat gaagggcgag cggcggaggg gcaagggcca cgacggcctg   1620

taccagggcc tgagcaccgc caccaaggat acctacgacg ccctgcacat gcaggccctg   1680

ccccccaga                                                           1689
```

```
<210> SEQ ID NO 617
<211> LENGTH: 563
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 617

Asp Ile Gln Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Thr Phe Ser Ser Tyr Ala Met Ser Trp Val Arg
145                 150                 155                 160

Gln Ala Pro Gly Lys Gly Leu Glu Trp Val Ser Ser Ile Ser Arg Gly
                165                 170                 175

Gly Thr Thr Tyr Tyr Pro Asp Ser Val Lys Gly Arg Phe Thr Ile Ser
            180                 185                 190

Arg Asp Asn Ser Lys Asn Thr Leu Tyr Leu Gln Met Asn Ser Leu Arg
        195                 200                 205

Ala Glu Asp Thr Ala Val Tyr Tyr Cys Gly Arg Tyr Asp Tyr Asp Gly
    210                 215                 220

Tyr Tyr Ala Met Asp Tyr Trp Gly Gln Gly Thr Leu Val Thr Val Ser
225                 230                 235                 240

Ser Lys Pro Thr Thr Thr Pro Ala Pro Arg Pro Pro Thr Pro Ala Pro
                245                 250                 255

Thr Ile Ala Ser Gln Pro Leu Ser Leu Arg Pro Glu Ala Ser Arg Pro
```

```
            260                 265                 270

Ala Ala Gly Gly Ala Val His Thr Arg Gly Leu Asp Phe Ala Ser Asp
        275                 280                 285

Lys Pro Thr Thr Thr Pro Ala Pro Arg Pro Pro Thr Pro Ala Pro Thr
    290                 295                 300

Ile Ala Ser Gln Pro Leu Ser Leu Arg Pro Glu Ala Ser Arg Pro Ala
305                 310                 315                 320

Ala Gly Gly Ala Val His Thr Arg Gly Leu Asp Phe Ala Ser Asp Lys
                325                 330                 335

Pro Thr Thr Thr Pro Ala Pro Arg Pro Pro Thr Pro Ala Pro Thr Ile
            340                 345                 350

Ala Ser Gln Pro Leu Ser Leu Arg Pro Glu Ala Cys Arg Pro Ala Ala
        355                 360                 365

Gly Gly Ala Val His Thr Arg Gly Leu Asp Phe Ala Cys Asp Ile Tyr
    370                 375                 380

Ile Trp Ala Pro Leu Ala Gly Thr Cys Gly Val Leu Leu Leu Ser Leu
385                 390                 395                 400

Val Ile Thr Leu Tyr Cys Asn His Arg Asn Arg Ser Lys Arg Ser Arg
                405                 410                 415

Gly Gly His Ser Asp Tyr Met Asn Met Thr Pro Arg Arg Pro Gly Pro
            420                 425                 430

Thr Arg Lys His Tyr Gln Pro Tyr Ala Pro Pro Arg Asp Phe Ala Ala
        435                 440                 445

Tyr Arg Ser Arg Val Lys Phe Ser Arg Ser Ala Asp Ala Pro Ala Tyr
    450                 455                 460

Gln Gln Gly Gln Asn Gln Leu Tyr Asn Glu Leu Asn Leu Gly Arg Arg
465                 470                 475                 480

Glu Glu Tyr Asp Val Leu Asp Lys Arg Arg Gly Arg Asp Pro Glu Met
                485                 490                 495

Gly Gly Lys Pro Arg Arg Lys Asn Pro Gln Glu Gly Leu Tyr Asn Glu
            500                 505                 510

Leu Gln Lys Asp Lys Met Ala Glu Ala Tyr Ser Glu Ile Gly Met Lys
        515                 520                 525

Gly Glu Arg Arg Arg Gly Lys Gly His Asp Gly Leu Tyr Gln Gly Leu
    530                 535                 540

Ser Thr Ala Thr Lys Asp Thr Tyr Asp Ala Leu His Met Gln Ala Leu
545                 550                 555                 560

Pro Pro Arg
```

<210> SEQ ID NO 618
<211> LENGTH: 1692
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 618

```
gatattcaga tgacccagtc accttcgagt ctgagcgcat ccgtgggcga cagagtgacc     60

attacctgta aggccagccc ggacattaac agctacctat cgtggtatca gcaaaagcct    120

ggtaaggccc ctaaactcct tatctacagg gctaataggt tggtagacgg ggtgcctagc    180

cggttctctg gttccggcag cggtacggac tttactctga ccataagctc tctgcaacca    240

gaagacatcg caacatacta ctgtttacaa tacgacgaat ttccttatac ctttggccag    300
```

gggaccaagt tagagatcaa ggggggcggc ggaagtggtg gagggggaag tggtggagga 360
ggaagcgaag tgcaactggt cgagtctggg ggcggccttg tgcaacctgg aggcagcctt 420
cgactcagtt gcgccgcgtc tggttttacc ttctcctctt acgcgatgag ctgggttcgc 480
caggcccccg gcaagggact tgagtgggtt agttcgatct cccgcggagg caccacatat 540
tatcctgact cggttaaggg acgcttcact atctctaggg acaattcaaa gaacacactg 600
tatctccaaa tgaactcctt gcgggccgag gacactgctg tgtattattg cggacgatac 660
gactacgatg ggtattacgc catggattac tgggggcaag gtacactggt cactgtgagt 720
tcgaagccta ccaccacccc cgcacctcgt cctccaaccc ctgcacctac gattgccagt 780
cagcctcttt cactgcggcc tgaggccagc agaccagctg ccggcggtgc cgtccataca 840
agaggactgg acttcgcgtc cgataaacct actaccactc cagccccaag gcccccaacc 900
ccagcaccga ctatcgcatc acagcctttg tcactgcgtc ctgaagccag ccggccagct 960
gcaggggggg ccgtccacac aaggggactc gactttgcga gtgataagcc caccaccacc 1020
cctgccccta gacctccaac cccagcccct acaatcgcca gccagcccct gagcctgagg 1080
cccgaagcct gtagacctgc cgctggcgga gccgtgcaca ccagaggcct ggatttcgcc 1140
tgcgacatct acatctgggc ccctctggcc ggcacctgtg gcgtgctgct gctgagcctg 1200
gtcatcaccc tgtactgcaa ccaccggaat aggagcaagc ggagcagagg cggccacagc 1260
gactacatga acatgacccc ccggaggcct ggccccaccc ggaagcacta ccagccctac 1320
gcccctccca gggacttcgc cgcctaccgg agccgggtga agttcagccg gagcgccgac 1380
gcccctgcct accagcaggg ccagaaccag ctgtacaacg agctgaacct gggccggagg 1440
gaggagtacg acgtgctgga caagcggaga ggccgggacc ctgagatggg cggcaagccc 1500
cggagaaaga accctcagga gggcctgtat aacgaactgc agaaagacaa gatggccgag 1560
gcctacagcg agatcggcat gaagggcgag cggcggaggg gcaagggcca cgacggcctg 1620
taccagggcc tgagcaccgc caccaaggat acctacgacg ccctgcacat gcaggccctg 1680
ccccccagat ga 1692

<210> SEQ ID NO 619
<211> LENGTH: 563
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 619

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ala Ser Ile Ser Arg Gly Gly Thr Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Gly
85 90 95

Arg Tyr Asp Tyr Asp Gly Tyr Tyr Ala Met Asp Tyr Trp Gly Gln Gly
100 105 110

-continued

```
Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Pro Asp Ile Asn Ser Tyr Leu Asn Trp Tyr Gln Gln Lys Pro Gly Lys
                165                 170                 175

Ala Pro Lys Leu Leu Ile Tyr Arg Ala Asn Arg Leu Val Asp Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Ile Ala Thr Tyr Tyr Cys Leu Gln
    210                 215                 220

Tyr Asp Glu Phe Pro Tyr Thr Phe Gly Gly Gly Thr Lys Val Glu Ile
225                 230                 235                 240

Lys Lys Pro Thr Thr Thr Pro Ala Pro Arg Pro Pro Thr Pro Ala Pro
                245                 250                 255

Thr Ile Ala Ser Gln Pro Leu Ser Leu Arg Pro Glu Ala Ser Arg Pro
            260                 265                 270

Ala Ala Gly Gly Ala Val His Thr Arg Gly Leu Asp Phe Ala Ser Asp
        275                 280                 285

Lys Pro Thr Thr Thr Pro Ala Pro Arg Pro Pro Thr Pro Ala Pro Thr
    290                 295                 300

Ile Ala Ser Gln Pro Leu Ser Leu Arg Pro Glu Ala Ser Arg Pro Ala
305                 310                 315                 320

Ala Gly Gly Ala Val His Thr Arg Gly Leu Asp Phe Ala Ser Asp Lys
                325                 330                 335

Pro Thr Thr Thr Pro Ala Pro Arg Pro Pro Thr Pro Ala Pro Thr Ile
            340                 345                 350

Ala Ser Gln Pro Leu Ser Leu Arg Pro Glu Ala Cys Arg Pro Ala Ala
        355                 360                 365

Gly Gly Ala Val His Thr Arg Gly Leu Asp Phe Ala Cys Asp Ile Tyr
    370                 375                 380

Ile Trp Ala Pro Leu Ala Gly Thr Cys Gly Val Leu Leu Leu Ser Leu
385                 390                 395                 400

Val Ile Thr Leu Tyr Cys Asn His Arg Asn Arg Ser Lys Arg Ser Arg
                405                 410                 415

Gly Gly His Ser Asp Tyr Met Asn Met Thr Pro Arg Arg Pro Gly Pro
            420                 425                 430

Thr Arg Lys His Tyr Gln Pro Tyr Ala Pro Pro Arg Asp Phe Ala Ala
        435                 440                 445

Tyr Arg Ser Arg Val Lys Phe Ser Arg Ser Ala Asp Ala Pro Ala Tyr
    450                 455                 460

Gln Gln Gly Gln Asn Gln Leu Tyr Asn Glu Leu Asn Leu Gly Arg Arg
465                 470                 475                 480

Glu Glu Tyr Asp Val Leu Asp Lys Arg Arg Gly Arg Asp Pro Glu Met
                485                 490                 495

Gly Gly Lys Pro Arg Arg Lys Asn Pro Gln Glu Gly Leu Tyr Asn Glu
            500                 505                 510

Leu Gln Lys Asp Lys Met Ala Glu Ala Tyr Ser Glu Ile Gly Met Lys
        515                 520                 525
```

-continued

```
Gly Glu Arg Arg Arg Gly Lys Gly His Asp Gly Leu Tyr Gln Gly Leu
    530                 535                 540

Ser Thr Ala Thr Lys Asp Thr Tyr Asp Ala Leu His Met Gln Ala Leu
545                 550                 555                 560

Pro Pro Arg


<210> SEQ ID NO 620
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 620

gaggttcaac ttgtggaatc cggcggcggg ttagtccagc ccggcgggag cttgcggctg     60

tcctgcgccg cctctggatt cacttttagc tcctatgcta tgtcttgggt aaggcaggcc    120

cctggtaaag gactagagtg ggtggcctcg atctcccgtg gtggcactac atactacgcc    180

gactccgtta aaggccggtt taccatctcc cgtgacaact ctaaaaatac tttgtacctg    240

caaatgaact ccctgcgggc agaagacaca gccgtgtact attgcgggcg ttacgattac    300

gacggatatt acgcaatgga ctactggggc cagggcacac tggtcaccgt gagcagcggg    360

ggcggaggaa gtggaggagg cggtagtggt gggggaggaa gcgatataca aatgactcag    420

tcccctagta gccttagtgc tagtgtggga gacagagtga ccatcacctg caaagcatct    480

cctgatatca attcctacct taactggtat caacagaagc ctggcaaagc tccaaagctc    540

ctgatttatc gcgcgaacag attggtcgat ggggtccctt ccagattcag cggctcaggg    600

tcagggaccg atttcaccct cacaattagt tcacttcagc ccgaggacat cgccacgtat    660

tattgccttc agtacgatga gttcccttac acctttggcg ggggaactaa agtcgaaatt    720

aagaagccta ccaccacccc cgcacctcgt cctccaaccc ctgcacctac gattgccagt    780

cagcctcttt cactgcggcc tgaggccagc agaccagctg ccggcggtgc cgtccataca    840

agaggactgg acttcgcgtc cgataaacct actaccactc cagccccaag gcccccaacc    900

ccagcaccga ctatcgcatc acagcctttg tcactgcgtc ctgaagccag ccggccagct    960

gcaggggggg ccgtccacac aaggggactc gactttgcga gtgataagcc caccaccacc   1020

cctgccccta gacctccaac cccagcccct acaatcgcca gccagcccct gagcctgagg   1080

cccgaagcct gtagacctgc cgctggcgga gccgtgcaca ccagaggcct ggatttcgcc   1140

tgcgacatct acatctgggc ccctctggcc ggcacctgtg gcgtgctgct gctgagcctg   1200

gtcatcaccc tgtactgcaa ccaccggaat aggagcaagc ggagcagagg cggccacagc   1260

gactacatga acatgacccc ccggaggcct ggccccaccc ggaagcacta ccagccctac   1320

gcccctccca gggacttcgc cgcctaccgg agccgggtga agttcagccg gagcgccgac   1380

gcccctgcct accagcaggg ccagaaccag ctgtacaacg agctgaacct gggccggagg   1440

gaggagtacg acgtgctgga caagcggaga ggccgggacc ctgagatggg cggcaagccc   1500

cggagaaaga accctcagga gggcctgtat aacgaactgc agaaagacaa gatggccgag   1560

gcctacagcg agatcggcat gaagggcgag cggcggaggg gcaagggcca cgacggcctg   1620

taccagggcc tgagcaccgc caccaaggat acctacgacg ccctgcacat gcaggccctg   1680

ccccccaga                                                           1689


<210> SEQ ID NO 621
```

<211> LENGTH: 563
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 621

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Pro Asp Ile Asn Ser Tyr Leu Asn Trp Tyr Gln Gln Lys Pro Gly Lys
                165                 170                 175

Ala Pro Lys Leu Leu Ile Tyr Arg Ala Asn Arg Leu Val Asp Gly Val
            180                 185                 190

Pro Ser Arg Phe Ser Gly Ser Gly Ser Gly Thr Asp Tyr Thr Leu Thr
        195                 200                 205

Ile Ser Ser Leu Gln Pro Glu Asp Phe Ala Thr Tyr Tyr Cys Leu Gln
    210                 215                 220

Tyr Asp Glu Phe Pro Tyr Thr Phe Gly Ala Gly Thr Lys Val Glu Ile
225                 230                 235                 240

Lys Lys Pro Thr Thr Thr Pro Ala Pro Arg Pro Pro Thr Pro Ala Pro
                245                 250                 255

Thr Ile Ala Ser Gln Pro Leu Ser Leu Arg Pro Glu Ala Ser Arg Pro
            260                 265                 270

Ala Ala Gly Gly Ala Val His Thr Arg Gly Leu Asp Phe Ala Ser Asp
        275                 280                 285

Lys Pro Thr Thr Thr Pro Ala Pro Arg Pro Pro Thr Pro Ala Pro Thr
    290                 295                 300

Ile Ala Ser Gln Pro Leu Ser Leu Arg Pro Glu Ala Ser Arg Pro Ala
305                 310                 315                 320

Ala Gly Gly Ala Val His Thr Arg Gly Leu Asp Phe Ala Ser Asp Lys
                325                 330                 335

Pro Thr Thr Thr Pro Ala Pro Arg Pro Pro Thr Pro Ala Pro Thr Ile
            340                 345                 350

Ala Ser Gln Pro Leu Ser Leu Arg Pro Glu Ala Cys Arg Pro Ala Ala
        355                 360                 365

Gly Gly Ala Val His Thr Arg Gly Leu Asp Phe Ala Cys Asp Ile Tyr
```

```
    370                 375                 380

Ile Trp Ala Pro Leu Ala Gly Thr Cys Gly Val Leu Leu Leu Ser Leu
385                 390                 395                 400

Val Ile Thr Leu Tyr Cys Asn His Arg Asn Arg Ser Lys Arg Ser Arg
                405                 410                 415

Gly Gly His Ser Asp Tyr Met Asn Met Thr Pro Arg Arg Pro Gly Pro
            420                 425                 430

Thr Arg Lys His Tyr Gln Pro Tyr Ala Pro Pro Arg Asp Phe Ala Ala
        435                 440                 445

Tyr Arg Ser Arg Val Lys Phe Ser Arg Ser Ala Asp Ala Pro Ala Tyr
    450                 455                 460

Gln Gln Gly Gln Asn Gln Leu Tyr Asn Glu Leu Asn Leu Gly Arg Arg
465                 470                 475                 480

Glu Glu Tyr Asp Val Leu Asp Lys Arg Arg Gly Arg Asp Pro Glu Met
                485                 490                 495

Gly Gly Lys Pro Arg Arg Lys Asn Pro Gln Glu Gly Leu Tyr Asn Glu
            500                 505                 510

Leu Gln Lys Asp Lys Met Ala Glu Ala Tyr Ser Glu Ile Gly Met Lys
        515                 520                 525

Gly Glu Arg Arg Arg Gly Lys Gly His Asp Gly Leu Tyr Gln Gly Leu
    530                 535                 540

Ser Thr Ala Thr Lys Asp Thr Tyr Asp Ala Leu His Met Gln Ala Leu
545                 550                 555                 560

Pro Pro Arg


<210> SEQ ID NO 622
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 622

gaagtgcagc ttgtggagtc aggaggaggg ctagttcagc caggcggctc tctgagacta      60

tcttgtgctg cctccggctt cacatttagc tcttatgcaa tgtcctgggt ccgccaggcc     120

cctggtaaag gcctggaatg ggttgcttct atctctagag gcggaaccac ttactaccct     180

gattcagtga aggggagatt cacaattagt agggacaacg tgcggaacat cctctaccta     240

cagatgtcaa gtttacgcag tgaggacact gcgatgtatt actgcggtcg atacgattat     300

gatggatatt atgcaatgga ttattggggc cagggcactc tggtcacagt atcttccggc     360

ggcggtggtt ctggcggtgg tggaagcgga gggggggggt ccgacatcca gatgacccaa     420

tcaccatcga gtcttagtgc atccgttggg gatagagtga caatcacttg taaggcatcc     480

ccggacatca actcatatct taattggtat cagcaaaagc cgggcaaggc ccctaagctc     540

ctgatttata gggccaaccg ccttgtggat ggagtcccct cccgctttag tggaagcggc     600

tctggcacag actacaccct gactatcagc tccttgcagc ctgaggattt tgctacctac     660

tactgtcttc agtacgatga atttccatac actttcggtg ctgggacaaa agtggagatc     720

aaaaagccta ccaccacccc cgcacctcgt cctccaaccc ctgcacctac gattgccagt     780

cagcctcttt cactgcggcc tgaggccagc agaccagctg ccggcggtgc cgtccataca     840

agaggactgg acttcgcgtc cgataaacct actaccactc cagccccaag gcccccaacc     900

ccagcaccga ctatcgcatc acagcctttg tcactgcgtc ctgaagccag ccggccagct     960
```

```
gcaggggggg ccgtccacac aaggggactc gactttgcga gtgataagcc caccaccacc   1020

cctgccccta gacctccaac cccagcccct acaatcgcca gccagcccct gagcctgagg   1080

cccgaagcct gtagacctgc cgctggcgga gccgtgcaca ccagaggcct ggatttcgcc   1140

tgcgacatct acatctgggc ccctctggcc ggcacctgtg gcgtgctgct gctgagcctg   1200

gtcatcaccc tgtactgcaa ccaccggaat aggagcaagc ggagcagagg cggccacagc   1260

gactacatga acatgacccc ccggaggcct ggccccaccc ggaagcacta ccagccctac   1320

gcccctccca gggacttcgc cgcctaccgg agccgggtga agttcagccg gagcgccgac   1380

gcccctgcct accagcaggg ccagaaccag ctgtacaacg agctgaacct gggccggagg   1440

gaggagtacg acgtgctgga caagcggaga ggccgggacc ctgagatggg cggcaagccc   1500

cggagaaaga accctcagga gggcctgtat aacgaactgc agaaagacaa gatggccgag   1560

gcctacagcg agatcggcat gaagggcgag cggcggaggg gcaagggcca cgacggcctg   1620

taccagggcc tgagcaccgc caccaaggat acctacgacg ccctgcacat gcaggccctg   1680

ccccccaga                                                           1689
```

```
<210> SEQ ID NO 623
<211> LENGTH: 563
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 623

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Gly Gly Thr Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Pro Asp Ile Asn Ser Tyr Leu Asn Trp Tyr Gln Gln Lys Pro Gly Lys
                165                 170                 175

Ala Pro Lys Leu Leu Ile Tyr Arg Ala Asn Arg Leu Val Asp Gly Val
            180                 185                 190

Pro Ser Arg Phe Ser Gly Ser Gly Ser Gly Thr Asp Tyr Thr Leu Thr
        195                 200                 205

Ile Ser Ser Leu Gln Pro Glu Asp Phe Ala Thr Tyr Tyr Cys Leu Gln
    210                 215                 220
```

```
Tyr Asp Glu Phe Pro Tyr Thr Phe Gly Ala Gly Thr Lys Val Glu Ile
225                 230                 235                 240

Lys Lys Pro Thr Thr Thr Pro Ala Pro Arg Pro Pro Thr Pro Ala Pro
            245                 250                 255

Thr Ile Ala Ser Gln Pro Leu Ser Leu Arg Pro Glu Ala Ser Arg Pro
            260                 265                 270

Ala Ala Gly Gly Ala Val His Thr Arg Gly Leu Asp Phe Ala Ser Asp
        275                 280                 285

Lys Pro Thr Thr Thr Pro Ala Pro Arg Pro Pro Thr Pro Ala Pro Thr
    290                 295                 300

Ile Ala Ser Gln Pro Leu Ser Leu Arg Pro Glu Ala Ser Arg Pro Ala
305                 310                 315                 320

Ala Gly Gly Ala Val His Thr Arg Gly Leu Asp Phe Ala Ser Asp Lys
                325                 330                 335

Pro Thr Thr Thr Pro Ala Pro Arg Pro Pro Thr Pro Ala Pro Thr Ile
            340                 345                 350

Ala Ser Gln Pro Leu Ser Leu Arg Pro Glu Ala Cys Arg Pro Ala Ala
        355                 360                 365

Gly Gly Ala Val His Thr Arg Gly Leu Asp Phe Ala Cys Asp Ile Tyr
    370                 375                 380

Ile Trp Ala Pro Leu Ala Gly Thr Cys Gly Val Leu Leu Leu Ser Leu
385                 390                 395                 400

Val Ile Thr Leu Tyr Cys Asn His Arg Asn Arg Ser Lys Arg Ser Arg
                405                 410                 415

Gly Gly His Ser Asp Tyr Met Asn Met Thr Pro Arg Arg Pro Gly Pro
            420                 425                 430

Thr Arg Lys His Tyr Gln Pro Tyr Ala Pro Pro Arg Asp Phe Ala Ala
        435                 440                 445

Tyr Arg Ser Arg Val Lys Phe Ser Arg Ser Ala Asp Ala Pro Ala Tyr
    450                 455                 460

Gln Gln Gly Gln Asn Gln Leu Tyr Asn Glu Leu Asn Leu Gly Arg Arg
465                 470                 475                 480

Glu Glu Tyr Asp Val Leu Asp Lys Arg Arg Gly Arg Asp Pro Glu Met
                485                 490                 495

Gly Gly Lys Pro Arg Arg Lys Asn Pro Gln Glu Gly Leu Tyr Asn Glu
            500                 505                 510

Leu Gln Lys Asp Lys Met Ala Glu Ala Tyr Ser Glu Ile Gly Met Lys
        515                 520                 525

Gly Glu Arg Arg Arg Gly Lys Gly His Asp Gly Leu Tyr Gln Gly Leu
    530                 535                 540

Ser Thr Ala Thr Lys Asp Thr Tyr Asp Ala Leu His Met Gln Ala Leu
545                 550                 555                 560

Pro Pro Arg


<210> SEQ ID NO 624
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 624

gaagtgcaac tggtcgagtc tgggggcggc cttgtgcaac ctggaggcag ccttcgactc     60
```

-continued

```
agttgcgccg cgtctggttt taccttctcc tcttacgcga tgagctgggt tcgccaggcc    120

cccggcaagg gacttgagtg ggttagttcg atctcccgcg gaggcaccac atattatcct    180

gactcggtta agggacgctt cactatctct agggacaatt caaagaacac actgtatctc    240

caaatgaact ccttgcgggc cgaggacact gctgtgtatt attgcggacg atacgactac    300

gatgggtatt acgccatgga ttactggggg caaggtacac tggtcactgt gagttcgggg    360

ggcggcggaa gtggtggagg gggaagtggt ggaggaggaa gcgatataca gatgacacag    420

agcccttcaa gtttatctgc aagcgtcggc gatcgtgtta caataacttg caaggcatct    480

cccgacatca attcctacct caactggtat cagcagaagc ctgggaaggc tcctaagctg    540

cttatttaca gagcaaatcg cctggtggac ggcgtgccca gtcggttttc cgggtctggg    600

agcggaacgg attacacact gaccatctca agcctgcaac ccgaagactt cgctacatat    660

tactgccttc agtatgatga gttcccatat accttcggcg ctgggaccaa ggtggagata    720

aagaagccta ccaccacccc cgcacctcgt cctccaaccc ctgcacctac gattgccagt    780

cagcctcttt cactgcggcc tgaggccagc agaccagctg ccggcggtgc cgtccataca    840

agaggactgg acttcgcgtc cgataaacct actaccactc cagccccaag gcccccaacc    900

ccagcaccga ctatcgcatc acagcctttg tcactgcgtc ctgaagccag ccggccagct    960

gcaggggggg ccgtccacac aaggggactc gactttgcga gtgataagcc caccaccacc   1020

cctgccccta gacctccaac cccagcccct acaatcgcca gccagcccct gagcctgagg   1080

cccgaagcct gtagacctgc cgctggcgga gccgtgcaca ccagaggcct ggatttcgcc   1140

tgcgacatct acatctgggc ccctctggcc ggcacctgtg gcgtgctgct gctgagcctg   1200

gtcatcaccc tgtactgcaa ccaccggaat aggagcaagc ggagcagagg cggccacagc   1260

gactacatga acatgacccc ccggaggcct ggccccaccc ggaagcacta ccagccctac   1320

gcccctccca gggacttcgc cgcctaccgg agccgggtga agttcagccg gagcgccgac   1380

gcccctgcct accagcaggg ccagaaccag ctgtacaacg agctgaacct gggccggagg   1440

gaggagtacg acgtgctgga caagcggaga ggccgggacc ctgagatggg cggcaagccc   1500

cggagaaaga accctcagga gggcctgtat aacgaactgc agaaagacaa gatggccgag   1560

gcctacagcg agatcggcat gaagggcgag cggcggaggg gcaagggcca cgacggcctg   1620

taccagggcc tgagcaccgc caccaaggat acctacgacg ccctgcacat gcaggccctg   1680

ccccccaga                                                            1689
```

<210> SEQ ID NO 625
<211> LENGTH: 563
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 625

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Gly Gly Thr Thr Tyr Tyr Pro Asp Ser Val Lys
    50                  55                  60
```

```
Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Pro Asp Ile Asn Ser Tyr Leu Asn Trp Tyr Gln Gln Lys Pro Gly Lys
                165                 170                 175

Ala Pro Lys Val Leu Ile Tyr Arg Ala Asn Arg Leu Val Asp Gly Val
            180                 185                 190

Pro Ser Arg Phe Ser Gly Ser Gly Ser Gly Thr Asp Tyr Thr Leu Thr
        195                 200                 205

Ile Ser Ser Leu Gln Pro Glu Asp Phe Ala Thr Tyr Tyr Cys Leu Gln
    210                 215                 220

Tyr Asp Glu Phe Pro Tyr Thr Phe Gly Gln Gly Thr Lys Val Glu Ile
225                 230                 235                 240

Lys Lys Pro Thr Thr Thr Pro Ala Pro Arg Pro Pro Thr Pro Ala Pro
                245                 250                 255

Thr Ile Ala Ser Gln Pro Leu Ser Leu Arg Pro Glu Ala Ser Arg Pro
            260                 265                 270

Ala Ala Gly Gly Ala Val His Thr Arg Gly Leu Asp Phe Ala Ser Asp
        275                 280                 285

Lys Pro Thr Thr Thr Pro Ala Pro Arg Pro Pro Thr Pro Ala Pro Thr
    290                 295                 300

Ile Ala Ser Gln Pro Leu Ser Leu Arg Pro Glu Ala Ser Arg Pro Ala
305                 310                 315                 320

Ala Gly Gly Ala Val His Thr Arg Gly Leu Asp Phe Ala Ser Asp Lys
                325                 330                 335

Pro Thr Thr Thr Pro Ala Pro Arg Pro Pro Thr Pro Ala Pro Thr Ile
            340                 345                 350

Ala Ser Gln Pro Leu Ser Leu Arg Pro Glu Ala Cys Arg Pro Ala Ala
        355                 360                 365

Gly Gly Ala Val His Thr Arg Gly Leu Asp Phe Ala Cys Asp Ile Tyr
    370                 375                 380

Ile Trp Ala Pro Leu Ala Gly Thr Cys Gly Val Leu Leu Leu Ser Leu
385                 390                 395                 400

Val Ile Thr Leu Tyr Cys Asn His Arg Asn Arg Ser Lys Arg Ser Arg
                405                 410                 415

Gly Gly His Ser Asp Tyr Met Asn Met Thr Pro Arg Arg Pro Gly Pro
            420                 425                 430

Thr Arg Lys His Tyr Gln Pro Tyr Ala Pro Pro Arg Asp Phe Ala Ala
        435                 440                 445

Tyr Arg Ser Arg Val Lys Phe Ser Arg Ser Ala Asp Ala Pro Ala Tyr
    450                 455                 460

Gln Gln Gly Gln Asn Gln Leu Tyr Asn Glu Leu Asn Leu Gly Arg Arg
465                 470                 475                 480

Glu Glu Tyr Asp Val Leu Asp Lys Arg Arg Gly Arg Asp Pro Glu Met
```

-continued

```
                485                 490                 495

Gly Gly Lys Pro Arg Arg Lys Asn Pro Gln Glu Gly Leu Tyr Asn Glu
            500                 505                 510

Leu Gln Lys Asp Lys Met Ala Glu Ala Tyr Ser Glu Ile Gly Met Lys
        515                 520                 525

Gly Glu Arg Arg Arg Gly Lys Gly His Asp Gly Leu Tyr Gln Gly Leu
    530                 535                 540

Ser Thr Ala Thr Lys Asp Thr Tyr Asp Ala Leu His Met Gln Ala Leu
545                 550                 555                 560

Pro Pro Arg


<210> SEQ ID NO 626
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 626

gaagtgcaac tggtcgagtc tgggggcggc cttgtgcaac ctggaggcag ccttcgactc     60

agttgcgccg cgtctggttt taccttctcc tcttacgcga tgagctgggt tcgccaggcc    120

cccggcaagg gacttgagtg ggttagttcg atctcccgcg gaggcaccac atattatcct    180

gactcggtta agggacgctt cactatctct agggacaatt caaagaacac actgtatctc    240

caaatgaact ccttgcgggc cgaggacact gctgtgtatt attgcggacg atacgactac    300

gatgggtatt acgccatgga ttactggggg caaggtacac tggtcactgt gagttcgggg    360

ggcggcggaa gtggtggagg gggaagtggt ggaggaggaa gcgatattca gatgacccag    420

tcgcccagca gtctctcggc ctcagtgggc gaccgggtca ctatcacttg caaagcaagt    480

cctgatataa actcctatct taattggtat cagcagaagc ccggcaaggc acctaaggtt    540

ctgatatatc gcgcaaatcg gctcgtggat ggagtaccca gccgattttc cggcagcggc    600

tcaggcactg actacacact gacaatcagc agcttgcagc ctgaagattt cgccacatac    660

tattgtctac agtacgacga gttcccttat acattcggcc aggggaccaa ggtcgagatc    720

aagaagccta ccaccacccc cgcacctcgt cctccaaccc ctgcacctac gattgccagt    780

cagcctcttt cactgcggcc tgaggccagc agaccagctg ccggcggtgc cgtccataca    840

agaggactgg acttcgcgtc cgataaacct actaccactc cagccccaag gcccccaacc    900

ccagcaccga ctatcgcatc acagcctttg tcactgcgtc ctgaagccag ccggccagct    960

gcaggggggg ccgtccacac aaggggactc gactttgcga gtgataagcc caccaccacc   1020

cctgccccta gacctccaac cccagcccct acaatcgcca gccagcccct gagcctgagg   1080

cccgaagcct gtagacctgc cgctggcgga gccgtgcaca ccagaggcct ggatttcgcc   1140

tgcgacatct acatctgggc ccctctggcc ggcacctgtg gcgtgctgct gctgagcctg   1200

gtcatcaccc tgtactgcaa ccaccggaat aggagcaagc ggagcagagg cggccacagc   1260

gactacatga acatgacccc ccggaggcct ggccccaccc ggaagcacta ccagccctac   1320

gcccctccca gggacttcgc cgcctaccgg agccgggtga agttcagccg gagcgccgac   1380

gcccctgcct accagcaggg ccagaaccag ctgtacaacg agctgaacct gggccggagg   1440

gaggagtacg acgtgctgga caagcggaga ggccgggacc ctgagatggg cggcaagccc   1500

cggagaaaga accctcagga gggcctgtat aacgaactgc agaaagacaa gatggccgag   1560
```

-continued

```
gcctacagcg agatcggcat gaagggcgag cggcggaggg gcaagggcca cgacggcctg   1620

taccagggcc tgagcaccgc caccaaggat acctacgacg ccctgcacat gcaggccctg   1680

ccccccaga                                                           1689


<210> SEQ ID NO 627
<211> LENGTH: 563
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 627

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met Ser Trp Val Arg Gln Val Pro Gly Lys Gly Leu Val Trp Ile
        35                  40                  45

Ser Ser Ile Ser Arg Gly Gly Thr Thr Tyr Tyr Ala Asp Ser Val Arg
    50                  55                  60

Gly Arg Phe Ile Ile Ser Arg Asp Asn Ala Lys Asn Thr Leu Tyr Leu
65                  70                  75                  80

Glu Met Asn Asn Leu Arg Gly Glu Asp Thr Ala Val Tyr Tyr Cys Ala
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Gln Ala Ser
145                 150                 155                 160

Pro Asp Ile Asn Ser Tyr Leu Asn Trp Tyr Gln Gln Lys Pro Gly Lys
                165                 170                 175

Ala Pro Lys Leu Leu Ile Tyr Arg Ala Asn Asn Leu Glu Thr Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Ile Ala Thr Tyr Tyr Cys Leu Gln
    210                 215                 220

Tyr Asp Glu Phe Pro Tyr Thr Phe Gly Gln Gly Thr Lys Leu Glu Ile
225                 230                 235                 240

Lys Lys Pro Thr Thr Thr Pro Ala Pro Arg Pro Pro Thr Pro Ala Pro
                245                 250                 255

Thr Ile Ala Ser Gln Pro Leu Ser Leu Arg Pro Glu Ala Ser Arg Pro
            260                 265                 270

Ala Ala Gly Gly Ala Val His Thr Arg Gly Leu Asp Phe Ala Ser Asp
        275                 280                 285

Lys Pro Thr Thr Thr Pro Ala Pro Arg Pro Pro Thr Pro Ala Pro Thr
    290                 295                 300

Ile Ala Ser Gln Pro Leu Ser Leu Arg Pro Glu Ala Ser Arg Pro Ala
305                 310                 315                 320

Ala Gly Gly Ala Val His Thr Arg Gly Leu Asp Phe Ala Ser Asp Lys
                325                 330                 335
```

Pro Thr Thr Thr Pro Ala Pro Arg Pro Pro Thr Pro Ala Pro Thr Ile
340 345 350

Ala Ser Gln Pro Leu Ser Leu Arg Pro Glu Ala Cys Arg Pro Ala Ala
355 360 365

Gly Gly Ala Val His Thr Arg Gly Leu Asp Phe Ala Cys Asp Ile Tyr
370 375 380

Ile Trp Ala Pro Leu Ala Gly Thr Cys Gly Val Leu Leu Leu Ser Leu
385 390 395 400

Val Ile Thr Leu Tyr Cys Asn His Arg Asn Arg Ser Lys Arg Ser Arg
405 410 415

Gly Gly His Ser Asp Tyr Met Asn Met Thr Pro Arg Arg Pro Gly Pro
420 425 430

Thr Arg Lys His Tyr Gln Pro Tyr Ala Pro Pro Arg Asp Phe Ala Ala
435 440 445

Tyr Arg Ser Arg Val Lys Phe Ser Arg Ser Ala Asp Ala Pro Ala Tyr
450 455 460

Gln Gln Gly Gln Asn Gln Leu Tyr Asn Glu Leu Asn Leu Gly Arg Arg
465 470 475 480

Glu Glu Tyr Asp Val Leu Asp Lys Arg Arg Gly Arg Asp Pro Glu Met
485 490 495

Gly Gly Lys Pro Arg Arg Lys Asn Pro Gln Glu Gly Leu Tyr Asn Glu
500 505 510

Leu Gln Lys Asp Lys Met Ala Glu Ala Tyr Ser Glu Ile Gly Met Lys
515 520 525

Gly Glu Arg Arg Arg Gly Lys Gly His Asp Gly Leu Tyr Gln Gly Leu
530 535 540

Ser Thr Ala Thr Lys Asp Thr Tyr Asp Ala Leu His Met Gln Ala Leu
545 550 555 560

Pro Pro Arg

<210> SEQ ID NO 628
<211> LENGTH: 1689
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 628
gaggttcaac tcgtggagtc tggaggcggg ctagtgcagc ctggcggctc cctgcgactg 60
tcttgcagcg catcaggctt tacattcagt tcttatgcca tgagctgggt gaggcaggtg 120
cccggcaagg gtctggtgtg gatcagctca atctccaggg gcgggactac atattacgcc 180
gattcggtca ggggtcgttt tatcattagc agggataatg ccaagaacac cttgtatttg 240
gagatgaaca acctaagagg cgaagacacc gctgtgtact attgtgcccg ttacgactac 300
gatgggtact acgccatgga ctattggggc cagggaacct tggtgactgt gtcaagtggc 360
gggggcggca gcggaggcgg tggcagcgga ggcggcggtt ctgatattca aatgacgcaa 420
agtcccagca gcctctccgc ctccgttgga gacagggtga ctattacatg ccaagccagc 480
cccgatatta atagctactt aaattggtat cagcagaaac ctgggaaggc acctaaactt 540
ctcatctacc gcgctaacaa tctggagacc ggcgtgccgt ctagattttc cggctctgga 600
tcagggaccg attttactct gacaattagt tccctgcaac ccgaagacat cgccacttat 660
tattgcctgc aatatgatga gtttccttac acatttggtc agggaactaa actagagatt 720

```
aagaagccta ccaccacccc cgcacctcgt cctccaaccc ctgcacctac gattgccagt    780

cagcctcttt cactgcggcc tgaggccagc agaccagctg ccggcggtgc cgtccataca    840

agaggactgg acttcgcgtc cgataaacct actaccactc cagccccaag gcccccaacc    900

ccagcaccga ctatcgcatc acagcctttg tcactgcgtc ctgaagccag ccggccagct    960

gcaggggggg ccgtccacac aaggggactc gactttgcga gtgataagcc caccaccacc   1020

cctgccccta gacctccaac cccagcccct acaatcgcca gccagcccct gagcctgagg   1080

cccgaagcct gtagacctgc cgctggcgga gccgtgcaca ccagaggcct ggatttcgcc   1140

tgcgacatct acatctgggc ccctctggcc ggcacctgtg gcgtgctgct gctgagcctg   1200

gtcatcaccc tgtactgcaa ccaccggaat aggagcaagc ggagcagagg cggccacagc   1260

gactacatga acatgacccc ccggaggcct ggccccaccc ggaagcacta ccagccctac   1320

gcccctccca gggacttcgc cgcctaccgg agccgggtga agttcagccg gagcgccgac   1380

gcccctgcct accagcaggg ccagaaccag ctgtacaacg agctgaacct gggccggagg   1440

gaggagtacg acgtgctgga caagcggaga ggccgggacc ctgagatggg cggcaagccc   1500

cggagaaaga accctcagga gggcctgtat aacgaactgc agaaagacaa gatggccgag   1560

gcctacagcg agatcggcat gaagggcgag cggcggaggg gcaagggcca cgacggcctg   1620

taccagggcc tgagcaccgc caccaaggat acctacgacg ccctgcacat gcaggccctg   1680

ccccccaga                                                           1689
```

```
<210> SEQ ID NO 629
<211> LENGTH: 563
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 629

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met Ser Trp Val Arg Gln Val Pro Gly Lys Gly Leu Val Trp Ile
        35                  40                  45

Ser Ser Ile Ser Arg Gly Gly Thr Thr Tyr Tyr Ala Asp Ser Val Arg
    50                  55                  60

Gly Arg Phe Ile Ile Ser Arg Asp Asn Ala Lys Asn Thr Leu Tyr Leu
65                  70                  75                  80

Glu Met Asn Asn Leu Arg Gly Glu Asp Thr Ala Val Tyr Tyr Cys Ala
                85                  90                  95

Arg Tyr Asp Tyr Asp Gly Tyr Tyr Ala Met Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Pro Asp Ile Asn Ser Tyr Leu Asn Trp Tyr Gln Gln Lys Pro Gly Lys
                165                 170                 175
```

-continued

Ala Pro Lys Leu Leu Ile Tyr Arg Ala Asn Arg Leu Val Asp Gly Val
180 185 190

Pro Ser Arg Phe Ser Gly Ser Gly Ser Gly Thr Asp Tyr Thr Leu Thr
195 200 205

Ile Ser Ser Leu Gln Pro Glu Asp Phe Ala Thr Tyr Tyr Cys Leu Gln
210 215 220

Tyr Asp Glu Phe Pro Tyr Thr Phe Gly Ala Gly Thr Lys Val Glu Ile
225 230 235 240

Lys Lys Pro Thr Thr Thr Pro Ala Pro Arg Pro Pro Thr Pro Ala Pro
245 250 255

Thr Ile Ala Ser Gln Pro Leu Ser Leu Arg Pro Glu Ala Ser Arg Pro
260 265 270

Ala Ala Gly Gly Ala Val His Thr Arg Gly Leu Asp Phe Ala Ser Asp
275 280 285

Lys Pro Thr Thr Thr Pro Ala Pro Arg Pro Pro Thr Pro Ala Pro Thr
290 295 300

Ile Ala Ser Gln Pro Leu Ser Leu Arg Pro Glu Ala Ser Arg Pro Ala
305 310 315 320

Ala Gly Gly Ala Val His Thr Arg Gly Leu Asp Phe Ala Ser Asp Lys
325 330 335

Pro Thr Thr Thr Pro Ala Pro Arg Pro Pro Thr Pro Ala Pro Thr Ile
340 345 350

Ala Ser Gln Pro Leu Ser Leu Arg Pro Glu Ala Cys Arg Pro Ala Ala
355 360 365

Gly Gly Ala Val His Thr Arg Gly Leu Asp Phe Ala Cys Asp Ile Tyr
370 375 380

Ile Trp Ala Pro Leu Ala Gly Thr Cys Gly Val Leu Leu Leu Ser Leu
385 390 395 400

Val Ile Thr Leu Tyr Cys Asn His Arg Asn Arg Ser Lys Arg Ser Arg
405 410 415

Gly Gly His Ser Asp Tyr Met Asn Met Thr Pro Arg Arg Pro Gly Pro
420 425 430

Thr Arg Lys His Tyr Gln Pro Tyr Ala Pro Pro Arg Asp Phe Ala Ala
435 440 445

Tyr Arg Ser Arg Val Lys Phe Ser Arg Ser Ala Asp Ala Pro Ala Tyr
450 455 460

Gln Gln Gly Gln Asn Gln Leu Tyr Asn Glu Leu Asn Leu Gly Arg Arg
465 470 475 480

Glu Glu Tyr Asp Val Leu Asp Lys Arg Arg Gly Arg Asp Pro Glu Met
485 490 495

Gly Gly Lys Pro Arg Arg Lys Asn Pro Gln Glu Gly Leu Tyr Asn Glu
500 505 510

Leu Gln Lys Asp Lys Met Ala Glu Ala Tyr Ser Glu Ile Gly Met Lys
515 520 525

Gly Glu Arg Arg Arg Gly Lys Gly His Asp Gly Leu Tyr Gln Gly Leu
530 535 540

Ser Thr Ala Thr Lys Asp Thr Tyr Asp Ala Leu His Met Gln Ala Leu
545 550 555 560

Pro Pro Arg

<210> SEQ ID NO 630
<211> LENGTH: 1689
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 630

```
gaggttcaac tcgtggagtc tggaggcggg ctagtgcagc ctggcggctc cctgcgactg     60

tcttgcagcg catcaggctt tacattcagt tcttatgcca tgagctgggt gaggcaggtg    120

cccggcaagg gtctggtgtg gatcagctca atctccaggg gcgggactac atattacgcc    180

gattcggtca ggggtcgttt tatcattagc agggataatg ccaagaacac cttgtatttg    240

gagatgaaca acctaagagg cgaagacacc gctgtgtact attgtgcccg ttacgactac    300

gatgggtact acgccatgga ctattggggc cagggaacct tggtgactgt gtcaagtggc    360

gggggcggca gcggaggcgg tggcagcgga ggcggcggtt ctgatataca gatgacacag    420

agcccttcaa gtttatctgc aagcgtcggc gatcgtgtta caataacttg caaggcatct    480

cccgacatca attcctacct caactggtat cagcagaagc ctgggaaggc tcctaagctg    540

cttatttaca gagcaaatcg cctggtggac ggcgtgccca gtcggttttc cgggtctggg    600

agcggaacgg attacacact gaccatctca agcctgcaac ccgaagactt cgctacatat    660

tactgccttc agtatgatga gttcccatat accttcggcg ctgggaccaa ggtggagata    720

aagaagccta ccaccacccc cgcacctcgt cctccaaccc ctgcacctac gattgccagt    780

cagcctcttt cactgcggcc tgaggccagc agaccagctg ccggcggtgc cgtccataca    840

agaggactgg acttcgcgtc cgataaacct actaccactc cagccccaag gcccccaacc    900

ccagcaccga ctatcgcatc acagcctttg tcactgcgtc ctgaagccag ccggccagct    960

gcagggggggg ccgtccacac aaggggactc gactttgcga gtgataagcc caccaccacc   1020

cctgccccta gacctccaac cccagcccct acaatcgcca gccagcccct gagcctgagg   1080

cccgaagcct gtagacctgc cgctggcgga gccgtgcaca ccagaggcct ggatttcgcc   1140

tgcgacatct acatctgggc ccctctggcc ggcacctgtg gcgtgctgct gctgagcctg   1200

gtcatcaccc tgtactgcaa ccaccggaat aggagcaagc ggagcagagg cggccacagc   1260

gactacatga acatgacccc ccggaggcct ggccccaccc ggaagcacta ccagccctac   1320

gcccctccca gggacttcgc cgcctaccgg agccgggtga agttcagccg gagcgccgac   1380

gcccctgcct accagcaggg ccagaaccag ctgtacaacg agctgaacct gggccggagg   1440

gaggagtacg acgtgctgga caagcggaga ggccgggacc ctgagatggg cggcaagccc   1500

cggagaaaga accctcagga gggcctgtat aacgaactgc agaaagacaa gatggccgag   1560

gcctacagcg agatcggcat gaagggcgag cggcggaggg gcaagggcca cgacggcctg   1620

taccagggcc tgagcaccgc caccaaggat acctacgacg ccctgcacat gcaggccctg   1680

ccccccaga                                                           1689
```

<210> SEQ ID NO 631
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 631

```
Glu Ser Lys Tyr Gly Pro Pro Cys Pro Pro Cys Pro
1               5                   10
```

<210> SEQ ID NO 632
<211> LENGTH: 86
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 632

Gly Pro Lys Lys Lys Arg Lys Val Ala Pro Pro Thr Asp Val Ser Leu
1 5 10 15

Gly Asp Glu Leu His Leu Asp Gly Glu Asp Val Ala Met Ala His Ala
20 25 30

Asp Ala Leu Asp Asp Phe Asp Leu Asp Met Leu Gly Asp Gly Asp Ser
35 40 45

Pro Gly Pro Gly Phe Thr Pro His Asp Ser Ala Pro Tyr Gly Ala Leu
50 55 60

Asp Met Ala Asp Phe Glu Phe Glu Gln Met Phe Thr Asp Ala Leu Gly
65 70 75 80

Ile Asp Glu Tyr Gly Gly
85

<210> SEQ ID NO 633
<211> LENGTH: 258
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 633
ggccccaaga agaaaaggaa ggtggccccc cccaccgacg tgagcctggg cgacgagctg 60
cacctggacg gcgaggacgt ggccatggcc cacgccgacg ccctggacga cttcgacctg 120
gacatgctgg gcgacggcga cagccccggc cccggcttca ccccccacga cagcgccccc 180
tacggcgccc tggacatggc cgacttcgag ttcgagcaga tgttcaccga cgccctgggc 240
atcgacgagt acggcggc 258

<210> SEQ ID NO 634
<211> LENGTH: 235
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 634

Glu Met Pro Val Asp Arg Ile Leu Glu Ala Glu Leu Ala Val Glu Gln
1 5 10 15

Lys Ser Asp Gln Gly Val Glu Gly Pro Gly Gly Thr Gly Gly Ser Gly
20 25 30

Ser Ser Pro Asn Asp Pro Val Thr Asn Ile Cys Gln Ala Ala Asp Lys
35 40 45

Gln Leu Phe Thr Leu Val Glu Trp Ala Lys Arg Ile Pro His Phe Ser
50 55 60

Ser Leu Pro Leu Asp Asp Gln Val Ile Leu Leu Arg Ala Gly Trp Asn
65 70 75 80

Glu Leu Leu Ile Ala Ser Phe Ser His Arg Ser Ile Asp Val Arg Asp
85 90 95

Gly Ile Leu Leu Ala Thr Gly Leu His Val His Arg Asn Ser Ala His

```
            100                 105                 110

Ser Ala Gly Val Gly Ala Ile Phe Asp Arg Val Leu Thr Glu Leu Val
        115                 120                 125

Ser Lys Met Arg Asp Met Arg Met Asp Lys Thr Glu Leu Gly Cys Leu
    130                 135                 140

Arg Ala Ile Ile Leu Phe Asn Pro Glu Val Arg Gly Leu Lys Ser Ala
145                 150                 155                 160

Gln Glu Val Glu Leu Leu Arg Glu Lys Val Tyr Ala Ala Leu Glu Glu
                165                 170                 175

Tyr Thr Arg Thr Thr His Pro Asp Glu Pro Gly Arg Phe Ala Lys Leu
            180                 185                 190

Leu Leu Arg Leu Pro Ser Leu Arg Ser Ile Gly Leu Lys Cys Leu Glu
        195                 200                 205

His Leu Phe Phe Phe Arg Leu Ile Gly Asp Val Pro Ile Asp Thr Phe
    210                 215                 220

Leu Met Glu Met Leu Glu Ser Pro Ser Asp Ser
225                 230                 235


<210> SEQ ID NO 635
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 635

gagatgcccg tggacaggat tctggaggcc gaactcgccg tggagcagaa aagcgaccag     60

ggcgtggagg gccccggcgg aaccggcggc agcggcagca gccccaacga ccccgtgacc    120

aacatctgcc aggccgccga caagcagctg ttcaccctgg tggagtgggc caagaggatt    180

ccccacttca gcagcctgcc cctggacgac caggtgatcc tgctgagggc cggatggaac    240

gagctgctga tcgccagctt cagccacagg agcatcgacg tgagggacgg catcctgctg    300

gccaccggcc tgcacgtcca taggaacagc gcccacagcg ccggagtggg cgccatcttc    360

gacagggtgc tgaccgagct ggtgagcaag atgagggaca tgaggatgga caagaccgag    420

ctgggctgcc tgagggccat catcctgttc aaccccgagg tgaggggcct gaaaagcgcc    480

caggaggtgg agctgctgag ggagaaggtg tacgccgccc tggaggagta caccaggacc    540

acccaccccg acgagcccgg cagattcgcc aagctgctgc tgaggctgcc cagcctgagg    600

agcatcggcc tgaagtgcct ggagcacctg ttcttcttca ggctgatcgg cgacgtgccc    660

atcgacacct tcctgatgga gatgctggag agccccagcg acagc                    705


<210> SEQ ID NO 636
<211> LENGTH: 323
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 636

Gly Pro Lys Lys Lys Arg Lys Val Ala Pro Pro Thr Asp Val Ser Leu
1               5                   10                  15

Gly Asp Glu Leu His Leu Asp Gly Glu Asp Val Ala Met Ala His Ala
            20                  25                  30

Asp Ala Leu Asp Asp Phe Asp Leu Asp Met Leu Gly Asp Gly Asp Ser
```

```
        35                  40                  45

Pro Gly Pro Gly Phe Thr Pro His Asp Ser Ala Pro Tyr Gly Ala Leu
    50                  55                  60

Asp Met Ala Asp Phe Glu Phe Glu Gln Met Phe Thr Asp Ala Leu Gly
65                  70                  75                  80

Ile Asp Glu Tyr Gly Gly Glu Phe Glu Met Pro Val Asp Arg Ile Leu
                85                  90                  95

Glu Ala Glu Leu Ala Val Glu Gln Lys Ser Asp Gln Gly Val Glu Gly
            100                 105                 110

Pro Gly Gly Thr Gly Gly Ser Gly Ser Ser Pro Asn Asp Pro Val Thr
        115                 120                 125

Asn Ile Cys Gln Ala Ala Asp Lys Gln Leu Phe Thr Leu Val Glu Trp
    130                 135                 140

Ala Lys Arg Ile Pro His Phe Ser Ser Leu Pro Leu Asp Asp Gln Val
145                 150                 155                 160

Ile Leu Leu Arg Ala Gly Trp Asn Glu Leu Leu Ile Ala Ser Phe Ser
                165                 170                 175

His Arg Ser Ile Asp Val Arg Asp Gly Ile Leu Leu Ala Thr Gly Leu
            180                 185                 190

His Val His Arg Asn Ser Ala His Ser Ala Gly Val Gly Ala Ile Phe
        195                 200                 205

Asp Arg Val Leu Thr Glu Leu Val Ser Lys Met Arg Asp Met Arg Met
    210                 215                 220

Asp Lys Thr Glu Leu Gly Cys Leu Arg Ala Ile Ile Leu Phe Asn Pro
225                 230                 235                 240

Glu Val Arg Gly Leu Lys Ser Ala Gln Glu Val Glu Leu Leu Arg Glu
                245                 250                 255

Lys Val Tyr Ala Ala Leu Glu Glu Tyr Thr Arg Thr Thr His Pro Asp
            260                 265                 270

Glu Pro Gly Arg Phe Ala Lys Leu Leu Leu Arg Leu Pro Ser Leu Arg
        275                 280                 285

Ser Ile Gly Leu Lys Cys Leu Glu His Leu Phe Phe Phe Arg Leu Ile
    290                 295                 300

Gly Asp Val Pro Ile Asp Thr Phe Leu Met Glu Met Leu Glu Ser Pro
305                 310                 315                 320

Ser Asp Ser


<210> SEQ ID NO 637
<211> LENGTH: 969
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 637

ggccccaaga agaaaaggaa ggtggccccc cccaccgacg tgagcctggg cgacgagctg     60

cacctggacg gcgaggacgt ggccatggcc cacgccgacg ccctggacga cttcgacctg    120

gacatgctgg gcgacggcga cagccccggc cccggcttca ccccccacga cagcgccccc    180

tacggcgccc tggacatggc cgacttcgag ttcgagcaga tgttcaccga cgccctgggc    240

atcgacgagt acggcggcga attcgagatg cccgtggaca ggattctgga ggccgaactc    300

gccgtggagc agaaaagcga ccagggcgtg gagggccccg gcggaaccgg cggcagcggc    360

agcagcccca acgaccccgt gaccaacatc tgccaggccg ccgacaagca gctgttcacc    420
```

ctggtggagt gggccaagag gattccccac ttcagcagcc tgcccctgga cgaccaggtg 480
atcctgctga gggccggatg gaacgagctg ctgatcgcca gcttcagcca caggagcatc 540
gacgtgaggg acggcatcct gctggccacc ggcctgcacg tccataggaa cagcgcccac 600
agcgccggag tgggcgccat cttcgacagg gtgctgaccg agctggtgag caagatgagg 660
gacatgagga tggacaagac cgagctgggc tgcctgaggg ccatcatcct gttcaacccc 720
gaggtgaggg gcctgaaaag cgcccaggag gtggagctgc tgagggagaa ggtgtacgcc 780
gccctggagg agtacaccag gaccacccac cccgacgagc ccggcagatt cgccaagctg 840
ctgctgaggc tgcccagcct gaggagcatc ggcctgaagt gcctggagca cctgttcttc 900
ttcaggctga tcggcgacgt gcccatcgac accttcctga tggagatgct ggagagcccc 960
agcgacagc 969

<210> SEQ ID NO 638
<211> LENGTH: 150
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 638

Met Lys Leu Leu Ser Ser Ile Glu Gln Ala Cys Asp Ile Cys Arg Leu
1 5 10 15

Lys Lys Leu Lys Cys Ser Lys Glu Lys Pro Lys Cys Ala Lys Cys Leu
20 25 30

Lys Asn Asn Trp Glu Cys Arg Tyr Ser Pro Lys Thr Lys Arg Ser Pro
35 40 45

Leu Thr Arg Ala His Leu Thr Glu Val Glu Ser Arg Leu Glu Arg Leu
50 55 60

Glu Gln Leu Phe Leu Leu Ile Phe Pro Arg Glu Asp Leu Asp Met Ile
65 70 75 80

Leu Lys Met Asp Ser Leu Gln Asp Ile Lys Ala Leu Leu Thr Gly Leu
85 90 95

Phe Val Gln Asp Asn Val Asn Lys Asp Ala Val Thr Asp Arg Leu Ala
100 105 110

Ser Val Glu Thr Asp Met Pro Leu Thr Leu Arg Gln His Arg Ile Ser
115 120 125

Ala Thr Ser Ser Ser Glu Glu Ser Ser Asn Lys Gly Gln Arg Gln Leu
130 135 140

Thr Val Ser Pro Glu Phe
145 150

<210> SEQ ID NO 639
<211> LENGTH: 450
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 639
atgaagctgc tgagcagcat cgagcaggct tgcgacatct gcaggctgaa gaagctgaag 60
tgcagcaagg agaagcccaa gtgcgccaag tgcctgaaga acaactggga gtgcagatac 120
agccccaaga ccaagaggag cccccctgacc agggcccacc tgaccgaggt ggagagcagg 180

-continued

```
ctggagaggc tggagcagct gttcctgctg atcttcccca gggaggacct ggacatgatc    240

ctgaagatgg acagcctgca agacatcaag gccctgctga ccggcctgtt cgtgcaggac    300

aacgtgaaca aggacgccgt gaccgacagg ctggccagcg tggagaccga catgcccctg    360

accctgaggc agcacaggat cagcgccacc agcagcagcg aggagagcag caacaagggc    420

cagaggcagc tgaccgtgag ccccgagttt                                     450
```

```
<210> SEQ ID NO 640
<211> LENGTH: 336
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 640

Ile Arg Pro Glu Cys Val Val Pro Glu Thr Gln Cys Ala Met Lys Arg
1               5                   10                  15

Lys Glu Lys Lys Ala Gln Lys Glu Lys Asp Lys Leu Pro Val Ser Thr
            20                  25                  30

Thr Thr Val Asp Asp His Met Pro Pro Ile Met Gln Cys Glu Pro Pro
        35                  40                  45

Pro Pro Glu Ala Ala Arg Ile His Glu Val Val Pro Arg Phe Leu Ser
    50                  55                  60

Asp Lys Leu Leu Val Thr Asn Arg Gln Lys Asn Ile Pro Gln Leu Thr
65                  70                  75                  80

Ala Asn Gln Gln Phe Leu Ile Ala Arg Leu Ile Trp Tyr Gln Asp Gly
                85                  90                  95

Tyr Glu Gln Pro Ser Asp Glu Asp Leu Lys Arg Ile Thr Gln Thr Trp
            100                 105                 110

Gln Gln Ala Asp Asp Glu Asn Glu Glu Ser Asp Thr Pro Phe Arg Gln
        115                 120                 125

Ile Thr Glu Met Thr Ile Leu Thr Val Gln Leu Ile Val Glu Phe Ala
    130                 135                 140

Lys Gly Leu Pro Gly Phe Ala Lys Ile Ser Gln Pro Asp Gln Ile Thr
145                 150                 155                 160

Leu Leu Lys Ala Cys Ser Ser Glu Val Met Met Leu Arg Val Ala Arg
                165                 170                 175

Arg Tyr Asp Ala Ala Ser Asp Ser Ile Leu Phe Ala Asn Asn Gln Ala
            180                 185                 190

Tyr Thr Arg Asp Asn Tyr Arg Lys Ala Gly Met Ala Glu Val Ile Glu
        195                 200                 205

Asp Leu Leu His Phe Cys Arg Cys Met Tyr Ser Met Ala Leu Asp Asn
    210                 215                 220

Ile His Tyr Ala Leu Leu Thr Ala Val Val Ile Phe Ser Asp Arg Pro
225                 230                 235                 240

Gly Leu Glu Gln Pro Gln Leu Val Glu Glu Ile Gln Arg Tyr Tyr Leu
                245                 250                 255

Asn Thr Leu Arg Ile Tyr Ile Leu Asn Gln Leu Ser Gly Ser Ala Arg
            260                 265                 270

Ser Ser Val Ile Tyr Gly Lys Ile Leu Ser Ile Leu Ser Glu Leu Arg
        275                 280                 285

Thr Leu Gly Met Gln Asn Ser Asn Met Cys Ile Ser Leu Lys Leu Lys
    290                 295                 300

Asn Arg Lys Leu Pro Pro Phe Leu Glu Glu Ile Trp Asp Val Ala Asp
```

305 310 315 320

Met Ser His Thr Gln Pro Pro Pro Ile Leu Glu Ser Pro Thr Asn Leu
325 330 335

<210> SEQ ID NO 641
<211> LENGTH: 1008
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 641
atcaggcccg agtgcgtggt gcccgagacc cagtgcgcca tgaaaaggaa ggagaagaag 60
gcccagaagg agaaggacaa gctgcccgtg agcaccacca ccgtcgatga ccacatgccc 120
cccatcatgc agtgcgagcc cccccccccc gaggccgcca ggattcacga ggtcgtgccc 180
aggttcctga gcgacaagct gctggtgacc aacaggcaga agaacatccc ccagctgacc 240
gccaaccagc agttcctgat cgccaggctg atctggtatc aggacggcta cgagcagccc 300
agcgacgagg acctgaaaag gatcacccag acctggcagc aggccgacga cgagaacgag 360
gagagcgaca ccccccttcag gcagatcacc gagatgacca tcctgaccgt gcagctgatc 420
gtggagttcg ccaagggcct gcccggattc gccaagatca gccagcccga ccagatcacc 480
ctgctgaagg cttgcagcag cgaggtgatg atgctgaggg tggccaggag gtacgacgcc 540
gccagcgaca gcatcctgtt cgccaacaac caggcttaca ccagggacaa ctacaggaag 600
gctggcatgg ccgaggtgat cgaggacctc ctgcacttct gcagatgtat gtacagcatg 660
gccctggaca acatccacta cgccctgctg accgccgtgg tgatcttcag cgacaggccc 720
ggcctggagc agccccagct ggtggaggag atccagaggt actacctgaa caccctgagg 780
atctacatcc tgaaccagct gagcggcagc gccaggagca gcgtgatcta cggcaagatc 840
ctgagcatcc tgagcgagct gaggaccctg ggaatgcaga acagcaatat gtgtatcagc 900
ctgaagctga agaacaggaa gctgccccccc ttcctggagg agatttggga cgtggccgac 960
atgagccaca cccagccccc ccccatcctg gagagcccca ccaacctg 1008

<210> SEQ ID NO 642
<211> LENGTH: 335
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 642

Arg Pro Glu Cys Val Val Pro Glu Thr Gln Cys Ala Met Lys Arg Lys
1 5 10 15

Glu Lys Lys Ala Gln Lys Glu Lys Asp Lys Leu Pro Val Ser Thr Thr
20 25 30

Thr Val Asp Asp His Met Pro Pro Ile Met Gln Cys Glu Pro Pro Pro
35 40 45

Pro Glu Ala Ala Arg Ile His Glu Val Val Pro Arg Phe Leu Ser Asp
50 55 60

Lys Leu Leu Val Thr Asn Arg Gln Lys Asn Ile Pro Gln Leu Thr Ala
65 70 75 80

Asn Gln Gln Phe Leu Ile Ala Arg Leu Ile Trp Tyr Gln Asp Gly Tyr
85 90 95

Glu Gln Pro Ser Asp Glu Asp Leu Lys Arg Ile Thr Gln Thr Trp Gln
            100                 105                 110

Gln Ala Asp Asp Glu Asn Glu Glu Ser Asp Thr Pro Phe Arg Gln Ile
        115                 120                 125

Thr Glu Met Thr Ile Leu Thr Val Gln Leu Ile Val Glu Phe Ala Lys
    130                 135                 140

Gly Leu Pro Gly Phe Ala Lys Ile Ser Gln Pro Asp Gln Ile Thr Leu
145                 150                 155                 160

Leu Lys Ala Cys Ser Ser Glu Val Met Met Leu Arg Val Ala Arg Arg
                165                 170                 175

Tyr Asp Ala Ala Ser Asp Ser Ile Leu Phe Ala Asn Asn Gln Ala Tyr
            180                 185                 190

Thr Arg Asp Asn Tyr Arg Lys Ala Gly Met Ala Glu Val Ile Glu Asp
        195                 200                 205

Leu Leu His Phe Cys Arg Cys Met Tyr Ser Met Ala Leu Asp Asn Ile
    210                 215                 220

His Tyr Ala Leu Leu Thr Ala Val Val Ile Phe Ser Asp Arg Pro Gly
225                 230                 235                 240

Leu Glu Gln Pro Gln Leu Val Glu Glu Ile Gln Arg Tyr Tyr Leu Asn
                245                 250                 255

Thr Leu Arg Ile Tyr Ile Leu Asn Gln Leu Ser Gly Ser Ala Arg Ser
            260                 265                 270

Ser Val Ile Tyr Gly Lys Ile Leu Ser Ile Leu Ser Glu Leu Arg Thr
        275                 280                 285

Leu Gly Met Gln Asn Ser Asn Met Cys Ile Ser Leu Lys Leu Lys Asn
    290                 295                 300

Arg Lys Leu Pro Pro Phe Leu Glu Glu Ile Trp Asp Val Ala Asp Met
305                 310                 315                 320

Ser His Thr Gln Pro Pro Pro Ile Leu Glu Ser Pro Thr Asn Leu
                325                 330                 335

<210> SEQ ID NO 643
<211> LENGTH: 1008
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 643
cggcctgagt gcgtagtacc cgagactcag tgcgccatga agcggaaaga gaagaaagca     60
cagaaggaga aggacaaact gcctgtcagc acgacgacgg tggacgacca catgccgccc    120
attatgcagt gtgaacctcc acctcctgaa gcagcaagga ttcacgaagt ggtcccaagg    180
tttctctccg acaagctgtt ggtgacaaac cggcagaaaa acatccccca gttgacagcc    240
aaccagcagt tccttatcgc caggctcatc tggtaccagg acgggtacga gcagccttct    300
gatgaagatt tgaagaggat tacgcagacg tggcagcaag cggacgatga aaacgaagag    360
tcggacactc ccttccgcca gatcacagag atgactatcc tcacggtcca acttatcgtg    420
gagttcgcga agggattgcc agggttcgcc aagatctcgc agcctgatca aattacgctg    480
cttaaggctt gctcaagtga ggtaatgatg ctccgagtcg cgcgacgata cgatgcggcc    540
tcagacagta ttctgttcgc gaacaaccaa gcgtacactc gcgacaacta ccgcaaggct    600
ggcatggccg aggtcatcga ggatctactg cacttctgcc ggtgcatgta ctctatggcg    660
ttggacaaca tccattacgc gctgctcacg gctgtcgtca tcttttctga ccggccaggg    720
ttggagcagc cgcaactggt ggaagagatc cagcggtact acctgaatac gctccgcatc 780
tatatcctga accagctgag cgggtcggcg cgttcgtccg tcatatacgg caagatcctc 840
tcaatcctct ctgagctacg cacgctcggc atgcaaaact ccaacatgtg catctccctc 900
aagctcaaga acagaaagct gccgcctttc ctcgaggaga tctgggatgt ggcggacatg 960
tcgcacaccc aaccgccgcc tatcctcgag tcccccacga atctctag 1008

<210> SEQ ID NO 644
<211> LENGTH: 488
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 644

Met Lys Leu Leu Ser Ser Ile Glu Gln Ala Cys Asp Ile Cys Arg Leu
1 5 10 15

Lys Lys Leu Lys Cys Ser Lys Glu Lys Pro Lys Cys Ala Lys Cys Leu
20 25 30

Lys Asn Asn Trp Glu Cys Arg Tyr Ser Pro Lys Thr Lys Arg Ser Pro
35 40 45

Leu Thr Arg Ala His Leu Thr Glu Val Glu Ser Arg Leu Glu Arg Leu
50 55 60

Glu Gln Leu Phe Leu Leu Ile Phe Pro Arg Glu Asp Leu Asp Met Ile
65 70 75 80

Leu Lys Met Asp Ser Leu Gln Asp Ile Lys Ala Leu Leu Thr Gly Leu
85 90 95

Phe Val Gln Asp Asn Val Asn Lys Asp Ala Val Thr Asp Arg Leu Ala
100 105 110

Ser Val Glu Thr Asp Met Pro Leu Thr Leu Arg Gln His Arg Ile Ser
115 120 125

Ala Thr Ser Ser Ser Glu Glu Ser Ser Asn Lys Gly Gln Arg Gln Leu
130 135 140

Thr Val Ser Pro Glu Phe Pro Gly Ile Arg Pro Glu Cys Val Val Pro
145 150 155 160

Glu Thr Gln Cys Ala Met Lys Arg Lys Glu Lys Lys Ala Gln Lys Glu
165 170 175

Lys Asp Lys Leu Pro Val Ser Thr Thr Thr Val Asp Asp His Met Pro
180 185 190

Pro Ile Met Gln Cys Glu Pro Pro Pro Pro Glu Ala Ala Arg Ile His
195 200 205

Glu Val Val Pro Arg Phe Leu Ser Asp Lys Leu Leu Val Thr Asn Arg
210 215 220

Gln Lys Asn Ile Pro Gln Leu Thr Ala Asn Gln Gln Phe Leu Ile Ala
225 230 235 240

Arg Leu Ile Trp Tyr Gln Asp Gly Tyr Glu Gln Pro Ser Asp Glu Asp
245 250 255

Leu Lys Arg Ile Thr Gln Thr Trp Gln Gln Ala Asp Asp Glu Asn Glu
260 265 270

Glu Ser Asp Thr Pro Phe Arg Gln Ile Thr Glu Met Thr Ile Leu Thr
275 280 285

Val Gln Leu Ile Val Glu Phe Ala Lys Gly Leu Pro Gly Phe Ala Lys
290 295 300

```
Ile Ser Gln Pro Asp Gln Ile Thr Leu Leu Lys Ala Cys Ser Ser Glu
305                 310                 315                 320

Val Met Met Leu Arg Val Ala Arg Arg Tyr Asp Ala Ala Ser Asp Ser
                325                 330                 335

Ile Leu Phe Ala Asn Asn Gln Ala Tyr Thr Arg Asp Asn Tyr Arg Lys
            340                 345                 350

Ala Gly Met Ala Glu Val Ile Glu Asp Leu Leu His Phe Cys Arg Cys
        355                 360                 365

Met Tyr Ser Met Ala Leu Asp Asn Ile His Tyr Ala Leu Leu Thr Ala
    370                 375                 380

Val Val Ile Phe Ser Asp Arg Pro Gly Leu Glu Gln Pro Gln Leu Val
385                 390                 395                 400

Glu Glu Ile Gln Arg Tyr Tyr Leu Asn Thr Leu Arg Ile Tyr Ile Leu
                405                 410                 415

Asn Gln Leu Ser Gly Ser Ala Arg Ser Ser Val Ile Tyr Gly Lys Ile
            420                 425                 430

Leu Ser Ile Leu Ser Glu Leu Arg Thr Leu Gly Met Gln Asn Ser Asn
        435                 440                 445

Met Cys Ile Ser Leu Lys Leu Lys Asn Arg Lys Leu Pro Pro Phe Leu
    450                 455                 460

Glu Glu Ile Trp Asp Val Ala Asp Met Ser His Thr Gln Pro Pro Pro
465                 470                 475                 480

Ile Leu Glu Ser Pro Thr Asn Leu
                485
```

```
<210> SEQ ID NO 645
<211> LENGTH: 1467
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 645

atgaagctac tgtcttctat cgaacaagca tgcgatattt gccgacttaa aaagctcaag     60

tgctccaaag aaaaaccgaa gtgcgccaag tgtctgaaga acaactggga gtgtcgctac    120

tctcccaaaa ccaaaaggtc tccgctgact agggcacatc tgacagaagt ggaatcaagg    180

ctagaaagac tggaacagct atttctactg atttttcctc gagaagacct tgacatgatt    240

ttgaaaatgg attctttaca ggatataaaa gcattgttaa caggattatt tgtacaagat    300

aatgtgaata aagatgccgt cacagataga ttggcttcag tggagactga tatgcctcta    360

acattgagac agcatagaat aagtgcgaca tcatcatcgg aagagagtag taacaaaggt    420

caaagacagt tgactgtatc gccggaattc ccggggatcc ggcctgagtg cgtagtaccc    480

gagactcagt gcgccatgaa gcggaaagag aagaaagcac agaaggagaa ggacaaactg    540

cctgtcagca cgacgacggt ggacgaccac atgccgccca ttatgcagtg tgaacctcca    600

cctcctgaag cagcaaggat tcacgaagtg gtcccaaggt ttctctccga caagctgttg    660

gtgacaaacc ggcagaaaaa catcccccag ttgacagcca accagcagtt ccttatcgcc    720

aggctcatct ggtaccagga cgggtacgag cagccttctg atgaagattt gaagaggatt    780

acgcagacgt ggcagcaagc ggacgatgaa aacgaagagt cggacactcc cttccgccag    840

atcacagaga tgactatcct cacggtccaa cttatcgtgg agttcgcgaa gggattgcca    900

gggttcgcca agatctcgca gcctgatcaa attacgctgc ttaaggcttg ctcaagtgag    960
```

```
gtaatgatgc tccgagtcgc gcgacgatac gatgcggcct cagacagtat tctgttcgcg   1020

aacaaccaag cgtacactcg cgacaactac cgcaaggctg gcatggccga ggtcatcgag   1080

gatctactgc acttctgccg gtgcatgtac tctatggcgt tggacaacat ccattacgcg   1140

ctgctcacgg ctgtcgtcat cttttctgac cggccagggt tggagcagcc gcaactggtg   1200

gaagagatcc agcggtacta cctgaatacg ctccgcatct atatcctgaa ccagctgagc   1260

gggtcggcgc gttcgtccgt catatacggc aagatcctct caatcctctc tgagctacgc   1320

acgctcggca tgcaaaactc caacatgtgc atctccctca agctcaagaa cagaaagctg   1380

ccgcctttcc tcgaggagat ctgggatgtg gcggacatgt cgcacaccca accgccgcct   1440

atcctcgagt cccccacgaa tctctag                                       1467
```

<210> SEQ ID NO 646
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 646

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Pro Gly Arg Pro Glu Cys Val Val Pro Glu
145                 150                 155                 160

Thr Gln Cys Ala Met Lys Arg Lys Glu Lys Lys Ala Gln Lys Glu Lys
                165                 170                 175

Asp Lys Leu Pro Val Ser Thr Thr Thr Val Asp Asp His Met Pro Pro
            180                 185                 190

Ile Met Gln Cys Glu Pro Pro Pro Pro Glu Ala Ala Arg Ile His Glu
        195                 200                 205

Val Val Pro Arg Phe Leu Ser Asp Lys Leu Leu Val Thr Asn Arg Gln
    210                 215                 220

Lys Asn Ile Pro Gln Leu Thr Ala Asn Gln Gln Phe Leu Ile Ala Arg
225                 230                 235                 240

Leu Ile Trp Tyr Gln Asp Gly Tyr Glu Gln Pro Ser Asp Glu Asp Leu
                245                 250                 255

Lys Arg Ile Thr Gln Thr Trp Gln Gln Ala Asp Asp Glu Asn Glu Glu
            260                 265                 270
```

-continued

Ser Asp Thr Pro Phe Arg Gln Ile Thr Glu Met Thr Ile Leu Thr Val
275 280 285

Gln Leu Ile Val Glu Phe Ala Lys Gly Leu Pro Gly Phe Ala Lys Ile
290 295 300

Ser Gln Pro Asp Gln Ile Thr Leu Leu Lys Ala Cys Ser Ser Glu Val
305 310 315 320

Met Met Leu Arg Val Ala Arg Arg Tyr Asp Ala Ala Ser Asp Ser Ile
325 330 335

Leu Phe Ala Asn Asn Gln Ala Tyr Thr Arg Asp Asn Tyr Arg Lys Ala
340 345 350

Gly Met Ala Glu Val Ile Glu Asp Leu Leu His Phe Cys Arg Cys Met
355 360 365

Tyr Ser Met Ala Leu Asp Asn Ile His Tyr Ala Leu Leu Thr Ala Val
370 375 380

Val Ile Phe Ser Asp Arg Pro Gly Leu Glu Gln Pro Gln Leu Val Glu
385 390 395 400

Glu Ile Gln Arg Tyr Tyr Leu Asn Thr Leu Arg Ile Tyr Ile Leu Asn
405 410 415

Gln Leu Ser Gly Ser Ala Arg Ser Ser Val Ile Tyr Gly Lys Ile Leu
420 425 430

Ser Ile Leu Ser Glu Leu Arg Thr Leu Gly Met Gln Asn Ser Asn Met
435 440 445

Cys Ile Ser Leu Lys Leu Lys Asn Arg Lys Leu Pro Pro Phe Leu Glu
450 455 460

Glu Ile Trp Asp Val Ala Asp Met Ser His Thr Gln Pro Pro Pro Ile
465 470 475 480

Leu Glu Ser Pro Thr Asn Leu
485

<210> SEQ ID NO 647
<211> LENGTH: 1464
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 647
atgaagctgc tgagcagcat cgagcaggct tgcgacatct gcaggctgaa gaagctgaag 60
tgcagcaagg agaagcccaa gtgcgccaag tgcctgaaga acaactggga gtgcagatac 120
agccccaaga ccaagaggag ccccctgacc agggcccacc tgaccgaggt ggagagcagg 180
ctggagaggc tggagcagct gttcctgctg atcttcccca gggaggacct ggacatgatc 240
ctgaagatgg acagcctgca agacatcaag gccctgctga ccggcctgtt cgtgcaggac 300
aacgtgaaca aggacgccgt gaccgacagg ctggccagcg tggagaccga catgcccctg 360
accctgaggc agcacaggat cagcgccacc agcagcagcg aggagagcag caacaagggc 420
cagaggcagc tgaccgtgag ccccgagttt cccgggcggc ctgagtgcgt agtacccgag 480
actcagtgcg ccatgaagcg gaaagagaag aaagcacaga aggagaagga caaactgcct 540
gtcagcacga cgacggtgga cgaccacatg ccgcccatta tgcagtgtga acctccacct 600
cctgaagcag caaggattca cgaagtggtc ccaaggtttc tctccgacaa gctgttggtg 660
acaaaccggc agaaaaacat cccccagttg acagccaacc agcagttcct tatcgccagg 720
ctcatctggt accaggacgg gtacgagcag ccttctgatg aagatttgaa gaggattacg 780
cagacgtggc agcaagcgga cgatgaaaac gaagagtcgg acactccctt ccgccagatc 840
acagagatga ctatcctcac ggtccaactt atcgtggagt tcgcgaaggg attgccaggg 900
ttcgccaaga tctcgcagcc tgatcaaatt acgctgctta aggcttgctc aagtgaggta 960
atgatgctcc gagtcgcgcg acgatacgat gcggcctcag acagtattct gttcgcgaac 1020
aaccaagcgt acactcgcga caactaccgc aaggctggca tggccgaggt catcgaggat 1080
ctactgcact tctgccggtg catgtactct atggcgttgg acaacatcca ttacgcgctg 1140
ctcacggctg tcgtcatctt ttctgaccgg ccagggttgg agcagccgca actggtggaa 1200
gagatccagc ggtactacct gaatacgctc cgcatctata tcctgaacca gctgagcggg 1260
tcggcgcgtt cgtccgtcat atacggcaag atcctctcaa tcctctctga gctacgcacg 1320
ctcggcatgc aaaactccaa catgtgcatc tccctcaagc tcaagaacag aaagctgccg 1380
cctttcctcg aggagatctg ggatgtggcg gacatgtcgc acacccaacc gccgcctatc 1440
ctcgagtccc ccacgaatct ctag 1464

<210> SEQ ID NO 648
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 648

Gln Val Gln Leu Gln Glu Ser Gly Pro Gly Leu Val Lys Pro Ser Asp
1 5 10 15

Thr Leu Ser Leu Thr Cys Ala Val Ser Gly Tyr Ser Ile Val Ser His
20 25 30

Tyr Tyr Trp His Trp Ile Arg Gln Pro Pro Gly Lys Gly Leu Glu Trp
35 40 45

Met Gly Tyr Ile Ser Ser Asp Gly Ser Asn Asp Phe Asn Pro Ser Leu
50 55 60

Lys Thr Arg Ile Thr Ile Ser Arg Asp Thr Ser Lys Asn Gln Phe Ser
65 70 75 80

Leu Lys Leu Ser Ser Val Thr Ala Val Asp Thr Ala Val Tyr Tyr Cys
85 90 95

Val Arg Gly Val Asp Tyr Trp Gly Gln Gly Thr Leu Val Thr Val Ser
100 105 110

Ser

<210> SEQ ID NO 649
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 649
caggtgcagc tgcaggagag cggccccggc ctggtgaagc ccagcgacac cctgagcctg 60
acctgcgccg tgagcggcta cagcatcgtg agccactact actggcactg gatcagacag 120
ccccccggca agggcctgga gtggatgggc tacatcagca gcgacggcag caacgacttc 180
aaccccagcc tgaagaccag aatcaccatc agcagagaca ccagcaagaa ccagttcagc 240
ctgaagctga gcagcgtgac cgccgtggac accgccgtgt actactgcgt gagaggcgtg 300
gactactggg gccagggcac cctggtgacc gtgagcagc 339

<210> SEQ ID NO 650
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 650

Gln Val Gln Leu Gln Glu Ser Gly Pro Gly Leu Val Lys Pro Ser Gln
1 5 10 15

Thr Leu Ser Leu Thr Cys Ala Val Tyr Gly Tyr Ser Ile Val Ser His
20 25 30

Tyr Tyr Trp Ser Trp Ile Arg Gln Pro Pro Gly Lys Gly Leu Glu Trp
35 40 45

Ile Gly Glu Ile Ser Ser Asp Gly Ser Asn Asn Tyr Asn Pro Ser Leu
50 55 60

Lys Ser Arg Val Thr Ile Ser Val Asp Thr Ser Lys Asn Gln Phe Ser
65 70 75 80

Leu Lys Leu Ser Ser Val Thr Ala Ala Asp Thr Ala Val Tyr Tyr Cys
85 90 95

Val Arg Gly Val Asp Tyr Trp Gly Gln Gly Thr Leu Val Thr Val Ser
100 105 110

Ser

<210> SEQ ID NO 651
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 651
caggtgcagc tgcaggagag cggccccggc ctggtgaagc ccagccagac cctgagcctg 60
acctgcgccg tgtacggcta cagcatcgtg agccactact actggagctg gatcagacag 120
ccccccggca agggcctgga gtggatcggc gagatcagca gcgacggcag caacaactac 180
aaccccagcc tgaagagcag agtgaccatc agcgtggaca ccagcaagaa ccagttcagc 240
ctgaagctga gcagcgtgac cgccgccgac accgccgtgt actactgcgt gagaggcgtg 300
gactactggg gccagggcac cctggtgacc gtgagcagc 339

<210> SEQ ID NO 652
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 652

Gln Val Gln Leu Gln Glu Ser Gly Pro Gly Leu Val Lys Pro Ser Glu
1 5 10 15

Thr Leu Ser Leu Thr Cys Ala Val Ser Gly Tyr Ser Ile Val Ser His
20 25 30

Tyr Tyr Trp Gly Trp Ile Arg Gln Pro Pro Gly Lys Gly Leu Glu Trp
35 40 45

Ile Gly Ser Ile Ser Ser Asp Gly Ser Asn Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Arg Gly Val Asp Tyr Trp Gly Gln Gly Thr Leu Val Thr Val Ser
            100                 105                 110

Ser

<210> SEQ ID NO 653
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 653
caggtgcagc tgcaggagag cggccccggc ctggtgaagc ccagcgagac cctgagcctg     60
acctgcgccg tgagcggcta cagcatcgtg agccactact actggggctg gatcagacag    120
ccccccggca agggcctgga gtggatcggc agcatcagca gcgacggcag caactactac    180
aaccccagcc tgaagagcag agtgaccatc agcgtggaca ccagcaagaa ccagttcagc    240
ctgaagctga gcagcgtgac cgccgccgac accgccgtgt actactgcgt gagaggcgtg    300
gactactggg gccagggcac cctggtgacc gtgagcagc                           339

<210> SEQ ID NO 654
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 654

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Ser Ile Val Ser His
            20                  25                  30

Tyr Tyr Trp Asn Trp Val Arg Gln Ala Pro Gly Lys Gly Leu Glu Trp
        35                  40                  45

Val Ala Tyr Ile Ser Ser Asp Gly Ser Asn Glu Tyr Asn Pro Ser Leu
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Gly Val Asp Tyr Trp Gly Gln Gly Thr Thr Val Thr Val Ser
            100                 105                 110

Ser

<210> SEQ ID NO 655
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 655
caggtgcagc tggtggagag cggcggcggc gtggtgcagc ccggcagaag cctgagactg 60
agctgcgccg ccagcggcta cagcatcgtg agccactact actggaactg ggtgagacag 120
gcccccggca agggcctgga gtgggtggcc tacatcagca gcgacggcag caacgagtac 180
aaccccagcc tgaagaacag attcaccatc agcagagaca acagcaagaa caccctgtac 240
ctgcagatga acagcctgag agccgaggac accgccgtgt actactgcgt gagaggcgtg 300
gactactggg gccagggcac caccgtgacc gtgagcagc 339

<210> SEQ ID NO 656
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 656

Gln Val Gln Leu Gln Glu Ser Gly Pro Gly Leu Val Lys Pro Ser Gln
1 5 10 15

Thr Leu Ser Leu Thr Cys Thr Val Ser Gly Tyr Ser Ile Val Ser His
20 25 30

Tyr Tyr Trp Asn Trp Ile Arg Gln His Pro Gly Lys Gly Leu Glu Trp
35 40 45

Ile Gly Tyr Ile Ser Ser Asp Gly Ser Asn Glu Tyr Asn Pro Ser Leu
50 55 60

Lys Asn Leu Val Thr Ile Ser Val Asp Thr Ser Lys Asn Gln Phe Ser
65 70 75 80

Leu Lys Leu Ser Ser Val Thr Ala Ala Asp Thr Ala Val Tyr Tyr Cys
85 90 95

Val Arg Gly Val Asp Tyr Trp Gly Gln Gly Thr Met Val Thr Val Ser
100 105 110

Ser

<210> SEQ ID NO 657
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 657
caggtgcagc tgcaggagag cggccccggc ctggtgaagc ccagccagac cctgagcctg 60
acctgcaccg tgagcggcta cagcatcgtg agccactact actggaactg gatcagacag 120
caccccggca agggcctgga gtggatcggc tacatcagca gcgacggcag caacgagtac 180
aaccccagcc tgaagaacct ggtgaccatc agcgtggaca ccagcaagaa ccagttcagc 240
ctgaagctga gcagcgtgac cgccgccgac accgccgtgt actactgcgt gagaggcgtg 300
gactactggg gccagggcac catggtgacc gtgagcagc 339

<210> SEQ ID NO 658
<211> LENGTH: 113
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 658

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Val Ser His
            20                  25                  30

Tyr Tyr Trp Asn Trp Ile Arg Gln Pro Pro Gly Lys Gly Leu Glu Trp
        35                  40                  45

Ile Gly Tyr Ile Ser Ser Asp Gly Ser Asn Glu Tyr Asn Pro Ser Leu
    50                  55                  60

Lys Asn Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Val Arg Gly Val Asp Tyr Trp Gly Gln Gly Thr Met Val Thr Val Ser
            100                 105                 110

Ser

<210> SEQ ID NO 659
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 659
caggtgcagc tgcaggagag cggccccggc ctggtgaagc ccagcgacac cctgagcctg      60
acctgcgccg tgagcggcta cagcatcgtg agccactact actggaactg gatcagacag     120
ccccccggca agggcctgga gtggatcggc tacatcagca gcgacggcag caacgagtac     180
aaccccagcc tgaagaacag agtgaccatg agcgtggaca ccagcaagaa ccagttcagc     240
ctgaagctga gcagcgtgac cgccgtggac accgccgtgt actactgcgt gagaggcgtg     300
gactactggg gccagggcac catggtgacc gtgagcagc                            339

<210> SEQ ID NO 660
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 660

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Ile Val Ser His
            20                  25                  30

Tyr Tyr Trp Asn Trp Val Arg Gln Ala Pro Gly Lys Gly Leu Glu Trp
        35                  40                  45

Val Ser Tyr Ile Ser Ser Asp Gly Ser Asn Glu Tyr Asn Pro Ser Leu
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Gly Val Asp Tyr Trp Gly Gln Gly Thr Leu Val Thr Val Ser
            100                 105                 110

Ser

<210> SEQ ID NO 661
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 661
gaggtgcagc tgctggagag cggcggcggc ctggtgcagc ccggcggcag cctgagactg     60
agctgcgccg ccagcggcta cagcatcgtg agccactact actggaactg ggtgagacag    120
gcccccggca agggcctgga gtgggtgagc tacatcagca gcgacggcag caacgagtac    180
aaccccagcc tgaagaacag attcaccatc agcagagaca acagcaagaa caccctgtac    240
ctgcagatga acagcctgag agccgaggac accgccgtgt actactgcgt gagaggcgtg    300
gactactggg gccagggcac cctggtgacc gtgagcagc                           339

<210> SEQ ID NO 662
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 662

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Asp Ile Asn Asn Phe
            20                  25                  30

Leu Ala Trp Tyr Gln Gln Lys Pro Gly Lys Ala Pro Lys Leu Leu Leu
        35                  40                  45

Tyr Arg Ala Asn Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Gly Asp Leu Tyr Thr
                85                  90                  95

Phe Gly Gly Gly Thr Lys Val Glu Ile Lys
            100                 105

<210> SEQ ID NO 663
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 663
gacatccaga tgacccagag ccccagcagc ctgagcgcca gcgtgggcga cagagtgacc     60
atcacctgca gagccagcag agacatcaac aacttcctgg cctggtacca gcagaagccc    120
ggcaaggccc ccaagctgct gctgtacaga gccaacagac tggagagcgg cgtgcccagc    180
agattcagcg gcagcggcag cggcaccgac tacaccctga ccatcagcag cctgcagccc    240
gaggacttcg ccacctacta ctgcctgcag tacggcgacc tgtacacctt cggcggcggc 300
accaaggtgg agatcaag 318

<210> SEQ ID NO 664
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 664

Asp Ile Gln Met Thr Gln Ser Pro Ser Ser Leu Ser Ala Ser Val Gly
1 5 10 15

Asp Arg Val Thr Ile Thr Cys Lys Ala Ser Arg Asp Ile Asn Asn Phe
20 25 30

Leu Ser Trp Tyr Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Leu Gln Tyr Gly Asp Leu Tyr Thr
85 90 95

Phe Gly Gly Gly Thr Lys Val Glu Ile Lys
100 105

<210> SEQ ID NO 665
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 665
gacatccaga tgacccagag ccccagcagc ctgagcgcca gcgtgggcga cagagtgacc 60
atcacctgca aggccagcag agacatcaac aacttcctga gctggtacca gcagaagccc 120
ggcaaggccc ccaagctgct gatctacaga gccaacagac tggtggacgg cgtgcccagc 180
agattcagcg gcagcggcag cggcaccgac ttcaccttca ccatcagcag cctgcagccc 240
gaggacatcg ccacctacta ctgcctgcag tacggcgacc tgtacacctt cggcggcggc 300
accaaggtgg agatcaag 318

<210> SEQ ID NO 666
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 666

Asp Ile Gln Met Thr Gln Ser Pro Ser Ser Leu Ser Ala Ser Val Gly
1 5 10 15

Asp Arg Val Thr Ile Thr Cys Lys Ala Ser Arg Asp Ile Asn Asn Phe
20 25 30

Leu Ser Trp Tyr Gln Gln Lys Pro Gly Lys Ala Pro Lys Leu Leu Ile
35 40 45

```
Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Gly Asp Leu Tyr Thr
                85                  90                  95

Phe Gly Gln Gly Thr Lys Val Glu Ile Lys
            100                 105
```

<210> SEQ ID NO 667
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 667

```
gacatccaga tgacccagag ccccagcagc ctgagcgcca gcgtgggcga cagagtgacc     60

atcacctgca aggccagcag agacatcaac aacttcctga gctggtacca gcagaagccc    120

ggcaaggccc ccaagctgct gatctacaga gccaacagac tggtggacgg cgtgcccagc    180

agattcagcg gcagcggcag cggcaccgac ttcaccctga ccatcagcag cctgcagccc    240

gaggacttcg ccacctacta ctgcctgcag tacggcgacc tgtacacctt cggccagggc    300

accaaggtgg agatcaag                                                  318
```

<210> SEQ ID NO 668
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 668

```
Glu Ile Val Leu Thr Gln Ser Pro Gly Thr Leu Ser Leu Ser Pro Gly
1               5                   10                  15

Glu Arg Ala Thr Leu Ser Cys Lys Ala Ser Arg Asp Ile Asn Asn Phe
            20                  25                  30

Leu Ser Trp Tyr Gln Gln Lys Pro Gly Gln Ala Pro Arg Leu Leu Ile
        35                  40                  45

Tyr Arg Ala Asn Arg Leu Val Asp Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Leu Gln Tyr Gly Asp Leu Tyr Thr
                85                  90                  95

Phe Gly Gln Gly Thr Lys Val Glu Ile Lys
            100                 105
```

<210> SEQ ID NO 669
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 669
gagatcgtgc tgacccagag ccccggcacc ctgagcctga gccccggcga gagagccacc 60
ctgagctgca aggccagcag agacatcaac aacttcctga gctggtacca gcagaagccc 120
ggccaggccc ccagactgct gatctacaga gccaacagac tggtggacgg catccccgac 180
agattcagcg gcagcggcag cggcaccgac ttcaccctga ccatcagcag actggagccc 240
gaggacttcg ccgtgtacta ctgcctgcag tacggcgacc tgtacacctt cggccagggc 300
accaaggtgg agatcaag 318

<210> SEQ ID NO 670
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 670

Glu Ile Val Leu Thr Gln Ser Pro Ala Thr Leu Ser Leu Ser Pro Gly
1 5 10 15

Glu Arg Ala Thr Leu Ser Cys Lys Ala Ser Arg Asp Ile Asn Asn Phe
20 25 30

Leu Ser Trp Tyr Gln Gln Lys Pro Gly Gln Ala Pro Arg Leu Leu Ile
35 40 45

Tyr Arg Ala Asn Arg Leu Val Asp Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Leu Gln Tyr Gly Asp Leu Tyr Thr
85 90 95

Phe Gly Gln Gly Thr Lys Val Glu Ile Lys
100 105

<210> SEQ ID NO 671
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 671
gagatcgtgc tgacccagag ccccgccacc ctgagcctga gccccggcga gagagccacc 60
ctgagctgca aggccagcag agacatcaac aacttcctga gctggtacca gcagaagccc 120
ggccaggccc ccagactgct gatctacaga gccaacagac tggtggacgg catccccgcc 180
agattcagcg gcagcggcag cggcaccgac ttcaccctga ccatcagcag cctggagccc 240
gaggacttcg ccgtgtacta ctgcctgcag tacggcgacc tgtacacctt cggccagggc 300
accaaggtgg agatcaag 318

<210> SEQ ID NO 672
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 672

Val Lys Leu Gln Glu Ser Gly Gly Gly Phe Val Lys Pro Gly Gly Ser

```
1               5                   10                  15

Leu Lys Val Ser Cys Ala Ala Ser Gly Phe Thr Phe Ser Ser Tyr Ala
            20                  25                  30

Met Ser Trp Val Arg Leu Ser Pro Glu Met Arg Leu Glu Trp Val Ala
        35                  40                  45

Thr Ile Ser Ser Ala Gly Gly Tyr Ile Phe Tyr Ser Asp Ser Val Gln
    50                  55                  60

Gly Arg Phe Thr Ile Ser Arg Asp Asn Ala Lys Asn Thr Leu His Leu
65                  70                  75                  80

Gln Met Gly Ser Leu Arg Ser Gly Asp Thr Ala Met Tyr Tyr Cys Ala
                85                  90                  95

Arg Gln Gly Phe Gly Asn Tyr Gly Asp Tyr Tyr Ala Met Asp Tyr Trp
            100                 105                 110

Gly Gln Gly Thr Thr Val Thr Val Ser Ser
        115                 120
```

<210> SEQ ID NO 673
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 673

```
gtgaagctgc aagagtccgg cggaggcttt gtgaagcctg gcggctctct gaaagtgtcc     60

tgtgccgcca gcggcttcac ctttagcagc tacgccatga gctgggtccg actgagccct    120

gagatgagac tggaatgggt cgccaccatc agtagcgcag gcggctacat cttctacagc    180

gactctgtgc agggcagatt caccatcagc cgggacaacg ccaagaacac cctgcacctc    240

cagatgggca gtctgagaag cggcgatacc gccatgtact actgcgccag acaaggcttc    300

ggcaactacg gcgactacta tgccatggat tactggggcc agggcaccac cgtgacagtc    360

tcttct                                                               366
```

<210> SEQ ID NO 674
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 674

```
Val Lys Leu Glu Glu Ser Gly Gly Gly Phe Val Lys Pro Gly Gly Ser
1               5                   10                  15

Leu Lys Ile Ser Cys Ala Ala Ser Gly Phe Thr Phe Arg Asn Tyr Ala
            20                  25                  30

Met Ser Trp Val Arg Leu Ser Pro Glu Met Arg Leu Glu Trp Val Ala
        35                  40                  45

Thr Ile Ser Ser Ala Gly Gly Tyr Ile Phe Tyr Ser Asp Ser Val Gln
    50                  55                  60

Gly Arg Phe Thr Ile Ser Arg Asp Asn Ala Lys Asn Thr His Leu Gln
65                  70                  75                  80

Met Gly Ser Leu Arg Ser Gly Asp Thr Ala Met Tyr Tyr Cys Ala Arg
                85                  90                  95

Gln Gly Phe Gly Asn Tyr Gly Asp Tyr Tyr Ala Met Asp Tyr Trp Gly
            100                 105                 110
```

Gln Gly Thr Thr Val Thr Val Ser Ser
115 120

<210> SEQ ID NO 675
<211> LENGTH: 365
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 675
gtgaagctgg aagagtccgg cggaggcttt gtgaagcctg gcggaagcct gaagatcagc 60
tgtgccgcca gcggcttcac cttcagaaac tacgccatga gctgggtccg actgagcccc 120
gagatgagac tggaatgggt cgccacaatc agcagcgcag gcggctacat cttctacagc 180
gatagcgtgc agggcagatt caccatcagc cgggacaacg ccaagaacac cctgcacctc 240
cagatgggca gtctgagatc tggcgacacc gccatgtact actggccaga caaggcttcg 300
gcaactacgg cgactactat gccatggatt actggggcca gggcaccacc gtgacagtct 360
cttct 365

<210> SEQ ID NO 676
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 676

Asp Val Gln Leu Leu Glu Ser Gly Pro Gly Leu Val Arg Pro Ser Gln
1 5 10 15

Ser Leu Ser Leu Thr Cys Ser Val Thr Gly Tyr Ser Ile Val Ser His
20 25 30

Tyr Tyr Trp Asn Trp Ile Arg Gln Phe Pro Gly Asn Lys Leu Glu Trp
35 40 45

Met Gly Tyr Ile Ser Ser Asp Gly Ser Asn Glu Tyr Asn Pro Ser Leu
50 55 60

Lys Asn Arg Ile Ser Ile Ser Leu Asp Thr Ser Lys Asn Gln Phe Phe
65 70 75 80

Leu Lys Phe Asp Phe Val Thr Thr Ala Asp Thr Ala Thr Tyr Phe Cys
85 90 95

Val Arg Gly Val Asp Tyr Trp Gly Gln Gly Thr Thr Leu Thr Val Ser
100 105 110

Ser

<210> SEQ ID NO 677
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 677
gacgtgcaac ttctggagag cgggccaggg ctagtcaggc cctcccagtc gctttcactg 60
acttgcagtg tgaccggtta ctctattgtg agtcactact attggaactg gattcggcag 120
ttcccaggca acaaactgga atggatgggg tacatatctt ccgatggctc gaatgaatat 180
aacccatcat tgaaaaatcg tatttccatc agtctggata cgagtaaaaa ccagtttttc 240
ctcaaattcg atttcgtgac tacagcagat actgccacat acttctgtgt acgaggtgtc 300
gattattggg gacagggcac aacgctgacc gtaagttct 339

<210> SEQ ID NO 678
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 678

Asp Val Gln Leu Gln Glu Ser Gly Pro Gly Leu Val Asn Pro Ser Gln
1 5 10 15

Ser Leu Ser Leu Thr Cys Thr Val Thr Gly Tyr Ser Ile Thr Asn Asp
20 25 30

Tyr Ala Trp Asn Trp Ile Arg Gln Phe Pro Gly Asn Lys Leu Glu Trp
35 40 45

Met Gly Tyr Ile Asn Tyr Ser Gly Tyr Thr Thr Tyr Asn Pro Ser Leu
50 55 60

Lys Ser Arg Ile Ser Ile Thr Arg Asp Thr Ser Lys Asn Gln Phe Phe
65 70 75 80

Leu His Leu Asn Ser Val Thr Thr Glu Asp Thr Ala Thr Tyr Tyr Cys
85 90 95

Ala Arg Trp Asp Gly Gly Leu Thr Tyr Trp Gly Gln Gly Thr Leu Val
100 105 110

Thr Val Ser Ala
115

<210> SEQ ID NO 679
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 679
gacgttcagc tgcaagagtc tggccctggc ctggtcaatc ctagccagag cctgagcctg 60
acatgtaccg tgaccggcta cagcatcacc aacgactacg cctggaactg gatcagacag 120
ttccccggca acaagctgga atggatgggc tacatcaact acagcggcta caccacctac 180
aatcccagcc tgaagtcccg gatctccatc accagagaca ccagcaagaa ccagttcttc 240
ctgcacctga acagcgtgac caccgaggat accgccacct actactgcgc tagatgggat 300
ggcggcctga catattgggg ccagggaaca ctggtcaccg tgtctgct 348

<210> SEQ ID NO 680
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 680

Glu Val Gln Leu Val Glu Ser Gly Gly Gly Leu Val Gln Pro Gly Gly
1 5 10 15

```
Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Asn Tyr Ser Gly Tyr Thr Thr Tyr Asn Pro Ser Leu
    50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Asp Gly Gly Leu Thr Tyr Trp Gly Gln Gly Thr Leu Val
            100                 105                 110

Thr Val Ser Ser
        115
```

<210> SEQ ID NO 681
<211> LENGTH: 348
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 681

```
gaggtgcagc tggtggagag cggcggcggc ctggtgcagc ccggcggcag cctgaggctg      60

agctgcgccg ccagcggcta cagcatcacc aacgactacg cctggaactg ggtgaggcag     120

gcccccggca agggcctgga gtgggtgggc tacatcaact acagcggcta caccacctac     180

aaccccagcc tgaagagcag gttcaccatc agcagggaca acagcaagaa caccctgtac     240

ctgcagatga acagcctgag ggccgaggac accgccgtgt actactgcgc caggtgggac     300

ggcggcctga cctactgggg ccagggcacc ctggtgaccg tgagcagc                  348
```

<210> SEQ ID NO 682
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 682

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Asn Tyr Ser Gly Tyr Thr Thr Tyr Asn Pro Ser Leu
    50                  55                  60

Lys Ser Arg Phe Thr Ile Ser Arg Asp Asn Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Trp Asp Gly Gly Leu Thr Tyr Trp Gly Gln Gly Thr Leu Val
            100                 105                 110

Thr Val Ser Ser
        115
```

<210> SEQ ID NO 683
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 683
gaggtgcagc tggtggagag cggcggcggc ctggtgcagc ccggcggcag cctgaggctg 60
agctgcgccg ccagcggcta cagcatcacc aacgactacg cctggaactg ggtgaggcag 120
gcccccggca agggcctgga gtgggtgggc tacatcaact acagcggcta caccacctac 180
aaccccagcc tgaagagcag gttcaccatc agcagggaca acagcaagaa caccttctac 240
ctgcagatga acagcctgag ggccgaggac accgccgtgt actactgcgc caggtgggac 300
ggcggcctga cctactgggg ccagggcacc ctggtgaccg tgagcagc 348

<210> SEQ ID NO 684
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 684

Glu Val Gln Leu Gln Gln Ser Gly Ala Glu Leu Val Lys Pro Gly Ala
1 5 10 15

Ser Val Lys Leu Ser Cys Thr Ala Ser Gly Phe Asn Ile Lys Asp Thr
20 25 30

Tyr Met His Trp Val Lys Gln Arg Pro Glu Gln Gly Leu Glu Trp Ile
35 40 45

Gly Arg Val Asp Pro Ala Asn Gly Asn Thr Lys Tyr Asp Pro Lys Phe
50 55 60

Gln Gly Lys Ala Thr Leu Thr Ala Asp Thr Ser Ser Asn Thr Ala Tyr
65 70 75 80

Leu Gln Leu Ser Ser Leu Thr Ser Glu Asp Thr Ala Val Tyr Phe Cys
85 90 95

Val Arg Asp Tyr Tyr Gly His Thr Tyr Gly Phe Ala Phe Cys Asp Gln
100 105 110

Gly Thr Thr Leu Thr Val Ser Ala
115 120

<210> SEQ ID NO 685
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 685
gaggttcagc tgcagcagtc tggcgccgaa cttgtgaaac ctggcgcctc tgtgaagctg 60
agctgtaccg ccagcggctt caacatcaag gacacctaca tgcactgggt caagcagagg 120
cctgagcagg gcctcgaatg gatcggaaga gtggatcccg ccaacggcaa caccaaatac 180
gaccccaagt tccagggcaa agccacactg accgccgaca cctctagcaa cacagcctac 240
ctgcagctgt ccagcctgac ctctgaagat accgccgtgt acttctgcgt gcgggactac 300
tacggccata cctacggctt cgccttctgc gaccaaggca caaccctgac agtgtctgct 360

<210> SEQ ID NO 686
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 686

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Met His Trp Val Arg Gln Ala Pro Gly Lys Gly Leu Glu Trp Val
35 40 45

Gly Arg Val Asp Pro Ala Asn Gly Asn Thr Lys Tyr Asp Pro Lys Phe
50 55 60

Gln Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Val Arg Asp Tyr Tyr Gly His Thr Tyr Gly Phe Ala Phe Trp Gly Gln
100 105 110

Gly Thr Leu Val Thr Val Ser Ser
115 120

<210> SEQ ID NO 687
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 687
gaggtgcagc tggttgaatc tggcggagga ctggttcagc ctggcggatc tctgagactg 60
tcttgtgccg ccagcggctt caacatcaag gacacctaca tgcactgggt ccgacaggcc 120
cctggcaaag gacttgagtg ggttggaaga gtggaccccg ccaacggcaa caccaaatac 180
gaccccaagt tccagggcag attcaccatc agcgccgaca ccagcaagaa caccgcctac 240
ctgcagatga acagcctgag agccgaggac accgccgtgt actattgcgt gcgggattac 300
tacggccata cctacggctt cgccttttgg ggccagggca cactggttac cgttagctct 360

<210> SEQ ID NO 688
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 688

Asp Ile Glu Leu Thr Gln Ser Pro Ser Ser Leu Ala Val Ser Ala Gly
1 5 10 15

Glu Lys Val Thr Met Ser Cys Lys Ser Ser Gln Ser Leu Leu Asn Ser
20 25 30

Arg Thr Arg Lys Asn Gln Leu Ala Trp Tyr Gln Gln Lys Pro Gly Gln
35 40 45

Ser Pro Glu Leu Leu Ile Tyr Trp Ala Ser Thr Arg Gln Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Ser Tyr Asn Leu Leu Thr Phe Gly Pro Gly Thr Lys Leu Glu Val Lys
            100                 105                 110

Arg

<210> SEQ ID NO 689
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 689
gacatcgagc tgacacagag cccatctagc ctggctgtgt ctgccggcga gaaagtgacc     60
atgagctgca agagcagcca gagcctgctg aacagccgga ccagaaagaa tcagctggcc    120
tggtatcagc agaagcccgg ccaatctcct gagctgctga tctactgggc cagcacaaga    180
cagagcggcg tgcccgatag attcacagga tctggcagcg gcaccgactt caccctgaca    240
atcagttctg tgcaggccga ggacctggcc gtgtactact gtcagcagag ctacaacctg    300
ctgaccttcg gacccggcac caagctggaa gtgaagaga                           339

<210> SEQ ID NO 690
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 690

Asp Ile Glu Leu Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Gln Leu Ala Trp Tyr Gln Gln Lys Thr Gly Gln
        35                  40                  45

Ser Pro Glu Leu Leu Ile Tyr Trp Ala Ser Thr Arg Gln Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Ser Tyr Asn Leu Leu Thr Phe Gly Pro Gly Thr Lys Leu Glu Ile Lys
            100                 105                 110

Arg

<210> SEQ ID NO 691
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 691
gacatcgagc tgacacagag cccatctagc ctggctgtgt ctgccggcga gaaagtgacc 60
atgagctgca agagcagcca gagcctgctg aacagccgga ccagaaagaa tcagctggcc 120
tggtatcagc agaaaaccgg acagagcccc gagctgctga tctactgggc cagcacaaga 180
cagagcggcg tgcccgatag attcacagga tctggcagcg gcaccgactt caccctgaca 240
atcagttctg tgcaggccga ggacctggcc gtgtactact gtcagcagag ctacaacctg 300
ctgaccttcg gacccggcac caagctggaa atcaagaga 339

<210> SEQ ID NO 692
<211> LENGTH: 106
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 692

Asp Ile Lys Met Ala Gln Ser Pro Ser Ser Val Asn Ala Ser Leu Gly
1 5 10 15

Glu Arg Val Thr Ile Thr Cys Lys Ala Ser Arg Asp Ile Asn Asn Phe
20 25 30

Leu Ser Trp Phe His Gln Lys Pro Gly Lys Ser Pro Lys Thr Leu Ile
35 40 45

Tyr Arg Ala Asn Arg Leu Val Asp Gly Val Pro Ser Arg Phe Ser Gly
50 55 60

Ser Gly Ser Gly Gln Asp Tyr Ser Phe Thr Ile Ser Ser Leu Glu Tyr
65 70 75 80

Glu Asp Val Gly Ile Tyr Tyr Cys Leu Gln Tyr Gly Asp Leu Tyr Thr
85 90 95

Phe Gly Gly Gly Thr Lys Leu Glu Ile Lys
100 105

<210> SEQ ID NO 693
<211> LENGTH: 318
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 693
gacatcaaga tggctcagtc cccttctagc gtgaatgctt cgctagggga gcgtgtgacc 60
atcacatgta aagcatcacg cgacataaat aatttccttt cctggtttca tcagaaaccg 120
ggcaagtcgc ctaagacgct gatttacaga gcaaatcggt tggtagatgg agtgccaagc 180
agattcagcg ggagcggaag tggacaggat tatagcttca ctatttcatc cctggaatac 240
gaggacgtag gtatctatta ttgcctccag tatggcgatc tttacacatt tggtgggggg 300
actaagctgg agattaag 318

<210> SEQ ID NO 694
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 694

Asp Ile Gln Met Thr Gln Ser Ser Ser Phe Leu Ser Val Ser Leu Gly
1               5                   10                  15

Gly Arg Val Thr Ile Thr Cys Lys Ala Ser Asp Leu Ile His Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Asn Asp Tyr Thr Leu Ser Ile Ala Ser Leu Gln Thr
65                  70                  75                  80

Glu Asp Ala Ala Thr Tyr Tyr Cys Gln Gln Tyr Trp Thr Thr Pro Phe
                85                  90                  95

Thr Phe Gly Ser Gly Thr Lys Leu Glu Ile Lys
            100                 105

<210> SEQ ID NO 695
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 695
gacatccaga tgacccagag cagcagcttc ctgagcgtgt cccttggcgg cagagtgacc     60
atcacctgta aagccagcga cctgatccac aactggctgg cctggtatca gcagaagcct    120
ggcaacgctc ccagactgct gattagcggc gccacctctc tggaaacagg cgtgccaagc    180
agattttccg gcagcggctc cggcaacgac tacacactgt ctattgccag cctgcagacc    240
gaggatgccg ccacctatta ctgccagcag tactggacca cacctttcac ctttggcagc    300
ggcaccaagc tggaaatcaa g                                              321

<210> SEQ ID NO 696
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 696

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Leu Ile His Asn Trp
            20                  25                  30

Leu Ala Trp Tyr Gln Gln Lys Pro Gly Lys Ala Pro Lys Leu Leu Ile
        35                  40                  45

Ser Gly Ala Thr Ser Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Thr Thr Pro Phe
                85                  90                  95

Thr Phe Gly Gln Gly Thr Lys Val Glu Ile Lys Arg
            100                 105

<210> SEQ ID NO 697
<211> LENGTH: 324
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 697
gacatccaga tgacccagag ccccagcagc ctgagcgcca gcgtgggcga cagggtgacc 60
atcacctgca aggccagcga cctgatccac aactggctgg cctggtacca gcagaagccc 120
ggcaaggccc ccaagctgct gatcagcggc gccaccagcc tggagaccgg cgtgcccagc 180
aggttcagcg gcagcggcag cggcaccgac ttcaccctga ccatcagcag cctgcagccc 240
gaggacttcg ccacctacta ctgccagcag tactggacca ccccttcac cttcggccag 300 ggcaccaagg tggagatcaa gagg 324

<210> SEQ ID NO 698
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 698

Asp Ile Val Leu Thr Gln Ser Pro Ala Ile Met Ser Ala Ser Leu Gly
1 5 10 15

Glu Arg Val Thr Met Thr Cys Thr Ala Ser Ser Ser Val Ser Ser Ser
20 25 30

Tyr Leu His Trp Tyr Gln Gln Lys Pro Gly Ser Ser Pro Lys Leu Trp
35 40 45

Ile Tyr Ser Thr Ser Asn Leu Ala Ser Gly Val Pro Gly Arg Phe Ser
50 55 60

Gly Ser Gly Ser Gly Thr Ser Tyr Ser Leu Thr Ile Ser Ser Met Glu
65 70 75 80

Ala Glu Asp Ala Ala Thr Tyr Tyr Cys His Gln Tyr His Arg Ser Pro
85 90 95

Tyr Thr Phe Gly Gly Gly Thr Lys Val Glu Ile Lys Arg
100 105

<210> SEQ ID NO 699
<211> LENGTH: 327
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 699
gacatcgtgc tgacacagag ccctgccatc atgtctgcca gcctcggcga gcgagtgacc 60
atgacatgta cagccagcag cagcgtgtcc agcagctacc tgcattggta tcagcagaag 120
cccggcagca gccccaagct gtggatctac agcacaagca atctggccag cggcgtgcca 180
ggcagatttt ctggttctgg cagcggcacc agctacagcc tgacaatcag cagcatggaa 240
gccgaggatg ccgccaccta ctactgccac cagtaccaca gaagccccta cacctttggc 300
ggaggcacca aggtggaaat caagcgg 327

<210> SEQ ID NO 700
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 700

Asp Ile Gln Met Thr Gln Ser Pro Ser Ser Leu Ser Ala Ser Val Gly
1 5 10 15

Asp Arg Val Thr Ile Thr Cys Thr Ala Ser Ser Ser Val Ser Ser Ser
20 25 30

Tyr Leu His Trp Tyr Gln Gln Lys Pro Gly Lys Ala Pro Lys Leu Leu
35 40 45

Ile Tyr Ser Thr Ser Asn Leu Ala Ser Gly Val Pro Ser Arg Phe Ser
50 55 60

Gly Ser Gly Ser Gly Thr Asp Phe Thr Leu Thr Ile Ser Ser Leu Gln
65 70 75 80

Pro Glu Asp Phe Ala Thr Tyr Tyr Cys His Gln Tyr His Arg Ser Pro
85 90 95

Tyr Thr Phe Gly Gln Gly Thr Lys Val Glu Ile Lys Arg
100 105

<210> SEQ ID NO 701
<211> LENGTH: 327
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 701
gacatccaga tgacacagag ccctagcagc ctgtctgcca gcgtgggaga cagagtgacc 60
atcacctgta cagccagcag cagcgtgtcc agcagctacc tgcattggta tcagcagaag 120
cccggcaagg cccctaagct gctgatctac agcaccagca atctggccag cggcgtgcca 180
agcagatttt ctggctctgg cagcggcacc gacttcaccc tgaccatatc tagcctgcag 240
cctgaggact tcgccaccta ctactgccac cagtaccaca gaagccccta cacctttggc 300
cagggcacca aggtggaaat caagcgg 327

<210> SEQ ID NO 702
<211> LENGTH: 570
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 702
ccccctctcc ctcccccccc cctaacgtta ctggccgaag ccgcttggaa taaggccggt 60
gtgcgtttgt ctatatgtta ttttccacca tattgccgtc ttttggcaat gtgagggccc 120
ggaaacctgg ccctgtcttc ttgacgagca ttcctagggg tctttcccct ctcgccaaag 180
gaatgcaagg tctgttgaat gtcgtgaagg aagcagttcc tctggaagct tcttgaagac 240
aaacaacgtc tgtagcgacc ctttgcaggc agcggaaccc cccacctggc gacaggtgcc 300
tctgcggcca aaagccacgt gtataagata cacctgcaaa ggcggcacaa ccccagtgcc 360
acgttgtgag ttggatagtt gtggaaagag tcaaatggct ctcctcaagc gtattcaaca 420
aggggctgaa ggatgcccag aaggtacccc attgtatggg atctgatctg gggcctcggt 480
gcacatgctt tacatgtgtt tagtcgaggt taaaaaacgt ctaggccccc cgaaccacgg 540
ggacgtggtt ttcctttgaa aaacacgatc 570

<210> SEQ ID NO 703
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 703
actagtttta taatttcttc ttccagaatt tctgacattt tataatttct tcttccagaa 60
gactcacaac ctc 73

<210> SEQ ID NO 704
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 704
ttcaggaatg ggttccaagg a 21

<210> SEQ ID NO 705
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 705
ttcaggaatg ggttccaagg atg 23

<210> SEQ ID NO 706
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 706
tcctggaagc tattcctgac g 21

<210> SEQ ID NO 707
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 707
tcctggaagc tattcctgac gt 22

<210> SEQ ID NO 708
<211> LENGTH: 23
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 708
tcctggaagc tattcctgac gtt 23

<210> SEQ ID NO 709
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 709
tataatataa tagaaccaca g 21

<210> SEQ ID NO 710
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 710
tataatataa tagaaccaca gga 23

<210> SEQ ID NO 711
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 711
tgtggttctg ttatatccat a 21

<210> SEQ ID NO 712
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 712
tgtggttctg ttatatccat at 22

<210> SEQ ID NO 713
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 713
tgtggttctg ttatatccat ata 23

<210> SEQ ID NO 714

<400> SEQUENCE: 714

000

<210> SEQ ID NO 715
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 715

Gly Phe Thr Phe Ser Ser Tyr Ala
1 5

<210> SEQ ID NO 716
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 716

Ile Ser Arg Gly Gly Thr Thr
1 5

<210> SEQ ID NO 717
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 717

Gly Arg Tyr Asp Tyr Asp Gly Tyr Tyr Ala Met Asp Tyr
1 5 10

<210> SEQ ID NO 718
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 718

Ser Tyr Ala Met Ser
1 5

<210> SEQ ID NO 719
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 719

Ala Ile Ser Arg Gly Gly Thr Thr Tyr Tyr Ala Asp Ser Val Lys Gly
1 5 10 15

<210> SEQ ID NO 720
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 720

Tyr Asp Tyr Asp Gly Tyr Tyr Ala Met Asp Tyr
1 5 10

<210> SEQ ID NO 721
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 721

Pro Asp Ile Asn Ser Tyr
1 5

<210> SEQ ID NO 722
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 722

Arg Ala Asn
1

<210> SEQ ID NO 723
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 723

Leu Gln Tyr Asp Glu Phe Pro Tyr Thr
1 5

<210> SEQ ID NO 724
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 724

Arg Ala Ser Pro Asp Ile Asn Ser Tyr Leu Ser
1 5 10

<210> SEQ ID NO 725
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 725

Arg Ala Asn Thr Leu Glu Ser
1 5

<210> SEQ ID NO 726
<211> LENGTH: 83
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 726

```
Gly Phe Thr Phe Ser Ser Tyr Ala Met Ser Trp Val Arg Gln Ala Pro
1               5                   10                  15

Gly Lys Gly Leu Glu Trp Val Ser Ser Ile Ser Arg Gly Gly Thr Thr
            20                  25                  30

Tyr Tyr Pro Asp Ser Val Lys Gly Arg Phe Thr Ile Ser Arg Asp Asn
        35                  40                  45

Ser Lys Asn Thr Leu Tyr Leu Gln Met Asn Ser Leu Arg Ala Glu Asp
    50                  55                  60

Thr Ala Val Tyr Tyr Cys Gly Arg Tyr Asp Tyr Asp Gly Tyr Tyr Ala
65                  70                  75                  80

Met Asp Tyr
```

<210> SEQ ID NO 727
<211> LENGTH: 73
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 727

```
Ala Ser Pro Asp Ile Asn Ser Tyr Leu Asn Trp Tyr Gln Gln Lys Pro
1               5                   10                  15

Gly Lys Ala Pro Lys Leu Leu Ile Tyr Arg Ala Asn Arg Leu Val Asp
            20                  25                  30

Gly Val Pro Ser Arg Phe Ser Gly Ser Gly Ser Gly Thr Asp Tyr Thr
        35                  40                  45

Leu Thr Ile Ser Ser Leu Gln Pro Glu Asp Phe Ala Thr Tyr Tyr Cys
    50                  55                  60

Leu Gln Tyr Asp Glu Phe Pro Tyr Thr
65                  70
```

<210> SEQ ID NO 728
<211> LENGTH: 78
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 728

```
Ser Tyr Ala Met Ser Trp Val Arg Gln Ala Pro Gly Lys Gly Leu Glu
1               5                   10                  15

Trp Val Ser Ser Ile Ser Arg Gly Gly Thr Thr Tyr Tyr Pro Asp Ser
            20                  25                  30

Val Lys Gly Arg Phe Thr Ile Ser Arg Asp Asn Ser Lys Asn Thr Leu
        35                  40                  45

Tyr Leu Gln Met Asn Ser Leu Arg Ala Glu Asp Thr Ala Val Tyr Tyr
    50                  55                  60

Cys Gly Arg Tyr Asp Tyr Asp Gly Tyr Tyr Ala Met Asp Tyr
65                  70                  75
```

<210> SEQ ID NO 729
<211> LENGTH: 71

-continued

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 729

Pro Asp Ile Asn Ser Tyr Leu Asn Trp Tyr Gln Gln Lys Pro Gly Lys
1               5                   10                  15

Ala Pro Lys Leu Leu Ile Tyr Arg Ala Asn Arg Leu Val Asp Gly Val
            20                  25                  30

Pro Ser Arg Phe Ser Gly Ser Gly Ser Gly Thr Asp Tyr Thr Leu Thr
        35                  40                  45

Ile Ser Ser Leu Gln Pro Glu Asp Phe Ala Thr Tyr Tyr Cys Leu Gln
    50                  55                  60

Tyr Asp Glu Phe Pro Tyr Thr
65                  70
```

CHIMERIC RECEPTOR THERAPY

CROSS-REFERENCE TO RELATED APPLICATION

The present application claims the priority benefit of U.S. Provisional Application No. 63/263,508, filed Nov. 3, 2021, U.S. Provisional Application No. 63/263,001, filed Oct. 25, 2021, U.S. Provisional Application No. 63/136,611, filed Jan. 12, 2021, and U.S. Provisional Application No. 63/136,074, filed Jan. 11, 2021, each of which is hereby incorporated by reference in its entirety.

REFERENCE TO SEQUENCE LISTING

The instant application contains a Sequence Listing which has been submitted electronically in ASCII format and is hereby incorporated by reference in its entirety. Said ASCII copy, created on Jan. 10, 2022, is named 75594-348568_SL.txt and is 579,627 bytes in size.

BACKGROUND OF THE DISCLOSURE

Chimeric antigen receptor (CAR-T) cell and T cell receptor (TCR) therapies have recently undergone rapid development and have been shown to successfully direct killing of tumor cells. Such therapies are, for example, useful in treating autoimmune disorders and cancers. Indeed, several targets for such therapies have been identified to date, including but not limited to CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, Folate receptor α, Mucins such as MUC1, MUC4 or MUC16, MAGE-A1, h5T4, PSMA, TAG-72, EGFR, CD20, EGFRvIII, CD123 or VEGF-R2. Among these, CD19, CD33, MUC1, MUC16, and ROR1 have shown particular promise as targets for immunotherapy.

CD19 is an attractive target for immunotherapy due to several factors. It is expressed on a variety of B cell lymphomas and leukemias and on normal B cells, but it is not found on hematopoietic stem cells, plasma cells, and other healthy tissues. In addition, CD19 has a broader expression profile than that of CD20, which is the target of monoclonal antibody therapies such as rituximab, and it is thought to be a better target for antibody-drug conjugates (ADC) compared with CD20, which suffers from inefficient internalization. CD19 has also been shown to be expressed in cases where monoclonal antibody treatment (e.g., rituximab) is ineffective due to CD20 downregulation or other factors. Additionally, because CD19-targeting agents have a mode of action that is distinct from that of anti-CD20 antibodies, they could complement existing monoclonal antibody regimens.

CD33 is an attractive target for immunotherapy due to its high expression in cancer and minimal expression in healthy adult tissues. CD33 is overexpressed on myeloid leukemia and leukemic stem cells. CD33 is overexpressed in acute myeloid leukemia (AML), which is the most common acute leukemia in adults. 85 to 90% of AML patients show expression of CD33 on blast cells. CD33 is also overexpressed in myelodysplastic syndromes (MDS), which are cancerous conditions of the bone marrow generally found in adults in their 70s.

MUC1 is an attractive target for immunotherapy because it is overexpressed in breast cancer, and is absent or expressed at low levels in normal mammary glands. In addition, MUC1 is mostly aberrantly underglycosylated in cancer and the antigens on the cancer surface are different from those on normal cells. Therefore targeting MUC1 for cancer immunotherapy can exploit the differences between cancerous and normal cells.

MUC16 is an attractive target for immunotherapy due to its high expression in cancer and minimal expression in healthy adult tissues. MUC16 is aberrantly expressed in ovarian cancer, breast cancer, pancreatic cancer, endothermal cancer, and lung cancer. For example, MUC16 is overexpressed in over 80% of ovarian tumors, which is the most lethal of the gynecologic malignancies. Meanwhile, limited expression of MUC16 has been found on healthy tissue. The current standard of care for ovarian cancer is surgery, followed by chemotherapy with a combination of platinum agents and taxanes. However, recurrence of the disease occurs in most patients after initial treatment, resulting in a cycle of repeated surgeries and additional rounds of chemotherapy.

Receptor tyrosine kinase-like orphan receptor 1 (ROR1) is an attractive target for immunotherapy due to its high expression in cancer and minimal expression in healthy adult tissues. ROR1 is aberrantly expressed in multiple hematological tumors, including chronic lymphocytic leukemia (CLL), mantle cell lymphoma (MCL), acute lymphoblastic leukemia (ALL), and diffuse B-cell lymphoma (DLBCL) and solid tumors, including breast adenocarcinomas encompassing triple negative breast cancer (TNBC), pancreatic cancer, ovarian cancer, and lung adenocarcinoma.

Although many patients have durable responses with CAR-T and TCR therapies, for some patients the anti-tumor effects of such therapies are either short-lived or ineffective. Another immunotherapy that has shown promise is immune checkpoint inhibition, which can prevent the switching off of T cells and promote the activity of these cells. Examples of checkpoint inhibitor targets include but are not limited to PD1, PD-L1, CTLA-4, TIGIT, 4-1BB, PIK3IP1, CD27, CD28, CD40, CD70, CD122, CD137, OX40 (CD134), GITR, ICOS, A2AR, B7-H3 (CD276), B7-H4 (VTCN1), BTLA, IDO, KIR, LAG3, TIM-3, or VISTA. Among these, targeting CTLA4, PD-1, PD-L1, TIM3, TIGIT, LAG3, and/or PIK3IP1 has shown the most promise. One of the most studied checkpoint inhibition pathway is the PD-1/programmed death ligand 1 (PD-L1) pathway, which plays a vital role in how tumor cells evade immune response. Immunotherapy utilizing PD-1/PD-L1 blocking antibodies has been extensively evaluated in the clinic and has been shown to improve tumor regression across multiple malignancies, especially when administered in conjunction with CAR-T cells. However, checkpoint inhibitor blocking antibodies have not performed consistently across cancer types, may have limited access to the tumor microenvironment, require repeated administration, and may lose effectiveness over time. Genome editing is an alternate approach to eliminate PD-1 mediated CAR-T cell exhaustion, and has the advantage of restricting the PD-1 blockade to only the engineered CAR-T cells. However, gene editing adds complexity to the manufacturing process, which increases the turnaround time and cost of the cell therapy.

There is accordingly a continuing need in the art to obtain safer, more effective, less expensive therapies to antigen-associated diseases and conditions, including treatments that combine CAR-T and/or TCR therapy with systemic checkpoint inhibition.

There is also a need to devise ways of diversifying treatment regimens to provide a multi-pronged targeting of antigens in order to address complex in vivo biological issues such as loss of immunological surveillance, genetic alterations in tumor antigen composition and tumor heterogeneity (giving rise to cancer cell phenotypic differences).

SUMMARY OF THE DISCLOSURE

The present invention relates in part to a non-naturally occurring polynucleotide encoding a miRNA that inhibits the expression of an immune checkpoint protein. In certain embodiments, the miRNA targets CTLA4, PD-1, PD-L1, TIM3, TIGIT, LAG3, GITR, or PIK3IP1. In certain embodiments, the miRNA targets PD-1.

In certain embodiments, the polynucleotide comprises a nucleic acid sequence having at least 80% sequence identity with any one of SEQ ID NOs: 72-87 or that is capable of hybridizing under stringent hybridization conditions to the complement of any one of SEQ ID NOs: 72-87. In certain such embodiments, the polynucleotide comprises a nucleic acid sequence having at least 80% sequence identity with any one of SEQ ID NOs: 72, 74, 76, 78, 80, 82, 84, and 86 or that is capable of hybridizing under stringent hybridization conditions to the complement of any one of SEQ ID NOs: 72, 74, 76, 78, 80, 82, 704, 705, 709, and 710. In certain embodiments, the polynucleotide comprises a nucleic acid sequence having at least 80% sequence identity with SEQ ID NO: 179 or 180 or that is capable of hybridizing under stringent hybridization conditions to the complement of SEQ ID NO: 179 or 180. In certain embodiments, the polynucleotide comprises a nucleic acid sequence having at least 80% sequence identity with SEQ ID NO: 267 or that is capable of hybridizing under stringent hybridization conditions to the complement of SEQ ID NO: 267.

In certain embodiments, the polynucleotide further comprises: a) a nucleic acid sequence having at least 80% sequence identity with SEQ ID NO: 292 or is capable of hybridizing under stringent hybridization conditions to the complement of SEQ ID NO: 291; and b) a nucleic acid sequence having at least 80% sequence identity with SEQ ID NO: 292 or is capable of hybridizing under stringent hybridization conditions to the complement of SEQ ID NO: 292.

In certain embodiments, the polynucleotide further encodes a chimeric receptor. In certain embodiments, the chimeric receptor is a T-cell receptor or a chimeric antigen receptor.

In certain embodiments, the chimeric antigen receptor comprises an antigen-binding domain that binds to an epitope on CD19, CD33, MUC1, MUC16, or ROR1. In certain embodiments, the antigen-binding domain binds to an epitope on ROR1.

In certain embodiments, the antigen-binding domain comprises a variable light chain domain comprising the amino acid sequence of any one of SEQ ID NOs: 347, 351, 355, 359, 363, 367, 371, 375, 379, 383, 387, 391, 395, 399, 403, 407, 411, 415, 419, 423, 427, 431, 435, 439, 443, 447, 451, 455, 459, and 463, or a functional fragment or variant thereof. In certain such embodiments, the variable light chain domain comprises the amino acid sequence of SEQ ID NO: 387 or a functional fragment or variant thereof.

In certain embodiments, the antigen-binding domain comprises a variable heavy chain domain comprising the amino acid sequence of any one of SEQ ID NOs: 349, 353, 357, 361, 365, 369, 373, 377, 381, 385, 389, 393, 397, 401, 405, 409, 413, 417, 421, 425, 429, 433, 437, 441, 445, 449, 453, 457, and 461, or a functional fragment or variant thereof. In certain such embodiments, the variable heavy chain domain comprises the amino acid sequence of SEQ ID NO: 349 or a functional fragment or variant thereof.

In certain embodiments, the chimeric antigen receptor comprises a spacer. In certain such embodiments, the spacer comprises a stalk region that is a CD8α hinge domain or a functional fragment or variant thereof. In certain such embodiments, the stalk region comprises the amino acid sequence of SEQ ID NO: 467 or a functional fragment or variant thereof. In certain embodiments, the spacer comprises a stalk extension region. In certain such embodiments, the stalk extension region comprises the amino acid sequence of SEQ ID NO: 473 or a functional fragment or variant thereof.

In certain embodiments, the chimeric antigen receptor further comprises a transmembrane domain. In certain such embodiments, the transmembrane domain comprises a CD8α transmembrane domain or a functional fragment or variant thereof. In certain such embodiments, the transmembrane domain comprises the amino acid sequence of SEQ ID NO: 475 or a functional fragment or variant thereof.

In certain embodiments, the chimeric antigen receptor further comprises an intracellular signaling domain. In certain such embodiments, the intracellular signaling domain comprises a CD3ζ signaling domain or a functional fragment or variant thereof. In certain such embodiments, the intracellular signaling domain comprises the amino acid sequence of SEQ ID NO: 479 or a functional fragment or variant thereof.

In certain embodiments, the intracellular signaling domain comprises a co-stimulatory domain. In certain such embodiments, the intracellular signaling domain comprises a CD28 signaling domain or a functional fragment or variant thereof. In certain embodiments, the intracellular signaling domain comprises the amino acid sequence of SEQ ID NO: 481 or a functional fragment or variant thereof.

In certain embodiments, the polynucleotide further encodes a cytokine. In certain embodiments, the cytokine is IL-15 or a functional fragment or variant thereof. In certain such embodiments, the cytokine comprises the amino acid sequence of SEQ ID NO: 519 or a functional fragment or variant thereof.

In certain embodiments, the IL-15, or functional fragment or variant thereof, is membrane bound. In certain such embodiments, the IL-15, or functional fragment or variant thereof, forms part of a fusion protein that also comprises IL-15Rα, or a functional fragment or variant thereof. In certain such embodiments, the fusion protein comprises the amino acid sequence of SEQ ID NO: 523 or a functional fragment or variant thereof. In certain embodiments, the fusion protein comprises the amino acid sequence of SEQ ID NO: 525 or a functional fragment or variant thereof.

In certain embodiments, the polynucleotide further encodes a cell tag. In certain embodiments, the cell tag comprises a truncated HER1, or a functional fragment or variant thereof. In certain embodiments, the truncated HER1 comprises a HER1 Domain III, or a functional fragment or variant thereof, and a truncated HER1 Domain IV, or a functional fragment or variant thereof. In certain such embodiments, the truncated HER1 comprises the amino acid sequence of SEQ ID NO: 565, or a functional fragment or variant thereof, and the amino acid sequence of SEQ ID NO: 567, or a functional fragment or variant thereof.

In certain embodiments, the cell tag further comprises a CD28 transmembrane domain or a functional fragment or variant thereof. In certain such embodiments, the cell tag comprises the amino acid sequence of SEQ ID NO: 571 or a functional fragment or variant thereof.

The present invention also relates to a vector comprising the aforementioned polynucleotide. The vector may be viral or non-viral. In certain embodiments, the vector comprises a Sleeping Beauty transposon.

The present invention further relates to a modified immune effector cell comprising the aforementioned polynucleotide. In certain embodiments, the cell is a T-cell.

The present invention additionally relates to compositions and kits comprising the aforementioned polynucleotide and/or cell.

A further aspect of the present invention is a method for treating a subject suffering from a disease or disorder, comprising administering the aforementioned cell to a subject in need thereof. The invention also relates to the use of the aforementioned cell in the manufacture of a medicament for the treatment of a disease or disorder. The disease or disorder may be one associated with the overexpression of an antigen, for example, CD19, CD33, ROR1, MUC1, or MUC16. In certain embodiments, the disease or disorder is one associated with the overexpression of ROR1.

In certain embodiments, the disease or disorder is cancer. In certain embodiments, the disease or disorder is chronic lymphocytic leukemia, mantle cell lymphoma, acute lymphoblastic leukemia, or diffuse large B-cell lymphoma, breast adenocarcinomas encompassing triple negative breast cancer, pancreatic cancer, ovarian cancer, or lung adenocarcinoma.

Another aspect of the present invention is a method for the detection of a disease or disorder associated with the overexpression of an antigen in a subject, the method comprising: a) contacting a sample from the subject with one or more of the antibodies, or antigen-binding fragments thereof; and b) detecting an increased level of binding of the antibody or fragment thereof to the sample as compared to such binding to a control sample lacking the disease, thereby detecting the disease in the subject.

A yet further aspect of the present invention is a method for the treatment of a disease or disorder, such as cancer and auto-immune disease or disorders, comprising the serial administration of cells, nucleic acids, viral vectors, or non-viral vectors comprising polynucleotides encoding chimeric antigen receptors selected from a collection of chimeric antigen receptors having different structural compositions and binding specificities for an array of antigen targets. In certain such embodiments, the method comprises a first administration of cells expressing one or more chimeric antigen receptors from the collection followed by a second administration of cells expressing one or more chimeric antigen receptors from the collection, wherein a period of time elapses between the first and second administrations.

BRIEF DESCRIPTION OF THE DRAWINGS

In FIG. 3A, the Y-axis plots the transcript counts from CAR-T cells containing an intron coding for 2 checkpoint inhibitor miRNAs targeting PD-1 and TIGIT (CD33 CAR-mbIL15-HER1t+ miRNA (PD-1+TIGIT)), and the X-axis plots the transcripts from CAR-T cells only (not containing any checkpoint inhibitory miRNA). The circles denote the genes of interest. In FIG. 3B, the Y-axis plots the transcript counts from PD-1 miRNA containing CAR-T cells (CD33 CAR-mbIL15-HER1t+miRNA (PD-1+PD-1)) and the X-axis plots the transcripts from CAR-T cells only. FIG. 3C plots the non-targeting miRNA control (CD33 CAR-mbIL15-HER1t+miRNA scrambled*) on the Y-axis and CAR-T cells without a miRNA containing intron on the X-axis. The circles denote the genes of interest and used to depict the on-target specificity of the checkpoint inhibitor miRNA designs. All three graphs were derived from one donor. * Scrambled controls are non-targeting miRNAs.

In FIG. 4A, the Y-axis plots the transcript counts from CAR-T cells containing an intron coding for miRNAs targeting two different sequences within PD-1 and a sequence for TIGIT (MUC16CAR-mbIL15-HER1t (collectively also referred to as "MUC16CAR")+miRNA (PD-1/PD-1/TIGIT)), and the X-axis plots the transcripts from CAR-T cells without a miRNA-containing intron (MUC16CAR-mbIL15-HER1t). The black circles denote the genes of interest. In FIG. 4B, the X-axis is the same, and the Y-axis plots the transcript counts from dual PD-1 targeting miRNA containing CAR-T cells (MUC16CAR-mbIL15-HER1t+miRNA (PD-1/PD-1)). FIG. 4C plots the non-targeting miRNA control (MUC16CAR-mbIL15-HER1t+miRNA (scrambled)) on the Y-axis and CAR-T cells without a miRNA-containing intron on the X-axis. All three graphs are from one donor.

FIGS. 15A-D show a comparison of predicted miRNA binding strength to transcript log fold change.

FIG. 19 provides an indication of additional embodiments of the present disclosure.

DETAILED DESCRIPTION OF THE DISCLOSURE

Figure 1A:
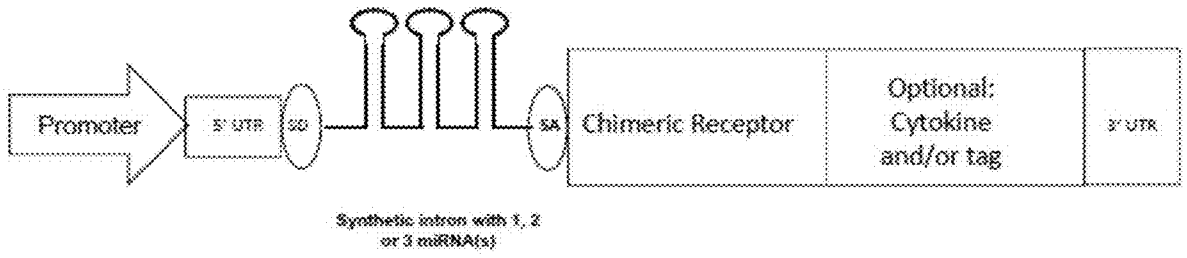
FIG. 1A is an exemplary depiction of a vector comprising a combination of one or more checkpoint inhibitor miRNAs with a chimeric receptor (SD=Splice Donor; SA=Splice Acceptor).

The following description and examples illustrate embodiments of the present disclosure in detail.

It is to be understood that the present disclosure is not limited to the particular embodiments described herein and as such can vary. Those of skill in the art will recognize that there are variations and modifications of the present disclosure, which are encompassed within the scope of the present invention.

Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the disclosure can be described in the context of a single embodiment, the features can also be provided separately or in any suitable combination. Conversely, although the present disclosure can be described herein in the context of separate embodiments for clarity, the present disclosure can also be implemented in a single embodiment.

The following definitions supplement those in the art and are directed to the current application and are not to be imputed to any related or unrelated case, e.g., to any commonly owned patent or application. The terminology used herein is for the purpose of describing particular embodiments only, and is not intended to be limiting.

I. Definitions

In this application, the use of the singular includes the plural unless specifically stated otherwise. As used in the specification, the singular forms "a," "an" and "the" include plural referents unless the context clearly dictates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

Furthermore, use of the term "including" as well as other forms, such as "include," "includes," and "included," is not limiting.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures.

As used in this specification and the claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the disclosure, and vice versa. Furthermore, compositions of the present disclosure can be used to achieve methods of the present disclosure.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. In another example, the amount "about 10" includes 10 and any amounts from 9 to 11. In yet another example, the term "about" in relation to a reference numerical value can also include a range of values plus or minus 10%, 9%, 8%, 7%, 6%, 5%, 4%, 3%, 2%, or 1% from that value. Alternatively, particularly with respect to biological systems or processes, the term "about" can mean within an order of magnitude, preferably within 5-fold, and more preferably within 2-fold, of a value. Where particular values are described in the application and claims, unless otherwise stated the term "about" meaning within an acceptable error range for the particular value should be assumed.

A "therapeutically-effective amount" or "therapeutically-effective dose" refers to an amount or dose effective, for periods of time necessary, to achieve a desired therapeutic result. The amount can vary according to factors such as the disease state, age, sex, and weight of the individual, and the ability of the inventive nucleic acid sequences to elicit a desired response in the individual.

"Polynucleotide" or "oligonucleotide" refers to a polymeric form of nucleotides or nucleic acids of any length, either ribonucleotides or deoxyribonucleotides. This term refers only to the primary structure of the molecule. Thus, this term includes double and single stranded DNA, triplex DNA, as well as double and single stranded RNA. It also includes modified, for example, by methylation and/or by capping, and unmodified forms of the polynucleotide. The term is also meant to include molecules that include non-naturally occurring or synthetic nucleotides as well as nucleotide analogs.

Unless otherwise stated, nucleic acid sequences in the text of this specification are given, when read from left to right, in the 5' to 3' direction.

The terms "transfection," "transformation," "nucleofection," or "transduction" as used herein refer to the introduction of one or more exogenous polynucleotides into a host cell or organism by using physical, chemical, and/or electrical methods. The nucleic acid sequences and vectors disclosed herein can be introduced into a cell or organism by any such methods, including, for example, by electroporation, calcium phosphate co-precipitation, strontium phosphate DNA co-precipitation, liposome mediated-transfection, DEAE dextran mediated-transfection, polycationic mediated-transfection, tungsten particle-facilitated microparticle bombardment, viral, and/or non-viral mediated transfection. In some cases, the method of introducing nucleic acids into the cell or organism involves the use of viral, retroviral, lentiviral, or transposon, or transposable element-mediated (e.g., Sleeping Beauty) vectors.

"Polypeptide," "peptide," and their grammatical equivalents as used herein refer to a polymer of amino acid residues. The polypeptide can optionally include glycosylation or other modifications typical for a given protein in a given cellular environment. Polypeptides and proteins disclosed herein (including functional fragments and functional variants thereof) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine. The present disclosure further contemplates that expression of polypeptides or proteins described herein in an engineered cell can be associated with post-translational modifications of one or more amino acids of the polypeptide or protein. Non-limiting examples of post-translational modifications include phosphorylation, acylation including acetylation and formylation, glycosylation (including N-linked and O-linked), amidation, hydroxylation, alkylation including methylation and ethylation, ubiquitylation, addition of pyrrolidone carboxylic acid, formation of disulfide bridges, sulfation, myristoylation, palmitoylation, isoprenylation, farnesylation, geranylation, glypiation, lipoylation and iodination.

The term "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and Schirmer, R. H., Principles of Protein Structure, Springer-Verlag, New York (1979)). According to such analyses, groups of amino acids can be defined where amino acids within a group exchange preferentially with each other, and therefore resemble each other most in their impact on the overall protein structure (Schulz, G. E. and Schirmer, R. H., supra). Examples of conservative mutations include amino acid substitutions of amino acids within the sub-groups below, for example, lysine for arginine and vice versa such that a positive charge can be maintained; glutamic acid for aspartic acid and vice versa such that a negative charge can be maintained; serine for threonine such that a free —OH can be maintained; and glutamine for asparagine such that a free $—NH_2$ can be maintained. Exemplary conservative amino acid substitutions are shown in the following chart:

| Type of Amino Acid | Substitutable Amino Acids |
|---|---|
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

An amino acid sequence that differs from a reference amino acid sequence by only conservative amino acid substitutions will be referred to herein as a "conservatively-substituted variant" of the reference sequence.

In some embodiments, the functional variants can comprise the amino acid sequence of the reference protein with at least one non-conservative amino acid substitution. The term "non-conservative mutations" involve amino acid substitutions between different groups, for example, lysine for tryptophan, or phenylalanine for serine, etc. In this case, it is preferable for the non-conservative amino acid substitution to not interfere with, or inhibit the biological activity of, the functional variant. The non-conservative amino acid substitution can enhance the biological activity of the functional variant, such that the biological activity of the functional variant is increased as compared to the homologous parent protein. Amino acid substitutability is discussed in more detail, for example, in L. Y. Yampolsky and A. Stoltzfus, "The Exchangeability of Amino acids in Proteins," *Genetics* 2005 August; 170(4):1459-1472.

The terms "identical" and its grammatical equivalents as used herein or "sequence identity" in the context of two nucleic acid sequences or amino acid sequences of polypeptides refer to the residues in the two sequences which are the same when aligned for maximum correspondence over a specified comparison window. A "comparison window," as used herein, refers to a segment of at least about 20 contiguous positions, usually about 50 to about 200, more usually about 100 to about 150 in which a sequence can be compared to a reference sequence of the same number of contiguous positions after the two sequences are aligned optimally. Methods of alignment of sequences for comparison are well-known in the art. Optimal alignment of sequences for comparison can be conducted by the local homology algorithm of Smith and Waterman, *Adv. Appl. Math.,* 2:482 (1981); by the alignment algorithm of Needleman and Wunsch, *J. Mol. Biol.,* 48:443 (1970); by the search for similarity method of Pearson and Lipman, *Proc. Nat. Acad. Sci U.S.A.,* 85:2444 (1988); by computerized implementations of these algorithms (including, but not limited to CLUSTAL in the PC/Gene program by Intelligentics, Mountain View Calif., GAP, BESTFIT, BLAST, FASTA, and TFASTA in the Wisconsin Genetics Software Package, Genetics Computer Group (GCG), 575 Science Dr., Madison, Wis., U.S.A.); the CLUSTAL program is well described by Higgins and Sharp, *Gene,* 73:237-244 (1988) and Higgins and Sharp, CABIOS, 5:151-153 (1989); Corpet et al., *Nucleic Acids Res.,* 16:10881-10890 (1988); Huang et al., *Computer Applications in the Biosciences,* 8:155-165 (1992); and Pearson et al., *Methods in Molecular Biology,* 24:307-331 (1994). Alignment is also often performed by inspection and manual alignment. In one class of embodiments, the polypeptides herein are at least 80%, 85%, 90%, 98% 99% or 100% identical to a reference polypeptide (i.e., the full length thereof), or a fragment thereof, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 98%, 99% or 100% identical to a reference nucleic acid (i.e., the full length thereof) or a fragment thereof, e.g., as measured by BLASTN (or CLUSTAL, or any other available alignment software) using default parameters. When one molecule is said to have certain percentage of sequence identity with a larger molecule, it means that when the two molecules are optimally aligned, the percentage of residues in the smaller molecule finds a match residue in the larger molecule in accordance with the order by which the two molecules are optimally aligned.

For purposes of this specification and the claims, it is understood that the phrase "having at least 50% sequence identity with" a reference sequence, or referencing any range therein (e.g., "at least 80% sequence identity with") encompasses the reference sequence itself. Thus, for example, a claim reciting "a nucleic acid having at least 80% sequence identity with SEQ ID NO: 0" encompasses SEQ ID NO: 0 itself.

The term "substantially identical" and its grammatical equivalents as applied to nucleic acid or amino acid sequences mean that a nucleic acid or amino acid sequence comprises a sequence that has at least 95% sequence identity with a reference sequence using the programs described above, e.g., BLAST, using standard parameters.

"Homology" is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95%, or 99% or more can also be used to establish homology. Methods for determining sequence identity percentages (e.g., BLASTP and BLASTN using default parameters) are described herein and are generally available. Nucleic acids and/or nucleic acid sequences are "homologous" when they are derived, naturally or artificially, from a common ancestral nucleic acid or nucleic acid sequence. Proteins and/or protein sequences are "homologous" when their encoding DNAs are derived, naturally or artificially, from a common ancestral nucleic acid or nucleic acid sequence. The homologous molecules can be termed "homologs." For example, any naturally occurring proteins can be modified by any available mutagenesis method. When expressed, this mutagenized nucleic acid encodes a polypeptide that is homologous to the protein encoded by the original nucleic acid.

Also contemplated and included herein are nucleic acid molecules that hybridize to the disclosed sequences. Hybridization conditions may be mild, moderate, or stringent, as is warranted.

Appropriate stringency conditions which promote DNA hybridization, for example, 6× sodium chloride/sodium citrate (SSC) at about 45° C., followed by a wash of 2×SSC at 50° C., are known or can be found in Current Protocols in Molecular Biology, John Wiley & Sons, N.Y. (1989), 6.3.1-6.3.6. "Stringent hybridization conditions" are those that include a salt concentration of 1.0 M NaCl in 50% formamide, at a temperature of 37° C. for 4 to 12 hours, followed by a wash in 0.1×SSC at 60-65° C.

As will be appreciated by the skilled practitioner, slight changes in nucleic acid sequence do not necessarily alter the amino acid sequence of the encoded polypeptide. This disclosure embraces the degeneracy of codon usage as would be understood by one of ordinary skill in the art. For example, as known in the art, different codons will code for the same amino acid as illustrated in the following chart.

| Amino Acid | Codons |
|---|---|
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, UGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |

-continued

| Amino Acid | Codons |
|---|---|
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |
| START | ATG |
| STOP | TAG, TGA, TAA |

As used herein, the phrase "codon degenerate variant" when used with reference to a nucleic acid sequence means a nucleic acid sequence that differs from the referenced sequence, but that encodes a polypeptide having the same amino acid sequence as that encoded by the referenced sequence.

Additionally, it will be appreciated by persons skilled in the art that partial sequences often work as effectively as full-length versions. The ways in which the nucleotide sequence can be varied or shortened are well known to persons skilled in the art, as are ways of testing the suitability or effectiveness of the altered genes. In certain embodiments, suitability and/or effectiveness of the altered gene may easily be tested by, for example, conventional gas chromatography. All such variations of the genes are therefore included as part of the present disclosure.

The term "isolated" and its grammatical equivalents as used herein refer to the removal of a nucleic acid from its natural environment. It is to be understood, however, that nucleic acids and proteins can be formulated with diluents or adjuvants and still for practical purposes be isolated.

The term "purified" and its grammatical equivalents as used herein refer to a molecule or composition, whether removed from nature (including genomic DNA and mRNA) or synthesized (including cDNA) and/or amplified under laboratory conditions, that has been increased in purity, wherein "purity" is a relative term, not "absolute purity." For example, nucleic acids typically are mixed with an acceptable carrier or diluent when used for introduction into cells. The term "substantially purified" and its grammatical equivalents as used herein refer to a nucleic acid sequence, polypeptide, protein or other compound that is essentially free, i.e., is more than about 50% free of, more than about 70% free of, more than about 90% free of, the polynucleotides, proteins, polypeptides and other molecules that the nucleic acid, polypeptide, protein or other compound is naturally associated with.

"T cell" or "T lymphocyte" as used herein is a type of lymphocyte that plays a central role in cell-mediated immunity. They can be distinguished from other lymphocytes, such as B cells and natural killer cells (NK cells), by the presence of a T-cell receptor (TCR) on the cell surface.

"Transposon," "transposable element" or "TE" refers to a vector DNA sequence that can change its position within the genome, sometimes creating or reversing mutations and altering the cell's genome size. Transposition often results in duplication of the transposon. Class I transposons are copied in two stages: first, they are transcribed from DNA to RNA, and the RNA produced is then reverse transcribed to DNA. This copied DNA is then inserted at a new position into the genome. The reverse transcription step is catalyzed by a reverse transcriptase, which can be encoded by the transposon itself. The characteristics of retrotransposons are similar to retroviruses, such as HIV. The cut-and-paste transposition mechanism of class II transposons does not involve an RNA intermediate. The transpositions are catalyzed by several transposase enzymes. Some transposases non-specifically bind to any target site in DNA, whereas others bind to specific DNA sequence targets. The transposase makes a staggered cut at the target site resulting in single-strand 5' or 3' DNA overhangs (sticky ends). This step cuts out the DNA transposon, which is then ligated into a new target site; this process involves activity of a DNA polymerase that fills in gaps and of a DNA ligase that closes the sugar-phosphate backbone. This results in duplication of the target site. The insertion sites of DNA transposons can be identified by short direct repeats which can be created by the staggered cut in the target DNA and filling in by DNA polymerase, followed by a series of inverted repeats important for the transposon excision by transposase. Cut-and-paste transposons can be duplicated if their transposition takes place during S phase of the cell cycle when a donor site has already been replicated, but a target site has not yet been replicated. Transposition can be classified as either "autonomous" or "non-autonomous" in both Class I and Class II transposons. Autonomous transposons can move by themselves while non-autonomous transposons require the presence of another transposon to move. This is often because non-autonomous transposons lack transposase (for class II) or reverse transcriptase (for class I).

"Transposase" refers an enzyme that binds to the end of a transposon and catalyzes the movement of the transposon to another part of the genome by a cut and paste mechanism or a replicative transposition mechanism. In some embodiments, the transposase's catalytic activity can be utilized to move gene(s) from a vector to the genome.

An "expression vector" or "vector" is any genetic element, e.g., a plasmid, a mini-circle, a nanoplasmid, chromosome, virus, transposon, behaving either as an autonomous unit of polynucleotide replication within a cell. (i.e. capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, transposons, bacteriophages and cosmids. Vectors can contain polynucleotide sequences that are necessary to effect ligation or insertion of the vector into a desired host cell and to effect the expression of the attached segment. Such sequences differ depending on the host organism; they include promoter sequences to effect transcription, enhancer sequences to increase transcription, ribosomal binding site sequences and transcription and translation termination sequences. Alternatively, expression vectors can be capable of directly expressing nucleic acid sequence products encoded therein without ligation or integration of the vector into host cell DNA sequences. In some embodiments, the vector is an "episomal expression vector" or "episome," which is able to replicate in a host cell, and persists as an extrachromosomal segment of DNA within the host cell in the presence of appropriate selective pressure (see, e.g., Conese et al., Gene Therapy, 11:1735-1742 (2004)). Representative commercially-available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP. A vector also can comprise a selectable marker gene. In certain embodiments where nano plasmids are utilized, strains such as R6K that utilizes an antisense RNA selection marker (e.g. sucrose tolerance) can be used.

The term "selectable marker gene" refers to a nucleic acid sequence that allows cells expressing the nucleic acid sequence to be specifically selected for or against, in the presence of a corresponding selective agent. Suitable selectable marker genes are known in the art and described in, e.g., International Patent Application Publications WO 1992/08796 and WO 1994/28143; Wigler et al., Proc. Natl. Acad. Sci. USA, 77: 3567 (1980); O'Hare et al., Proc. Natl. Acad. Sci. USA, 78: 1527 (1981); Mulligan & Berg, Proc. Natl. Acad. Sci. USA, 78: 2072 (1981); Colberre-Garapin et al., J. Mol. Biol., 150:1 (1981); Santerre et al., Gene, 30: 147 (1984); Kent et al., Science, 237: 901-903 (1987); Wigler et al., Cell, 11: 223 (1977); Szybalska & Szybalski, Proc. Natl. Acad. Sci. USA, 48: 2026 (1962); Lowy et al., Cell, 22: 817 (1980); and U.S. Pat. Nos. 5,122,464 and 5,770,359.

The term "coding sequence" refers to a segment of a polynucleotide that encodes for protein or polypeptide. The region or sequence is bounded nearer the 5' end by a start codon and nearer the 3' end with a stop codon. Coding sequences can also be referred to as open reading frames.

The term "operably linked" refers to refers to the physical and/or functional linkage of a DNA segment to another DNA segment in such a way as to allow the segments to function in their intended manners. A DNA sequence encoding a gene product is operably linked to a regulatory sequence when it is linked to the regulatory sequence, such as, for example, promoters, enhancers and/or silencers, in a manner, that allows modulation of transcription of the DNA sequence, directly or indirectly. For example, a DNA sequence is operably linked to a promoter when it is ligated to the promoter downstream with respect to the transcription initiation site of the promoter and in the correct reading frame with respect to the transcription initiation site so as to allow transcription elongation to proceed through the DNA sequence. An enhancer or silencer is operably linked to a DNA sequence coding for a gene product when it is ligated to the DNA sequence in such a manner as to, respectively, increase or decrease the transcription of the DNA sequence. Enhancers and silencers can be located upstream or downstream of or embedded within the coding regions of the DNA sequence. A DNA for a signal sequence is operably linked to DNA coding for a polypeptide if the signal sequence is expressed as a pre-protein that participates in the secretion of the polypeptide. Linkage of DNA sequences to regulatory sequences is typically accomplished by ligation at suitable restriction sites or via adapters or linkers inserted in the sequence using restriction endonucleases known to one of skill in the art.

The terms "induce," "induction" and their grammatical equivalents as used herein refer to an increase in nucleic acid sequence transcription, promoter activity and/or expression brought about by a transcriptional regulator, relative to some basal level of transcription.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer).

The term "enhancer," as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream or downstream of coding sequences or within coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), Fundamental Immunology, 3rd Edition, Raven Press, New York (1993), pages 353-363; and U.S. Pat. No. 5,885,827).

The term "promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter. The term "promoter activity" and its grammatical equivalents as used herein refer to the extent of expression of nucleotide sequence that is operably linked to the promoter whose activity is being measured. Promoter activity can be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" refers to a promoter, that is induced into activity by the presence or absence of transcriptional regulators, e.g., biotic or abiotic factors. Inducible promoters are useful because the expression of genes operably linked to them can be turned on or off at certain stages of development of an organism or in a particular tissue. Non-limiting examples of inducible promoters include alcohol-regulated promoters, tetracycline-regulated promoters, steroid-regulated promoters, metal-regulated promoters, pathogenesis-regulated promoters, temperature-regulated promoters and light-regulated promoters. The inducible promoter can be part of a gene switch or genetic switch.

"T cell" or "T lymphocyte" as used herein is a type of lymphocyte that plays a central role in cell-mediated immunity. They can be distinguished from other lymphocytes, such as B cells and natural killer cells (NK cells), by the presence of a T-cell receptor (TCR) on the cell surface.

As used herein, the phrase "functional fragment" when used with reference to a polypeptide refers to a fragment of such polypeptide that possesses the primary function of the referenced polypeptide. For example, a functional fragment of a polypeptide that serves as a transmembrane domain is a fragment of that polypeptide that also serves as a transmembrane domain. In certain embodiments, the functional fragment of a polypeptide is shorter than the referenced polypeptide by at most 30, 25, 20, 15, 10, 9, 8, 7, 6, 5, 4, 3, 2, or 1 amino acid residues at the N- and/or C-terminus. When used with reference to a nucleic acid, the phrase "functional fragment" refers to a fragment of the referenced nucleic acid that encodes a polypeptide having the same primary function as the polypeptide encoded by the referenced nucleic acid.

As used herein, the phrase "functional variant" when used with reference to a polypeptide refers to a polypeptide that differs from the referenced polypeptide but possesses the primary function of the referenced polypeptide. For example, a functional variant of a polypeptide that serves as a transmembrane domain is a fragment of that polypeptide that also serves as a transmembrane domain. In certain embodiments, the functional variant has at least 80%, 85%, 90%, 95%, 96%, 97%, 98%, or 99% sequence identity with the referenced amino acid sequence and/or is a conservatively-substituted variant of the referenced sequence. When used with reference to a nucleic acid, the phrase "functional variant" refers to a nucleic acid that differs from the referenced nucleic acid but encodes a polypeptide having the same primary function as the polypeptide encoded by the referenced nucleic acid. In certain embodiments, the functional variant has at least 80%, 85%, 90%, 95%, 96%, 97%, 98%, or 99% sequence identity with the referenced nucleic acid sequence, hybridizes under stringent hybridization conditions with the complement of the referenced nucleic acid sequence, or is a codon degenerate variant of the nucleic acid sequence.

The term "antibody," also known as immunoglobulin (Ig), as used herein can refer to a monoclonal or polyclonal antibody. The term "monoclonal antibodies," as used herein, refers to antibodies that are produced by a single clone of B-cells and bind to the same epitope. In contrast, "polyclonal antibodies" refer to a population of antibodies that is produced by different B-cells and bind to different epitopes of the same antigen. The antibodies can be from any animal origin. An antibody can be IgG (including IgG1, IgG2, IgG3, and IgG4), IgA (including IgA1 and IgA2), IgD, IgE, or IgM, and IgY. In some embodiments, the antibody can a single-chain whole antibody. An antibody typically consists of four polypeptides: two identical copies of a heavy (H) chain polypeptide and two identical copies of a light (L) chain polypeptide. Each of the heavy chains contains one N-terminal variable ($V_H$) region and three C-terminal constant (CH1, CH2 and CH3) regions, and each light chain contains one N-terminal variable ($V_L$) region and one C-terminal constant ($C_L$) region. The variable regions of each pair of light and heavy chains form the antigen-binding site of an antibody. The $V_H$ and $V_L$ regions have a similar general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding. These particular regions have been described by Kabat et al., J. Biol. Chem. 252, 6609-6616 (1977) and Kabat et al., Sequences of protein of immunological interest. (1991), by Chothia et al., J. Mol. Biol. 196:901-917 (1987), and by MacCallum et al., J. Mol. Biol. 262:732-745 (1996), where the definitions include overlapping or subsets of amino acid residues when compared against each other. Preferably, the term "CDR" is a CDR as defined by Kabat, based on sequence comparisons. CDRH1, CDRH2 and CDRH3 denote the heavy chain CDRs, and CDRL1, CDRL2 and CDRL3 denote the light chain CDRs.

The terms "fragment of an antibody," "antibody fragment," "fragment of an antibody," "antigen-binding portion" and their grammatical equivalents are used interchangeably herein to mean one or more fragments or portions of an antibody that retain the ability to specifically bind to an antigen (see, generally, Holliger et al., Nat. Biotech., 23(9): 1126-1129 (2005)). The antibody fragment desirably comprises, for example, one or more CDRs, the variable region (or portions thereof), the constant region (or portions thereof), or combinations thereof. Non-limiting examples of antibody fragments include (1) a Fab fragment, which is a monovalent fragment consisting of the $V_L$, $V_H$, $C_L$, and CH1 domains; (2) a F(ab')2 fragment, which is a bivalent fragment comprising two Fab fragments linked by a disulfide bridge at the stalk region; (3) a Fv fragment consisting of the $V_L$ and $V_H$ domains of a single arm of an antibody; (4) a single chain Fv (scFv), which is a monovalent molecule consisting of the two domains of the Fv fragment (i.e., $V_L$ and $V_H$) joined by a linker that enables the two domains to be synthesized as a single polypeptide chain (see, e.g., Bird et al., Science, 242: 423-426 (1988); Huston et al., Proc. Natl. Acad. Sci. USA, 85: 5879-5883 (1988); and Osbourn et al., Nat. Biotechnol., 16: 778 (1998)) and (5) a diabody, which is a dimer of polypeptide chains, wherein each polypeptide chain comprises a $V_H$ connected to a $V_L$ by a peptide linker that is too short to allow pairing between the $V_H$ and $V_L$ on the same polypeptide chain, thereby driving the pairing between the complementary domains on different $V_H$-$V_L$ polypeptide chains to generate a dimeric molecule having two functional antigen-binding sites. Antibody fragments are known in the art and are described in more detail in, e.g., U.S. Pat. No. 8,603,950.

The terms "antigen recognition moiety," "antigen recognition domain," "antigen-binding domain," and "antigen binding region" refer to a molecule or portion of a molecule that specifically binds to an antigen. In one embodiment, the antigen recognition moiety is an antibody, antibody like molecule or fragment thereof.

The term "proliferative disease" refers to a unifying concept in which excessive proliferation of cells and/or turnover of cellular matrix contributes significantly to the pathogenesis of the disease, including cancer. In some embodiments, the proliferative disease is cancer.

"Patient" or "subject" refers to a mammalian subject diagnosed with or suspected of having or developing a proliferative disorder such as cancer. In some embodiments, the term "patient" refers to a mammalian subject with a higher than average likelihood of developing a proliferative disorder such as cancer. Exemplary patients can be humans, apes, dogs, pigs, cattle, cats, horses, goats, sheep, rodents and other mammalians that can benefit from the therapies disclosed herein. Exemplary human patients can be male and/or female. "Patient in need thereof" or "subject in need thereof" means a patient diagnosed with or suspected of having a disease or disorder, for instance, but not restricted to cancer.

"Administering" refers to herein as providing one or more compositions described herein to a patient or a subject. By way of example and not limitation, composition administration, e.g., injection, can be performed by intravenous (i.v.) injection, sub-cutaneous (s.c.) injection, intradermal (i.d.) injection, intraperitoneal (i.p.) injection, or intramuscular (i.m.) injection. One or more such routes can be employed. Parenteral administration can be, for example, by bolus injection or by gradual perfusion over time. Alternatively, or concurrently, administration can be by the oral route. Additionally, administration can also be by surgical deposition of a bolus or pellet of cells, or positioning of a medical device.

As used herein, the terms "treatment," "treating," and their grammatical equivalents refer to obtaining a desired pharmacologic and/or physiologic effect. In some embodiments, the effect is therapeutic, i.e., the effect partially or completely cures a disease and/or adverse symptom attributable to the disease. In some embodiments, the term "treating" can include "preventing" a disease or a condition.

As used herein, a "treatment interval" refers to a treatment cycle, for example, a course of administration of a therapeutic agent that can be repeated, e.g., on a regular schedule. In some embodiments, a dosage regimen can have one or more periods of no administration of the therapeutic agent in between treatment intervals.

The terms "administered in combination," "co-administration," "co-administering," and "co-providing" as used herein, mean that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In some embodiments, the first treatment and second treatment can be administered simultaneously (e.g., at the same time), in the same or in separate compositions, or sequentially. Sequential administration refers to administration of one treatment before (e.g., immediately before, less than 5, 10, 15, 30, 45, 60 minutes; 1, 2, 3, 4, 6, 8, 10, 12, 16, 20, 24, 48, 72, 96 or more hours; 4, 5, 6, 7, 8, 9 or more days; 1, 2, 3, 4, 5, 6, 7, 8 or more weeks before) administration of an additional, e.g., secondary, treatment. The order of administration of the first and secondary treatment can also be reversed.

The terms "therapeutically effective amount," therapeutic amount," "immunologically effective amount," "anti-tumor effective amount," "tumor-inhibiting effective amount," and their grammatical equivalents refer to an amount effective, at dosages and for periods of time necessary, to achieve a desired therapeutic result. The therapeutically effective amount can vary according to factors such as the disease state, age, sex, and weight of the individual, and the ability of a composition described herein to elicit a desired response in one or more subjects. The precise amount of the compositions of the present disclosure to be administered can be determined by a physician with consideration of individual differences in age, weight, tumor size, extent of infection or metastasis, and condition of the patient (subject).

Alternatively, the pharmacologic and/or physiologic effect of administration of one or more compositions described herein to a patient or a subject of can be "prophylactic," i.e., the effect completely or partially prevents a disease or symptom thereof. A "prophylactically effective amount" refers to an amount effective, at dosages and for periods of time necessary, to achieve a desired prophylactic result (e.g., prevention of disease onset).

As used herein, the term "immune checkpoint protein" refers to a molecule that transmits a suppressive signal or has an immunosuppressive function. Examples of such immune checkpoint proteins include, but are not limited to, CTLA-4, PD-1, PD-L1 (programmed cell death-ligand 1), PD-L2 (programmed cell death-ligand 2), LAG-3 (Lymphocyte activation gene 3), TIM3 (T cell immunoglobulin and mucin-3), BTLA (B and T lymphocyte attenuator), B7H3, B7H4, CD160, CD39, CD70, CD73, A2aR (adenosine A2a receptor), KIR (killer inhibitory receptor), VISTA (V-domain Ig-containing suppressor of T cell activation), IDO1 (Indoleamine 2,3-dioxygenase), Arginase I, TIGIT (T cell immunoglobulin and ITIM domain), CD115, and the like (see, Nature Reviews Cancer, 12, p. 252-264, 2012 and Cancer Cell, 27, p. 450-461, 2015).

As used herein, terms used in the identification of biological moieties may include, or may not include, a dash "-" within the term. The presence or absence of a dash does not change the intended meaning or identification of the biological moiety. By way of illustration only, and without limitation to these biological moieties, each of the following paired terms (shown with/without a dash) indicate and identify the same biological entities: CCR-4/CCR4, CD-3/CD3, CD-4/CD4, CD-33/CD33, EGFR-2/EGFR2, FLT-1/FLT1, HER-1/HER1, HER-1t/HER1t, IL-12/IL12, IL-15/IL15, IL-15Ra/IL15Rα MUC-1/MUC1, MUC-16/MUC16, ROR-1/ROR1, ROR-1R/ROR1R, TGF-Beta/TGFBeta, VEGF-1/VEGF1, VEGF-R2/VEGFR2."

II. Combinations

In certain embodiments, miRNA(s) or polynucleotides encoding the miRNA(s) as described herein can be used in combination with a chimeric receptor or can further comprise a nucleic acid sequence encoding a chimeric receptor, respectively. In some cases, the chimeric receptor is a chimeric antigen receptor (CAR). In some instances, the CAR comprises a pattern-recognition receptor. In other cases, the chimeric receptor comprises an engineered T-cell receptor (TCR). The miRNA(s) can be used in combination with specific CARs, cytokines, and cell tags, for example MUC16-specific CAR with a fusion protein comprising IL15 and IL-15Rα (mbIL15) and truncated HER1 (HER1t), MUC1-specific CAR with mbIL15 and HER1t, or CD33-specific CAR with mbIL15 and HER1t.

In certain embodiments, the genetic construct can include a 5' untranslated region (5'UTR) and/or a 3' untranslated region (3'UTR). In some embodiments, the sequences encoding the miRNA(s) can be located in the 5'UTR and/or the 3'UTR. In some embodiments, the 5'UTR and/or the 3'UTR do not contain an intron.

In certain embodiments, a nucleic acid sequence encoding a synthetic intron with checkpoint inhibitor miRNAs is inserted into the same genetic construct as that encoding the chimeric receptor (for example, in the portion of the construct corresponding to the 5'UTR of the mRNA encoding the chimeric receptor). An exemplary depiction of the order of polynucleotide sequences can be found in FIG. 1A. In one embodiment, the 5'UTR contains one or more mature miRNAs. In some embodiments, the one or more mature miRNA(s) can be directed to the same immune checkpoint protein target, for example PD-1. In certain other embodiments, the mature miRNAs can be directed to more than one immune checkpoint protein target, for example PD-1 and TIGIT, PD1 and CTLA4, or TIGIT and CTLA4.

III. miRNA(s)

As used herein, the terms "miR," "mir" and "miRNA" are used to refer to microRNA, a class of small non-coding RNA molecules that are capable of affecting the expression of a gene (the "target gene") by modulating the translation of messenger RNA transcribed therefrom (either increasing or decreasing the gene's expression) and/or destabilizing such messenger RNA.

The miRNAs can be non-naturally occurring. The terms "non-naturally occurring," "synthetic," and "artificial," as used to describe miRNA(s) herein, are used interchangeably and refer to an miRNA having a sequence that does not occur in nature. In some embodiments, a non-naturally occurring miRNA effectively mimics naturally-occurring miRNA. Non-naturally occurring miRNA can be designed such that the desired hairpins or loops of the corresponding naturally-occurring miRNA are maintained when a naturally-occurring mature miRNA sequence is replaced with a synthetic sequence designed to target a specific transcript. For example, the non-naturally occurring miRNA can have at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or greater sequence identity with naturally-occurring miRNA and/or can hybridize under stringent hybridization conditions with naturally-occurring miRNA. The term "miRNA," unless otherwise indicated, refers generically to the mature, pri-, and pre-forms of a particular microRNA and functional fragments and variants thereof.

Figure 1B:
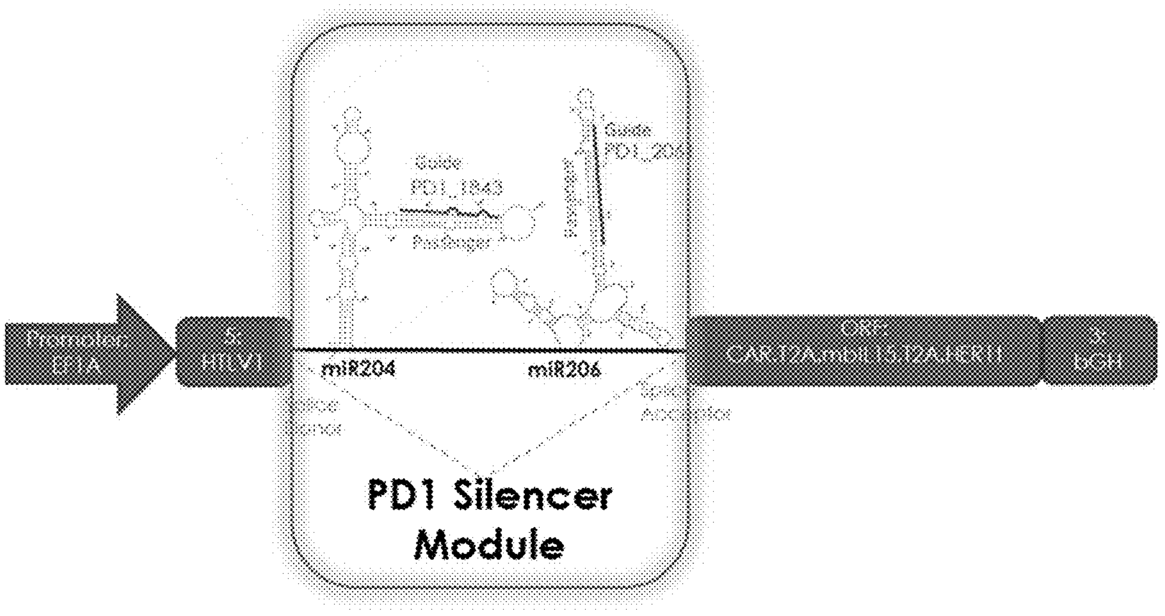
FIG. 1B is an exemplary depiction of hairpin and loop design of various pri-miRNAs including target miRNA and complementary sequences at various 5' or 3' positions.
Figure 1C:
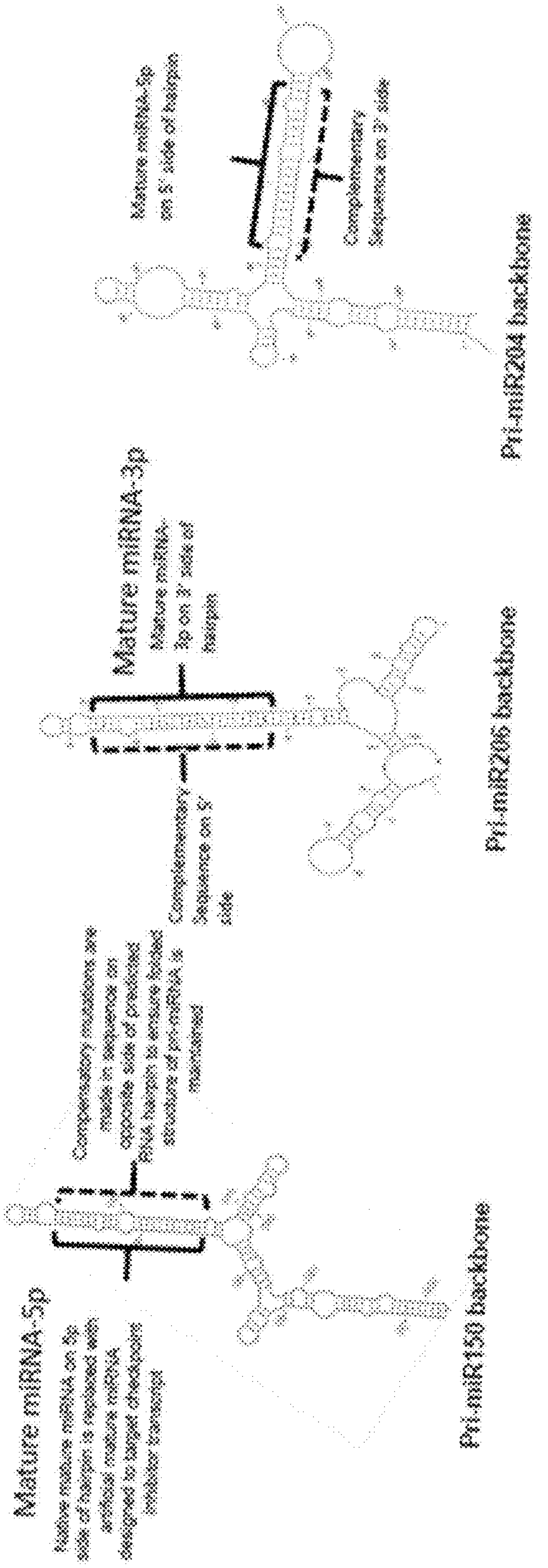
FIG. 1C is exemplary depiction of hairpin and loop design of various pri-miRNAs including its position in a transgene cassette.

The term "pri-miRNA" refers to the primary miRNA transcript containing at least one RNA hairpin. Exemplary depictions of pri-miRNA are illustrated in FIG. 1B. The RNA hairpin(s) are cleaved from the pri-miRNA in the cell nucleus to form one or more precursor miRNAs ("pre-miRNAs). This pre-miRNA is exported into the cytoplasm where the stem loop structure is cleaved to produce a double-stranded miRNA comprising a miRNA-5p strand from the former 5' arm of the hairpin loop and a miRNA-3p strand from the former 3' arm of the hairpin loop. The Argonaute protein then binds the double-stranded miRNA and one of the strands (either the miRNA-5p sequence or the miRNA-3p sequence) is released. The remaining bound strand become the "guide strand" whereas the released strand is known as the "passenger strand" and preferably degrades. The guide strand then goes on to interact with the messenger RNA derived from the target gene, thus affecting its translation.

Both the miRNA-5p and miRNA-3p strand sequences will be referred to herein as "mature miRNA" sequences. The remaining portions of the pri-miRNA (the portion thereof 5' to the miRNA-5p sequence, the portion thereof 3' to the miRNA-3p sequence, and the stem loop sequence in between the miRNA-5p and miRNA-3p sequences) will be collectively referred to as miRNA backbone sequences. The term "5' backbone sequence" will be used herein to refer to the backbone sequence that, in a pri-miRNA, is 5' of the miRNA-5p sequence. The term "3' backbone sequence" will be used herein to refer to the backbone sequence that, in a pri-miRNA, is 3' of the miRNA-3p sequence. The term "stem loop sequence" refers to the backbone sequence that, in a pri-miRNA, is between the miRNA-5p and miRNA-3p sequences.

The pri-miRNA of the present invention may be produced from naturally-occurring pri-miRNAs by removing the native mature miRNA sequences and replacing them with non-native mature miRNA sequences wherein one of the sequences is capable of serving as a guide miRNA targeting a gene of interest. In the design of a non-naturally occurring pri-miRNA, backbone miRNA nucleic acid sequences can be derived from mouse, rat, or human miRNA sequences. As a non-limiting example, backbone miRNA sequences can be derived from miR150, miR206, miR204, miR17, miR16, miR30a, miR126, miR122, miR213, miR29b1 or miR133a1.

Examples of backbone sequences that may be used in the practice of the present invention include, but are not limited, to those encoded by the DNA sequences listed in Table 1 below. The symbols of "X" and "Y" in Table 1 indicate nucleic acid sequences encoding, respectively, the guide miRNA (which may be either miRNA-5p or miRNA-3p) and the passenger miRNA (which may be either miRNA-5p or miRNA-3p), whereas the symbol of "n" indicates the number of nucleotides in such sequences, for example 16-30, preferably 18-25. In some embodiments, n can be 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 nucleotides. In certain embodiments, the backbone miRNA sequences are those that are encoded by sequences that hybridize under stringent hybridization conditions with the complement of any one of the sequences listed in Table 1.

TABLE 1

Nucleic acids encoding miRNA backbone sequences

| Synthetic miRNA | Nucleic acid sequences encoding 5' Backbone Sequence $X_n$-Stem Loop Sequence $Y_n$-3' Backbone Sequence |
|---|---|
| miR204 | SEQ ID NO: 1-**Xn**-SEQ ID NO: 2-**Yn**-SEQ ID NO: 3 |
| miR206 | SEQ ID NO: 4-**Yn**-SEQ ID NO: 5-**Xn**-SEQ ID NO: 6 |
| miR17 | SEQ ID NO: 7-**Xn**-SEQ ID NO: 8-**Yn**-SEQ ID NO: 9 |
| miR150 | SEQ ID NO: 10-**Xn**-SEQ ID NO: 11-**Yn**-SEQ ID NO: 12 |
| miR150 | SEQ ID NO: 13-**Yn**-SEQ ID NO: 14-**Xn**-SEQ ID NO: 15 |
| miR16 | SEQ ID NO: 16-**Xn**-SEQ ID NO: 17-**Yn**-SEQ ID NO: 18 |
| miR30a | SEQ ID NO: 19-**Xn(or Yn)**-SEQ ID NO: 20-**Yn(or Xn)**-SEQ ID NO: 21 |
| miR126 | SEQ ID NO: 22-**Yn**-SEQ ID NO: 23-**Xn**-SEQ ID NO: 24 |
| miR122 | SEQ ID NO: 25-**Xn**-SEQ ID NO: 26-**Yn**-SEQ ID NO: 27 |
| miR214 | SEQ ID NO: 28-**Yn**-SEQ ID NO: 29-**Xn**-SEQ ID NO: 30 |
| miR214 | SEQ ID NO: 31-**Xn**-SEQ ID NO: 32-**Yn**-SEQ ID NO: 33 |
| miR29b1 | SEQ ID NO: 34-**Yn**-SEQ ID NO: 35-**Yn**-SEQ ID NO: 36 |
| miR29b1 | SEQ ID NO: 37-**Xn**-SEQ ID NO: 38-**Xn**-SEQ ID NO: 39 |
| miR133a1 | SEQ ID NO: 40-**Yn**-SEQ ID NO: 41-**Xn**-SEQ ID NO: 42 |
| miR26a | SEQ ID NO: 43-**Xn**-SEQ ID NO: 44-**Yn**-SEQ ID NO: 45 |
| miR412 | SEQ ID NO: 46-**Xn**-SEQ ID NO: 47-**Yn**-SEQ ID NO: 48 |
| miR-19 | SEQ ID NO: 49-**Xn**-SEQ ID NO: 50-**Yn**-SEQ ID NO: 51 |
| miR-21 | SEQ ID NO: 52-**Xn**-SEQ ID NO: 53-**Yn**-SEQ ID NO: 54 |
| miR-142 | SEQ ID NO: 55-**Xn**-SEQ ID NO: 56-**Yn**-SEQ ID NO: 57 |
| miR-494 | SEQ ID NO: 58-**Xn**-SEQ ID NO: 59-**Yn**-SEQ ID NO: 60 |
| miR-1915 | SEQ ID NO: 61-**Xn**-SEQ ID NO: 62-**Yn**-SEQ ID NO: 63 |

While the miRNA-5p and miRNA-3p sequences hybridize with each other, they are not necessarily exactly complementary. In the design of a non-naturally occurring miRNA, compensatory mutations can be made in the miRNA-5p and/or miRNA-3p sequences so as to maintain the RNA folding and free energy of the native miRNA. In certain embodiments, the sequence encoding the miRNA-3p sequence has at least 50%, 60%, 70%, 80%, 85%, 90%, 95%, 96%, 97%, 98%, or 99% sequence identity with the complement to the sequence encoding the miRNA-5p sequence or is capable of hybridizing under stringent hybridization conditions with the sequence encoding the miRNA-5p sequence.

In certain embodiments, the target gene encodes a checkpoint inhibitor protein. Thus, the present invention relates in part to a polynucleotide encoding a non-naturally occurring miRNA that inhibits the expression of an immune checkpoint protein. In certain such embodiments, the target gene encodes CTLA4, PD-1, PD-L1, TIGIT, TIM3, LAG3, GITR, or PIK3IP1. Non-limiting examples of nucleic acid sequences encoding the guide miRNA targeting genes encoding such checkpoint inhibitors are listed in Table 2. Table 2 also lists the sequences encoding the passenger strand. As previous discussed, the guide and passenger strand are not necessarily complementary. It is contemplated that the passenger strand may also serve to target the messenger RNA associated with the target gene. It is also contemplated that sequences that sequences that hybridize under stringent hybridization conditions with the compliments of the sequences listed in Table 2 may also be used. The mature miRNA sequences used may be combined with a specific pri-miRNA backbone. Table 2 also lists backbones that can be combined with the mature guide and passenger miRNAs listed therein.

TABLE 2

Nucleic acid sequences encoding mature miRNA sequences

| miRNA Target | Backbone | DNA encoding guide miRNA | DNA encoding passenger miRNA |
|---|---|---|---|
| CTLA4 | miR-204 | (SEQ ID NO: 64) | (SEQ ID NO: 65) |
| CTLA4 | miR-26a | (SEQ ID NO: 66) | (SEQ ID NO: 67) |
| CTLA4 | miR-30a | (SEQ ID NO: 68) | (SEQ ID NO: 69) |
| CTLA4 | miR-206 | (SEQ ID NO: 70) | (SEQ ID NO: 71) |
| PD1 | miR-204 | (SEQ ID NO: 72) | (SEQ ID NO: 73) |
| PD1 | miR-204 | (SEQ ID NO: 704) | |
| PD1 | miR-204 | (SEQ ID NO: 705) | |
| PD1 | miR-204 | | (SEQ ID NO: 706) |
| PD1 | miR-204 | | (SEQ ID NO: 707) |
| PD1 | miR-204 | | (SEQ ID NO: 708) |
| PD1 | miR-206 | (SEQ ID NO: 74) | (SEQ ID NO: 75) |
| PD1 | miR-206 | (SEQ ID NO: 709) | |
| PD1 | miR-206 | (SEQ ID NO: 710) | |
| PD1 | miR-206 | | (SEQ ID NO: 711) |
| PD1 | miR-206 | | (SEQ ID NO: 712) |
| PD1 | miR-206 | | (SEQ ID NO: 713) |
| PD1 | miR-30a | (SEQ ID NO: 76) | (SEQ ID NO: 77) |
| PD1 | miR-412 | (SEQ ID NO: 78) | (SEQ ID NO: 79) |
| PD1 | miR122 | (SEQ ID NO: 80) | (SEQ ID NO: 81) |
| PD1 | miR-17 | (SEQ ID NO: 82) | (SEQ ID NO: 83) |
| PD1 | miR-150 | (SEQ ID NO: 74) | (SEQ ID NO: 85) |
| PD1 | miR-486 | (SEQ ID NO: 76) | (SEQ ID NO: 87) |
| TIGIT | miR-17 | (SEQ ID NO: 88) | (SEQ ID NO: 89) |
| TIGIT | miR-150 | (SEQ ID NO: 90) | (SEQ ID NO: 91) |
| TIGIT | miR-204 | (SEQ ID NO: 92) | (SEQ ID NO: 93) |
| TIGIT | miR29b1 | (SEQ ID NO: 94) | (SEQ ID NO: 95) |
| TIGIT | miR214 | (SEQ ID NO: 96) | (SEQ ID NO: 97) |
| TIGIT | miR-206 | (SEQ ID NO: 98) | (SEQ ID NO: 99) |
| TIGIT | miR-204 | (SEQ ID NO: 100) | (SEQ ID NO: 101) |
| TIGIT | miR-22 | (SEQ ID NO: 102) | (SEQ ID NO: 103) |
| TIGIT | miR-16 | (SEQ ID NO: 104) | (SEQ ID NO: 105) |
| TIGIT | miR-21 | (SEQ ID NO: 106) | (SEQ ID NO: 107) |
| TIGIT | miR-494 | (SEQ ID NO: 108) | (SEQ ID NO: 109) |
| TIGIT | miR-142 | (SEQ ID NO: 110) | (SEQ ID NO: 111) |
| TIGIT | miR-19 | (SEQ ID NO: 112) | (SEQ ID NO: 113) |
| TIGIT | miR-1915 | (SEQ ID NO: 114) | (SEQ ID NO: 115) |
| TIGIT | miR-206 | (SEQ ID NO: 116) | (SEQ ID NO: 117) |
| TIGIT | miR-204 | (SEQ ID NO: 118) | (SEQ ID NO: 119) |
| TIGIT | miR-22 | (SEQ ID NO: 120) | (SEQ ID NO: 121) |

TABLE 2-continued

Nucleic acid sequences encoding mature miRNA sequences

| miRNA Target | Backbone | DNA encoding guide miRNA | DNA encoding passenger miRNA |
|---|---|---|---|
| TIGIT | miR-142 | (SEQ ID NO: 122) | (SEQ ID NO: 123) |
| TIGIT | miR-16 | (SEQ ID NO: 124) | (SEQ ID NO: 125) |
| TIGIT | miR-206 | (SEQ ID NO: 126) | (SEQ ID NO: 127) |
| TIGIT | miR-204 | (SEQ ID NO: 128) | (SEQ ID NO: 129) |
| TIGIT | miR-21 | (SEQ ID NO: 130) | (SEQ ID NO: 131) |
| TIGIT | miR-494 | (SEQ ID NO: 132) | (SEQ ID NO: 133) |
| TIGIT | miR-19 | (SEQ ID NO: 134) | (SEQ ID NO: 135) |
| TIGIT | miR-1915 | (SEQ ID NO: 136) | (SEQ ID NO: 137) |
| TIGIT | miR-204 | (SEQ ID NO: 138) | (SEQ ID NO: 139) |
| TIGIT | miR-206 | (SEQ ID NO: 140) | (SEQ ID NO: 141) |
| TIGIT | miR-21 | (SEQ ID NO: 142) | (SEQ ID NO: 143) |
| TIGIT | miR-22 | (SEQ ID NO: 144) | (SEQ ID NO: 145) |
| TIM3 | miR204 | (SEQ ID NO: 146) | (SEQ ID NO: 147) |
| TIM3 | miR206 | (SEQ ID NO: 148) | (SEQ ID NO: 149) |
| TIM3 | miR17 | (SEQ ID NO: 150) | (SEQ ID NO: 151) |
| TIM3 | miR126 | (SEQ ID NO: 152) | (SEQ ID NO: 153) |
| TIM3 | miR122 | (SEQ ID NO: 154) | (SEQ ID NO: 155) |
| TIM3 | miR214 | (SEQ ID NO: 156) | (SEQ ID NO: 157) |
| LAG3 | miR-30a | (SEQ ID NO: 158) | (SEQ ID NO: 159) |
| LAG3 | miR122 | (SEQ ID NO: 160) | (SEQ ID NO: 161) |
| GITR | miR206 | (SEQ ID NO: 162) | (SEQ ID NO: 163) |
| GITR | miR29b1 | (SEQ ID NO: 164) | (SEQ ID NO: 165) |
| PIK3IP1 | miR206 | (SEQ ID NO: 166) | (SEQ ID NO: 167) |
| PIK3IP1 | miR126 | (SEQ ID NO: 168) | (SEQ ID NO: 169) |
| PIK3IP1 | miR30a | (SEQ ID NO: 170) | (SEQ ID NO: 171) |

In certain embodiments, the present invention relates to a polynucleotide comprising a nucleic acid sequence having at least 80% sequence identity with any one of SEQ ID NOs: 64-83, 85, 87-171, and 704-713 or that is capable of hybridizing under stringent hybridization conditions to the complement of any one of SEQ ID NOs: 64-83, 85, 87-171, and 704-713. In certain such embodiments, the present invention relates to a polynucleotide comprising a nucleic acid sequence having at least 80%, 85%, 90%, 95%, 96%, 97%, 98%, or 99% sequence identity with any one of SEQ ID NOs: 64, 66, 68, 70, 72, 74, 76, 78, 80, 82, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 704, 705, 709, and 710 or that is capable of hybridizing under stringent hybridization conditions to the complement of any one of SEQ ID NOs: 64, 66, 68, 70, 72, 74, 76, 78, 80, 82, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 704, 705, 709, and 710.

In certain embodiments, the miRNA targets PD-1. In certain such embodiments, the present invention relates to a polynucleotide comprising a nucleic acid sequence having at least 80%, 85%, 90%, 95%, 96%, 97%, 98%, or 99% sequence identity with any one of SEQ ID NOs: 72-83, 85, 87, and 704-713 or that is capable of hybridizing under stringent hybridization conditions to the complement of any one of SEQ ID NOs: 72-83, 85, 87, and 704-713. In certain embodiments, the present invention relates to a polynucleotide comprising a nucleic acid sequence having at least 80%, 85%, 90%, 95%, 96%, 97%, 98%, or 99% sequence identity with any one of SEQ ID NOs: 72, 74, 76, 78, 80, 82, 704, 705, 709, and 710 or that is capable of hybridizing under stringent hybridization conditions to the complement of any one of SEQ ID NOs: 72, 74, 76, 78, 80, 82, 704, 705, 709, and 710.

In certain embodiments, the present invention relates to a polynucleotide comprising a nucleic acid sequence having at least 80%, 85%, 90%, 95%, 96%, 97%, 98%, or 99% sequence identity with any one of SEQ ID NOs: 72-75 or that is capable of hybridizing under stringent hybridization conditions to the complement of any one of SEQ ID NOs: 72-75. In certain such embodiments, the present invention relates to a polynucleotide comprising a nucleic acid sequence having at least 80%, 85%, 90%, 95%, 96%, 97%, 98%, or 99% sequence identity with SEQ ID NO: 72 or 74 or that is capable of hybridizing under stringent hybridization conditions to the complement of SEQ ID NO: 72 or 74.

In certain embodiments, the present invention relates to a polynucleotide comprising:

a) a sequence encoding a 5' miRNA backbone sequence;

b) a sequence encoding a guide miRNA sequence;

c) a sequence encoding a stem loop sequence;

d) a sequence encoding a passenger miRNA sequence; and e) a sequence encoding a 3' backbone sequence.

In certain embodiments, the sequence encoding the guide miRNA sequence has at least 80%, 85%, 90%, 95%, 96%, 97%, 98%, or 99% sequence identity with any one of SEQ ID NOs: 64, 66, 68, 70, 72, 74, 76, 78, 80, 82, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 704, 705, 709, and 710; or is capable of hybridizing under stringent hybridization conditions to the complement of any one of such sequences.

In certain embodiments, the sequence encoding the passenger miRNA sequence has at least 80%, 85%, 90%, 95%, 96%, 97%, 98%, or 99% sequence identity to any one of SEQ ID NOs: 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 706-708, and 711-713; or is capable of hybridizing under stringent hybridization conditions to the complement of any one of such sequences.

In certain embodiments, the polynucleotide encoding a pri-miRNA encodes:

a) a guide miRNA sequence having at least 80%, 85%, 90%, 95%, 96%, 97%, 98%, or 99% sequence identity with any one of SEQ ID NOs: 64, 66, 68, 70, 72, 74, 76, 78, 80, 82, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 704, 705, 709, and 710, or that is capable of hybridizing under stringent hybridization conditions to the complement of any one of such sequences; and b) a passenger sequence having at least 80%, 85%, 90%, 95%, 96%, 97%, 98%, or 99% sequence identity to, respectively, any one of SEQ ID NOs: 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 706-708, and 711-713, or that is capable of hybridizing under stringent hybridization conditions to the complement of any one of such sequences.

In any of the foregoing embodiments, the sequences encoding the 5' miRNA backbone sequence, the stem loop sequence, and the 3' miRNA backbone sequence can each comprise:

SEQ ID NO: 1, SEQ ID NO: 2, and SEQ ID NO: 3, respectively;

SEQ ID NO: 4, SEQ ID NO: 5, and SEQ ID NO: 6, respectively;

SEQ ID NO: 7, SEQ ID NO: 8, and SEQ ID NO: 9, respectively;

SEQ ID NO: 10, SEQ ID NO: 11, and SEQ ID NO: 12, respectively;

SEQ ID NO: 13, SEQ ID NO: 14, and SEQ ID NO: 15, respectively;

SEQ ID NO: 16, SEQ ID NO: 17, and SEQ ID NO: 18, respectively;

SEQ ID NO: 19, SEQ ID NO: 20, and SEQ ID NO: 21, respectively;

SEQ ID NO: 22, SEQ ID NO: 23, and SEQ ID NO: 24, respectively;

SEQ ID NO: 25, SEQ ID NO: 26, and SEQ ID NO: 27, respectively;

SEQ ID NO: 28, SEQ ID NO: 29, and SEQ ID NO: 30, respectively;

SEQ ID NO: 31, SEQ ID NO: 32, and SEQ ID NO: 33, respectively;

SEQ ID NO: 34, SEQ ID NO: 35, and SEQ ID NO: 36, respectively;

SEQ ID NO: 37, SEQ ID NO: 38, and SEQ ID NO: 39, respectively;

SEQ ID NO: 40, SEQ ID NO: 41, and SEQ ID NO: 42, respectively;

SEQ ID NO: 43, SEQ ID NO: 44, and SEQ ID NO: 45, respectively;

SEQ ID NO: 46, SEQ ID NO: 47, and SEQ ID NO: 48, respectively;

SEQ ID NO: 49, SEQ ID NO: 50, and SEQ ID NO: 51, respectively;

SEQ ID NO: 52, SEQ ID NO: 53, and SEQ ID NO: 54, respectively;

SEQ ID NO: 55, SEQ ID NO: 56, and SEQ ID NO: 57, respectively;

SEQ ID NO: 58, SEQ ID NO: 59, and SEQ ID NO: 60, respectively; or

SEQ ID NO: 61, SEQ ID NO: 62, and SEQ ID NO: 63, respectively;

or sequences having at least 80%, 85%, 90%, 95%, 96%, 97%, 98%, or 99% sequence identity with such sequences, or that are capable of hybridizing under stringent hybridization conditions to the complements of such sequences.

Nucleic acids encoding exemplary non-naturally occurring pri-miRNA sequences targeting specific checkpoint inhibitors are described in Table 3. In certain embodiments, the non-naturally occurring pri-miRNA sequence may be a sequence that is capable of hybridizing under stringent hybridization conditions with the complement of any one of the sequences listed in Table 3.

TABLE 3

Nucleic acid sequences encoding non-naturally occurring pri-miRNA sequences

| miRNA Target | Encoded pri-miRNA(s) | DNA Sequence |
|---|---|---|
| CTLA4 | miR204 | (SEQ ID NO: 178) |
| PD1 | miR204 | (SEQ ID NO: 179) |
| PD1 | miR206 | (SEQ ID NO: 180) |
| TIGIT | miR17 | (SEQ ID NO: 181) |
| TIGIT | miR150 | (SEQ ID NO: 182) |
| TIGIT | miR204 | (SEQ ID NO: 183) |
| TIGIT | miR-206 | (SEQ ID NO: 184) |
| TIGIT | miR-204 | (SEQ ID NO: 185) |
| TIGIT | miR-22 | (SEQ ID NO: 186) |

TABLE 3-continued

Nucleic acid sequences encoding non-naturally occurring pri-miRNA sequences

| miRNA Target | Encoded pri-miRNA(s) | DNA Sequence |
|---|---|---|
| TIGIT | miR-16 | (SEQ ID NO: 187) |
| TIGIT | miR-16 | (SEQ ID NO: 188) |
| TIGIT | miR-21 | (SEQ ID NO: 189) |
| TIGIT | miR-494 | (SEQ ID NO: 190) |
| TIGIT | miR-142 | (SEQ ID NO: 191) |
| TIGIT | miR-19 | (SEQ ID NO: 192) |
| TIGIT | miR-1915 | (SEQ ID NO: 193) |
| TIGIT | miR-206 | (SEQ ID NO: 194) |
| TIGIT | miR-204 | (SEQ ID NO: 195) |
| TIGIT | miR-22 | (SEQ ID NO: 196) |
| TIGIT | miR-142 | (SEQ ID NO: 197) |
| TIGIT | miR-16 | (SEQ ID NO: 198) |
| TIGIT | miR-206 | (SEQ ID NO: 199) |
| TIGIT | miR-204 | (SEQ ID NO: 200) |
| TIGIT | miR-21 | (SEQ ID NO: 201) |
| TIGIT | miR-494 | (SEQ ID NO: 202) |
| TIGIT | miR-19 | (SEQ ID NO: 203) |
| TIGIT | miR-1915 | (SEQ ID NO: 204) |
| TIGIT | miR-204 | (SEQ ID NO: 205) |
| TIGIT | miR-206 | (SEQ ID NO: 206) |
| TIGIT | miR-21 | (SEQ ID NO: 207) |
| TIGIT | miR-22 | (SEQ ID NO: 208) |
| TIM3 | miR204 | (SEQ ID NO: 209) |
| TIM3 | miR150 | (SEQ ID NO: 210) |
| TIM3 | miR30a | (SEQ ID NO: 211) |
| TIM3 | miR206 | (SEQ ID NO: 212) |
| TIM3 | miR16 | (SEQ ID NO: 213) |
| TIM3 | miR17 | (SEQ ID NO: 214) |
| TIM3 | miR126 | (SEQ ID NO: 215) |
| TIM3 | miR122 | (SEQ ID NO: 216) |
| TIM3 | miR214 | (SEQ ID NO: 217) |
| TIM3 | miR29b1 | (SEQ ID NO: 218) |
| TIM3 | miR204 | (SEQ ID NO: 219) |
| TIM3 | miR133a1 | (SEQ ID NO: 220) |
| LAG3 | miR30a | (SEQ ID NO: 221) |
| LAG3 | miR206 | (SEQ ID NO: 222) |
| LAG3 | miR204 | (SEQ ID NO: 223) |
| LAG3 | miR150 | (SEQ ID NO: 224) |
| LAG3 | miR17 | (SEQ ID NO: 225) |
| LAG3 | miR122 | (SEQ ID NO: 226) |
| LAG3 | miR126 | (SEQ ID NO: 227) |
| GITR | miR30a | (SEQ ID NO: 228) |
| GITR | miR206 | (SEQ ID NO: 229) |
| GITR | miR17 | (SEQ ID NO: 230) |
| GITR | miR122 | (SEQ ID NO: 231) |
| GITR | miR150 | (SEQ ID NO: 232) |
| GITR | miR29 | (SEQ ID NO: 233) |
| GITR | miR181a1 | (SEQ ID NO: 234) |
| TIGIT | miR206 | (SEQ ID NO: 235) |
| TIGIT | miR30a | (SEQ ID NO: 236) |
| TIGIT | miR133a1 | (SEQ ID NO: 237) |
| TIGIT | miR122 | (SEQ ID NO: 238) |
| TIGIT | miR29b1 | (SEQ ID NO: 239) |
| TIGIT | miR214 | (SEQ ID NO: 240) |
| PD1 | miR30a | (SEQ ID NO: 241) |
| PD1 | miR412 | (SEQ ID NO: 242) |
| PD1 | miR17 | (SEQ ID NO: 243) |
| PD1 | miR122 | (SEQ ID NO: 244) |
| PD1 | miR150 | (SEQ ID NO: 245) |
| PD1 | miR486 | (SEQ ID NO: 246) |
| PD1 | miR206 | (SEQ ID NO: 247) |
| PD1 | miR122 | (SEQ ID NO: 248) |
| PD1 | miR30a | (SEQ ID NO: 249) |
| CTLA4 | miR206 | (SEQ ID NO: 250) |
| CTLA4 | miR26a | (SEQ ID NO: 251) |
| CTLA4 | miR30a | (SEQ ID NO: 252) |
| PIK3IP1 | miR206 | (SEQ ID NO: 253) |
| PIK3IP1 | miR126 | (SEQ ID NO: 254) |
| PIK3IP1 | miR30a | (SEQ ID NO: 255) |
| TCRa3'UTR | miR150 | (SEQ ID NO: 256) |
| TCRa3'UTR | miR204 | (SEQ ID NO: 257) |
| TCRa3'UTR | miR206 | (SEQ ID NO: 258) |
| TCRa3'UTR | miR26a | (SEQ ID NO: 259) |
| TCRa3'UTR | miR150 | (SEQ ID NO: 260) |
| TCRa3'UTR | miR16 | (SEQ ID NO: 261) |
| TCRa3'UTR | miR206 | (SEQ ID NO: 262) |
| TCRa3'UTR | miR26a | (SEQ ID NO: 263) |

In certain such embodiments, the present invention relates to a polynucleotide comprising a nucleic acid sequence having at least 80%, 85%, 90%, 95%, 96%, 97%, 98%, or 99% sequence identity with any one of SEQ ID NOs: 178-263 or that is capable of hybridizing under stringent hybridization conditions to the complement of any one of SEQ ID NOs: 178-263.

In certain embodiments, the miRNA targets PD-1. In certain such embodiments, the present invention relates to a polynucleotide comprising a nucleic acid sequence having at least 80%, 85%, 90%, 95%, 96%, 97%, 98%, or 99% sequence identity with any one of SEQ ID NOs: 179, 180, and 241-249 or that is capable of hybridizing under stringent hybridization conditions to the complement of any one of SEQ ID NOs: 179, 180, and 241-249. In certain embodiments, the present invention relates to a polynucleotide comprising a nucleic acid sequence having at least 80%, 85%, 90%, 95%, 96%, 97%, 98%, or 99% sequence identity with any one of SEQ ID NO: 179 or 180 or that is capable of hybridizing under stringent hybridization conditions to the complement of any one of SEQ ID NOs: 179 or 180.

Certain embodiments of the present relate to a polynucleotide that comprises nucleic acid sequences encoding at least two pri-miRNAs. The two or more pri-miRNAs may contain guide miRNA sequences that target the same target gene or the various guide miRNAs may target different genes. In the case of multiple pri-miRNAs, each design may be based on a different native miRNA backbone to reduce the likelihood of misfolding of one miRNA with another. Table 4 provides examples of nucleic acid sequences encoding one or more pri-miRNAs.

TABLE 4

Non-naturally occurring miRNA sequences comprising two or more pri-miRNAs

| miRNA Target | miRNA backbone | DNA Sequence |
|---|---|---|
| PD1 | miR204 + miR206 | (SEQ ID NO: 267) |
| PD1 + TIGIT | miR204 + miR150 | (SEQ ID NO: 268) |
| PD1 + TIGIT | miR206 + miR150 | (SEQ ID NO: 269) |
| TIGIT + PD1 | miR17 + miR204 | (SEQ ID NO: 270) |
| TIGIT + PD1 | miR17 + miR206 | (SEQ ID NO: 271) |
| TIGIT + PD1 | miR204 + miR206 | (SEQ ID NO: 272) |
| TIGIT + PD1 | miR150 + miR204 | (SEQ ID NO: 273) |
| TIGIT + PD1 | miR150 + miR206 | (SEQ ID NO: 274) |
| TIGIT + PD1 + PD1 | miR17 + miR204 + miR206 | (SEQ ID NO: 275) |
| TIGIT + PD1 + | miR17 + miR204 + | (SEQ ID NO: 276) |

TABLE 4-continued

Non-naturally occurring miRNA sequences comprising two or more pri-miRNAs

| miRNA Target | miRNA backbone | DNA Sequence |
|---|---|---|
| PD1 | miR206 extra spacing 1 | |
| TIGIT + PD1 + PD1 | miR17 + miR204 + miR206 extra spacing 2 | (SEQ ID NO: 277) |
| PD1 + PD1 + TIGIT | miR204 + miR206 + miR17 | (SEQ ID NO: 278) |
| PD1 + PD1 + TIGIT | miR204 + miR206 + miR17 extra spacing 1 | (SEQ ID NO: 279) |
| PD1 + PD1 + TIGIT | miR204 + miR206 + miR17 extra spacing 2 | (SEQ ID NO: 280) |
| PD1 + CTLA4 | miR204 + miR26a | (SEQ ID NO: 281) |
| PD1 + PD1 | miR204 + miR206 | (SEQ ID NO: 282) |
| PD1 + CTLA4 | miR206 + miR26a | (SEQ ID NO: 283) |
| PD1 + CTLA4 | miR206 + miR204 | (SEQ ID NO: 284) |
| TIGIT + CTLA4 | miR17 + miR26a | (SEQ ID NO: 285) |
| TIGIT + CTLA4 | miR17 + miR204 | (SEQ ID NO: 286) |
| TIGIT + PD1 | miR17 + miR204 | (SEQ ID NO: 287) |
| TIGIT + PD1 | miR17 + 206 | (SEQ ID NO: 288) |
| TIGIT + CTLA4 | miR204 + miR26a | (SEQ ID NO: 289) |
| TIGIT + PD1 | miR204 + miR206 | (SEQ ID NO: 290) |

In certain such embodiments, the present invention relates to a polynucleotide comprising a nucleic acid sequence having at least 80%, 85%, 90%, 95%, 96%, 97%, 98%, or 99% sequence identity with any one of SEQ ID NOs: 267-290 or that is capable of hybridizing under stringent hybridization conditions to the complement of any one of SEQ ID NOs: 267-290.

In certain such embodiments, the pri-miRNA comprises at least two pre-miRNAs that target PD-1. In certain embodiments, the present invention relates to a polynucleotide comprising a nucleic acid sequence having at least 80%, 85%, 90%, 95%, 96%, 97%, 98%, or 99% sequence identity with any one of SEQ ID NO: 267 or that is capable of hybridizing under stringent hybridization conditions to the complement of any one of SEQ ID NOs: 267.

In certain embodiments, the nucleic acid encoding the pri-miRNA(s) is contained in the same genetic construct as that comprising one or more genes encoding protein(s) of interest (e.g., a chimeric antigen receptor, a cytokine, or a cell tag). In certain embodiments, such a genetic construct includes a nucleic acid sequence encoding a 5' untranslated region (5'UTR) directly upstream of the gene(s) of interest and the sequence encoding the miRNA is included in the 5'UTR. In certain embodiments, such a genetic construct includes a nucleic acid sequence encoding a 3' untranslated region (3'UTR) directly downstream of the gene(s) of interest and the sequence encoding the miRNA is included in the 3'UTR.

In embodiments wherein the sequence encoding the pri-miRNA is included in the sequence corresponding to the 5' UTR, the transcribed RNA can include additional sequences such as splice donor, branchpoint and/or acceptor site sequences. The inclusion of splice donor, branchpoint, and acceptor sites is important for splicing of the miRNAs from the transcribed RNA. Without splicing, the highly structured miRNA sequence is likely to impede ribosome scanning to the translation initiation sequence relating to the gene of interest. Examples of sequences encoding such splice donor/acceptor sites include SEQ ID NOs: 291 and 292, sequences having at least 80%, 85%, 90%, 95%, 96%, 97%, 98%, or 99% sequence identity with such sequences and sequences that are capable of hybridizing with the complement of such sequences under stringent hybridization conditions.

Thus, in certain embodiments, the polynucleotide of the present invention further comprises: a) a nucleic acid sequence having at least 80% sequence identity with SEQ ID NO: 291 or that is capable of hybridizing under stringent hybridization conditions to the complement of SEQ ID NO: 291; and b) a nucleic acid sequence having at least 80% sequence identity with SEQ ID NO: 292 or that is capable of hybridizing under stringent hybridization conditions to the complement of SEQ ID NO: 292.

IV. Chimeric Antigen Receptors (CARs)

In any of the foregoing embodiments, a polynucleotide of the present disclosure can further encode a chimeric receptor, such as a chimeric antigen receptor (CAR). Thus, a polynucleotide of the present disclosure can encode miRNA(s) and a CAR as described herein. In any of the embodiments of the present disclosure, a modified immune effector cell can comprise a chimeric receptor as described herein.

A CAR is an engineered receptor that grafts an exogenous specificity onto an immune effector cell. In some instances, a CAR comprises an extracellular domain (ectodomain) that comprises an antigen-binding domain, a transmembrane domain, and an intracellular (endodomain) domain. The intracellular domain comprises an intracellular signaling domain. In certain embodiments, the extracellular domain further comprises a spacer between the antigen-binding domain and the transmembrane domain.

A. Antigen-Binding Domain

An antigen-binding domain can comprise complementary determining regions of a monoclonal antibody and/or antigen binding fragments thereof. A complementarity determining region (CDR) is a short amino acid sequence found in the variable domains of antigen receptor (e.g., immunoglobulin and T-cell receptor) proteins that bind an antigen and therefore provides the receptor with its specificity for that particular antigen. Each polypeptide chain of an antigen receptor can contain three CDRs (CDR1, CDR2, and CDR3).

In certain embodiments, the antigen-binding domain comprises an antibody, or functional fragment or variant thereof, that binds to a target antigen. The functional fragment or variant may comprise the variable domain of the heavy chain of an antibody ($V_H$) and/or the variable domain of the light chain of an antibody ($V_L$), or functional fragments or variants thereof. In certain embodiments, the antigen-binding domain comprises a Fv, Fab, $Fab_2$, Fab', $F(ab')_2$, or $F(ab')_3$ fragment of an antibody. In certain embodiments, the antigen-binding domain comprises a scFv, $sc(Fv)_2$, a dsFv, a diabody, a minibody, a nanobody, or binding fragments thereof. In certain embodiments, the antigen-binding domain further comprises an $F_c$ fragment of an antibody, for example it may comprise an scFv linked with an $F_c$ fragment.

In some embodiments, the CAR targets an antigen that is elevated in cancer cells, in autoimmune cells, or in cells that are infected by a virus, bacteria or parasite. Pathogens that may be targeted include, without limitation, *Plasmodium*, trypanosome, *Aspergillus, Candida*, Hepatitis A, Hepatitis B, Hepatitis C, HSV, HPV, RSV, EBV, CMV, JC virus, BK virus, or Ebola pathogens. Autoimmune diseases can include graft-versus-host disease, rheumatoid arthritis, lupus, celiac disease, Crohn's disease, Sjogren Syndrome, polymyalgia rheumatic, multiple sclerosis, neuromyelitis optica, ankylosing spondylitis, Type 1 diabetes, alopecia areata, vasculitis, temporal arteritis, bullous pemphigoid, psoriasis, pemphigus vulgaris, and autoimmune uveitis.

The pathogen recognized by a CAR may be essentially any kind of pathogen, but in some embodiments, the pathogen is a fungus, bacteria, or virus. Exemplary viral pathogens include those of the families of Adenoviridae, Epstein-Barr virus (EBV), Cytomegalovirus (CMV), Respiratory Syncytial Virus (RSV), JC virus, BK virus, HPV, HSV, HHV family of viruses, Hepatitis family of viruses, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Exemplary pathogenic viruses cause smallpox, influenza, mumps, measles, chickenpox, ebola, and rubella. Exemplary pathogenic fungi include *Candida, Aspergillus, Cryptococcus, Histoplasma, Pneumocystis*, and *Stachybotrys*. Exemplary pathogenic bacteria include *Streptococcus, Pseudomonas, Shigella, Campylobacter, Staphylococcus, Helicobacter, E. coli, Rickettsia, Bacillus, Bordetella, Chlamydia*, Spirochetes, and *Salmonella*. In some embodiments, the pathogen receptor Dectin-1 may be used to generate a CAR that recognizes the carbohydrate structure on the cell wall of fungi such as *Aspergillus*. In another embodiment, CARs can be made based on an antibody recognizing viral determinants (e.g., the glycoproteins from CMV and Ebola) to interrupt viral infections and pathology.

In some embodiments, a CAR described herein comprises an antigen-binding domain that binds to an epitope on B7H4, BCMA, BTLA, CAIX, CA125, CCR4, CD3, CD4, CD5, CD7, CD16, CD19, CD20, CD22, CD24, CD25, CD28, CD30, CD33, CD38, CD40, CD44, CD44v6, CD44v7/v8, CD47, CD52, CD56, CD70, CD79b, CD80, CD81, CD86, CD123, CD133, CD137, CD138, CD151, CD171, CD174, CD276, CEA, CEACAM6, CLL-1, c-MET, CS1, CSPG4, CTLA-4, DLL3, EDB-F, EGFR, EGFR2, EGFRvIII, EGP-2, EGP-40, EphA2, FAP, FLT1, FLT4, Folate-binding Protein, Folate Receptor, Folate receptor $\alpha$, $\alpha$-Folate receptor, Frizzled, GD2, GD3, GHR, GHRHR, GITR, GPC3, Gp100, gp130, HBV antigens, HER1, HER2, HER3, HER4, HER1/HER3, h5T4, HPV antigens, HVEM, IGF1R, IgKAppa, IL-1-RAP, IL-2R, IL6R, IL-11R$\alpha$, IL-13R-a2, KDR, KRASG12V, LewisA, LewisY, L1-CAM, LIFRP, LRP5, LTPR, MAGE-A, MAGE-A1, MAGE-A10, MAGE-A3, MAGEA3/A6, MAGE-A4, MAGE-A6, MART-1, MCAM, mesothelin, PSCA, Mucins such as MUC1, MUC-4 or MUC16, NGFR, NKG2D, Notch-1-4, NY-ESO-1, O-acetylGD2, O-acetylGD3, OX40, P53, PD1, PDE10A, PD-L1, PD-L2, PMSA, PRAME, PSCA, PSMA, PTCH1, RANK, Robol, ROR1, ROR1R, ROR-2, TACI, TAG-72, TCR$\alpha$, TCRp, TGF, TGFBeta, TGFBeta-II, TGFBR1, TGFBR2, Titin, TLR7, TLR9, TNFR1, TNFR2, TNFRSF4, TRBC1, TWEAK-R, VEGF, VEGF-R2, or WT-1.

In some embodiments, a CAR described herein comprises an antigen-binding domain that binds to an epitope on CD19, CD33, MUC1, MUC16, or ROR1. In some instances, a CAR described herein comprises an antigen-binding domain that binds to an epitope on CD19. In some cases, a CAR described herein comprises an antigen-binding domain that binds to an epitope on CD33. In some instances, a CAR described herein comprises an antigen-binding domain that binds to an epitope on MUC1. In some instances, a CAR described herein comprises an antigen-binding domain that binds to an epitope on MUC16. In some instances, a CAR described herein comprises an antigen-binding domain that binds to an epitope on ROR1. In further embodiments, a CAR described herein comprises an autoantigen or an antigen binding domain that binds to an epitope on HLA-A2, myelin oligodendrocyte glycoprotein (MOG), factor VIII (FVIII), MAdCAM1, SDF1, or collagen type II.

Antigen binding can be assessed by flow cytometry or a cell based assay or any other equivalent assay. Cell based assays may utilize a cell type expressing antigen of interest on the surface to assess antigen-binding. An antigen or a fragment thereof expressed as a soluble protein can be utilized to assess antigen-binding using flow cytometry or similar assay. Improvements in antigen-binding may be indirectly assessed by functional measurement of antigen-binding domain or a chimeric receptor. For example, improved antigen-binding of a chimeric receptor or a CAR, as described herein, can be measured by increased specific cytotoxicity against target cells expressing the antigen.

Cell surface expression level of a polypeptide of the present disclosure can be assessed, for example, using a flow cytometry based assay. Improved expression of an antigen-binding polypeptide can be measured as percentage of analyzed cells expressing said antigen-binding polypeptide or alternatively as average density of said antigen-binding polypeptide on the surface of a cell. Additional suitable methods that can be used for assessing cell surface expression of the antigen-binding polypeptides described herein include western blotting or any other equivalent assay.

1. CD19-Specific Antigen-Binding Domain

CD19 is a cell surface glycoprotein of the immunoglobulin superfamily and is found predominately in malignant B-lineage cells. In some instances, CD19 has also been detected in solid tumors such as pancreatic cancer, liver cancer, and prostate cancer.

In some embodiments, the CAR comprises a CD19-specific antigen-binding domain, in which the antigen-binding domain comprises a $F(ab')_2$, Fab', Fab, Fv, or scFv. In some embodiments, the antigen-binding domain recognizes an epitope on CD19 that is also recognized by FMC63. In some embodiments the scFv and/or VH/VL domains is/are derived from FMC63. FMC63 generally refers to a mouse monoclonal IgG1 antibody raised against Nalm-1 and -16 cells expressing CD19 of human origin (Ling, N. R., et al. (1987). Leucocyte typing III. 302).

In some embodiments, the antigen-binding domain recognizes an epitope on CD19 that is also recognized by JCAR014, JCAR015, JCAR017, or 19-28z CAR (Juno Therapeutics).

In some embodiments, the antigen-binding domain comprises a scFv antigen-binding domain that recognizes an epitope on CD19 that is also recognized by JCAR014, JCAR015, JCAR017, or 19-28z CAR (Juno Therapeutics).

In some embodiments, the antigen-binding domain comprises an anti-CD19 antibody described in U.S. Patent Application Publication No. 2016/0152723. In some embodiments, the antigen-binding domain comprises an anti-CD19 antibody described in International Patent Application Publication No. WO2015/123642. In some embodiments, the antigen-binding domain comprises an anti-CD19 scFv derived from clone FMC63 (Nicholson et al., Construction and characterization of a functional CD19 specific single chain Fv fragment for immunotherapy of B lineage leukemia and lymphoma., Mol. Immunol. 34:1157-1165 (1997)).

In some embodiments, the antigen-binding domain recognizes an epitope on CD19 that is also recognized by KTE-C19 (Kite Pharma, Inc.).

In some embodiments, the antigen-binding domain comprises a scFv antigen-binding domain, and the antigen-binding domain recognizes an epitope on CD19 that is also recognized by KTE-C19.

In some embodiments, the antigen-binding domain comprises an anti-CD19 antibody described in International Patent Application Publication No. WO2015/187528 or fragment or variant thereof.

In some embodiments, the antigen-binding domain recognizes an epitope on CD19 that is also recognized by CTL019 (Novartis).

In some embodiments, the antigen-binding domain comprises a scFv antigen-binding domain, and the antigen-binding domain recognizes an epitope on CD19 that is also recognized by CTL019.

In some embodiments, the antigen-binding domain recognizes an epitope on CD19 that is also recognized by UCART19 (Cellectis).

In some embodiments, the antigen-binding domain comprises a scFv antigen-binding domain, and the antigen-binding domain recognizes an epitope on CD19 that is also recognized by UCART19.

In some embodiments, the antigen-binding domain recognizes an epitope on CD19 that is also recognized by BPX-401 (Bellicum).

In some embodiments, the antigen-binding domain comprises a scFv antigen-binding domain, and the antigen-binding domain recognizes an epitope on CD19 that is also recognized by BPX-401.

In some cases, the antigen-binding domain recognizes an epitope on CD19 that is also recognized by blinatumomab (Amgen), coltuximabravtansine (ImmunoGen Inc./Sanofi-aventis), MOR208 (Morphosys AG/Xencor Inc.), MEDI-551 (Medimmune), denintuzumabmafodotin (Seattle Genetics), B4 (or DI-B4) (Merck Serono), taplitumomabpaptox (National Cancer Institute), XmAb 5871 (Amgen/Xencor, Inc.), MDX-1342 (Medarex) or AFM11 (Affimed).

In some embodiments, the antigen-binding domain comprises a F(ab') 2, Fab', Fab, Fv, or scFv, and the antigen-binding domain recognizes an epitope on CD19 that is also recognized by blinatumomab (Amgen), coltuximabravtansine (ImmunoGen Inc./Sanofi-aventis), MOR208 (Morphosys AG/Xencor Inc.), MEDI-551 (Medimmune), denintuzumabmafodotin (Seattle Genetics), B4 (or DI-B4) (Merck Serono), taplitumomabpaptox (National Cancer Institute), XmAb 5871 (Amgen/Xencor, Inc.), MDX-1342 (Medarex) or AFM11 (Affimed).

In some cases, the antigen-binding domain comprises a scFv antigen-binding domain, and the antigen-binding domain recognizes an epitope on CD19 that is also recognized by FMC63, blinatumomab (Amgen), coltuximabravtansine (ImmunoGen Inc./Sanofi-aventis), MOR208 (Morphosys AG/Xencor Inc.), MEDI-551 (Medimmune), denintuzumabmafodotin (Seattle Genetics), B4 (or DI-B4) (Merck Serono), taplitumomabpaptox (National Cancer Institute), XmAb 5871 (Amgen/Xencor, Inc.), MDX-1342 (Medarex) or AFM11 (Affimed).

2. CD33-specific Antigen-Binding Domain

"CD33," is a 67 kDa single pass transmembrane glycoprotein and is a member of the sialic acid-binding immunoglobulin-like lectins (Siglecs) super-family. CD33 is characterized by a V-set Ig-like domain responsible for sialic acid binding and a C2-set Ig-like domain in its extracellular domain. CD33 is expressed in myeloid lineage cells and has also been detected in lymphoid cells. Alternative splicing of CD33 mRNA leads to a shorter isoform (CD33m) lacking the V-set Ig-like domain as well as the disulfide bond linking the V- and C2-set Ig-like domains. In healthy subjects, CD33 is primarily expressed as a myeloid differentiation antigen found on normal multipotent myeloid precursors, unipotent colony-forming cells, monocytes and maturing granulocytes. CD33 is expressed on more than 80% of myeloid leukemia cells but not on normal hematopoietic stem cells or mature granulocytes. (Andrews, R. et al., The L4F3 antigen is expressed by unipotent and multipotent colony-forming cells but not by their precursors, *Blood,* 68(5):1030-5 (1986)). CD33 has been reported to be expressed on malignant myeloid cells, activated T cells and activated NK cells and is found on at least a subset of blasts in the vast majority of AML patients (Pollard, J. et al., Correlation of CD33 expression level with disease characteristics and response to gemtuzumab ozogamicin containing chemotherapy in childhood AML, *Blood,* 119(16):3705-11(2012)). In addition to broad expression on AML blasts, CD33 may be expressed on stem cells underlying AML.

In some embodiments, the antigen-binding domain of a CAR described herein is specific to CD33 (CD33 CAR). The CD33-specific CAR, when expressed on the cell surface, redirects the specificity of T cells to human CD33. In some embodiments, the antigen-binding domain comprises a single chain antibody fragment (scFv) comprising a variable domain light chain (VL) and variable domain heavy chain (VH) of a target antigen specific monoclonal anti-CD33 antibody joined by a flexible linker, such as a glycine-serine linker or a Whitlow linker. In some embodiments, the scFv is M195, m2H12, DRB2, and/or My9-6. In some embodiments, the scFv is humanized, for example, hM195. In some embodiments, the antigen-binding domain may comprise VH and VL that are directionally linked, for example, from N to C terminus, VH-linker-VL or VL-linker-VH. In some embodiments, the antigen-binding domain comprises a $F(ab')_2$, Fab', Fab, Fv, or scFv that binds CD33. In some embodiments, the antigen-binding region recognizes an epitope on CD33 that is also recognized by Lintuzumab (Seattle Genetics), BI 836858 (Boehringer Ingelheim).

In some embodiments, a CAR described herein comprises an antigen-binding domain comprising a VL polypeptide.

In certain embodiments, the antigen-binding domain comprises a VL domain comprising the amino acid sequence of SEQ ID NO: 293 (hM195 VL domain), SEQ ID NO: 296 (M2H12 VL domain), SEQ ID NO: 298 (DRB2 VL domain), SEQ ID NO: 300 (My9-6 VL domain) or a functional fragment or variant thereof. In certain embodiments, the functional fragment is shorter than any one of the aforementioned sequences by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of any one of SEQ ID NOs: 293, 296, 298, and 300, and/or is a conservatively-substituted variant of any one of such sequences.

In certain embodiments, the antigen-binding domain comprises a VL domain encoded by SEQ ID NO: 301 (nucleic acid encoding the VL domain for hM195). In certain embodiments, the functional variant has at least 80%, 85%, 90%, 95%, 96%, 97%, 98%, or 99% sequence identity with SEQ ID NO: 301; hybridizes under stringent hybridization conditions with the complement of the nucleic acid sequence of SEQ ID NO: 301; or is a codon degenerate variant of SEQ ID NO: 301.

In some embodiments, a CAR described herein comprises an antigen-binding domain comprising a VH polypeptide.

In certain embodiments, the antigen-binding domain comprises a VH domain comprising the amino acid sequence of SEQ ID NO: 294 (hM195 VH domain), SEQ ID NO: 295 (M2H12 VH domain), SEQ ID NO: 297 (DRB2 VH domain), SEQ ID NO: 299 (My9-6 VH domain) or a functional fragment or variant thereof. In certain embodiments, the functional fragment is shorter than any one of the aforementioned sequences by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of any one of SEQ ID NOs: 294, 295, 297, or 299, and/or is a conservatively-substituted variant of the amino acid sequence of any one of SEQ ID NOs: 294, 295, 297, or 299.

In certain embodiments, the antigen-binding domain comprises a VH domain encoded by SEQ ID NO: 302 (nucleic acid encoding the VH domain for hM195), or a functional fragment or variant thereof. In certain embodiments, the functional variant has at least 80%, 85%, 90%, 95%, 96%, 97%, 98%, or 99% sequence identity with SEQ ID NO: 302; hybridizes under stringent hybridization conditions with the complement of the nucleic acid sequence of SEQ ID NO: 302; or is a codon degenerate variant of SEQ ID NO: 302.

In some embodiments, the antigen-binding domain can comprise VH and VL that are directionally linked, for example, from N to C terminus, VH-linker-VL or VL-linker-VH. Any linker as described herein can be used to link the VH and VL domains.

In certain embodiments, the antigen-binding domain comprises scFv. In certain such embodiments, the domain comprises the amino acid sequence of SEQ ID NO: 303, or a functional fragment or variant thereof. In certain embodiments, the functional fragment is shorter than any one of the aforementioned sequence by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 303, and/or is a conservatively-substituted variant of the amino acid sequence of SEQ ID NO: 303.

In certain embodiments, the antigen-binding domain is encoded by SEQ ID NO: 304, or a functional fragment or variant thereof. In certain embodiments, the functional variant has at least 80%, 85%, 90%, 95%, 96%, 97%, 98%, or 99% sequence identity with SEQ ID NO: 304; hybridizes under stringent hybridization conditions with the complement of the nucleic acid sequence of SEQ ID NO: 304; or is a codon degenerate variant of SEQ ID NO: 304.

3. MUC1-Specific Antigen-Binding Domain

In one embodiment, the antigen-binding domain binds to an epitope on MUC1. In some embodiments, the anti-MUC1 antibody fragment is a Fab, $Fab_2$, $(Fab')_2$, Fv, $(Fv)_2$, scFv, scFv-$F_C$, $F_C$, diabody, triabody, or minibody of the anti-MUC1. In some embodiments, the anti-MUC1 antibody fragment is a single-domain antibody of the anti-MUC1 antibody. In some embodiments, the single-domain antibody is a $V_{NAR}$ or $V_H$H fragment of the anti-MUC1 antibody.

In some embodiments, a CAR described herein comprises an antigen-binding domain comprising a VL polypeptide of MUC1.

In certain embodiments, the antigen-binding domain comprises a VL domain comprising the amino acid sequence of any one of SEQ ID NOs: 310-314, or a functional fragment or variant thereof. In certain embodiments, the functional fragment is shorter than the amino acid sequence of any one of SEQ ID NOs: 310-314 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of any one of SEQ ID NOs: 310-314, and/or is a conservatively-substituted variant of the amino acid sequence of any one of SEQ ID NOs: 310-314.

In some embodiments, a CAR described herein comprises an antigen-binding domain comprising a VH polypeptide of MUC1.

In certain embodiments, the antigen-binding domain comprises a VH domain comprising the amino acid sequence of any one of SEQ ID NOs: 305-309, or a functional fragment or variant thereof. In certain embodiments, the functional fragment is shorter than the amino acid sequence of any one of SEQ ID NOs: 305-309 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of any one of SEQ ID NOs: 305-309, and/or is a conservatively-substituted variant of the amino acid sequence of any one of SEQ ID NOs: 305-309.

In some embodiments, the antigen binding moiety can comprise VH and VL that are directionally linked, for example, from N to C terminus, VH-linker-VL or VL-linker-VH. Any linker as described herein can be used to link the VH and VL domains.

4. MUC16-Specific Antigen-Binding Domain

In some embodiments, the antigen binding moiety of a CAR described herein is specific to MUC16 (MUC16 CAR). The MUC16-specific CAR, when expressed on the cell surface, redirects the specificity of T cells to human MUC16.

In certain embodiments, the antigen-binding domain comprises a VL domain comprising the amino acid sequence of any one of SEQ ID NOs: 329, 331, 333, 335, 337, 339, 341, 662, 664, 666, 668, 670, 688, 690, 692, 694, 696, 698, and 700, or a functional fragment or variant thereof. In certain embodiments, the functional fragment is shorter than the amino acid sequence of any one of the aforementioned sequences by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of any one of SEQ ID NOs: 329, 331, 333, 335, 337, 339, 341, 662, 664, 666, 668, 670, 688, 690, 692, 694, 696, 698, and 700; and/or is a conservatively-substituted variant of the amino acid sequence of any one of SEQ ID NOs: 329, 331, 333, 335, 337, 339, 341, 662, 664, 666, 668, 670, 688, 690, 692, 694, 696, 698, and 700.

In certain embodiments, the antigen-binding domain comprises a VL domain encoded by any one of SEQ ID NOs: 330, 332, 334, 336, 338, 340, 342, 663, 665, 667, 669, 671, 689, 691, 693, 695, 697, 699, and 701, or a functional fragment or variant thereof. In certain embodiments, the functional variant has at least 80%, 85%, 90%, 95%, 96%, 97%, 98%, or 99% sequence identity with any one of SEQ ID NOs: 330, 332, 334, 336, 338, 340, 342, 663, 665, 667, 669, 671, 689, 691, 693, 695, 697, 699, and 701; or hybridizes under stringent hybridization conditions with the complement of any one of SEQ ID NOs: 330, 332, 334, 336, 338, 340, 342, 663, 665, 667, 669, 671, 689, 691, 693, 695, 697, 699, and 701.

In certain embodiments, the antigen-binding domain comprises a VL domain comprising the amino acid sequence of SEQ ID NO: 692, or a functional fragment or variant thereof. In certain embodiments, the functional fragment is shorter than SEQ ID NO: 692 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 692; and/or is a conservatively-substituted variant of the amino acid sequence of SEQ ID NO: 692.

In certain embodiments, the antigen-binding domain comprises a VL domain encoded by SEQ ID NO: 693, or a functional fragment or variant thereof. In certain embodiments, the functional variant has at least 80%, 85%, 90%, 95%, 96%, 97%, 98%, or 99% sequence identity with SEQ ID NO: 693; or hybridizes under stringent hybridization conditions with the complement of SEQ ID NO: 693.

In certain embodiments, the antigen-binding domain comprises a VH domain comprising the amino acid sequence of any one of SEQ ID NOs: 315, 317, 319, 321, 323, 325, 327, 648, 650, 652, 654, 656, 658, 660, 672, 674, 676, 678, 680, 682, 684, and 686, or a functional fragment or variant thereof. In certain embodiments, the functional fragment is shorter than the amino acid sequence of any one of the aforementioned sequences by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with any one of SEQ ID NOs: 315, 317, 319, 321, 323, 325, 327, 648, 650, 652, 654, 656, 658, 660, 672, 674, 676, 678, 680, 682, 684, and 686; and/or is a conservatively-substituted variant of the amino acid sequence of any one of SEQ ID NOs: 315, 317, 319, 321, 323, 325, 327, 648, 650, 652, 654, 656, 658, 660, 672, 674, 676, 678, 680, 682, 684, and 686.

In certain embodiments, the antigen-binding domain comprises a VH domain encoded by any one of SEQ ID NOs: 316, 318, 320, 322, 324, 326, 328, 649, 651, 653, 655, 657, 659, 661, 673, 675, 677, 679, 681, 683, 685, and 687, or a functional fragment or variant thereof. In certain embodiments, the functional variant has at least 80%, 85%, 90%, 95%, 96%, 97%, 98%, or 99% sequence identity with any one of SEQ ID NOs: 316, 318, 320, 322, 324, 326, 328, 649, 651, 653, 655, 657, 659, 661, 673, 675, 677, 679, 681, 683, 685, and 687; or hybridizes under stringent hybridization conditions with the complement of any one of SEQ ID NOs: 316, 318, 320, 322, 324, 326, 328, 649, 651, 653, 655, 657, 659, 661, 673, 675, 677, 679, 681, 683, 685, and 687.

In certain embodiments, the antigen-binding domain comprises a VH domain comprising the amino acid sequence of SEQ ID NO: 676, or a functional fragment or variant thereof. In certain embodiments, the functional fragment is shorter than SEQ ID NO: 676 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 676; and/or is a conservatively-substituted variant of the amino acid sequence of SEQ ID NO: 676.

In certain embodiments, the antigen-binding domain comprises a VH domain encoded by SEQ ID NO: 677, or a functional fragment or variant thereof. In certain embodiments, the functional variant has at least 80%, 85%, 90%, 95%, 96%, 97%, 98%, or 99% sequence identity with SEQ ID NO: 677; or hybridizes under stringent hybridization conditions with the complement of SEQ ID NO: 677.

In some embodiments, the antigen binding moiety can comprise VH and VL that are directionally linked, for example, from N to C terminus, VH-linker-VL or VL-linker-VH. Any linker as described herein can be used to link the VH and VL domains.

In some embodiments, the antigen-binding domain comprises a single chain antibody fragment (scFv) comprising a variable domain light chain (VL) and variable domain heavy chain (VH) of a target antigen specific monoclonal anti-MUC16 antibody joined by a flexible linker, such as a glycine-serine linker or a Whitlow linker. In certain embodiments, the scFv comprises the VH and VL from MUC16-3 and a linker. In certain such embodiments, the scFv comprises the amino acid sequence of SEQ ID NO: 343, or a functional fragment or variant thereof. In certain embodiments, the functional fragment is shorter than the amino acid sequence of SEQ ID NO: 343 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 343; and/or is a conservatively-substituted variant of the amino acid sequence of SEQ ID NO: 343.

In certain embodiments, the antigen-binding domain comprises a scFv encoded by SEQ ID NO: 344, or a functional fragment or variant thereof. In certain embodiments, the functional variant has at least 80%, 85%, 90%, 95%, 96%, 97%, 98%, or 99% sequence identity with SEQ ID NO: 344; or hybridizes under stringent hybridization conditions with the complement of SEQ ID NO: 344.

5. ROR1-Specific Antigen-Binding Domain

In some embodiments, a CAR described herein comprises an antigen-binding domain comprising the $V_L$domain of an anti-ROR1 antibody.

In certain such embodiments, the antigen-binding domain may comprise an amino acid sequence of any one of SEQ ID NOs: 347, 351, 355, 359, 363, 367, 371, 375, 379, 383, 387, 391, 395, 399, 403, 407, 411, 415, 419, 423, 427, 431, 435, 439, 443, 447, 451, 455, 459, and 463, or a functional fragment or variant thereof. In certain embodiments, the functional fragment is shorter than any one of the aforementioned sequences by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with any one of SEQ ID NOs: 347, 351, 355, 359, 363, 367, 371, 375, 379, 383, 387, 391, 395, 399, 403, 407, 411, 415, 419, 423, 427, 431, 435, 439, 443, 447, 451, 455, 459, and 463, and/or is a conservatively-substituted variant of the amino acid sequence of any one of SEQ ID NOs: 347, 351, 355, 359, 363, 367, 371, 375, 379, 383, 387, 391, 395, 399, 403, 407, 411, 415, 419, 423, 427, 431, 435, 439, 443, 447, 451, 455, 459, and 463.

In certain embodiments, the antigen-binding domain comprises a $V_L$ domain encoded by any one of SEQ ID NOs: 348, 352, 356, 360, 364, 368, 372, 376, 380, 384, 388, 392, 396, 400, 404, 408, 412, 416, 420, 424, 428, 432, 436, 440, 444, 448, 452, 456, 460, and 464, or a functional fragment or variant thereof. In certain embodiments, the functional variant has at least 80%, 85%, 90%, 95%, 96%, 97%, 98%, or 99% sequence identity with any one of SEQ ID NOs: 348, 352, 356, 360, 364, 368, 372, 376, 380, 384, 388, 392, 396, 400, 404, 408, 412, 416, 420, 424, 428, 432, 436, 440, 444, 448, 452, 456, 460, and 464; hybridizes under stringent hybridization conditions with the complement of any one of SEQ ID NOs: 348, 352, 356, 360, 364, 368, 372, 376, 380, 384, 388, 392, 396, 400, 404, 408, 412, 416, 420, 424, 428, 432, 436, 440, 444, 448, 452, 456, 460, and 464; or is a codon degenerate variant of any one of SEQ ID NOs: 348, 352, 356, 360, 364, 368, 372, 376, 380, 384, 388, 392, 396, 400, 404, 408, 412, 416, 420, 424, 428, 432, 436, 440, 444, 448, 452, 456, 460, and 464.

In some embodiments, a CAR described herein comprises the VH domain of an anti-ROR1 antibody.

In certain such embodiments, the antigen-binding domain may comprise an amino acid sequence of any one of SEQ ID NOs: 349, 353, 357, 361, 365, 369, 373, 377, 381, 385, 389, 393, 397, 401, 405, 409, 413, 417, 421, 425, 429, 433, 437, 441, 445, 449, 453, 457, and 461, or a functional fragment or variant thereof. In certain embodiments, the functional fragment is shorter than any one of the aforementioned sequences by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with any one of SEQ ID NOs: 349, 353, 357, 361, 365, 369, 373, 377, 381, 385, 389, 393, 397, 401, 405, 409, 413, 417, 421, 425, 429, 433, 437, 441, 445, 449, 453, 457, and 461, and/or is a conservatively-substituted variant of the amino acid sequence of any one of SEQ ID NOs: 349, 353, 357, 361, 365, 369, 373, 377, 381, 385, 389, 393, 397, 401, 405, 409, 413, 417, 421, 425, 429, 433, 437, 441, 445, 449, 453, 457, and 461.

In certain embodiments, the antigen-binding domain comprises a VH domain encoded by any one of SEQ ID NOs: 350, 354, 358, 362, 366, 370, 374, 378, 382, 386, 390, 394, 398, 402, 406, 410, 414, 418, 422, 426, 430, 434, 438, 442, 446, 450, 454, 458, and 462, or a functional fragment or variant thereof. In certain embodiments, the functional variant has at least 80%, 85%, 90%, 95%, 96%, 97%, 98%, or 99% sequence identity with any one of SEQ ID NOs: 350, 354, 358, 362, 366, 370, 374, 378, 382, 386, 390, 394, 398, 402, 406, 410, 414, 418, 422, 426, 430, 434, 438, 442, 446, 450, 454, 458, and 462; hybridizes under stringent hybridization conditions with the complement of any one of SEQ ID NOs: 350, 354, 358, 362, 366, 370, 374, 378, 382, 386, 390, 394, 398, 402, 406, 410, 414, 418, 422, 426, 430, 434, 438, 442, 446, 450, 454, 458, and 462; or is a codon degenerate variant of any one of SEQ ID NOs: 350, 354, 358, 362, 366, 370, 374, 378, 382, 386, 390, 394, 398, 402, 406, 410, 414, 418, 422, 426, 430, 434, 438, 442, 446, 450, 454, 458, and 462.

In certain embodiments, the antigen-binding domain comprises at least one CDR selected from those comprising the amino acid sequence of any one of the CDRs that bind ROR1 or a functional fragment or variant thereof.

In certain embodiments, the antigen-binding domain comprises the amino acid sequence of any one of SEQ ID NOs: 715-725, or a functional fragment or variant thereof. In certain embodiments, the functional fragment is shorter than the sequence of any one of the aforementioned sequences by at most 5, 4, 3, 2, or 1 amino acid residues at the N- and/or C-terminus. In certain embodiments, the functional variant has at least 80%, 85%, 90%, 95%, 96%, 97%, 98%, or 99% sequence identity with any one of SEQ ID NOs: 715-725, and/or is a conservatively-substituted variant of any one of SEQ ID NOs: 715-725.

In certain embodiments, the antigen-binding domain comprises a $V_H$ domain comprising the amino acid sequences of SEQ ID NO: 715, SEQ ID NO: 716, and SEQ ID NO: 717.

In certain embodiments, the antigen-binding domain comprises a $V_H$ domain comprising the amino acid sequences of SEQ ID NO: 718, SEQ ID NO: 719, and SEQ ID NO: 720.

In certain embodiments, the antigen-binding domain comprises a $V_L$ domain comprising the amino acid sequences of SEQ ID NO: 721, SEQ ID NO: 722, and SEQ ID NO: 723.

In certain embodiments, the antigen-binding domain comprises a $V_L$ domain comprising the amino acid sequences of SEQ ID NO: 724, SEQ ID NO: 725, and SEQ ID NO: 723.

In certain embodiments, the antigen-binding domain comprises both the aforementioned $V_H$ and VL domains.

In certain embodiments, the antigen-binding domain comprises a variable heavy chain domain comprising the amino acid sequence of SEQ ID NO: 349 or a functional fragment or variant thereof. In certain embodiments, the functional fragment is shorter than SEQ ID NO: 349 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 349, and/or is a conservatively-substituted variant of the amino acid sequence of SEQ ID NO: 349.

In certain embodiments, the antigen-binding domain comprises a $V_H$ domain encoded by SEQ ID NO: 350, or a functional fragment or variant thereof. In certain embodiments, the functional variant has at least 80%, 85%, 90%, 95%, 96%, 97%, 98%, or 99% sequence identity with SEQ ID NO: 350; hybridizes under stringent hybridization conditions with the complement SEQ ID NO: 350; or is a codon degenerate variant of SEQ ID NO: 350.

In certain embodiments, the antigen-binding domain comprises a variable light chain domain comprising the amino acid sequence of SEQ ID NO: 387 or a functional fragment or variant thereof. In certain embodiments, the functional fragment is shorter than SEQ ID NO: 387 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 387, and/or is a conservatively-substituted variant of the amino acid sequence of SEQ ID NO: 387.

In certain embodiments, the antigen-binding domain comprises a $V_L$ domain encoded by SEQ ID NO: 388, or a functional fragment or variant thereof. In certain embodiments, the functional variant has at least 80%, 85%, 90%, 95%, 96%, 97%, 98%, or 99% sequence identity with SEQ ID NO: 388; hybridizes under stringent hybridization conditions with the complement SEQ ID NO: 388; or is a codon degenerate variant of SEQ ID NO: 388.

In certain embodiments, the antigen-binding domain comprises a variable heavy chain domain comprising the amino acid sequence of SEQ ID NO: 349 or a functional fragment or variant thereof, wherein the variable heavy chain domain comprises, in N-terminal to C-terminal order, the sequences of SEQ ID NO: 715, SEQ ID NO: 716, and SEQ ID NO: 717. In certain embodiments, the functional fragment is shorter than SEQ ID NO: 349 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 349, and/or is a conservatively-substituted variant of the amino acid sequence of SEQ ID NO: 349.

In certain embodiments, the antigen-binding domain comprises a variable heavy chain domain comprising the amino acid sequence of SEQ ID NO: 349 or a functional fragment or variant thereof, wherein the variable heavy chain domain comprises, in N-terminal to C-terminal order, the sequences of SEQ ID NO: 718, SEQ ID NO: 719, and SEQ ID NO: 720. In certain embodiments, the functional fragment is shorter than SEQ ID NO: 349 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 349, and/or is a conservatively-substituted variant of the amino acid sequence of SEQ ID NO: 349.

In certain embodiments, the antigen-binding domain comprises a variable light chain domain comprising the amino acid sequence of SEQ ID NO: 387 or a functional fragment or variant thereof, wherein the variable heavy chain domain comprises, in N-terminal to C-terminal order, the sequences of SEQ ID NO: 721, SEQ ID NO: 722, and SEQ ID NO: 723. In certain embodiments, the functional fragment is shorter than SEQ ID NO: 387 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 387, and/or is a conservatively-substituted variant of the amino acid sequence of SEQ ID NO: 387.

In certain embodiments, the antigen-binding domain comprises a variable light chain domain comprising the amino acid sequence of SEQ ID NO: 387 or a functional fragment or variant thereof, wherein the variable heavy chain domain comprises, in N-terminal to C-terminal order, the sequences of SEQ ID NO: 724, SEQ ID NO: 725, and SEQ ID NO: 723. In certain embodiments, the functional fragment is shorter than SEQ ID NO: 387 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 387, and/or is a conservatively-substituted variant of the amino acid sequence of SEQ ID NO: 387.

In certain embodiments, the antigen-binding domain comprises a variable heavy chain domain comprising the amino acid sequence of SEQ ID NO: 726 or a functional fragment or variant thereof. In certain embodiments, the functional fragment is shorter than SEQ ID NO: 726 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 726, and/or is a conservatively-substituted variant of the amino acid sequence of SEQ ID NO: 726.

In certain embodiments, the antigen-binding domain comprises a variable light chain domain comprising the amino acid sequence of SEQ ID NO: 727 or a functional fragment or variant thereof. In certain embodiments, the functional fragment is shorter than SEQ ID NO: 727 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 727, and/or is a conservatively-substituted variant of the amino acid sequence of SEQ ID NO: 727.

In certain embodiments, the antigen-binding domain comprises a variable heavy chain domain comprising the amino acid sequence of SEQ ID NO: 728 or a functional fragment or variant thereof. In certain embodiments, the functional fragment is shorter than SEQ ID NO: 728 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 728, and/or is a conservatively-substituted variant of the amino acid sequence of SEQ ID NO: 728.

In certain embodiments, the antigen-binding domain comprises a variable light chain domain comprising the amino acid sequence of SEQ ID NO: 729 or a functional fragment or variant thereof. In certain embodiments, the functional fragment is shorter than SEQ ID NO: 729 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 729, and/or is a conservatively-substituted variant of the amino acid sequence of SEQ ID NO: 729.

In certain embodiments, the antigen-binding domain comprises a linker that links the $V_H$ and VL domains. In certain such embodiments, the linker comprises: (a) the amino acid sequence of SEQ ID NO: 424 ($(G_4S)_3$) or a conservatively-substituted variant thereof; or (b) an amino acid sequence having at least 80%, 85%, 90%, 95%, 96%, 97%, 98%, or 99% sequence identity with SEQ ID NO: 424. In certain such embodiments, the linker is encoded by SEQ ID NO: 425, hybridizes under stringent conditions to the complement of SEQ ID NO: 425, or is a codon degenerate version of SEQ ID NO: 425. Any linker as described herein can be used to link the VH and VL domains.

In certain embodiments, the antigen-binding domain comprises an scFv. In certain such embodiments, the domain comprises an amino acid sequence of SEQ ID NO: 465, or a functional fragment or variant thereof. In certain embodiments, the functional fragment is shorter than SEQ ID NO: 465 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 465, and/or is a conservatively-substituted variant of the amino acid sequence of SEQ ID NO: 465.

In certain embodiments, the antigen-binding domain comprises an scFv encoded by SEQ ID NO: 466, or a functional fragment or variant thereof. In certain embodiments, the functional variant has at least 80%, 85%, 90%, 95%, 96%, 97%, 98%, or 99% sequence identity with SEQ ID NO: 466; hybridizes under stringent hybridization conditions with the complement SEQ ID NO: 466; or is a codon degenerate variant of SEQ ID NO: 466.

6. EGFRvIII-Specific Antigen-Binding Domain

In another embodiment, a CAR described herein is a EGFRvIII-specific CAR. "EGFRvIII", "EGFR variant III", "EGFR type III mutant", "EGFR.D2-7" or "de2-7EGFR" is a mutated form of epidermal growth factor receptor (EGFR; ErbB-1; HER1), a transmembrane protein that is a receptor for members of the epidermal growth factor (EGF) family of extracellular protein ligands in human and non-human subjects. EGFRvIII is characterized by a deletion of exons 2-7 of the wild type EGFR gene, which results in an in-frame deletion of 267 amino acids in the extracellular domain of the full length wild type EGFR protein. EGFRvIII also contains a novel glycine residue inserted at the fusion junction compared to wild type EGFR. The truncated receptor EGFRvIII is unable to bind any known EGFR ligand; however, it shows constitutive tyrosine kinase activity. This constitutive activation is important to its pro-oncogenic effect. A kinase-deficient EGFRvIII is unable to confer a similar oncogenic advantage. EGFRvIII is highly expressed in glioblastoma (GBM) and can be detected in some other solid tumor types but not in normal tissues.

In some embodiments, the antigen binding moiety of a CAR described herein is specific to EGFRvIII (EGFRvIII CAR). The EGFRvIII-specific CAR, when expressed on the cell surface, redirects the specificity of T cells to human EGFRvIII. In embodiments, the antigen binding domain comprises a single chain antibody fragment (scFv) comprising a variable domain light chain (VL) and variable domain heavy chain (VH) of a target antigen specific monoclonal anti-EGFRvIII antibody joined by a flexible linker, such as a glycine-serine linker or a Whitlow linker. In some embodiments, the antigen binding moiety may comprise VH and VL that are directionally linked, for example, from N to C terminus, VH-linker-VL or VL-linker-VH.

B. Spacer

In some embodiments, a chimeric antigen receptor of the present disclosure further includes a spacer that is used to link the antigen-binding domain to the transmembrane domain. In some embodiments, the spacer is flexible enough to allow the antigen-binding domain to orient in different directions to facilitate antigen recognition.

In certain embodiments, a chimeric antigen receptor comprising a spacer has improved functional activity compared to an otherwise identical antigen-binding polypeptide lacking the spacer. In certain embodiments, a chimeric antigen receptor comprising a spacer has increased expression on a cell surface compared to an otherwise identical polypeptide lacking the spacer. In an embodiment, a chimeric antigen receptor comprising a spacer is a polypeptide that, were it not for the spacer, would not express on the cell membrane surface and/or would not be able to bind its target due to lack of proximity or steric hindrance.

In certain embodiments, the spacer comprises a stalk region, for example a hinge region from an antibody. In some instances, the stalk region comprises the hinge region from an IgG, for example IgG1. In alternative instances, the stalk region comprises the $CH_2CH_3$ region of immunoglobulin and, optionally, portions of CD3. In some cases, the stalk region comprises a CD8α hinge region (SEQ ID NO: 426), an IgG4-Fc 12 amino acid hinge region (SEQ ID NO: 631), or an IgG4 hinge region as described in WO2016/073755. The stalk region can be an extracellular portion of the CAR that links the antigen-binding domain to the cell surface and/or transmembrane region.

In some embodiments, the stalk region can be from about 20 to about 300 amino acids in length. In some cases, the stalk region can be about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or greater amino acids in length. In other cases, the stalk region can be about: 100, 125, 150, 175, 200, 225, 250, 275 or 300 amino acids in length. In some cases a stalk region can be less than 20 amino acids in length.

In some embodiments, the stalk region comprises a CD8α hinge domain, a CD28 hinge domain or a CTLA-4 hinge domain, or a functional fragment or variant thereof.

In certain embodiments, the stalk region comprises a CD8α hinge region, or a functional fragment or variant thereof. In certain such embodiments, the spacer comprises the amino acid sequence of SEQ ID NO: 426 or a functional fragment or variant thereof. In certain embodiments, the functional fragment is shorter than the amino acid sequence of SEQ ID NO: 467 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 467, and/or is a conservatively-substituted variant of the amino acid sequence of SEQ ID NO: 467.

In certain embodiments, the CD8α hinge region, or functional fragment or variant thereof, is encoded by SEQ ID NO: 468, or a functional fragment or variant thereof. In certain embodiments, the functional variant has at least 80%, 85%, 90%, 95%, 96%, 97%, 98%, or 99% sequence identity with SEQ ID NO: 468, hybridizes under stringent hybridization conditions with the complement of SEQ ID NO: 468, or is a codon degenerate variant of SEQ ID NO: 468.

In some embodiments, the stalk region can be capable of dimerizing with a homologous stalk region of a second CAR.

In certain embodiments, in addition to a stalk region, the spacer may comprise one or more stalk extension region(s). In certain embodiments, the stalk extension region is a polypeptide that is homologous to the stalk region. For example, it may comprise at least one amino acid residue substitution as compared with the stalk region. In some embodiments, the stalk region comprises a sequence with at least about 70%, 75%, 80%, 85%, 90%, 95%, 96%, 97%, 98%, or 99% identity to the stalk region to which it is attached, for example a CD8α hinge domain, a CD28 hinge domain, or a CTLA-4 hinge domain.

In some embodiments, the spacer comprises 1, 2, 3, 4, 5, 6, 7, 8, 9, 10, 11, 12, 13, 14, 15, 16, 17, 18, 19, or 20 stalk extension regions.

In certain embodiments, the stalk region can be linked to the stalk extension region by way of a linker.

In certain embodiments, the stalk extension region can comprise about 1, 2, 3, 4, 5, 6, 7, 8, 9, or 10 times the length of the stalk region as measured by number of amino acids.

In some embodiments, the stalk region comprises at least one dimerization site. In certain embodiments, the stalk region may comprise one or more dimerization sites to form homo- or hetero-dimerized chimeric polypeptides. In other embodiments, the stalk region or one or more stalk extension regions may contain mutations that eliminate dimerization sites altogether.

In certain embodiments, the stalk extension region has at least one fewer dimerization site as compared to a stalk region. For example, if a stalk region comprises two dimerization sites, a stalk extension region can comprise one or zero dimerization sites. As another example, if a stalk region comprises one dimerization site, a stalk extension region can comprise zero dimerization sites. In some examples, a stalk extension region lacks a dimerization site. In some cases, one or more dimerization site(s) can be membrane proximal. In other cases, one or more dimerization site(s) can be membrane distal.

In certain embodiments, the dimerization site is a cysteine residue capable of forming a disulfide bond. In certain embodiments, the stalk extension region is capable of forming fewer disulfide bond(s) as compared to a stalk region. For example, if a stalk region is capable of forming two disulfide bonds, a stalk extension region may be capable of forming one or no disulfide bonds. As another example, if a stalk region is capable of forming one disulfide bond, a stalk extension region may be capable of forming no such bonds.

Each of the stalk extension regions can be about 10, 15, 20, 25, 30, 35, 40, 45, 50, 55, 60, 65, or greater amino acids in length.

In certain embodiments, the stalk extension region is homologous to the CD8α hinge region. In certain such embodiments, the stalk extension region comprises the amino acid sequence of SEQ ID NO: 469 or a functional fragment or variant thereof. In certain embodiments, the functional fragment is shorter than the amino acid sequence of SEQ ID NO: 469 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 469, and/or is a conservatively-substituted variant of the amino acid sequence of SEQ ID NO: 469.

In certain embodiments, the stalk extension region is encoded by any one of SEQ ID NOs: 470-472, or a functional fragment or variant thereof. In certain embodiments, the functional variant has at least 80%, 85%, 90%, 95%, 96%, 97%, 98%, or 99% sequence identity with any one of SEQ ID NOs: 470-472, hybridizes under stringent hybridization conditions with the complement of any one of SEQ ID NOs: 470-472, or is a codon degenerate variant of any one of SEQ ID NOs: 470-472.

In certain embodiments, the spacer comprises a stalk region and 1 to 3 stalk extension regions. In certain such embodiments, the spacer comprises a stalk region and 2 stalk extension regions, for example a CD8α hinge region and 2 stalk extension regions wherein each stalk extension region is homologous to the CD8α hinge region.

In some embodiments, each of the stalk region and stalk extension region(s) can be derived from at least one of a CD8α hinge domain, a CD28 hinge domain, a CTLA-4 hinge domain, a LNGFR extracellular domain, IgG1 hinge, IgG4 hinge and CH2-CH3 domain. The stalk and stalk extension region(s) can be separately derived from any combination of CD8α hinge domain, CD28 hinge domain, CTLA-4 hinge domain, LNGFR extracellular domain, IgG1 hinge, IgG4 hinge or CH2-CH3 domain. As an example, the stalk region can be derived from CD8α hinge domain and at least one stalk extension region can be derived from CD28 hinge domain thus creating a hybrid spacer. As another example, the stalk region can be derived from an IgG1 hinge or IgG4 hinge and at least one stalk extension region can be derived from a CH2-CH3 domain of IgG.

In certain such embodiments, the spacer comprises the amino acid sequence of SEQ ID NO: 473 or a functional fragment or variant thereof. In certain embodiments, the functional fragment is shorter than the amino acid sequence of SEQ ID NO: 473 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 473, and/or is a conservatively-substituted variant of the amino acid sequence of SEQ ID NO: 473.

In certain embodiments, the spacer is encoded by SEQ ID NO: 474, or a functional fragment or variant thereof. In certain embodiments, the functional variant has at least 80%, 85%, 90%, 95%, 96%, 97%, 98%, or 99% sequence identity with SEQ ID NO: 474, hybridizes under stringent hybridization conditions with the complement of SEQ ID NO: 474, or is a codon degenerate variant of SEQ ID NO: 474.

C. Transmembrane Domain

The transmembrane domain can be derived from either a natural or a synthetic source. Where the source is natural, the domain can, for example, be derived from any membrane-bound or transmembrane protein. Suitable transmembrane domains include transmembrane domains from a TCR-alpha chain, a TCR-beta chain, a TCR-γ1 chain, a TCR-δ chain, a TCR-zeta chain, CD28, CD3 epsilon, CD3ζ CD45, CD4, CD5, CD8α, CD9, CD16, CD22, CD33, CD37, CD64, CD80, CD86, CD134, CD137, ICOS, GITR, CD152 (CTLA-4), or CD154, or a functional fragment or variant thereof. Alternatively, the transmembrane domain can be synthetic, and can comprise hydrophobic residues such as leucine and valine. In some embodiments, a triplet of phenylalanine, tryptophan and valine is found at one or both termini of a synthetic transmembrane domain. In some embodiments, the transmembrane domain comprises a CD8α transmembrane domain, a CD152 (CTLA-4), TCRγ1, TCRδ or a CD3ζ transmembrane domain.

Optionally, a short oligonucleotide or polypeptide linker, in some embodiments between 2 and 10 amino acids in length, may link the transmembrane domain with the intracellular signaling domain of a CAR. In some embodiments, the linker is a glycine-serine linker.

In some embodiments, the transmembrane domain comprises a CD8α transmembrane domain or a CD3ζ transmembrane domain, or a functional fragments or variants thereof.

In certain embodiments, the transmembrane domain comprises a CD8α transmembrane domain, or a functional fragment or variant thereof. In certain such embodiments, the transmembrane domain comprises the amino acid sequence of SEQ ID NO: 475 or a functional fragment or variant thereof. In certain embodiments, the functional fragment is shorter than the amino acid sequence of SEQ ID NO: 475 by at most 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 475, and/or is a conservatively-substituted variant of the amino acid sequence of SEQ ID NO: 475.

In certain embodiments, the CD8α transmembrane domain, or functional fragment or variant thereof, is encoded by SEQ ID NO: 476 or a functional fragment or variant thereof. In certain embodiments, the functional variant has at least 80%, 85%, 90%, 95%, 96%, 97%, 98%, or 99% sequence identity with SEQ ID NO: 476, hybridizes under stringent hybridization conditions with the complement of SEQ ID NO: 476, or is a codon degenerate variant of SEQ ID NO: 476.

In certain embodiments, the transmembrane domain comprises a CD28 transmembrane domain, or a functional fragment or variant thereof. In certain such embodiments, the transmembrane domain comprises the amino acid sequence of SEQ ID NO: 477 or a functional fragment or variant thereof. In certain embodiments, the functional fragment is shorter than the amino acid sequence of SEQ ID NO: 477 by at most 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 477, and/or is a conservatively-substituted variant of the amino acid sequence of SEQ ID NO: 477.

In certain embodiments, the CD28 transmembrane domain, or functional fragment or variant thereof, is encoded by SEQ ID NO: 478 or a functional fragment or variant thereof. In certain embodiments, the functional variant has at least 80%, 85%, 90%, 95%, 96%, 97%, 98%, or 99% sequence identity with SEQ ID NO: 478, hybridizes under stringent hybridization conditions with the complement of SEQ ID NO: 478, or is a codon degenerate variant of SEQ ID NO: 438.

D. Intracellular Signaling Domain

The intracellular signaling domain of the CAR may be responsible for activation of at least one of the normal effector functions of the immune cell in which the CAR has been placed. The term "effector function" refers to a specialized function of a cell. Effector function of a T cell, for example, can be cytolytic activity or helper activity including the secretion of cytokines. While usually the entire intracellular signaling domain can be employed, in many cases it is not necessary to use the entire chain. To the extent that a truncated portion of the intracellular signaling domain is used, such truncated portion can be used in place of the intact chain as long as it transduces the effector function signal. In some embodiments, the intracellular domain further comprises a signaling domain for T-cell activation.

In some embodiments, the intracellular cell signaling domain interacts with a T cell, a Natural Killer (NK) cell, a cytotoxic T lymphocyte (CTL), or a regulatory T cell.

The intracellular domain can comprise an amino acid sequence derived from FCER1G, CD19, CD40, KIR3DL1, KIR3DL2, KIR2DL3, KIR2DL4, KIR2DL5, KIR3DL1, KIR3DL2, KIR3DL3, SIRPA, FCRL1, FCRL2, FCRL3, FCRL4, FCRL5, FCRL6, FCGR1A, FCGR2A, FCGR2B, FCGR3A, TLR1, TLR2, TLR3, TLR4, TLR5, TLR6, TLR7, TLR8, TLR9, TLR10, PILRB, NCR1, NCR2, NCR3, NKG2A, NKG2C, NKG2D, DAP12, FCER1G, DAP10, CD84, CD19, KIR3DL1, KIR3DL2, KIR2DL2, KIR2DL3, KIR2DL4, KIR2DL5, KIR3DL2, KIR3DL3, SIRPA, FCRL1, FCRL2, FCRL3, FCRL4, FCRL5, FCRL6, CD4, CD8A, CD8B, LAT, FCGR1A, FCGR2A, FCGR2B, FCGR3A, TLR1, TLR2, TLR3, TLR4, TLR5, TLR6, TLR7, TLR8, TLR9, TLR10, NCR1, NCR2, NCR3, LY9, NKG2C, TCR zeta, FcR gamma, FcR beta, CD3 gamma, CD3 delta, CD3 epsilon, CD3ζ, CD5, CD22, CD79a, CD79b or CD66d, or a functional fragment or variant thereof. In some cases, the signaling domain for T-cell activation comprises a domain derived from CD3ζ. or a functional fragment or variant thereof.

In certain embodiments, the intracellular signaling domain comprises a CD3ζ domain, or a functional fragment or variant thereof. In certain such embodiments, the intracellular signaling domain comprises the amino acid sequence of SEQ ID NO: 479 or a functional fragment or variant thereof. In certain embodiments, the functional fragment is shorter than SEQ ID NO: 479 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 479, and/or is a conservatively-substituted variant of the amino acid sequence of SEQ ID NO: 479.

In certain embodiments, the CD3 domain, or functional fragment or variant thereof, is encoded by a nucleic acid comprising SEQ ID NO: 480 or a functional fragment or variant thereof. In certain embodiments, the functional variant has at least 80%, 85%, 90%, 95%, 96%, 97%, 98%, or 99% sequence identity with SEQ ID NO: 480, hybridizes under stringent hybridization conditions with the complement of SEQ ID NO: 480, or is a codon degenerate variant of SEQ ID NO: 480.

The intracellular signaling domain can further comprise one or more co-stimulatory domains. Exemplary co-stimulatory domains include, but are not limited to, CD8, CD27, CD28, 4-1BB (CD137), ICOS, DAP10, DAP12, OX40 (CD134), and CD3-zeta co-stimulatory domains and functional fragments or variants thereof. In some instances, a CAR described herein comprises one or more, or two or more of co-stimulatory domains selected from CD8, CD27, CD28, 4-1BB (CD137), ICOS, DAP10, DAP12, and OX40 (CD134) co-stimulatory domains and functional fragments or variants thereof. In some instances, a CAR described herein comprises one or more, or two or more of co-stimulatory domains selected from CD27, CD28, 4-1BB (CD137), ICOS, and OX40 (CD134) co-stimulatory domains and functional fragments or variants thereof. In some instances, a CAR described herein comprises one or more, or two or more of co-stimulatory domains selected from CD8, CD28, 4-1BB (CD137), DAP10, and DAP12 co-stimulatory domains and functional fragments or variants thereof. In some instances, a CAR described herein comprises one or more, or two or more co-stimulatory domains selected from CD28 and 4-1BB (CD137) co-stimulatory domains and functional fragments or variants thereof. In some instances, a CAR described herein comprises CD28 and 4-1BB (CD137) co-stimulatory domains or their respective functional fragments or variants. In some instances, a CAR described herein comprises CD28 and OX40 (CD134) co-stimulatory domains or their respective functional fragments and variants. In some instances, a CAR described herein comprises CD8 and CD28 co-stimulatory domains or their respective functional fragments and variants. In some instances, a CAR described herein comprises a CD28 co-stimulatory domains or a functional fragment or variant thereof. In some instances, a CAR described herein comprises a 4-1BB (CD137) co-stimulatory domain or a functional fragment or variant thereof. In some instances, a CAR described herein comprises an OX40 (CD134) co-stimulatory domain or a functional fragment or variant thereof. In some instances, a CAR described herein comprises a CD8 co-stimulatory domain or a functional fragment or variant thereof. In some instances, the CAR described herein comprises a DAP10 co-stimulatory domain or a functional fragment or variant thereof. In some instances, the CAR described herein comprises a DAP12 co-stimulatory domain or a functional fragment or variant thereof.

In certain embodiments, the intracellular signaling domain comprises a CD28 co-stimulatory domain, or a functional fragment or variant thereof. In certain such embodiments, the intracellular signaling domain comprises the amino acid sequence of SEQ ID NO: 481 or a functional fragment or variant thereof. In certain embodiments, the functional fragment is shorter than the amino acid sequence of SEQ ID NO: 481 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 481, and/or is a conservatively-substituted variant of the amino acid sequence of SEQ ID NO: 481.

In certain embodiments, the CD28 co-stimulatory domain, or functional fragment or variant thereof, is encoded by a nucleic acid comprising SEQ ID NO: 482 or a functional fragment or variant thereof. In certain embodiments, the functional variant has at least 80%, 85%, 90%, 95%, 96%, 97%, 98%, or 99% sequence identity with SEQ ID NO: 482, hybridizes under stringent hybridization conditions with the complement of SEQ ID NO: 482, or is a codon degenerate variant of SEQ ID NO: 442.

In certain embodiments, the intracellular signaling domain comprises a 4-1BB co-stimulatory domain, or a functional fragment or variant thereof. In certain such embodiments, the intracellular signaling domain comprises the amino acid sequence of SEQ ID NO: 483 or a functional fragment or variant thereof. In certain embodiments, the functional fragment is shorter than the amino acid sequence of SEQ ID NO: 483 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 483, and/or is a conservatively-substituted variant of SEQ ID NO: 483.

In certain embodiments, the 4-1BB co-stimulatory domain, or functional fragment or variant thereof, is encoded by SEQ ID NO: 484 or a functional fragment or variant thereof. In certain embodiments, the functional variant has at least 80%, 85%, 90%, 95%, 96%, 97%, 98%, or 99% sequence identity with SEQ ID NO: 484, hybridizes under stringent hybridization conditions with the complement of SEQ ID NO: 484, or is a codon degenerate variant of SEQ ID NO: 484.

In certain embodiments, the intracellular signaling domain comprises a DAP10 co-stimulatory domain, or a functional fragment or variant thereof. In certain embodiments, the intracellular signaling domain comprises the amino acid sequence of SEQ ID NO: 485 or a functional fragment or variant thereof. In certain embodiments, the functional fragment is shorter than the amino acid sequence of SEQ ID NO: 485 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 485, and/or is a conservatively-substituted variant of SEQ ID NO: 485.

In certain embodiments, the DAP10 co-stimulatory domain, or functional fragment or variant thereof, is encoded by the sequence of SEQ ID NO: 486, or a functional fragment or variant thereof. In certain embodiments, the functional variant has at least 80%, 85%, 90%, 95%, 96%, 97%, 98%, or 99% sequence identity with SEQ ID NO: 486, hybridizes under stringent hybridization conditions with the complement of SEQ ID NO: 486, or is a codon degenerate variant of SEQ ID NO: 486.

In certain embodiments, the intracellular signaling domain comprises a DAP12 co-stimulatory domain, or a functional fragment or variant thereof. In certain embodiments, the intracellular signaling domain comprises the amino acid sequence of SEQ ID NO: 487 or a functional fragment or variant thereof. In certain embodiments, the functional fragment is shorter than the amino acid sequence of SEQ ID NO: 487 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 487, and/or is a conservatively-substituted variant of SEQ ID NO: 487.

In certain embodiments, the DAP12 co-stimulatory domain, or functional fragment or variant thereof, is encoded by the sequence of SEQ ID NO: 488, or functional fragment or variant thereof. In certain embodiments, the functional variant has at least 80%, 85%, 90%, 95%, 96%, 97%, 98%, or 99% sequence identity with SEQ ID NO: 488, hybridizes under stringent hybridization conditions with the complement of SEQ ID NO: 488, or is a codon degenerate variant of SEQ ID NO: 488.

In certain embodiments, the intracellular signaling domain comprises both a CD28 co-signaling domain and a 4-1BB co-signaling domain, or respective functional fragments or variants thereof, as described above.

E. Signal Peptide

In an embodiment, a signal peptide directs the nascent CAR protein into the endoplasmic reticulum. This is, for example, if the receptor is to be glycosylated and anchored in the cell membrane. Any eukaryotic signal peptide sequence is envisaged to be functional. Generally, the signal peptide natively attached to the protein or, in the case of a fusion protein, the component closest to the N-terminus is used (e.g., in a scFv with the $V_L$ component at closest to the N-terminus, the native signal of the light chain is used). In some embodiments, the signal peptide is native for GM-CSFRa (SEQ ID NO: 489) or IgK (SEQ ID NO: 491), IgE (SEQ ID NO: 493) or a functional fragment or variant thereof. Other signal peptides that can be used include those native to CD8α (SEQ ID NO: 495) and CD28. In some embodiments, the signal peptide is that native to Mouse Ig $V_H$ region 3 (SEQ ID NO: 497), β2M signal peptide (SEQ ID NO: 499), Azurocidin (SEQ ID NO: 501), Human Serum Albumin signal peptide (SEQ ID NO: 503), A2M receptor associated protein signal peptide (SEQ ID NO: 505), IGHV3-23 (SEQ ID NO: 507), IGKV1-D33 (HuL1) (SEQ ID NO: 509), IGKV1-D33 (L14F) (HuH7) (SEQ ID NO: 511), or a functional fragment or variant thereof.

In certain embodiments, the CAR is linked to a GM-CSFRa signal peptide, or a functional fragment or variant thereof. In certain such embodiments, the GM-CSFRa signal peptide has the amino acid sequence of SEQ ID NO: 489 or a functional fragment or variant thereof. In certain embodiments, the functional fragment is shorter than SEQ ID NO: 489 by at most 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 489, and/or is a conservatively-substituted variant of SEQ ID NO: 489.

In certain embodiments, the GM-CSFRa signal peptide, or functional fragment or variant thereof, is encoded by a nucleic acid comprising SEQ ID NO: 490 or a functional fragment or variant thereof. In certain embodiments, the functional variant has at least 80%, 85%, 90%, 95%, 96%, 97%, 98%, or 99% sequence identity with SEQ ID NO: 490, hybridizes under stringent hybridization conditions with the complement of SEQ ID NO: 490, or is a codon degenerate variant of SEQ ID NO: 490.

In certain embodiments, the CAR is linked to an IgK signal peptide, or a functional fragment or variant thereof. In certain such embodiments, the IgK signal peptide has the amino acid sequence of SEQ ID NO: 491 or a functional fragment or variant thereof. In certain embodiments, the functional fragment is shorter than SEQ ID NO: 491 by at most 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 491, and/or is a conservatively-substituted variant of SEQ ID NO: 491.

In certain embodiments, the Igκ signal peptide, or functional fragment or variant thereof, is encoded by a nucleic acid comprising SEQ ID NO: 492 or a functional fragment or variant thereof. In certain embodiments, the functional variant has at least 80%, 85%, 90%, 95%, 96%, 97%, 98%, or 99% sequence identity with SEQ ID NO: 492, hybridizes under stringent hybridization conditions with the complement of SEQ ID NO: 492, or is a codon degenerate variant of SEQ ID NO: 492.

In certain embodiments, the CAR is linked to an IgE signal peptide native to IgE ("IgE signal peptide"), or a functional fragment or variant thereof. In certain such embodiments, the IgE signal peptide the amino acid sequence of SEQ ID NO: 493 or a functional fragment or variant thereof. In certain embodiments, the functional fragment is shorter than SEQ ID NO: 493 by at most 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 493, and/or is a conservatively-substituted variant of SEQ ID NO: 493.

In certain embodiments, the IgE signal peptide, or functional fragment or variant thereof, is encoded by a nucleic acid comprising SEQ ID NO: 494 or a functional fragment or variant thereof. In certain embodiments, the functional variant has at least 80%, 85%, 90%, 95%, 96%, 97%, 98%, or 99% sequence identity with SEQ ID NO: 494, hybridizes under stringent hybridization conditions with the complement of SEQ ID NO: 494, or is a codon degenerate variant of SEQ ID NO: 494.

In certain embodiments, the CAR is linked to an CD8α signal peptide native to CD8α, or a functional fragment or variant thereof. In certain such embodiments, the CD8α signal peptide comprises the amino acid sequence of SEQ ID NO: 495 or a functional fragment or variant thereof. In certain embodiments, the functional fragment is shorter than SEQ ID NO: 495 by at most 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 495, and/or is a conservatively-substituted variant of SEQ ID NO: 495.

In certain embodiments, the CD8α signal peptide, or functional fragment or variant thereof, is encoded by a nucleic acid comprising SEQ ID NO: 496 or a functional fragment or variant thereof. In certain embodiments, the functional variant has at least 80%, 85%, 90%, 95%, 96%, 97%, 98%, or 99% sequence identity with SEQ ID NO: 496, hybridizes under stringent hybridization conditions with the complement of SEQ ID NO: 496 or is a codon degenerate variant of SEQ ID NO: 496.

In certain embodiments, the CAR is linked to a Mouse Ig VH region 3 signal peptide, or a functional fragment or variant thereof. In certain such embodiments, the Mouse Ig VH region 3 signal peptide has the amino acid sequence of SEQ ID NO: 497 or a functional fragment or variant thereof. In certain embodiments, the functional fragment is shorter than SEQ ID NO: 497 by at most 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 497, and/or is a conservatively-substituted variant of SEQ ID NO: 497.

In certain embodiments, the Mouse Ig VH region 3 signal peptide, or functional fragment or variant thereof, is encoded by a nucleic acid comprising SEQ ID NO: 498 or a functional fragment or variant thereof. In certain embodiments, the functional variant has at least 80%, 85%, 90%, 95%, 96%, 97%, 98%, or 99% sequence identity with SEQ ID NO: 498, hybridizes under stringent hybridization conditions with the complement of SEQ ID NO: 498, or is a codon degenerate variant of SEQ ID NO: 498.

In certain embodiments, the CAR is linked to a β2M signal peptide, or a functional fragment or variant thereof. In certain such embodiments, the β2M signal peptide has the amino acid sequence of SEQ ID NO: 499 or a functional fragment or variant thereof. In certain embodiments, the functional fragment is shorter than SEQ ID NO: 499 by at most 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 499, and/or is a conservatively-substituted variant of SEQ ID NO: 499.

In certain embodiments, the β2M signal peptide, or functional fragment or variant thereof, is encoded by a nucleic acid comprising SEQ ID NO: 500 or a functional fragment or variant thereof. In certain embodiments, the functional variant has at least 80%, 85%, 90%, 95%, 96%, 97%, 98%, or 99% sequence identity with SEQ ID NO: 500, hybridizes under stringent hybridization conditions with the complement of SEQ ID NO: 500, or is a codon degenerate variant of SEQ ID NO: 500.

In certain embodiments, the CAR is linked to an Azurocidin signal peptide, or a functional fragment or variant thereof. In certain such embodiments, the Azurocidin signal peptide has the amino acid sequence of SEQ ID NO: 501 or a functional fragment or variant thereof. In certain embodiments, the functional fragment is shorter than SEQ ID NO: 501 by at most 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 501, and/or is a conservatively-substituted variant of SEQ ID NO: 501.

In certain embodiments, the Azurocidin signal peptide, or functional fragment or variant thereof, is encoded by a nucleic acid comprising SEQ ID NO: 502 or a functional fragment or variant thereof. In certain embodiments, the functional variant has at least 80%, 85%, 90%, 95%, 96%, 97%, 98%, or 99% sequence identity with SEQ ID NO: 502, hybridizes under stringent hybridization conditions with the complement of SEQ ID NO: 502, or is a codon degenerate variant of SEQ ID NO: 502.

In certain embodiments, the CAR is linked to a human serum albumin signal peptide, or a functional fragment or variant thereof. In certain such embodiments, the human serum albumin signal peptide has the amino acid sequence of SEQ ID NO: 503 or a functional fragment or variant thereof. In certain embodiments, the functional fragment is shorter than SEQ ID NO: 503 by at most 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 503, and/or is a conservatively-substituted variant of SEQ ID NO: 503.

In certain embodiments, the human serum albumin signal peptide, or functional fragment or variant thereof, is encoded by a nucleic acid comprising SEQ ID NO: 504 or a functional fragment or variant thereof. In certain embodiments, the functional variant has at least 80%, 85%, 90%, 95%, 96%, 97%, 98%, or 99% sequence identity with SEQ ID NO: 504, hybridizes under stringent hybridization conditions with the complement of SEQ ID NO: 504, or is a codon degenerate variant of SEQ ID NO: 504.

In certain embodiments, the CAR is linked to an A2M receptor associated protein signal peptide, or a functional fragment or variant thereof. In certain such embodiments, A2M receptor associated protein signal peptide has the amino acid sequence of SEQ ID NO: 505 or a functional fragment or variant thereof. In certain embodiments, the functional fragment is shorter than SEQ ID NO: 505 by at most 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 505, and/or is a conservatively-substituted variant of SEQ ID NO: 505.

In certain embodiments, the A2M receptor associated protein signal peptide, or functional fragment or variant thereof, is encoded by a nucleic acid comprising SEQ ID NO: 506 or a functional fragment or variant thereof. In certain embodiments, the functional variant has at least 80%, 85%, 90%, 95%, 96%, 97%, 98%, or 99% sequence identity with SEQ ID NO: 506, hybridizes under stringent hybridization conditions with the complement of SEQ ID NO: 506, or is a codon degenerate variant of SEQ ID NO: 506.

In certain embodiments, the CAR is linked to an IGHV3-23 signal peptide, or a functional fragment or variant thereof. In certain such embodiments, the IGHV3-23 signal peptide has the amino acid sequence of SEQ ID NO: 507 or a functional fragment or variant thereof. In certain embodiments, the functional fragment is shorter than SEQ ID NO: 507 by at most 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 507, and/or is a conservatively-substituted variant of SEQ ID NO: 507.

In certain embodiments, the IGHV3-23 signal peptide, or functional fragment or variant thereof, is encoded by a nucleic acid comprising SEQ ID NO: 508 or a functional fragment or variant thereof. In certain embodiments, the functional variant has at least 80%, 85%, 90%, 95%, 96%, 97%, 98%, or 99% sequence identity with SEQ ID NO: 508, hybridizes under stringent hybridization conditions with the complement of SEQ ID NO: 508, or is a codon degenerate variant of SEQ ID NO: 508.

In certain embodiments, the CAR is linked to an IGKV1-D33 signal peptide, or a functional fragment or variant thereof. In certain such embodiments, the IGKV1-D33 signal peptide has the amino acid sequence of SEQ ID NO: 509 or a functional fragment or variant thereof. In certain embodiments, the functional fragment is shorter than SEQ ID NO: 509 by at most 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 509, and/or is a conservatively-substituted variant of SEQ ID NO: 509.

In certain embodiments, the IGKV1-D33 signal peptide, or functional fragment or variant thereof, is encoded by a nucleic acid comprising SEQ ID NO: 510 or a functional fragment or variant thereof. In certain embodiments, the functional variant has at least 80%, 85%, 90%, 95%, 96%, 97%, 98%, or 99% sequence identity with SEQ ID NO: 510, hybridizes under stringent hybridization conditions with the complement of SEQ ID NO: 510, or is a codon degenerate variant of SEQ ID NO: 510.

In certain embodiments, the CAR is linked to an IGHV3-33 (L14F) signal peptide, or a functional fragment or variant thereof. In certain such embodiments, the IGHV3-33 (L14F) signal peptide has the amino acid sequence of SEQ ID NO: 511 or a functional fragment or variant thereof. In certain embodiments, the functional fragment is shorter than SEQ ID NO: 511 by at most 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 511, and/or is a conservatively-substituted variant of SEQ ID NO: 511.

In certain embodiments, the IGHV3-33 (L14F) signal peptide, or functional fragment or variant thereof, is encoded by a nucleic acid comprising SEQ ID NO: 512 or a functional fragment or variant thereof. In certain embodiments, the functional variant has at least 80%, 85%, 90%, 95%, 96%, 97%, 98%, or 99% sequence identity with SEQ ID NO: 512, hybridizes under stringent hybridization conditions with the complement of SEQ ID NO: 512, or is a codon degenerate variant of SEQ ID NO: 512.

In certain embodiments, the CAR is linked to an TVB2 (T21A) signal peptide, or a functional fragment or variant thereof. In certain such embodiments, the TVB2 (T21A) signal peptide has the amino acid sequence of SEQ ID NO: 513 or a functional fragment or variant thereof. In certain embodiments, the functional fragment is shorter than SEQ ID NO: 513 by at most 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 513, and/or is a conservatively-substituted variant of SEQ ID NO: 513.

In certain embodiments, the TVB2 (T21A) signal peptide, or functional fragment or variant thereof, is encoded by a nucleic acid comprising SEQ ID NO: 514 or a functional fragment or variant thereof. In certain embodiments, the functional variant has at least 80%, 85%, 90%, 95%, 96%, 97%, 98%, or 99% sequence identity with SEQ ID NO: 514, hybridizes under stringent hybridization conditions with the complement of SEQ ID NO: 514, or is a codon degenerate variant of SEQ ID NO: 514.

In certain embodiments, the CAR is linked to an CD52 signal peptide, or a functional fragment or variant thereof. In certain such embodiments, the CD52 signal peptide has the amino acid sequence of SEQ ID NO: 515 or a functional fragment or variant thereof. In certain embodiments, the functional fragment is shorter than SEQ ID NO: 515 by at most 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 515, and/or is a conservatively-substituted variant of SEQ ID NO: 515.

In certain embodiments, the CD52 signal peptide, or functional fragment or variant thereof, is encoded by a nucleic acid comprising SEQ ID NO: 516 or a functional fragment or variant thereof. In certain embodiments, the functional variant has at least 80%, 85%, 90%, 95%, 96%, 97%, 98%, or 99% sequence identity with SEQ ID NO: 516, hybridizes under stringent hybridization conditions with the complement of SEQ ID NO: 516, or is a codon degenerate variant of SEQ ID NO: 516.

In certain embodiments, the CAR is linked to an LNGFR signal peptide, or a functional fragment or variant thereof. In certain such embodiments, the LNGFR signal peptide has the amino acid sequence of SEQ ID NO: 517 or a functional fragment or variant thereof. In certain embodiments, the functional fragment is shorter than SEQ ID NO: 517 by at most 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 517, and/or is a conservatively-substituted variant of SEQ ID NO: 517.

In certain embodiments, the LNGFR signal peptide, or functional fragment or variant thereof, is encoded by a nucleic acid comprising SEQ ID NO: 518 or a functional fragment or variant thereof. In certain embodiments, the functional variant has at least 80%, 85%, 90%, 95%, 96%, 97%, 98%, or 99% sequence identity with SEQ ID NO: 518, hybridizes under stringent hybridization conditions with the complement of SEQ ID NO: 518, or is a codon degenerate variant of SEQ ID NO: 518.

F. Exemplary CAR Constructs

By way of example, but not limitation, the CAR can comprise an amino acid sequence having at least 80%, 85%, 90%, 95%, 96%, 97%, 98%, or 99% sequence identity with any one of SEQ ID NOs: 591, 593, 595, 597, 599, 601, 603, 605, 607, 609, 611, 613, 615, 617, 619, 621, 623, 625, 627, and 629 or a conservatively-substituted variant thereof. By way of further example, but not limitation, a polynucleotide encoding the CAR can comprise a nucleic acid sequence having at least 80%, 85%, 90%, 95%, 96%, 97%, 98%, or 99% sequence identity with the sequence of any one of SEQ ID NOs: 592, 594, 596, 598, 600, 602, 604, 606, 608, 610, 612, 614, 616, 618, 620, 622, 624, 626, 628, and 630; a sequence that hybridizes under stringent hybridization conditions with the complement of any one of such sequences; or a codon degenerate variant of any one of such sequences.

In certain embodiments, the CAR can comprise an amino acid sequence having at least 80%, 85%, 90%, 95%, 96%, 97%, 98%, or 99% sequence identity with SEQ ID NO: 623 or a conservatively-substituted variant thereof. In certain such embodiments, the polynucleotide encoding the CAR can comprise a nucleic acid sequence having at least 80%, 85%, 90%, 95%, 96%, 97%, 98%, or 99% sequence identity with the sequence of SEQ ID NO: 624; a sequence that hybridizes under stringent hybridization conditions with the complement of any one of such sequences; or a codon degenerate variant of any one of such sequences.

CARs and CAR construction as well as compositions are also described, for example, in:

Chimeric Antigen Receptor (CAR) T-Cell Therapies for Cancer: A Practical Guide, Edited by: Daniel W. Lee and Nirali N. Shah, 2020 (ISBN 978-0-323-66181-2;

Second Generation Cell and Gene-based Therapies, Biological Advances, Clinical Outcomes and Strategies for Capitalisation, Editors-in-Chief: Alain A. Vertès, Devyn M. Smith, Nathan J. Dowden, 2020 (ISBN 978-0-12-812034-7;

Basics of Chimeric Antigen Receptor (CAR) Immunotherapy, Author: Mumtaz Yaseen Balkhi, 2020 (ISBN 978-0-12-819573-4;

Engineering and Design of Chimeric Antigen Receptors, Authors: Sonia Guedan, Hugo Calderon, Avery D. Posey, Jr., and Marcela V. Maus, *Molecular Therapy: Methods & Clinical Development*, Vol. 12, March (2019);

Chimeric Antigen Receptor T Cell Therapy Pipeline at a Glance: A Retrospective and Systematic Analysis from Clinicaltrials.Gov, Authors: Eider F Moreno Cortes, Caleb K Stein, Paula A Lengerke Diaz, Cesar A Ramirez-Segura, Januario E. Castro, MD, *Blood* (2019) 134 (Supplement_1): 5629;

WO2020209934 (PCT/US2020/017794)—Novel chimeric antigen receptors and libraries (MIT);

WO2020037142 (PCT/US2019/046691)—Compositions and methods for high-throughput activation screening to boost t cell effector function (Yale);

WO2015123642 (PCT/US2015/016057)—Chimeric antigen receptors and methods of making (Univ. TX);

WO2020014366 (PCT/US2019/041213)—Ror-1 specific chimeric antigen receptors and uses thereof (Precigen);

WO2019236577 (PCT/US2019/035384)—Muc16 specific chimeric antigen receptors and uses thereof (Precigen)

WO2019079486 (PCT/US2018/056334)—Polypeptide compositions comprising spacers (Precigen)

WO2017214333 (PCT/US2017/036440)—Cd33 specific chimeric antigen receptors (Precigen)

V. Cytokine

In some embodiments, the modified immune effector cell of the present invention can comprise a cytokine. The cytokine may, for example, be encoded by the polynucleotide of the present disclosure. For example, the polynucleotide may encode the miRNA(s), CAR and cytokine, or the miRNA(s) and cytokine.

In some cases, the cytokine comprises at least one chemokine, interferon, interleukin, lymphokine, tumor necrosis factor, or variant or combination thereof. In certain embodiments, the cytokine is an interferon, GM-CSF, G-CSF, M-CSF, LT-beta, TNF-alpha, growth factors, hGH, and/or a ligand of human Toll-like receptors TLR1, TLR2, TLR3, TLR4, TLR5, TLR6, TLR7, TLR8, TLR9, TLR10, IFN-alpha, IFN-beta, or IFN-gamma.

In certain embodiments, the cytokine is an interleukin. In some cases the interleukin is IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, or a functional variant or fragment thereof.

In certain embodiments, the cytokine may be IL-12, or a functional fragment or variant thereof. In some embodiments, the IL-12 is a single chain IL-12 (scIL-12), protease sensitive IL-12, destabilized IL-12, membrane bound IL-12, intercalated IL-12. In some instances, the IL-12 variants are as described in WO2015/095249, WO2016/048903, WO2017/062953.

In certain embodiments, the cytokine may be IL-15, or a functional fragment or variant thereof. In certain embodiments, the IL-15, or functional fragment or variant thereof, is membrane-bound. Such may occur when IL-15, or a functional fragment or variant thereof, is bound to membrane-bound IL-15Rα, or a functional fragment or variant thereof. Thus, certain embodiments of the present invention may involve a fusion protein comprising IL-15 and IL-15Rα, or their respective functional fragments or variants.

In certain embodiments, the IL-15, or functional fragment or variant thereof, comprises the amino acid sequence of SEQ ID NO: 519, or a functional fragment or variant thereof. In certain embodiments, the functional fragment is shorter than the amino acid sequence of SEQ ID NO: 519 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 519, and/or is a conservatively-substituted variant of the amino acid sequence of SEQ ID NO: 519.

In certain embodiments, the IL-15, or functional fragment or variant thereof, is encoded by a nucleic acid comprising the sequence of SEQ ID NO: 520, or a functional fragment or variant thereof. In certain embodiments, the functional variant has at least 80%, 85%, 90%, 95%, 96%, 97%, 98%, or 99% sequence identity with SEQ ID NO: 520, hybridizes under stringent hybridization conditions with the complement of SEQ ID NO: 520, or is a codon degenerate variant of SEQ ID NO: 520.

In certain embodiments, the IL-15Rα, or functional fragment or variant thereof, comprises the amino acid sequence of SEQ ID NO: 521 or a functional fragment or variant thereof. In certain embodiments, the functional fragment is shorter than the amino acid sequence of SEQ ID NO: 521 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 521, and/or is a conservatively-substituted variant of the amino acid sequence of SEQ ID NO: 521.

In certain embodiments, the IL-15Rα, or functional fragment or variant thereof, is encoded by a nucleic acid comprising SEQ ID NO: 522, or a functional fragment or variant thereof. In certain embodiments, the functional variant has at least 80%, 85%, 90%, 95%, 96%, 97%, 98%, or 99% sequence identity with SEQ ID NO: 522, hybridizes under stringent hybridization conditions with the complement of SEQ ID NO: 522, or is a codon degenerate variant of SEQ ID NO: 522.

In certain embodiments, the IL-15, or functional fragment or variant thereof, is linked to the IL-15Rα, or functional fragment thereof by way of a linker.

In certain embodiments, the linker comprises the amino acid sequence of SEQ ID NO: 529 or a functional fragment or variant thereof. In certain embodiments, the functional fragment is shorter than SEQ ID NO: 529 by at most 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 529, and/or is a conservatively-substituted variant of SEQ ID NO: 529.

In certain embodiments, the linker is encoded by a nucleic acid comprising SEQ ID NO: 530 or a functional fragment or variant thereof. In certain embodiments, the functional variant has at least 80%, 85%, 90%, 95%, 96%, 97%, 98%, or 99% sequence identity with SEQ ID NO: 530, hybridizes under stringent hybridization conditions with SEQ ID NO: 530, or is a codon degenerate variant of SEQ ID NO: 530.

In certain embodiments, the fusion protein comprising IL-15 and IL-15Rα comprises the amino acid sequence of SEQ ID NO: 523 or a functional fragment or variant thereof. In certain embodiments, the functional fragment is shorter than the amino acid sequence of SEQ ID NO: 523 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 523, and/or is a conservatively-substituted variant of the amino acid sequence of SEQ ID NO: 523.

In certain embodiments, the fusion protein comprising IL-15 and IL-15Rα is encoded by a nucleic acid comprising SEQ ID NO: 524 or a functional fragment or variant thereof. In certain embodiments, the functional variant has at least 80%, 85%, 90%, 95%, 96%, 97%, 98%, or 99% sequence identity with SEQ ID NO: 524, hybridizes under stringent hybridization conditions with the complement of SEQ ID NO: 524, or is a codon degenerate variant of SEQ ID NO: 603.

In certain embodiments, the cytokine is linked to a signal peptide. Any signal for use in eukaryotic cells, including those described above for use with the CARs may be linked to the cytokine. In certain embodiments, the cytokine is linked to an IgE signal peptide.

In certain embodiments, the fusion protein comprising IL-15 and IL-15Rα comprises the amino acid sequence of SEQ ID NO: 525 or a functional fragment or variant thereof. In certain embodiments, the functional fragment is shorter than the amino acid sequence of SEQ ID NO: 525 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 525, and/or is a conservatively-substituted variant of the amino acid sequence of SEQ ID NO: 525.

In certain embodiments, the fusion protein comprising IL-15 and IL-15Rα is encoded by a nucleic acid comprising SEQ ID NO: 526 or a functional fragment or variant thereof. In certain embodiments, the functional variant has at least 80%, 85%, 90%, 95%, 96%, 97%, 98%, or 99% sequence identity with SEQ ID NO: 526, hybridizes under stringent hybridization conditions with the complement of SEQ ID NO: 526, or is a codon degenerate variant of SEQ ID NO: 526.

VI. Cell Tag

In some embodiments, the modified immune effector cell of the present invention can comprise a cell tag. The cell tag may, for example, be encoded by the polynucleotide of the present disclosure. For example, the polynucleotide may encode the miRNA(s), CAR and/or cytokine described herein as well as a cell tag. In some aspects, the cell tag is used as a kill switch, selection marker, a biomarker, or a combination thereof.

In certain embodiments, the cell tag is capable of being bound by a predetermined binding partner. In certain such embodiments, the cell tag is non-immunogenic. In certain such embodiments, the cell tag comprises a polypeptide that is truncated so that it is non-immunogenic.

In certain embodiments, the administration of the predetermined binding partner allows for depletion of infused CAR-T cells. For example, the administration of cetuximab or any antibody that recognizes HER1 allows for the elimination of cells expressing a cell tag comprising truncated non-immunogenic HER1. The truncation of the HER1 sequence eliminates the potential for EGF ligand binding, homo- and hetero-dimerization of EGFR, and/or EGFR-mediated signaling while keeping cetuximab-binding ability intact (Ferguson, K., 2008. A structure-based view of Epidermal Growth Factor Receptor regulation. *Annu Rev Biophys*, Volume 37, pp. 353-373).

In certain embodiments, the cell tag comprises at least one of a truncated non-immunogenic HER1 polypeptide, a truncated non-immunogenic LNGFR polypeptide, a truncated non-immunogenic CD20 polypeptide, or a truncated non-immunogenic CD52 polypeptide, or a functional fragment or variant thereof.

In certain embodiments, the cell tag comprises a truncated non-immunogenic HER1 polypeptide comprising a HER1 Domain III and a truncated HER1 Domain IV. Such domains and the nucleic acid sequences encoding the same include those described in WO 2018/226897.

In certain embodiments, the HER1 Domain III comprises the amino acid sequence of SEQ ID NO: 604 or a functional fragment or variant thereof. In certain embodiments, the functional fragment is shorter than the amino acid sequence of SEQ ID NO: 565 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 565, and/or is a conservatively-substituted variant the amino acid sequence of sequence of SEQ ID NO: 565.

In certain embodiments, the HER1 Domain III, or functional fragment or variant thereof, is encoded by a nucleic acid comprising SEQ ID NO: 566 or a functional fragment or variant thereof. In certain embodiments, the functional variant has at least 80%, 85%, 90%, 95%, 96%, 97%, 98%, or 99% sequence identity with SEQ ID NO: 566, hybridizes under stringent hybridization conditions with the complement of SEQ ID NO: 566, or is a codon degenerate variant of SEQ ID NO: 566.

In certain embodiments, the truncated HER1 Domain IV comprises the amino acid sequence of SEQ ID NO: 567 or a functional fragment or variant thereof. In certain embodiments, the functional fragment is shorter than the amino acid sequence of SEQ ID NO: 567 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 567, and/or is a conservatively-substituted variant the amino acid sequence of sequence of SEQ ID NO: 567.

In certain embodiments, the truncated HER1 Domain IV, or functional fragment or variant thereof, is encoded by a nucleic acid comprising SEQ ID NO: 568 or a functional fragment or variant thereof. In certain embodiments, the functional variant has at least 80%, 85%, 90%, 95%, 96%, 97%, 98%, or 99% sequence identity with SEQ ID NO: 568, hybridizes under stringent hybridization conditions with the complement of SEQ ID NO: 568, or is a codon degenerate variant of SEQ ID NO: 568.

In certain such embodiments, the truncated non-immunogenic HER1 comprises the amino acid sequence of SEQ ID NO: 569 or a functional fragment or variant thereof. In certain embodiments, the functional fragment is shorter than the amino acid sequence of SEQ ID NO: 569 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 569, and/or is a conservatively-substituted variant the amino acid sequence of sequence of SEQ ID NO: 569.

In certain embodiments, the truncated non-immunogenic HER1, or functional fragment or variant thereof, is encoded by a nucleic acid comprising SEQ ID NO: 570 or a functional fragment or variant thereof. In certain embodiments, the functional variant has at least 80%, 85%, 90%, 95%, 96%, 97%, 98%, or 99% sequence identity with SEQ ID NO: 570, hybridizes under stringent hybridization conditions with the complement of SEQ ID NO: 570, or is a codon degenerate variant of SEQ ID NO: 570.

In certain embodiments, the cell tag comprises a truncated non-immunogenic CD20, or CD20t-1, or a functional fragment or variant thereof. In certain such embodiments, the cell tag comprises the amino acid sequence of SEQ ID NO: 573, SEQ ID NO: 575, or a functional fragment or variant thereof. In certain embodiments, the functional fragment is shorter than the amino acid sequences of SEQ ID NO: 573 or SEQ ID NO: 575 by at most 30, 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with SEQ ID NO: 573 or SEQ ID NO: 575, and/or is a conservatively-substituted variant of the amino acid sequence of SEQ ID NO: 573 or SEQ ID NO: 575.

In certain embodiments, the truncated non-immunogenic CD20, or CD20t-1, or functional fragment or variant thereof, is encoded by a nucleic acid comprising SEQ ID NO: 574 or SEQ ID NO: 576 or a functional fragment or variant thereof. In certain embodiments, the functional variant has at least 80%, 85%, 90%, 95%, 96%, 97%, 98%, or 99% sequence identity with SEQ ID NO: 574 or SEQ ID NO: 576, hybridizes under stringent hybridization conditions with the complement of SEQ ID NO: 574 or SEQ ID NO: 576, or is a codon degenerate variant of SEQ ID NO: 574 or SEQ ID NO: 576.

In certain embodiments, the cell tag further comprises a transmembrane domain. The transmembrane domain can be derived from either a natural or a synthetic source. Where the source is natural, the domain can, for example, be derived from any membrane-bound or transmembrane protein. Suitable transmembrane domains can include the transmembrane domain(s) of alpha, beta or zeta chain of the T-cell receptor; or a transmembrane domain from CD28, CD3 epsilon, CD3, CD45, CD4, CD5, CD8, CD9, CD16, CD22, CD33, CD37, CD64, CD80, CD86, CD134, CD137 or CD154, or a functional fragment or variant thereof. Alternatively, the transmembrane domain can be synthetic, and can comprise hydrophobic residues such as leucine and valine. In some embodiments, a triplet of phenylalanine, tryptophan and valine is found at one or both termini of a synthetic transmembrane domain.

In some embodiments, the transmembrane domain comprises a CD28 transmembrane domain, or a functional fragment or variant thereof. In certain such embodiments, the transmembrane domain comprises the amino acid sequence of SEQ ID NO: 477 or a functional fragment or variant thereof. In certain embodiments, the functional fragment is shorter than the amino acid sequence of SEQ ID NO: 477 by at most 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 477, and/or is a conservatively-substituted variant of the amino acid sequence of SEQ ID NO: 477.

In certain embodiments, the CD28 transmembrane domain, or functional fragment or variant thereof, is encoded by a nucleic acid comprising SEQ ID NO: 478, or a functional fragment or variant thereof. In certain embodiments, the functional variant has at least 80%, 85%, 90%, 95%, 96%, 97%, 98%, or 99% sequence identity with SEQ ID NO: 478, hybridizes under stringent hybridization conditions with the complement of SEQ ID NO: 478, or is a codon degenerate variant of SEQ ID NO: 478.

In certain embodiments, the cell tag comprises a truncated HER1, or functional fragment or variant thereof, and a transmembrane domain, or a functional fragment or variant thereof. In some embodiments, the cell comprises the amino acid sequence of SEQ ID NO: 571 or a functional fragment or variant thereof. In certain embodiments, the functional fragment is shorter than the amino acid sequence of SEQ ID NO: 571 by at most 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 571, and/or is a conservatively-substituted variant of the amino acid sequence of SEQ ID NO: 571.

In certain embodiments, the cell tag is encoded by a nucleic acid comprising SEQ ID NO: 572, or a functional fragment or variant thereof. In certain embodiments, the functional variant has at least 80%, 85%, 90%, 95%, 96%, 97%, 98%, or 99% sequence identity with SEQ ID NO: 572, hybridizes under stringent hybridization conditions with the complement of SEQ ID NO: 572, or is a codon degenerate variant of SEQ ID NO: 572.

In certain embodiments, the cell tag is linked with a signal peptide. The signal peptide can be any signal peptide suitable for use in a eukaryotic cell including those described with respect to CARs herein. In certain embodiments, the signal peptide is a Igκ signal peptide comprising the amino acid sequence of SEQ ID NO: 491, or a functional fragment or variant thereof

VII. Genetic Construct

Figure 16:
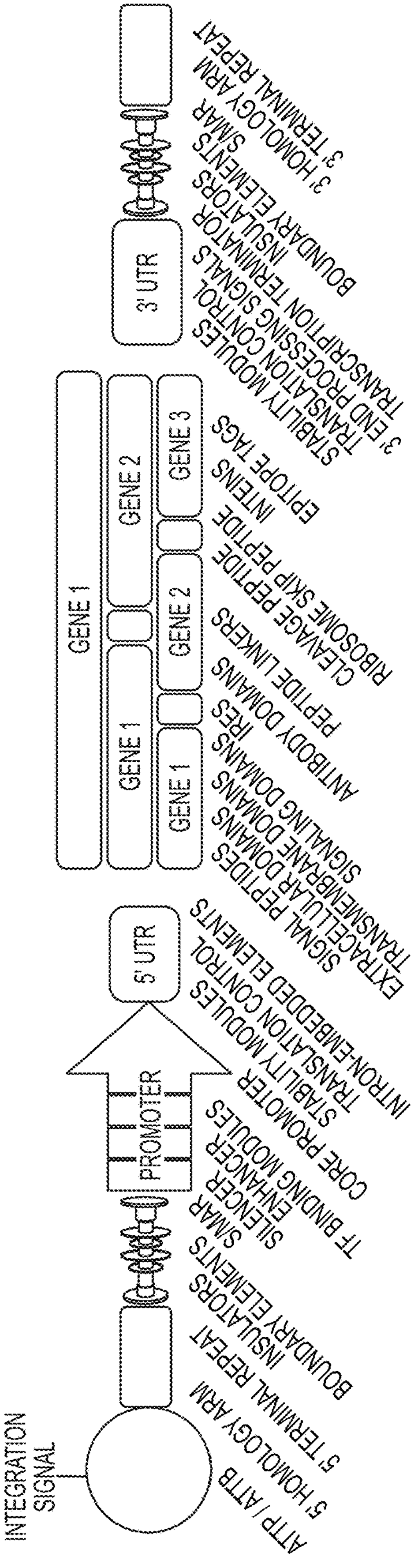
FIG. 16 provides an exemplary scheme for a genetic construct of the present disclosure.
Figure 17:
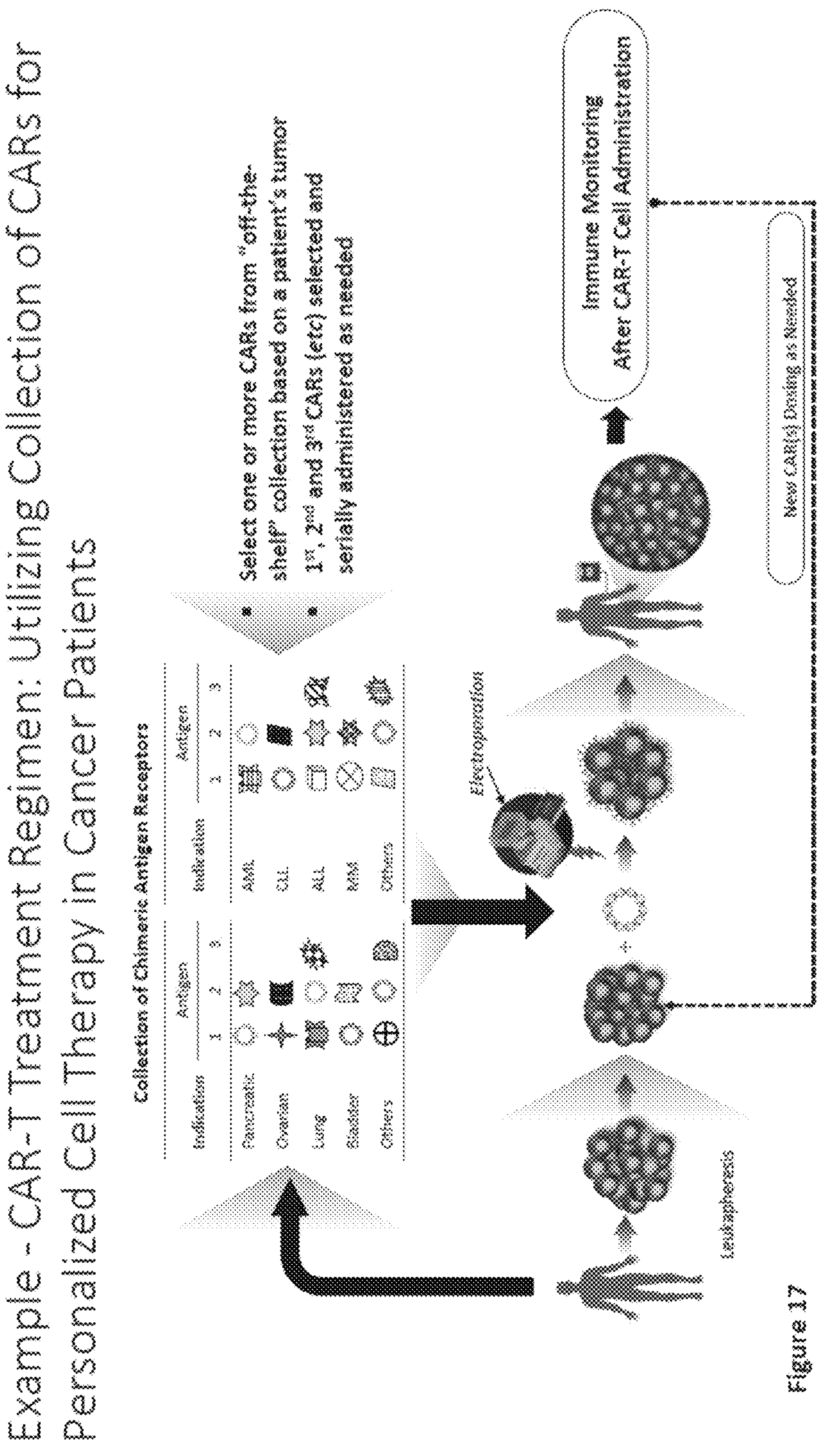
FIG. 17 provides a schematic depiction of pathways and elements of the present disclosure.
Figure 18:
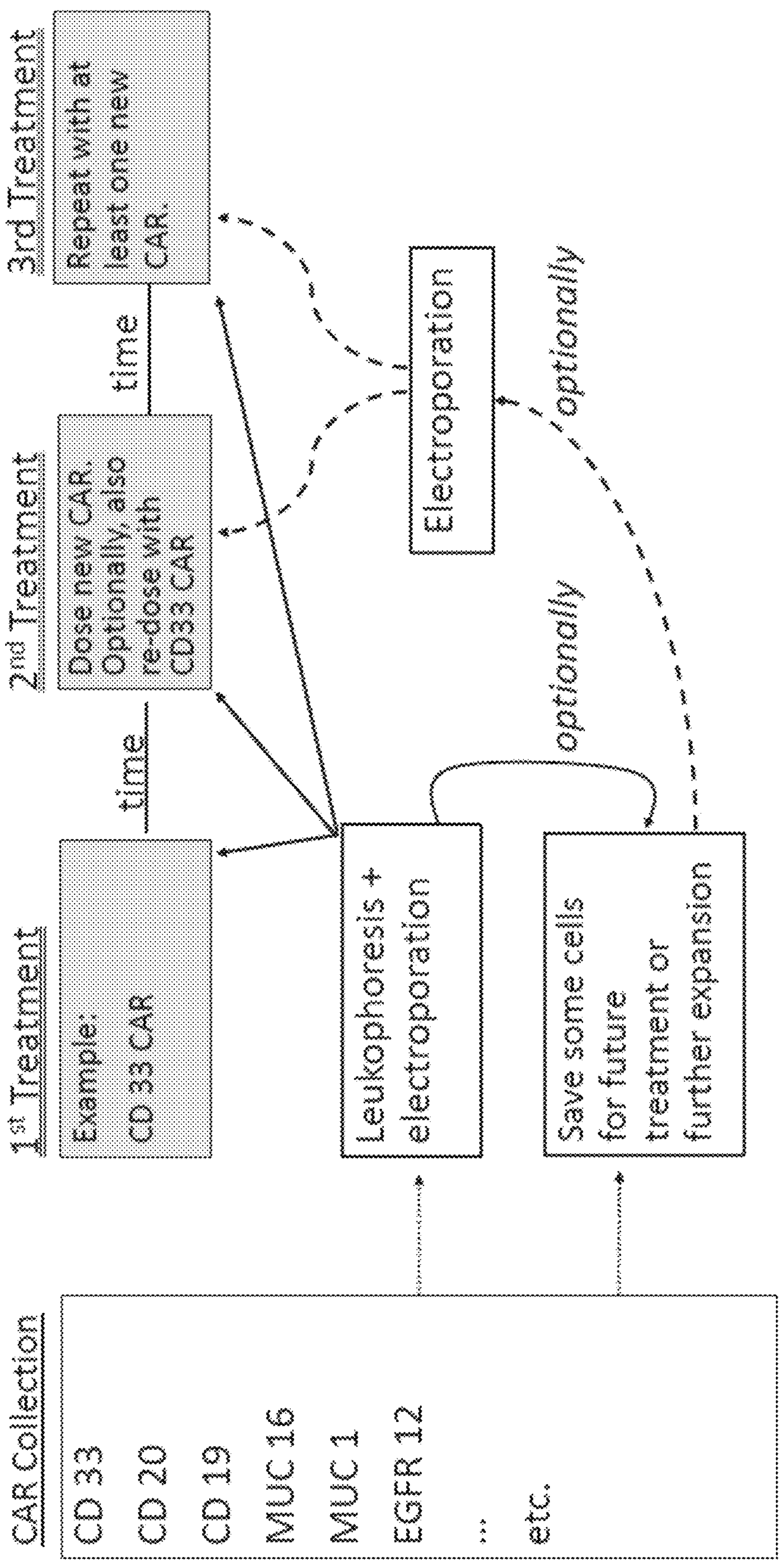
FIG. 18 provides examples of pathways by which treatment regimens of the present disclosure can proceed.
Figure 20:
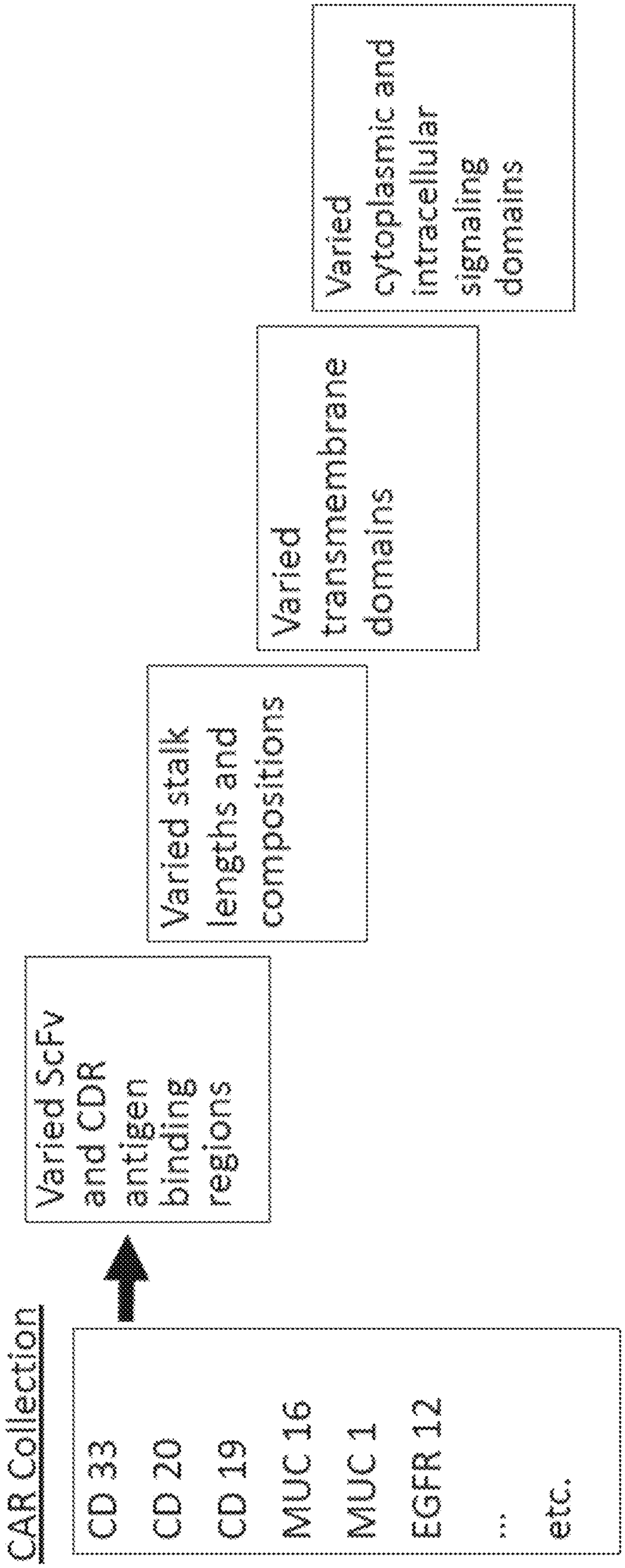
FIG. 20 provides an indication of additional embodiments of the present disclosure.

As shown in FIG. 16, an exemplary polynucleotide is provided which can be used as template for the expression of various genes and other regulatory elements in cells. It should be understood that various elements can be included or omitted in the polynucleotide and that different options are shown for various exemplary sites in the polynucleotide.

As shown, the polynucleotide can include an integration signal for attP/attB phage integration of the polynucleotide into a bacterial genome. The polynucleotide can further include a 5' homology arm or 5' terminal repeat and a 3' homology arm or 3' terminal repeat. The polynucleotide can further include insulators, boundary elements and S/MAR positioned 3' adjacent to the 5' homology arm or 5' terminal repeat and 5' adjacent to the 3' homology arm or 3' terminal repeat. Between the insulators, boundary elements, or S/MAR, the polynucleotide can include, from 5' to 3', a promoter which can include a silencer, enhancer, TF binding modules and a core promoter; a 5' untranslated region which can include stability modules, translation control elements, and intron-embedded elements such as miRNA encoding sequences; one or more genes which can include signal peptides, extracellular domains, transmembrane domains, signaling domains, antibody domains, peptide linkers, inteins and epitope tags; and a 3' untranslated region that can include stability modules, translation control, 3' end processing signals and a transcription terminator. It should be understood that the genes to be expressed can be separated by IRES, cleavage peptides, or ribosomal skipping peptides.

The CAR may be encoded in the same genetic construct with the miRNA, the cytokine, and/or the cell tag. An advantage of having two or more of such components expressed using one genetic construct is stoichiometric expression of such components.

A. Linkers

In certain embodiments, the polypeptides of the present invention (e.g., the CAR, the cytokine, and the cell tag) are linked by linker polypeptide(s). The linkers may also be used to link domains of a polypeptide (e.g., the VH and VL domains of a CAR, the truncated HER1 and transmembrane domains of the cell tag, and the IL-15 and IL-15Rα domains).

Linkers suitable in the present invention include flexible linkers, rigid linkers, and in vivo cleavable linkers. In some cases, the linker acts to link functional domains together (as in flexible and rigid linkers) or to release a free functional domain in vivo as in in vivo cleavable linkers.

As noted, in some cases, the linker sequence may include a flexible linker. Flexible linkers can be applied when a joined domain requires a certain degree of movement or interaction. Flexible linkers can be composed of small, non-polar (e.g., Gly) or polar (e.g., Ser or Thr) amino acids. A flexible linker can have sequences consisting primarily of stretches of Gly and Ser residues ("GS" linker). An example of a flexible linker can have the sequence of (Gly-Gly-Gly-Gly-Ser)n. By adjusting the copy number "n", the length of this exemplary GS linker can be optimized to achieve appropriate separation of functional domains, or to maintain necessary inter-domain interactions. For example, (Gly-Gly-Gly-Gly-Ser)n, wherein n is 4 is a (G4S)4 linker as shown in SEQ ID NO: 608 or a conservatively substituted amino acid sequence thereof. Besides GS linkers, other flexible linkers can be utilized for recombinant fusion proteins. In some cases, flexible linkers can contain additional amino acids such as Thr and Ala to maintain flexibility. In other cases, polar amino acids such as Lys and Glu can be used to improve solubility.

Flexible linkers can be suitable choices when certain movements or interactions are desired for fusion protein domains. In addition, although flexible linkers do not have rigid structures, in some cases they can serve as a passive linker to keep a distance between functional domains. The length of a flexible linker may be adjusted to allow for proper folding or to achieve optimal biological activity of the fusion proteins.

A rigid linker can be utilized to maintain a fixed distance between domains of a polypeptide. Examples of rigid linkers include Alpha helix-forming linkers, Pro-rich sequence, (XP)n, X-Pro backbone, A(EAAAK)nA (n=2-5) (SEQ ID NO: 563) and functional fragments and variants thereof, to name a few. Rigid linkers can exhibit relatively stiff structures by adopting α-helical structures or by containing multiple Pro residues in some cases.

A linker useful in the present invention can be cleavable in some cases. In other cases, the linker is not cleavable. Linkers that are not cleavable can covalently join functional domains together to act as one molecule throughout an in vivo processes or an ex vivo process. A linker can also be cleavable in vivo. A cleavable linker can be introduced to release free functional domains in vivo.

A cleavable linker can be cleaved by the presence of reducing reagents, proteases, to name a few. For example, a reduction of a disulfide bond can be utilized to produce a cleavable linker. In the case of a disulfide linker, a cleavage event through disulfide exchange with a thiol, such as glutathione, could produce a cleavage. In some cases, a cleavable linker can allow for targeted cleavage. For example, an in vivo cleavage of a linker in a recombinant fusion protein can also be carried out by proteases that can be expressed in vivo under pathological conditions (e.g., cancer or inflammation), in specific cells or tissues, or constrained within certain cellular compartments. A cleavable linker can comprise a hydrazone, peptides, a disulfide, or a thioesther. For example, a hydrazone can confer serum stability. In other cases, a hydrazone can allow for cleavage in an acidic compartment. An acidic compartment can have a pH up to 7. A linker can also include a thioether. A thioether can be nonreducible A thioether can be designed for intracellular proteolytic degradation. Examples of cleavable linkers include Furinlink, fmdv, and 2A linkers (e.g., P2A, GSG-P2A, FP2A, T2A, and Furin-T2A), or functional fragments or variants thereof.

A fmdv linker may comprise the amino acid sequence of SEQ ID NO: 539 or a functional fragment or variant thereof. In certain embodiments, the functional fragment is shorter than the amino acid sequence of SEQ ID NO: 539 by at most 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 539, and/or is a conservatively-substituted variant of the amino acid sequence of SEQ ID NO: 539.

In certain embodiments, the fmdv linker is encoded by a nucleic acid comprising SEQ ID NO: 540, or a functional fragment or variant thereof. In certain embodiments, the functional variant has at least 80%, 85%, 90%, 95%, 96%, 97%, 98%, or 99% sequence identity with SEQ ID NO: 540, hybridizes under stringent hybridization conditions with the complement of SEQ ID NO: 540, or is a codon degenerate variant of SEQ ID NO: 540.

A P2A linker may comprise the amino acid sequence of SEQ ID NO: 547 or a functional fragment or variant thereof. In certain embodiments, the functional fragment is shorter than the amino acid sequence of SEQ ID NO: 547 by at most 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 547, and/or is a conservatively-substituted variant of the amino acid sequence of SEQ ID NO: 547.

In certain embodiments, the P2A linker is encoded by a nucleic acid comprising SEQ ID NO: 548, or a functional fragment or variant thereof. In certain embodiments, the functional variant has at least 80%, 85%, 90%, 95%, 96%, 97%, 98%, or 99% sequence identity with SEQ ID NO: 548, hybridizes under stringent hybridization conditions with the complement of SEQ ID NO: 548, or is a codon degenerate variant of SEQ ID NO: 548.

A GSG-P2A linker may comprise the amino acid sequence of SEQ ID NO: 549 or a functional fragment or variant thereof. In certain embodiments, the functional fragment is shorter than the amino acid sequence of SEQ ID NO: 549 by at most 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 549, and/or is a conservatively-substituted variant of the amino acid sequence of SEQ ID NO: 549.

In certain embodiments, the GSG-P2A linker is encoded by a nucleic acid comprising SEQ ID NO: 550, or a functional fragment or variant thereof. In certain embodiments, the functional variant has at least 80%, 85%, 90%, 95%, 96%, 97%, 98%, or 99% sequence identity with SEQ ID NO: 550, hybridizes under stringent hybridization conditions with the complement of SEQ ID NO: 550, or is a codon degenerate variant of SEQ ID NO: 550.

A FP2A linker may comprise the amino acid sequence of SEQ ID NO: 555 or a functional fragment or variant thereof. In certain embodiments, the functional fragment is shorter than the amino acid sequence of SEQ ID NO: 555 by at most 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 555, and/or is a conservatively-substituted variant of the amino acid sequence of SEQ ID NO: 555.

In certain embodiments, the FP2A linker is encoded by a nucleic acid comprising SEQ ID NO: 556, or a functional fragment or variant thereof. In certain embodiments, the functional variant has at least 80%, 85%, 90%, 95%, 96%, 97%, 98%, or 99% sequence identity with SEQ ID NO: 556, hybridizes under stringent hybridization conditions with the complement of SEQ ID NO: 556, or is a codon degenerate variant of SEQ ID NO: 556.

A T2A linker may comprise the amino acid sequence of SEQ ID NO: 541 or a functional fragment or variant thereof. In certain embodiments, the functional fragment is shorter than the amino acid sequence of SEQ ID NO: 541 by at most 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 541, and/or is a conservatively-substituted variant of the amino acid sequence of SEQ ID NO: 541.

In certain embodiments, the T2A linker is encoded by a nucleic acid comprising SEQ ID NO: 475428, or a functional fragment or variant thereof. In certain embodiments, the functional variant has at least 80%, 85%, 90%, 95%, 96%, 97%, 98%, or 99% sequence identity with SEQ ID NO: 542, hybridizes under stringent hybridization conditions with the complement of SEQ ID NO: 54, or is a codon degenerate variant of SEQ ID NO: 542.

In some embodiments, the linker comprises a furin polypeptide and a 2A polypeptide, wherein the furin polypeptide and the 2A polypeptide are connected by a polypeptide linker comprising at least three hydrophobic amino acids. Such linkers are called "Furin-T2A" linkers. In some cases, the at least three hydrophobic amino acids are selected from the list consisting of glycine (Gly)(G), alanine (Ala)(A), valine (Val)(V), leucine (Leu)(L), isoleucine (Ile)(I), proline (Pro)(P), phenylalanine (Phe)(F), methionine (Met)(M), tryptophan (Trp)(W). In some cases, the polypeptide linker can include one or more GS linker sequences, for instance (GS)n, (SG)n, and (GSG)n, wherein n can be any number from zero to thirty.

A Furin-T2A linker may comprise the amino acid sequence of SEQ ID NO: 543 or 545 or a functional fragment or variant thereof. In certain embodiments, the functional fragment is shorter than the amino acid sequence of SEQ ID NO: 543 or 545 by at most 25, 20, 15, 10, 9, 8, 7, 6, 5, 4, 3, 2, or 1 amino acid residues at the N- and/or C-terminus. In certain embodiments, the functional variant has at least 80%, 85%, 90%, 95%, 96%, 97%, 98%, or 99% sequence identity with the amino acid sequence of SEQ ID NO: 543 or 545, and/or is a conservatively-substituted variant of the amino acid sequence of SEQ ID NO: 543 or 545.

In certain embodiments, the Furin-T2A linker is encoded by a nucleic acid comprising SEQ ID NO: 544 or 546, or a functional fragment or variant thereof. In certain embodiments, the functional variant has at least 80%, 85%, 90%, 95%, 96%, 97%, 98%, or 99% sequence identity with SEQ ID NO: 544 or 546, hybridizes under stringent hybridization conditions with the complement of SEQ ID NO: 544 or 546, or is a codon degenerate variant of SEQ ID NO: 544 or 546.

A linker can be an engineered linker. For example, a linker can be designed to comprise chemical characteristics such as hydrophobicity. Methods of designing linkers can be computational. In some cases, computational methods can include graphic techniques. Computation methods can be used to search for suitable peptides from libraries of three-dimensional peptide structures derived from databases. For example, a Brookhaven Protein Data Bank (PDB) can be used to span the distance in space between selected amino acids of a linker.

Further exemplary linkers are provided in the Sequence Listing.

In some cases, at least two linker sequences can be included in the same protein. For example, polypeptides of interest within a fusion protein can be separated by at least two linkers. In some cases, polypeptides can be separated by 2, 3, 4, 5, 6, 7, 8, 9, or up to 10 linkers.

The CAR, cell tag, and/or cytokine of the present invention may be expressed as a fusion protein. In such embodiments, such components may be linked together using a self-cleaving peptide, for example a 2A peptide.

In certain embodiments, the self-cleaving peptide is a T2A peptide, or a functional fragment or variant thereof.

In certain embodiments, the self-cleaving peptide is a Furin-T2A peptide, or a functional fragment or variant thereof.

In certain such embodiments, the CAR, the cytokine, and the cell tag are expressed as a fusion protein with the CAR and the cytokine linked by a self-cleaving linker, for example one comprising Furin-T2A, and the cytokine and cell tag linked by a self-cleaving linker, for example one comprising T2A.

B. Promoters

The polynucleotide of the invention can be present in the construct in operable linkage with a promoter. Appropriate promoters can be selected based on the host cell and effect sought. Suitable promoters include constitutive and inducible promoters. The promoters can be tissue specific, such promoters being well known in the art.

Examples of constitutive promoters for use in the present invention include immediate early cytomegalovirus (CMV) promoter; human elongation growth factor 1 alpha 1 (hEF1A1); simian virus 40 (SV40) early promoter; mouse mammary tumor virus (MMTV); human immunodeficiency virus (HIV) long terminal repeat (LTR) promoter; MoMuLV promoter; avian leukemia virus promoter; Epstein-Barr virus immediate early promoter; Rous sarcoma virus promoter; and human gene promoters such as, but not limited to, the actin promoter, the myosin promoter, the hemoglobin promoter, and the creatine kinase promoter; and functional fragments and variants thereof.

In certain embodiments, the promoter is a hEF1A1 promoter. A hEF1A1 promoter may comprise the sequence of SEQ ID NO: 577, or a functional fragment or variant thereof. In certain embodiments, the functional variant has at least 80%, 85%, 90%, 95%, 96%, 97%, 98%, or 99% sequence identity with SEQ ID NO: 577, or hybridizes under stringent hybridization conditions with the complement of SEQ ID NO: 577. In certain embodiments, the promoter is a CMV promoter. A CMV promoter may comprise the sequence of SEQ ID NO: 578, or a functional fragment or variant thereof. In certain embodiments, the functional variant has at least 80%, 85%, 90%, 95%, 96%, 97%, 98%, or 99% sequence identity with SEQ ID NO: 578, or hybridizes under stringent hybridization conditions with the complement of SEQ ID NO: 578.

In contrast to constitutive promoters, the use of an inducible promoter provides a molecular switch capable of turning on the expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. In one aspect, the inducible promoter can be a gene switch ligand inducible promoter. In some cases, an inducible promoter can be a small molecule ligand-inducible two polypeptide ecdysone receptor-based gene switch, such as a RHEOSWITCH® gene switch.

VIII. Vectors and Delivery Systems

In certain embodiments, the polynucleotide of the present invention can be delivered to a target cell by any suitable delivery system, including non-viral and viral delivery systems. In some embodiments, a vector can include a polynucleotide of the present disclosure encoding the miRNA, CAR, cytokine, cell tag, or any combination thereof.

In certain cases, the miRNA(s), CAR, cytokine, and/or cell tag are expressed in separate vectors. In other aspects, the miRNA(s), CAR, cytokine, and/or cell tag are expressed from one single vector. In certain cases, the CAR and the miRNA(s) are expressed in separate vectors. In other aspects, the miRNA(s), CAR and cytokine are expressed from one single vector. In specific cases, the vectors can be lentiviral vectors, retroviral vectors, Sleeping Beauty transposons or vectors containing sequences for serine recombinase mediated integration. In some aspects, the vector is a plasmid, a mini-circle DNA or a nanoplasmid.

In certain embodiments, where the vector is a plasmid, mini-circle DNA or a nanoplasmid, the plasmid, mini-circle DNA or nanoplasmid can further include a bacterial origin of replication. In certain embodiments, the bacterial origin of replication can be from a ColE1 plasmid. In certain embodiments, the bacterial origin of replication comprises the sequence of SEQ ID NO: 579, or a functional fragment or variant thereof. In certain embodiments, the functional variant has at least 80%, 85%, 90%, 95%, 96%, 97%, 98%, or 99% sequence identity with SEQ ID NO: 579, or hybridizes under stringent hybridization conditions with the complement of SEQ ID NO: 579.

In order to assess the expression of one or more miRNA(s) and a CAR described herein or portions thereof, the expression vector to be introduced into a cell can also contain either a selectable marker gene or a reporter gene or both to facilitate identification and selection of expressing cells from the population of cells sought to be transfected or infected through viral vectors or non-viral vectors. In other aspects, the selectable marker can be carried on a separate piece of DNA and used in a co-transfection procedure. Both selectable markers and reporter genes can be flanked with appropriate regulatory sequences to enable expression in the host cells. Useful selectable markers include, for example, antibiotic-resistance genes, such as neomycin resistance gene (neo) and ampicillin resistance gene and the like. In some embodiments, a truncated epidermal growth factor receptor (HER1t or HER1t-1) tag can be used as a selectable marker gene.

Reporter genes can be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes include genes encoding luciferase, beta-galactosidase, chloramphenicol acetyl transferase, secreted alkaline phosphatase, or the green fluorescent protein gene (e.g., Ui-Tei et al., FEBS Letters 479: 79-82 (2000)). Suitable expression systems are well known and can be prepared using known techniques or obtained commercially. In general, the construct with the minimal 5' flanking region showing the highest level of expression of reporter gene is identified as the promoter. Such promoter regions can be linked to a reporter gene and used to evaluate agents for the ability to modulate promoter-driven transcription.

In some embodiments, a viral vector described herein can comprise a hEF1A1 promoter to drive expression of transgenes, a bovine growth hormone polyA sequence to enhance transcription, a woodchuck hepatitis virus posttranscriptional regulatory element (WPRE), as well as LTR sequences derived from the pFUGW plasmid.

A. Methods for Introducing Nucleic Acids into Cells

Methods of introducing and expressing genes into a cell are well known. In the context of an expression vector, the vector can be readily introduced into a host cell, e.g., mammalian, bacterial, yeast, or insect cell by any method in the art. For example, the expression vector can be transferred into a host cell by physical, chemical, or biological means.

1. Physical Methods

Physical methods for introducing a polynucleotide into a host cell, for instance an immune effector cell, include calcium phosphate precipitation, lipofection, particle bombardment, microinjection, electroporation, and the like. Methods for producing cells comprising vectors and/or exogenous nucleic acids are well-known in the art. See, for example, Sambrook et al. (Molecular Cloning: A Laboratory Manual, Cold Spring Harbor Laboratory, New York (2001)). In some embodiments, a method for the introduction of a polynucleotide into a host cell is calcium phosphate transfection or polyethylenimine (PEI) Transfection. In some embodiments, a method for introduction of a polynucleotide into a host cell is electroporation.

a. Electroporation (EP) Buffers

Various buffers can be used for electroporation. The buffers disclosed herein were found to have improved properties, including enhanced transfection capabilities, notwithstanding that these buffers comprise fewer components as compared to other known electroporation buffers.

Table 4 provides differing amounts of monobasic and dibasic phosphate used as buffering agents. Table 5 provides buffers 1-20 which contain buffering agents and glucose. Table Z provides buffers 21-37 which contain buffering agents and mannitol. Table 7 provides pH, conductivity, and osmolality for Buffers 1, 2 and 3 compared to a control buffer (Mirus Bio™ Ingenio™ electroporation solution, Catalog No. MIR-50117; Mirus Bio LLC, Madison, WI, USA) ("Control 1").

TABLE 4

Differing Amounts of Monobasic and Dibasic Phosphate Used as a Buffering Agent

| 0.2M $NaH_2PO_4$ (mL) | 0.2M $Na_2HPO_4$ (mL) | pH |
|---|---|---|
| 92.0 | 8.0 | 5.8 |
| 90.0 | 10.0 | 5.9 |
| 87.7 | 12.3 | 6.0 |
| 85.5 | 15.0 | 6.1 |
| 81.5 | 19.5 | 6.2 |
| 77.5 | 22.5 | 6.3 |
| 73.5 | 26.5 | 6.4 |
| 68.5 | 31.5 | 6.5 |
| 62.5 | 37.5 | 6.6 |
| 56.5 | 43.5 | 6.7 |
| 51.0 | 49.0 | 6.8 |
| 45.0 | 55.0 | 6.9 |
| 39.0 | 61.0 | 7.0 |

TABLE 4-continued

Differing Amounts of Monobasic and Dibasic Phosphate Used as a Buffering Agent

| 0.2M $NaH_2PO_4$ (mL) | 0.2M $Na_2HPO_4$ (mL) | pH |
|---|---|---|
| 33.0 | 67.0 | 7.1 |
| 28.0 | 72.0 | 7.2 |
| 23.0 | 77.0 | 7.3 |
| 19.0 | 81.0 | 7.4 |
| 16.0 | 84.0 | 7.5 |
| 13.0 | 87.0 | 7.6 |
| 10.5 | 89.5 | 7.7 |
| 8.5 | 91.5 | 7.8 |

TABLE 5

Buffers 1 through 20 - Buffering Agents and Glucose

| Sample No. | Glucose (mM) | HEPES (mM) | $Na_2HPO_4$/ $NaH_2PO_4$ (mM) | KCl (mM) | $MgCl_2$ (mM) | DMSO (%) |
|---|---|---|---|---|---|---|
| 1 | 30 | 5 | 105 | 10 | 20 | 0 |
| 2 | 31 | 0 | 90 | 5 | 15 | 0 |
| 3 | 30 | 10 | 90 | 5 | 15 | 0 |
| 4 | 25 | 10 | 120 | 15 | 25 | 0 |
| 5 | 30 | 25 | 50 | 2 | 10.5 | 5 |
| 6 | 0 | 5 | 160 | 10 | 10.5 | 0 |
| 7 | 0 | 5 | 160 | 2 | 20 | 5 |
| 8 | 15 | 25 | 160 | 10 | 20 | 5 |
| 9 | 30 | 5 | 160 | 2 | 1 | 2.5 |
| 10 | 15 | 15 | 105 | 6 | 10.5 | 2.5 |
| 11 | 30 | 25 | 50 | 10 | 1 | 0 |
| 12 | 30 | 5 | 50 | 6 | 20 | 5 |
| 13 | 30 | 15 | 160 | 10 | 1 | 5 |
| 14 | 15 | 5 | 50 | 2 | 1 | 0 |
| 15 | 0 | 5 | 50 | 10 | 1 | 5 |
| 16 | 0 | 25 | 50 | 10 | 20 | 2.5 |
| 17 | 30 | 25 | 160 | 2 | 20 | 0 |
| 18 | 0 | 15 | 50 | 2 | 20 | 0 |
| 19 | 0 | 25 | 160 | 6 | 1 | 0 |
| 20 | 0 | 25 | 105 | 2 | 1 | 5 |

TABLE 6

Buffers 21 through 37 - Buffering Agents and Mannitol

| Sample No. | Mannitol (mM) | HEPES (mM) | $Na_2HPO_4$/ $NaH_2PO_4$ (mM) | KCl (mM) | $MgCl_2$ (mM) | DMSO (%) |
|---|---|---|---|---|---|---|
| 21 | 5 | 25 | 160 | 6 | 1 | 0 |
| 22 | 150 | 25 | 50 | 2 | 10.5 | 5 |
| 23 | 5 | 15 | 50 | 2 | 20 | 0 |
| 24 | 150 | 25 | 50 | 10 | 1 | 0 |
| 25 | 5 | 25 | 105 | 2 | 1 | 5 |
| 26 | 77.5 | 5 | 50 | 2 | 1 | 0 |
| 27 | 150 | 5 | 160 | 2 | 1 | 2.5 |
| 28 | 150 | 15 | 160 | 10 | 1 | 5 |
| 29 | 5 | 5 | 50 | 10 | 1 | 5 |
| 30 | 150 | 25 | 160 | 2 | 20 | 0 |
| 31 | 150 | 5 | 105 | 10 | 20 | 0 |
| 32 | 77.5 | 15 | 105 | 6 | 10.5 | 2.5 |
| 33 | 77.5 | 25 | 160 | 10 | 20 | 5 |
| 34 | 150 | 5 | 50 | 6 | 20 | 5 |
| 35 | 5 | 25 | 50 | 10 | 20 | 2.5 |
| 36 | 5 | 5 | 160 | 10 | 10.5 | 0 |
| 37 | 5 | 5 | 160 | 2 | 20 | 5 |

TABLE 7

Composition, pH, Conductivity, and Osmolality of Buffers 1, 2, and 3 Compared to Control 1

| Sample No. | Glucose (mM) | HEPES (mM) | Na2HPO4/ NaH2PO4 (mM) | KCl (mM) | MgCl2 (mM) | pH | Conductivity (ms/cm) | osm (mOsm/ kgH20) |
|---|---|---|---|---|---|---|---|---|
| 1 | 30 | 5 | 105 | 10 | 20 | 7.0 | 14.3 | 340 |
| 2 | 31 | 0 | 90 | 5 | 15 | 7.1 | 11.6 | 280 |
| 3 | 30 | 10 | 90 | 5 | 15 | 7.1 | 12.8 | 292 |
| Control 1 | X | X | | | | 7.3 | 16.9 | 575 |

In some embodiments, the buffer comprises a solvent, such as water. In some embodiments, the water may be purified and/or sterilized. For example, the water may be subjected to deionization (e.g., capacitive deionization or electrodeionization), reverse osmosis, carbon filtering, microfiltration, ultrafiltration, and/or ultraviolet sterilization. In some embodiments, the water is deionized. In some embodiments, the water is of a quality designated as "water for injection"; also known as "sterile water for injection." Water for injection is generally made by distillation or reverse osmosis. Water for injection is a sterile, nonpyrogenic, solute-free preparation of water, chemically designated "$H_2O$," and having a pH of between about 5.0 and about 7.0, preferably about 5.5.

In some embodiments, the solvent comprises between 0.1% and 99.9% by volume of the total buffer volume. For example, the solvent may comprise at least about 0.1%, 1%, 5%, 10%, 15%, 20%, 25%, 30%, 35%, 40%, 45%, 50%, 55%, 60%, 65%, 70%, 75%, 80%, 85%, 90%, 95%, 99%, or 99.1% by volume of the total buffer volume.

In some embodiments, the buffer comprises a solute, for example a sugar or an organic compound derived from sugar, for example a sugar alcohol. In embodiments wherein the buffer comprises a sugar, the sugar may comprise a monosaccharide, a disaccharide, and/or a polysaccharide. In some embodiments, the sugar comprises a monosaccharide, for example glucose, fructose, and/or galactose. In some embodiments, the sugar comprises a disaccharide, for example sucrose, lactose, and maltose. In some embodiments, the sugar comprises a polysaccharide, for example cellulose or starch. In embodiments wherein the buffer comprises a sugar alcohol, the sugar alcohol may comprise mannitol, sorbitol, xylitol, lactitol, isomalt, maltitol, and/or hydrogenated starch hydrolysates (HSH).

In some embodiments, the sugar is present in an amount less than about 50 millimolar (mM). For example, the sugar may be present in an amount less than about 45 mM, 40 mM, 35 mM, 30 mM, 25 mM, 20 mM, 15 mM, 10 mM, or 5 mM. In some embodiments, the sugar is present in an amount that ranges between about 10 mM and about 50 mM, about 10 mM and about 40 mM, about 10 mM and about 20 mM, or about 25 mM and about 35 mM. In some embodiments, the sugar is present in an amount of about 25 mM, 26 mM, 27 mM, 28 mM, 29 mM, 30 mM, 31 mM, 32 mM, 33 mM, 34 mM, or 35 mM.

In some embodiments, the sugar is glucose. In these embodiments, the glucose may be present in an amount less than about 50 millimolar (mM). For example, the glucose may be present in an amount less than about 45 mM, 40 mM, 35 mM, 30 mM, 25 mM, 20 mM, 15 mM, 10 mM, or 5 mM. In some embodiments, the glucose is present in an amount that ranges between about 10 mM and about 50 mM, about 10 mM and about 40 mM, about 10 mM and about 20 mM, or about 25 mM and about 35 mM. In some embodiments, the glucose is present in an amount of about 25 mM, 26 mM, 27 mM, 28 mM, 29 mM, 30 mM, 31 mM, 32 mM, 33 mM, 34 mM, or 35 mM. In certain embodiments, the glucose is present in an amount of about 30 mM or 31 mM.

In some embodiments, the sugar is mannitol. In these embodiments, the mannitol may be present in an amount less than about 50 millimolar (mM). For example, the mannitol may be present in an amount less than about 45 mM, 40 mM, 35 mM, 30 mM, 25 mM, 20 mM, 15 mM, 10 mM, or 5 mM. In some embodiments, the mannitol is present in an amount that ranges between about 10 mM and about 50 mM, about 10 mM and about 40 mM, about 10 mM and about 20 mM, or about 25 mM and about 35 mM. In some embodiments, the mannitol is present in an amount of about 25 mM, 26 mM, 27 mM, 28 mM, 29 mM, 30 mM, 31 mM, 32 mM, 33 mM, 34 mM, or 35 mM.

In some embodiments, the EP buffer comprises one or more chloride salts, for example potassium chloride (KCl) and/or magnesium chloride ($MgCl_2$). In some embodiments, the buffer further comprises one or more buffering agents, for example, $Na_2HPO_4$, $NaH_2PO_4$, or $Na_2HPO_4/NaH_2PO_4$. In some embodiments, the buffer further comprises one or more of HEPES and/or DMSO. In other embodiments, the buffer specifically excludes one or more buffering agents commonly found in commercial electroporation (EP) buffers. For example, in some embodiments, the buffer excludes one or both of DMSO and/or HEPES.

In some embodiments, the buffer comprises water ($H_2O$), glucose, KCl, $MgCl_2$, and $Na_2HPO_4/NaH_2PO_4$. In some embodiments, the buffer comprises water ($H_2O$), glucose, KCl, $MgCl_2$, $Na_2HPO_4/NaH_2PO_4$, and HEPES. In other embodiments, the buffer comprises water ($H_2O$), glucose, KCl, $MgCl_2$, $Na_2HPO_4/NaH_2PO_4$, HEPES, and DMSO.

In some embodiments, the buffer consists essentially of water ($H_2O$), glucose, KCl, $MgCl_2$, and $Na_2HPO_4/NaH_2PO_4$. In some embodiments, the buffer consists essentially of water ($H_2O$), glucose, KCl, $MgCl_2$, $Na_2HPO_4/NaH_2PO_4$, and HEPES. In other embodiments, the buffer consists essentially of water ($H_2O$), glucose, KCl, $MgCl_2$, $Na_2HPO_4/NaH_2PO_4$, HEPES, and DMSO.

In some embodiments, the buffer consists of water ($H_2O$), glucose, KCl, $MgCl_2$, and $Na_2HPO_4/NaH_2PO_4$. In some embodiments, the buffer consists of water ($H_2O$), glucose, KCl, $MgCl_2$, $Na_2HPO_4/NaH_2PO_4$, and HEPES. In other embodiments, the buffer consists of water ($H_2O$), glucose, KCl, $MgCl_2$, $Na_2HPO_4/NaH_2PO_4$, HEPES, and DMSO.

In some embodiments, the buffering agent has a pH ranging from about 6.0 to 8.0, 6.5 to 8.0, 7.0 to 8.0, 7.5 to 8.0, 6.0 to 7.5, 6.0 to 7.0, 6.0 to 6.5, 6.5 to 7.5, or 6.5 to 7.0. In some embodiments, the buffering agent has a pH of about 6.5, 6.6, 6.7, 6.8, 6.9, 7.0, 7.1, 7.2, 7.3, 7.4, 7.5, 7.6, 7.7, 7.8, 7.9, or 8.0.

In some embodiments, the buffer comprising the one or more buffering agents has a pH ranging from about 6.0 to 8.0, 6.5 to 8.0, 7.0 to 8.0, 7.5 to 8.0, 6.0 to 7.5, 6.0 to 7.0, 6.0 to 6.5, 6.5 to 7.5, or 6.5 to 7.0. In some embodiments, the buffer has a pH of about 6.5, 6.6, 6.7, 6.8, 6.9, 7.0, 7.1, 7.2, 7.3, 7.4, 7.5, 7.6, 7.7, 7.8, 7.9, or 8.0.

In some embodiments, the buffer comprises one or both of $Na_2HPO_4$ and/or $NaH_2PO_4$. In embodiments wherein the buffer comprises both buffering agents, the ratio of the two (i.e., $Na_2HPO_4/NaH_2PO_4$) may be about 1:1, 1:2, 1:3, 1:4, 1:5, 1:6, 1:7, 1:8, 1:9, 9:1, 8:1, 7:1, 6:1 5:1, 4:1, 3:1, 2:1, or 2:3. In some embodiments, the ratio of $Na_2HPO_4/NaH_2PO_4$ has a pH of 6.5, 6.6, 6.7, 6.8, 6.9, 7.0, 7.1, 7.2, 7.3, 7.4, 7.5, 7.6, 7.7, 7.8, or 7.9.

In some embodiments, a mixture of $Na_2HPO_4$ and $NaH_2PO_4$ (also referred to "$Na_2HPO_4/NaH_2PO_4$" or "sodium phosphate") may be present in the buffer in an amount ranging from about 50 mM and 160 mM, 60 mM to 150 mM, 70 mM to 140 mM, 75 mM to 130 mM, 80 mM to 125 mM, 90 mM to 125 mM, 90 mM to 120 mM, 90 mM to 115 mM, or 90 mM to 105 mM. In some embodiments, the $Na_2HPO_4/NaH_2PO_4$ is present in an amount of at least 50 mM, 60 mM, 70 mM, 80 mM, 90 mM, or 100 mM. In some embodiments, the $Na_2HPO_4/NaH_2PO_4$ is present in an amount of 80 mM, 81 mM, 82 mM, 83 mM, 84 mM, 85 mM, 86 mM, 87 mM, 88 mM, 89 mM, 90 mM, 91 mM, 92 mM, 93 mM, 94 mM, 95 mM, 96 mM, 97 mM, 98 mM, 99 mM, 100 mM, 101 mM, 102 mM, 103 mM, 104 mM, 105 mM, 106 mM, 107 mM, 108 mM, 109 mM, 110 mM, 111 mM, 112 mM, 113 mM, 114 mM, 115 mM, 116 mM, 117 mM, 118 mM, 119 mM, or 120 mM. In certain embodiments, the $Na_2HPO_4/NaH_2PO_4$ is present in an amount of 90 mM or 105 mM.

In embodiments wherein the buffer comprises KCl, the KCl may be present in an amount less than about 30 mM. For example, the KCl may be present in an amount less than about 25 mM, 20 mM, 15 mM, 10 mM, or 5 mM. In some embodiments, the KCl is present in an amount that ranges between about 1 mM and about 30 mM, about 2 mM and about 25 mM, about 3 mM and about 20 mM, about 4 mM and about 15 mM, about 5 mM and about 10 mM, or about 5 mM to about 15 mM. In some embodiments, the KCl is present in an amount of about 1 mM, 2 mM, 3 mM, 4 mM, 5 mM, 6 mM, 7 mM, 8 mM, 9 mM, 10 mM, 11 mM, 12 mM, 13 mM, 14 mM, or 15 mM. In certain embodiments, the KCl is present in an amount of about 5 mM or 10 mM. In some embodiments, the KCl has a pH of about 6.5, 6.6, 6.7, 6.8, 6.9, 7.0, 7.1, 7.2, 7.3, 7.4, 7.5, 7.6, 7.7, 7.8, or 7.9.

In embodiments wherein the buffer comprises $MgCl_2$, the $MgCl_2$ may be present in an amount less than about 50 mM. For example, the $MgCl_2$ may be present in an amount less than about 45 mM, 35 mM, 30 mM 25 mM, 20 mM, 15 mM, 10 mM, or 5 mM. In some embodiments, the $MgCl_2$ is present in an amount that ranges between about 5 mM and about 50 mM, about 6 mM and about 45 mM, about 7 mM and about 40 mM, about 8 mM and about 35 mM, about 9 mM and about 30 mM, about 10 mM and about 25 mM, or about 15 mM and about 25 mM. In some embodiments, the $MgCl_2$ is present in an amount of about 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, or 30 mM. In certain embodiments, the $MgCl_2$ is present in an amount of about 15 mM or 20 mM. In some embodiments, the $MgCl_2$ has a pH of about 6.5, 6.6, 6.7, 6.8, 6.9, 7.0, 7.1, 7.2, 7.3, 7.4, 7.5, 7.6, 7.7, 7.8, or 7.9.

In embodiments wherein the buffer comprises HEPES, the HEPES may be present in an amount less than about 30 mM. For example, the HEPES may be present in an amount less than about 25 mM, 20 mM, 15 mM, 10 mM, 5 mM, 4 mM, 3 mM, 2 mM, 1 mM, 0.5 mM, or 0.1 mM. In some embodiments, the HEPES is present in an amount that ranges between about 1 mM and about 30 mM, about 2 mM and about 25 mM, about 3 mM and about 20 mM, about 4 mM and about 15 mM, about 5 mM and about 10 mM. In some embodiments, the HEPES is present in an amount of about 0.1 mM, 0.5 mM, 1 mM, 2 mM, 3 mM, 4 mM, 5 mM, 6 mM, 7 mM, 8 mM, 9 mM, 10 mM, 11 mM, 12 mM, 13 mM, 14 mM, or 15 mM. In certain embodiments, the HEPES is present in an amount of 0 mM, 5 mM, or 10 mM. In some embodiments, the HEPES has a pH of about 6.5, 6.6, 6.7, 6.8, 6.9, 7.0, 7.1, 7.2, 7.3, 7.4, 7.5, 7.6, 7.7, 7.8, or 7.9.

In embodiments wherein the buffer comprises DMSO, the DMSO may be present in an amount equal to or less than 5%, 4%, 3%, 2%, 1%, 0.9%, 0.8%, 0.7%, 0.6%, 0.5%, 0.4%, 0.3%, 0.2%, or 0.1% by volume of the total buffer volume. In some embodiments, DMSO is present from about 0% to about 2.5% by volume of the total buffer volume. In some embodiments, DMSO is present in an amount ranging from about 0.1% to 5%, 1% to 5%, 2% to 5%, 3% to 5%, or 4% to 5% by volume of the total buffer volume. In some embodiments, the DMSO has a pH of about 6.5, 6.6, 6.7, 6.8, 6.9, 7.0, 7.1, 7.2, 7.3, 7.4, 7.5, 7.6, 7.7, 7.8, or 7.9. In other embodiments, DMSO is not included in the buffer at all.

In certain embodiments, the buffer comprises a sugar in an amount equal to or less than 50 mM; HEPES in an amount equal to or less than 25 mM; $Na_2HPO_4/NaH_2PO_4$ in an amount equal to or less than 160 mM; KCl in an amount equal to or less than 10 mM; $MgCl_2$ in an amount equal to or less than 20 mM; and DMSO in an amount equal to or less than 5% by volume of the total buffer volume. In some of these embodiments, the sugar may comprise a monosaccharide and/or a sugar alcohol. In some of these embodiments, the sugar is mannitol and/or glucose. In some of these embodiments, the sugar is glucose. In some embodiments, the buffer does not comprise DMSO.

In certain embodiments, the buffer comprises a sugar in an amount of at least about 15 mM; HEPES in an amount equal to or less than 25 mM; $Na_2HPO_4/NaH_2PO_4$ in an amount of at least about 90 mM; KCl in an amount of at least about 2 mM; $MgCl_2$ in an amount of at least 15 mM; and DMSO in an amount equal to or less than 5% by volume of the total buffer volume. In some of these embodiments, the sugar may comprise a monosaccharide and/or a sugar alcohol. In some of these embodiments, the sugar is mannitol and/or glucose. In some of these embodiments, the sugar is glucose. In some embodiments, the buffer does not comprise DMSO.

In certain embodiments, the buffer comprises a sugar in an amount ranging from about 15 mM to about 35 mM; KCl in an amount ranging from about 5 mM to about 10 mM; $MgCl_2$ in an amount ranging from about 10.5 mM to about 20 mM; $Na_2HPO_4/NaH_2PO_4$ in an amount ranging from about 90 mM to about 105 mM; HEPES in an amount equal to or less than 25 mM; and DMSO in an amount equal to or less than 5% by volume of the total buffer volume. In some of these embodiments, the sugar may comprise a monosaccharide and/or a sugar alcohol. In some of these embodiments, the sugar is mannitol and/or glucose. In some of these embodiments, the sugar is glucose. In some embodiments, the buffer does not comprise DMSO.

In certain embodiments, the buffer comprises glucose in an amount of about 15 mM; KCl in an amount of about 6 mM; $MgCl_2$ in an amount of about 10.5 mM $Na_2HPO_4/NaH_2PO_4$ in an amount of about 105 mM; HEPES in an amount ranging from about 15 mM; and DMSO in an amount of about 2.5% by volume of total buffer volume.

In certain embodiments, the buffer comprises glucose in an amount of about 30 mM; KCl in an amount of about 10 mM; $MgCl_2$ in an amount of about 20 mM; $Na_2HPO_4$/$NaH_2PO_4$ in an amount of about 105 mM; and HEPES in an amount of about 5 mM. In some embodiments, DMSO is specifically excluded from the buffer.

In certain embodiments, the buffer comprises glucose in an amount of about 31 mM; KCl in an amount of about 5 mM; and $MgCl_2$ in an amount of about 15 mM; and $Na_2HPO_4$/$NaH_2PO_4$ in an amount of about 90 mM. In some embodiments, one or more of HEPES and DMSO is/are specifically excluded from the buffer.

In certain embodiments, the buffer comprises glucose in an amount of about 30 mM; KCl in an amount of about 5 mM; and $MgCl_2$ in an amount of about 15 mM; $Na_2HPO_4$/$NaH_2PO_4$ in an amount of about 90 mM; and HEPES in an amount of about 10 mM. In some embodiments, DMSO is specifically excluded from the buffer.

In certain embodiments, the buffer comprises glucose in an amount of about 25 mM; KCl in an amount of about 15 mM; and $MgCl_2$ in an amount of about 25 mM; $Na_2HPO_4$/$NaH_2PO_4$ in an amount of about 120 mM; and HEPES in an amount of about 10 mM. In some embodiments, DMSO is specifically excluded from the buffer.

In certain embodiments, the pH of the buffer may be adjusted. In some embodiments, the buffer is adjusted to a pH of between 6.5 and 8. In some embodiments, the buffer is adjusted to a pH between about 7.0 and 7.6. In some embodiments, the buffer is adjusted to a pH between about 6.9 and 7.2, or between about 7.0 and 7.1. In some embodiments, the buffer is adjusted to a pH of about 6.5, 6.6, 6.7, 6.8, 6.9, 7.0, 7.1, 7.2, 7.3, 7.4, 7.5, 7.6, 7.7, 7.8, 7.9, or 8.0. In certain embodiments, the buffer is adjusted to a pH of about 7.0 or 7.1.

In certain embodiments, the conductivity of the buffer is between about 7.0 ms/cm to about 16.0 ms/cm, about 9.0 ms/cm to about 16.0 ms/cm, about 11.0 ms/cm to about 16.0 ms/cm, or about 13.0 ms/cm to about 16.0 ms/cm. In some embodiments, the conductivity of the buffer is between about 7.0 ms/cm to about 15.0 ms/cm, about 9.0 ms/cm to about 15.0 ms/cm, about 11.0 ms/cm to about 15.0 ms/cm, or about 13.0 ms/cm to about 15.0 ms/cm. In some embodiments, the conductivity of the buffer is about 7.0 ms/cm, about 7.1 ms/cm, about 7.2 ms/cm, about 7.3 ms/cm, about 7.4 ms/cm, about 7.5 ms/cm, about 7.6 ms/cm, about 7.7 ms/cm, about 7.8 ms/cm, about 7.9 ms/cm, about 8.0 ms/cm, about 8.1 ms/cm, about 8.2 ms/cm, about 8.3 ms/cm, about 8.4 ms/cm, about 8.5 ms/cm, about 8.6 ms/cm, about 8.7 ms/cm, about 8.8 ms/cm, about 8.9 ms/cm, about 9.0 ms/cm, about 9.1 ms/cm, about 9.2 ms/cm, about 9.3 ms/cm, about 9.4 ms/cm, about 9.5 ms/cm, about 9.6 ms/cm, about 9.7 ms/cm, about 9.8 ms/cm, about 9.9 ms/cm, about 10.0 ms/cm, about 10.1 ms/cm, about 10.2 ms/cm, about 10.3 ms/cm, about 10.4 ms/cm, about 10.5 ms/cm, about 10.6 ms/cm, about 10.7 ms/cm, about 10.8 ms/cm, about 10.9 ms/cm, about 11.0 ms/cm, about 11.1 ms/cm, about 11.2 ms/cm, about 11.3 ms/cm, about 11.4 ms/cm, about 11.5 ms/cm, about 11.6 ms/cm, about 11.7 ms/cm, about 11.8 ms/cm, about 11.9 ms/cm, about 12.0 ms/cm, about 12.1 ms/cm, about 12.2 ms/cm, about 12.3 ms/cm, about 12.4 ms/cm, about 12.5 ms/cm, about 12.6 ms/cm, about 12.7 ms/cm, about 12.8 ms/cm, about 12.9 ms/cm, about 13.0 ms/cm, about 13.1 ms/cm, about 13.2 ms/cm, about 13.3 ms/cm, about 13.4 ms/cm, about 13.5 ms/cm, about 13.6 ms/cm, about 13.7 ms/cm, about 13.8 ms/cm, about 13.9 ms/cm, about 14.0 ms/cm, about 14.1 ms/cm, about 14.2 ms/cm, about 14.3 ms/cm, about 14.4 ms/cm, about 14.5 ms/cm, about 14.6 ms/cm, about 14.7 ms/cm, about 14.8 ms/cm, about 14.9 ms/cm, about 15.0 ms/cm, about 15.1 ms/cm, about 15.2 ms/cm, about 15.3 ms/cm, about 15.4 ms/cm, about 15.5 ms/cm, about 15.6 ms/cm, about 15.7 ms/cm, about 15.8 ms/cm, about 15.9 ms/cm, or about 16.0 ms/cm. In certain embodiments, the conductivity of the buffer is about 11.6, 12.8, or 14.3.

In some embodiments, the osmolality of the buffer is lower than the osmolality of the cells being transfected (i.e., also known as "intracellular osmolality"). In some embodiments, the osmolality of the buffer ranges from about 250 mOsm/kg $H_2O$ to about 1255 mOsm/kg $H_2O$, about 250 mOsm/kg $H_2O$ to about 1100 mOsm/kg $H_2O$, about 250 mOsm/kg $H_2O$ to about 900 mOsm/kg $H_2O$, about 250 mOsm/kg $H_2O$ to about 700 mOsm/kg $H_2O$, about 250 mOsm/kg $H_2O$ to about 500 mOsm/kg $H_2O$, about 250 mOsm/kg $H_2O$ to about 400 mOsm/kg $H_2O$, or about 250 mOsm/kg $H_2O$ to about 360 mOsm/kg $H_2O$. In some embodiments, the osmolality is about 360 mOsm/kg $H_2O$ to about 1255 mOsm/kg $H_2O$, about 360 mOsm/kg $H_2O$ to about 1100 mOsm/kg $H_2O$, about 360 mOsm/kg $H_2O$ to about 900 mOsm/kg $H_2O$, about 360 mOsm/kg $H_2O$ to about 700 mOsm/kg $H_2O$, about 360 mOsm/kg $H_2O$ to about 500 mOsm/kg $H_2O$, about 360 mOsm/kg $H_2O$ to about 400 mOsm/kg $H_2O$. In some embodiments, the osmolality is about 250 mOsm/kg $H_2O$, 255 mOsm/kg $H_2O$, 260 mOsm/kg $H_2O$, 270 mOsm/kg $H_2O$, 275 mOsm/kg $H_2O$, about 280 mOsm/kg $H_2O$, about 285 mOsm/kg $H_2O$, about 290 mOsm/kg $H_2O$, about 300 mOsm/kg $H_2O$, about 305 mOsm/kg $H_2O$, about 310 mOsm/kg $H_2O$, about 315 mOsm/kg $H_2O$, about 320 mOsm/kg $H_2O$, about 325 mOsm/kg $H_2O$, about 330 mOsm/kg $H_2O$, about 335 mOsm/kg $H_2O$, about 340 mOsm/kg $H_2O$, about 345 mOsm/kg $H_2O$, about 350 mOsm/kg $H_2O$, about 355 mOsm/kg $H_2O$, about 360 mOsm/kg $H_2O$, about 365 mOsm/kg $H_2O$, about 370 mOsm/kg $H_2O$, about 375 mOsm/kg $H_2O$, about 380 mOsm/kg $H_2O$, about 385 mOsm/kg $H_2O$, about 390 mOsm/kg $H_2O$, about 395 mOsm/kg $H_2O$, or about 400 mOsm/kg $H_2O$. In certain embodiments, the osmolality is about 280 mOsm/kg $H_2O$, about 292 mOsm/kg $H_2O$, about 340 mOsm/kg $H_2O$, or about 362 mOsm/kg $H_2O$.

In some embodiments, the buffer is selected from one or more of the exemplary buffers set forth in Tables 5 and 6. In certain embodiments, the buffer is selected from Buffer 1, Buffer 2, or Buffer 3.

In some embodiments, the buffer of the invention is used in conjunction with an UltraPorator™ electroporation apparatus and cartridge (or, cassette); see, PCT/US20/59984 (filed Nov. 11, 2020) and U.S. patent application Ser. No. 17/095,028 (filed Nov. 11, 2020). This apparatus is designed to enable rapid manufacturing for a range of gene and cell therapies. UltraPorator™ is a high-throughput, semi-closed electroporation system for electroporation of large quantities of cells in a single operation. The UltraPorator™ system is an advancement over current electroporation devices by significantly reducing the processing time and contamination risk. For example, UltraPorator may be utilized as a scale-up and commercialization solution for decentralized chimeric antigen receptor (CAR) T-cell manufacturing, such as in the UltraCAR-T™ manufacturing of T-cells reprogrammed to target cancer antigens in vivo.

Buffers of the invention are surprisingly effective in producing high cell transfection efficiencies when electroporation is performed using the buffers in the UltraPorator™ electroporation apparatus and/or cartridge (or, cassette); see, PCT/US20/59984 (filed Nov. 11, 2020) and U.S. patent application Ser. No. 17/095,028.

b. Methods Utilizing the EP Buffer and Recombinant Cells Produced Using Those Methods In another aspect of the invention, a method is provided that utilizes the buffer according to the invention to introduce biologically active material (e.g., DNA or RNA) into cells via electric current (i.e., electroporation). The method comprises forming a suspension by combining cells obtained from a human along with an exogenous biological material into the buffer of the invention, and then applying an electric current in the form of a voltage pulse to the suspension, thereby facilitating the introduction of the biological material into the cells.

In certain embodiments, the voltage pulse may have a field strength of up to 1 to 10 kV*cm-1 and a duration of 5 to 250 μs and a current density of at least 2 A*cm-2. In certain embodiments, the voltage pulse permits the biologically active material (e.g., DNA) to be transfected directly into the cell nucleus of animal and human cells. In certain embodiments, a current flow following the voltage pulse without interruption, having a current density of 2 to 14 A*cm-2, preferably up to 5 A*cm-2, and a duration of 1 to 100 ms, may also be applied.

Using the method according to the invention, the transfection of biologically active material into cells, including into the nucleus of animal cells, may be optimized. In this case, the biologically active material (e.g., nucleic acids, polypeptides, or the like) can be introduced into quiescent or dividing animal cells with a high efficiency.

In some embodiments, the cells are exposed to the buffer for less than 10 minutes. For example, the cells may be exposed to the buffer for less than 9 minutes, less than 8 minutes, less than 7 minutes, less than 6 minutes, less than 5 minutes, less than 4 minutes, less than 3 minutes, less than 2 minutes, or less than 1 minute.

In some embodiments, the method is used to introduce biologically active material into primary human blood cells, pluripotent precursor cells of human blood, as well as primary human fibroblasts and endothelial cells. In some embodiments, the cells are human blood cells, for example immune cells. In certain embodiments, the immune cells are neutrophils, eosinophils, basophils, mast cells, monocytes, macrophages, dendritic cells, natural killer cells, and lymphocytes (B cells and T cells), or some combination thereof. In some embodiments, the lymphocytes are T-cells. In certain embodiments, the cells are obtained from a patient.

In some embodiments, the biological material includes a nucleic acid, peptide, polypeptide, protein, enzyme, RNP, or some combination thereof. In some embodiments, the biological material is heterologous to the cells. In some embodiments, the biological material is partially or fully synthetic.

In some embodiments, the nucleic acid is selected from DNA or RNA. In some embodiments, the DNA may comprise cDNA. In some embodiments, the RNA may comprise mRNA, tRNA, mRNA, lncRNA, sRNA, or a combination thereof. In some embodiments, the nucleic acid is a recombinant nucleic acid. In some embodiments, the peptide comprises a polypeptide, protein, enzyme, antibody, antibody fragment, or combination thereof. In some embodiments, the peptide is recombinant.

Methods utilizing the buffer of the invention result in desirably high transfection yields, especially as compared to methods utilizing other electroporation buffers. In some embodiments, the transfection yield with a buffer of the invention is at least about 1.1 times that of the transfection yield with a control (prior art) buffer. For example, the transfection yield with a buffer of the invention may be about 1.1, 1.2, 1.3, 1.4, 1.5, 1.6, 1.7, 2.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 times higher than that of a control (prior art) buffer. In some embodiments, the transfection yield with a buffer of the invention may be greater than 5 times than that of a control (prior art) buffer, such as 6, 7, 8, 9, or 10 times higher. In certain embodiments, the transfection yield with a buffer of the invention is 1.35, 1.41, 1.46, 1.97, 1.98, 2.05, 2.12, 2.40, or 2.44 times higher than that of a control (prior art) buffer.

Methods utilizing the buffer of the invention result in desirably high transfected cell recovery yields, especially as compared to methods utilizing other electroporation buffers. In some embodiments, the transfected cell recovery yield with a buffer of the invention is at least about 1.1 times that of the transfected cell recovery yield with a control (prior art) buffer. For example, the transfected cell recovery yield with a buffer of the invention may be about 1.1, 1.2, 1.3, 1.4, 1.5, 1.6, 1.7, 2.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 higher than that of a control (prior art) buffer. In some embodiments, the transfected cell recovery yield with a buffer of the invention may be greater than 5 times than that of a control (prior art) buffer. In certain embodiments, the transfected cell recovery yield with a buffer of the invention is 1.53, 1.66, 1.72, 1.80, 2.06, 2.17, 2.23, 2.34, or 2.61 times higher than that of a control (prior art) buffer.

In another aspect of the invention, recombinant cells are provided. In some embodiments, recombinant immune cells are produced using the method of the invention. In certain embodiments, the recombinant immune cell is a modified T-cell. In some embodiments, the modified T-cell is a chimeric antigen receptor (CAR) T-cell. In some embodiments, the CAR-T cell is administered to a patient for therapeutic purposes.

c. Electroporation Apparatuses and Their Methods of Use

An exemplary electroporation apparatus comprises: one or more chambers configured to store the buffer and cells during an electroporation process; one or more pairs of electrodes configured to generate electric fields within the one or more chambers during the electroporation process, each electric field corresponding to one chamber; and a flow channel configured to transport the cells during a cell collection process after the electroporation process.

In some embodiments, the apparatus comprises one chamber, two chambers, three chambers, four chambers, five chambers, six chambers, seven chambers, eight chambers, nine chambers, ten chambers, or ten or more chambers. In certain embodiments, the apparatus utilizes continuous flow or a microfluidic system.

In some embodiments, the electroporation apparatus further comprises a pump for pumping a liquid medium from the flow channel into at least one of the chambers during a collection process, wherein the liquid medium is obtained at the inlet port. In some embodiments, the pump comprises a valve or valves connecting the one or more chambers to the flow channel. In some embodiments, the valve or valves are opened one at a time. In some embodiments, the valve or valves permit only one-directional flow of fluid. In some embodiments, each valve corresponds to one chamber. In some embodiments, each valve corresponding to the chamber valves is a pinch-valve or pinch-type valve. In some embodiments, each of the valves operates using a spring motion, a lever motion, or a piston motion.

In some embodiments, the one or more chambers comprises a given chamber; each electrode of the pair of electrodes is located on opposite sides of the given chamber; and each electrode of the pair of electrodes comprises both an interior portion inside the given chamber and an exterior portion external to the given chamber.

In some embodiments, the electroporation apparatus further comprises: an inlet port; an outlet port; and one or more flanking flow channels connecting the inlet port and the outlet port to the flow channel.

In some embodiments, the electroporation apparatus further comprises: a pump for pumping a liquid medium from the flow channel into at least one of the chambers during a collection process, wherein the liquid medium is obtained at the inlet port.

In some embodiments, the electroporation apparatus further comprises: a surface comprising a one or more openings leading to the one or more chambers; and an airflow channel below the openings and connecting airflow between the chambers.

In some embodiments, the electroporation apparatus further comprises: a vent or air filter connecting the airflow channel to an exterior of the electroporation apparatus.

In some embodiments, the electroporation apparatus further comprises: a seal configured to cover the one or more openings. In some embodiments, each chamber in the electroporation apparatus comprises a shape which narrows toward the respective valve(s). In some embodiments, the electroporation apparatus further comprises a pair of electrodes wherein each electrode of the electrode pair is located on opposite sides of each chamber. The distance between the two electrodes in an electrode pair is referred to as the "gap distance" or "separation distance." This distance spans the width of the chamber.

In some embodiments, each of the one or more chambers comprises a gap distance of about 0.1 mm to about 20 mm, about 0.5 mm to about 10 mm, about 1 mm to about 7 mm, or about 1 mm to about 4 mm. In some embodiments, the gap distance is about 0.5 mm, 1.0 mm, 1.5 mm, 2.0 mm, 2.5 mm, 3.0 mm, 3.5 mm, 4.0 mm, 4.5 mm, 5.0 mm, 5.5 mm, 6.0 mm, 6.5 mm, 7.0 mm, 7.5 mm, or 8.0 mm. In some embodiments, a gap distance of about 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, or 4.0 mm. In some embodiments, the gap distance is less than about 4 mm, less than about 3.5 mm, less than about 3.0 mm, less than about 2.5 mm, less than about 2.0 mm, less than about 1.5 mm, or less than about 1.0 mm. In some embodiments, a gap distance of less than about 4.0 mm improves the electroporation performance of the buffer provided herein.

In some embodiments, each electrode of the pair of electrodes of the electroporation apparatus comprises: an interior portion inside the given chamber; and an exterior portion external to the given chamber, wherein each pair of electrodes is configured to connect to an electric circuit. In some embodiments, the interior portion inside the given chamber has an elliptical face and comprises a gold coating.

In some embodiments, each chamber of the electroporation apparatus is configured to store a volume of at least about 50 μL, at least about 100 μL, at least about 150 at least about μL, at least about 200 μL, at least about 250 μL, at least about 300 μL, at least about 350 μL, at least about 400 μL, at least about 450 μL, at least about 150 μL, at least about 500 μL, at least about 550 μL, at least about 600 μL, at least about 650 μL, at least about 700 μL, at least about 750 μL, at least about 800 μL, at least about 850 μL, at least about 900 μL, at least about 950 μL, or at least about 1000 μL (1.0 mL).

In some embodiments, the chambers of the electroporation apparatus, in combination, are configured to store at least about 500 μL, at least about 1.0 mL, at least about 1.2 mL, at least about 1.4 mL, at least about 1.6 mL, at least about 1.8 mL, at least about 2.0 mL, at least about 2.2 mL, at least about 2.4 mL, at least about 2.6 mL, at least about 2.8 mL, at least about 3.0 mL, at least about 3.2 mL, at least about 3.4 mL, at least about 3.6 mL, at least about 3.8 mL, at least about 4.0 mL, at least about 4.2 mL, at least about 4.4 mL, at least about 4.6 mL, at least about 4.8 mL, at least about 5.0 mL, at least about 5.2 mL, at least about 5.4 mL, at least about 5.6 mL, at least about 5.8 mL, at least about 6.0 mL, at least about 6.2 mL, at least about 6.4 mL, at least about 6.6 mL, at least about 6.8 mL, or at least about 7.0 mL of cells in liquid suspension for electroporation.

In some embodiments, the cells involved in the electroporation process comprises a population selected from a group consisting of: at least $1\times10^8$ cells, at least $2\times10^8$ cells, at least $3\times10^8$ cells, at least $4\times10^8$ cells, at least $5\times10^8$ cells, at least $6\times10^8$ cells, at least $7\times10^8$ cells, at least $8\times10^8$ cells, at least $9\times10^8$ cells, at least $1\times10^9$ cells, at least $2\times10^9$ cells, at least $3\times10^9$ cells, at least $4\times10^9$ cells, at least $5\times10^9$ cells, at least $6\times10^9$ cells, at least $7\times10^9$ cells, at least $8\times10^9$ cells, at least $9\times10^9$ cells, at least $1\times10^{10}$ cells, at least $2\times10^{10}$ cells, at least $3\times10^{10}$ cells, at least $4\times10^{10}$ cells, at least $5\times10^{10}$ cells, at least $6\times10^{10}$ cells, at least $7\times10^{10}$ cells, at least $8\times10^{10}$ cells, at least $9\times10^{10}$ cells, at least $1\times10^{11}$ cells, at least $2\times10^{11}$ cells, at least $3\times10^{11}$ cells, at least $4\times10^{11}$ cells, at least $5\times10^{11}$ cells, at least $6\times10^{11}$ cells, at least $7\times10^{11}$ cells, at least $8\times10^{11}$ cells, at least $9\times10^{11}$ cells, at least $1\times10^{12}$ cells, at least $2\times10^{12}$ cells, at least $3\times10^{12}$ cells, at least $4\times10^{12}$ cells, at least $5\times10^{12}$ cells, at least $6\times10^{12}$ cells, at least $7\times10^{12}$ cells, at least $8\times10^{12}$ cells, and at least $9\times10^{12}$.

In some embodiments, the apparatus of the invention comprises an UltraPorator™ electroporation apparatus and cartridge (see, PCT/US20/59984 and U.S. patent application Ser. No. 17/095,028). As noted above, the UltraPorator™ electroporation apparatus is designed to enable rapid manufacturing for a range of gene and cell therapies. The apparatus may be utilized as a scale-up and commercialization solution for decentralized CAR T-cell manufacturing, such as in the UltraCAR-T™ manufacturing of T-cells reprogrammed to target cancer antigens in vivo.

In some embodiments, the apparatus of the invention is used in a method of electroporation, the method comprising: executing an electroporation process by generating an electric field within a chamber using a pair of electrodes, wherein the chamber is configured to store the buffer and cells during the electroporation process; and executing a cell collection process by: opening a valve connected to the chamber; and transporting the buffer and cells to an outlet port using a flow channel connected to the valve, wherein the chamber, the electrode pair, the valve, the outlet port, and the flow channel are each located within an electroporation apparatus.

In some embodiments, the step of executing a cell collection process further comprises: pumping, through use of a pump, a liquid medium from the flow channel into the chamber, wherein the liquid medium is obtained at an inlet port, and wherein the inlet port and the outlet port are connected to the flow channel by a flanking flow channel within the electroporation apparatus.

In some embodiments, the cell collection process further comprises: draining the chamber into the flow channel, wherein pressure within the chamber is maintained via a vent or air filter connected to an air flow channel running between the chamber and another chamber.

In some embodiments, the method of electroporation further comprises: depositing the cells into an opening leading to the chamber holding the buffer; applying a seal to the opening; and connecting the electrode pair to at least one circuit by, for example, inserting the electroporation apparatus into a docking station.

In some embodiments, the method utilizes one or more of the exemplary buffers set forth in Tables 5 and 6. In certain embodiments, the method utilizes Buffer 1, Buffer 2, or Buffer 3.

In some embodiments, the method is performed in an UltraPorator™ electroporation apparatus (see, PCT/US20/59984 and U.S. patent application Ser. No. 17/095,028). In certain embodiments, the method is performed in an UltraPorator™ electroporation apparatus and utilizes one or more of the exemplary buffers set forth in Tables 5 and 6. In certain embodiments, the method is performed in an UltraPorator™ electroporation apparatus and utilizes Buffer 1, Buffer 2, or Buffer 3 (as set forth in Table 5).

d. Electroporation Systems

In another aspect of the invention, a system for electroporation is provided. In some embodiments, the system for electroporation comprises an electroporation apparatus, as described herein, and an electroporation buffer, as described herein. In some embodiments, the electroporation system comprises and UltraPorator™ electroporation apparatus and cartridge (see, PCT/US20/59984 and U.S. patent application Ser. No. 17/095,028). As noted above, the UltraPorator™ electroporation apparatus is designed to enable rapid manufacturing for a range of gene and cell therapies. The device may be utilized as a scale-up and commercialization solution for decentralized CAR T-cell manufacturing, such as in the UltraCAR-T™ manufacturing of T-cells reprogrammed to target cancer antigens in vivo.

In some embodiments, the system for electroporation further comprises a buffer is from one or more of the exemplary buffers set forth in Tables 5 and 6. In certain embodiments, the system for electroporation comprises a buffer selected from Buffer 1, Buffer 2, or Buffer 3. It has been found that systems comprising an UltraPorator™ device and one of Buffers 1, 2, or 3 result in surprisingly high cell transfection efficiencies, as compared to systems comprising an UltraPorator™ device and a control buffer.

e. Kits for Electroporation

In another aspect of the invention, a kit for electroporation is provided. The kit may include any of the buffers as described herein. In some embodiments, the kit comprises one or more of the exemplary buffers set forth in Tables 5 and 6. In certain embodiments, the kit comprises a buffer selected from Buffer 1, Buffer 2, or Buffer 3.

In some embodiments, the kit includes one or more containers filled with a buffer according to the invention and other suitable reagents and/or devices. For example, the kit may additionally comprise a vector comprising a nucleic acid of interest. In some embodiments, the kit may include a dropper, pipette, and/or cuvette. In some embodiments, the buffer may be packaged in aliquoted containers or as a stock solution.

In some embodiments, the kit further comprises packaging to safely transport the buffer and any additional reagents and/or devices. In some embodiments, the kit includes information about the contents of the buffer and any additional reagents. Further, the kit may comprise written materials, for example a user manual or answers to frequently asked questions.

2. Chemical Methods

Chemical methods for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

3. Viral Vectors and Delivery Methods

In the case where a viral delivery system is utilized, an exemplary delivery vehicle is a liposome. Lipid formulations can be used for the introduction of the nucleic acids into a host cell (in vitro, ex vivo, or in vivo). In another aspect, the nucleic acid can be associated with a lipid. The nucleic acid associated with a lipid can be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they can be present in a bilayer structure, as micelles, or with a "collapsed" structure. They can also simply be interspersed in a solution, possibly forming aggregates that are not uniform in size or shape. Lipids are fatty substances which can be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids can be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., Glycobiology 5: 505-10 (1991)). However, compositions that have different structures in solution than the normal vesicular structure are also encompassed. For example, the lipids can assume a micellar structure or merely exist as nonuniform aggregates of lipid molecules. Also contemplated are lipofectamine-nucleic acid complexes.

Also provided herein are viral-based delivery systems, in which a nucleic acid of the present invention is inserted. Representative viral expression vectors include, but are not limited to, the adenovirus-based vectors (e.g., the adenovirus-based Per.C6 system available from Crucell, Inc. (Leiden, The Netherlands)), adeno-associated virus based vectors, lentivirus-based vectors (e.g., the lentiviral-based pLPI from Life Technologies (Carlsbad, Calif.)), retroviral vectors (e.g., the pFB-ERV plus pCFB-EGSH), and herpes virus-based vectors. In an embodiment, the viral vector is a lentivirus vector. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In general, and in embodiments, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In some embodiments, a lentiviral vector is provided comprising a backbone and a nucleic acid sequence encoding one or more miRNA(s) and a CAR. Optionally, the vector further comprises a nucleic acid encoding a cytokine and a cell tag such as truncated HER1, CD20t-1 or a full length CD20.

In some embodiments, the nucleic acid encoding one or more miRNA(s) and a CAR is cloned into a vector comprising lentiviral backbone components. Exemplary backbone components include, but are not limited to, pFUGW, and pSMPUW. The pFUGW lentiviral vector backbone is a self-inactivating (SIN) lentiviral vector backbone and has unnecessary HIV-1 viral sequences removed resulting in reduced potential for the development of neoplasia, harmful mutations, and regeneration of infectious particles. In some embodiments, the vector encoding one or more miRNA(s) and a CAR also encodes a cytokine in a single construct. In some embodiments, the one or more miRNA(s) and a CAR and cytokine are encoded on two separate lentiviral vectors. In some embodiments, the cytokine is expressed with a cell tag. In some embodiments, one or more miRNA(s) and a CAR can be co-expressed with the cytokine and the cell tag from a single lentiviral vector. In further embodiments, one or more miRNA(s) and a CAR can be under the control of an inducible promoter. In another embodiment, the cytokine can be under the control of an inducible promoter. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

Other suitable vectors include integrating expression vectors, which can randomly integrate into the host cell's DNA, or can include a recombination site to enable the specific recombination between the expression vector and the host cell's chromosome. Such integrating expression vectors can utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNA™5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), and pCI or pFN10A (ACT) FLEXI™ from Promega (Madison, Wis.). Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

In some embodiments, the cell tag gene is cloned into a lentiviral plasmid backbone in frame with the CAR gene. In other embodiments, the cell tag is cloned into a separate lentiviral vector.

4. Non-Viral Vectors and Delivery Systems a. Sleeping Beauty Transposon System

A polynucleotide encoding one or more miRNA(s) alone or a polynucleotide encoding one or more miRNA(s) and a chimeric receptor, cytokine, and/or cell tag as described herein can be introduced into immune effector cells using non-viral based delivery systems, such as the "Sleeping Beauty (SB) Transposon System," which refers to a synthetic DNA transposon system for introducing DNA sequences into the chromosomes of vertebrates. An exemplary Sleeping Beauty transposon system is described for example, in U.S. Pat. Nos. 6,489,458 and 8,227,432. As used herein, the Sleeping Beauty transposon system can comprise Sleeping Beauty transposase polypeptides as well as derivatives, functional fragments, and variants thereof, and Sleeping Beauty transposon polynucleotides, derivatives, and functional variants and fragments thereof. In certain embodiments, the Sleeping Beauty transposase is encoded by an mRNA. In some embodiments, the mRNA encodes for a SB10, SB11, SB100x or SB110 transposase. In some embodiments, the mRNA comprises a cap and a poly-A tail.

DNA transposons translocate from one DNA site to another in a simple, cut-and-paste manner. Transposition is a precise process in which a defined DNA segment is excised from one DNA molecule and moved to another site in the same or different DNA molecule or genome. As with other Tc 1/mariner-type transposases, SB transposase inserts a transposon into a TA dinucleotide base pair in a recipient DNA sequence. The insertion site can be elsewhere in the same DNA molecule, or in another DNA molecule (or chromosome). In mammalian genomes, including humans, there are approximately 200 million TA sites. The TA insertion site is duplicated in the process of transposon integration. This duplication of the TA sequence is a hallmark of transposition and used to ascertain the mechanism in some experiments. The transposase can be encoded either within the transposon or the transposase can be supplied by another source, in which case the transposon becomes a non-autonomous element. Non-autonomous transposons are most useful as genetic tools because after insertion they cannot independently continue to excise and re-insert. Sleeping Beauty transposons envisaged to be used as non-viral vectors for introduction of genes into genomes of vertebrate animals and for gene therapy.

Briefly, the Sleeping Beauty system (Hackett et al., Mol Ther 18:674-83, (2010)) was adapted to genetically modify the immune effector cells (Cooper et al., Blood 105:1622-31, (2005)). In one embodiment, this involves two steps: (i) the electro-transfer of DNA plasmids expressing a Sleeping Beauty transposon (Jin et al., Gene Ther 18:849-56, (2011); Kebriaei et al., Hum Gene Ther 23:444-50, (2012)) and Sleeping Beauty transposase and (ii) the propagation and expansion of T cells stably expressing integrants on designer artificial antigen-presenting cells (AaPC) derived from the K562 cell line (also known as AaPCs (Activating and Propagating Cells). In another, embodiment, the second step (ii) is eliminated and the genetically modified T cells are cryopreserved or immediately infused into a patient.

In one embodiment, the Sleeping Beauty transposon systems are described for example in Hudecek et al., Critical Reviews in Biochemistry and Molecular Biology, 52:4, 355-380 (2017), Singh et al., Cancer Res (8):68 (2008). Apr. 15, 2008 and Maiti et al., J Immunother. 36(2): 112-123 (2013).

In some embodiments, one or more miRNA(s), a CAR, a cytokine, and a cell tag can be encoded by a single transposon DNA plasmid vector. In some embodiments, the one or more miRNA(s), CAR, cytokine, and cell tag can be encoded by different transposon DNA plasmid vectors. In further embodiments, one or more miRNA(s) and a CAR can be under the control of an inducible promoter. In another embodiment, the cytokine can be under the control of an inducible promoter. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch further described below. In certain embodiments, the CAR, cytokine, and cell tag can be configured in one, two or more transposons.

In some embodiments, the MUC16, CD33, or ROR1-specific CARs and other genetic elements are delivered to a cell using the SB11 transposon system, the SB100X transposon system, the SB110 transposon system, the piggyBac transposon system (see, e.g., U.S. Pat. Nos. 6,489,458; 8,227,432, 9,228,180, Wilson et al, "PiggyBac Transposon-mediated Gene Transfer in Human Cells," Molecular Therapy 15:139-145 (2007) and WO 2016/145146) and/or the piggyBat transposon system (see, e.g., Mitra et al., "Functional characterization of piggyBat from the bat *Myotis lucifugus* unveils an active mammalian DNA transposon," Proc. Natl. Acad. Sci USA 110:234-239 (2013). Additional transposases and transposon systems are provided in U.S. Pat. Nos. 7,148,203; 8,227,432; U.S. Patent Publn. No. 2011/0117072; Mates et al., *Nat Genet,* 41(6):753-61 (2009). doi: 10.1038/ng.343. Epub 2009 May 3, *Gene Ther.,* 18(9):849-56 (2011). doi: 10.1038/gt.2011.40. Epub 2011 Mar. 31 and in Ivics et al., *Cell.* 91(4):501-10, (1997).

In certain embodiments, the vector is a Sleeping Beauty plasmid that comprises a left transposon repeat region and a right transposon repeat region. In certain embodiments, the left transposon repeat region comprises a nucleic acid comprising SEQ ID NO: 580 or a functional fragment or variant thereof. In certain embodiments, the functional variant has at least 80%, 85%, 90%, 95%, 96%, 97%, 98%, or 99% sequence identity with SEQ ID NO: 580, or hybridizes under stringent hybridization conditions with the complement of SEQ ID NO: 580. In certain embodiments, the right transposon repeat region comprises a nucleic acid comprising SEQ ID NO: 581 or a functional fragment or variant thereof. In certain embodiments, the functional variant has at least 80%, 85%, 90%, 95%, 96%, 97%, 98%, or 99% sequence identity with SEQ ID NO: 581, or hybridizes under stringent hybridization conditions with the complement of SEQ ID NO: 581.

b. Recombinase-Based Delivery Systems

In other embodiments, nucleic acids encoding one or more miRNA(s), a CAR, a cytokine, and/or a cell tag can be integrated into the immune effector cell's DNA through a recombinase and integrating expression vectors. Such vectors can randomly integrate into the host cell's DNA, or can include a recombination site to enable the specific recombination between the expression vector and the host cell's chromosome. Such integrating expression vectors can utilize the endogenous expression control sequences of the host cell's chromosomes to effect expression of the desired protein. In some embodiments, targeted integration is promoted by the presence of sequences on the donor polynucleotide that are homologous to sequences flanking the integration site. For example, targeted integration using the donor polynucleotides described herein can be achieved following conventional transfection techniques, e.g. techniques used to create gene knockouts or knockins by homologous recombination. In other embodiments, targeted integration is promoted both by the presence of sequences on the donor polynucleotide that are homologous to sequences flanking the integration site, and by contacting the cells with donor polynucleotide in the presence of a site-specific recombinase. By a site-specific recombinase, or simply a recombinase, it is meant a polypeptide that catalyzes conservative site-specific recombination between its compatible recombination sites. As used herein, a site-specific recombinase includes native polypeptides as well as derivatives, variants and/or fragments that retain activity, and native polynucleotides, derivatives, variants, and/or fragments that encode a recombinase that retains activity.

The recombinases can be introduced into a target cell before, concurrently with, or after the introduction of a targeting vector. The recombinase can be directly introduced into a cell as a protein, for example, using liposomes, coated particles, or microinjection. Alternately, a polynucleotide, either DNA or messenger RNA, encoding the recombinase can be introduced into the cell using a suitable expression vector. The targeting vector components described above are useful in the construction of expression cassettes containing sequences encoding a recombinase of interest. However, expression of the recombinase can be regulated in other ways, for example, by placing the expression of the recombinase under the control of a regulatable promoter (i.e., a promoter whose expression can be selectively induced or repressed).

A recombinase can be from the Integrase or Resolvase families. The Integrase family of recombinases has over one hundred members and includes, for example, FLP, Cre, and lambda integrase. The Integrase family, also referred to as the tyrosine family or the lambda integrase family, uses the catalytic tyrosine's hydroxyl group for a nucleophilic attack on the phosphodiester bond of the DNA. Typically, members of the tyrosine family initially nick the DNA, which later forms a double strand break. Examples of tyrosine family integrases include Cre, FLP, SSV1, and lambda (λ) integrase. In the resolvase family, also known as the serine recombinase family, a conserved serine residue forms a covalent link to the DNA target site (Grindley, et al., (2006) Ann Rev Biochem 16:16).

In one embodiment, the recombinase is an isolated polynucleotide sequence comprising a nucleic acid sequence that encodes a recombinase selecting from the group consisting of a SPβc2 recombinase, a SF370.1 recombinase, a Bxb1 recombinase, an A118 recombinase and a ϕRv1 recombinase. Examples of serine recombinases are described in detail in U.S. Pat. No. 9,034,652.

Recombinases for use in the practice of the present invention can be produced recombinantly or purified as previously described. Polypeptides having the desired recombinase activity can be purified to a desired degree of purity by methods known in the art of protein ammonium sulfate precipitation, purification, including, but not limited to, size fractionation, affinity chromatography, HPLC, ion exchange chromatography, heparin agarose affinity chromatography (e.g., Thorpe & Smith, Proc. Nat. Acad. Sci. 95:5505-5510, 1998.)

In one embodiment, the recombinases can be introduced into the eukaryotic cells that contain the recombination attachment sites at which recombination is desired by any suitable method. Methods of introducing functional proteins, e.g., by microinjection or other methods, into cells are well known in the art. Introduction of purified recombinase protein ensures a transient presence of the protein and its function, which is often a preferred embodiment. Alternatively, a gene encoding the recombinase can be included in an expression vector used to transform the cell, in which the recombinase-encoding polynucleotide is operably linked to a promoter which mediates expression of the polynucleotide in the eukaryotic cell. The recombinase polypeptide can also be introduced into the eukaryotic cell by messenger RNA that encodes the recombinase polypeptide. It is generally preferred that the recombinase be present for only such time as is necessary for insertion of the nucleic acid fragments into the genome being modified. Thus, the lack of permanence associated with most expression vectors is not expected to be detrimental. One can introduce the recombinase gene into the cell before, after, or simultaneously with, the introduction of the exogenous polynucleotide of interest. In one embodiment, the recombinase gene is present within the vector that carries the polynucleotide that is to be inserted; the recombinase gene can even be included within the polynucleotide.

In one embodiment, a method for site-specific recombination comprises providing a first recombination site and a second recombination site; contacting the first and second recombination sites with a prokaryotic recombinase polypeptide, resulting in recombination between the recombination sites, wherein the recombinase polypeptide can mediate recombination between the first and second recombination sites, the first recombination site is attP or attB, the second recombination site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP, and when the first recombination attachment site is attP, the second recombination attachment site is attB Further embodiments provide for the introduction of a site-specific recombinase into a cell whose genome is to be modified. One embodiment relates to a method for obtaining site-specific recombination in an eukaryotic cell comprises providing a eukaryotic cell that comprises a first recombination attachment site and a second recombination attachment site; contacting the first and second recombination attachment sites with a prokaryotic recombinase polypeptide, resulting in recombination between the recombination attachment sites, wherein the recombinase polypeptide can mediate recombination between the first and second recombination attachment sites, the first recombination attachment site is a phage genomic recombination attachment site (attP) or a bacterial genomic recombination attachment site (attB), the second recombination attachment site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP, and when the first recombination attachment site is attP, the second recombination attachment site is attB. In an embodiment the recombinase is selected from the group consisting of an A118 recombinase, a SF370.1 recombinase, a SPβc2 recombinase, a ϕRv1 recombinase, and a Bxb1 recombinase. In one embodiment the recombination results in integration.

c. Other Non-Viral Delivery Systems

In other embodiments, nucleic acids encoding one or more miRNA(s), a CAR, a cytokine, and/or a cell tag, can be integrated into the immune effector cell's DNA through gene editing systems that utilize CRISPR, TALEN or Zinc-Finger nucleases.

Regardless of the method used to introduce exogenous nucleic acids into a host cell, in order to confirm the presence of the recombinant DNA sequence in the host cell, a variety of assays can be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify peptides or proteins or nucleic acids falling within the scope of the invention.

IX. Engineered T-Cell Receptor (TCR)

In some embodiments, the chimeric receptor comprises an engineered T-cell receptor. The T cell receptor (TCR) is composed of two chains (αβ or γδ) that pair on the surface of the T cell to form a heterodimeric receptor. In some instances, the αβ TCR is expressed on most T cells in the body and is known to be involved in the recognition of specific MHC-restricted antigens. Each α and β chain are composed of two domains: a constant domain (C) that anchors the protein to the cell membrane and is associated with invariant subunits of the CD3 signaling apparatus; and a variable domain (V) that confers antigen recognition through six loops, referred to as complementarity determining regions (CDRs). In some instances, each of the V domains comprises three CDRs; e.g., CDR1, CDR2 and CDR3 with CDR3 as the hypervariable region. These CDRs interact with a complex formed between an antigenic peptide bound to a protein encoded by the major histocompatibility complex (pepMHC) (e.g., HLA-A, HLA-B, HLA-C, HLA-DPA1, HLA-DPB1, HLA-DQA1, HLA-DQB1, HLA-DRA, or HLA-DRB1 complex). In some instances, the constant domain further comprises a joining region that connects the constant domain to the variable domain. In some cases, the beta chain further comprises a short diversity region which makes up part of the joining region.

Both the α and β chains are highly variable, although the T-cell receptor α chain contains a constant (preserved region), i.e., the Va24-Ja18 junction (amino acid sequence GSTLGR or a conservatively substituted amino acid sequence thereof).

In some cases, such TCR are reactive to specific tumor antigen, e.g. NY-ESO, Mage A3, Titin, MART-1, HPV, HBV, MAGE-A4, MAGE-A10, MAGE A3/A6, gp100, MAGE-A 1, or PRAME. In other cases, such TCR are reactive to specific neoantigens expressed within a patient's tumor (i.e. patient-specific, somatic, non-synonymous mutations expressed by tumors). In some cases, engineered TCRs can be affinity-enhanced.

In some embodiments, a TCR is described using the International Immunogenetics (IMGT) TCR nomenclature, and links to the IMGT public database of TCR sequences. For example, there can be several types of alpha chain variable (Vα) regions and several types of beta chain variable (Vβ) regions distinguished by their framework, CDR1, CDR2, and CDR3 sequences. As such, a Vα type can be referred to in IMGT nomenclature by a unique TRAV number. For example, "TRAV21" defines a TCR Vα region having unique framework and CDR1 and CDR2 sequences, and a CDR3 sequence, which is partly defined by an amino acid sequence which is preserved from TCR to TCR but which also includes an amino acid sequence which varies from TCR to TCR Similarly, "TRBV5-1" defines a TCR Vβ region having unique framework and CDR1 and CDR2 sequences, but with only a partly defined CDR3 sequence.

In some cases, the beta chain diversity region is referred to in IMGT nomenclature by the abbreviation TRBD.

In some instances, the unique sequences defined by the IMGT nomenclature are widely known and accessible to those working in the TCR field. For example, they can be found in the IMGT public database and in "T cell Receptor Factsbook", (2001) LeFranc and LeFranc, Academic Press, ISBN 0-12-441352-8.

In some embodiments, an αβ heterodimeric TCR is, for example, transfected as full length chains having both cytoplasmic and transmembrane domains. In some cases, the TCRs contain an introduced disulfide bond between residues of the respective constant domains, as described, for example, in WO 2006/000830.

In some instances, TCRs described herein are in single chain format, for example see WO 2004/033685. Single chain formats include αβ TCR polypeptides of the Vα-L-Vβ, Vβ-L-Vα, Vα-Cα-L-Vβ, Vα-L-Vβ-Cβ, Vα-Cα-L-Vβ-Cβ types, wherein Vα and Vβ are TCR α and β variable regions respectively, Cα and Cβ are TCR α and β constant regions respectively, and L is a linker sequence. In certain embodiments single chain TCRs of the invention may have an introduced disulfide bond between residues of the respective constant domains, as described in WO 2004/033685.

In some embodiments, the TCR can be an αβ TCR. In some embodiments, the TCR can be a γδ TCR. It should be understood that a TCR of the present disclosure can bind to any of the antigen targets described herein.

In some embodiments, the TCR may be any one of the Vδ1, Vδ2, and Vδ1negVδ2neg TCR subsets. In some embodiments, the engineered cell may express any combination of a Vδ1, Vδ2, Vδ3, Vδ5, Vδ7, or Vδ8 TCR chain with a Vγ2, Vγ3, Vγ7, Vγ8, Vγ9, Vγ10, or Vγ11 TCR chain. In some embodiments, the engineered cell may have essentially identical genetic material. In one aspect, the engineered cell may not contain a chimeric antigen receptor.

The TCR described herein may be associated with a detectable label, a therapeutic agent or a PK modifying moiety. Exemplary detectable labels for diagnostic purposes include, but are not limited to, fluorescent labels, radiolabels, enzymes, nucleic acid probes and contrast reagents.

In some cases, each chain of TCR disclosed herein, for example αβ or γδ, comprises a modified spacer region connecting the constant region of a TCR chain to the transmembrane region. In some cases, a spacer region of each chain of TCR disclosed herein comprises 1) a stalk region and 1 or more stalk extension region(s) adjacent to said stalk region. The stalk and stalk extension regions may, for example, be those as previously described for use in chimeric antigen receptors. In some embodiments, each chain of TCR disclosed herein incorporates a spacer that comprises a stalk region (s) and up to 20 stalk extension regions.

In some instances, the stalk region comprises the extracellular hinge region from TCRα or TCRβ chain or the stalk region comprises a sequence with at least 80% homology to the extracellular hinge region from TCRα or TCRβ chain. In alternative instances, the stalk region comprises any portion of extracellular region of TCRα or TCRβ constant region with at least 80% homology to the extracellular region of TCRα or TCRβ constant region respectively. For example, the stalk region can comprise a sequence with at least 80%, 85%, 90%, 95%, or greater than 95% homology to the any portion of extracellular region of TCRα or TCRβ constant region.

TCR chain heterodimers are formed by inter-chain disulfide bonds in extracellular hinge region of α and β chains. In some embodiments, the stalk region comprises a dimerization site. A dimerization site can comprise a disulfide bond formation site. A dimerization site can comprise cysteine residue(s). A stalk region can be capable of forming a disulfide bond. Such a disulfide bond can be formed at a disulfide bond forming site or a dimerization site. In some examples, the dimerization occurs between α and β chains of TCR.

In some embodiments, a stalk extension region is used to link the stalk region to the transmembrane region TCR α and β chains. In certain embodiments, a stalk extension region is used to link the stalk region to constant region of TCR α and β chains. In certain embodiments, the stalk region and the stalk extension region(s) can be connected via a linker.

In some instances, the stalk extension domain comprises a sequence that is partially homologous to the stalk region. In some instances, each of the stalk extension region comprises a sequence that is homologous to the stalk region, except that the stalk extension region lacks the dimerization site of the stalk region. In some cases, each of the stalk extension region comprises a sequence identical to the stalk region. In other cases, each of the stalk extension regions comprise a sequence identical to the stalk region with at least one amino acid residue substitution relative to the stalk region. In some cases, each of the stalk extension region is not capable of forming a disulfide bond or is not capable of dimerization with a homologous stalk extension region.

In other embodiments, one stalk extension region can be connected to another stalk extension region via a linker. Examples of such linkers can include glycine-serine rich linkers.

In some embodiments, the addition of stalk extension region(s) prevents mispairing of transgenic TCR α and β chains with native TCR α and β chains expressed by T cells that are genetically modified.

In some embodiments, a modified immune effector cell of the present disclosure can comprise a TCR of the present disclosure and a cytokine of the present disclosure. In certain embodiments, the modified immune effector cell can comprise a TCR and a fusion protein comprising IL-15 and IL-15Rα, or a fusion protein comprising functional fragments or variants of such domains.

X. Immune Checkpoint Inhibitors

In some embodiments, an engineered cell of the present disclosure can include an immune checkpoint inhibitor. In certain embodiments, a polynucleotide of the present disclosure can further encode an immune checkpoint inhibitor. In certain embodiments, an engineered cell of the present disclosure can comprise such a polynucleotide.

In certain embodiments, the immune checkpoint inhibitor can be an antibody or a functional fragment or variant thereof. In certain embodiments, the immune checkpoint inhibitor can inhibit the activity of an immune checkpoint protein such as PD1, PD-L1, CTLA-4, TIGIT, 4-1BB, PIK3IP1, CD27, CD28, CD40, CD70, CD122, CD137, OX40 (CD134), GITR, ICOS, A2AR, B7-$H_3$ (CD276), B7-$H_4$ (VTCN1), BTLA, IDO, KIR, LAGS, TIM-3, or VISTA.

In some embodiments, the immune checkpoint inhibitor can be an anti-CTLA-4 antibody. The anti-CTLA-4 antibody (e.g., ipilimumab) has shown durable anti-tumor activities and prolonged survival in participants with advanced melanoma, resulting in its Food and Drug Administration (FDA) approval in 2011. See Hodi et al., Improved survival with ipilimumab in patients with metastatic melanoma. N Engl J Med. (2010) Aug. 19; 363(8):711-23. In some embodiments, the one or more checkpoint inhibitors can be an anti-PD-L1 antibody. In some embodiments, the anti-PD-L1 antibody can be a full-length atezolizumab (anti-PD-L1), avelumab (anti-PD-L1), durvalumab (anti-PD-L1), or a fragment or a variant thereof. In some embodiments, the one or more checkpoint inhibitors can be any one or more of CD27 inhibitor, CD28 inhibitor, CD40 inhibitor, CD122 inhibitor, CD137 inhibitor, OX40 (also known as CD134) inhibitor, GITR inhibitor, ICOS inhibitor, or any combination thereof. In some embodiments, the one or more checkpoint inhibitors can be any one or more of A2AR inhibitor, B7-$H_3$ (also known as CD276) inhibitor, B7-$H_4$ (also known as VTCN1) inhibitor, BTLA inhibitor, IDO inhibitor, KIR inhibitor, LAG3 inhibitor, TIM-3 inhibitor, VISTA inhibitor, or any combination thereof.

In some embodiments, the immune checkpoint inhibitor is an anti-PD-L1 antibody, an anti-CTLA-4 antibody, an anti-CD28 antibody, an anti-TIGIT antibody, an anti-LAG3 antibody, an anti-TIM3 antibody, an anti-GITR antibody, an anti-4-1BB antibody, or an anti-OX-40 antibody. In some embodiments, the additional therapeutic agent is an anti-TIGIT antibody. In some embodiments, the immune checkpoint inhibitor is an anti-PD-L1 antibody selected from the group consisting of: BMS935559 (MDX-1105), atexolizumab (MPDL3280A), durvalumab (MEDI4736), and avelumab (MSB0010718C). In some embodiments, the immune checkpoint inhibitor is an anti-CTLA-4 antibody selected from the group consisting of: ipilimumab (YERVOY) and tremelimumab. In some embodiments, the additional therapeutic agent is an anti-LAG-3 antibody selected from the group consisting of: BMS-986016 and LAG525. In some embodiments, the immune checkpoint inhibitor is an anti-OX-40 antibody selected from the group consisting of: MEDI6469, MEDI0562, and MOXR0916. In some embodiments, the additional therapeutic agent is an anti-4-1BB antibody selected from the group consisting of: PF-05082566.

In some embodiments, the engineered cell can include an immune checkpoint inhibitor comprising a PD1-binding moiety. In some embodiments, the PD1-binding moiety (referred to herein as an "anti-PD-1") is selected from an antibody identified in Table 8 (below), or a functional fragment or variant thereof.

TABLE 8

| PD-1 Antibodies | | | |
|---|---|---|---|
| Name | Also Known as | Company | Reference(s) |
| cemiplimab | Libtayo, cemiplimab. REGN2810 | Regeneron, Sanofi | WO 2015/112800 |
| pembrolizumab | Keytruda, MK-3475, SCH 900475, lambrolizumab | Merck (MSD), Schering-Plough | WO 2008/156712, U.S. Pat. No. 8,354,509. U.S. Pat. No. 8,952,136, U.S. Pat. No. 8,900,587 |
| nivolumab | Opdivo, ONO-4538, MDX-1106, BMS-936558, 5C4 | BMS, Medarex, Ono | U.S. Pat. No. 8,728,474. U.S. Pat. No. 8,779,105, U.S. Pat. No. 8.008,449, U.S. Pat. No. 9,067,999, U.S. Pat. No. 9,073,994 |
| toripalimab | JS001, JS-001, TAB001, triprizumab | Junmeng Biosciences, Shanghai Junshi, TopAlliance Bio | Si-Yang Liu et al., *J. Hematol. Oncol.* 10: 136 (2017) |
| sintilimab | Tyvyt, IBI308 | Adimab, Innovent, Lilly | WO 2017/024465, WO 2017/025016, WO 2017/132825, WO 2017/133540 |
| LY3434172 | — | Lilly, Zymeworks | ClinicalTrials.gov Identifier: NCT03936959 |
| JTX-4014 | — | Jounce Therapeutics Inc. | U.S. 2018/0118829; ClinicalTrials.gov Identifier: NCT03790488; Papdopolous et al., *Cancer Immunol Immunother* 70(3): 763-772 (2021)) |
| 609 A | 609A | 3S Bio; Sunshine Guojian Pharma | ClinicalTrials.gov Identifier: NCT03998345 |
| Sym021 | — | Symphogen A/S | Gjetting et al., mAbs 11(4): 666-680 (2019 |

TABLE 8-continued

| PD-1 Antibodies | | | |
|---|---|---|---|
| Name | Also Known as | Company | Reference(s) |
| LZM009 | — | Livzon Pharmaceutical Group | ClinicalTrials.gov Identifier: NCT03286296 |
| budigalimab | ABBV-181, PR-1648817 | Abbvie | Powderly et al., *Annals of Oncology* 29(8) (2018); ClinicalTrials.gov Identifier: NCT03000257 |
| IB | IBI-318 | Innovent, Lilly | ClinicalTrials.gov Identifier: NCT03875157 |
| SCT-I10A | — | Sinocelltech Ltd. | ClinicalTrials.gov Identifier: NCT03821363 |
| SG001 | — | CSPC ZhongQi Pharmaceutical Technology Co., Ltd. | ClinicalTrials.gov Identifier: NCT03852823 |
| AMP-224 | GSK-2661380 | Astra Zeneca, Glaxo Smith Kline | Floudas et al., *Clin. Colorectal Cancer* 18(4) (2019) |
| AMG 404 | AMG404 | Amgen | ClinicalTrials.gov Identifier: NCT03853109 |
| AK112 | — | Akesobio Australia Pty Ltd | ClinicalTrials.gov Identifier: NCT04047290 |
| CS1003 | — | CStone Pharma | Li et al., *Acta Pharmacologica Sinica* 42: 142-148 (2021) |
| MEDI0680 | AMP-514 | Astra Zeneca, Amplimmune, Medimmune | WO 2012/145493, WO 2014/194293 |
| RO7121661 | — | Roche | ClinicalTrials.gov Identifier: NCT03708328 |
| F520 | — | Shandong New Time Pharmaceutical Co. | ClinicalTrials.gov Identifier: NCT03657381 |
| sasanlimab | PF-06801591, RN-888 | Pfizer | Cho et al., *Annals of Oncology* 30(5) (2019) |
| BI 754091 | BI754091 | Boehringer Ingelheim | Kang et al., *J. Clin. Oncology* 38(15) (2020) |
| cetrelimab | JNJ-63723283 | Janssen Biotech | Rutkowski et al., *J. Clin. Oncology* 37: 8 (2019) |
| HerinCAR-PD-1 | — | Ningbo Cancer Hospital | ClinicalTrials.gov Identifier: NCT02873390 |
| HX008 | — | Taizhou Hanzhong Bio | Zhang et al, *mAbs* 12(1) (2020); ClinicalTrials.gov Identifier: NCT03704246 |
| zimberelimab | WBP3055, GLS-010, AB122 | Arcus, Guangzhou Gloria Bio, Harbin Gloria Pharma, WuXi Biologies | US 2019/0270815, Si-Yang Liu et al., *J. Hematol. Oncol.* 10: 136 (2017) |
| retifanlimab | MGA012, INCMGA00012 | Incyte, MacroGenics | WO 2017/19846 |
| balstilimab | AGEN2034, AGEN-2034 | Agenus, Ludwig Inst., Sloan-Kettering | WO 2017/040790 |
| pidilizumab | CT-011, hBat-1, MDV9300 | CureTech, Medivation, Teva | Rosenblatt et al., *J Immunother.* 34(5): 409-418 (2011) |
| teripalimab | — | Henan Cancer Hospital | ClinicalTrials.gov Identifier: NCT03985670 |
| CBT-501 | GB226, GB 226, Genolimzumab, Genormab | CBT Pharmaceuticals, Genor | ClinicalTrials.gov Identifier: NCT03053466. |
| BAT1306 | — | Bio-Thera Solutions | Wu et al., *J. Clin. Oncol.* 37(4)(2019) |
| tislelizumab | BGB-A317 | BeiGene, Celgene | WO 2015/35606, US 2015/0079109 |
| AK105 | — | Akeso, HanX Bio | ClinicalTrials.gov Identifier: NCT03866967 |
| spartalizumab | PDR001, BAP049 | Dana-Farber, Novartis | WO 2015/112900; Lin et al., *Ann. of Oncology*, 29: 8 (2018) |
| prolgolimab | BCD-100 | Biocad | Kaplon et al., *mAbs* 10(2): 183-203 (2018) |
| serplulimab | HLX10 | Henlix Biotech | ClinicalTrials.gov Identifier: NCT04297995 |
| dostarlimab | ANB011, TSR-042, ABT1, WBP-285 | AnaptysBio, Tesaro | WO 2014/179664 |
| camrelizumab | SHR-1210 | Incyte, Jiangsu Hengrui, Shanghai Hengrui | WO 2015/085847; Si-Yang Liu et al., *J. Hematol.* Oncol. 10: 136(2017) |

TABLE 8-continued

| PD-1 Antibodies | | | |
|---|---|---|---|
| Name | Also Known as | Company | Reference(s) |
| IBI319 | IBI-319 | Innovent Biologies (Suzhou) Co. Ltd., Lilly | ClinicalTrials.gov Identifier: NCT04708210 |
| KY1043 | — | Kymab | Van Krinks, Kymab poster no. P625, "KY1043, a novel PD-L1 IL-2 immunocytokine directed towards CD25, delivers potent anti-tumour activity in vitro and in vivo" |
| STI-1110 | — | Sorrento Therapeutics | WO 2014/194302 |
| CA05100948 | Antibody 948 | UCB Biopharma | U.S. Pat. No. 8.993,731 |
| Nb97 | MY2935, MY2626 | Fudan University, Novamab | Xian et al., *Biochem. & Biophys. Res. Comm's* 519(3), 267-273 (2019) |
| ENUM 388D4 | — | Enumeral | Scheuplein et al., *Immunology*, Abstract 4871 (2016) |
| hAb-10D3 | hAb-10D3 | BPS Bioscience | U.S. Pat. No. 10,759,859 |
| Unknown | — | Isis Innovation | WO 2010/029434 |
| ANB030 | — | AnaptysBio Inc. | Grebinoski et al., *Current Opinion in Immunol.* 67: 1-9 (2020) |
| MCLA-134 | — | Merus N.V. | WO 2019/009727 |
| hAb21 | — | Suzhou Stainwei Biotech Inc. | U.S. 2020/0277376 |
| — | — | Ampsource | U.S. 2019/0367617 |
| — | — | Reyoung(Suzhou) Biology Science & Technology Co. | U.S. 2019/0071501 |
| — | — | Xencor, Inc. | WO 2018/071918 |
| — | — | Crown Bio science Inc. | WO 2016/014688 |
| — | — | Beijing Hanmi | U.S. 2020/0299412 |
| — | — | Beijing Hanmi | U.S. 2021/0032343 |
| — | — | Beijing Hanmi | U.S. 2019/0367615 |
| — | — | MabQuest | WO 2016/020856 |
| — | — | Fuso Pharma, Hokkaido U. | WO 2018/034226 |
| — | — | Eureka Therapeutics, Inc., Sloan-Kettering | WO 2016/210129 |
| — | — | Sutro Biopharma, Inc. | WO 2016/077397 |
| — | — | Y-Biologics | U.S. 2019/0248900 |
| — | — | Harbour Biomed Ltd. | WO 2017/016497 |
| — | — | Shanghai PharmaExplorer Co. | Liu et al., *Sci. Rep* 9(1) (2019) |
| — | — | Bio X Cell | Grasselly et al., *Front Immunol* 9: 2100 (2018) |
| — | — | Tongji University | Cai et al., *Invest. New Drugs* 37(5): 799-809 (2019) |
| — | — | Janssen Biotech | U.S. 2018/0355061 |
| — | — | Shanghai Henlius Biotech, Inc. | U.S. 2019/0218295 |
| — | — | Ultrahuman Nine Ltd. | WO 2019/170898 |
| — | — | CytomX | WO 2017/011580 |
| — | — | Nanjing Legend Biotech | WO 2017/133633 |
| — | — | Aduro Biotech | U.S. Pat. No. 10,494,436 |
| — | — | Sutro Biopharm | U.S. Pat. No. 10,822,414 |
| — | — | Versitech Ltd. | U.S. Pat. No. 10,047,137 |
| — | — | STCube & Co., University of Texas | WO 2016/160792 |
| — | — | Tayu Huaxia Biotech Medivcal Group Co. | U.S. 2019/0144543 |
| — | — | Hangzhou Sumgen Biotechnology | U.S. 2019/0016799 |
| — | — | Jiangsu Hengrui Medicine Co, Shanghai Hengrui Pharmaceutical Co | WO 2015/085847 |
| — | — | Salubris (Chengdu) Biotech Co. | WO 2019/201169 |
| — | — | Kadmon Corp. | U.S. Pat. No. 10,407,502 |
| — | — | Augusta University Research Institute | WO 2019/051164 |

TABLE 8-continued

| PD-1 Antibodies | | | |
|---|---|---|---|
| Name | Also Known as | Company | Reference(s) |
| — | — | Abbvie Biotherapeutics Inc. | WO 2018/053106 |
| — | — | Lyvgen Biopharma Holdings Ltd. | WO 2017/087599 |
| — | — | Crescendo Biologies Ltd. | WO 2018/127711 |
| — | — | Zhejiang Teruisi Pharmaceutics Inc. | U.S. 2019/0322747 |
| — | — | Biosion Inc. | WO 2019/204132 |
| — | — | Celgene Corp. | U.S. 2017/0088618 |
| — | — | Asia Biotech Pte. Ltd. | WO 2017/058115 |
| — | — | The Brigham and Women's Hospital | U.S. Pat. No. 10,934,352 |
| — | — | Singapore Immunology Network (SIgN), Institute of Medical Biology, Agency for Science, Technology and Research (A*STAR) | Seidel et al., *Front. Oncol.* 28 (2018) |
| — | — | Chinese People Liberation Army General Hospital | Sun et al., *J Gastrointest Oncol.* 11(6): 1421-1430 (2020) |
| — | — | Immunomedics Inc. | U.S. Pat. No. 10,669,338 |
| — | — | Xiangtan Tenghua Bio | WO 2018/162944 |
| — | — | Beijing Dongfang Biotech | U.S. 2019/0144541 |
| — | — | REMD Biotherapeutics | WO 2018/119474 |
| — | — | Rinat Neuroscience Corp. | U.S. Pat. No. 10,155,037 |
| — | — | Medimmune, Wyeth | WO 2004/056875 |
| — | — | Fudan University | Yuan et al., *Invest. New Drugs* 39(1): 34-51 (2021) |

XI. Gene Switch

Provided herein are gene switch polypeptides, polynucleotides encoding ligand-inducible gene switch polypeptides, and methods and systems incorporating these polypeptides and/or polynucleotides. The term "gene switch" refers to the combination of a response element associated with a promoter, and for instance, an ecdysone receptor (EcR) based system which, in the presence of one or more ligands, modulates the expression of a gene into which the response element and promoter are incorporated. Tightly regulated inducible gene expression systems or gene switches are useful for various applications such as gene therapy, large scale production of proteins in cells, cell based high throughput screening assays, functional genomics and regulation of traits in transgenic plants and animals. Such inducible gene expression systems can include ligand inducible heterologous gene expression systems.

In some embodiments, the polynucleotide or an additional polynucleotide encodes polypeptides for a gene switch system for ligand-inducible control of heterologous gene expression, wherein the gene switch polypeptides include: (a) a first gene switch polypeptide that comprises a DNA binding domain fused to a first nuclear receptor ligand binding domain; and (b) a second gene switch polypeptide that comprises a transactivation domain fused to a second nuclear receptor ligand binding domain; wherein the first gene switch polypeptide and the second gene switch polypeptide are connected by a linker.

In some embodiments, the gene switch system comprises: (a) a first gene switch polypeptide comprising a transactivation domain; (b) a second gene switch polypeptide comprising a DNA binding domain fused to a ligand binding domain; and (c) at least one heterologous polypeptide; wherein one of said first gene switch polypeptide, said second gene switch polypeptide and said heterologous polypeptide is connected by a linker to another one of said first gene switch polypeptide, said second gene switch polypeptide and said heterologous polypeptide, and wherein said polypeptide linker comprises a cleavable linker or ribosome skipping linker sequence.

The heterologous polypeptide may, for example, be a chimeric receptor (e.g., a CAR), a cell tag, or a cytokine as described herein.

In certain embodiments, the gene switch system is of the type described in WO 2018/132494.

In some embodiments, the DNA binding domain comprises at least one of GAL4 (GAL4 DBD), a LexA DBD, a transcription factor DBD, a steroid/thyroid hormone nuclear receptor superfamily member DBD, a bacterial LacZ DBD, and a yeast DBD. In other embodiments, the DNA binding domain comprises the amino acid sequence of SEQ ID NO: 638 or a functional fragment or variant thereof. In some embodiments, the transactivation domain comprises at least one of a VP16 transactivation domain and a B42 acidic activator transactivation domain. In other cases, the transactivation domain comprises an amino acid sequence as shown in SEQ ID NO: 632 or a functional fragment or variant thereof. In some embodiments, at least one of the first nuclear receptor ligand binding domain and the second nuclear receptor ligand binding domain comprises at least one of an ecdysone receptor (EcR), a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a farnesol receptor, or a functional fragment or variant thereof. In some embodiments, at least one of the first nuclear receptor ligand binding domain, the second nuclear receptor ligand binding domain, and the ligand binding domain is derived from the Ecdysone Receptor polypeptide sequence of SEQ ID NOs: 640 or 642 or a functional fragment or variant thereof. In some embodiments, the nuclear receptor ligand binding domain is a RxR domain of SEQ ID NO: 634 or a functional fragment or variant thereof.

In some embodiments, the polynucleotide encodes at least one of GAL4 (GAL4 DBD), a LexA DBD, a transcription factor DBD, a steroid/thyroid hormone nuclear receptor superfamily member DBD, a bacterial LacZ DBD, and a yeast DBD, or a functional fragment or variant thereof. In other embodiments, the DNA binding domain is encoded by a nucleotide sequence as shown in SEQ ID NO: 639 or a functional fragment or variant thereof. In some embodiments, the polynucleotide encodes at least one of a VP16 transactivation domain and a B42 acidic activator transactivation domain. In other cases, the transactivation domain is encoded by a nucleotide sequence as shown in SEQ ID NO: 633 or a functional fragment or variant thereof. In some embodiments, at least one of the first nuclear receptor ligand binding domain, the second nuclear receptor ligand binding domain, and the ligand binding domain is encoded by SEQ ID NO: 641 or 643 or a functional fragment or variant thereof. In some embodiments, at least one of the first nuclear receptor ligand binding domain, the second nuclear receptor ligand binding domain, and the ligand binding domain is encoded by SEQ ID NO: 635 or a functional fragment or variant thereof.

In yet another embodiment, the first gene switch polypeptide comprises a GAL4 DBD, or a functional fragment or variant thereof, fused to an EcR nuclear receptor ligand binding domain, or a functional fragment or variant thereof, and the second gene switch polypeptide comprises a VP16 transactivation domain, or a functional fragment or variant thereof, fused to a retinoid receptor X (RXR) nuclear receptor ligand binding domain, or a functional fragment or variant thereof. In some cases, the first gene switch polypeptide and the second gene switch polypeptide are connected by a linker, which is selected from the group consisting of 2A, GSG-2A, GSG linker (SEQ ID NO: 531), SGSG linker (SEQ ID NO: 533), furinlink variants and derivatives thereof.

In some cases, at least one of the first nuclear receptor ligand binding domain and the second nuclear receptor ligand binding domain comprise any one of amino acid sequences as shown in SEQ ID NOs: 640 or 642 or a functional fragment or variant thereof. In some embodiments, the first gene switch polypeptide comprises a GAL4 DBD, or a functional fragment or variant thereof, fused to an EcR nuclear receptor ligand binding domain, or a functional fragment or variant thereof, and the second gene switch polypeptide comprises a VP16 transactivation domain, or a functional fragment or variant thereof, fused to a retinoid receptor X (RXR) nuclear receptor ligand binding domain, or a functional fragment or variant thereof. In some embodiments, the Gal4 DBD, or a functional fragment or variant thereof, fused to the EcR nuclear receptor ligand binding domain, or a functional fragment or variant thereof, comprises an amino acid sequence as shown in SEQ ID NOs: 644 or 646, or a functional fragment or variant thereof, and the VP16 transactivation domain, or a functional fragment or variant thereof, fused to the retinoid receptor X (RXR) nuclear receptor ligand binding domain, or a functional fragment or variant thereof, comprises an amino acid sequence as shown in SEQ ID NO: 636, or a functional fragment or variant thereof.

In some cases, at least one of the first nuclear receptor ligand binding domain and the second nuclear receptor ligand binding domain are encoded by the amino acid sequences as shown in SEQ ID NOs: 641 or 643, or a functional fragment or variant thereof. In some embodiments, the Gal4 DBD, or a functional fragment or variant thereof, fused to the EcR nuclear receptor ligand binding domain, or a functional fragment or variant thereof, is encoded by the nucleotide sequence as shown in SEQ ID NOs: 645 or 647, or a functional fragment or variant thereof, and the VP16 transactivation domain, or a functional fragment or variant thereof, fused to the retinoid receptor X (RXR) nuclear receptor ligand binding domain, or a functional fragment or variant thereof, is encoded by the nucleotide sequence of SEQ ID NO: 637, or a functional fragment or variant thereof.

In any of the foregoing gene switch embodiments, the linker can be a cleavable linker, a ribosome skipping linker sequence or an IRES linker. In some cases, the linker is an IRES linker and is encoded by a nucleic acid comprising the sequence of SEQ ID NOs: 702 or 703 or a functional fragment or variant thereof. In other cases, the linker is a cleavable linker or ribosome skipping linker sequence. In some embodiments, the cleavable linker or the ribosome skipping linker sequence comprises one or more of a 2A linker, p2A linker, T2A linker, F2A linker, E2A linker, GSG-2A linker, GSG linker, SGSG linker, furinlink linker variants and derivatives thereof. In other embodiments, the cleavable linker or said ribosome skipping linker sequence has a sequence as shown in any one of SEQ ID NOs: 527, 529, 531, 533, 535, 537, 539, 541, 543, 545, 547, 549, 551, 553, 555, 557 and 559 or is encoded by the sequence as shown in any one of SEQ ID NOs: 528, 530, 532, 534, 536, 538, 540, 542, 544, 546, 548, 550, 552, 554, 556, 558, and 560.

In any of the gene switch embodiments, expression of at least one of the first gene switch polypeptide, the second gene switch polypeptide, the antigen-binding polypeptide, and the heterologous polypeptide of any of the compositions as provided herein can be modulated by a promoter, where the promoter is a tissue-specific promoter or an EF1A promoter or functional fragment or variant thereof. In some cases, the promoter comprises the sequence of SEQ ID NOs: 58 and 59 of WO 2018/132494, or a functional fragment or variant thereof. In other cases, the promoter is a tissue-specific promoter comprising a T-cell-specific response element. In another case, the tissue-specific promoter comprises one or more NFAT response element(s). In yet another case, the NFAT response element has a sequence of any one of SEQ ID NOs: 51 to 57 of WO 2018/132494 or a functional fragment or variant thereof.

In an embodiment, expression of the at least one heterologous polypeptide is modified by an inducible promoter. In some embodiments, the inducible promoter has a sequence of any one of SEQ ID NOs: 40 to 64 of WO 2018/132494 or a functional fragment or variant thereof. In other embodiments, the inducible promoter is modulated by at least one of the first gene switch polypeptide and the second gene switch polypeptide.

It should be understood that any of the foregoing polynucleotides can be included in a vector as described herein.

Also provided herein is a method of regulating the expression of a heterologous gene in an effector cell, the method comprising: (a) introducing into the effector cell one or more polynucleotides encoding the polypeptides of the first and second gene switch polypeptides as described herein and the heterologous polypeptide; and (b) contacting the effector cell with a ligand in an amount sufficient to induce expression of the gene encoding the heterologous polypeptide.

In certain embodiments, the ligand in the method of regulating the expression of the heterologous gene in the effector cell as provided herein comprises at least one of: (2S,3R,5R,9R,10R,13R,14S,17R)-17-[(2S,3R)-3,6-dihydroxy-6-methylheptan-2-yl]-2,3,14-trihydroxy-10,13-dimethyl-2,3,4,5,9,11,12,15,16,17-decahydro-1H-cyclopenta[a]phenanthren-6-one; N'-(3,5-Dimethylbenzoyl)-N'-[(3R)-2,2-dimethyl-3-hexanyl]-2-ethyl-3-methoxybenzohydrazide; 5-Methyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Methyl-2,3-dihydro-benzo [1,4]dioxine-6-carboxylic acid N'-(3,5-dimethoxy-4-methyl-benzoyl)-N'-(1-ethyl-2,2-dimethyl-propyl)-hydrazide; 5-Methyl-2,3-dihydro-benzo[1,4]dioxine-6-carboxylic acid N'-(1-tert-butyl-butyl)-N'-(3,5-dimethyl-benzoyl)-hydrazide; 5-Methyl-2,3-dihydro-benzo[1,4]dioxine-6-carboxylic acid N'-(1-tert-butyl-butyl)-N'-(3,5-dimethoxy-4-methyl-benzoyl)-hydrazide; 5-Ethyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Ethyl-2,3-dihydro-benzo[1,4]dioxine-6-carboxylic acid N'-(3,5-dimethoxy-4-methyl-benzoyl)-N '-(1-ethyl-2,2-dimethyl-propyl)-hydrazide; 5-Ethyl-2,3-dihydro-benzo[1,4]dioxine-6-carboxylic acid N'-(1-tert-butyl-butyl)-N '-(3,5-dimethyl-benzoyl)-hydrazide; 5-Ethyl-2,3-dihydro-benzo[1,4]dioxine-6-carboxylic acid N'-(1-tert-butyl-butyl)-N '-(3,5-dimethoxy-4-methyl-benzoyl)-hydrazide; 3,5-Dimethyl-benzoic acid N-(1-ethyl-2,2-dimethyl-propyl)-N'-(3-methoxy-2-methyl-benzoyl)-hydrazide; 3,5-Dimethoxy-4-methyl-benzoic acid N-(1-ethyl-2,2-dimethyl-propyl)-N'-(3-methoxy-2-methyl-benzoyl)-hydrazide; 3,5-Dimethyl-benzoic acid N-(1-tert-butyl-butyl)-N'-(3-methoxy-2-methyl-benzoyl)-hydrazide; 3,5-Dimethoxy-4-methyl-benzoic acid N-(1-tert-butyl-butyl)-N'-(3-methoxy-2-methyl-benzoyl)-hydrazide; 3,5-Dimethyl-benzoic acid N-(1-ethyl-2,2-dimethyl-propyl)-N'-(2-ethyl-3-methoxy-benzoyl)-hydrazide; 3,5-Dimethoxy-4-methyl-benzoic acid N-(1-ethyl-2,2-dimethyl-propyl)-N'-(2-ethyl-3-methoxy-benzoyl)-hydrazide; 3,5-Dimethyl-benzoic acid N-(1-tert-butyl-butyl)-N'-(2-ethyl-3-methoxy-benzoyl)-hydrazide; 3,5-Dimethoxy-4-methyl-benzoic acid N-(1-tert-butyl-butyl)-N'-(2-ethyl-3-methoxy-benzoyl)-hydrazide; 2-Methoxy-nicotinic acid N-(1-tert-butyl-pentyl)-N'-(4-ethyl-benzoyl)-hydrazide; 3,5-Dimethyl-benzoic acid N-(2,2-dimethyl-1-phenyl-propyl)-N'-(4-ethyl-benzoyl)-hydrazide; 3,5-Dimethyl-benzoic acid N-(1-tert-butyl-pentyl)-N'-(3-methoxy-2-methyl-benzoyl)-hydrazide; and 3,5-Dimethoxy-4-methyl-benzoic acid N-(1-tert-butyl-pentyl)-N'-(3-methoxy-2-methyl-benzoyl)-hydrazide.

In some cases, the expression of the gene encoding the polypeptide in the effector cell as provided herein is reduced or eliminated in the absence of the ligand, as compared to the expression in the presence of the ligand. In certain cases, the expression of said heterologous polypeptide is restored by providing additional amounts of the ligand.

In some embodiments, the one or more expression cassettes of the gene switch system further comprise one or more of the following: (a) one or more recombinase attachment sites; and (b) a sequence encoding a serine recombinase. In other embodiments, the one or more expression cassettes further comprise one or more of the following: (a) a non-inducible promoter; and (b) an inducible promoter.

In some embodiments, one of the first and second gene switch polypeptides can be connected to the heterologous polypeptide by a linker.

In some embodiments, the first and second gene switch polypeptides are connected by a polypeptide linker that is an IRES linker.

In some embodiments, the expression cassette can further comprise a second gene encoding a second heterologous polypeptide.

In some embodiments, the gene switch system as provided is for integrating a heterologous gene in a host cell, wherein upon contacting the host cell with the one or more expression cassettes in the presence of the serine recombinase and the one or more recombinase attachment sites, the heterologous gene is integrated in the host cell. In certain embodiments, the gene switch system further comprises a ligand, wherein the heterologous gene is expressed in the host cell upon contact of the host cell by the ligand. In certain embodiments, the one or more recombinase attachment sites can comprise a phage genomic recombination attachment site (attP) or a bacterial genomic recombination attachment site (attB). In some cases, the serine recombinase can be SF370.

In some cases, the expression cassette has the sequence of any one of SEQ ID NOs: 131 to 126 of WO 2018/132494 or a functional fragment or variant thereof.

In certain embodiments, the inducible promoter of the gene switch system can be activated by the transactivation domain. It should be understood that the gene switch system can be included in a single vector or in multiple vectors.

An early version of EcR-based gene switch used *Drosophila melanogaster* EcR (DmEcR) and *Mus musculus* RXR (MmRXR) polypeptides and showed that these receptors in the presence of steroid, ponasteroneA, transactivate reporter genes in mammalian cell lines and transgenic mice (Christopherson et al., 1992; No et al., 1996). Later, Suhr et al., 1998 showed that non-steroidal ecdysone agonist, tebufenozide, induced high level of transactivation of reporter genes in mammalian cells through *Bombyx mori* EcR (BmEcR) in the absence of exogenous heterodimer partner.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. In this example, the ecdysone receptor was isolated from *Drosophila melanogaster*. Typically, such systems require the presence of the silent partner, preferably retinoid X receptor (RXR), in order to provide optimum activation. In mammalian cells, insect ecdysone receptor (EcR) is capable of heterodimerizing with mammalian retinoid X receptor (RXR) and, thereby, be used to regulate expression of target genes or heterologous genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 6,265,173 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S.

Pat. No. 5,880,333 discloses a *Drosophila melanogaster* EcR and ultraspiracle (USP) heterodimer system used in plants in which the transactivation domain and the DNA binding domain are positioned on two different hybrid proteins. In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

International Patent Application No. PCT/US01/0905 discloses an ecdysone receptor-based inducible gene expression system in which the transactivation and DNA binding domains are separated from each other by placing them on two different proteins results in greatly reduced background activity in the absence of a ligand and significantly increased activity over background in the presence of a ligand. This two-hybrid system is a significantly improved inducible gene expression modulation system compared to the two systems disclosed in applications PCT/US97/05330 and PCT/US98/14215. The two-hybrid system is believed to exploit the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). The two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, it is believed that a conformational change is induced which promotes interaction of the antibody with the TGF-β cytokine trap, thereby resulting in dimerization of the DNA binding domain and the transactivation domain. Since the DNA binding and transactivation domains reside on two different molecules, the background activity in the absence of ligand is greatly reduced.

Certain modifications of the two-hybrid system could also provide improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provided higher gene transcription activity at a lower ligand concentration. Furthermore, the two-hybrid system avoids some side effects due to overexpression of RXR that can occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell, thereby resulting in reduced side effects.

The ecdysone receptor (EcR) is a member of the nuclear receptor superfamily and is classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; Cell 97: 161-163). In addition to the ecdysone receptor, other members of this nuclear receptor subfamily 1, group H include: ubiquitous receptor (UR), Orphan receptor 1 (OR-1), steroid hormone nuclear receptor 1 (NER-1), RXR interacting protein-15 (RIP-15), liver x receptor β (LXRβ), steroid hormone receptor like protein (RLD-1), liver x receptor (LXR), liver x receptor α (LXRα), farnesoid x receptor (FXR), receptor interacting protein 14 (RIP-14), and farnesol receptor (HRR-1).

In some cases, an inducible promoter ("IP") can be a small molecule ligand-inducible two polypeptide ecdysone receptor-based gene switch, such as Intrexon Corporation's RHEOSWITCH® gene switch. In some cases, a gene switch can be selected from ecdysone-based receptor components as described in, but without limitation to, any of the systems described in: PCT/US2001/009050 (WO 2001/070816); U.S. Pat. Nos. 7,091,038; 7,776,587; 7,807,417; 8,202,718; PCT/US2001/030608 (WO 2002/029075); U.S. Pat. Nos. 8,105,825; 8,168,426; PCT/US52002/005235 (WO 2002/066613); U.S. application Ser. No. 10/468,200 (U.S. Pub. No. 20120167239); PCT/US2002/005706 (WO 2002/066614); U.S. Pat. Nos. 7,531,326; 8,236,556; 8,598,409; PCT/US2002/005090 (WO 2002/066612); U.S. Pat. No. 8,715,959 (U.S. Pub. No. 20060100416); PCT/US2002/005234 (WO 2003/027266); U.S. Pat. Nos. 7,601,508; 7,829,676; 7,919,269; 8,030,067; PCT/US2002/005708 (WO 2002/066615); U.S. application Ser. No. 10/468,192 (U.S. Pub. No. 20110212528); PCT/US2002/005026 (WO 2003/027289); U.S. Pat. Nos. 7,563,879; 8,021,878; 8,497,093; PCT/US2005/015089 (WO 2005/108617); U.S. Pat. Nos. 7,935,510; 8,076,454; PCT/US2008/011270 (WO 2009/045370); U.S. application Ser. No. 12/241,018 (U.S. Pub. No. 20090136465); PCT/US2008/011563 (WO 2009/048560); U.S. application Ser. No. 12/247,738 (U.S. Pub. No. 20090123441); PCT/US2009/005510 (WO 2010/042189); U.S. application Ser. No. 13/123,129 (U.S. Pub. No. 20110268766); PCT/US2011/029682 (WO 2011/119773); U.S. application Ser. No. 13/636,473 (U.S. Pub. No. 20130195800); PCT/US2012/027515 (WO 2012/122025); WO 2018/132494 (PCT/US2018/013196); and, U.S. Pat. No. 9,402,919.

As used herein, the term "ligand," as applied to ligand-activated ecdysone receptor-based gene switches are small molecules of varying solubility (such as diacylhydrazine compounds) having the capability of activating a gene switch to stimulate gene expression (i.e., therein providing ligand inducible expression of polynucleotides (e.g., mRNAs, miRNAs, etc) and/or polypeptides). Examples of such ligands include, but are not limited to those described in: WO 2004/072254 (PCT/US2004/003775); WO 2004/005478 (PCT/US2003/021149); WO 2005/017126 (PCT/US2004/005149); WO 2004/078924 (PCT/US2004/005912); WO 2008/153801 (PCT/US2008/006757); WO 2009/114201 (PCT/US2009/001639); WO 2013/036758 (PCT/US2012/054141); WO 2014/144380 (PCT/US2014/028768); and, WO 2016/044390 (PCT/US2015/050375).

Examples of ligands also include, without limitation, an ecdysteroid, such as ecdysone, 20-hydroxyecdysone, ponasterone A, muristerone A, and the like, 9-cis-retinoic acid, synthetic analogs of retinoic acid, N, N'-diacylhydrazines such as those disclosed in U.S. Pat. Nos. 6,258,603; 6,013,836; 5,117,057; 5,530,028; 5,378,726; 7,304,161; 7,851,220; 8,748,125; 9,272,986; 7,456,315; 7,563,928; 8,524,948; 9,102,648; 9,169,210; 9,255,273; and, 9,359,289; oxadiazolines as described in U.S. Pat. Nos. 8,669,072; and, 8,895,306; dibenzoylalkyl cyanohydrazines such as those disclosed in European Application No. 2,461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; amidoketones such as those described in U.S. Pat. Nos. 7,375,093; 8,129,355; and, 9,802,936; and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, famesol, bile acids, 1,1-biphosphonate esters, juvenile hormone III, and the like. Examples of diacylhydrazine ligands useful in the present invention include RG-115819 (3,5-Dimethyl-benzoic acid N-(1-ethyl-2,2-dimethyl-propyl)-N'-(2-methyl-3-methoxybenzoyl)-hydrazide), RG-115932 ((R)-3,5-Dimethyl-benzoic acid N-(1-tert-butyl-butyl)N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide). See, e.g., WO 2008/153801 (PCT/US2008/006757); and, WO 2013/036758 (PCT/US2012/054141).

For example, a ligand for the ecdysone receptor-based gene switch may be selected from any suitable ligands. Both naturally occurring ecdysone or ecdysone analogs (e.g., 20-hydroxyecdysone, muristerone A, ponasterone A, ponasterone B, ponasterone C, 26-iodoponasterone A, inokosterone or 26-mesylinokosterone) and non-steroid inducers may be used as a ligand for gene switch of the present invention. U.S. Pat. No. 6,379,945, describes an insect steroid receptor isolated from *Heliothis virescens* ("HEcR") which is capable of acting as a gene switch responsive to both steroid and certain non-steroidal inducers. Non-steroidal inducers have a distinct advantage over steroids, in this and many other systems which are responsive to both steroids and non-steroid inducers, for several reasons including, for example: lower manufacturing cost, metabolic stability, absence from insects, plants, or mammals, and environmental acceptability. U.S. Pat. No. 6,379,945 describes the utility of two dibenzoylhydrazines, 1,2-dibenzoyl-1-tert-butyl-hydrazine and tebufenozide (N-(4-ethylbenzoyl)-N'-(3,5-dimethylbenzoyl)-N'-tert-butyl-hydrazine) as ligands for an ecdysone-based gene switch. Also included in the present invention as a ligand are other dibenzoylhydrazines, such as those disclosed in U.S. Pat. No. 5,117,057. Use of tebufenozide as a chemical ligand for the ecdysone receptor from *Drosophila melanogaster* is also disclosed in U.S. Pat. No. 6,147,282. Additional, non-limiting examples of ecdysone ligands are 3,5-di-tert-butyl-4-hydroxy-N-isobutyl-benzamide, 8-O-acetylharpagide, a 1,2-diacyl hydrazine, an N'-substituted-N,N'-disubstituted hydrazine, a dibenzoylalkyl cyanohydrazine, an N-substituted-N-alkyl-N,N-diaroyl hydrazine, an N-substituted-N-acyl-N-alkyl, carbonyl hydrazine or an N-aroyl-N'-alkylN'-aroyl hydrazine. (See U.S. Pat. No. 6,723,531).

In one embodiment, the ligand for an ecdysone-based gene switch system is a diacylhydrazine ligand or chiral diacylhydrazine ligand. The ligand used in the gene switch system may be compounds of Formula I Formula I

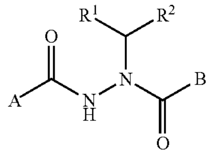

wherein A is alkoxy, arylalkyloxy or aryloxy; B is optionally substituted aryl or optionally substituted heteroaryl; and R1 and R2 are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl; or pharmaceutically acceptable salts, hydrates, crystalline forms or amorphous forms thereof.

In another embodiment, the ligand may be enantiomerically enriched compounds of Formula II Formula II

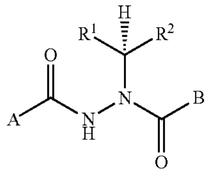

wherein A is alkoxy, arylalkyloxy, aryloxy, arylalkyl, optionally substituted aryl or optionally substituted heteroaryl; B is optionally substituted aryl or optionally substituted heteroaryl; and R1 and R2 are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl; with the proviso that R1 does not equal R2; wherein the absolute configuration at the asymmetric carbon atom bearing R1 and R2 is predominantly S; or pharmaceutically acceptable salts, hydrates, crystalline forms or amorphous forms thereof.

In certain embodiments, the ligand may be enantiomerically enriched compounds of Formula III Formula III

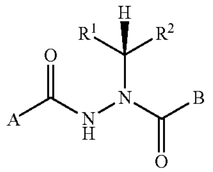

wherein A is alkoxy, arylalkyloxy, aryloxy, arylalkyl, optionally substituted aryl or optionally substituted heteroaryl; B is optionally substituted aryl or optionally substituted heteroaryl; and R1 and R2 are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl; with the proviso that R1 does not equal R2; wherein the absolute configuration at the asymmetric carbon atom bearing R1 and R2 is predominantly R; or pharmaceutically acceptable salts, hydrates, crystalline forms or amorphous forms thereof.

In one embodiment, a ligand may be (R)-3,5-dimethyl-benzoic acid N-(1-tertbutyl-butyl)-N'-(2-ethyl-3-methoxy-benzoyl)-hydrazide having an enantiomeric excess of at least 95% or a pharmaceutically acceptable salt, hydrate, crystalline form or amorphous form thereof.

The diacylhydrazine ligands of Formula I and chiral diacylhydrazine ligands of Formula II or III, when used with an ecdysone-based gene switch system, provide the means for external temporal regulation of expression of a therapeutic polypeptide or therapeutic polynucleotide of the present invention. See U.S. Pat. Nos. 8,076,517; 8,884,060; and, 9,598,355.

The ligands used in the present invention may form salts. The term "salt(s)" as used herein denotes acidic and/or basic salts formed with inorganic and/or organic acids and bases. In addition, when a compound of Formula I, II or III contains both a basic moiety and an acidic moiety, zwitterions ("inner salts") may be formed and are included within the term "salt(s)" as used herein. Pharmaceutically acceptable (i.e., non-toxic, physiologically acceptable) salts are used, although other salts are also useful, e.g., in isolation or purification steps which may be employed during preparation. Salts of the compounds of Formula I, II or III may be formed, for example, by reacting a compound with an amount of acid or base, such as an equivalent amount, in a medium such as one in which the salt precipitates or in an aqueous medium followed by lyophilization.

The ligands which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The ligands which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Non-limiting examples of the ligands for the inducible gene expression system also includes those utilizing the FK506 binding domain are FK506, Cyclosporin A, or Rapamycin. FK506, rapamycin, and their analogs are disclosed in U.S. Pat. Nos. 6,649,595; 6,187,757; 7,276,498; and, 7,273,874.

In some embodiments, a diacylhydrazine ligand for inducible gene expression is administered at unit daily dose of about 5, 10, 15, 20, 25, 30, 35, 40, 50, 60, 70, 80, 90, 100 or 120 mg. In some embodiments, the diacylhydrazine ligand is administered at a unit daily dose of about 5 mg. In some embodiments, the diacylhydrazine ligand is administered at a unit daily dose of about 10 mg. In some embodiments, the diacylhydrazine ligand is administered at a unit daily dose of about 15 mg. In some embodiments, the diacylhydrazine ligand is administered daily at a unit daily dose of about 20 mg.

In some embodiments, the cytokine, cell tag and/or CAR can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch. In some cases, the gene switch system used may be the one described in WO 2018/132494.

In some embodiments, the cytokines described above can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch. In some cases, the gene switch system used may be the one described in WO 2018/132494.

In some embodiments, the modified immune effector cells as described herein can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch as described in WO2018/132494.

XII. Modified Immune Effector Cells

Provided herein are modified immune effector cells expressing one or more miRNAs, CARs, cytokines, and/or cell tags as described herein. In some embodiments, modified immune effector cells are modified T cells and/or natural killer (NK) cells. T cells or T lymphocytes are a subtype of white blood cells that are involved in cell-mediated immunity. Exemplary T cells include T helper cells, cytotoxic T cells, TH17 cells, stem memory T cells (TSCM), naïve T cells, memory T cells, effector T cells, regulatory T cells, or natural killer T cells. In certain aspects, the embodiments described herein include making and/or expanding the modified immune effector cells (e.g., T-cells, Tregs, NK-cell or NK T-cells). Such may be accomplished by transfecting the cells with an expression vector containing a DNA (or RNA) construct encoding the one or more miRNAs, CARs, cytokines, and/or cell tags as described herein. It should be understood that the cells of the present disclosure can be human or animal cells.

T helper cells (TH cells) assist other white blood cells in immunologic processes, including maturation of B cells into plasma cells and memory B cells, and activation of cytotoxic T cells and macrophages. In some instances, TH cells are known as CD4+ T cells due to expression of the CD4 glycoprotein on the cell surfaces. T helper cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including TH1, TH2, TH3, TH17, Th9, or TFH, which secrete different cytokines to facilitate different types of immune responses. Signaling from the APC directs T cells into particular subtypes.

Cytotoxic T cells (TC cells or CTLs) destroy virus-infected cells and tumor cells, and are also implicated in transplant rejection. These cells are also known as CD8+ T cells since they express the CD8 glycoprotein on their surfaces. These cells recognize their targets by binding to antigen associated with MHC class I molecules, which are present on the surface of all nucleated cells. Through IL-10, adenosine, and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise subtypes: stem memory T cells (TSCM), central memory T cells (TCM cells) and two types of effector memory T cells (TEM cells and TEMRA cells). Memory cells can be either CD4+ or CD8+. Memory T cells can express the cell surface proteins CD45RO, CD45RA and/or CCR7.

Regulatory T cells (Treg cells), formerly known as suppressor T cells, play a role in the maintenance of immunological tolerance. Their major role is to shut down T cell-mediated immunity toward the end of an immune reaction and to suppress autoreactive T cells that escaped the process of negative selection in the thymus.

Natural killer T cells (NKT cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d. Once activated, these cells can perform functions ascribed to both Th and Tc cells (i.e., cytokine production and release of cytolytic/cell killing molecules). They are also able to recognize and eliminate some tumor cells and cells infected with herpes viruses.

Natural killer (NK) cells are a type of cytotoxic lymphocyte of the innate immune system. In some instances, NK cells provide a first line defense against viral infections and/or tumor formation. NK cells can detect MHC presented on infected or cancerous cells, triggering cytokine release, and subsequently induce lysis and apoptosis. NK cells can further detect stressed cells in the absence of antibodies and/or MHC, thereby allowing a rapid immune response.

A. Immune Effector Cell Sources

In certain aspects, the embodiments described herein include methods of making and/or expanding the modified (antigen-specific redirected) immune effector cells (e.g., T-cells, Tregs, NK-cell or NK T-cells) that comprise transfecting the cells with an expression vector containing a DNA (or RNA) construct encoding the CAR, then, optionally, stimulating the cells with feeder cells, recombinant antigen, or an antibody to the receptor to cause the cells to proliferate. In certain aspects, the cell (or cell population) engineered to express a CAR is a stem cell, CD34+ cord blood cells, iPS cell, T cell differentiated from iPS cell, immune effector cell or a precursor of these cells.

Sources of immune effector cells can include both allogeneic and autologous sources. In some cases immune effector cells can be differentiated from stem cells or induced pluripotent stem cells (iPSCs). Thus, cells for engineering according to the embodiments can be isolated from umbilical cord blood, peripheral blood, human embryonic stem cells, or iPSCs. For example, allogeneic T cells can be modified to include a chimeric antigen receptor (and optionally, to lack functional TCR). In some aspects, the immune effector cells are primary human T cells such as T cells derived from human peripheral blood mononuclear cells (PBMC). PBMCs can be collected from the peripheral blood or after stimulation with G-CSF (Granulocyte colony stimulating factor) from the bone marrow, or umbilical cord blood. In one aspect, the immune effector cells are Pan T cells. Following transfection or transduction (e.g., with a CAR expression construct), the cells can be immediately infused or can be cryo-preserved. In certain aspects, following transfection or transduction, the cells can be preserved in a cytokine bath that can include IL-2 and/or IL-21 until ready for infusion. In certain aspects, following transfection, the cells can be propagated for days, weeks, or months ex vivo as a bulk population within about 1, 2, 3, 4, 5 days or more following gene transfer into cells. In a further aspect, following transfection, the transfectants are cloned and a clone demonstrating presence of a single integrated or episomally maintained expression cassette or plasmid, and expression of the chimeric antigen receptor is expanded ex vivo. The clone selected for expansion demonstrates the capacity to specifically recognize and lyse antigen-expressing target cells. The recombinant T cells can be expanded by stimulation with IL-2, or other cytokines that bind the common gamma-chain (e.g., IL-7, IL-12, IL-15, IL-21, and others). The recombinant T cells can be expanded by stimulation with artificial antigen presenting cells. The recombinant T cells can be expanded on artificial antigen presenting cell or with an antibody, such as OKT3, which cross links CD3 on the T cell surface. Subsets of the recombinant T cells can be further selected with the use of magnetic bead based isolation methods and/or fluorescence activated cell sorting technology and further cultured with the AaPCs. In a further aspect, the genetically modified cells can be cryopreserved. In some embodiments, the genetically modified cells are not cryopreserved.

T cells can also be obtained from a number of sources, including bone marrow, lymph node tissue, cord blood, thymus tissue, tissue from a site of infection, ascites, pleural effusion, spleen tissue, and tumors. In certain embodiments of the present invention, any number of T cell lines available in the art, can be used. In certain embodiments of the present invention, T cells can be obtained from a unit of blood collected from a subject using any number of techniques known to the skilled artisan, such as Ficoll® separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis can be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and can lack magnesium or can lack many if not all divalent cations. Initial activation steps in the absence of calcium lead to magnified activation. As those of ordinary skill in the art would readily appreciate a washing step can be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells can be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample can be removed and the cells directly resuspended in culture media.

In another embodiment, T cells are isolated from peripheral blood lymphocytes by lysing the red blood cells and depleting the monocytes, for example, by centrifugation through a PERCOLL® gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. In another embodiment, CD14+ cells are depleted from the T-cell population. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours. In one embodiment, the incubation time period is 24 hours. For isolation of T cells from patients with leukemia, use of longer incubation times, such as 24 hours, can increase cell yield. Longer incubation times can be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it can be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it can be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-CD25 conjugated beads or other similar method of selection.

For isolation of a desired population of cells by positive or negative selection, the concentration of cells and surface (e.g., particles such as beads) can be varied. In certain embodiments, it can be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that can weakly express target antigens of interest, such as CD28-negative T cells, or from samples where there are many tumor cells present (i.e., leukemic blood, tumor tissue, etc.). Such populations of cells can have therapeutic value and would be desirable to obtain. For example, using high concentration of cells allows more efficient selection of CD8+ T cells that normally have weaker CD28 expression.

In a related embodiment, it can be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells can be incubated on a rotator for varying lengths of time at varying speeds at either 2-10° C. or at room temperature.

T cells for stimulation can also be frozen after a washing step. After the washing step that removes plasma and platelets, the cells can be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° C. per minute and stored in the vapor phase of a liquid nitrogen storage tank. Other methods of controlled freezing can be used as well as uncontrolled freezing immediately at −20° C. or in liquid nitrogen. In certain embodiments, cryopreserved cells are thawed and washed as described herein and allowed to rest for one hour at room temperature prior to activation using the methods of the present invention.

Also provided in certain embodiments is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells can be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., *Cell* 66:807-815, (1991); Henderson et al., *Immun* 73:316-321, (1991); Bierer et al., *Curr. Opin. Immun* 5:763-773, (1993)). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained can be optimal or improved for their ability to expand ex vivo. Likewise, following ex vivo manipulation using the methods described herein, these cells can be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

B. Activation and Expansion of Immune Effector Cells

Whether prior to or after engineering of the immune effector cells to express a CAR described herein, the cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the immune effector cells described herein are expanded by contact with a surface having attached thereto an agent that stimulates a CD3/TCR complex associated signal and a ligand that stimulates a co-stimulatory molecule on the surface of the cells. In particular, cell populations can be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, (1998); Haanen et al., *J. Exp. Med.* 190(9):13191328, (1999); Garland et al., *J. Immunol Meth.* 227(1-2):53-63, (1999)).

In certain embodiments, the primary stimulatory signal and the co-stimulatory signal for the immune effector cell can be provided by different protocols. For example, the agents providing each signal can be in solution or coupled to a surface. When coupled to a surface, the agents can be coupled to the same surface (i.e., in "cis" formation) or to separate surfaces (i.e., in "trans" formation). Alternatively, one agent can be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents can be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In some embodiments, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between can be used to stimulate T cells or other target cells. As those of ordinary skill in the art can readily appreciate, the ratio of particles to cells can depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one ratio being at least 1:1 particles per T cell. In one embodiment, a ratio of particles to cells of 1:1 or less is used. In one particular embodiment, the particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios can be suitable for use in the present invention. In particular, ratios will vary depending on particle size and on cell size and type.

In further embodiments described herein, the immune effector cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins can be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1, or MACS® MicroBeads from Miltenyi Biotec) are combined in a buffer, for example, PBS (without divalent cations such as, calcium and magnesium). Again, those of ordinary skill in the art can readily appreciate any cell concentration can be used. For example, the target cell can be very rare in the sample and comprise only 0.01% of the sample or the entire sample (i.e., 100%) can comprise the target cell of interest. Accordingly, any cell number is within the context of the present invention. In certain embodiments, it can be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that can weakly express target antigens of interest, such as CD28-negative T cells. Such populations of cells can have therapeutic value and would be desirable to obtain in certain embodiments. For example, using high concentration of cells allows more efficient selection of $CD8^+$ T cells that normally have weaker CD28 expression.

In one embodiment described herein, the mixture can be cultured for several hours (about 3 hours) to about 14 days or any hourly integer value in between. In another embodiment, the mixture can be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that can contain factors necessary for proliferation and viability, including serum (e.g., fetal bovine or human serum), interleukin-2 (IL-2), insulin, IFN-.gamma., IL-4, IL-7, GM-CSF, IL-10, IL-12, IL-15, TGFbeta, and TNF-alpha or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, alpha-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

Ex vivo procedures are well known and are discussed more fully below. Briefly, cells are isolated from a mammal (for example, a human) and genetically modified (i.e., transduced or transfected in vitro) with a vector expressing a CAR disclosed herein. The CAR-modified cell can be administered to a mammalian recipient to provide a therapeutic benefit. The mammalian recipient can be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, can be applied to the cells of the present invention. Other suitable methods are known in the art, therefore the present invention is not limited to any particular method of ex vivo expansion of the cells. Briefly, ex vivo culture and expansion of effector cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

Effector cells that have been exposed to varied stimulation times can exhibit different characteristics. For example, typical blood or apheresed peripheral blood mononuclear cell products have a helper T cell population ($T_H$, $CD4^+$) that is greater than the cytotoxic or suppressor T cell population (Tc, $CD8^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of Tc cells. Accordingly, depending on the purpose of treatment, infusing a subject with a T cell population comprising predominately of $T_H$ cells can be advantageous. Similarly, if an antigen-specific subset of Tc cells has been isolated it can be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In some cases, immune effector cells of the embodiments (e.g., T-cells) are co-cultured with activating and propagating cells (AaPCs), to aid in cell expansion. AaPCs can also be referred to as artificial Antigen Presenting cells (aAPCs). For example, antigen presenting cells (APCs) are useful in preparing therapeutic compositions and cell therapy products of the embodiments. In one aspect, the AaPCs can be genetically modified K562 cells. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009. In yet a further aspect of the embodiments, culturing the genetically modified CAR cells comprises culturing the genetically modified CAR cells in the presence of dendritic cells or activating and propagating cells (AaPCs) that stimulate expansion of the CAR-expressing immune effector cells. In still further aspects, the AaPCs comprise a CAR-binding antibody or fragment thereof expressed on the surface of the AaPCs. The AaPCs can comprise additional molecules that activate or co-stimulate T-cells in some cases. The additional molecules can, in some cases, comprise membrane-bound Cy cytokines. In yet still further aspects, the AaPCs are inactivated or irradiated, or have been tested for and confirmed to be free of infectious material. In still further aspects, culturing the genetically modified CAR cells in the presence of AaPCs comprises culturing the genetically modified CAR cells in a medium comprising soluble cytokines, such as IL-15, IL-21 and/or IL-2. The cells can be cultured at a ratio of about 10:1 to about 1:10; about 3:1 to about 1:5; about 1:1 to about 1:3 (immune effector cells to AaPCs); or any range derivable therein. For example, the co-culture of T cells and AaPCs can be at a ratio of about 1:1, about 1:2 or about 1:3.

In one aspect, the AaPCs can express CD137L. In some aspects, the AaPCs can further express the antigen that is targeted by the CAR cell, for example MUC16, CD33, or ROR1 (full length, truncate or any variant thereof). In other aspects, the AaPCs can further express CD64, CD86, or mIL15. In certain aspects, the AaPCs can express at least one anti-CD3 antibody clone, such as, for example, OKT3 and/or UCHT1. In one aspect, the AaPCs can be inactivated (e.g., irradiated). In one aspect, the AaPCs have been tested and confirmed to be free of infectious material. Methods for producing such AaPCs are known in the art. In one aspect, culturing the CAR-modified T cell population with AaPCs can comprise culturing the cells at a ratio of about 10:1 to about 1:10; about 3:1 to about 1:5; about 1:1 to about 1:3 (T cells to AaPCs); or any range derivable therein. For example, the co-culture of T cells and AaPCs can be at a ratio of about 1:1, about 1:2 or about 1:3. In one aspect, the culturing step can further comprise culturing with an aminobisphosphonate (e.g., zoledronic acid).

In one aspect, the population of genetically modified CAR cells is immediately infused into a subject or cryopreserved. In another aspect, the population of genetically modified CAR cells is placed in a cytokine bath prior to infusion into a subject. In a further aspect, the population of genetically modified CAR cells is cultured and/or stimulated for no more than 1, 2, 3, 4, 5, 6, 7, 14, 21, 28, 35 42 days, 49, 56, 63 or 70 days. In some embodiments, the population of CAR-T cells is cultured and/or stimulated for at least 0, 2, 4, 6, 8, 10, 12, 14, 16, 18, 20, 22, 24, 26, 28, 30 or more days. In some embodiments, the population of CAR-T cells is cultured and/or stimulated for at least 5, 10, 15, 20, 25, 30, 35, 40, 45, 50, 55, 60 or more days. In some embodiments, the population of CAR expressing effector cells is cultured and/or stimulated for at least 7, 14, 21, 28, 35, 42, 49, 56, 63 or more days. In an embodiment, a stimulation includes the co-culture of the genetically modified CAR-T cells with AaPCs to promote the growth of CAR positive T cells. In another aspect, the population of genetically modified CAR cells is stimulated for not more than: 1× stimulation, 2× stimulation, 3× stimulation, 4× stimulation, 5× stimulation, 5× stimulation, 6× stimulation, 7× stimulation, 8× stimulation, 9× stimulation or 10× stimulation. In some instances, the genetically modified cells are not cultured ex vivo in the presence of AaPCs. In some specific instances, the method of the embodiment further comprises enriching the cell population for CAR-expressing immune effector cells (e.g., T-cells) after the transfection and/or culturing step. The enriching can comprise fluorescence-activated cell sorting (FACS) to sort for CAR-expressing cells. In a further aspect, the sorting for CAR-expressing cells comprises use of a CAR-binding antibody. The enriching can also comprise depletion of CD56+ cells. In yet still a further aspect of the embodiment, the method further comprises cryopreserving a sample of the population of genetically modified CAR cells.

In some cases, AaPCs are incubated with a peptide of an optimal length that allows for direct binding of the peptide to the MHC molecule without additional processing. Alternatively, the cells can express an antigen of interest (i.e., in the case of MHC-independent antigen recognition). Furthermore, in some cases, APCs can express an antibody that binds to either a specific CAR polypeptide or to CAR polypeptides in general (e.g., a universal activating and propagating cell (uAPC). Such methods are disclosed in WO2014/190273. In addition to peptide-MHC molecules or antigens of interest, the AaPC systems can also comprise at least one exogenous assisting molecule. Any suitable number and combination of assisting molecules can be employed. The assisting molecule can be selected from assisting molecules such as co-stimulatory molecules and adhesion molecules. Exemplary co-stimulatory molecules include CD70 and B7.1 (B7.1 was previously known as B7 and also known as CD80), which among other things, bind to CD28 and/or CTLA-4 molecules on the surface of T cells, thereby affecting, for example, T-cell expansion, Th1 differentiation, short-term T-cell survival, and cytokine secretion such as interleukin (IL)-2. Adhesion molecules can include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs) that promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001.

Cells selected to become AaPCs, preferably have deficiencies in intracellular antigen-processing, intracellular peptide trafficking, and/or intracellular MHC Class I or Class II molecule-peptide loading, or are poikilothermic (i.e., less sensitive to temperature challenge than mammalian cell lines), or possess both deficiencies and poikilothermic properties. Preferably, cells selected to become AaPCs also lack the ability to express at least one endogenous counterpart (e.g., endogenous MHC Class I or Class II molecule and/or endogenous assisting molecules as described above) to the exogenous MHC Class I or Class II molecule and assisting molecule components that are introduced into the cells. Furthermore, AaPCs preferably retain the deficiencies and poikilothermic properties that were possessed by the cells prior to their modification to generate the AaPCs. Exemplary AaPCs either constitute or are derived from a transporter associated with antigen processing (TAP)-deficient cell line, such as an insect cell line. An exemplary poikilothermic insect cells line is a Drosophila cell line, such as a Schneider 2 cell line (see, e.g., Schneider 1972 Illustrative methods for the preparation, growth, and culture of Schneider 2 cells, are provided in U.S. Pat. Nos. 6,225,042, 6,355,479, and 6,362,001.

In one embodiment, AaPCs are also subjected to a freeze-thaw cycle. In an exemplary freeze-thaw cycle, the AaPCs can be frozen by contacting a suitable receptacle containing the AaPCs with an appropriate amount of liquid nitrogen, solid carbon dioxide (i.e., dry ice), or similar low-temperature material, such that freezing occurs rapidly. The frozen APCs are then thawed, either by removal of the AaPCs from the low-temperature material and exposure to ambient room temperature conditions, or by a facilitated thawing process in which a lukewarm water bath or warm hand is employed to facilitate a shorter thawing time. Additionally, AaPCs can be frozen and stored for an extended period of time prior to thawing. Frozen AaPCs can also be thawed and then lyophilized before further use. Preferably, preservatives that might detrimentally impact the freeze-thaw procedures, such as dimethyl sulfoxide (DMSO), polyethylene glycols (PEGs), and other preservatives, are absent from media containing AaPCs that undergo the freeze-thaw cycle, or are essentially removed, such as by transfer of AaPCs to media that is essentially devoid of such preservatives.

In further embodiments, xenogenic nucleic acid and nucleic acid endogenous to the AaPCs, can be inactivated by crosslinking, so that essentially no cell growth, replication or expression of nucleic acid occurs after the inactivation. In one embodiment, AaPCs are inactivated at a point subsequent to the expression of exogenous MHC and assisting molecules, presentation of such molecules on the surface of the AaPCs, and loading of presented MHC molecules with selected peptide or peptides. Accordingly, such inactivated and selected peptide loaded AaPCs, while rendered essentially incapable of proliferating or replicating, retain selected peptide presentation function. Preferably, the crosslinking also yields AaPCs that are essentially free of contaminating microorganisms, such as bacteria and viruses, without substantially decreasing the antigen-presenting cell function of the AaPCs. Thus crosslinking maintains the important AaPC functions of while helping to alleviate concerns about safety of a cell therapy product developed using the AaPCs. For methods related to crosslinking and AaPCs, see for example, U.S. Patent Application Publication No. 20090017000.

In certain embodiments there are further provided an engineered antigen presenting cell (APC). Such cells can be used, for example, as described above, to propagate immune effector cells ex vivo. In further aspects, engineered APCs can, themselves be administered to a patient and thereby stimulate expansion of immune effector cells in vivo. Engineered APCs of the embodiments can, themselves, be used as a therapeutic agent. In other embodiments, the engineered APCs can used as a therapeutic agent that can stimulate activation of endogenous immune effector cells specific for a target antigen and/or to increase the activity or persistence of adoptively transferred immune effector cells specific to a target antigen.

As used herein the term "engineered APC" refers to cell(s) that comprises at least a first transgene, wherein the first transgene encodes a HLA. Such engineered APCs can further comprise a second transgene for expression of an antigen, such that the antigen is presented at the surface on the APC in complex with the HLA. In some aspects, the engineered APC can be a cell type that presented antigens (e.g., a dendritic cell). In further aspects, engineered APC can be produced from a cell type that does not normally present antigens, such a T-cell or T-cell progenitor (referred to as "T-APC"). Thus, in some aspects, an engineered APC of the embodiments comprises a first transgene encoding a target antigen and a second transgene encoding a human leukocyte antigen (HLA), such that the HLA is expressed on the surface of the engineered APC in complex with an epitope of the target antigen. In certain specific aspects, the HLA expressed in the engineered APC is HLA-A2.

In some aspects, an engineered APC of the embodiments can further comprise at least a third transgene encoding co-stimulatory molecule. The co-stimulatory molecule can be a co-stimulatory cytokine that can be a membrane-bound Cy cytokine. In certain aspects, the co-stimulatory cytokine is IL-15, such as membrane-bound IL-15. In some further aspects, an engineered APC can comprise an edited (or deleted) gene. For example, an inhibitory gene, such as PD-1, LIM-3, CTLA-4 or a TCR, can be edited to reduce or eliminate expression of the gene. An engineered APC of the embodiments can further comprise a transgene encoding any target antigen of interest. For example, the target antigen can be an infectious disease antigen or a tumor-associated antigen (TAA).

C. Rapid Manufacturing

In one embodiment of the present disclosure, the immune effector cells described herein are modified at a point-of-care site. In one embodiment of the present disclosure, the immune effector cells described herein are modified at or near a point-of-care site. In some cases, modified immune effector cells are also referred to as engineered T cells. In some cases, the facility or treatment site is at a hospital, at a facility (e.g., a medical facility), or at a treatment site near a subject in need of treatment. The subject undergoes apheresis and peripheral blood mononuclear cells (PBMCs)

or a sub population of PBMC can be enriched for example, by elutriation or Ficoll separation. Enriched PBMC or a subpopulation of PBMC can be cryopreserved in any appropriate cryopreservation solution prior to further processing. In one instance, the elutriation process is performed using a buffer solution containing human serum albumin. Immune effector cells, such as T cells can be isolated by selection methods described herein. In one instance, the selection method for T cells includes beads specific for CD3 or beads specific for CD4 and CD8 on T cells. In one case, the beads can be paramagnetic beads. The harvested immune effector cells can be cryopreserved in any appropriate cryopreservation solution prior to modification. The immune effector cells can be thawed up to 24 hours, 36 hours, 48 hours, 72 hours or 96 hours ahead of infusion. The thawed cells can be placed in cell culture buffer, for example in cell culture buffer (e.g. RPMI) supplemented with fetal bovine serum (FBS) or human serum AB or placed in a buffer that includes cytokines such as IL-2 and IL-21, prior to modification. In another aspect, the harvested immune effector cells can be modified immediately without the need for cryopreservation. In one aspect, the elutriation step is eliminated completely.

In some cases, the immune effector cells are modified by engineering/introducing a one or more miRNA(s), a chimeric receptor, one or more cell tag(s), and/or cytokine(s) into the immune effector cells and then rapidly infused into a subject. In some cases, the sources of immune effector cells can include both allogeneic and autologous sources. In one case, the immune effector cells can be T cells or NK cells. In one case, the chimeric receptor can be a CAR. In another case, the cytokine can be IL-15 (for example, as part of a fusion protein with IL-15Rα) or IL-12. In yet another case, expression of cytokine is modulated by ligand inducible gene-switch expression systems described herein. For example, a ligand such as veledimex can be delivered to the subject to modulate the expression of the cytokine.

In another aspect, veledimex is provided at 5 mg, 10 mg, 15 mg, 20 mg, 30 mg, 40 mg, 50 mg, 60 mg, 70 mg, 80 mg, 90 mg or 100 mg. In a further aspect, lower doses of veledimex are provided, for example, 0.5 mg, 1 mg, 5 mg, 10 mg, 15 mg or 20 mg. In one embodiment, veledimex is administered to the subject 0, 1, 2, 3, 4, 5, 6, 7, 8, 9, 10, 11, 12, 13, 14, 15, 16, 17, 18, 19, 20, or 21 days prior to infusion of the modified immune effector cells. In a further embodiment, veledimex is administered about once every 12 hours, about once every 24 hours, about once every 36 hours or about once every 48 hours, for an effective period of time to a subject post infusion of the modified immune effector cells. In one embodiment, an effective period of time for veledimex administration is about: 7, 8, 9, 10, 11, 12, 13, 14, 15, 16, 17, 18, 19, 20, 21, 22, 23, 24, 25, 26, 27, 28, 29, 30 days. In other embodiments, veledimex can be re-administered after a rest period, after a drug holiday or when the subject experiences a relapse.

In certain cases, where an adverse effect on a subject is observed or when treatment is not needed, the cell tag can be activated, for example via cetuximab, for conditional in vivo ablation of modified immune effector cells comprising cell tags such as truncated epidermal growth factor receptor tags as described herein.

In some embodiments, such immune effectors cells are modified by the constructs as described herein through electroporation. In one instance, electroporation is performed with electroporators such as Lonza's Nucleofector™ electroporators. In other embodiments, the vector comprising the above-mentioned constructs is a non-viral or viral vector. In one case, the non-viral vector includes a Sleeping Beauty transposon-transposase system. In one instance, the immune effector cells are electroporated using a specific sequence. For example, the immune effector cells can be electroporated with one transposon followed by the DNA encoding the transposase followed by a second transposon. In another instance, the immune effector cells can be electroporated with all transposons and transposase at the same time. In another instance, the immune effector cells can be electroporated with a transposase followed by both transposons or one transposon at a time. While undergoing sequential electroporation, the immune effector cells can be rested for a period of time prior to the next electroporation step.

In some cases, the modified immune effector cells do not undergo a propagation and activation step. In some cases, the modified immune effector cells do not undergo an incubation or culturing step (e.g. ex vivo propagation). In some cases, the modified immune effector cells are place in PBS/EDTA buffer. In certain cases, the modified immune effector cells are placed in a buffer that includes IL-2 and IL-21 prior to infusion. In other instances, the modified immune effector cells are placed or rested in cell culture buffer, for example in cell culture buffer (e.g. RPMI) supplemented with fetal bovine serum (FBS) prior to infusion. Prior to infusion, the modified immune effector cells can be harvested, washed and formulated in saline buffer in preparation for infusion into the subject.

In one instance, the subject has been lymphodepleted prior to infusion. In other instances, lymphodepletion is not required and the modified immune effector cells are rapidly infused into the subject.

In a further instance, the subject undergoes minimal lymphodepletion. Minimal lymphodepletion herein refers to a reduced lymphodepletion protocol such that the subject can be infused within 1 day, 2 days or 3 days following the lymphodepletion regimen. In one instance, a reduced lymphodepletion protocol can include lower doses of fludarabine and/or cyclophosphamide. In another instance, a reduced lymphodepletion protocol can include a shortened period of lymphodepletion, for example 1 day or 2 days.

In some embodiments, the subject is not lymphodepleted prior to infusion.

In one embodiment, the immune effector cells are modified by engineering/introducing one or more miRNA(s), a chimeric receptor and a cytokine into said immune effector cells and then rapidly infused into a subject. In other cases, the immune effector cells are modified by engineering/introducing one or more miRNA(s), a chimeric receptor and a cytokine into said cells and then infused within at least: 0, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 hours into a subject. In other cases, immune effector cells are modified by engineering/introducing one or more miRNA(s), a chimeric receptor and a cytokine into the immune effector cells and then infused in 0 days, <1 day, <2 days, <3 days, <4 days, <5 days, <6 days or <7 days into a subject.

In other embodiments, a method of stimulating the proliferation and/or survival of engineered cells comprises obtaining a sample of cells from a subject, and transfecting cells of the sample of cells with one or more polynucleotides that comprise one or more transposons. In one embodiment, the transposons encode one or more miRNA(s), a chimeric antigen receptor (CAR), a cytokine, one or more cell tags, and a transposase effective to integrate said one or more polynucleotides into the genome of said cells, to provide a population of engineered cells. In an embodiment, the transposons encode one or more miRNA(s), a chimeric antigen receptor (CAR), a cytokine, one or more cell tags, gene switch polypeptides for ligand-inducible control of the cytokine and a transposase effective to integrate said one or more polynucleotides into the genome of said cells, to provide a population of engineered cells. In an embodiment, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain. In some embodiments, the first gene switch polypeptide and the second gene switch polypeptide are connected by a linker. In one instance, lymphodepletion is not required prior to administration of the engineered cells to a subject.

In one instance, a method of in vivo propagation of engineered cells comprises obtaining a sample of cells from a subject, and transfecting cells of the sample of cells with one or more polynucleotides that comprise one or more transposons. In one embodiment, the transposons encode one or more miRNA(s), a chimeric antigen receptor (CAR), a cytokine, one or more cell tags, and a transposase effective to integrate said one or more polynucleotides into the genome of said cells, to provide a population of engineered cells. In an embodiment, the transposons encode one or more miRNA(s), a chimeric antigen receptor (CAR), a cytokine, one or more cell tags, gene switch polypeptides for ligand-inducible control of the cytokine and a transposase effective to integrate said one or more polynucleotides into the genome of said cells, to provide a population of engineered cells. In an embodiment, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain. In some embodiments, the first gene switch polypeptide and the second gene switch polypeptide are connected by a linker. In one instance, lymphodepletion is not required prior to administration of the engineered cells to a subject.

In another embodiment, a method of enhancing in vivo persistence of engineered cells in a subject in need thereof comprises obtaining a sample of cells from a subject, and transfecting cells of the sample of cells with one or more polynucleotides that comprise one or more transposons. In some cases, one or more transposons encode one or more miRNA(s), a chimeric antigen receptor (CAR), a cytokine, one or more cell tags, and a transposase effective to integrate the DNA into the genome of said cells, to provide a population of engineered cells. In some cases, one or more transposons encode one or more miRNA(s), a chimeric antigen receptor (CAR), a cytokine, one or more cell tags, gene switch polypeptides for ligand-inducible control of the cytokine and a transposase effective to integrate the DNA into the genome of said cells, to provide a population of engineered cells. In some cases, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain, wherein the first gene switch polypeptide and the second gene switch polypeptide are connected by a linker. In one instance, lymphodepletion is not required prior to administration of the engineered cells to a subject.

XIII. Kits and Compositions

One aspect of the disclosure relates to kits and compositions that comprise: a CAR, a cytokine, a cell tag, and/or one or more miRNAs as described previously, or nucleic acids encoding the same. In another aspect, the kits and compositions can include RHEOSWITCH® gene switch components. These kits and compositions can include multiple vectors each encoding different proteins or subsets of proteins. These vectors can be viral, non-viral, episomal, or integrating. In some embodiments, the vectors are transposons, e.g., Sleeping Beauty transposons. In other embodiments, the vectors can comprise sequences for serine recombinase-mediated integration.

In some embodiments, the kits and compositions include not only vectors but also cells and agents such as interleukins, cytokines, interleukins and chemotherapeutics, adjuvants, wetting agents, or emulsifying agents. In one embodiment the cells are T cells. In one embodiment the kits and composition includes IL-2. In one embodiment, the kits and compositions include IL-21. In one embodiment, the kits and compositions include Bcl-2, STAT3 or STATS inhibitors. In some embodiments, the kit includes IL-15, for example as part of a fusion protein with IL-15Rα.

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include CAR-T cells (e.g., MUC16-, CD33-, and ROR1-specific CAR-T cells described herein), and optionally in addition with cytokines and/or chemotherapeutic agents disclosed herein. Such kits optionally include an identifying description or label or instructions relating to its use in the methods described herein.

A kit typically includes labels listing contents and/or instructions for use, and package inserts with instructions for use. A set of instructions will also typically be included.

In some embodiments, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

The present invention relates also to pharmaceutical compositions comprising a modified immune effector cell as described above. In certain embodiments, the composition comprising an immune effector cell (e.g., T cell) modified with sequences comprising one or more miRNA(s), a CAR, one or more cell tags, and/or one or more cytokines and optionally, components of the gene switch system as described herein. In certain embodiments, the immune effector cell is modified with Sleeping Beauty transposon(s) and Sleeping Beauty transposase. For example, the Sleeping Beauty transposon or transposons can include one or more miRNA(s), a CAR, one or more cell tags, one or more cytokines and optionally, components of the gene switch system as described herein. Therefore, in some instances, the modified T-cell can elicit a CAR-mediated T-cell response.

The cells activated and expanded as described herein can be utilized in the treatment and prevention of diseases that arise in individuals who are immunocompromised. In particular, the modified T cells of the invention are used in the treatment of malignancies. In certain embodiments, the cells of the invention are used in the treatment of patients at risk for developing malignancies. Thus, the methods for the treatment or prevention of malignancies comprising administering to a subject in need thereof, a therapeutically effective amount of the modified T cells of the invention. In embodiments, the cells activated and expanded as described herein can be utilized in the treatment of malignancies.

In addition to using a cell-based vaccine in terms of ex vivo immunization, the present invention also provides compositions and methods for in vivo immunization to elicit an immune response directed against an antigen in a patient.

Briefly, pharmaceutical compositions described herein can comprise a population comprising modified immune effector cells as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In some embodiments, compositions of the present invention are formulated for intravenous administration.

Pharmaceutical compositions described herein can be administered in a manner appropriate to the disease to be treated (or prevented). The quantity and frequency of administration will be determined by such factors as the condition of the patient, and the type and severity of the patient's disease.

When "an immunologically effective amount", or "therapeutic amount" is indicated, the precise amount of the compositions described herein to be administered can be determined by a physician with consideration of individual differences in age, weight, and condition of the patient (subject). It can generally be stated that a pharmaceutical composition comprising the T cells described herein can be administered at a dosage of $10^4$ to $10^9$ cells/kg body weight, $10^5$ to $10^6$ cells/kg body weight, including all integer values within those ranges. T cell compositions can also be administered multiple times at these dosages. The cells can be administered by using infusion techniques that are commonly known in immunotherapy (see, e.g., Rosenberg et al., New Eng. J. of Med. 319:1676, (1988)). The optimal dosage and treatment regime for a particular patient can readily be determined by one skilled in the art of medicine by monitoring the patient for signs of disease and adjusting the treatment accordingly.

In certain embodiments, it can be desired to administer activated T cells to a subject and then subsequently redraw blood (or have an apheresis performed), activate T cells therefrom, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol can serve to select out certain populations of T cells. In another embodiment, it can be desired to administer activated T cells of the subject composition following lymphodepletion of the patient, either via radiation or chemotherapy.

Formulations described herein can benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

A "carrier" or "carrier materials" include any commonly used excipients in pharmaceutics and should be selected on the basis of compatibility with the polynucleotides, vectors, and/or cells disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" can include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), non-crystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term “diluent” refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner’s sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

“Filling agents” include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

“Lubricants” and “glidants” are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™ sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

“Plasticizers” are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

“Solubilizers” include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

“Stabilizers” include compounds such as any antioxidation agents, buffers, acids, preservatives and the like.

“Suspending agents” include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

“Surfactants” include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants can be included to enhance physical stability or for other purposes.

“Viscosity enhancing agents” include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

XIV. Methods of Treatment

The present invention also relates to a method of treating a disease or disorder comprising administering a modified immune effector cell of the present disclosure to a subject in need thereof. In certain embodiments, the cell is administered in a therapeutically effective amount.

The present invention also relates to the use of a modified immune effector cell of the present disclosure in the manufacture of a medicament for the treatment of a disease or disorder.

In some embodiments, the disease can be cancer. In certain aspects, the cancer can be hematological or a solid tumor. In other instances, the cancer is a hematologic malignancy. In some cases, the cancer is a metastatic cancer. In some cases, the cancer is a relapsed or refractory cancer. In certain aspects, the cancer is selected from B cell cancer, e.g., multiple myeloma, Waldenstrom's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer (e.g., metastatic, hormone refractory prostate cancer), pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers that can be treated by the methods of the present disclosure include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's sarcoma, Ewing's tumor, leiomyosarcoma, rhabdomyosarcoma, colon carcinoma, colorectal cancer, pancreatic cancer, breast cancer, beast adenocarcinomas e.g. triple negative breast cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, hepatocellular carcinoma (HCC), choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute myeloid leukemia, acute lymphocytic leukemia, mantle cell lymphoma, acute lymphoblastic leukemia, and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); diffuse large B-cell lymphoma; and polycythemia vera, lymphoma (Hodgkin's disease and non-Hodgkin's disease), multiple myeloma, Waldenstrom's macroglobulinemia, and heavy chain disease.

In some instances, the cancer is a solid tumor. Exemplary solid tumors include, but are not limited to, anal cancer; appendix cancer; bile duct cancer (i.e., cholangiocarcinoma); bladder cancer; brain tumor; breast cancer; cervical cancer; colon cancer; cancer of Unknown Primary (CUP); esophageal cancer; eye cancer; fallopian tube cancer; gastroenterological cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer; stomach cancer; testicular cancer; throat cancer; thyroid cancer; uterine cancer; vaginal cancer; or vulvar cancer.

In some instances, the cancer is a hematologic malignancy. In some cases, a hematologic malignancy comprises a lymphoma, a leukemia, a myeloma, or a B-cell malignancy. In some cases, a hematologic malignancy comprises a lymphoma, a leukemia or a myeloma. In some instances, exemplary hematologic malignancies include chronic lymphocytic leukemia (CLL), small lymphocytic lymphoma (SLL), high risk CLL, non-CLL/SLL lymphoma, prolymphocytic leukemia (PLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the hematologic malignancy comprises a myeloid leukemia. In some embodiments, the hematologic malignancy comprises acute myeloid leukemia (AML) or chronic myeloid leukemia (CML).

In some instances, disclosed herein are methods of administering to a subject having a hematologic malignancy selected from chronic lymphocytic leukemia (CLL), small lymphocytic lymphoma (SLL), high risk CLL, non-CLL/SLL lymphoma, prolymphocytic leukemia (PLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis a modified effector cell described herein. In some instances, disclosed herein are methods of administering to a subject having a hematologic malignancy selected from AML or CML a modified effector cell to the subject.

In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers can be characterized in various other ways including, but not limited to, serous, endometrioid, mucinous, clear cell, brenner, or undifferentiated. In some embodiments, the methods and compositions of the present disclosure are used in the treatment, diagnosis, and/or prognosis of lymphoma or its subtypes, including, but not limited to, mantle cell lymphoma.

In some embodiments, the disease or disorder is associated with the overexpression of an antigen. In certain embodiments, the antigen is CD19, CD33, ROR1, MUC1, or MUC16. In some embodiments, the disease is ovarian cancer, a myelodysplastic syndrome (MDS).

In some embodiments, disclosed herein are methods of administering a modified effector cell comprising a polypeptide described herein to a subject having a disorder, for instance a cancer. In some cases, the cancer is a cancer associated with an expression of CD19, CD20, CD33, CD44, BCMA, CD123, EGFRvIII, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, GPC3, CSPG4, HER1/HER3, HER2, CD44v6, CD44v7/v8, CD20, CD174, CD138, L1-CAM, FAP, c-MET, PSCA, CS1, CD38, IL-11Rα, EphA2, CLL-1, CD22, EGFR, Folate receptor α, Mucins such as MUC1 or MUC16, MAGE-A1, h5T4, PSMA, CSPG4, TAG-72 or VEGF-R2.

In some embodiments, the disease is associated with the overexpression of MUC16. In certain such embodiments, the disease is ovarian cancer, breast cancer, pancreatic cancer, endometrial cancer, or lung cancer.

In some embodiments, the disease is associated with the overexpression of CD33. In certain such embodiments, the disease is acute myeloid leukemia (AML) or a myelodysplastic syndrome (MDS).

In some embodiments, the disease is associated with the overexpression of ROR1. In certain such embodiments, the disease involves a hematological tumor, for example chronic lymphocytic leukemia (CLL), mantle cell lymphoma (MCL), acute lymphoblastic leukemia (ALL), and diffuse large B-cell lymphoma (DLBCL). In certain such embodiments, the disease involves a solid tumor, for example breast adenocarcinomas encompassing triple negative breast cancer (TNBC), pancreatic cancer, ovarian cancer, and lung adenocarcinoma.

In another embodiment, a method of treating a subject with a solid tumor comprises obtaining a sample of cells from a subject, transfecting cells of the sample with one or more polynucleotides that comprise one or more transposons, and administering the population of engineered cells to the subject. In one instance, lymphodepletion is not required prior to administration of the engineered cells to a subject. In some embodiments, genetically modified T cells can be expanded and transferred into patients treated with or without preconditioning lymphodepletion according to well-known protocols. In some cases, the one or more transposons encode one or more miRNA(s), a chimeric antigen receptor (CAR), a cytokine, one or more cell tags, and a transposase effective to integrate the DNA into the genome of the cells. In some cases, the one or more transposons encode one or more miRNA(s), a chimeric antigen receptor (CAR), a cytokine, one or more cell tags, gene switch polypeptides for ligand-inducible control of the cytokine and a transposase effective to integrate the DNA into the genome of the cells. In some cases, the gene switch polypeptides comprise: i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain, wherein the first gene switch polypeptide and second gene switch polypeptide are connected by a linker. In some cases, the cells are transfected via electroporation. In some cases, the polynucleotides encoding the gene switch polypeptides are modulated by a promoter. In some cases, the promoter is a tissue-specific promoter or an EF1A promoter or functional variant thereof. In some cases, the tissue-specific promoter comprises a T cell specific response element or an NFAT response element. In some cases, the cytokine comprises at least one of IL-1, IL-2, IL-15, IL-12, IL-21, a fusion of IL-15, IL-15R or an IL-15 variant. In some cases, the cytokine is in secreted form. In some cases, the cytokine is in membrane-bound form. In some cases, the cells are NK cells, NKT cells, T-cells or T-cell progenitor cells. In some cases, the cells are administered to a subject (e.g. by infusing the subject with the engineered cells). In some cases, the method further comprises administering an effective amount of a ligand (e.g. veledimex) to induce expression of the cytokine. In some cases, the transposase is salmonid-type Tc 1-like transposase. In some cases, the transposase is SB11 or SB100x transposase. In other cases, the transposase is PiggyBac. In some cases, the cell tag comprises at least one of a HER1 truncated variant or a CD20 truncated variant.

Studies conducted in patients with metastatic melanoma demonstrated that lymphodepletion prior to adoptive cell transfer dramatically improves the efficacy of therapy with in vitro expanded tumor-infiltrating lymphocytes (TILs). Muranski P, et al., "Increased intensity lymphodepletion and adoptive immunotherapy—how far can we go?" *Nat Clin Pract Oncol.* 2006; 3(12):668-681. Lymphodepletion likely works by multiple mechanisms, including eliminating sinks for homeostatic cytokines, such as interleukin-2 (IL-2), IL-7, and IL-15, eradicating immunosuppressive elements, such as regulatory T cells and myeloid-derived suppressor cells, inducing costimulatory molecules and downregulating indoleamine 2,3-dioxygenase in tumor cells, and promoting expansion, function, and persistence of adoptively transferred T cells. These experiences led to the use of lymphodepletion in clinical trials with CAR T-cell therapy. Kochenderfer et al showed an association between an increase in serum IL-15 levels post-lymphodepletion and clinical response after anti-CD19 CAR T-cell therapy. Kochenderfer J N, et al., "Lymphoma remissions caused by anti-CD19 chimeric antigen receptor T cells are associated with high serum interleukin-15 levels," *J Clin Oncol.* 2017; 35(16):1803-1813. Turtle and colleagues showed that the addition of fludarabine to cyclophosphamide (Cy/Flu) in the lymphodepleting regimen was associated with improved anti-CD19 CAR T-cell expansion and persistence and better clinical outcome compared with non-Flu lymphodepleting regimens in patients with non-Hodgkin lymphoma. Turtle C J, et al., "Immunotherapy of non-Hodgkin's lymphoma with a defined ratio of CD8+ and CD4+ CD19-specific chimeric antigen receptor-modified T cells," *Sci Transl Med.* 2016; (8)355-355ra116. Other studies indicated that the magnitude of the CAR T-cell expansion in vivo with respect to both the peak and the area under the curve over the first month may be associated with response and/or durability. Neelapu S S, et al., "Axicabtagene ciloleucel CAR T-cell therapy in refractory large B-cell lymphoma," *N Engl J Med.* 2017; 377(26):2531-2544.

In some embodiments, the subject is subjected to lymphodepletion before the step of administering the modified immune effector cells to the subject. As used herein, "lymphodepletion" involves methods that reduce the number of lymphocytes in a subject, for example by administration of a lymphodepletion agent. Examples of lymphodepletion include nonmyeloablative lymphodepleting chemotherapy, myeloablative lymphodepleting chemotherapy. Lymphodepletion can also be attained by partial body or whole body fractioned radiation therapy. A lymphodepletion agent can be a chemical compound or composition capable of decreasing the number of functional lymphocytes in a mammal when administered to the mammal. One example of such an agent is one or more chemotherapeutic agents. Such agents and dosages are known, and can be selected by a treating physician depending on the subject to be treated. Examples of lymphodepletion agents include, but are not limited to, fludarabine, cyclophosphamide, cladribine, denileukin diftitox, or combinations thereof. In some embodiments, the subject is not subjected to lymphodepletion before the step of administering the modified immune effector cells to the subject.

In some embodiments, lymphodepletion is performed by administration of cyclophosphamide at a dose of about 10 mg/kg to about 100 mg/kg, preferably about 40 mg/kg to about 80 mg/kg, for example about 60 mg/kg. In such embodiments, the cyclophosphamide can be administered concomitantly with fludarabine at a dose of about 10 $mg/m^2$ to about 50 $mg/m^2$, preferably about 20 $mg/m^2$ to about 40 $mg/m^2$, for example about 30 $mg/m^2$. In some embodiments, lymphodepletion is performed by administration of fludarabine at a dose of about 10 $mg/m^2$ to about 50 $mg/m^2$, preferably about 20 $mg/m^2$ to about 40 $mg/m^2$, for example about 30 $mg/m^2$. In such embodiments, the fludarabine can be administered concomitantly with cyclophosphamide at a dose of about 200 $mg/m^2$ to about 900 $mg/m^2$, preferably about 400 to about 600 $mg/m^2$, for example 500 $mg/m^2$.

In some embodiments, patients or subjects are not lymphodepleted prior to blood being withdrawn to produce the autologous modified immune effector cells.

In some embodiments, the modified immune effector cells are autologous to the subject. In some embodiments, the modified immune effector cells are allogeneic to the subject.

In some embodiments, an amount of modified immune effector cells that is administered to a subject in need thereof and the amount is determined based on the efficacy and the potential of inducing a cytokine-associated toxicity.

The administration of compositions described herein can be carried out in any convenient manner, including by aerosol inhalation, injection, ingestion, transfusion, implantation or transplantation. The compositions described herein can be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the immune effector cell compositions of the present invention are administered by i.v. injection. The compositions of T cells can be injected directly into a lymph node, or site of primary tumor or metastasis.

The dosage of the above treatments to be administered to a patient will vary with the precise nature of the condition being treated and the recipient of the treatment. The scaling of dosages for human administration can be performed according to art-accepted practices. For example, the dose of the above treatment can be in the range of $1\times10^4$ CAR+ cells/kg to $5\times10^6$ CAR+ cells/kg. Exemplary doses can be $1\times10^2$ CAR+ cells/kg, $1\times10^3$ CAR+ cells/kg, $1\times10^4$ CAR+ cells/kg, $1\times10^5$ CAR+ cells/kg, $3\times10^5$ CAR+ cells/kg, $1\times10^6$ CAR+ cells/kg, $5\times10^6$ CAR+ cells/kg, $1\times10^7$ CAR+ cells/kg, $1\times10^8$ CAR+ cells/kg or $1\times10^9$ CAR+ cells/kg. The appropriate dose can be adjusted accordingly for an adult or a pediatric patient.

Alternatively, a typical amount of immune effector cells administered to a mammal (e.g., a human) can be, for example, in the range of one hundred, one thousand, ten thousand, one million to 100 billion cells; however, amounts below or above this exemplary range are within the scope of the invention. For example, the dose of inventive host cells can be about 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells, or a range defined by any two of the foregoing values).

Therapeutic or prophylactic efficacy can be monitored by periodic assessment of treated patients. For repeated administrations over several days or longer, depending on the condition, the treatment is repeated until a desired suppression of disease symptoms occurs. However, other dosage regimens can be useful and are within the scope of the invention. The desired dosage can be delivered by a single bolus administration of the composition, by multiple bolus administrations of the composition, or by continuous infusion administration of the composition.

In some embodiments, an amount of modified effector cells is administered to a subject in need thereof and the amount is determined based on the efficacy and the potential of inducing a cytokine-associated toxicity. In another embodiment, the modified effector cells are CARP and $CD3^+$ cells. In some cases, an amount of modified effector cells comprises about $10^4$ to about $10^9$ modified effector cells/kg. In some cases, an amount of modified effector cells comprises about $10^4$ to about $10^5$ modified effector cells/kg. In some cases, an amount of modified effector cells comprises about $10^5$ to about $10^6$ modified effector cells/kg. In some cases, an amount of modified effector cells comprises about $10^6$ to about $10^7$ modified effector cells/kg. In some cases, an amount of modified effector cells comprises $>10^4$ but $\leq10^5$ modified effector cells/kg. In some cases, an amount of modified effector cells comprises $>10^5$ but $\leq10^6$ modified effector cells/kg. In some cases, an amount of modified effector cells comprises $>10^6$ but $\leq10^7$ modified effector cells/kg.

In one embodiment, the modified immune effector cells are targeted to the cancer via regional delivery directly to the tumor tissue. For example, in ovarian cancer, the modified immune effector cells can be delivered intraperitoneally (IP) to the abdomen or peritoneal cavity. Such IP delivery can be performed via a port or pre-existing port placed for delivery of chemotherapy drugs. Other methods of regional delivery of modified immune effector cells can include catheter infusion into resection cavity, ultrasound guided intratumoral injection, hepatic artery infusion or intrapleural delivery.

In one embodiment, a subject in need thereof, can begin therapy with a first dose of modified immune effector cells delivered via IP followed by a second dose of modified immune effector cells delivered via IV. In a further embodiment, the second dose of modified immune effector cells can be followed by subsequent doses which can be delivered via IV or IP. In one embodiment, the duration between the first and second or further subsequent dose can be about: 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days. In one embodiment, the duration between the first and second or further subsequent dose can be about: 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months. In another embodiment, the duration between the first and second or further subsequent dose can be about: 0, 1, 2, 3, 4, 5, 6, 7, 8, 9 or 10 years.

In another embodiment, a catheter can be placed at the tumor or metastasis site for further administration of 1, 2, 3, 4, 5, 6, 7, 8, 9, 10 doses of modified immune effector cells. In some cases, doses of modified effector cells can comprise about $10^2$ to about $10^9$ modified effector cells/kg. In cases where toxicity is observed, doses of modified effector cells can comprise about $10^2$ to about $10^5$ modified effector cells/kg. In some cases, doses of modified effector cells can start at about $10^2$ modified effector cells/kg and subsequent doses can be increased to about: $10^4$, $10^5$, $10^6$, $10^7$, $10^8$ or $10^9$ modified effector cells/kg.

The immune effector cells expressing the disclosed nucleic acid sequences, or a vector comprising the those nucleic acid sequences, can be administered with one or more additional therapeutic agents, which can be co-administered to the mammal. By "co-administering" is meant administering one or more additional therapeutic agents and the inventive host cells or the inventive vector sufficiently close in time to enhance the effect of one or more additional therapeutic agents, or vice versa. In this regard, the immune effector cells described herein or a vector described herein can be administered simultaneously with one or more additional therapeutic agents, or first, and the one or more additional therapeutic agents can be administered second, or vice versa. Alternatively, the disclosed immune effector cells or the vectors described herein and the one or more additional therapeutic agents can be administered simultaneously.

An example of a therapeutic agents that can be included in or co-administered with the inventive host cells and/or the inventive vectors are interleukins, cytokines, interferons, adjuvants and chemotherapeutic agents. In some embodiments, the additional therapeutic agents are IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, and TLR10.

A. Modified Immune Effector Cell Doses

In some embodiments, an amount of modified immune effector cells administered comprises about $10^2$ to about $10^9$ modified effector cells/kg of the subject's body weight. In some embodiments, an amount of modified immune effector cells administered comprises about $10^3$ to about $10^9$ modified effector cells/kg of the subject's body weight. In some embodiments, an amount of modified immune effector cells administered comprises about $10^4$ to about $10^9$ modified effector cells/kg of the subject's body weight. In some cases, an amount of modified effector cells comprises about $10^5$ to about $10^9$ modified effector cells/kg of the subject's body weight. In some cases, an amount of modified effector cells comprises about $10^5$ to about $10^8$ modified effector cells/kg of the subject's body weight. In some cases, an amount of modified effector cells comprises about $10^5$ to about $10^7$ modified effector cells/kg of the subject's body weight. In some cases, an amount of modified effector cells comprises about $10^6$ to about $10^9$ modified effector cells/kg of the subject's body weight. In some cases, an amount of modified effector cells comprises about $10^6$ to about $10^8$ modified effector cells/kg of the subject's body weight. In some cases, an amount of modified effector cells comprises about $10^7$ to about $10^9$ modified effector cells/kg of the subject's body weight. In some cases, an amount of modified effector cells comprises about $10^5$ to about $10^6$ modified effector cells/kg of the subject's body weight. In some cases, an amount of modified effector cells comprises about $10^6$ to about $10^7$ modified effector cells/kg of the subject's body weight. In some cases, an amount of modified effector cells comprises about $10^7$ to about $10^8$ modified effector cells/kg of the subject's body weight. In some cases, an amount of modified effector cells comprises about $10^8$ to about $10^9$ modified effector cells/kg of the subject's body weight. In some instances, an amount of modified effector cells comprises about $10^9$ modified effector cells/kg of the subject's body weight. In some instances, an amount of modified effector cells comprises about $10^8$ modified effector cells/kg of the subject's body weight. In some instances, an amount of modified effector cells comprises about $10^7$ modified effector cells/kg of the subject's body weight. In some instances, an amount of modified effector cells comprises about $10^6$ modified effector cells/kg of the subject's body weight. In some instances, an amount of modified effector cells comprises about $10^5$ modified effector cells/kg of the subject's body weight. In some instances, an amount of modified effector cells comprises about $10^4$ modified effector cells/kg of the subject's body weight. In some instances, an amount of modified effector cells comprises about $10^3$ modified effector cells/kg of the subject's body weight. In some instances, an amount of modified effector cells comprises about $10^2$ modified effector cells/kg of the subject's body weight.

In some embodiments, the modified immune effector cells are modified CAR-T cells. In some instances, the modified CAR-T cells further comprise one or more miRNA(s) as described herein. In some cases, an amount of modified CAR-T cells comprises about $10^4$ to about $10^9$ modified CAR-T cells/kg of the subject's body weight. In some cases, an amount of modified CAR-T cells comprises about $10^5$ to about $10^9$ modified CAR-T cells/kg of the subject's body weight. In some cases, an amount of modified CAR-T cells comprises about $10^5$ to about $10^8$ modified CAR-T cells/kg of the subject's body weight. In some cases, an amount of modified CAR-T cells comprises about $10^5$ to about $10^7$ modified CAR-T cells/kg of the subject's body weight. In some cases, an amount of modified CAR-T cells comprises about $10^6$ to about $10^9$ modified CAR-T cells/kg of the subject's body weight. In some cases, an amount of modified CAR-T cells comprises about $10^6$ to about $10^8$ modified CAR-T cells/kg of the subject's body weight. In some cases, an amount of modified CAR-T cells comprises about $10^7$ to about $10^9$ modified CAR-T cells/kg of the subject's body weight. In some cases, an amount of modified CAR-T cells comprises about $10^5$ to about $10^6$ modified CAR-T cells/kg of the subject's body weight. In some cases, an amount of modified CAR-T cells comprises about $10^6$ to about $10^7$ modified CAR-T cells/kg of the subject's body weight. In some cases, an amount of modified CAR-T cells comprises about $10^7$ to about $10^8$ modified CAR-T cells/kg of the subject's body weight. In some cases, an amount of modified CAR-T cells comprises about $10^8$ to about $10^9$ CAR-T cells/kg of the subject's body weight. In some instances, an amount of modified CAR-T cells comprises about $10^9$ modified CAR-T cells/kg of the subject's body weight. In some instances, an amount of modified CAR-T cells comprises about $10^8$ modified CAR-T cells/kg of the subject's body weight. In some instances, an amount of modified CAR-T cells comprises about $10^7$ modified CAR-T cells/kg of the subject's body weight. In some instances, an amount of modified CAR-T cells comprises about $10^6$ modified CAR-T cells/kg of the subject's body weight. In some instances, an amount of modified CAR-T cells comprises about $10^5$ modified CAR-T cells/kg of the subject's body weight.

In some embodiments, the modified CAR-T cells are CD19-specific CAR-T cells. In some cases, an amount of CD19-specific CAR-T cells comprises about $10^5$ to about $10^9$ CAR-T cells/kg of the subject's body weight. In some cases, an amount of CD19-specific CAR-T cells comprises about $10^5$ to about $10^8$ CAR-T cells/kg of the subject's body weight. In some cases, an amount of CD19-specific CAR-T cells comprises about $10^5$ to about $10^7$ CAR-T cells/kg of the subject's body weight. In some cases, an amount of CD19-specific CAR-T cells comprises about $10^6$ to about $10^9$ CAR-T cells/kg of the subject's body weight. In some cases, an amount of CD19-specific CAR-T cells comprises about $10^6$ to about $10^8$ CAR-T cells/kg of the subject's body weight. In some cases, an amount of CD19-specific CAR-T cells comprises about $10^7$ to about $10^9$ CAR-T cells/kg of the subject's body weight. In some cases, an amount of CD19-specific CAR-T cells comprises about $10^5$ to about $10^6$ CAR-T cells/kg of the subject's body weight. In some cases, an amount of CD19-specific CAR-T cells comprises about $10^6$ to about $10^7$ CAR-T cells/kg of the subject's body weight. In some cases, an amount of CD19-specific CAR-T cells comprises about $10^7$ to about $10^8$ CAR-T cells/kg of the subject's body weight. In some cases, an amount of CD19-specific CAR-T cells comprises about $10^8$ to about $10^9$ CAR-T cells/kg of the subject's body weight. In some instances, an amount of CD19-specific CAR-T cells comprises about $10^9$ CAR-T cells/kg of the subject's body weight. In some instances, an amount of CD19-specific CAR-T cells comprises about $10^8$ CAR-T cells/kg of the subject's body weight. In some instances, an amount of CD19-specific CAR-T cells comprises about $10^7$ CAR-T cells/kg of the subject's body weight. In some instances, an amount of CD19-specific CAR-T cells comprises about $10^6$ CAR-T cells/kg of the subject's body weight. In some instances, an amount of CD19-specific CAR-T cells comprises about $10^5$ CAR-T cells/kg of the subject's body weight.

In some embodiments, the modified CAR-T cells are CD33-specific CAR-T cells. In some cases, an amount of CD33-specific CAR-T cells comprises about $10^5$ to about $10^9$ CAR-T cells/kg of the subject's body weight. In some cases, an amount of CD33-specific CAR-T cells comprises about $10^5$ to about $10^8$ CAR-T cells/kg of the subject's body weight. In some cases, an amount of CD33-specific CAR-T cells comprises about $10^5$ to about $10^7$ CAR-T cells/kg of the subject's body weight. In some cases, an amount of CD33-specific CAR-T cells comprises about $10^6$ to about $10^9$ CAR-T cells/kg of the subject's body weight. In some cases, an amount of CD33-specific CAR-T cells comprises about $10^6$ to about $10^8$ CAR-T cells/kg of the subject's body weight. In some cases, an amount of CD33-specific CAR-T cells comprises about $10^7$ to about $10^9$ CAR-T cells/kg of the subject's body weight. In some cases, an amount of CD33-specific CAR-T cells comprises about $10^5$ to about $10^6$ CAR-T cells/kg of the subject's body weight. In some cases, an amount of CD33-specific CAR-T cells comprises about $10^6$ to about $10^7$ CAR-T cells/kg of the subject's body weight. In some cases, an amount of CD33-specific CAR-T cells comprises about $10^7$ to about $10^8$ CAR-T cells/kg of the subject's body weight. In some cases, an amount of CD33-specific CAR-T cells comprises about $10^8$ to about $10^9$ CAR-T cells/kg of the subject's body weight. In some instances, an amount of CD33-specific CAR-T cells comprises about $10^9$ CAR-T cells/kg of the subject's body weight. In some instances, an amount of CD33-specific CAR-T cells comprises about $10^8$ CAR-T cells/kg of the subject's body weight. In some instances, an amount of CD33-specific CAR-T cells comprises about $10^7$ CAR-T cells/kg of the subject's body weight. In some instances, an amount of CD33-specific CAR-T cells comprises about $10^6$ CAR-T cells/kg of the subject's body weight. In some instances, an amount of CD33-specific CAR-T cells comprises about $10^5$ CAR-T cells/kg of the subject's body weight.

In some embodiments, the modified CAR-T cells are MUC1-specific CAR-T cells. In some cases, an amount of MUC1-specific CAR-T cells comprises about $10^5$ to about $10^9$ CAR-T cells/kg of the subject's body weight. In some cases, an amount of MUC1-specific CAR-T cells comprises about $10^5$ to about $10^8$ CAR-T cells/kg of the subject's body weight. In some cases, an amount of MUC1-specific CAR-T cells comprises about $10^5$ to about $10^7$ CAR-T cells/kg of the subject's body weight. In some cases, an amount of MUC1-specific CAR-T cells comprises about $10^6$ to about $10^9$ CAR-T cells/kg of the subject's body weight. In some cases, an amount of MUC1-specific CAR-T cells comprises about $10^6$ to about $10^8$ CAR-T cells/kg of the subject's body weight. In some cases, an amount of MUC1-specific CAR-T cells comprises about $10^7$ to about $10^9$ CAR-T cells/kg of the subject's body weight. In some cases, an amount of MUC1-specific CAR-T cells comprises about $10^5$ to about $10^6$ CAR-T cells/kg of the subject's body weight. In some cases, an amount of MUC1-specific CAR-T cells comprises about $10^6$ to about $10^7$ CAR-T cells/kg of the subject's body weight. In some cases, an amount of MUC1-specific CAR-T cells comprises about $10^7$ to about $10^8$ CAR-T cells/kg of the subject's body weight. In some cases, an amount of MUC1-specific CAR-T cells comprises about $10^8$ to about $10^9$ CAR-T cells/kg of the subject's body weight. In some instances, an amount of MUC1-specific CAR-T cells comprises about $10^9$ CAR-T cells/kg of the subject's body weight. In some instances, an amount of MUC1-specific CAR-T cells comprises about $10^8$ CAR-T cells/kg of the subject's body weight. In some instances, an amount of MUC1-specific CAR-T cells comprises about $10^7$ CAR-T cells/kg of the subject's body weight. In some instances, an amount of MUC1-specific CAR-T cells comprises about $10^6$ CAR-T cells/kg of the subject's body weight. In some instances, an amount of MUC1-specific CAR-T cells comprises about $10^5$ CAR-T cells/kg of the subject's body weight.

In some embodiments, the modified CAR-T cells are MUC16-specific CAR-T cells. In some cases, an amount of MUC16-specific CAR-T cells comprises about $10^5$ to about $10^9$ CAR-T cells/kg of the subject's body weight. In some cases, an amount of MUC16-specific CAR-T cells comprises about $10^5$ to about $10^8$ CAR-T cells/kg of the subject's body weight. In some cases, an amount of MUC16-specific CAR-T cells comprises about $10^5$ to about $10^7$ CAR-T cells/kg of the subject's body weight. In some cases, an amount of MUC16-specific CAR-T cells comprises about $10^6$ to about $10^9$ CAR-T cells/kg of the subject's body weight. In some cases, an amount of MUC16-specific CAR-T cells comprises about $10^6$ to about $10^8$ CAR-T cells/kg of the subject's body weight. In some cases, an amount of MUC16-specific CAR-T cells comprises about $10^7$ to about $10^9$ CAR-T cells/kg of the subject's body weight. In some cases, an amount of MUC16-specific CAR-T cells comprises about $10^5$ to about $10^6$ CAR-T cells/kg of the subject's body weight. In some cases, an amount of MUC16-specific CAR-T cells comprises about $10^6$ to about $10^7$ CAR-T cells/kg of the subject's body weight. In some cases, an amount of MUC16-specific CAR-T cells comprises about $10^7$ to about $10^8$ CAR-T cells/kg of the subject's body weight. In some cases, an amount of MUC16-specific CAR-T cells comprises about $10^8$ to about $10^9$ CAR-T cells/kg of the subject's body weight. In some instances, an amount of MUC16-specific CAR-T cells comprises about $10^9$ CAR-T cells/kg of the subject's body weight. In some instances, an amount of MUC16-specific CAR-T cells comprises about $10^8$ CAR-T cells/kg of the subject's body weight. In some instances, an amount of MUC16-specific CAR-T cells comprises about $10^7$ CAR-T cells/kg of the subject's body weight. In some instances, an amount of MUC16-specific CAR-T cells comprises about $10^6$ CAR-T cells/kg of the subject's body weight. In some instances, an amount of MUC16-specific CAR-T cells comprises about $10^5$ CAR-T cells/kg of the subject's body weight.

In some embodiments, the modified CAR-T cells are ROR1-specific CAR-T cells. In some cases, an amount of ROR1-specific CAR-T cells comprises about $10^5$ to about $10^9$ CAR-T cells/kg of the subject's body weight. In some cases, an amount of ROR1-specific CAR-T cells comprises about $10^5$ to about $10^8$ CAR-T cells/kg of the subject's body weight. In some cases, an amount of ROR1-specific CAR-T cells comprises about $10^5$ to about $10^7$ CAR-T cells/kg of the subject's body weight. In some cases, an amount of ROR1-specific CAR-T cells comprises about $10^6$ to about $10^9$ CAR-T cells/kg of the subject's body weight. In some cases, an amount of ROR1-specific CAR-T cells comprises about $10^6$ to about $10^8$ CAR-T cells/kg of the subject's body weight. In some cases, an amount of ROR1-specific CAR-T cells comprises about $10^7$ to about $10^9$ CAR-T cells/kg of the subject's body weight. In some cases, an amount of ROR1-specific CAR-T cells comprises about $10^5$ to about $10^6$ CAR-T cells/kg of the subject's body weight. In some cases, an amount of ROR1-specific CAR-T cells comprises about $10^6$ to about $10^7$ CAR-T cells/kg of the subject's body weight. In some cases, an amount of ROR1-specific CAR-T cells comprises about $10^7$ to about $10^8$ CAR-T cells/kg of the subject's body weight. In some cases, an amount of ROR1-specific CAR-T cells comprises about $10^8$ to about $10^9$ CAR-T cells/kg of the subject's body weight. In some instances, an amount of ROR1-specific CAR-T cells comprises about $10^9$ CAR-T cells/kg of the subject's body weight. In some instances, an amount of ROR1-specific CAR-T cells comprises about $10^8$ CAR-T cells/kg of the subject's body weight. In some instances, an amount of ROR1-specific CAR-T cells comprises about $10^7$ CAR-T cells/kg of the subject's body weight. In some instances, an amount of ROR1-specific CAR-T cells comprises about $10^6$ CAR-T cells/kg of the subject's body weight. In some instances, an amount of ROR1-specific CAR-T cells comprises about $10^5$ CAR-T cells/kg of the subject's body weight.

In some embodiments, the modified T cells are engineered TCR T-cells. In some cases, an amount of engineered TCR T-cells comprises about $10^5$ to about $10^9$ TCR cells/kg of the subject's body weight. In some cases, an amount of engineered TCR cells comprises about $10^5$ to about $10^8$ TCR cells/kg of the subject's body weight. In some cases, an amount of engineered TCR cells comprises about $10^5$ to about $10^7$ TCR cells/kg of the subject's body weight. In some cases, an amount of engineered TCR cells comprises about $10^6$ to about $10^9$ TCR cells/kg of the subject's body weight. In some cases, an amount of engineered TCR cells comprises about $10^6$ to about $10^8$ TCR cells/kg of the subject's body weight. In some cases, an amount of engineered TCR cells comprises about $10^7$ to about $10^9$ TCR cells/kg of the subject's body weight. In some cases, an amount of engineered TCR cells comprises about $10^5$ to about $10^6$ TCR cells/kg of the subject's body weight. In some cases, an amount of engineered TCR cells comprises about $10^6$ to about $10^7$ TCR cells/kg of the subject's body weight. In some cases, an amount of engineered TCR cells comprises about $10^7$ to about $10^8$ TCR cells/kg of the subject's body weight. In some cases, an amount of engineered TCR cells comprises about $10^8$ to about $10^9$ TCR cells/kg of the subject's body weight. In some instances, an amount of engineered TCR cells comprises about $10^9$ TCR cells/kg of the subject's body weight. In some instances, an amount of engineered TCR cells comprises about $10^8$ TCR cells/kg of the subject's body weight. In some instances, an amount of engineered TCR cells comprises about $10^7$ TCR cells/kg of the subject's body weight. In some instances, an amount of engineered TCR cells comprises about $10^6$ TCR cells/kg of the subject's body weight. In some instances, an amount of engineered TCR cells comprises about $10^5$ TCR cells/kg of the subject's body weight.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In some embodiments, the cancer whose phenotype is determined by the method of the present disclosure is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer.

B. Combination Therapies

In certain embodiments, the modified immune effector cells and compositions thereof described herein may be used, alone or with other therapies, to treat cancers that have about 0, 5, 10, 15, 20, 25, 30, 35, 40, 45, 50, 55, 60, 65, 70, 75, 80, 85, 90, 95%, 96%, 97%, 98%, or 99% average response rate to standard therapy (including but not limited to chemotherapy, chemotherapy and current clinical trial therapies). Such cancers include but are not limited to, Hodgkin's lymphoma, melanoma, non-small cell lung cancer (NSCLC), microsatellite instability (MSI)-high or mismatch repair (MMR)-deficient solid tumors, CSCC, RCC, CRC, melanoma, Merkel cell cancer, bladder cancer, RCC, hepatocellular carcinoma (HCC), head & neck cancer (H&N), cervical cancer, gastric cancer, small cell lung cancer (SCLC), endometrial cancer, mesothelioma, ovarian cancer, triple negative breast cancer (TNBC), breast cancer, colorectal cancer (CRC), pancreatic cancer, prostate cancer.

In some embodiments, the compositions described herein can be administered as a combination therapy with an additional therapeutic agent. In some embodiments, an additional therapeutic agent comprises a biological molecule, such as an antibody. For example, treatment can involve the combined administration of the modified immune effector cells as described herein with antibodies against tumor-associated antigens including, but not limited to, antibodies that bind EGFR, HER2/ErbB2, and/or VEGF. In certain embodiments, the additional therapeutic agent is an antibody specific for a cancer stem cell marker. In certain embodiments, the additional therapeutic agent is an antibody that is an angiogenesis inhibitor (e.g., an anti-VEGF or VEGF receptor antibody). In certain embodiments, the additional therapeutic agent is bevacizumab (AVASTIN), ramucirumab, trastuzumab (HERCEPTIN), pertuzumab (OMNITARG), panitumumab (VECTIBIX), nimotuzumab, zalutumumab, or cetuximab (ERBITUX). In some embodiments, an additional therapeutic agent comprises an agent such as a small molecule. For example, treatment can involve the combined administration of the modified immune effector cells as described herein with a small molecule that acts as an inhibitor against tumor-associated antigens including, but not limited to, EGFR, HER2 (ErbB2), and/or VEGF. In some embodiments, the modified immune effector cells as described herein administered in combination with a protein kinase inhibitor selected from the group consisting of: gefitinib (IRESSA), erlotinib (TARCEVA), sunitinib (SUTENT), lapatanib, vandetanib (ZACTIMA), AEE788, CI-1033, cediranib (RECENTIN), sorafenib (NEXAVAR), and pazopanib (GW786034B). In some embodiments, an additional therapeutic agent comprises an mTOR inhibitor. In another embodiment, the additional therapeutic agent is chemotherapy or other inhibitors that reduce the number of $T_{RE}G$ cells. In certain embodiments, the therapeutic agent is cyclophosphamide or an anti-CTLA4 antibody. In another embodiment, the additional therapeutic reduces the presence of myeloid-derived suppressor cells. In a further embodiment, the additional therapeutic is carbotaxol. In a further embodiment, the additional therapeutic agent is ibrutinib. In some embodiments, an additional therapeutic agent comprises an anti-PD-1 or anti-PDL1 inhibitor. In some embodiments, the method can further comprise one or more checkpoint inhibitors in combination with modified immune effector cells as described herein. In some embodiments, the additional checkpoint inhibitor can be an anti-CTLA-4 antibody. The anti-CTLA-4 antibody (e.g., ipilimumab) has shown durable anti-tumor activities and prolonged survival in participants with advanced melanoma, resulting in its Food and Drug Administration (FDA) approval in 2011. See Hodi et al., Improved survival with ipilimumab in patients with metastatic melanoma. N Engl J Med. (2010) Aug. 19; 363(8):711-23. In some embodiments, the one or more checkpoint inhibitors can be an anti-PD-L1 antibody. In some embodiments, the anti-PD-L1 antibody can be a full length atezolizumab (anti-PD-L1), avelumab (anti-PD-L1), durvalumab (anti-PD-L1), or a fragment or a variant thereof. In some embodiments, the one or more checkpoint inhibitors can be any one or more of CD27 inhibitor, CD28 inhibitor, CD40 inhibitor, CD122 inhibitor, CD137 inhibitor, OX40 (also known as CD134) inhibitor, GITR inhibitor, ICOS inhibitor, or any combination thereof. In some embodiments, the one or more checkpoint inhibitors can be any one or more of A2AR inhibitor, B7-H3 (also known as CD276) inhibitor, B7-H4 (also known as VTCN1) inhibitor, BTLA inhibitor, IDO inhibitor, KIR inhibitor, LAG3 inhibitor, TIM-3 inhibitor, VISTA inhibitor, or any combination thereof.

In certain embodiments, an additional therapeutic agent comprises a second immunotherapeutic agent. In some embodiments, the additional immunotherapeutic agent includes, but is not limited to, a colony stimulating factor, an interleukin, an antibody that blocks immunosuppressive functions (e.g., an anti-CTLA-4 antibody, anti-CD28 antibody, anti-CD3 antibody, anti-PD-L1 antibody, anti-TIGIT antibody), an antibody that enhances immune cell functions (e.g., an anti-GITR antibody, an anti-OX-40 antibody, an anti-CD40 antibody, or an anti-4-1BB antibody), a toll-like receptor (e.g., TLR4, TLR7, TLR9), a soluble ligand (e.g., GITRL, GITRL-Fc, OX-40L, OX-40L-Fc, CD40L, CD40L-Fc, 4-1BB ligand, or 4-1BB ligand-Fc), or a member of the B7 family (e.g., CD80, CD86). In some embodiments, the additional immunotherapeutic agent targets CTLA-4, CD28, CD3, PD-L1, TIGIT, GITR, OX-40, CD-40, or 4-1BB.

In some embodiments, the additional therapeutic agent is an additional immune checkpoint inhibitor. As used herein, "an immune checkpoint inhibitor" is an agent that inhibits the activity of an immune checkpoint protein. In some embodiments, the additional immune checkpoint inhibitor is an anti-PD-L1 antibody, an anti-CTLA-4 antibody, an anti-CD28 antibody, an anti-TIGIT antibody, an anti-LAG3 antibody, an anti-TIM3 antibody, an anti-GITR antibody, an anti-4-1BB antibody, or an anti-OX-40 antibody. In some embodiments, the additional therapeutic agent is an anti-TIGIT antibody. In some embodiments, the additional therapeutic agent is an anti-PD-L1 antibody selected from the group consisting of: BMS935559 (MDX-1105), atexolizumab (MPDL3280A), durvalumab (MEDI4736), and avelumab (MSB0010718C). In some embodiments, the additional therapeutic agent is an anti-CTLA-4 antibody selected from the group consisting of: ipilimumab (YERVOY) and tremelimumab. In some embodiments, the additional therapeutic agent is an anti-LAG-3 antibody selected from the group consisting of: BMS-986016 and LAG525. In some embodiments, the additional therapeutic agent is an anti-OX-40 antibody selected from the group consisting of: MEDI6469, MEDI0562, and MOXR0916. In some embodiments, the additional therapeutic agent is an anti-4-1BB antibody selected from the group consisting of: PF-05082566. In some embodiments, the modified immune effector cells as described herein can be administered in combination with a biologic molecule selected from the group consisting of: cytokines, adrenomedullin (AM), angiopoietin (Ang), BMPs, BDNF, EGF, erythropoietin (EPO), FGF, GDNF, granulocyte colony stimulating factor (G-CSF), granulocyte-macrophage colony stimulating factor (GM-CSF), macrophage colony stimulating factor (M-CSF), stem cell factor (SCF), GDF9, HGF, HDGF, IGF, migration-stimulating factor, myostatin (GDF-8), NGF, neurotrophins, PDGF, thrombopoietin, TGF-α, TGF-β, TNF-α, VEGF, P1GF, gamma-IFN, IL-1, IL-2, IL-3, IL-4, IL-5, IL-6, IL-7, IL-12, IL-15, and IL-18.

XVI. Personalized Therapy

In an embodiment, the invention involves the detection of a disease or disorder associated with the overexpression of an antigen in a subject. The method of detection comprises:

a) contacting a sample from a subject with one or more of the antibodies, or antigen-binding fragments thereof, that are described herein; and b) detecting an increased level of binding of the antibody or fragment thereof to the sample as compared to such binding to a control sample lacking the disease, thereby detecting the disease in the subject. In certain embodiments, the disease is cancer. In certain such embodiments, the cancer is selected from the group of ovarian cancer and breast cancer. While not intending to limit the method of detection, in one embodiment detection of binding is immunohistochemical, for example by enzyme-linked immunosorbent assay (ELISA), fluorescence-activated cell sorting (FACS), Western blot, immunoprecipitation, and/or radiographic imaging.

In an embodiment of the invention, a collection approach is used to transform the personalized cell therapy landscape for patients, including cancer patients. The approach includes the use of a developed and validated collection of non-viral plasmids to target tumor-associated antigens. These design and manufacturing advantages include the use of UltraCAR-T™ technology for generation of genetically modified cells, coupled with the capabilities of the UltraPorator™ electroporation system. These methods, compounds and compositions allow therapies and treatment options to assist cancer centers and physicians deliver personalized, autologous genetically modified cell treatments with overnight manufacturing to cancer patients. Based on the patient's cancer indication and/or biomarker profile, one or more non-viral plasmids may be selected from the library to build a personalized UltraCAR-T cell treatment. After initial treatment, this approach has potential to allow re-dosing of UltraCAR-T cells targeting the same or new tumor antigen(s) based on the treatment response and the changes in antigen expression of the patient's tumor. The combination of the advanced UltraVector™ DNA construction platform and the ease of overnight manufacturing gives this library approach an advantage over traditional T-cell therapies.

Provided herein is a method for the treatment of a disease or disorder comprising the serial administration of polynucleotides encoding a chimeric antigen receptor or a cell comprising the same. The disease or disorder may, for example, be a cancer or auto-immune disease or disorders. The polynucleotides may be present in a viral or non-viral vector. The chimeric antigen receptors selected from a collection of chimeric antigen receptors having different structural compositions and binding specificities for an array of antigen targets.

In certain embodiments, the collection of chimeric antigen receptors comprises a chimeric antigen receptor that targets at least one of the following antigens: BCMA, CAIX, CA125, CCR4, CD3, CD4, CD5, CD7, CD16, CD19, CD20, CD22, CD24, CD25, CD28, CD30, CD33, CD38, CD40, CD44, CD44v6, CD44v7/v8, CD47, CD52, CD56, CD70, CD79b, CD80, CD81, CD86, CD123, CD133, CD138, CD151, CD171, CD174, CD276, CEA, CEACAM6, CLL-1, c-MET, CS1, CSPG4, CTLA-4, DLL3, EDB-F, EGFR, EGFR2, EGFRvIII, EGP-2, EGP-40, EphA2, FAP, FLT1, FLT4, Folate-binding Protein, Folate Receptor, Folate receptor α, α-Folate receptor, Frizzled, GD2, GD3, GHR, GHRHR, GITR, GPC3, Gp100, gp130, HBV antigens, HER1, HER2, HER3, HER4, h5T4, HVEM, IGF1R, IgKAppa, IL-1-RAP, IL-2R, IL6R, IL-11Rα, IL-13R-a2, KDR, KRASG12V, LewisA, LewisY, L1-CAM, LIFRP, LRP5, LTPR, MAGE-A, MAGE-A1, MAGE-A10, MAGE-A3, MAGEA3/A6, MAGE-A4, MAGE-A6, MART-1, MCAM, mesothelin, PSCA, Mucins such as MUC1, MUC4 or MUC16, NGFR, NKG2D, Notch-1-4, NY-ESO-1, O-acetylGD2, O-acetylGD3, OX40, P53, PD1, PDE10A, PD-L1, PD-L2, PRAME, PSMA, PTCH1, RANK, Robol, ROR1, ROR1R, ROR-2, TACI, TAG-72, TCRa, TCRp, TGF, TGFBeta, TGFBeta-II, TGFBR1, TGFBR2, Titin, TLR7, TLR9, TNFR1, TNFR2, TNFRSF4, TRBC1, TWEAK-R, VEGF, VEGF-R2, and WT-1. In certain embodiments, the collection of chimeric antigen receptors comprises a chimeric antigen receptor that targets at least one of the following antigens: B7H4, BCMA, BTLA, CA125, CAIX, CCR4, CD123, CD133, CD137, CD138, CD151, CD16, CD171, CD174, CD19, CD20, CD22, CD24, CD25, CD276, CD28, CD3, CD30, CD33, CD38, CD4, CD40, CD44, CD44v6, CD44v7/v8, CD47, CD5, CD52, CD56, CD7, CD70, CD79b, CD80, CD81, CD86, CEA, CEACAM6, CLL-1, c-MET, CS1, CSPG4, CTLA-4, DLL3, EDB-F, EGFR, EGFR2, EGFRvIII, EGP-2, EGP-40, EphA2, HER1, HER2, HER3, HER4, FAP, FLT1, FLT4, Folate receptor α, Folate-binding protein, folate receptor, Frizzled, GD2, GD3, GHR, GHRHR, GITR, Gp100, gp130, GPC3, h5T4, HBV antigens, HER1/HER3, HPV antigens, HVEM, IGF1R, IgKAppa, IL-11Rα, IL-13R-a2, IL-1-RAP, IL-2R, IL6R, KDR, KRASG12V, L1-CAM, LewisA, LewisY, LIFRP, LRP5, LTPR, MAGE-A, MAGE-A1, MAGE-A10, MAGE-A3, MAGEA3/A6, MAGE-A4, MAGE-A6, MART-1, MCAM, Mesothelin, mucins such as MUC1 and MUC16, NGFR, NKG2D, Notch 1-4, NY-ESO-1, O-acetylGD2, O-acetylGD3, OX40, P53, PD1, PDE10A, PD-L1, PD-L2, PMSA, PRAME, PSCA, PSMA, PTCH1, RANK, Robol, ROR1, ROR1R, ROR-2, TACI, TAG-72, TCRα, TCRp, TGF, TGFβ, TGFβ-II, TGFBR1, TGFBR2, Titin, TLR7, TLR9, TNFR1, TNFR2, TNFRSF4, TRBC1, TWEAK-R, VEGF, VEGF-R2, and WT-1.

In certain embodiments, the method comprises a first administration of cells expressing one or more chimeric antigen receptors from the collection followed by a second administration of cells expressing one or more chimeric antigen receptors from the collection, wherein a period of time elapses between the first and second administrations. In certain embodiments, the same one or more CARs in the first administration are administered again. In certain other embodiments, at least one of the CARs expressed by cells in the second administration is different from CARs in the first administration. In certain embodiments, the invention comprises a third, fourth, fifth, sixth, seventh, eighth, ninth, tenth or any additional number of rounds of administration of cells expressing CARs selected from the collection, wherein in each subsequent round of administration a different CAR is administered which was not administered in a previous round of treatment.

In certain embodiments, the dose of the cells is autologous. In certain embodiments, the dose of cells is allogenic. In certain embodiments, one dose of the cells is autologous and another dose is allogenic.

In certain embodiments, prior to a second or subsequent administration of a CAR or CARs, a period of time is allowed to elapse that is sufficient for biologic or therapeutic activity of one or more CARs in a preceding administration to become diminished from peak biologic or therapeutic activity, become negligible or become undetectable. In certain embodiments, a subsequent administration of a CAR takes place at least one day following the previous administration of a CAR.

The polynucleotide encoding the CAR may be introduced into the cells of a subject by way of viral transduction, non-viral transfection or electroporation methods of delivery.

In certain embodiments, the polynucleotide encoding the CAR may be administered as part of a vector, such as those described herein. In certain embodiments of the invention, one or more polynucleotides encoding a CAR further comprises nucleotide sequences encoding a cytokine, a cell tag, and/or a gene switch, as described previously. In certain embodiments, the vector comprises the polynucleotide encoding the CAR and one or more polynucleotides encoding the cytokine, cell tag, and/or a gene switch.

In certain embodiments, the vector is a "regulatory approved vector," meaning that it has been approved by a Regulatory Authority, national, supra-national (e.g., the U.S. Food and Drug Administration (FDA), the European Commission or the Council of the EU), regional, state or local regulatory agency, department, bureau, commission, council or other governmental entity, wherein such approval is necessary or sufficient for the manufacture, distribution, use or sale of a vector in a regulatory jurisdiction. In certain embodiments, such a "regulatory approved vector" means a vector which has been approved, at a minimum, for use in human clinical safety trials (sometimes referred to as "phase 1 clinical trial") in a regulatory jurisdiction. "Clinical safety" or "Phase 1" trial means a trial to assess at least safety, optionally to assess safety and dosages, for analysis of side effects associated with the test article, optionally to assess side effects in conjunction with varying dosages. In certain embodiments, "regulatory approved vector" means a vector which has been approved, at a minimum, for use in "Phase 2" studies. A "Phase 2" study is one in which the test article is administered to a larger group human subjects (as compared to a smaller Phase 1 group of subjects) for evaluation of a larger group of patients (typically up to a few hundred) with a disease, disorder or condition for which the test article is developed, to initially assess its effectiveness and to further study its safety. In certain embodiments, a Phase 2 study is to assess the optimal dose or doses of a test article to maximize benefits, while minimizing risks. In certain embodiments, "regulatory approved vector" means a vector which has been approved, at a minimum, for use in "Phase 3" studies. A Phase 3 study (sometimes referred to as "pivotal trials") typically involves about 300 to 3,000 participants from a patient population for which the test article is intended to be used. Participants in a Phase 3 study are typically assigned to receive either the test article or a placebo (a substance that has no therapeutic effect). A Phase 3 study is intended to demonstrate whether or not a test article offers a treatment benefit to a specific population and to provide more detailed safety data, and to serve as the basis for product labeling in regard to diseases or conditions for which the test article may be used. In certain embodiments, "regulatory approved vector" means a vector which has been approved for commercial manufacturing, use or sale for treatment of a disease, disorder or condition in humans by a regulatory authority in the regulatory jurisdiction (e.g., approval by U.S. FDA for manufacturing, use or sale in the United States of America). In certain embodiments, the "regulatory approved vector" is a regulatory approved lentivirus vector, a regulatory approved retroviral vector, or a regulatory approved non-viral vector. In some embodiments, the regulatory approved vector is a non-viral vector that is a Sleeping Beauty vector.

In certain embodiments, the regulatory authority governs approval of pharmaceuticals, biologics, or other medicines or medical treatments in a country selected from the United Arab Emirates, Antigua and Barbuda, Albania, Armenia, Angola, Austria, Australia, Azerbaijan, Bosnia and Herzegovina, Barbados, Belgium, Burkina Faso, Bulgaria, Bahrain, Benin, Brunei Darussalam, Brazil, Botswana, Belarus, Belize, Canada, Central African Republic, Congo, Switzerland, Cote d'Ivoire, Chile, Cameroon, China (People's Republic of China (PCR)), Colombia, Costa Rica, Cuba, Cyprus, Czech, Germany, Djibouti, Denmark, Dominica, Dominican Republic, Algeria, Ecuador, Estonia, Egypt, Spain, Finland, France, Gabon, United Kingdom, Grenada, Georgia, Ghana, Gambia, Guinea, Equatorial Guinea, Greece, Guatemala, Guinea-Bissau, Honduras, Croatia, Hungary, Indonesia, Ireland, Israel, India, Iran (Islamic Republic of), Iceland, Italy, Jordan, Japan, Kenya, Kyrgyzstan, Cambodia, Comoros, Saint Kitts and Nevis, Democratic People's Republic of Korea, Republic of Korea, Kuwait, Kazakhstan, Lao People's Democratic Republic, Saint Lucia, Liechtenstein, Sri Lanka, Liberia, Lesotho, Lithuania, Luxembourg, Latvia, Libya, Morocco, Monaco, Republic of Moldova, Montenegro, Madagascar, North Macedonia, Mali, Mongolia, Mauritania, Malta, Malawi, Mexico, Malaysia, Mozambique, Namibia, Niger, Nigeria, Nicaragua, Netherlands, Norway, New Zealand, Oman, Panama, Peru, Papua New Guinea, Philippines, Poland, Portugal, Qatar, Romania, Serbia, Russian Federation, Rwanda, Saudi Arabia, Seychelles, Sudan, Sweden, Singapore, Slovenia, Slovakia, Sierra Leone, San Marino, Senegal, Sao Tome and Principe, El Salvador, Syrian Arab Republic, Eswatini, Chad, Togo, Thailand, Tajikistan, Turkmenistan, Tunisia, Turkey, Trinidad and Tobago, United Republic of Tanzania, Ukraine, Uganda, United States of America, Uzbekistan, Saint Vincent and the Genadines, Viet Nam, Samoa, South Africa, Zambia, Zimbabwe, Afghanistan, Andorra, ARIPO, Bangladesh, Bolivia, Cayman Islands, Ethiopia, Fiji, Gibraltar, Guam, Haiti, Iraq, Lebanon, Martinique, Micronesia, federated states of, Nauru, OAPI, Palestinian territory, occupied (Gaza), Pitcairn, Saint Barthélemy, Somalia, Taiwan, Tonga, Vanuatu, Yemen, Åland Islands, Anguilla, Aruba, Bermuda, Burundi, Congo (Democratic Republic of the), Eurasian Patent Organization, French Guiana, Greenland, Guernsey, Holy see (Vatican), Jamaica, Macau, Mauritius, Montserrat, Nepal, Pakistan, Palestinian territory, occupied (West Bank), Puerto Rico, Saint Helena, South Sudan, Timor-Leste, Tuvalu, Venezuela, American Samoa, Argentina, Bahamas, Bhutan, Cape Verde, Eritrea, European Union, French Polynesia, Guadeloupe, Guyana, Hong Kong, Kiribati, Maldives, Mayotte, Myanmar, New Caledonia, Palau, Paraguay, Réunion, Saint Pierre and Miquelon, Suriname, Tokelau, Uruguay, and Western Sahara.

In certain embodiments, the regulatory authority is selected from a multinational organization, such as the World Health Organization, the Pan-American Health Organization, the World Trade Organization (WTO), the International Conference on Harmonization (ICH), and the World Intellectual Property Organization (WIPO); and a national health authority, such as, in Asia and the Pacific, the Australian Government: Department of Health and Ageing, Australian Government: Therapeutic Goods Administration (TGA), Brunei: Ministry of Health, People's Republic of China: State Food and Drug Administration, People's Republic of China: Ministry of Health, People's Republic of China: National Medical Products Administration, People's Republic of China: National Institute for the Control of Pharmaceutical and Biological Products, People's Republic of China: Ministry of Agriculture, Fiji: Ministry of Health, Hong Kong: Department of Health, India: Ministry of Consumer Affairs, Food & Public Distribution, India: Central Drug Standards Control Organization (CDSCO), India: Ministry of Food and Consumer Affairs, Indonesia: Ministry of Health, Japan: Ministry of Health, Labor and Welfare, Japan: Pharmaceuticals and Medical Devices Evaluation Agency, Korea: Food and Drug Administration, Malaysia: Ministry of Health, Malaysia: National Pharmaceutical Regulatory Agency, New Zealand: Ministry of Health, New Zealand: Medicines and Medical Devices Safety Authority, New Zealand: Food Safety Authority, Papua New Guinea: Department of Health, Philippines: Department of Health, Philippines: National Food Authority, Singapore: Ministry of Health, Singapore: Health Sciences Authority, Sri Lanka: Ministry of Health, Taiwan: Department of Health, Taiwan: National Laboratories of Foods and Drugs, Thailand: Ministry of Public Health, Thailand: Food and Drug Administration, Thailand: Ministry of Agriculture and Co-operatives, in Europe, the European Medicines Agency (EMA), European Commission Directorate General: Medicinal Products for Veterinary Use, Andorra: Ministry of Health and Welfare, Armenia: Ministry of Health, Armenia: Drug and Medical Technology Agency, Austria: Secretariat of Health, Belgium: Health, Food Chain Safety and Environment, Belgium: Pharmaceutical Inspectorate, Belgium: Federal Agency for the Safety of the Food Chain, Bulgaria: Ministry of Health, Bulgaria: Drug Agency, Croatia: Ministry of Health and Social Care, Czech Republic: Ministry of Health, Czech Republic: State Institute for Drug Control, Denmark: Ministry of Health, Denmark: Danish Medicines Agency, Denmark: Veterinary and Food Administration, Estonia: State Agency of Medicines, Finland: Ministry of Social Affairs and Health, Finnish Medicines Agency, France: Ministry of Health, France: National Agency for Veterinary Medicinal Products, Georgia: Ministry of Labor, Health and Social Affairs, Germany: Ministry of Health, Germany: Federal Institute for Drugs and Medical Devices, Germany: Robert Koch Institute, Germany: Paul Ehrlich Institute, Germany: Federal Institute for Risk Assessment, Germany: Ministry of Consumer Protection, Food and Agriculture, Greece: Ministry of Health and Social Solidarity, Greece: National Organization for Medicines, Hungary: Ministry of Health, Social and Family Affairs, Hungary: National Institute of Pharmacy, Iceland: Ministry for Health and Social Security, Icelandic Medicines Agency, Iceland: The Environment Agency, Ireland: Department of Health and Children, Irish Medicines Board, Italy: Ministry of Health, Italy: National Institute of Health, Latvia: State Agency of Medicines, Lithuania: Ministry of Health, Lithuania: State Medicines Control Agency, Luxembourg: Ministry of Health, Malta: Ministry of Health, Elderly and Community Care, Netherlands: Ministry of Health, Welfare and Sport, Netherlands: Medicines Evaluation Board, Netherlands: Inspectorate for Health Protection and Veterinary Public Health, Norway: Ministry of Health and Care Services, Norway: Norwegian Board of Health Supervision, Norway: Norwegian Medicines Agency, Norway: Ministry of Agriculture and Food, Poland: Ministry of Health and Social Security, Poland: Drug Institute, Portugal: Ministry of Health, Portugal: National Authority of Medicines and Health Products, Romania: Ministry of Health and the Family, Russian Federation: Scientific Centre for Expert Evaluation of Medicinal Products, Russian Federation: State Institute of Drugs and Good Practices, San Marino, Ministry of Health and Social Security, National Insurance and Gender Equality (in Italian), Slovak Republic: Ministry of Health, Slovak Republic: State Institute for Drug Control, Slovak Republic: State Veterinary and Food Administration, Slovenia: Ministry of Health, Slovenia: Institute of Public Health, Spain: Ministry of Health and Consumption; Spanish Agency for Medicines and Health Products, Sweden: Medical Products Agency, Sweden: National Board of Health and Welfare, Sweden: National Food Administration, Switzerland: Federal Office of Public Health, Switzerland: Agency for Therapeutic Products, Switzerland: Federal Veterinary Office, Turkey: Ministry of Health (in Turkish), Ukraine: Ministry of Health, UK: Department of Health, UK: Health Protection Agency, UK: Medicines and Healthcare Products Regulatory Agency (MHRA), UK: National Institute for Biological Standards and Control, UK: Veterinary Medicines Directorate, in the Middle East, the Bahrain: Ministry of Health, Israel: Ministry of Health, Israel: Ministry of Industry, Trade and Labor, Jordan: Ministry of Health, Lebanon: Ministry of Public Health, Palestinian Authority: Ministry of Health, Saudi Arabia: Ministry of Health, United Arab Emirates: Ministry of Health, United Arab Emirates: Federal Department of Pharmacies, Yemen: Ministry of Public Health & Population, in Africa, the Benin: Ministry of Health, Botswana: Ministry of Health, Egypt: Ministry of Agriculture and Land Reclamation, Ghana: Ministry of Health, Ghana: Ministry of Food and Agriculture, Kenya: Ministry of Health, Maldives: Ministry of Health, Mauritius: Ministry of Health & Quality of Life, Mauritius: Ministry of Agro Industry and Food Security, Morocco: Ministry of Public Health, Namibia: Ministry of Health and Social Services, Senegal: Ministry of Health and Prevention, South Africa: Department of Health, Swaziland: Ministry of Health and Social Welfare, Tanzania: Ministry of Health, Tunisia: Ministry of Public Health, Tunisia: Office of Pharmacy and Medicines, Uganda: Ministry of Health, Zimbabwe: Ministry of Health and Child Welfare, and in the Americas, the Argentina: Ministry of Health, Argentina: National Administration of Drugs, Foods and Medical Technology, Belize: Ministry of Health, Bolivia: Ministry of Health and Social Welfare, Brazil: Ministry of Health, Brazil: National Health Surveillance Agency, Brazil: Fundacao Oswaldo Cruz, Canada: Health Canada, Canada: Health Products and Food Branch, Chile: Health Ministry, Chile: Institute of Public Health, Colombia: Ministry of Health, Colombia: INVIMA Instituto Nacional de Vigilancia de Medicamentos y Alimentos, Costa Rica: Ministry of Health, Dominican Republic: Ministry of Agriculture, Ecuador: Ministry of Public Health, El Salvador: Ministry of Public Health and Social Assistance, El Salvador: Ministry of Agriculture, Guatemala: Ministry of Health, Guyana: Ministry of Health, Guyana: National Bureau of Standards, Jamaica: Ministry of Health, Mexico: Ministry of Health, Mexico: Federal Commission for the Protection Against Sanitary Risks, Netherlands Antilles: Department of Public Health and Environmental Protection, Nicaragua: Ministry of Health, Panama: Ministry of Health, Peru: Ministry of Health, Peru: General Directorate of Medicines, Supplies and Drugs, St. Lucia: Ministry of Agriculture, Lands Forestry and Fisheries, Trinidad and Tobago: Ministry of Health, Trinidad & Tobago: Bureau of Standards, United States of America (USA/U.S.): Food and Drug Administration (FDA), Uruguay: Ministry of Public Health, and the Venezuela: Ministry of Health and Social Development.

In certain embodiments, cells expressing one or more CARs are isolated for continued ex vivo expansion and/or are cryopreserved for future use.

The present invention also relates to a composition comprising a chimeric antigen receptor as described above.

The present invention further relates to a kit comprising a first vector encoding a CAR as described above and a second vector encoding a CAR as described above.

EXAMPLES

These Examples are provided for illustrative purposes only and not to limit the scope of the claims provided herein.

The following table includes abbreviations and special terms that apply to the Examples only. These abbreviations and special terms are not otherwise limiting, and neither replace nor narrow the broader definitions set forth above, which shall continue to apply to the claims.

TABLE 9

Abbreviations and Special Terms for Use in the Examples

| Abbreviation of Special Term | Explanation |
|---|---|
| Artificial miRNA | A non-naturally occurring miRNA designed to target a specific gene |
| CAR-T | Chimeric Antigen Receptor T Cell |
| Guide miRNA | The mature miRNA processed from the pre-miRNA that is complementary to an intended target gene |
| LFC | Log2 fold change |
| Mature miRNA | The fully processed 21-23nt miRNA |
| mbIL15 | A fusion protein comprising IL-15 and IL-15Rα, the protein comprising the amino acid sequence of SEQ ID NO: 525 |
| miRNA | microRNA, a small RNA species generally 21-23nt in length that is complementary to a target mRNA transcript and reduces expression of the target transcript through either RNA degradation or inhibition of translation |
| Passenger miRNA | A mature miRNA that may be processed from the side opposite of the guide miRNA in the RNA stem-loop |
| PD1 Silencer Module | A genetic module encoded within the VVN-5351 transgene cassette designed to reduce expression of PD1 within ROR1 + PD1 silencer cells. The module consists of a splice unit containing a non-coding RNA that is processed by internal cellular machinery into 2 unique microRNAs with homology to PD1 mRNA. |
| Pre-miRNA | Precursor miRNA, which is the intermediate miRNA species that has undergone the first processing step to remove the RNA stem-loop structure from the primary mRNA transcript. Pre-miRNA undergoes a second processing step in which the mature miRNA is cleaved and loaded into the RNA-induced silencing complex (RISC). |
| ROR1 + PD1 silencer cells | ROR1 CAR-T cells expressing mbIL15 and HER1t with anti-PD-1 miRNAs |
| Pri-miRNA/ pri-miRNA scaffold | The primary transcript encoding RNA stem-loop structures that are processed by the endogenous cellular machinery into precursor and then mature miRNA. The artificial pri-miRNA sequence and structures are based on endogenous human pri-miRNAs, herein referred to as a scaffold, with the natural guide and passenger strands replaced with a guide miRNA to target PD1 and a passenger miRNA to maintain the predicted folded RNA structure. |
| UTR | Untranslated region |
| VVN-5351 | A DNA transposon plasmid encoding the ROR1 UltraCAR-T transgene cassette plus a dual PD1-targeting miRNA in the 5'UTR encoded within a synthetic splice unit. |
| VVN-5355 | A DNA transposon plasmid encoding the ROR1 UltraCAR-T transgene cassette. |

Example 1. PD1 Module Design

The PD1-silencing module of miRNA-expressing ROR1 UltraCAR-T cells encodes two artificial miRNAs designed to specifically reduce expression of PD-1 mRNA within UltraCAR-T cells while avoiding off-target silencing of other endogenous transcripts. The two artificial miRNAs of miRNA-expressing ROR1 UltraCAR-T cells are encoded within a dual primary miRNA (pri-miRNA) sequence placed within a 5' UTR splice unit of the UltraCAR-T transgene cassette (FIG. 1B). The dual pri-miRNA forms stem-loop structures that are recognized and processed by cellular complexes to generate two unique 21-24 nucleotide mature guide miRNAs that are homologous to specific sequences within the PD1 target transcript. Interaction of the guide miRNAs with the PD1 target sequence is expected to trigger the silencing of PD1 by induction of RNA degradation or translational inhibition (Guo et al, 2010).

The guide miRNAs encoded within miRNA-expressing ROR1 UltraCAR-T cells were designed to be highly specific for the PD1 target transcript NM_005018.3 by implementation of an internally-designed computational workflow using a combination of twenty-one ranking parameters based on three validated rules-based siRNA prediction algorithms (Amarzguioui and Prydz, 2004; Reynolds et al, 2004; Ui-Tei et al, 2004). Multi-level specificity profiling was performed against the human reference exome (RefSeq) and the activated T-cell transcriptome (Zhao et al, 2014) to ensure that the mature miRNAs are highly specific for the PD1 target gene. To further reduce risk of off-target silencing by the non-PD1 targeting passenger strand miRNAs, pri-miRNA scaffolds were selected that produce a high ratio of guide:passenger miRNA (Miniarikova et al, 2016). The PD1-targeting guide miRNA PD1_1843 was incorporated into a pri-miRNA scaffold based on human miRNA hsa-miR-204 (accession #MI0000284) while the PD1_2061 guide miRNA was incorporated into the hsa-miR-206 (accession #MI0000490) scaffold. Mutations were created on the passenger strand side of each pri-miRNA to assure the specific miRNA structure was maintained and that thermodynamic stability was not substantially altered. RNA structures were predicted using CLC Main Workbench software. The PD1 silencing module contains the miR204 PD1_1843 pri-miRNA placed directly upstream of miR206 PD1_2061 pri-miRNA within a synthetic splice unit in the 5' UTR of the CAR-T transgene expression cassette. The splice units were ordered as gBlock from IDT and can be cloned into Sleeping Beauty CAR vectors and can be cut using ClaI/NheI for cloning into the 5'UTR of any other Sleeping Beauty CAR vector.

Example 2. Reduction of PD1 Transcript Expression by miRNAs

Figure 2:
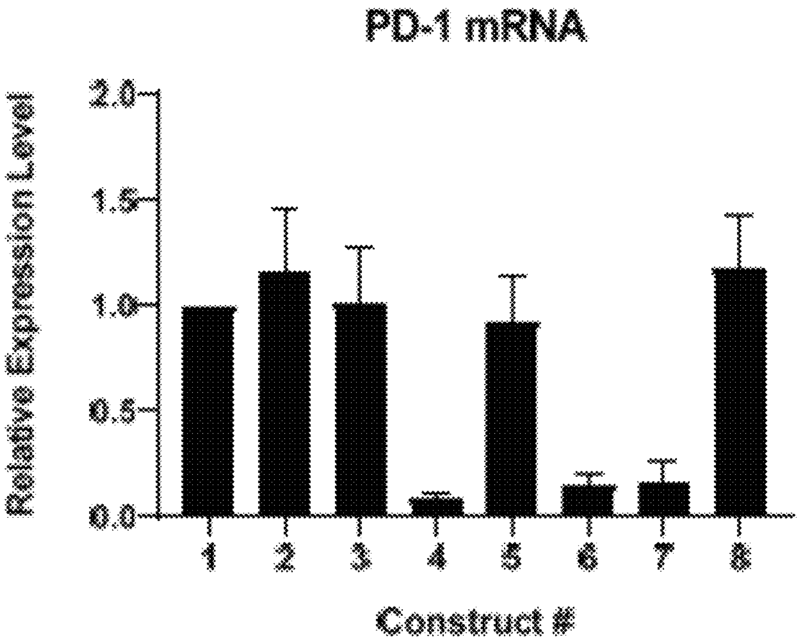
FIG. 2 is a graph depicting PD1 relative RNA expression following transfection of various combinations of miRNA constructs in the presence or absence of MUC16-specific CAR. Constructs #1-8 as depicted on the X-axis are as schematically presented in Table 10.

Primary human T cells were transfected with the constructs listed in Table 10 and expanded in vitro with the use of AaPC cells expressing cognate antigen that were grown in large batches and then frozen into aliquots. The generated CAR-T cells were then further activated using anti-CD3/anti-CD28 beads at a bead: T cell ratio of 1:1 and $1\times10^6$ T cells/mL for 48 hrs prior to harvesting the cells for RNA isolation. RNA isolation was performed according to manufacturer's recommended protocol (Qiagen) then subjected to RT-qPCR analysis using the SuperScript VILO Master Mix® (Thermo Fisher) reagent with ezDNase® (Invitrogen) DNase and TaqMan FAST Advanced Master Mix® (Thermo Fisher) reagent for qPCR to evaluate PD-1 expression levels using specific primer/probes (Human PD1: Hs00169472_m1; Human TIGIT: Hs00545087_m1; and Human ACTb: Hs99999903_m1). All samples were also normalized to beta-actin expression levels. The relative expression values are based upon ΔΔCT method by normalizing to construct #1 (MUC16 CAR-T cells only). Results are shown in FIG. 2. Shown is the mean±SD from 3 donors.

TABLE 10

Description of constructs 1-8 as utilized in FIG. 2 sequences of miRNA are as described in Table 4)

| Construct # | miRNA | Effector Genes |
|---|---|---|
| 1 | N/A | MUC16 CAR-mbIL15-HER1t |
| 2 | Scrambled 1 (SEQ ID NO: 586) | MUC16 CAR-mbIL15-HER1t |
| 3 | Scrambled 2 (SEQ ID NO: 582) | MUC16 CAR-mbIL15-HER1t |
| 4 | miR204 PD1 + miR206 PD1 | MUC16 CAR-mbIL15-HER1t |
| 5 | miR17 TIGIT | MUC16 CAR-mbIL15-HER1t |
| 6 | miR150 TIGIT + miR206 PD1 | MUC16 CAR-mbIL15-HER1t |
| 7 | miR204 PD1 + miR206 PD1 + miR17 TIGIT | MUC16 CAR-mbIL15-HER1t |
| 8 | N/A | MUC16 CAR + HER1t |

The data demonstrates the specificity of PD-1 checkpoint inhibitor miRNA targeting the intended sequence. CAR constructs that expressed the scrambled miRNA (Constructs 2 and 3) along with the CAR construct that did not express mbIL-15 (construct #8) did not show any decrease in PD-1 expression whereas CAR constructs that contain PD-1 miRNA (construct 4) or a combination of PD-1 and TIGIT miRNA (constructs 6 and 7) did show a decrease in PD-1 expression. On the other hand, the CAR construct containing only a TIGIT miRNA sequence (construct 5) did not show any decrease in PD-1 mRNA expression levels further demonstrating the specificity in targeting.

Example 3. Downregulation of Targeted mRNA

Primary human T cells were transfected with a vector encoding CD33-specific CAR or a vector encoding MUC16-specific CAR. The vectors comprise a synthetic intron containing miRNA sequences that target PD-1, PD-1 and/or TIGIT or a non-targeting scrambled control miRNA. T cell cultures were in vitro expanded using antigen presenting cells with cognate tumor antigen that were K562 cells modified to express either CD33 or MUC16 plus other co-stimulatory molecules (based on “Clone 1”) and at a ratio of 1:1 (AaPC: T cell). The generated CAR+ cells were then stimulated with anti-CD3/anti-CD28 beads (1:1 bead: T cell ratio) in the absence of cytokines for 48 hrs. RNA was isolated using AllPrep® Universal DNA/RNA/miRNA kit #80224 (Quiagen) as per manufacturer’s protocol and utilized for the nCoutner® Human PanCancer Immune gene set panel Kit (Nanostring). Briefly, the RNA was hybridized with capture and reporter probe sets and samples processed then hybridized to the slide using the nCounter® Prep Station (Nanostring) automated liquid handling instrument and transcript counts were generated by the nCounter® Digital Analyzer according to the manufacturer’s protocol (Nanostring). Data validation, QC and normalization were performed by nSolver® software (Nanostring-Technologies).

Figure 3A:
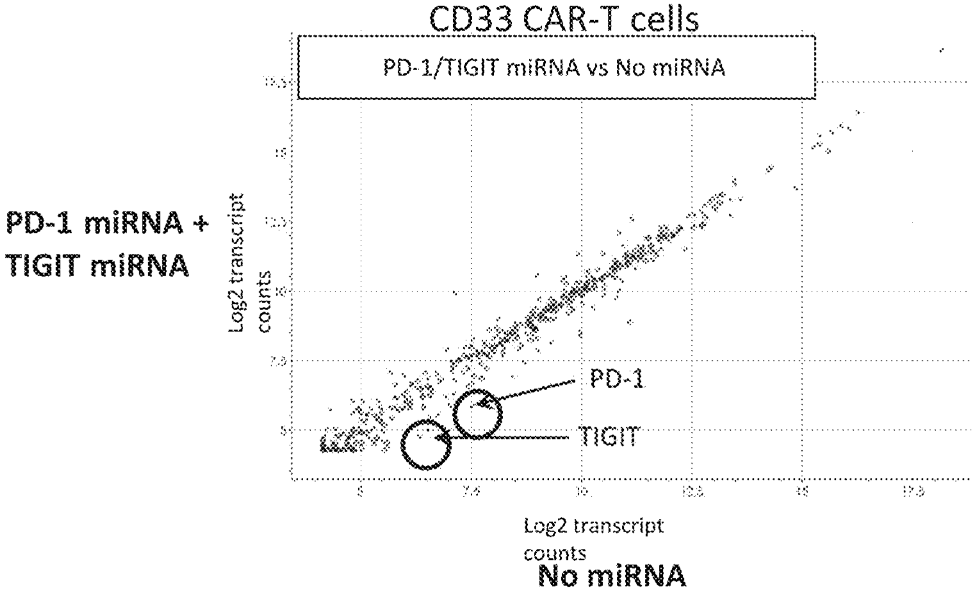
FIGS. 3A, 3B and 3C are graphs depicting normalized absolute transcript counts obtained from gene analysis of >700 genes using a Nanostring human gene panel code set with CD3/CD28 bead-stimulated CD33 CAR-T cells.
Figure 3B:
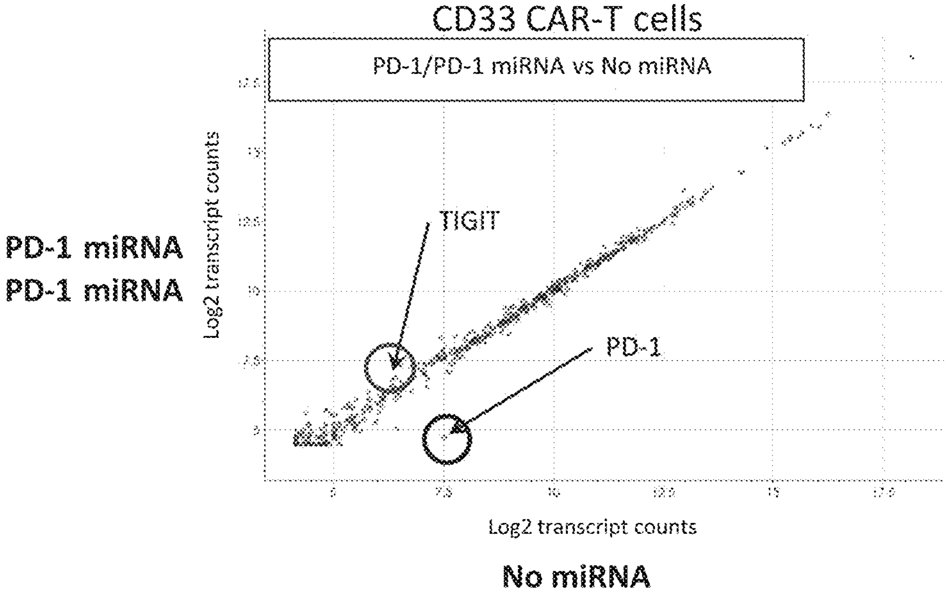
Figure 3C:
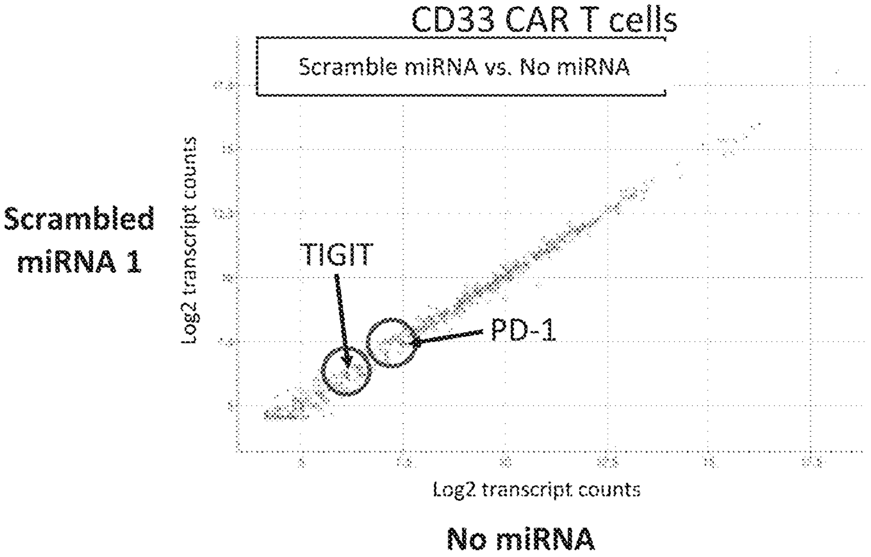
Figure 4A:
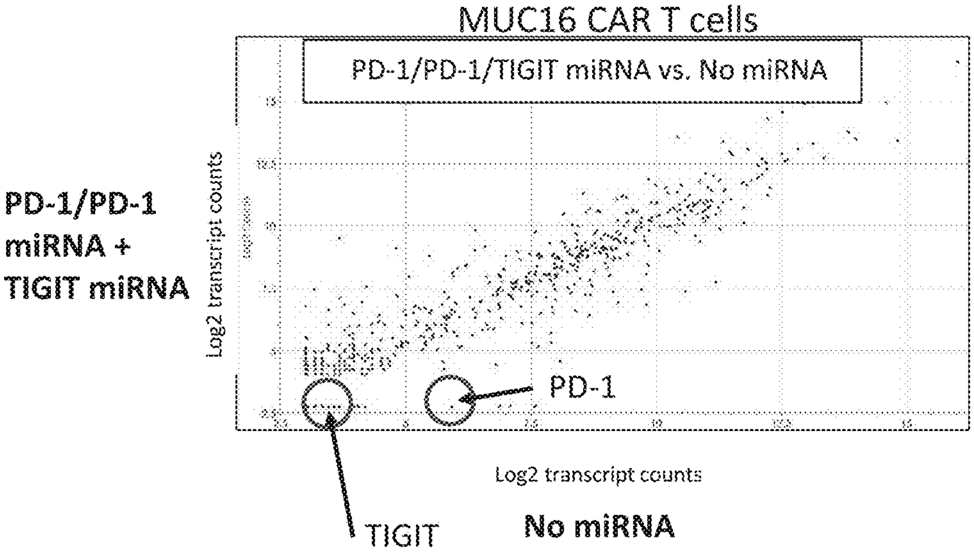
FIG. 4A-C are graphs depicting the normalized absolute transcript counts obtained from gene analysis of >700 genes using a Nanostring human gene panel code set with CD3/CD28 bead stimulated MUC16-specific CAR-T cells.
Figure 4B:
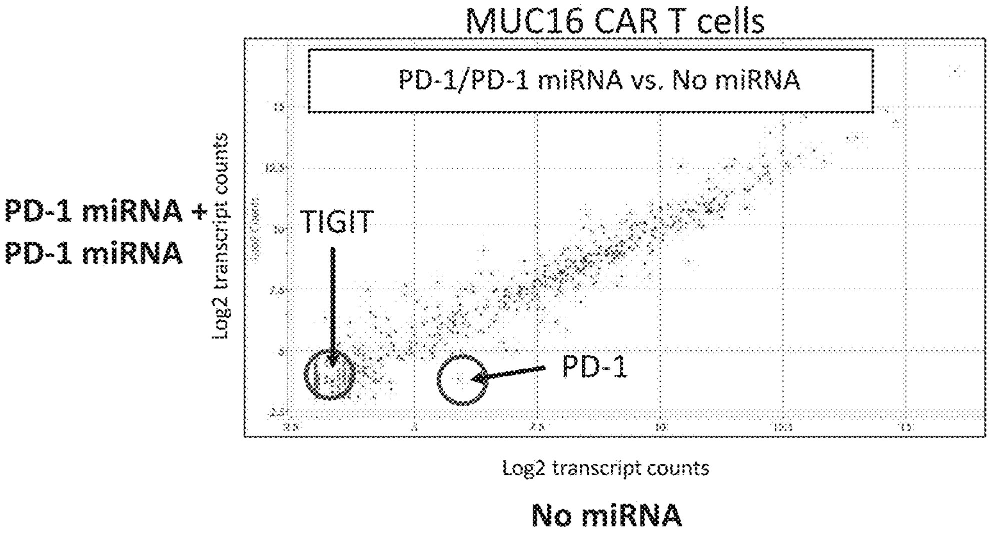
Figure 4C:
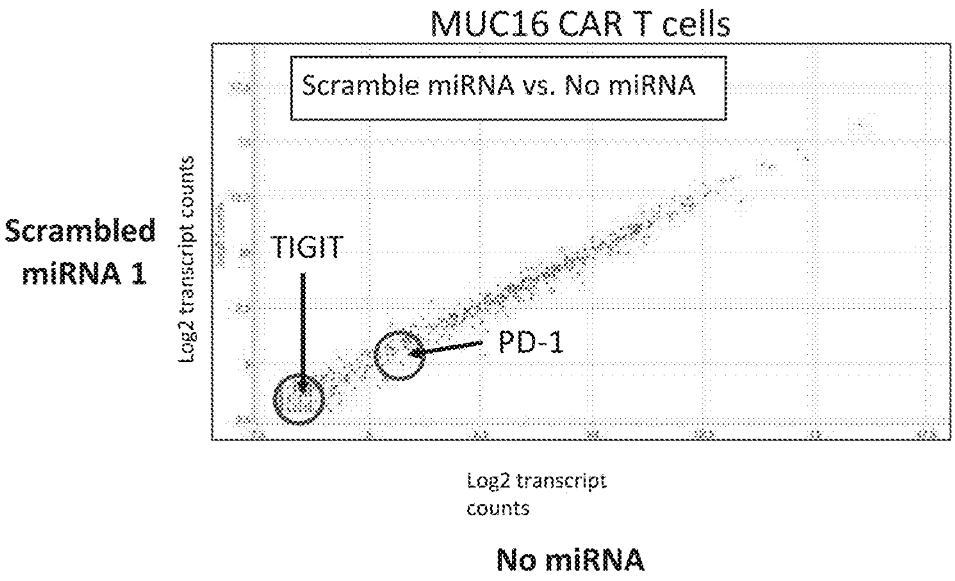

The distribution of the transcript count data on the graph would be a line (from lower left to top right corner) with the slope of 1 if the samples were identical. Data points falling off this line represent variations in transcript counts between the two samples. Counts that were found below the main line represent reduced expression whereas counts above the main line represent increased expression to the sample being compared. The transcript targeted by the miRNA, either PD-1 or TIGIT expressed in the CAR-T cells, specifically showed lower expression of the transcripts of their respective targeted genes compared to the CAR-T cells without the miRNA. See FIG. 3A-B. In addition, to further demonstrate the specificity of targeting, the CAR-T cells with the scrambled control miRNA had no alterations to the transcript levels of either PD-1 or TIGIT, as the data distribution in this graph remained close to the diagonal indicating very little variation in transcript levels. See FIG. 3C. Similar results were observed in T cells transfected with the MUC16 CAR vector comprising a synthetic intron containing miRNA sequences that target PD-1, PD-1 and/or TIGIT (see FIG. 4A-C).

Example 4. Enhancement of Tumor Cell Cytotoxicity Effect of miRNA MUC16 CAR-T Cells Primary human T cells were transfected with a vector encoding MUC16-specific CAR and miRNA sequences that target two sequences within the PD-1 transcript, or with a vector that encodes the MUC16-specific CAR but not an miRNA. CAR-T cells used in this assay were in vitro expanded, normalized for CAR expression then seeded in triplicates with GFP+ K562 cells expressing MUC16 (“tumor cells”) in 96 well plates at the 3:1 E: T ratios. The plate was loaded into the IncuCyteS3® (Sartorius) live-cell analysis system and 4 images per well were taken every 2 hr for 7 days. The IncuCyte® Software (Sartorius) for live-cell analysis was used to analyze the data and normalize the GFP+ cell counts/image to the 0 hr time point.

Figure 5A:
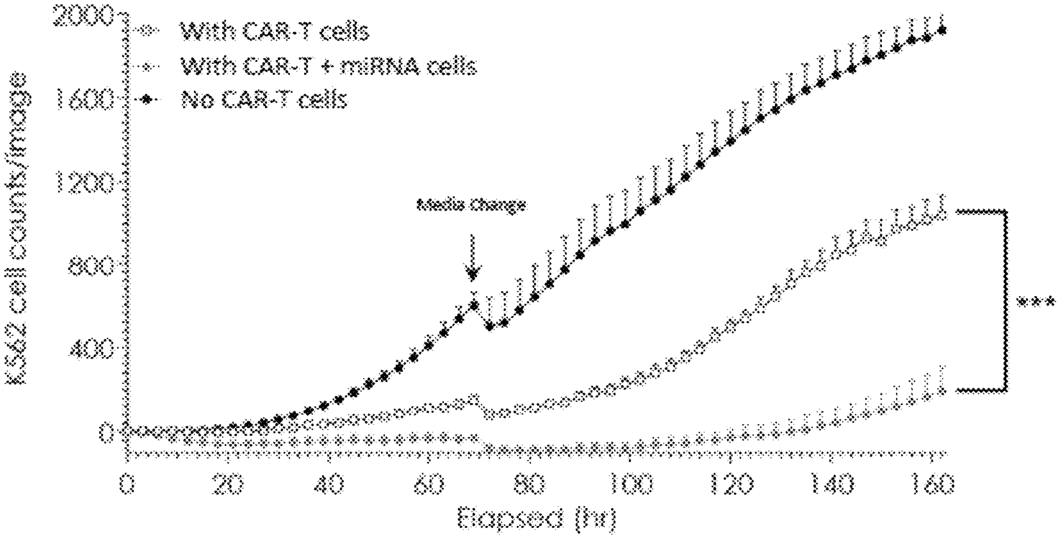
FIG. 5A is a graph depicting the number of GFP+K562 cells expressing MUC16 over time. The line with black circle filled dots at each time point denotes number GFP+ target cells in wells without CAR-T cells. The line with square open points denotes target cell counts in wells with MUC16 CAR-mbIL15-HER1t CAR-T cells without a miRNA-containing intron, (("with CAR-T cells")). The line with grey circle filled points denotes the target cell counts in wells with CAR-T cells containing a synthetic intron with dual PD-1 targeting miRNAs (MUC16 CAR-mbIL15-HER1t+miRNA (PD-1/PD-1) ("with CAR-T+miRNA cells"). Data are from one donor, plotted is the mean+SD of triplicate wells. ***P<0.001 based on a 2-way ANOVA with Dunnett's Multiple Comparison post hoc test.

The outgrowth assay determines the rate of target cell growth in the presence or absence of CAR-T cells over the course of 7 days in culture. The lower target cell count in cultures containing CAR-T cells indicate the CAR-T cytolytic activity. FIG. 5A depicts the difference between the tumor target cells only (black circle, filled) and the cells expressing the MUC16-specific CAR only (open square), demonstrating the killing capacity of the MUC16 CAR-T cells. The cells further expressing miRNA targeting PD-1 (grey circle filled) further demonstrates improved cytolytic activity, based upon the sustained low GFP+ counts over the time course evaluation, compared to the cells expressing MUC16 specific CAR only (open square). This data demonstrates the enhanced cytolytic activity of CAR-T cells containing PD-1 targeting miRNA.

Figure 5B:
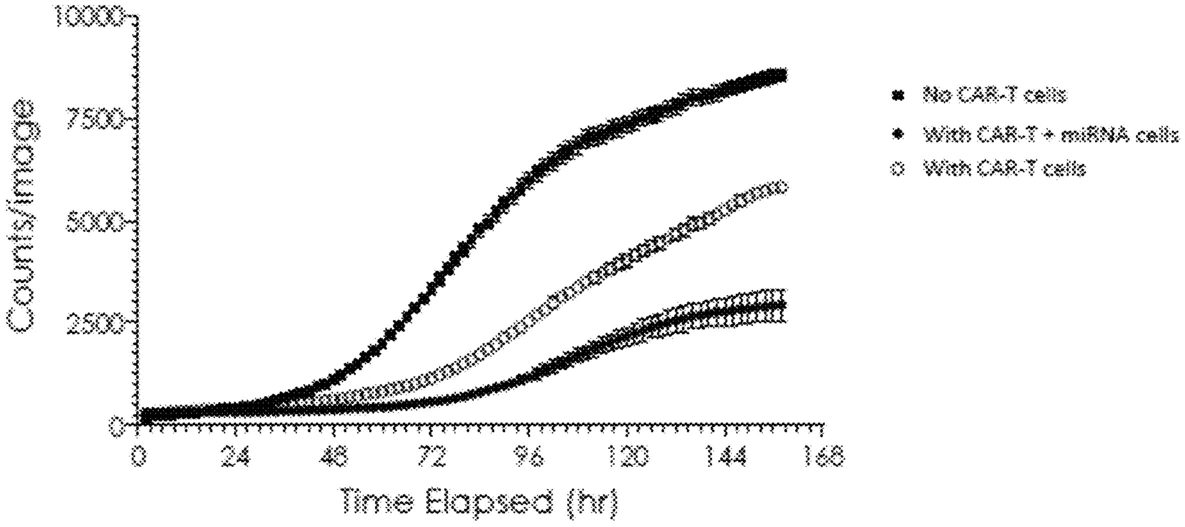
FIG. 5B is a graph depicting the number of GFP+K562/MUC16+/PD-L1+/CD155+ cells over time. The line with square filled points at each time point denotes number GFP+ target cells only in wells. The line with open circle points denotes target cell counts in wells with MUC16-specific CAR-T cells without a miRNA-containing intron (MUC16 CAR-mbIL15-HER1t (with CAR-T cells)). The line with open circle filled points denotes the target cell counts in wells with CAR-T cells containing a synthetic intron with dual PD-1 and a TIGIT targeting miRNAs (MUC16CAR-mbIL15-HER1t+miRNA (PD-1/PD-1/TIGIT)(with CAR-T+miRNA cells)). Data are from one donor, plotted is the mean+SD of triplicate wells.
Figure 6A:
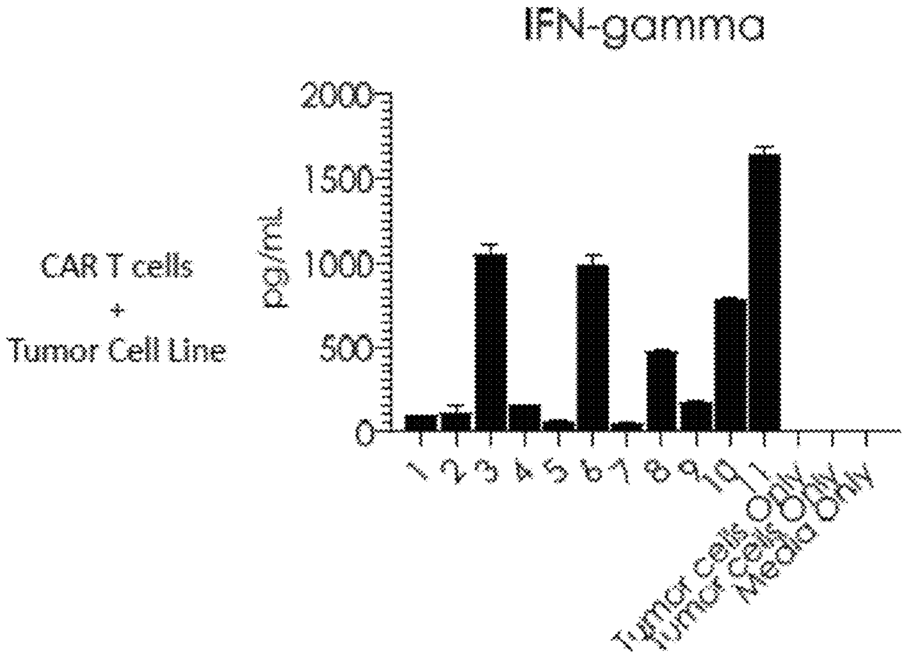
FIG. 6A-B depicts cytokine expression levels of IFN gamma and GM-CSF in MUC16 CAR-T cells with a combination of one or more checkpoint inhibitor miRNAs following co-culture with tumor target cells (K562/MUC16t).
Figure 6B:
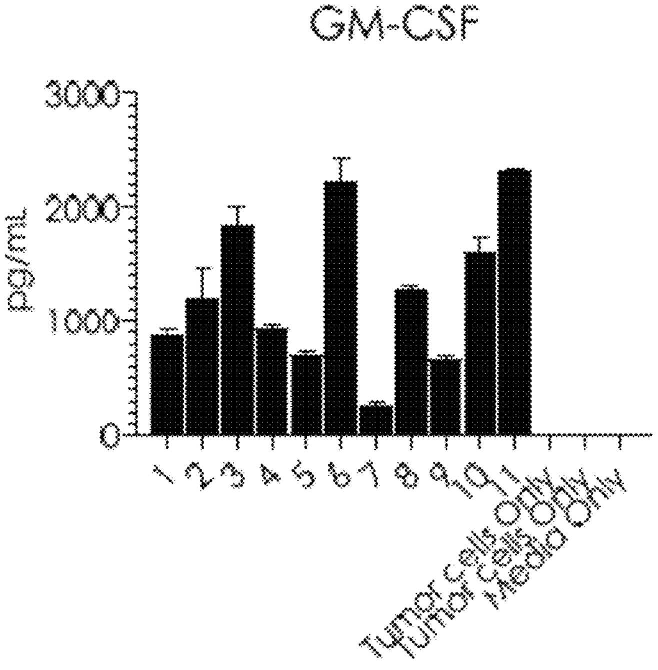
Figure 6C:
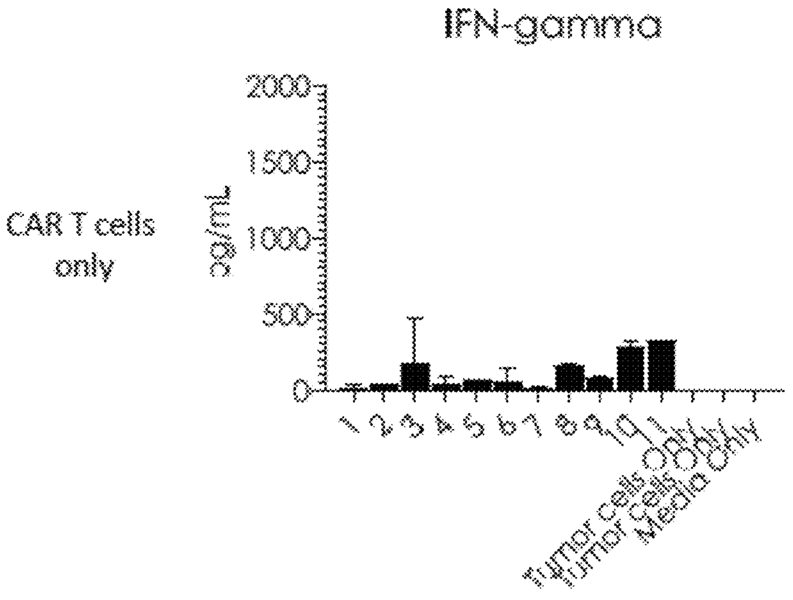
FIG. 6C-D depicts cytokine expression levels of IFN gamma and GM-CSF in MUC16 CAR-T cells with a combination of one or more checkpoint inhibitor miRNAs without co-culture with tumor target cells. Constructs #1-11 as depicted on the X-axis are as schematically presented in Table 11.
Figure 6D:
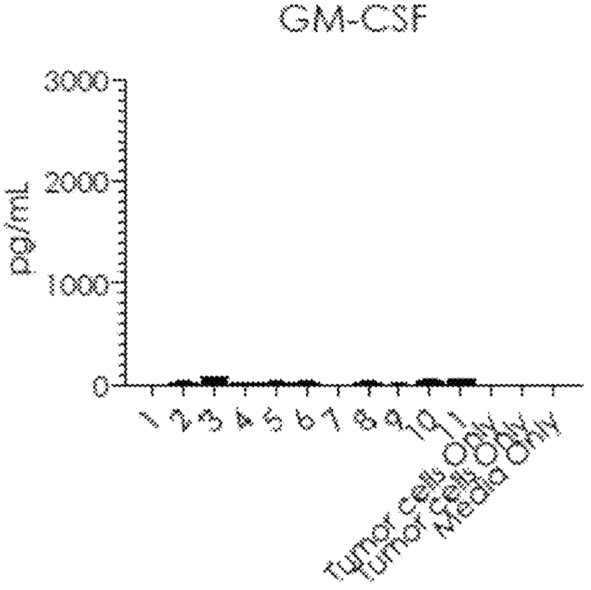

A similar experiment was conducted utilizing GFP+ K562 cells expressing MUC16, PD-L1, and CD155. As shown in FIG. 5B, the difference between the tumor target cells only (square, filled) and cells expressing the CAR only (circle, open), demonstrates the killing capacity of the MUC16 CAR-T cells. The CAR-T cells incorporating miRNAs targeting both PD-1 and TIGIT (circle, filled) further demonstrates improved cytolytic activity, based upon the sustained low GFP+ counts over the time course evaluation, compared to the MUC16 CAR-T cells only (circle, filled). This data demonstrates the enhanced cytolytic activity of CAR-T cells containing 3 targeting miRNAs (2 for PD-1 and 1 for TIGIT) in a single construct.

Example 5. Improvement of Cytokine Expression

Primary human T cells were transfected with vectors encoding MUC16-specific CAR but not miRNA targeting sequences, and vectors encoding MUC16-specific CAR and single or combinations of miRNA targeting sequences of PD-1 and TIGIT (see Table 11). In vitro expanded CAR-T cells were in vitro expanded, normalized for CAR expression then seeded in triplicates in 96 well plates with K562 tumor target cells expressing truncated MUC16 9MUC16t) at an effector to target ratio of 1:1 or the CAR-T cells were cultured in media alone. Culture supernatants were collected after co-culturing for 3 days. Culture supernatants were collected and interferon-gamma (IFNγ) and granulocyte/macrophage-colony stimulating factor (GM-CSF) was assessed by multiplex cytokine analysis (Luminex) according to manufacturer's protocol. Shown in FIG. 6 is the mean±SD from duplicate wells.

For the CAR-T cell constructs cultured in media only had basal levels of IFNγ and GM-CSF detected. No cytokines were observed from the use of target cells or media only. The supernatants following co-culture of MUC16 CAR-T cells only (Vector 1) with the tumor cells provided a baseline value for expression levels of IFNγ and GM-CSF. With the inclusion of checkpoint inhibitor miRNA into the CAR constructs, improved cytokine expression may be observed, particularly through inhibition via the PD-1 pathway. In the constructs that contained dual PD-1 (Construct #3) or the combination of a single PD-1 and TIGIT miRNA (Construct #6) or dual PD-1 and a TIGIT miRNA (Constructs #10 and 11) provided higher levels of cytokine expression.

TABLE 11

Description of Constructs #1-11 in FIGS. 6A-D
(sequences of miRNA are as described in Table 4)

| Constructs | miRNA | Effector genes |
|---|---|---|
| 1 | N/A | MUC16 CAR-mbIL15-HER1t |
| 2 | Scrambled control 1 | MUC16 CAR-mbIL15-HER1t |
| 3 | miR204 PD1 + miR206 PD1 | MUC16 CAR-mbIL15-HER1t |
| 4 | miR17 TIGIT | MUC16 CAR-mbIL15-HER1t |
| 5 | miR17 TIGIT + miR206 PD1 | MUC16 CAR-mbIL15-HER1t |
| 6 | miR150 TIGIT + miR206 PD1 | MUC16 CAR-mbIL15-HER1t |
| 7 | miR17 TIGIT + miR204 PD1 + miR206 PD1 | MUC16 CAR-mbIL15-HER1t |
| 8 | miR17 TIGIT + miR204 PD1 + miR206 PD1extended v1 | MUC16 CAR-mbIL15-HER1t |
| 9 | miR17 TIGIT + miR204 PD1 + miR206 PD1extended v2 | MUC16 CAR-mbIL15-HER1t |
| 10 | miR204 PD1 + miR206 PD1 + miR17 TIGIT | MUC16 CAR-mbIL15-HER1t |
| 11 | miR204 PD1 + miR206 PD1 + miR17 TIGITextended v1 | MUC16 CAR-mbIL15-HER1t |

Example 6. Tumor Burden in Treated Mice

Non-obese diabetic/severe combined immunodeficiency (NOD/SCID) gamma mice (NSG) mice were intraperitoneally implanted with fLUC-GFP+ SK-OV-3 tumor cells expressing MUCt on Day 0. Tumor burden was monitored in these mice throughout the study using an in vivo imaging system (IVIS®) by luminescence with an IVIS® Spectrum instrument (Perkin Elmer). Data was analyzed using Living Image Software® (Version 4.1) (Perkin Elmer) based upon a defined region of interest to obtain total flux values (photons/sec). Prior to administration of the CAR-T cells, mice were randomized based upon tumor burden and body weight into the different groups then administered the test articles on Day 6 All CARs tested expressed the MUC16-specific CAR along with mbIL15 and HER1t and are referred to as MUC16 CAR. All test articles were normalized to a $0.5\times10^6$ CAR-T cells/mouse and administered intraperitoneally. IVIS® imaging was performed twice/week to monitor overall tumor burden in the mice. Data shown is the mean±SEM from n=4-8 mice/group.

Figure 7:
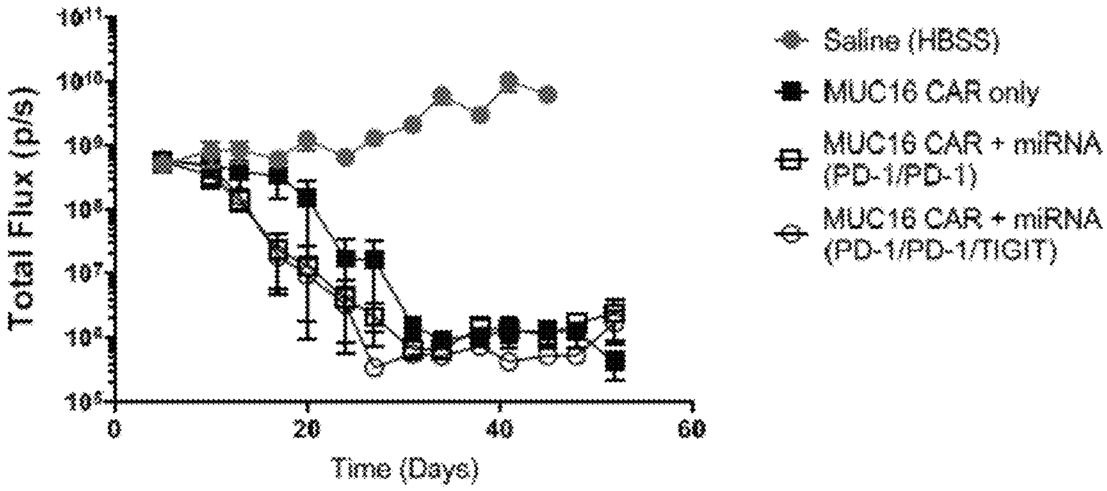
FIG. 7 shows the tumor burden in mice treated with MUC16 CAR+mbIL-15+HER1t (shown as "MUC16 CAR") in combination with various miRNAs.

As shown in FIG. 7, mice given saline only (gray-filled circles), had continuous tumor growth as evidenced by the increasing total flux levels observed throughout the course of the study. Eventually, these mice succumbed to the tumor burden and were euthanized. Mice given the MUC16 CAR only (black-filled squares) were able to control tumor burden. CAR-T cells expressing the checkpoint inhibitor miRNA to PD-1 and TIGIT within the constructs (open squares and circles) were found to maintain anti-tumor activity, based upon the decrease in tumor flux values to background levels. In addition, the CAR-T cells expressing the checkpoint inhibitor miRNA to PD-1 and TIGIT showed a faster time frame and the rate of tumor burden decrease compared to the MUC16 CAR only construct.

Example 7. In Vivo Phenotyping Experiment

Figure 8A:
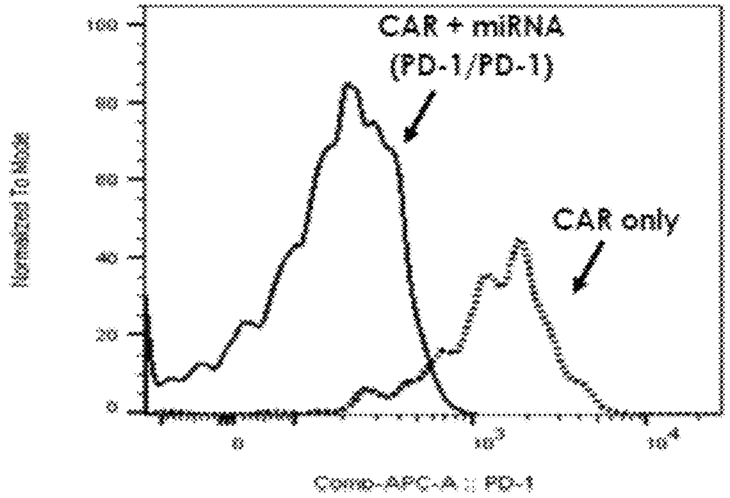
FIG. 8A demonstrates PD-1 levels in cell populations following gating hCD45/CD3+/HER1t+ expression in the blood of MUC16CAR+mbIL15+HER1t (CAR only) and MUC16CAR+mbIL15+HER1t+miRNA (PD1/PD-1) (CAR+miRNA (PD-1/PD-1)) treated mice.
Figure 8B:
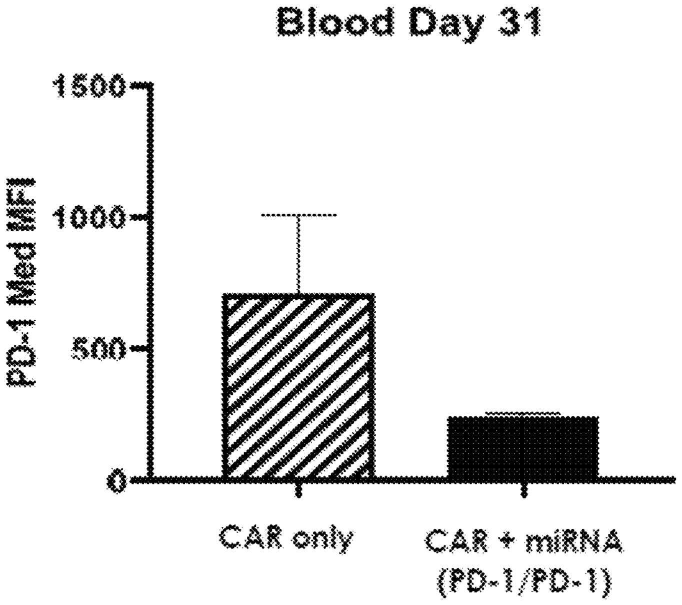
FIG. 8B shows PD-1 levels as measured by median fluorescent intensity (MFI) in CAR and CAR+miRNA (PD-1/PD-1) treated mice.

SKOV-3/MUC16 tumor bearing mice were administered CAR-T cells (expressing MUC16-specific CAR, mbIL15 and HER1t) of either CAR only or CAR with PD-1/PD-1 miRNA on Study Day 6. Whole blood from mice were taken on Study Day 31 for phenotypic evaluation by flow cytometry of the administered CAR-T cells. Briefly, cocktails of fluorescently conjugated antibodies were used to stain the whole blood samples then concurrently fixed along with red blood cells lysis using a one-step Fix/Lyse® buffer (BD Biosciences). The fixed samples were read on a BD LSR-FortessaX-20® (BD Biosciences) flow cytometer. CAR-T cells were identified based upon gating of hCD45/CD3$^+$/HER1t+ expression. In, FIG. 8A, the sample of CAR only (dotted line) shows high PD-1 expression, whereas the CAR with PD-1/PD-1 miRNA (solid line) shows a significant decrease in the level of PD-1 expression detected. To further quantify the reduced expression of PD-1 detected on the CAR+ miRNA (PD-1/PD-1) group, the median fluorescent intensity (MFI) was examined (FIG. 8B). The mean MFI of PD1 expression in mice given CAR-T cells (stripe bar) only was ~709 whereas the mean MFI of the CAR-T cells with a PD-1/PD-1 miRNA (solid bar) was reduced down to ~236. The mean±SEM from 5-8 mice is shown.

Example 8. Specific PD-1 and TIGIT Downregulation

SKOV-3 tumor bearing mice were administered CAR-T cells (expressing MUC16-specific CAR ("MUC16 CAR"), mbIL15 and HER1t) of either CAR only or CAR with different checkpoint miRNA inhibitors (PD-1 and TIGIT) on Study Day 6. See Table 12.

TABLE 12

Figure 9A:
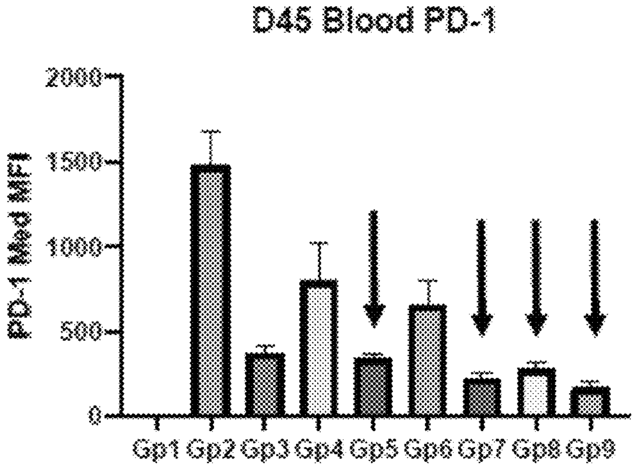
FIGS. 9A and 9B demonstrates PD-1 and TIGIT MFI levels in cell populations following gating hCD45/CD3+/HER1t+ expression in the blood of various CAR and CAR+miRNA treated mice. Groups #1-9 as depicted on the X-axis are as schematically presented in Table 12.
Figure 9B:
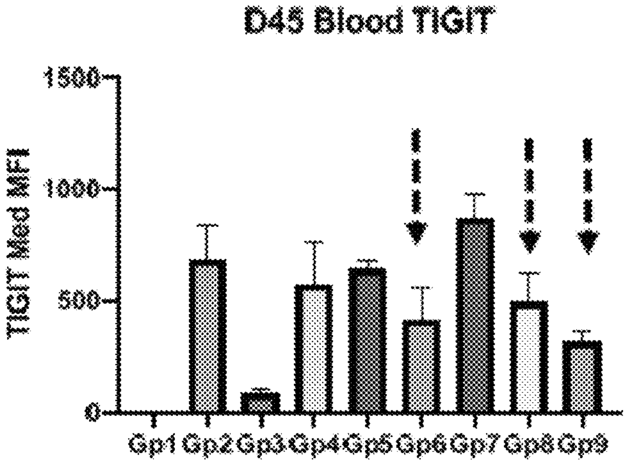

Description of Groups #1-9 in FIGS. 9A-B

| Group | CAR-T Cells |
|---|---|
| 1 | Saline control |
| 2 | MUC16 CAR/mbIL15/HER1t |
| 3 | MUC16 CAR/mbIL15/HER1t + anti-PD1 |
| 4 | MUC16 CAR/mbIL15/HER1t + scrambled miRNA 2 |
| 5 | MUC16 CAR/mbIL15/HER1t + miR206 PD1 |
| 6 | MUC16 CAR/mbIL15/HER1t + miR17 TIGIT |
| 7 | MUC16 CAR/mbIL15/HER1t + miR204 PD1/miR206 PD1 |
| 8 | MUC16 CAR/mbIL15/HER1t + miR150 TIGIT/miR206 PD-1 |

TABLE 12-continued

| Description of Groups #1-9 in FIGS. 9A-B | |
|---|---|
| Group | CAR-T Cells |
| 9 | MUC16 CAR/mbIL15/HER1t + miR204 PD1/miR206 PD1/miR150 TIGIT |

Whole blood from mice were taken on Study Day 45 (D45) for phenotypic evaluation by flow cytometry of the administered CAR-T cells. Briefly, cocktails of fluorescently conjugated antibodies, which included specific antibodies for human PD-1 and human TIGIT, were used to stain the whole blood samples then fixed using a one step Fix/Lyse® buffer (BD Biosciences). The fixed samples were read on a BD LSRFortessaX-20® (BD Biosciences) flow cytometer. CAR-T cells were identified in the mouse based upon gating of hCD45/$CD3^+$/HER1t+ expression. To further evaluate the specificity of miRNA used in the CAR vector for the checkpoint inhibitor, the median fluorescent intensity (MFI) for expression of PD-1 and TIGIT was analyzed (FIGS. 9A and B). The MFI for PD-1 is shown on the left and the MFI for TIGIT is shown on the right for a quantitative assessment of the expression levels for the same set of vectors. As shown in FIG. 9A, reduced expression of PD-1 was seen on the CAR-T cells for the groups indicated with the down arrows (solid line for PD-1), which are constructs with a PD-1 miRNA (single, double and in combination with another miRNA checkpoint inhibitor), when compared to the CAR vector only. On the right side (downward dashed arrows) highlights cell populations with a reduced expression of TIGIT expression seen on the CAR-T cells. The downregulated expression of TIGIT corresponded to the samples that contained an a miRNA for TIGIT (either as a single or in combination with other checkpoint miRNA inhibitors). The mean±SEM from 5-8 mice is shown.

Example 9. Expression of PD1-Targeting miRNAs in ROR1-Targeted CAR-T Cells

Briefly, miRNA-expressing ROR1 UltraCAR-T cells or control ROR1 UltraCAR-T cells were generated from T cells from five donors. PanT cells from five healthy donors were transfected with an indicated transposon vector (VVN-5355 or VVN-5351) plus SB11 transposase vector, and expanded by weekly stimulations for 4 weeks (~35 days before adding beads) with ROR1 antigen presenting cells. Following a rest period of 7-8 days, UltraCAR-T cells were activated with CD3/CD28 dynabeads (1:1 bead: T cell ratio, T cells at $1\times10^6$ cells/mL) for 48 hours prior to RNA harvest, 7-8 days after the last AaPC stimulation. Expression of PD1-targeting guide miRNAs and the impact on PD1 mRNA expression were verified by RT-qPCR. Small RNAseq, which is an established method to identify the predicted and alternate miRNA sequences that may arise from a pri-miRNA (Borel et al, 2018; Miniarikova et al, 2016), was performed to compare expression levels of the PD1-targeting guide miRNAs to additional small RNA species, such as passenger miRNA, that may be generated from the PD1 silencer module. Small RNAseq was also used to assess potential changes on global endogenous miRNA expression (Mueller et al, 2012). RNAseq analysis was performed to evaluate global transcript expression and to identify changes in molecular pathway signaling or off-target gene silencing attributed to the PD1 silencer. In silico miRNA target prediction was performed using the miRanda algorithm to identify most likely targets of miRNAs generated from the PD1 silencer module. Expression of the predicted target genes was evaluated by RNAseq. Details of each method is included in the sections below.

To characterize expression of miRNAs encoded by the PD1 silencer and impact on PD1 transcript levels, RT-qPCR and small RNAseq were performed. To characterize changes in specific genes or cellular pathways, RNAseq was performed.

Nucleic acids were purified from cell pellets using AllPrep® DNA/RNA/miRNA Universal kit (Cat #80224) (Qiagen) following the manufacturers protocol. Total RNA was eluted in 50 uL nuclease-free water and concentration measured on a Nanodrop® 2000 spectrophotometer.

To quantify the expression of PD1 guide and passenger miRNAs, total RNA was used as input for cDNA synthesis using miRCURY® LNA RT Kit (#339340) (Qiagen). Per the manufacturer's protocol, cDNA was diluted 1:60 with nuclease-free water and 3 μL of the diluted cDNA was used as input for qPCR using miRCURY® LNA SYBR Green PCR Kit (Qiagen #339345) with custom miRCURY® LNA primers specific to the two PD1 guide miRNAs. An endogenous miRNA, hsa-let-7a-5p, was quantified as a reference small RNA to allow for input normalization (Qiagen product #339306 with custom #YP00205727). Samples were run in a 384 well format on a QuantStudio 6 Flex® (Thermo Fisher) PCR instrument. Relative quantification (dCT) calculations were performed in Microsoft Excel® and data graphed in GraphPad Prism 98 (Graph Pad Software). Calculations for dCT were performed on each technical replicate as follows:

$$dCT=CT(\text{guide miRNA})-CT(hsa\text{-let-}7a)$$

$$ddCT=dCT(\text{miRNACART replicate})-dCT(\text{average of } VVN\text{-5355 technical replicates})$$

$$\text{Fold Change}=2\hat{}-ddCT$$

The VVN-5355 ROR1 UltraCAR-T control sample serves as the reference control sample for comparison to miRNA expressing ROR1 UltraCAR-T cells within each donor set. Average fold change and standard deviation of technical replicates was calculated and reported in FIG. 10A.

To quantify and compare the production of guide and passenger miRNAs originating from the PD1 silencing module, RT-qPCR was performed as described above, except this second experiment included primer assays to detect the passenger miRNAs as well as an additional endogenous reference small RNA, RNU1A1. Expression calculations were performed to compare expression of each guide or passenger strand mature miRNA relative to the average of the endogenous control small RNAs as follows:

$$dCT=CT(\text{mature miRNA})-CT(\text{average of } hsa\text{-let-}7a \text{ and } RNU1A1)$$

$$\text{Fold change}=2\hat{}-dCT$$

Figure 11:
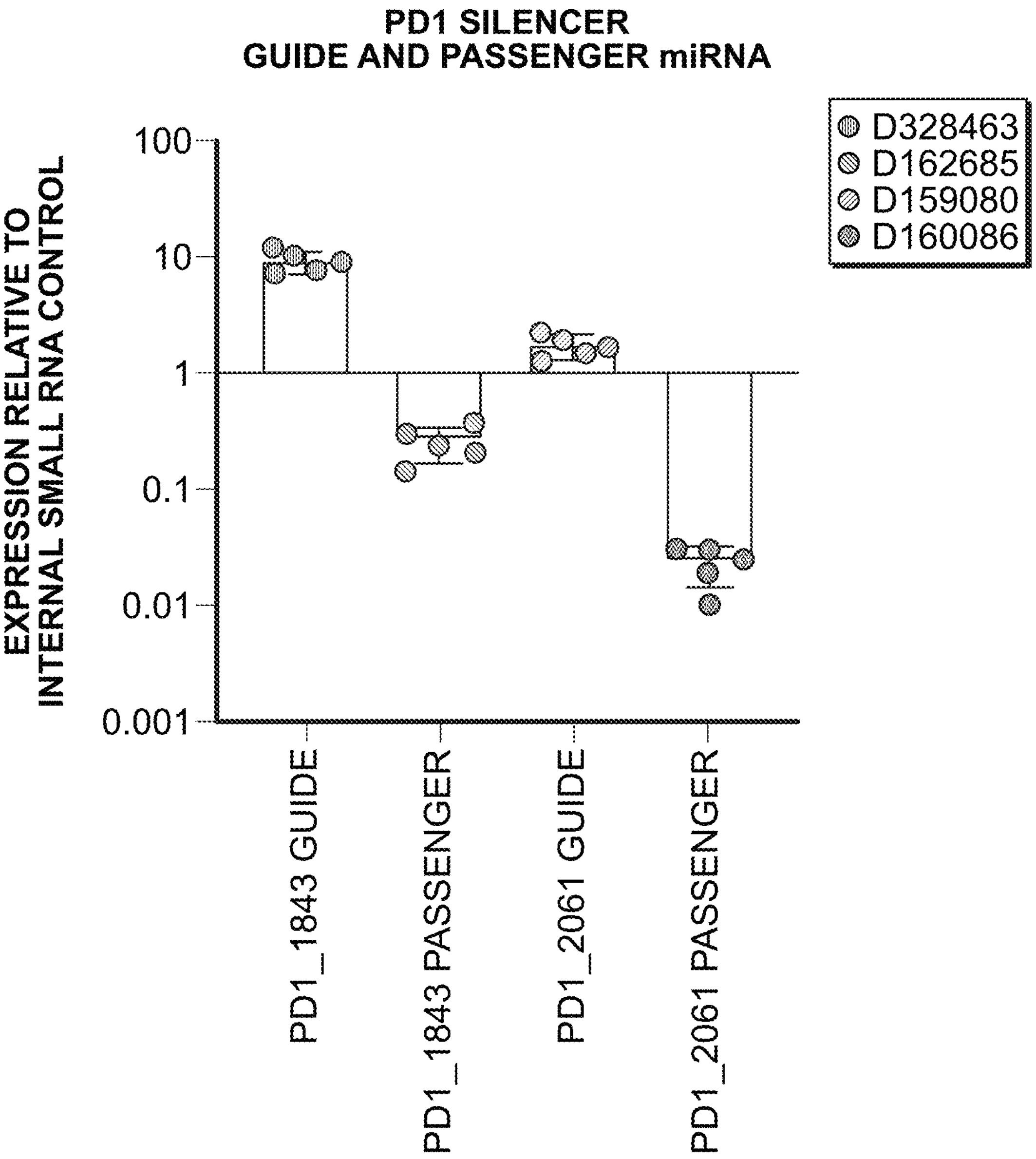
FIG. 11 demonstrates that the PD1 silencing module preferentially produced PD1-targeting guide miRNAs over non-targeting passenger miRNAs.

Average fold change was calculated from three technical replicates. These values are plotted in FIG. 11 with mean and standard deviation shown for the donor sample sets tested.

To quantify the expression of endogenous PD1 mRNA, cDNA synthesis was performed using a final RNA concentration of 5 ng/μL using SuperScript IV VILO Master Mix® (Invitrogen) with ezDNase (Invitrogen) enzyme kit (#11766050). Multiplex Taqman qPCR® (Invitrogen) was performed using Invitrogen's TaqMan MastAdvanced Master Mix® (#4444963) (Invitrogen) with 1 microliter of cDNA and Invitrogen (ThermoFisher Scientific) Taqman® assays. Human PD1 Taqman® assay (Invitrogen

#Hs00169472_m1) was FAM labeled and the internal normalizer gene, ACTb (Invitrogen #Hs99999903_m1), which was VIC-labelled. Samples were run in a 384 well format on a QuantStudio 6 Flex® (Thermo Fisher) PCR instrument. Relative quantification (dCT) calculations were performed in Microsoft Excel® as described above and data graphed in GraphPad Prism 9.

TABLE 13

Test and Control Articles

| Sample Name | Description | Designation |
|---|---|---|
| VVN-5355 | CAR-T cells generated using *Sleeping Beauty* transposon plasmid VVN-5355, which contains a transgene cassette to express ROR1-specific CAR + mbIL-15 + HER1t. | Control |
| VVN-5351 | CAR-T cells generated using *Sleeping Beauty* transposon plasmid VVN-5351, which contains a transgene cassette to express ROR1-specific CAR + mbIL-15 + HER1t plus a PD1 silencer module. | Test Article |

Figure 10A:
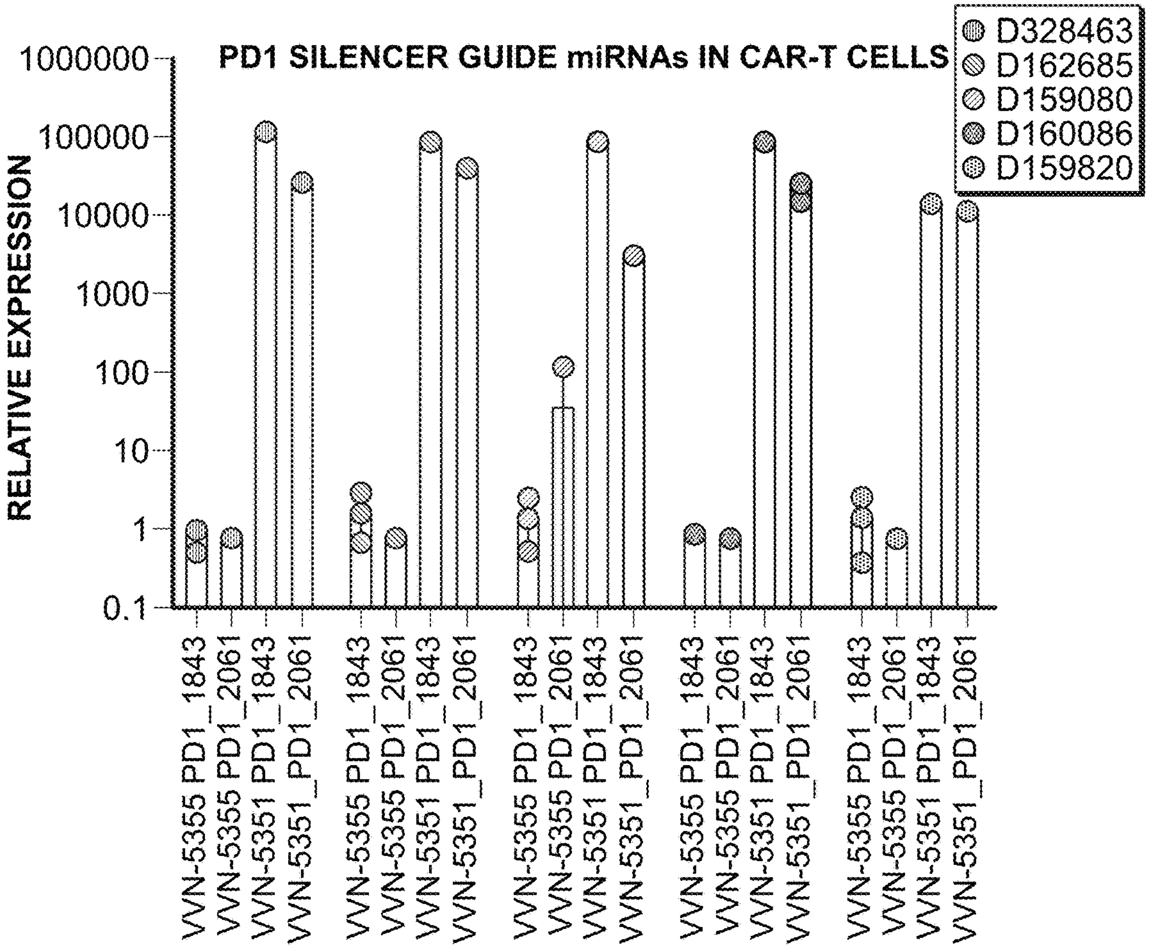
FIG. 10A demonstrates that the PD1 silencer module produces guide miRNAs and a corresponding decrease in PD1 mRNA expression in UltraCAR-T cells generated from 5 T cell donors. RT-qPCR results of PD1-targeting guide miRNAs are depicted.
Figure 10B:
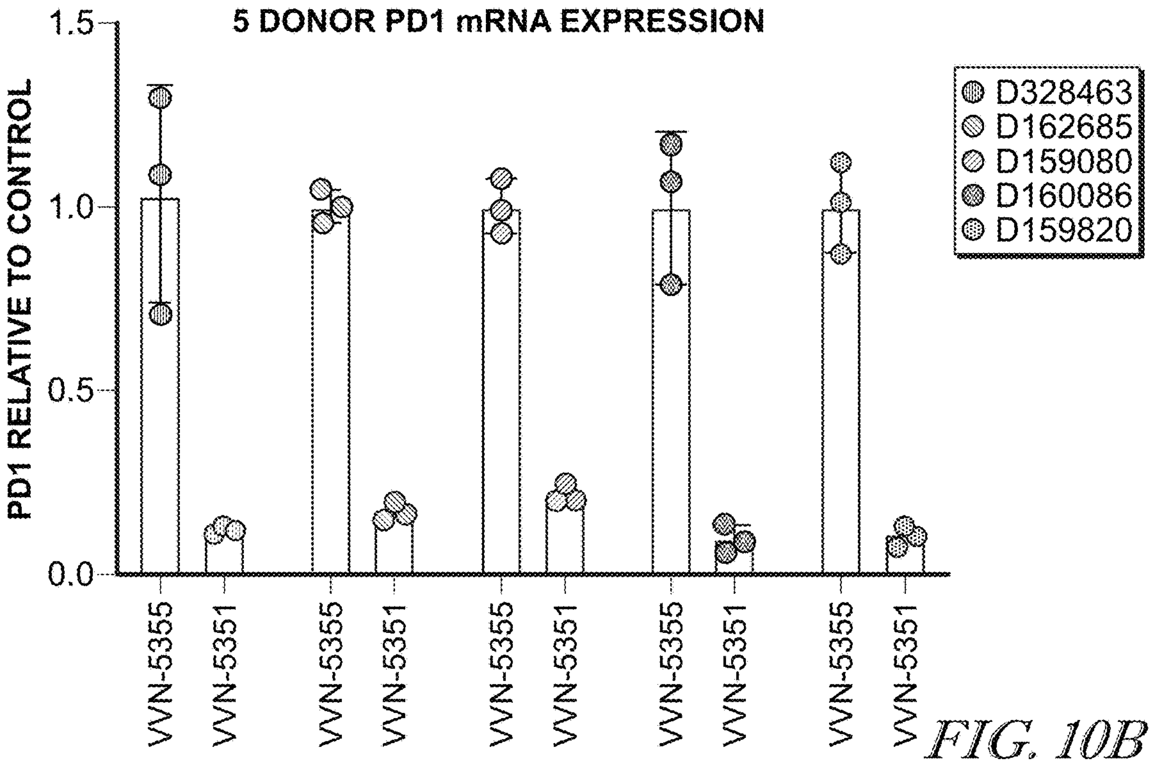
FIG. 10B demonstrates that the PD1 silencer module produced guide miRNAs and a corresponding decrease in PD1 mRNA expression in ultraCAR-T cells generated from 5 T cell donors. RT-qPCR results of PD1 mRNA are depicted.

The PD1 Silencer Module is designed to produce two mature guide miRNAs that bind to the PD1 transcript to silence PD1 expression. Expression of the two PD1-targeting guide miRNAs, referred to as PD1_1843 and PD1_2061, was confirmed in miRNA expressing ROR1 UltraCAR-T cells generated from multiple donors (FIG. 10A). A corresponding reduction in PD1 mRNA expression was verified in the miRNA-expressing ROR1 UltraCAR-T cells from all donors tested (FIG. 10B). This result demonstrated that the PD1 Silencer module produces the intended guide miRNAs and functions as designed.

Figures 12A, 12B, 12C, 12D, 12E:
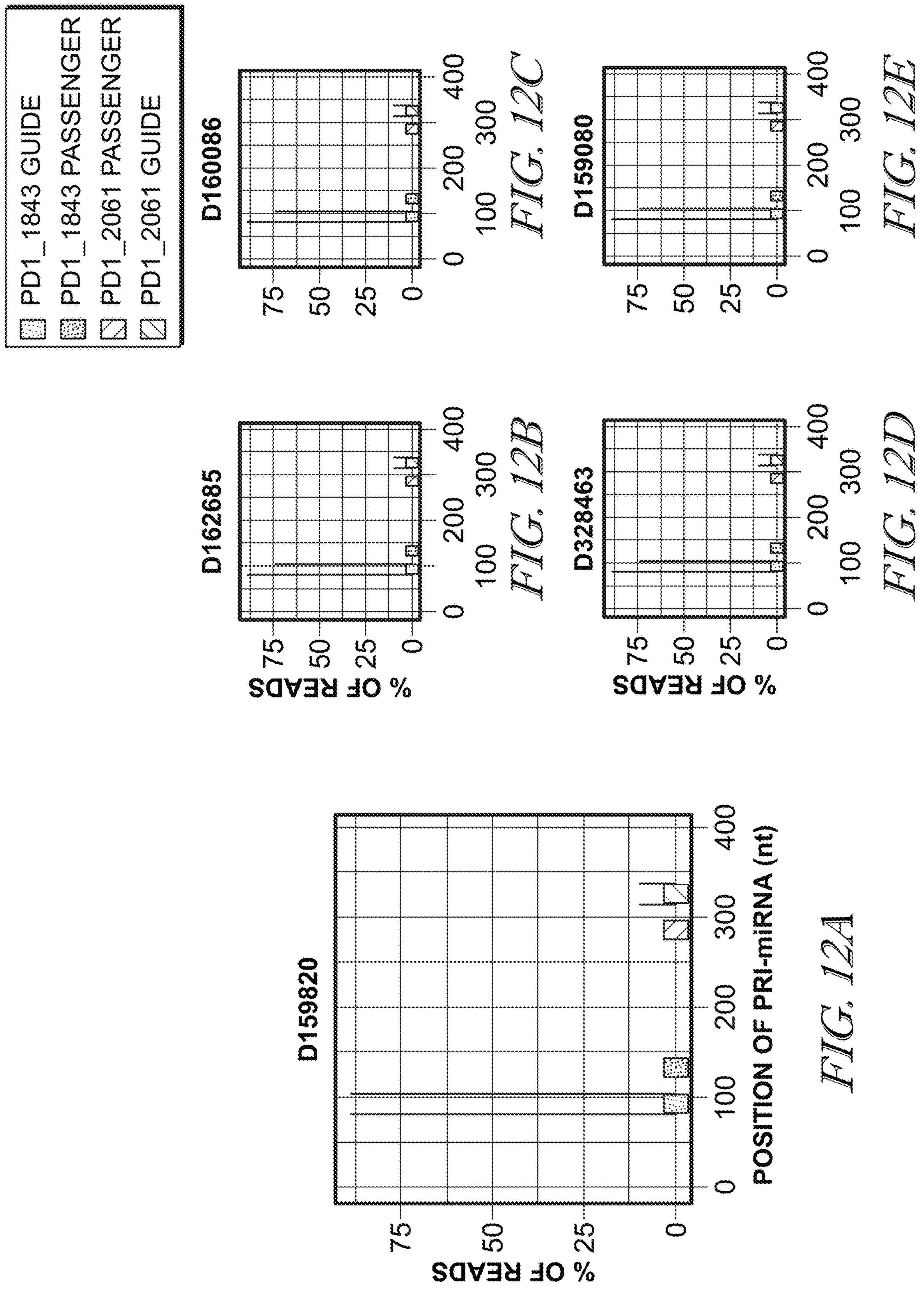
FIGS. 12A-E demonstrate that guide miRNAs are the predominant small RNA species originating from the PD1 silencer module.

To reduce the risk of silencing genes other than PD1, the PD1 silencer module was designed using pri-miRNA scaffolds that preferentially produce PD1-targeting guide miRNA over the non-targeting passenger miRNA. Both guide and passenger mature miRNAs were quantified from miRNA expressing ROR1 UltraCAR-T cells by RT-qPCR, which verified PD1 targeting guide miRNAs as the predominant species compared to non-targeting passenger strand miRNA (FIG. 4). The strong processing preference for the PD1 targeted guide miRNA was confirmed by small RNAseq, with 99.7% of reads mapping to the PD1 Silencer Module matching the intended PD1 targeting guide miRNAs (FIGS. 12 A-E). Furthermore, the start and stop position of the miRNAs was as expected, with miRNAs of 21-23 nucleotides detected that had the same 5' end and variable length at the 3' end (FIGS. 12 A-E). The extremely low incidence of passenger strand miRNAs and lack of unexpected small RNAs generated by aberrant RNA processing substantially reduced the risk for off-target gene silencing.

Figure 13:
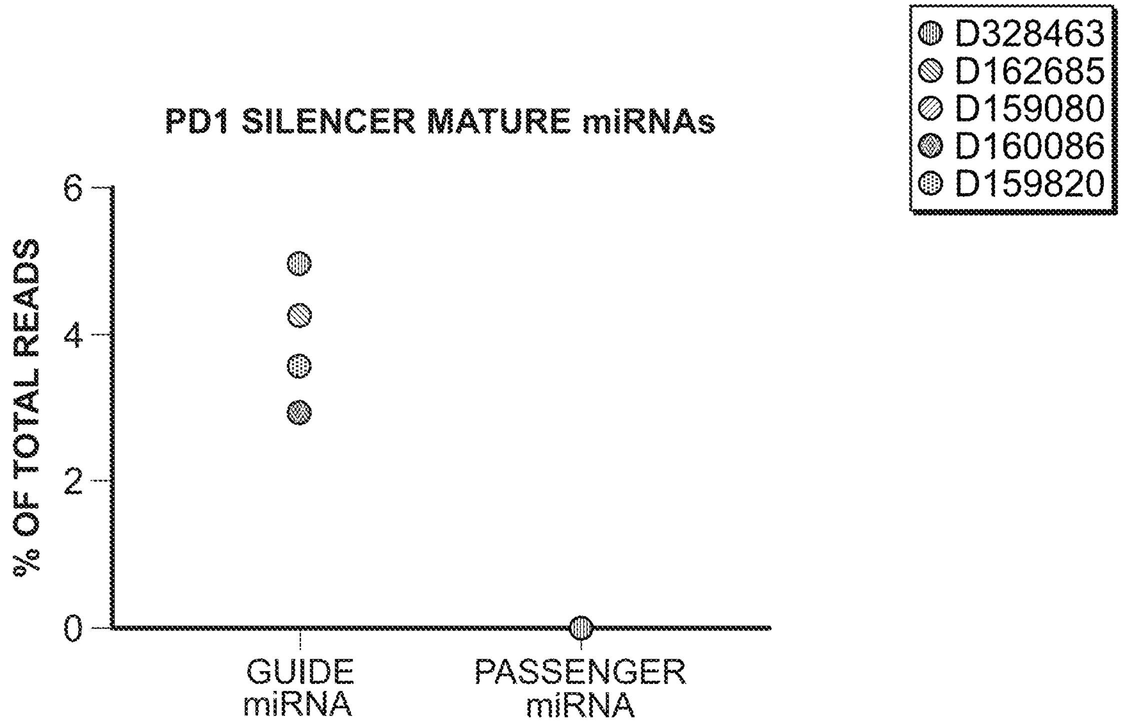
FIG. 13 shows quantification of mature miRNAs mapping to the PD1 silencer module as a percentage of total small RNAseq reads.

To ensure that expression of the PD1 Silencer module does not overwhelm the internal cellular RNAi machinery, endogenous miRNA counts were compared from miRNA expressing ROR1 UltraCAR-T cells vs control ROR1 UltraCAR-T cells. Examination of the top twenty expressed endogenous miRNAs demonstrated no statistically significant changes in expression across the samples (Table 15). Furthermore, the mature miRNAs generated from the PD1 silencer module accounted for approximately 4% of all quantified small RNAs (FIG. 13). The data indicated that expression of miRNAs from the PD1 silencer module did not saturate the cellular RNAi machinery and had no detectable impact on global endogenous miRNA expression.

TABLE 14

Small RNAseq Comparison of Guide and Passenger miRNA Counts

| Mature miRNA_Length (Sequence) | Normalized Mean | % Total |
|---|---|---|
| Guide PD1_204_21nt (TTCAGGAATGGGTTCCAAGGA; SEQ ID NO: 704) | 486,432.3 | 88.2% |
| Guide PD1_204_22nt (TTCAGGAATGGGTTCCAAGGAT; SEQ ID NO: 72) | 12,763.5 | |
| Guide PD1_204_23nt (TTCAGGAATGGGTTCCAAGGATG; SEQ ID NO: 705) | 59,759.4 | |
| Passenger PD1_204_21nt (TCCTGGAAGCTATTCCTGACG; SEQ ID NO: 706) | 380.6 | 0.1% |
| Passenger PD1_204_22nt (TCCTGGAAGCTATTCCTGACGT; SEQ ID NO: 707) | 20.2 | |
| Passenger PD1_204_23nt (TCCTGGAAGCTATTCCTGACGTT; SEQ ID NO: 708) | 54.7 | |
| Guide PD1_206_21nt (TATAATATAATAGAACCACAG; SEQ ID NO: 709) | 3,752.7 | 11.5% |
| Guide PD1_206_22nt (TATAATATAATAGAACCACAGG; SEQ ID NO: 74) | 49,181.3 | |
| Guide PD1_206_23nt (TATAATATAATAGAACCACAGGA; SEQ ID NO: 710) | 19,695.3 | |
| Passenger PD1_206_21nt (TGTGGTTCTGTTATATCCATA; SEQ ID NO: 711) | 1,581.0 | 0.3% |
| Passenger PD1_206_22nt (TGTGGTTCTGTTATATCCATAT; SEQ ID NO: 712) | 3.1 | |
| Passenger PD1_206_23nt (TGTGGTTCTGTTATATCCATATA; SEQ ID NO: 713) | 13.2 | |

TABLE 15

| Top 20 Expressed Endogenous Mature miRNAs Detected by Small RNAseq | | | |
|---|---|---|---|
| Endogenous miRNA | Base Mean | Log2 Fold Change | P-value Adjusted |
| hsa-miR-181a-5p | 796180.25 | 0.11 | 0.7948 |
| hsa-miR-191-5p | 421094.34 | −0.19 | 0.5622 |
| hsa-miR-21-5p | 386727.78 | 0.03 | 0.9411 |
| hsa-miR-92a-3p | 368149.34 | 0.26 | 0.2298 |
| hsa-miR-142-5p | 345451.62 | 0.08 | 0.8549 |
| hsa-miR-146b-5p | 286127.09 | 0.24 | 0.5471 |
| hsa-miR-16-5p | 261883.66 | 0.00 | 0.9954 |
| hsa-miR-146a-5p | 229059.23 | −0.27 | 0.4569 |
| hsa-let-7f-5p | 188491.61 | 0.16 | 0.6018 |
| hsa-miR-22-3p | 123453.58 | −0.01 | 0.9899 |
| hsa-miR-26a-5p | 110714.77 | 0.19 | 0.5166 |
| hsa-let-7a-5p | 104253.31 | 0.00 | 0.9921 |
| hsa-miR-155-5p | 72533.08 | −0.29 | 0.2298 |
| hsa-miR-181b-5p | 67527.35 | 0.12 | 0.7687 |
| hsa-let-7i-5p | 64631.72 | 0.30 | 0.2116 |
| hsa-miR-21-3p | 52519.27 | 0.25 | 0.5358 |
| hsa-miR-186-5p | 52479.56 | −0.20 | 0.4189 |
| hsa-miR-25-3p | 50411.16 | 0.02 | 0.9696 |
| hsa-miR-27a-3p | 47911.68 | −0.10 | 0.7818 |
| hsa-let-7g-5p | 47159.42 | 0.01 | 0.9811 |

Example 10: PD1 Silencer Module Specifically Reduces Expression of PD-1

An in silico miRNA target prediction algorithm, miRanda (Betel et al, 2008; Betel et al, 2010), was used to predict the most likely target transcripts for the guide and passenger miRNAs generated from the PD1 silencer module. The algorithm assigned a score for each potential miRNA target gene, with higher scores indicating higher likelihood of silencing by the input miRNA sequence. A summary of the top ten hits for each mature miRNA generated from the PD1 silencing module is listed in Table 16. PD1 is the only gene with perfect homology to any of the guide and passenger miRNAs and has the highest predicted miRanda score of any potential target gene. Expression of each predicted target gene was characterized from the RNAseq differential expression data set. PD1 was the most downregulated of all predicted target genes, with a log 2 fold change (LFC) of −2.63 (~84% PD1 reduction in miRNA expressing ROR1 UltraCAR-T cells compared to control ROR1 CAR-T cells) and a highly significant adjusted p-value. The expression of other predicted target genes was unchanged; those genes with adjusted p-values below 0.05 had LFC in the range of −0.33 to 0.22, which is an expression decrease or increase of <20%. One exception is a weakly predicted target gene of PD1_2061 guide miRNA, HDAC9, which has a LFC of ~1.51. HDAC9 is a transcriptional repressor that is mechanistically linked to PD1 expression through BCL6 (Xie et al, 2017; Gil et al, 2016). It is likely that HDAC9 is not directly targeted by PD1_2061 guide miRNA, and that the reduction in HDAC9 is an indirect effect of reduced PD1 expression.

TABLE 16

| In silico Predicted miRNA Target Genes | | | | | | | | | |
|---|---|---|---|---|---|---|---|---|---|
| miRNA | Target Gene | miRanda Score | free energy kcal/mol | % Identity to Target | Base Mean Count | log2 FoldChange | lfcSE | P value | Adjusted P Value |
| PD1_1843 | PD1 | 200 | −41.9 | 100.0 | 84 | −2.63 | 0.293 | 2.51E−19 | 2.64E−16 |
| miR204 | MIER3 | 184 | −32.1 | 84.2 | 1073 | 0.01 | 0.063 | 0.9104 | 0.9688 |
| Guide | SLFN12L | 182 | −34.2 | 89.5 | 1404 | −0.22 | 0.068 | 0.0015 | 0.0134 |
| miRNA | FMO4 | 180 | −28.5 | 84.2 | 15 | −0.18 | 0.461 | 0.6975 | NA |
| | GIGYF1 | 180 | −33.5 | 84.2 | 2749 | −0.07 | 0.046 | 0.1123 | 0.3211 |
| | FAM83G | 180 | −31.5 | 84.2 | 171 | 0.33 | 0.144 | 0.0214 | 0.1026 |
| | PPRC1 | 180 | −31.2 | 84.2 | 2679 | −0.18 | 0.045 | 0.0001 | 0.0011 |
| | PRMT9 | 180 | −29.1 | 84.2 | 335 | 0.09 | 0.100 | 0.3704 | 0.6432 |
| | MGAT4B | 179 | −29.3 | 88.9 | 4480 | −0.21 | 0.063 | 0.0007 | 0.0076 |
| | BRWD1 | 179 | −25.0 | 88.9 | 1816 | 0.05 | 0.052 | 0.3581 | 0.6328 |
| PD1_1843 | DOCK9 | 179 | −28.5 | 83.3 | 1239 | −0.12 | 0.077 | 0.1240 | 0.3428 |
| miR204 | NFYA | 179 | −27.5 | 83.3 | 1615 | −0.02 | 0.052 | 0.7446 | 0.8911 |
| Passenger | IFIT5 | 178 | −30.4 | 89.5 | 379 | −0.11 | 0.102 | 0.2629 | 0.5351 |
| miRNA | OTUB2 | 178 | −33.7 | 84.2 | 248 | −0.32 | 0.131 | 0.0154 | 0.0805 |
| | UBIAD1 | 177 | −32.1 | 88.9 | 1064 | −0.07 | 0.066 | 0.3085 | 0.5859 |
| | MYO15A | 176 | −29.5 | 93.3 | 11 | −0.25 | 0.510 | 0.6263 | NA |
| | ADRB2 | 175 | −27.1 | 83.3 | 62 | 0.61 | 0.264 | 0.0206 | 0.0997 |
| | HIC2 | 175 | −28.5 | 83.3 | 312 | −0.01 | 0.102 | 0.8962 | 0.9621 |
| | NECTIN3 | 175 | −33.5 | 72.2 | 662 | 0.05 | 0.081 | 0.5587 | 0.7864 |
| | TBC1D10C | 175 | −27.3 | 77.8 | 7562 | 0.03 | 0.041 | 0.4409 | 0.7056 |
| PD1_2061 | PD1 | 200 | −34.3 | 100.0 | 84 | −2.63 | 0.293 | 2.51E−19 | 2.64E−16 |
| miR206 | LCOR | 180 | −16.7 | 84.2 | 1321 | −0.19 | 0.064 | 0.0029 | 0.0230 |
| Guide | STARD4 | 179 | −16.7 | 88.9 | 6871 | −0.18 | 0.055 | 0.0013 | 0.0120 |
| miRNA | UQCRC2 | 179 | −19.1 | 81.0 | 4759 | 0.03 | 0.043 | 0.4641 | 0.7216 |
| | EXD2 | 178 | −17.5 | 88.2 | 58 | 0.18 | 0.265 | 0.5055 | 0.7511 |
| | NOL8 | 177 | −18.6 | 88.9 | 2190 | −0.08 | 0.050 | 0.1007 | 0.2996 |
| | ATP23 | 176 | −18.6 | 84.2 | 318 | 0.22 | 0.100 | 0.0265 | 0.1201 |
| | ELAPOR2 | 176 | −20.6 | 84.2 | 70 | −0.08 | 0.211 | 0.7139 | 0.8793 |
| | HDAC9 | 176 | −19.5 | 84.2 | 73 | −1.51 | 0.280 | 6.77E−08 | 3.53E−06 |
| | WDR47 | 176 | −19.6 | 79.0 | 625 | 0.08 | 0.089 | 0.3892 | 0.6617 |
| PD1_2061 | COG2 | 172 | −18.9 | 93.3 | 1244 | 0.06 | 0.060 | 0.3399 | 0.6170 |
| miR206 | NRG4 | 171 | −25.6 | 77.8 | | | | | |
| Passenger | AGBL3 | 170 | −19.2 | 79.0 | 49 | 0.01 | 0.250 | 0.9811 | 0.9934 |
| miRNA | PDK3 | 170 | −20.9 | 100.0 | 605 | 0.18 | 0.081 | 0.0256 | 0.1169 |
| | PDXK | 170 | −21.7 | 82.4 | 1786 | 0.22 | 0.058 | 0.0002 | 0.0022 |
| | N4BP2 | 169 | −25.1 | 77.8 | 2834 | −0.33 | 0.051 | 1.86E−10 | 1.95E−08 |

TABLE 16-continued

In silico Predicted miRNA Target Genes

| miRNA | Target Gene | miRanda Score | free energy kcal/mol | % Identity to Target | Base Mean Count | log2 FoldChange | lfcSE | P value | Adjusted P Value |
|---|---|---|---|---|---|---|---|---|---|
| | ZNF271P | 169 | −23.8 | 83.3 | 777 | 0.03 | 0.074 | 0.7197 | 0.8812 |
| | NFKB1 | 168 | −18.8 | 88.2 | 7889 | −0.11 | 0.039 | 0.0036 | 0.0269 |
| | XYLT1 | 168 | −26.9 | 82.4 | 5281 | 0.08 | 0.051 | 0.1100 | 0.3177 |
| | CNOT6 | 167 | −20.1 | 72.2 | 2030 | −0.24 | 0.052 | 0.0000 | 0.0001 |

Figure 14A:
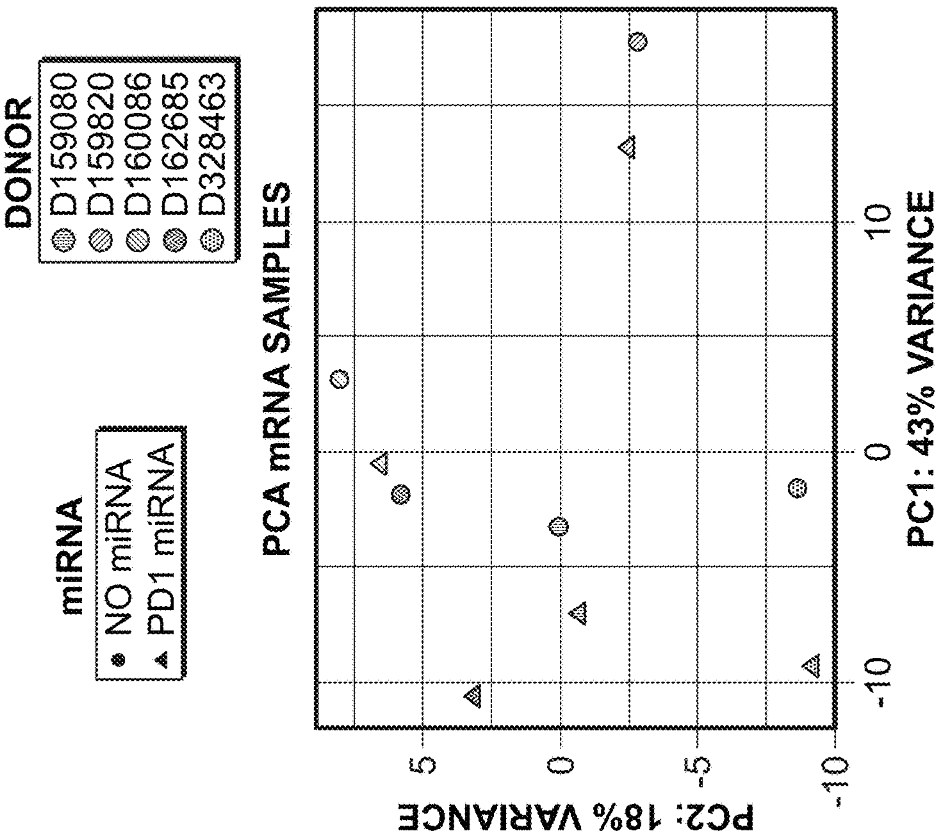
FIGS. 14 A and B shows differential gene expression in ROR1+PD1 silencer cells compared to ROR1 UltraCAR-T control cells.
Figure 14B:
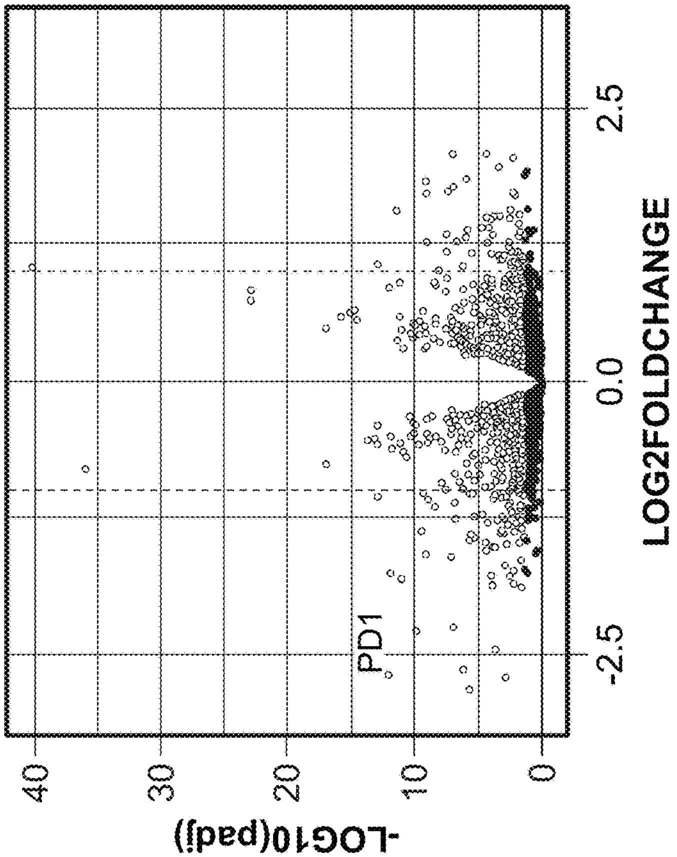

It is expected that changes in PD1 expression will impact expression of other genes in downstream pathways. As expected, analysis of RNAseq data confirmed the differential expression of several genes in miRNA expressing ROR1 UltraCAR-T cells compared to the control ROR1 UltraCAR-T cells (FIGS. 14A and B, Table 17). To elucidate direct versus indirect changes in gene expression, the differential expression (LFC) in miRNA expressing ROR1 UltraCAR-T cells compared to control ROR1 CAR-T cells was plotted against the predicted binding potential (predicted free energy) of the PD1 miRNAs for genes, which were in silico predicted as potential PD1 miRNA targets (FIGS. 15A-D). Genes with a highly negative free energy and a statistically significant reduction in expression are likely to be directly targeted by miRNA, while downregulated genes with a weak free energy are likely to be indirectly impacted by the miRNAs. PD1 is clearly separated from all other genes in the plots with a strong reduction in expression and high miRNA binding potential, which suggests a strong and preferential direct targeting of PD1, but not other genes, by the PD1 silencer miRNAs.

TABLE 17

Top 10 Down- and Up-Regulated Genes in ROR1 + PD1 Silencer Cells Relative to Control ROR1 UltraCAR-T Cells

| Ensembl_ID | Symbol | base Mean | Log2Fold Change | lfcSE | stat | pvalue | padj |
|---|---|---|---|---|---|---|---|
| ENSG00000188389 | PDCD1 | 84.2 | −2.6 | 0.3 | −9.0 | 2.51E−19 | 2.64E−16 |
| ENSG00000172020 | GAP43 | 71.6 | −2.2 | 0.4 | −5.7 | 1.37E−08 | 9.21E−07 |
| ENSG00000171951 | SCG2 | 110.5 | −2.2 | 0.4 | −6.1 | 1.13E−09 | 9.89E−08 |
| ENSG00000105974 | CAV1 | 172.3 | −2.1 | 0.5 | −4.2 | 2.93E−05 | 5.78E−04 |
| ENSG00000136193 | SCRN1 | 37.4 | −1.9 | 0.5 | −3.8 | 0.000136 | 1.97E−03 |
| ENSG00000130287 | NCAN | 206.1 | −1.7 | 0.4 | −4.4 | 1.23E−05 | 2.84E−04 |
| ENSG00000156052 | GNAQ | 145.0 | −1.7 | 0.2 | −7.8 | 6.88E−15 | 2.18E−12 |
| ENSG00000135898 | GPR55 | 84.5 | −1.6 | 0.3 | −5.7 | 1.47E−08 | 9.48E−07 |
| ENSG00000152495 | CAMK4 | 856.5 | −1.6 | 0.2 | −7.5 | 9.08E−14 | 2.21E−11 |
| ENSG00000102271 | KLHL4 | 184.3 | −1.6 | 0.3 | −4.7 | 3.00E−06 | 8.90E−05 |
| ENSG00000165025 | SYK | 120.2 | 1.6 | 0.4 | 4.0 | 6.65E−05 | 1.10E−03 |
| ENSG00000276597 | TRBV11-3 | 123.1 | 1.6 | 0.6 | 2.7 | 0.006913 | 4.44E−02 |
| ENSG00000082781 | ITGB5 | 329.1 | 1.7 | 0.3 | 5.7 | 1.45E−08 | 9.44E−07 |
| ENSG00000244242 | IFITM10 | 555.8 | 1.7 | 0.2 | 7.6 | 4.18E−14 | 1.10E−11 |
| ENSG00000143842 | SOX13 | 116.9 | 1.7 | 0.2 | 7.6 | 3.87E−14 | 1.06E−11 |
| ENSG00000180549 | FUT7 | 318.7 | 1.7 | 0.4 | 4.3 | 1.71E−05 | 3.71E−04 |
| ENSG00000137474 | MYO7A | 1057.3 | 1.8 | 0.2 | 8.2 | 3.56E−16 | 1.62E−13 |
| ENSG00000177508 | IRX3 | 317.9 | 1.8 | 0.5 | 3.3 | 0.001046 | 1.03E−02 |
| ENSG00000136689 | IL1RN | 242.1 | 1.9 | 0.5 | 4.0 | 5.65E−05 | 9.70E−04 |
| ENSG00000189013 | KIR2DL4 | 800.0 | 1.9 | 0.3 | 6.4 | 1.51E−10 | 1.62E−08 |

Example 11

In one instance a patient is diagnosed with a particular cancer. In this example the patient is diagnosed with breast cancer. The patient is identified to receive a particular chimeric antigen receptor therapy. The patient provides an initial blood sample for isolation of the desired cell type. In this example, the isolated cell type is a T-cell. In this example only a portion of the isolated T-cells are transfected with the desired initial CAR selected from the collection of CARs. The remaining T-cells are coded and stored in appropriate condition for potential future use by the patient. The remaining T-cells are transfected through an appropriate means. In this example, the transfection occurs through a non-viral means. In particular, the non-viral means utilizes a single sleeping beauty vector that encodes for at least the selected CAR, a T-cell expansion cytokine, and a termination switch. The patient is treated within 48 hours from the initial T-cell isolation.

Once the above round of treatment is complete the patient is followed in accordance with monitoring protocols. In the event there is an expansion of the cancer, in this example breast cancer, the patient is reevaluated. The patient may be redosed with the initial CAR, however, in the event the evaluation demonstrates that after the initial or potential redose there is antigen escape the protocol will call for a dosing of a new CAR from the CAR collection. In this instance, the patient's stored T-cells will be selected for use in the transfection of the newly selected CAR. The patient will be able to be redosed in a timely fashion. Further as the patient has already received each portion of the follow-on therapy except the newly selected CAR, the risk of toxicities and or adverse events is reduced. Further the knowledge of previous T-cell expansion for this patient is informed by the levels of expansion from the initial CAR selection. This further allows for a potential change in the dosage size, be it greater or less than the initial dose.

Example 12

In one instance a patient is not diagnosed with a particular cancer, but rather a specific antigen has been identified as causing undesired proliferation of cells or expansion of an infective agent. The initial CAR is selected based on antigen being presented in the patient. The patient provides an initial blood sample for isolation of the desired cell type. In this example, the isolated cell type is a T-cell. In this example all of the isolated T-cells are transfected with the desired initial CAR selected from the collection of CARs. The T-cells are transfected through an appropriate means. In this example, the transfection occurs through a non-viral means. In particular, the non-viral means utilizes a single sleeping beauty vector that encodes for at least the selected CAR, a T-cell expansion cytokine, and a kill switch. The patient is treated within 48 hours from the initial T-cell isolation.

Once the above round of treatment is complete the patient is followed in accordance with monitoring protocols. Following further evaluation the patient demonstrates that there is antigen escape. The patient is then dosed with a new CAR from the CAR collection following collection of new T-cells. Further as the patient has already received each portion of the follow-on therapy except the newly selected CAR, the risk of toxicities and or adverse events is reduced. Further the knowledge of previous T-cell expansion for this patient is informed by the levels of expansion from the initial CAR selection. This further allows for a potential change in the dosage size, be it greater or less than the initial dose.

Example 13

The clinician develops a treatment plan for a patient that involves use of an initial CAR from the CAR collection. The treatment plan includes a dosing of different CARs from the collection in consecutive manner to prevent antigen escape.

Example 14

In one instance a patient is diagnosed with a particular cancer. In this example the patient is diagnosed with pancreatic cancer. The patient is identified to receive a particular chimeric antigen receptor therapy. The patient provides an initial blood sample for isolation of the desired cell type. In this example, the isolated cell type is a T-cell. In this example the isolated T-cell's are transfected with the desired initial CAR selected from the collection of CARs. The T-cells are transfected through a non-viral means utilizing a single sleeping beauty vector that encodes for at least the selected CAR, a T-cell expansion cytokine, and a kill switch. The patient is treated within 48 hours from the initial T-cell isolation.

Once the above round of treatment is complete the patient is followed in accordance with monitoring protocols. In this instance, the patient through reevaluation is noted to suffer antigen escape. In this instance the patient requires dosing with a new CAR. However, due to the condition of the patient a sufficient sample of autologous T-cell may not be obtained. As a result the method allows for the inclusion of allogenic T-cells to be incorporated to the therapy. The CAR from the library is transduced into the allogenic T-cells and the patient is dosed in a timely fashion. Further as the patient has already received each portion of the follow-on therapy, the risk of toxicities and or adverse events is reduced.

Example 15

In one instance a patient is not diagnosed with a particular cancer, but rather a specific antigen has been identified as causing undesired proliferation of cells or expansion of an infective agent. The initial CAR is selected based on antigen being presented in the patient. The patient is unable to provide an initial blood sample for isolation of the desired cell type due to the current health of the patient. As such, allogenic T-cells are transfected with the desired initial CAR selected from the collection of CARs. The T-cells are transfected through an appropriate means utilizing a single attsite vector that encodes for at least the selected CAR, a T-cell expansion cytokine, and a termination switch.

Once the above round of treatment is complete the patient is followed in accordance with monitoring protocols. Following further evaluation the patient demonstrates that there is antigen escape. The patient is then dosed with a new CAR using the same source of allogenic T-cells. Further as the patient has already received each portion of the follow-on therapy except the newly selected CAR, the risk of toxicities and or adverse events is reduced. Further the knowledge of previous T-cell expansion for this patient is informed by the levels of expansion from the initial CAR selection. This further allows for a potential change in the dosage size, be it greater or less than the initial dose.

Example 16

The clinician develops a treatment plan for a patient that involves use of an initial CAR from the CAR collection. The treatment plan includes a dosing of different CARs from the collection in consecutive manner to prevent antigen escape. This treatment plan may include the use of both autologous and allogenic cells.

Example 17

In one instance a patient is diagnosed with a specific antigen has been identified as causing undesired proliferation of cells or expansion of an infective agent. The initial CAR is selected based on antigen being presented in the patient. The patient is unable to provide an initial blood sample for isolation of the desired cell type due to the current health of the patient. As such, allogenic cells are transfected with the desired initial CAR selected from the collection of CARs. The cells are transfected through an appropriate means utilizing a single sleeping beauty vector that encodes for at least the selected CAR and a termination switch.

Once the above round of treatment is complete the patient is followed in accordance with monitoring protocols. Following further evaluation the patient demonstrates that there is antigen escape. The patient is then dosed with a new CAR using a source of allogenic T-cells or if the patient show sufficient improvement autologous T-cells.

Example 18

In one instance a patient is not diagnosed with a particular cancer, but rather a specific antigen has been identified as causing undesired proliferation of cells or expansion of an infective agent. The initial CAR is selected based on antigen being presented in the patient. The patient provides an initial blood sample for isolation of T-cells. The T-cells are transfected with the desired initial CAR selected from the collection of CARs utilizing a single sleeping beauty vector that encodes for the selected CAR, a T-cell expansion cytokine, and a kill switch. The patient is treated within 48 hours from the initial T-cell isolation.

Once the above round of treatment is complete the patient is followed in accordance with monitoring protocols. Following further evaluation the patient demonstrates that there is antigen escape. The patient is then dosed with the same CAR and a new CAR from the CAR collection.

Example 19

In one instance a patient is diagnosed with a particular cancer. In this example the patient is diagnosed with AML. The patient is identified to receive a particular chimeric antigen receptor therapy. The patient provides an initial blood sample for isolation of the desired cell type. The cells are transfected with the desired two different CARs selected from the collection of CARs. The cells are transfected through a non-viral means utilizing a single vector that encodes for both selected CARs and a kill switch.

Once the above round of treatment is complete the patient is followed in accordance with monitoring protocols. In this instance, the patient through reevaluation is noted to suffer antigen escape. In this instance the patient requires dosing with a new CAR. However, due to the condition of the patient a sufficient sample of autologous cell may not be obtained. As a result the method allows for the inclusion of allogenic T-cells to be incorporated to the therapy. The CAR from the library is transduced into the allogenic cells and the patient is dosed in a timely fashion.

Nucleic Acid Sequences Encoding Backbone miRNA Sequences

| Synthetic miRNA | DNA encoding 5' backbone sequence | DNA encoding stem loop | DNA encoding 3' backbone sequence |
|---|---|---|---|
| miR204 | AGGAGGGTGGGGGTGG AGGCAAGCAGAGGACTT CCTGATCGCGTACCCATG GCTACAGTCTTTCTTCATG TGACTCGTGGAC (SEQ ID NO: 1) | GAGAATATATGAAGG (SEQ ID NO: 2) | GTTCAATTGTCATCACTG GCATCTTTTTTGATCATTG CACCATCATCAAATGCAT TGGGATAACCATGAC (SEQ ID NO: 3) |
| miR206 | GATGCTACAAGTGGCCCA CTTCTGAGATGCGGGCTG CTTCTGGATGACACTGCT TCCCGAGG (SEQ ID NO: 4) | TATGGATTACTTTGCTA (SEQ ID NO: 5) | TTTCGGCAAGTGCCTCCT CGCTGGCCCCAGGGTACC ACCCGGAGCACAGGTTTG GTGACCTT (SEQ ID NO: 6) |
| miR17 | TTAGCAGGAAAAAAGAG AACATCACCTTGTAAAAC TGAAGATTGTGACCAGTC AGAATAATGT (SEQ ID NO: 7) | TGATATGTGCAT (SEQ ID NO: 8) | GCATTATGGTGACAGCTG CCTCGGGAAGCCAAGTTG GGCTTTAAAGTGCAGGG CCTGCTGATGT (SEQ ID NO: 9) |
| miR150 | AGGGACTGGGCCCACGG GGAGGCAGCGTCCCCGA GGCAGCAGCGGCAGCGG CGGCTCCTCTCCCCATGG CCCTG (SEQ ID NO: 10) | CTGGGCTCAG (SEQ ID NO: 11) | CAGGGACCTGGGGACCC CGGCACCGGCAGGCCCC AAGGGGTGAGGTGAGCG GGCATTGGGACCTCCCCT CCCTGTACTC (SEQ ID NO: 12) |
| miR150 | AGGGACTGGGCCCACGG GGAGGCAGCGTCCCCGA GGCAGCAGCGGCAGCGG CGGCTCCTCTCCCCATGG CC (SEQ ID NO: 13) | TGCTGGGCTCAGACC (SEQ ID NO: 14) | GGACCTGGGGACCCCGG CACCGGCAGGCCCCAAG GGGTGAGGTGAGCGGGC ATTGGGACCTCCCCTCCC TGTACTC (SEQ ID NO: 15) |
| miR16 | CTTCTGAAGAAAATATAT TTCTTTTTATTCATAGCTC TTATGATAGCAATGTCAG CAGTGCCT (SEQ ID NO: 16) | TTAAGATTCTAAAATTATC T (SEQ ID NO: 17) | AAGTAAGGTTGACCATAC TCTACAGTTGTGTTTTAAT GTATATTAATGTTACTAAT GTGTTTT (SEQ ID NO: 18) |
| miR30a | CAGGTTAACCCAACAGAA GGCTAAAGAAGGTATATT GCTGTTGACAGTGAGCG AC (SEQ ID NO: 19) | CTGTGAAGCCACAGATG GG (SEQ ID NO: 20) | TGCCTACTGCCTCGGACT TCAAGGGGCTACTTTAGG AGCAATTATCTTGTTTA (SEQ ID NO: 21) |
| miR126 | CCGGGGTCCTGTCTGCAT CCAGCGCAGCATTCTGGA AGACGCCACGCCTCCGCT GGCGACGG (SEQ ID NO: 22) | CTGTGACACTTCAAAC (SEQ ID NO: 23) | CCGTCCACGGCACCGCAT CGAAAACGCCGCTGAGA CCTCAGCCTTGACCTCCCT CAGCGTGG (SEQ ID NO: 24) |

-continued

Nucleic Acid Sequences Encoding Backbone miRNA Sequences

| Synthetic miRNA | DNA encoding 5' backbone sequence | DNA encoding stem loop | DNA encoding 3' backbone sequence |
|---|---|---|---|
| miR122 | CAATGGTGGAATGTGGA GGTGAAGTTAACACCTTC GTGGCTACAGAGTTTCCT TAGCAGAGCTG (SEQ ID NO: 25) | TGTCTAAACTAT (SEQ ID NO: 26) | TAGCTACTGCTAGGCAAT CCTTCCCTCGATAAATGTC TTGGCATCGTTTGCTTTG AGCAAGAAGGTTCATCTG ATATCAGTCTTCTCAATCT (SEQ ID NO: 27) |
| miR214 | ACAGGCTGATTGTATCTG TCTATGAGCAAAGGAAAC CTGAAGGAACCAAGGGC CTGGCTGGACAGAGTTGT CATGTG (SEQ ID NO: 28) | GCAGAACATCCGCTCACC TGT (SEQ ID NO: 29) | CACATGACAACCCAGCCT GAATGACAACCAGCCATT GAAAGAAAGCAGCCCTC ACACCATAGCATCTA (SEQ ID NO: 30) |
| miR214 | ACAGGCTGATTGTATCTG TCTATGAGCAAAGGAAAC CTGAAGGAACCAAGGGC CTGGCTGGACAGAGTTGT CATGTGTC (SEQ ID NO: 31) | AGAACATCCGCTCACCT (SEQ ID NO: 32) | CACATGACAACCCAGCCT GAATGACAACCAGCCATT GAAAGAAAGCAGCCCTC ACACCATAGCATCTA (SEQ ID NO: 33) |
| miR29b1 | GGGTTTATTGTAAGAGAG CATTATGAAGAAAAAAAT AGATCATAAAGCTTCTTC AGG (SEQ ID NO: 34) | GATTTAAATAGTGATTGT C (SEQ ID NO: 35) | CTTGGGGGAGACCAGCT GCGCTGCACTACCAACAG CAAAAGAAGTGAATGGG ACAGCT (SEQ ID NO: 36) |
| miR29b1 | GGGTTTATTGTAAGAGAG CATTATGAAGAAAAAAAT AGATCATAAAGCTTCTTC AGGAA (SEQ ID NO: 37) | TTTAAATAGTGATTG (SEQ ID NO: 38) | GTTCTTGGGGGAGACCA GCTGCGCTGCACTACCAA CAGCAAAAGAAGTGAAT GGGACAGCT (SEQ ID NO: 39) |
| miR133a1 | TTTACCAATGAAAAGCAT TTAACTGTTTTGGATTCCA AACTAGCAGCACTACAAT GCTTTGCTA (SEQ ID NO: 40) | TCGCCTCTTCAATGGA (SEQ ID NO: 41) | TAGCTATGCATTGATTAC TACGGGACAACCAACGTT TTCATTTGTGAATATCAAT TACTTGCCA (SEQ ID NO: 42) |
| miR26a | TGAAGCCACAGGAGCCA AGAGCAGGAGGACCAAG GCCCTGGCGAAGGCCGT GGCCTCG (SEQ ID NO: 43) | GTGCAGGTCCCAATG (SEQ ID NO: 44) | CGGGGACGCGGGCCTGG ACGCCGGCATCCGGGCTC AGGACCCCCCTCTCTGCC AGAGGC (SEQ ID NO: 45) |
| miR412 | GTCTTGGAGGCTGGGGC ACCTCGGGGAAGGACGC CGGCATCAGCACCATTCT GGGGTACGGGGATGGA (SEQ ID NO: 46) | GTTTCT (SEQ ID NO: 47) | GCCGTCCGTATCCGCTGC AGCCTGTGGGGCCTGCG GGCCGGGGAGCCGATCG CGCTTCAGCTCAGCGCCT (SEQ ID NO: 48) |
| miR-19 | CCAATAATTCAAGCCAAG CAAGTATATAGGTGTTTT AATAGTTTTTGTTTGCAGT CCTCTG (SEQ ID NO: 49) | TACAAGAAGAATGTAGT (SEQ ID NO: 50) | TGGTGGCCTGCTATTTCC TTCAAATGAATGATTTTTA CTAATTTTGTGTACTTTTA TTGTG (SEQ ID NO: 51) |
| miR-21 | TGTCTGCTTGTTTTGCCTA CCATCGTGACATCTCCAT GGCTGTACCACCTTGTCG GG (SEQ ID NO: 52) | CTGTTGAATCTCATGG (SEQ ID NO: 53) | TCTGACATTTTGGTATCTT TCATCTGACCATCCATATC CAATGTTCTCATTTAAACA (SEQ ID NO: 54) |
| miR-142 | GGAGTCAGGAGGCCTGG GCAGCCTGAAGAGTACA CGCCGACGGACAGACAG ACAGTGCAGTCACC (SEQ ID NO: 55) | AACAGCACTGGAGGG (SEQ ID NO: 56) | GATGAGTGTACTGTGGG CTTCGGAGATCACGCCAC TGCTGCCGCCCGCTGCCC GCCACCATCTTC (SEQ ID NO: 57) |

-continued

| Nucleic Acid Sequences Encoding Backbone miRNA Sequences | | | |
|---|---|---|---|
| Synthetic miRNA | DNA encoding 5' backbone sequence | DNA encoding stem loop | DNA encoding 3' backbone sequence |
| miR-494 | CAGTTCTGTTTTGATTTTT TTTGTTTGTTTTTTGATCA GTGCTAATCTTCGATACT CGAAGGA (SEQ ID NO: 58) | TCTTTATTTATGA (SEQ ID NO: 59) | TTTTTTAGTATCAAATCCC ACCCTGGAGGCACTTCCT GTTCCTGATGCAGCCTTC AGGGAGG (SEQ ID NO: 60) |
| miR-1915 | CGGACCACGGTGTCCCCT TCTCTCCAGCTGGGGGTC TCGGGTCCTGGCGCTGAG AGGCCGC (SEQ ID NO: 61) | GTGCACCCGTG (SEQ ID NO: 62) | GCGGCCCTAGCGACCTGC GGCGGCGCCGGGAAAGC CCTGCCTCTGCAGCGGGT CCCAGGGGTC (SEQ ID NO: 63) |

| Nucleic acid sequences encoding mature miRNA sequences | | | |
|---|---|---|---|
| miRNA Target | Backbone | DNA encoding guide miRNA | DNA encoding passenger miRNA |
| CTLA4 | miR-204 | AATATAGTCTTCTCCCTCGCTT (SEQ ID NO: 64) | AAGCAGGGACAGGACTATATT (SEQ ID NO: 65) |
| CTLA4 | miR-26a | AATATAGTCTTCTCCCTCGCTT (SEQ ID NO: 66) | GAGCGAGGGATAGGACTATACT (SEQ ID NO: 67) |
| CTLA4 | miR-30a | AATATAGTCTTCTCCCTCGCTG (SEQ ID NO: 68) | CAGTGAGGGAAGACTATGTT (SEQ ID NO: 69) |
| CTLA4 | miR-206 | AATATAGTCTTCTCCCTCGCTG (SEQ ID NO: 70) | CAGCGAGGGAGAAGATTAC CATT (SEQ ID NO: 71) |
| PD1 | miR-204 | TTCAGGAATGGGTTCCAAGGAT (SEQ ID NO: 72) | ATCCTGGAAGCTATTCCTGAC (SEQ ID NO: 73) |
| PD1 | miR-206 | TATAATATAATAGAACCACAGG (SEQ ID NO: 74) | CCTGTGGTTCTGTTATATCCA TA (SEQ ID NO: 75) |
| PD1 | miR-30a | TTCAGGAATGGGTTCCAAGGAG (SEQ ID NO: 76) | CTCCTTGGACCATTCCTGAA (SEQ ID NO: 77) |
| PD1 | miR-412 | TTCAGGAATGGGTTCCAAGGAATT (SEQ ID NO: 78) | AATGTCCTGAAGCCATTCAT GGA (SEQ ID NO: 79) |
| PD1 | miR122 | TTCAGGAATGGGTTCCAAGGAG (SEQ ID NO: 80) | CTCCTTGGAACACATTCCTAC A (SEQ ID NO: 81) |
| PD1 | miR-17 | TTCAGGAATGGGTTCCAAGGAAG (SEQ ID NO: 82) | CTTCTTGGTACACGTTCCTGC TCA (SEQ ID NO: 83) |
| PD1 | miR-150 | TATAATATAATAGAACCACAGG (SEQ ID NO: 74) | ACGTGTGGTTTATCCTGTTGT A (SEQ ID NO: 85) |
| PD1 | miR-486 | TATAATATAATAGAACCACAGG (SEQ ID NO: 74) | CCAGCTTGTGGTTCTATTATG TTATA (SEQ ID NO: 87) |
| TIGIT | miR-17 | AGATCCACGTTACTCACCCTAG (SEQ ID NO: 88) | CTAGGGTGTGTCATGTGGAT GAA (SEQ ID NO: 89) |
| TIGIT | miR-150 | AGATCCACGTTACTCACCCGTG (SEQ ID NO: 90) | ACCCGGGTGATAATATGGAT CT (SEQ ID NO: 91) |

-continued

Nucleic acid sequences encoding mature miRNA sequences

| miRNA Target | Backbone | DNA encoding guide miRNA | DNA encoding passenger miRNA |
|---|---|---|---|
| TIGIT | miR-204 | AGATCCACGTTACTCACCCCCT (SEQ ID NO: 92) | AGGGGTGAGAAGCGTGGAT CC (SEQ ID NO: 93) |
| TIGIT | miR29b1 | AGATCCACGTTACTCACCCTTA (SEQ ID NO: 94) | TAGGTGAGTTACGTGGATCT GTT (SEQ ID NO: 95) |
| TIGIT | miR214 | AGATCCACGTTACTCACCCTGC (SEQ ID NO: 96) | GTAGGGTGAGACTCGTGGA TCT (SEQ ID NO: 97) |
| TIGIT | miR-206 | ACCACGATGACTGCTGTGCAGA (SEQ ID NO: 98) | TCTGCGTAGCAGTCATCGCC GGT (SEQ ID NO: 99) |
| TIGIT | miR-204 | ACCACGATGACTGCTGTGCAGA (SEQ ID NO: 100) | TCTGATGGCCGTCATCGTGGC (SEQ ID NO: 101) |
| TIGIT | miR-22 | ACCACGATGACTGCTGTGCAGA (SEQ ID NO: 102) | TCTGTACAGCAGCATCGATG GT (SEQ ID NO: 103) |
| TIGIT | miR-16 | ACCACGATGACTGCTGTGCAGA (SEQ ID NO: 104) | TGCGCAGCTGTTCATCGTGGT (SEQ ID NO: 105) |
| TIGIT | miR-21 | ACCACGATGACTGCTGTGCAGA (SEQ ID NO: 106) | CTGCGAAGCAGCATCGTGGC (SEQ ID NO: 107) |
| TIGIT | miR-494 | ACCACGATGACTGCTGTGCAGA (SEQ ID NO: 108) | TCTGCAACGCAGTCTCGCTGG (SEQ ID NO: 109) |
| TIGIT | miR-142 | ACCACGATGACTGCTGTGCAGA (SEQ ID NO: 110) | GATGCACAGCAATCATCGTG GT (SEQ ID NO: 111) |
| TIGIT | miR-19 | ACCACGATGACTGCTGTGCAGAT (SEQ ID NO: 112) | ATCTGCACAGCAGTTCGTGG (SEQ ID NO: 113) |
| TIGIT | miR-1915 | ACCACGATGACTGCTGTGCAGA (SEQ ID NO: 114) | TCTGCCAATAGCTGTAATCG TGG (SEQ ID NO: 115) |
| TIGIT | miR-206 | TATCGTTCACGGTCAGCGACTG (SEQ ID NO: 116) | CAGTCGTTGACTGTGGACTT ATA (SEQ ID NO: 117) |
| TIGIT | miR-204 | TATCGTTCACGGTCAGCGACTG (SEQ ID NO: 118) | CAGTGCTGAACGTGAACGATC (SEQ ID NO: 119) |
| TIGIT | miR-22 | TATCGTTCACGGTCAGCGACTG (SEQ ID NO: 120) | TAGTCGCTGACTTGAACAGA TA (SEQ ID NO: 121) |
| TIGIT | miR-142 | TATCGTTCACGGTCAGCGACT (SEQ ID NO: 122) | TGTCGCTGACAGTGAACGATA (SEQ ID NO: 123) |
| TIGIT | miR-16 | TATCGTTCACGGTCAGCGACTG (SEQ ID NO: 124) | GTCGCTGAGCGCTGAACGATG (SEQ ID NO: 125) |
| TIGIT | miR-206 | TAACTCAGGACATTGAAGTAGT (SEQ ID NO: 126) | ACTACTTCAATGTCCTGACCT TA (SEQ ID NO: 127) |
| TIGIT | miR-204 | TAACTCAGGACATTGAAGTAGT (SEQ ID NO: 128) | ACTATTCAGAGTCCTGAGTTC (SEQ ID NO: 129) |
| TIGIT | miR-21 | TAACTCAGGACATTGAAGTAGT (SEQ ID NO: 130) | CTACTCCAATGCCTGAGTTG (SEQ ID NO: 131) |
| TIGIT | miR-494 | TAACTCAGGACATTGAAGTAGT (SEQ ID NO: 132) | ACTACTGTAATGTCTGACGTT (SEQ ID NO: 133) |

-continued

| Nucleic acid sequences encoding mature miRNA sequences | | | |
|---|---|---|---|
| miRNA Target | Backbone | DNA encoding guide miRNA | DNA encoding passenger miRNA |
| TIGIT | miR-19 | TAACTCAGGACATTGAAGTAGTC (SEQ ID NO: 134) | GACTACTTCAATGTTGAGTT (SEQ ID NO: 135) |
| TIGIT | miR-1915 | AGATCCACGTTACTCACCCTAG (SEQ ID NO: 136) | CTAGGCAGTGAGCAAAGTG GATC (SEQ ID NO: 137) |
| TIGIT | miR-204 | AGATCCACGTTACTCACCCTAG (SEQ ID NO: 138) | CTAGGTGAGAAACGTGGATCG (SEQ ID NO: 139) |
| TIGIT | miR-206 | AGATCCACGTTACTCACCCTAG (SEQ ID NO: 140) | CTAGGGTGAGTAACGTGGCC TCT (SEQ ID NO: 141) |
| TIGIT | miR-21 | AGATCCACGTTACTCACCCTAG (SEQ ID NO: 142) | TAGGGCGAGTACGTGGATCG (SEQ ID NO: 143) |
| TIGIT | miR-22 | AGATCCACGTTACTCACCCTAG (SEQ ID NO: 144) | CTAGGGTGAGTACGTGGCAT CT (SEQ ID NO: 145) |
| TIM3 | miR204 | CATTATGCCTGGGATTTGGATC (SEQ ID NO: 146) | GATCAGATCGCAGGCATAATT (SEQ ID NO: 147) |
| TIM3 | miR206 | CATTATGCCTGGGATTTGGATC (SEQ ID NO: 148) | GATCCGGATCCTAGGTATCC ATG (SEQ ID NO: 149) |
| TIM3 | miR17 | CATTATGCCTGGGATTTGGATCG (SEQ ID NO: 150) | CGGCCAGAACCAAGGCATAA GTA (SEQ ID NO: 151) |
| TIM3 | miR126 | CATTATGCCTGGGATTTGGATC (SEQ ID NO: 152) | ACTCCAAATCCCGTGCATAA TCG (SEQ ID NO: 153) |
| TIM3 | miR122 | CATTATGCCTGGGATTTGGATC (SEQ ID NO: 154) | GATTCGAATCCAAGGCATAT GG (SEQ ID NO: 155) |
| TIM3 | miR214 | TAATTCACATCCCTTTCATCAG (SEQ ID NO: 156) | ATGATGAAAGGACAGTGAA TTA (SEQ ID NO: 157) |
| LAG3 | miR-30a | TAGTCGTTGGGTAAAGTCGCCA (SEQ ID NO: 158) | TGGTGACTTCTCAACGATTA (SEQ ID NO: 159) |
| LAG3 | miR122 | GTTGCTTTCCGCTAAGTGGTGA (SEQ ID NO: 160) | TCACCACTTAGAGGAAAGCC TC (SEQ ID NO: 161) |
| GITR | miR206 | TTTGCAGTGGCCTTCGTGGCCC (SEQ ID NO: 162) | GGGCTATGAAGGCCATTGA GAAA (SEQ ID NO: 163) |
| GITR | miR29b1 | AGCCTCCCGTCCTAAGACCCCAC (SEQ ID NO: 164) | GTGGGTCTTAGGTCGGGAG CTGCT (SEQ ID NO: 165) |
| PIK3IP1 | miR206 | TGAACGACCAGTGTTTAACCGG (SEQ ID NO: 166) | CCGGTTGAACATTGGTTGCC TCA (SEQ ID NO: 167) |
| PIK3IP1 | miR126 | TTCTCCTTGGAGTTCATCCGCG (SEQ ID NO: 168) | ATGAACTTAGAGGAGACG (SEQ ID NO: 169) |
| PIK3IP1 | miR30a | TTCTCCTTGGAGTTCATCCGCG (SEQ ID NO: 170) | CGCGGATGATCCAAGGAGGA (SEQ ID NO: 171) |

| Nucleic acid sequences encoding non-naturally occurring pri-miRNA sequences | | |
|---|---|---|
| miRNA Target | Encoded pri-miRNA(s) | DNA Sequence |
| CTLA4 | miR204 | AGGAGGGTGGGGGTGGAGGCAAGCAGAGGACTTCCTGATCGC GTACCCATGGCTACAGTCTTTCTTCATGTGACTCGTGGACAATA TAGTCTTCTCCCTCGCTTGAGAATATATGAAGGAAGCAGGGAC AGGACTATATTGTTCAATTGTCATCACTGGCATCTTTTTTGATCA TTGCACCATCATCAAATGCATTGGGATAACCATGAC (SEQ ID NO: 178) |
| PD1 | miR204 | AGGAGGGTGGGGGTGGAGGCAAGCAGAGGACTTCCTGATCGC GTACCCATGGCTACAGTCTTTCTTCATGTGACTCGTGGACTTCA GGAATGGGTTCCAAGGATGAGAATATATGAAGGATCCTGGAA GCTATTCCTGACGTTCAATTGTCATCACTGGCATCTTTTTTGATC ATTGCACCATCATCAAATGCATTGGGATAACCATGAC (SEQ ID NO: 179) |
| PD1 | miR206 | GATGCTACAAGTGGCCCACTTCTGAGATGCGGGCTGCTTCTGG ATGACACTGCTTCCCGAGGCCTGTGGTTCTGTTATATCCATATAT GGATTACTTTGCTATATAATATAATAGAACCACAGGTTTCGGCA AGTGCCTCCTCGCTGGCCCCAGGGTACCACCCGGAGCACAGGT TTGGTGACCTT (SEQ ID NO: 180) |
| TIGIT | miR17 | TTAGCAGGAAAAAAGAGAACATCACCTTGTAAAACTGAAGATT GTGACCAGTCAGAATAATGTAGATCCACGTTACTCACCCTAGTG ATATGTGCATCTAGGGTGTGTCATGTGGATGAAGCATTATGGT GACAGCTGCCTCGGGAAGCCAAGTTGGGCTTTAAAGTGCAGGG CCTGCTGATGT (SEQ ID NO: 181) |
| TIGIT | miR150 | AGGGACTGGGCCCACGGGGAGGCAGCGTCCCCGAGGCAGCAG CGGCAGCGGCGGCTCCTCTCCCCATGGCCCTGAGATCCACGTTA CTCACCCGTGCTGGGCTCAGACCCGGGTGATAATATGGATCTC AGGGACCTGGGGACCCCGGCACCGGCAGGCCCCAAGGGGTGA GGTGAGCGGGCATTGGGACCTCCCCTCCCTGTACTC (SEQ ID NO: 182) |
| TIGIT | miR204 | AGGAGGGTGGGGGTGGAGGCAAGCAGAGGACTTCCTGATCGC GTACCCATGGCTACAGTCTTTCTTCATGTGACTCGTGGACAGAT CCACGTTACTCACCCCCTGAGAATATATGAAGGAGGGGTGAGA AGCGTGGATCCGTTCAATTGTCATCACTGGCATCTTTTTTGATCA TTGCACCATCATCAAATGCATTGGGATAACCATGAC (SEQ ID NO: 183) |
| TIGIT | miR-206 | GATGCTACAAGTGGCCCACTTCTGAGATGCGGGCTGCTTCTGG ATGACACTGCTTCCCGAGGTCTGCGTAGCAGTCATCGCCGGTTA TGGATTACTTTGCTAACCACGATGACTGCTGTGCAGATTTCGGC AAGTGCCTCCTCGCTGGCCCCAGGGTACCACCCGGAGCACAGG TTTGGTGACCTT (SEQ ID NO: 184) |
| TIGIT | miR-204 | AGGAGGGTGGGGGTGGAGGCAAGCAGAGGACTTCCTGATCGC GTACCCATGGCTACAGTCTTTCTTCATGTGACTCGTGGACACCA CGATGACTGCTGTGCAGAGAGAATATATGAAGGTCTGATGGCC GTCATCGTGGCGTTCAATTGTCATCACTGGCATCTTTTTTGATCA TTGCACCATCATCAAATGCATTGGGATAACCATGAC (SEQ ID NO: 185) |
| TIGIT | miR-22 | CATTTTCCCTCCCTTTCCCTTAGGAGCCTGTTCCTCTCACGCCCTC ACCTGGCTGAGCCGCATCTGTACAGCAGCATCGATGGTTATGTC CTGACCCAGCTAACCACGATGACTGCTGTGCAGATGCCCTCTGC CCCTGGCTTCGAGGAGGAGGAGGAGCTGCTTTCCCCATCATCT GGAAGGTG (SEQ ID NO: 186) |
| TIGIT | miR-16 | cttcTGAAGAAAATATATTTCTTTTTATTCATAGCTCTTATGATAG CAATGTCAGCAGTGCCTACCACGATGACTGCTGTGCAGATTAA GATTCTAAAATTATCTTGCGCAGCTGTTCATCGTGGTAGTAAGG TTGACCATACTCTACAGTTGTGTTTTAATGTATATTAATGTTACT AATGTGTTTT (SEQ ID NO: 187) |

-continued

| Nucleic acid sequences encoding non-naturally occurring pri-miRNA sequences | | |
|---|---|---|
| miRNA Target | Encoded pri-miRNA(s) | DNA Sequence |
| TIGIT | miR-16 | cttcTGAAGAAAATATATTTCTTTTTATTCATAGCTCTTATGATAGCAATGTCAGCAGTGCCTACCACGATGACTGCTGTGCAGATTAAGATTCTAAAATTATCTTGCGCAGCTGTTCATCGTGGTAAGTAAGGTTGACCATACTCTACAGTTGTGTTTTAATGTATATTAATGTTACTAATGTGTTTT (SEQ ID NO: 188) |
| TIGIT | miR-21 | TGTCTGCTTGTTTTGCCTACCATCGTGACATCTCCATGGCTGTACCACCTTGTCGGGACCACGATGACTGCTGTGCAGACTGTTGAATCTCATGGCTGCGAAGCAGCATCGTGGCTCTGACATTTTGGTATCTTTCATCTGACCATCCATATCCAATGTTCTCATTTAAACA (SEQ ID NO: 189) |
| TIGIT | miR-494 | CAGTTCTGTTTTGATTTTTTTTGTTTGTTTTTTGATCAGTGCTAATCTTCGATACTCGAAGGATCTGCAACGCAGTCTCGCTGGTCTTTATTTATGAACCACGATGACTGCTGTGCAGATTTTTTAGTATCAAATCCCACCCTGGAGGCACTTCCTGTTCCTGATGCAGCCTTCAGGGAGG (SEQ ID NO: 190) |
| TIGIT | miR-142 | GGAGTCAGGAGGCCTGGGCAGCCTGAAGAGTACACGCCGACGGACAGACAGACAGTGCAGTCACCACCACGATGACTGCTGTGCAGAACAGCACTGGAGGGATGCACAGCAATCATCGTGGTGATGAGTGTACTGTGGGCTTCGGAGATCACGCCACTGCTGCCGCCCGCTGCCCGCCACCATCTTC (SEQ ID NO: 191) |
| TIGIT | miR-19 | CCAATAATTCAAGCCAAGCAAGTATATAGGTGTTTTAATAGTTTTTGTTTGCAGTCCTCTGATCTGCACAGCAGTTCGTGGTACAAGAAGAATGTAGTACCACGATGACTGCTGTGCAGATTGGTGGCCTGCTATTTCCTTCAAATGAATGATTTTTACTAATTTTGTGTACTTTTATTGTG (SEQ ID NO: 192) |
| TIGIT | miR-1915 | CGGACCACGGTGTCCCCTTCTCTCCAGCTGGGGGTCTCGGGTCCTGGCGCTGAGAGGCCGCACCACGATGACTGCTGTGCAGAGTGCACCCGTGTCTGCCAATAGCTGTAATCGTGGGCGGCCCTAGCGACCTGCGGCGGCGCCGGGAAAGCCCTGCCTCTGCAGCGGGTCCCAGGGGTC (SEQ ID NO: 193) |
| TIGIT | miR-206 | GATGCTACAAGTGGCCCACTTCTGAGATGCGGGCTGCTTCTGGATGACACTGCTTCCCGAGGCAGTCGTTGACTGTGGACTTATATATGGATTACTTTGCTATATCGTTCACGGTCAGCGACTGTTTCGGCAAGTGCCTCCTCGCTGGCCCCAGGGTACCACCCGGAGCACAGGTTTGGTGACCTT (SEQ ID NO: 194) |
| TIGIT | miR-204 | AGGAGGGTGGGGGTGGAGGCAAGCAGAGGACTTCCTGATCGCGTACCCATGGCTACAGTCTTTCTTCATGTGACTCGTGGACTATCGTTCACGGTCAGCGACTGGAGAATATATGAAGGCAGTGCTGAACGTGAACGATCGTTCAATTGTCATCACTGGCATCTTTTTTGATCATTGCACCATCATCAAATGCATTGGGATAACCATGAC (SEQ ID NO: 195) |
| TIGIT | miR-22 | CATTTTCCCTCCCTTTCCCTTAGGAGCCTGTTCCTCTCACGCCCTCACCTGGCTGAGCCGCATAGTCGCTGACTTGAACAGATATATGTCCTGACCCAGCTATATCGTTCACGGTCAGCGACTGTGCCCTCTGCCCCTGGCTTCGAGGAGGAGGAGGAGCTGCTTTCCCCATCATCTGGAAGGTG (SEQ ID NO: 196) |
| TIGIT | miR-142 | GGAGTCAGGAGGCCTGGGCAGCCTGAAGAGTACACGCCGACGGACAGACAGACAGTGCAGTCACCTATCGTTCACGGTCAGCGACTAACAGCACTGGAGGGTGTCGCTGACAGTGAACGATAGATGAGTGTACTGTGGGCTTCGGAGATCACGCCACTGCTGCCGCCCGCTGCCCGCCACCATCTTC (SEQ ID NO: 197) |

-continued

Nucleic acid sequences encoding non-naturally occurring pri-miRNA sequences

| miRNA Target | Encoded pri-miRNA(s) | DNA Sequence |
|---|---|---|
| TIGIT | miR-16 | cttcTGAAGAAAATATATTTCTTTTTATTCATAGCTCTTATGATAGCAATGTCAGCAGTGCCTTATCGTTCACGGTCAGCGACTGTTAAGATTCTAAAATTATCTGTCGCTGAGCGCTGAACGATGAAGTAAGGTTGACCATACTCTACAGTTGTGTTTTAATGTATATTAATGTTACTAATGTGTTTT (SEQ ID NO: 198) |
| TIGIT | miR-206 | GATGCTACAAGTGGCCCACTTCTGAGATGCGGGCTGCTTCTGGATGACACTGCTTCCCGAGGACTACTTCAATGTCCTGACCTTATATGGATTACTTTGCTATAACTCAGGACATTGAAGTAGTTTTCGGCAAGTGCCTCCTCGCTGGCCCCAGGGTACCACCCGGAGCACAGGTTTGGTGACCTT (SEQ ID NO: 199) |
| TIGIT | miR-204 | AGGAGGGTGGGGGTGGAGGCAAGCAGAGGACTTCCTGATCGCGTACCCATGGCTACAGTCTTTCTTCATGTGACTCGTGGACTAACTCAGGACATTGAAGTAGTGAGAATATATGAAGGACTATTCAGAGTCCTGAGTTCGTTCAATTGTCATCACTGGCATCTTTTTTGATCATTGCACCATCATCAAATGCATTGGGATAACCATGAC (SEQ ID NO: 200) |
| TIGIT | miR-21 | TGTCTGCTTGTTTTGCCTACCATCGTGACATCTCCATGGCTGTACCACCTTGTCGGGTAACTCAGGACATTGAAGTAGTCTGTTGAATCTCATGGCTACTCCAATGCCTGAGTTGTCTGACATTTTGGTATCTTTCATCTGACCATCCATATCCAATGTTCTCATTTAAACA (SEQ ID NO: 201) |
| TIGIT | miR-494 | CAGTTCTGTTTTGATTTTTTTTGTTTGTTTTTTGATCAGTGCTAATCTTCGATACTCGAAGGAACTACTGTAATGTCTGACGTTTCTTTATTTATGATAACTCAGGACATTGAAGTAGTTTTTTTAGTATCAAATCCCACCCTGGAGGCACTTCCTGTTCCTGATGCAGCCTTCAGGGAGG (SEQ ID NO: 202) |
| TIGIT | miR-19 | CCAATAATTCAAGCCAAGCAAGTATATAGGTGTTTTAATAGTTTTTGTTTGCAGTCCTCTGGACTACTTCAATGTTGAGTTTACAAGAAGAATGTAGTTAACTCAGGACATTGAAGTAGTCTGGTGGCCTGCTATTTCCTTCAAATGAATGATTTTTACTAATTTTGTGTACTTTTATTGTG (SEQ ID NO: 203) |
| TIGIT | miR-1915 | CGGACCACGGTGTCCCCTTCTCTCCAGCTGGGGGTCTCGGGTCCTGGCGCTGAGAGGCCGCAGATCCACGTTACTCACCCTAGGTGCACCCGTGCTAGGCAGTGAGCAAAGTGGATCGCGGCCCTAGCGACCTGCGGCGGCGCCGGGAAAGCCCTGCCTCTGCAGCGGGTCCCAGGGGTC (SEQ ID NO: 204) |
| TIGIT | miR-204 | AGGAGGGTGGGGGTGGAGGCAAGCAGAGGACTTCCTGATCGCGTACCCATGGCTACAGTCTTTCTTCATGTGACTCGTGGACAGATCCACGTTACTCACCCTAGGAGAATATATGAAGGCTAGGTGAGAAACGTGGATCGGTTCAATTGTCATCACTGGCATCTTTTTTGATCATTGCACCATCATCAAATGCATTGGGATAACCATGAC (SEQ ID NO: 205) |
| TIGIT | miR-206 | GATGCTACAAGTGGCCCACTTCTGAGATGCGGGCTGCTTCTGGATGACACTGCTTCCCGAGGCTAGGGTGAGTAACGTGGCCTCTTATGGATTACTTTGCTAAGATCCACGTTACTCACCCTAGTTTCGGCAAGTGCCTCCTCGCTGGCCCCAGGGTACCACCCGGAGCACAGGTTTGGTGACCTT (SEQ ID NO: 206) |
| TIGIT | miR-21 | TGTCTGCTTGTTTTGCCTACCATCGTGACATCTCCATGGCTGTACCACCTTGTCGGGAGATCCACGTTACTCACCCTAGCTGTTGAATCTCATGGTAGGGCGAGTACGTGGATCGTCTGACATTTTGGTATCTTTCATCTGACCATCCATATCCAATGTTCTCATTTAAACA (SEQ ID NO: 207) |

-continued

Nucleic acid sequences encoding non-naturally occurring pri-miRNA sequences

| miRNA Target | Encoded pri-miRNA(s) | DNA Sequence |
|---|---|---|
| TIGIT | miR-22 | CATTTTCCCTCCCTTTCCCTTAGGAGCCTGTTCCTCTCACGCCCTC ACCTGGCTGAGCCGCACTAGGGTGAGTACGTGGCATCTTATGT CCTGACCCAGCTAAGATCCACGTTACTCACCCTAGTGCCCTCTG CCCCTGGCTTCGAGGAGGAGGAGGAGCTGCTTTCCCCATCATC TGGAAGGTG (SEQ ID NO: 208) |
| TIM3 | miR204 | AGGAGGGTGGGGGTGGAGGCAAGCAGAGGACTTCCTGATCGC GTACCCATGGCTACAGTCTTTCTTCATGTGACTCGTGGACCATT ATGCCTGGGATTTGGATCGAGAATATATGAAGGGATCAGATCG CAGGCATAATTGTTCAATTGTCATCACTGGCATCTTTTTTGATCA TTGCACCATCATCAAATGCATTGGGATAACCATGAC (SEQ ID NO: 209) |
| TIM3 | miR150 | AGGGACTGGGCCCACGGGGAGGCAGCGTCCCCGAGGCAGCAG CGGCAGCGGCGGCTCCTCTCCCCATGGCCCTGCATTATGCCTGG GATTTGGATCCTGGGCTCAGACCTCCAAATCCACACATAGTGCA GGGACCTGGGGACCCCGGCACCGGCAGGCCCCAAGGGGTGAG GTGAGCGGGCATTGGGACCTCCCCTCCCTGTACTC (SEQ ID NO: 210) |
| TIM3 | miR30a | CAGGTTAACCCAACAGAAGGCTAAAGAAGGTATATTGCTGTTG ACAGTGAGCGACCATTATGCCTGGGATTTGGATCCTGTGAAGC CACAGATGGGGATCCAGATCAGGCATAGTGGCTGCCTACTGCC TCGGACTTCAAGGGGCTACTTTAGGAGCAATTATCTTGTTTA (SEQ ID NO: 211) |
| TIM3 | miR206 | GATGCTACAAGTGGCCCACTTCTGAGATGCGGGCTGCTTCTGG ATGACACTGCTTCCCGAGGGATCCGGATCCTAGGTATCCATGTA TGGATTACTTTGCTACATTATGCCTGGGATTTGGATCTTTCGGC AAGTGCCTCCTCGCTGGCCCCAGGGTACCACCCGGAGCACAGG TTTGGTGACCTT (SEQ ID NO: 212) |
| TIM3 | miR16 | CTTCTGAAGAAAATATATTTCTTTTTATTCATAGCTCTTATGATA GCAATGTCAGCAGTGCCTCATTATGCCTGGGATTTGGATCTTAA GATTCTAAAATTATCTTCCGAATCACATGGCATAATGAAGTAAG GTTGACCATACTCTACAGTTGTGTTTTAATGTATATTAATGTTAC TAATGTGTTTT (SEQ ID NO: 213) |
| TIM3 | miR17 | TTAGCAGGAAAAAAGAGAACATCACCTTGTAAAACTGAAGATT GTGACCAGTCAGAATAATGTCATTATGCCTGGGATTTGGATCGT GATATGTGCATCGGCCAGAACCAAGGCATAAGTAGCATTATGG TGACAGCTGCCTCGGGAAGCCAAGTTGGGCTTTAAAGTGCAGG GCCTGCTGATGT (SEQ ID NO: 214) |
| TIM3 | miR126 | CCGGGGTCCTGTCTGCATCCAGCGCAGCATTCTGGAAGACGCC ACGCCTCCGCTGGCGACGGACTCCAAATCCCGTGCATAATCGCT GTGACACTTCAAACCATTATGCCTGGGATTTGGATCCCGTCCAC GGCACCGCATCGAAAACGCCGCTGAGACCTCAGCCTTGACCTC CCTCAGCGTGG (SEQ ID NO: 215) |
| TIM3 | miR122 | CAATGGTGGAATGTGGAGGTGAAGTTAACACCTTCGTGGCTAC AGAGTTTCCTTAGCAGAGCTGCATTATGCCTGGGATTTGGATCT GTCTAAACTATGATTCGAATCCAAGGCATATGGTAGCTACTGCT AGGCAATCCTTCCCTCGATAAATGTCTTGGCATCGTTTGCTTTGA GCAAGAAGGTTCATCTGATATCAGTCTTCTCAATCT (SEQ ID NO: 216) |
| TIM3 | miR214 | ACAGGCTGATTGTATCTGTCTATGAGCAAAGGAAACCTGAAGG AACCAAGGGCCTGGCTGGACAGAGTTGTCATGTGATGATGAAA GGACAGTGAATTAGCAGAACATCCGCTCACCTGTTAATTCACAT CCCTTTCATCAGCACATGACAACCCAGCCTGAATGACAACCAGC CATTGAAAGAAAGCAGCCCTCACACCATAGCATCTA (SEQ ID NO: 217) |

-continued

Nucleic acid sequences encoding non-naturally occurring pri-miRNA sequences

| miRNA Target | Encoded pri-miRNA(s) | DNA Sequence |
|---|---|---|
| TIM3 | miR29b1 | GGGTTTATTGTAAGAGAGCATTATGAAGAAAAAAATAGATCAT AAAGCTTCTTCAGGACGATGGAAGGGTTGTGAACGTTAGATTT AAATAGTGATTGTCTAATTCACATCCCTTTCATCAGTCTTGGGG GAGACCAGCTGCGCTGCACTACCAACAGCAAAAGAAGTGAATG GGACAGCT (SEQ ID NO: 218) |
| TIM3 | miR204 | AGGAGGGTGGGGGTGGAGGCAAGCAGAGGACTTCCTGATCGC GTACCCATGGCTACAGTCTTTCTTCATGTGACTCGTGGACTAATT CACATCCCTTTCATCAGGAGAATATATGAAGGCTGAGGAAGAG GTGTGAATTCGTTCAATTGTCATCACTGGCATCTTTTTTGATCAT TGCACCATCATCAAATGCATTGGGATAACCATGAC (SEQ ID NO: 219) |
| TIM3 | miR133a1 | TTTACCAATGAAAAGCATTTAACTGTTTTGGATTCCAAACTAGC AGCACTACAATGCTTTGCTAGTGATGAATAGGCTGCGAATTATC GCCTCTTCAATGGATAATTCACATCCCTTTCATCAGTAGCTATGC ATTGATTACTACGGGACAACCAACGTTTTCATTTGTGAATATCA ATTACTTGCCA (SEQ ID NO: 220) |
| LAG3 | miR30a | CAGGTTAACCCAACAGAAGGCTAAAGAAGGTATATTGCTGTTG ACAGTGAGCGACTAGTCGTTGGGTAAAGTCGCCACTGTGAAGC CACAGATGGGTGGTGACTTCTCAACGATTAGCTGCCTACTGCCT CGGACTTCAAGGGGCTACTTTAGGAGCAATTATCTTGTTTA (SEQ ID NO: 221) |
| LAG3 | miR206 | GATGCTACAAGTGGCCCACTTCTGAGATGCGGGCTGCTTCTGG ATGACACTGCTTCCCGAGGTGGCGATTTTACCCAATGCTCTATA TGGATTACTTTGCTATAGTCGTTGGGTAAAGTCGCCATTTCGGC AAGTGCCTCCTCGCTGGCCCCAGGGTACCACCCGGAGCACAGG TTTGGTGACCTT (SEQ ID NO: 222) |
| LAG3 | miR204 | AGGAGGGTGGGGGTGGAGGCAAGCAGAGGACTTCCTGATCGC GTACCCATGGCTACAGTCTTTCTTCATGTGACTCGTGGACTAGT CGTTGGGTAAAGTCGCCAGAGAATATATGAAGGTGGCACTTTC CTCAACGACTCGTTCAATTGTCATCACTGGCATCTTTTTTGATCA TTGCACCATCATCAAATGCATTGGGATAACCATGAC (SEQ ID NO: 223) |
| LAG3 | miR150 | AGGGACTGGGCCCACGGGGAGGCAGCGTCCCCGAGGCAGCAG CGGCAGCGGCGGCTCCTCTCCCCATGGCCCTGTAGTCGTTGGG TAAAGTCGCCACTGGGCTCAGACCGCGACTTACCACACGACTAC AGGGACCTGGGGACCCCGGCACCGGCAGGCCCCAAGGGGTGA GGTGAGCGGGCATTGGGACCTCCCCTCCCTGTACTC (SEQ ID NO: 224) |
| LAG3 | miR17 | TTAGCAGGAAAAAAGAGAACATCACCTTGTAAAACTGAAGATT GTGACCAGTCAGAATAATGTGTTGCTTTCCGCTAAGTGGTGAGT GATATGTGCATCTCCCACTCAGAGGAAAGCACTAGCATTATGGT GACAGCTGCCTCGGGAAGCCAAGTTGGGCTTTAAAGTGCAGGG CCTGCTGATGT (SEQ ID NO: 225) |
| LAG3 | miR122 | CAATGGTGGAATGTGGAGGTGAAGTTAACACCTTCGTGGCTAC AGAGTTTCCTTAGCAGAGCTGGTTGCTTTCCGCTAAGTGGTGAT GTCTAAACTATTCACCACTTAGAGGAAAGCCTCTAGCTACTGCT AGGCAATCCTTCCCTCGATAAATGTCTTGGCATCGTTTGCTTTGA GCAAGAAGGTTCATCTGATATCAGTCTTCTCAATCT (SEQ ID NO: 226) |
| LAG3 | miR126 | CCGGGGTCCTGTCTGCATCCAGCGCAGCATTCTGGAAGACGCC ACGCCTCCGCTGGCGACGGGAACCACTTAGCGCGAAGCAAGGC TGTGACACTTCAAACGTTGCTTTCCGCTAAGTGGTGACCGTCCA CGGCACCGCATCGAAAACGCCGCTGAGACCTCAGCCTTGACCT CCCTCAGCGTGG (SEQ ID NO: 227) |

-continued

Nucleic acid sequences encoding non-naturally occurring pri-miRNA sequences

| miRNA Target | Encoded pri-miRNA(s) | DNA Sequence |
|---|---|---|
| GITR | miR30a | CAGGTTAACCCAACAGAAGGCTAAAGAAGGTATATTGCTGTTG ACAGTGAGCGACTTTGCAGTGGCCTTCGTGGCCCCTGTGAAGC CACAGATGGGGGGTCACGAGCCACTGCGAAGCTGCCTACTGCC TCGGACTTCAAGGGGCTACTTTAGGAGCAATTATCTTGTTTA (SEQ ID NO: 228) |
| GITR | miR206 | GATGCTACAAGTGGCCCACTTCTGAGATGCGGGCTGCTTCTGG ATGACACTGCTTCCCGAGGGGGCTATGAAGGCCATTGAGAAAT ATGGATTACTTTGCTATTTGCAGTGGCCTTCGTAGCCCTTTCGGC AAGTGCCTCCTCGCTGGCCCCAGGGTACCACCCGGAGCACAGG TTTGGTGACCTT (SEQ ID NO: 229) |
| GITR | miR17 | TTAGCAGGAAAAAAGAGAACATCACCTTGTAAAACTGAAGATT GTGACCAGTCAGAATAATGTTTTGCAGTGGCCTTCGTGGCCCGT GATATGTGCATCGGTCACGTAGACTACTGCACTCGCATTATGGT GACAGCTGCCTCGGGAAGCCAAGTTGGGCTTTAAAGTGCAGGG CCTGCTGATGT (SEQ ID NO: 230) |
| GITR | miR122 | CAATGGTGGAATGTGGAGGTGAAGTTAACACCTTCGTGGCTAC AGAGTTTCCTTAGCAGAGCTGTTTGCAGTGGCCTTCGTGGCCCT GTCTAAACTATGGGTCACGAAGACCACTGCCCATAGCTACTGCT AGGCAATCCTTCCCTCGATAAATGTCTTGGCATCGTTTGCTTTGA GCAAGAAGGTTCATCTGATATCAGTCTTCTCAATCT (SEQ ID NO: 231) |
| GITR | miR150 | AGGGACTGGGCCCACGGGGAGGCAGCGTCCCCGAGGCAGCAG CGGCAGCGGCGGCTCCTCTCCCCATGGCCCTGAGCCTCCCGTCC TAAGACCCCACTGGGCTCAGACAGGGTCTTGGAAAGGAGGCTC AGGGACCTGGGGACCCCGGCACCGGCAGGCCCCAAGGGGTGA GGTGAGCGGGCATTGGGACCTCCCCTCCCTGTACTC (SEQ ID NO: 232) |
| GITR | miR29 | GGGTTTATTGTAAGAGAGCATTATGAAGAAAAAAATAGATCAT AAAGCTTCTTCAGGGTGGGTCTTAGGTCGGGAGCTGCTGATTT AAATAGTGATTGTCAGCCTCCCGTCCTAAGACCCCACCTTGGGG GAGACCAGCTGCGCTGCACTACCAACAGCAAAAGAAGTGAATG GGACAGCT (SEQ ID NO: 233) |
| GITR | miR181a1 | TCTCCCATCCCCTTCAGATACTTACAGATACTGTAAAGTGAGTA GAATTCTGAGTTTTGAGGTTGCTTCAGTGAGCCTCCCGTCCTAA GACCCCACTTGGAATTAAAATCAAGTGGGTCTTGACGGGTGGC ACCCTATGGCTAACCATCATCTACTCCATGGTGCTCAGAATTCG CTGAAGACAGGAAACCAAAGGTGGACACACCAGG (SEQ ID NO: 234) |
| TIGIT | miR206 | GATGCTACAAGTGGCCCACTTCTGAGATGCGGGCTGCTTCTGG ATGACACTGCTTCCCGAGGCCAGGGTGAGTAACGTGGCCTCTT ATGGATTACTTTGCTAAGATCCACGTTACTCACCCTGGTTTCGG CAAGTGCCTCCTCGCTGGCCCCAGGGTACCACCCGGAGCACAG GTTTGGTGACCTT (SEQ ID NO: 235) |
| TIGIT | miR30a | CAGGTTAACCCAACAGAAGGCTAAAGAAGGTATATTGCTGTTG ACAGTGAGCGACAGATCCACGTTACTCACCCAAGCTGTGAAGC CACAGATGGGCTTGGGTGAGACGTGGATCTGCTGCCTACTGCC TCGGACTTCAAGGGGCTACTTTAGGAGCAATTATCTTGTTTA (SEQ ID NO: 236) |
| TIGIT | miR133a1 | TTTACCAATGAAAAGCATTTAACTGTTTTGGATTCCAAACTAGC AGCACTACAATGCTTTGCTAGAGGGGTGTATACCGCGGATCTTC GCCTCTTCAATGGAAGATCCACGTTACTCACCCCTGTAGCTATG CATTGATTACTACGGGACAACCAACGTTTTCATTTGTGAATATC AATTACTTGCCA (SEQ ID NO: 237) |

-continued

Nucleic acid sequences encoding non-naturally occurring pri-miRNA sequences

| miRNA Target | Encoded pri-miRNA(s) | DNA Sequence |
| --- | --- | --- |
| TIGIT | miR122 | CAATGGTGGAATGTGGAGGTGAAGTTAACACCTTCGTGGCTAC AGAGTTTCCTTAGCAGAGCTGAGATCCACGTTACTCACCCTTGT GTCTAAACTATCAAGGGTGAGTCACGTGGAGATTAGCTACTGC TAGGCAATCCTTCCCTCGATAAATGTCTTGGCATCGTTTGCTTTG AGCAAGAAGGTTCATCTGATATCAGTCTTCTCAATCT (SEQ ID NO: 238) |
| TIGIT | miR29b1 | GGGTTTATTGTAAGAGAGCATTATGAAGAAAAAAATAGATCAT AAAGCTTCTTCAGGAAAGATCCACGTTACTCACCCTTAGATTTA AATAGTGATTGTCTAGGTGAGTTACGTGGATCTGTTCTTGGGG GAGACCAGCTGCGCTGCACTACCAACAGCAAAAGAAGTGAATG GGACAGCT (SEQ ID NO: 239) |
| TIGIT | miR214 | ACAGGCTGATTGTATCTGTCTATGAGCAAAGGAAACCTGAAGG AACCAAGGGCCTGGCTGGACAGAGTTGTCATGTGTCAGATCCA CGTTACTCACCCTGCAGAACATCCGCTCACCTGTAGGGTGAGAC TCGTGGATCTGTCACATGACAACCCAGCCTGAATGACAACCAGC CATTGAAAGAAAGCAGCCCTCACACCATAGCATCTA (SEQ ID NO: 240) |
| PD1 | miR30a | CAGGTTAACCCAACAGAAGGCTAAAGAAGGTATATTGCTGTTG ACAGTGAGCGACTTCAGGAATGGGTTCCAAGGAGCTGTGAAGC CACAGATGGGCTCCTTGGACCATTCCTGAAGCTGCCTACTGCCT CGGACTTCAAGGGGCTACTTTAGGAGCAATTATCTTGTTTA (SEQ ID NO: 241) |
| PD1 | miR412 | GTCTTGGAGGCTGGGGCACCTCGGGGAAGGACGCCGGCATCA GCACCATTCTGGGGTACGGGGATGGATTCAGGAATGGGTTCCA AGGAATTGTTTCTAATGTCCTGAAGCCATTCATGGAGCCGTCCG TATCCGCTGCAGCCTGTGGGGCCTGCGGGCCGGGGAGCCGATC GCGCTTCAGCTCAGCGCCT (SEQ ID NO: 242) |
| PD1 | miR17 | TTAGCAGGAAAAAAGAGAACATCACCTTGTAAAACTGAAGATT GTGACCAGTCAGAATAATGTTTCAGGAATGGGTTCCAAGGAAG TGATATGTGCATCTTCTTGGTACACGTTCCTGCTCACATTATGGT GACAGCTGCCTCGGGAAGCCAAGTTGGGCTTTAAAGTGCAGGG CCTGCTGATGT (SEQ ID NO: 243) |
| PD1 | miR122 | CAATGGTGGAATGTGGAGGTGAAGTTAACACCTTCGTGGCTAC AGAGTTTCCTTAGCAGAGCTGTTCAGGAATGGGTTCCAAGGAG TGTCTAAACTATCTCCTTGGAACACATTCCTACATAGCTACTGCT AGGCAATCCTTCCCTCGATAAATGTCTTGGCATCGTTTGCTTTGA GCAAGAAGGTTCATCTGATATCAGTCTTCTCAATCT (SEQ ID NO: 244) |
| PD1 | miR150 | AGGGACTGGGCCCACGGGGAGGCAGCGTCCCCGAGGCAGCAG CGGCAGCGGCGGCTCCTCTCCCCATGGCCCTGTATAATATAATA GAACCACAGGCTGGGCTCAGACGTGTGGTTTATCCTGTTGTAC AGGGACCTGGGGACCCCGGCACCGGCAGGCCCCAAGGGGTGA GGTGAGCGGGCATTGGGACCTCCCCTCCCTGTACTC (SEQ ID NO: 245) |
| PD1 | miR486 | TGTGGTGCTGGGGGCTTCAGCGGCCGGCTCTGATCTCCATCCTC CCTGGGGCATATAATATAATAGAACCACAGGGCCCTTCATGCTG CCCAGCTTGTGGTTCTATTATGTTATAACTCGGGGTGGGAGTCA GCAGGAGGTGAGGGGGCATGGTGGCCCCAGTGCAGC (SEQ ID NO: 246) |
| PD1 | miR206 | GATGCTACAAGTGGCCCACTTCTGAGATGCGGGCTGCTTCTGG ATGACACTGCTTCCCGAGGCGTGCTGAACTGGTATCGAAATGT ATGGATTACTTTGCTACATGCGGTACCAGTTTAGCACGTTTCGG CAAGTGCCTCCTCGCTGGCCCCAGGGTACCACCCGGAGCACAG GTTTGGTGACCTT (SEQ ID NO: 247) |

-continued

Nucleic acid sequences encoding non-naturally occurring pri-miRNA sequences

| miRNA Target | Encoded pri-miRNA(s) | DNA Sequence |
|---|---|---|
| PD1 | miR122 | CAATGGTGGAATGTGGAGGTGAAGTTAACACCTTCGTGGCTAC AGAGTTTCCTTAGCAGAGCTGCATGCGGTACCAGTTTAGCACGT GTCTAAACTATCGTGCTAGACTTGTACTGTCAGTAGCTACTGCT AGGCAATCCTTCCCTCGATAAATGTCTTGGCATCGTTTGCTTTGA GCAAGAAGGTTCATCTGATATCAGTCTTCTCAATCT (SEQ ID NO: 248) |
| PD1 | miR30a | CAGGTTAACCCAACAGAAGGCTAAAGAAGGTATATTGCTGTTG ACAGTGAGCGACCATGCGGTACCAGTTTAGCACGCTGTGAAGC CACAGATGGGCGTGCTAGAGGTGTCGCATGGCTGCCTACTGCC TCGGACTTCAAGGGGCTACTTTAGGAGCAATTATCTTGTTTA (SEQ ID NO: 249) |
| CTLA4 | miR206 | GATGCTACAAGTGGCCCACTTCTGAGATGCGGGCTGCTTCTGG ATGACACTGCTTCCCGAGGCAGCGAGGGAGAAGATTACCATTT ATGGATTACTTTGCTAAATATAGTCTTCTCCCTCGCTGTTTCGGC AAGTGCCTCCTCGCTGGCCCCAGGGTACCACCCGGAGCACAGG TTTGGTGACCTT (SEQ ID NO: 250) |
| CTLA4 | miR26a | TGAAGCCACAGGAGCCAAGAGCAGGAGGACCAAGGCCCTGGC GAAGGCCGTGGCCTCGAATATAGTCTTCTCCCTCGCTTGTGCAG GTCCCAATGGAGCGAGGGATAGGACTATACTCGGGGACGCGG GCCTGGACGCCGGCATCCGGGCTCAGGACCCCCCTCTCTGCCA GAGGC (SEQ ID NO: 251) |
| CTLA4 | miR30a | CAGGTTAACCCAACAGAAGGCTAAAGAAGGTATATTGCTGTTG ACAGTGAGCGACAATATAGTCTTCTCCCTCGCTGCTGTGAAGCC ACAGATGGGCAGTGAGGGAAGACTATGTTGCTGCCTACTGCCT CGGACTTCAAGGGGCTACTTTAGGAGCAATTATCTTGTTTA (SEQ ID NO: 252) |
| PIK3IP1 | miR206 | GATGCTACAAGTGGCCCACTTCTGAGATGCGGGCTGCTTCTGG ATGACACTGCTTCCCGAGGCCGGTTGAACATTGGTTGCCTCATA TGGATTACTTTGCTATGAACGACCAGTGTTTAACCGGTTTCGGC AAGTGCCTCCTCGCTGGCCCCAGGGTACCACCCGGAGCACAGG TTTGGTGACCTT (SEQ ID NO: 253) |
| PIK3IP1 | miR126 | CCGGGGTCCTGTCTGCATCCAGCGCAGCATTCTGGAAGACGCC ACGCCTCCGCTGGCGACGGGACGGATGAACTTAGAGGAGACG CTGTGACACTTCAAACTTCTCCTTGGAGTTCATCCGCGCCGTCCA CGGCACCGCATCGAAAACGCCGCTGAGACCTCAGCCTTGACCT CCCTCAGCGTGG (SEQ ID NO: 254) |
| PIK3IP1 | miR30a | CAGGTTAACCCAACAGAAGGCTAAAGAAGGTATATTGCTGTTG ACAGTGAGCGACTTCTCCTTGGAGTTCATCCGCGCTGTGAAGCC ACAGATGGGCGCGGATGATCCAAGGAGGAGCTGCCTACTGCCT CGGACTTCAAGGGGCTACTTTAGGAGCAATTATCTTGTTTA (SEQ ID NO: 255) |
| TCRa3'UTR | miR150 | AGGGACTGGGCCCACGGGGAGGCAGCGTCCCCGAGGCAGCAG CGGCAGCGGCGGCTCCTCTCCCCATGGCCCTGATACACATCAGA ATCCTTACTGCTGGGCTCAGACCGTAAGGATCTCCTGTGTATCA GGGACCTGGGGACCCCGGCACCGGCAGGCCCCAAGGGGTGAG GCGAGCGGGCATTGGGACCTCCCCTCCCTGTACTC (SEQ ID NO: 256) |
| TCRa3'UTR | miR204 | AGGAGGGTGGGGGTGGAGGCAAGCAGAGGACTTCCTGATCGC GTACCCATGGCTACAGTCTTTCTTCATGTGACTCGTGGACATAC ACATCAGAATCCTTACTTGAGAATATATGAAGGAGGTAGGATA CTGATGTGTACGTTCAATTGTCATCACTGGCATCTTTTTTGATCA TTGCACCATCATCAAATGCATTGGGATAACCATGAC (SEQ ID NO: 257) |

-continued

Nucleic acid sequences encoding non-naturally occurring pri-miRNA sequences

| miRNA Target | Encoded pri-miRNA(s) | DNA Sequence |
| --- | --- | --- |
| TCRa3'UTR | miR206 | GATGCTACAAGTGGCCCACTTCTGAGATGCGGGCTGCTTCTGG ATGACACTGCTTCCCGAGGCGGTAAGGATTCTGATGTAATATTA TGGATTACTTTGCTAATACACATCAGAATCCTTACTGTTTCGGCA AGTGCCTCCTCGCTGGCCCCAGGGTACCACCCGGAGCACAGGT TTGGTGACCTT (SEQ ID NO: 258) |
| TCRa3'UTR | miR26a | TGAAGCCACAGGAGCCAAGAGCAGGAGGACCAAGGCCCTGGC GAAGGCCGTGGCCTCGATACACATCAGAATCCTTACTTGTGCAG GTCCCAATGGAGTAAGGATCCTGATGTGTCTCGGGGACGCGGG CCTGGACGCCGGCATCCGGGCTCAGGACCCCCCTCTCTGCCAG AGGC (SEQ ID NO: 259) |
| TCRa3'UTR | miR150 | AGGGACTGGGCCCACGGGGAGGCAGCGTCCCCGAGGCAGCAG CGGCAGCGGCGGCTCCTCTCCCCATGGCCCTGTTGTTGAAGGC GTTTGCACATGCTGGGCTCAGACCTGTGCAATGCGATCAATAG CAGGGACCTGGGGACCCCGGCACCGGCAGGCCCCAAGGGGTG AGGCGAGCGGGCATTGGGACCTCCCCTCCCTGTACTC (SEQ ID NO: 260) |
| TCRa3'UTR | miR16 | CTTCTGAAGAAAATATATTTCTTTTTATTCATAGCTCTTATGATA GCAATGTCAGCAGTGCCTTTGTTGAAGGCGTTTGCACATGTTAA GATTCTAAAATTATCTTGTGCGGAAGCACTTCAATAAAAGTAAG GTTGACCATACTCTACAGTTGTGTTTTAATGTATATTAATGTTAC TAATGTGTTTT (SEQ ID NO: 261) |
| TCRa3'UTR | miR206 | GATGCTACAAGTGGCCCACTTCTGAGATGCGGGCTGCTTCTGG ATGACACTGCTTCCCGAGGCGTGTGTGAACGCCTTCACATAATA TGGATTACTTTGCTATTGTTGAAGGCGTTTGCACATGTTTCGGC AAGTGCCTCCTCGCTGGCCCCAGGGTACCACCCGGAGCACAGG TTTGGTGACCTT (SEQ ID NO: 262) |
| TCRa3'UTR | miR26a | TGAAGCCACAGGAGCCAAGAGCAGGAGGACCAAGGCCCTGGC GAAGGCCGTGGCCTCGTTGTTGAAGGCGTTTGCACATTGTGCA GGTCCCAATGGGTGTGCAAAGGTCTTCAATCACGGGGACGCGG GCCTGGACGCCGGCATCCGGGCTCAGGACCCCCCTCTCTGCCA GAGGC (SEQ ID NO: 263) |

Non-naturally occurring miRNA sequences (two or more pri-miRNAs)

| miRNA Target | miRNA backbone | DNA Sequence |
| --- | --- | --- |
| PD1 | miR204 + miR206 | AGGAGGGTGGGGGTGGAGGCAAGCAGAGGACTTCCTGATCGCGTACCC ATGGCTACAGTCTTTCTTCATGTGACTCGTGGACTTCAGGAATGGGTTCC AAGGATGAGAATATATGAAGGATCCTGGAAGCTATTCCTGACGTTCAATT GTCATCACTGGCATCTTTTTTGATCATTGCACCATCATCAAATGCATTGGG ATAACCATGACGATGCTACAAGTGGCCCACTTCTGAGATGCGGGCTGCTT CTGGATGACACTGCTTCCCGAGGCCTGTGGTTCTGTTATATCCATATATG GATTACTTTGCTATATAATATAATAGAACCACAGGTTTCGGCAAGTGCCT CCTCGCTGGCCCCAGGGTACCACCCGGAGCACAGGTTTGGTGACCTT (SEQ ID NO: 267) |
| PD1 + TIGIT | miR204 + miR150 | AGGAGGGTGGGGGTGGAGGCAAGCAGAGGACTTCCTGATCGCGTACCC ATGGCTACAGTCTTTCTTCATGTGACTCGTGGACTTCAGGAATGGGTTCC AAGGATGAGAATATATGAAGGATCCTGGAAGCTATTCCTGACGTTCAATT GTCATCACTGGCATCTTTTTTGATCATTGCACCATCATCAAATGCATTGGG ATAACCATGACAGGGACTGGGCCCACGGGGAGGCAGCGTCCCCGAGGC AGCAGCGGCAGCGGCGGCTCCTCTCCCCATGGCCCTGAGATCCACGTTA CTCACCCGTGCTGGGCTCAGACCCGGGTGATAATATGGATCTCAGGGAC CTGGGGACCCCGGCACCGGCAGGCCCCAAGGGGTGAGGTGAGCGGGCA TTGGGACCTCCCCTCCCTGTACTC (SEQ ID NO: 268)22 |

-continued

Non-naturally occurring miRNA sequences (two or more pri-miRNAs)

| miRNA Target | miRNA backbone | DNA Sequence |
|---|---|---|
| PD1 + TIGIT | miR206 + miR150 | GATGCTACAAGTGGCCCACTTCTGAGATGCGGGCTGCTTCTGGATGACA CTGCTTCCCGAGGCCTGTGGTTCTGTTATATCCATATATGGATTACTTTGC TATATAATATAATAGAACCACAGGTTTCGGCAAGTGCCTCCTCGCTGGCC CCAGGGTACCACCCGGAGCACAGGTTTGGTGACCTTAGGGACTGGGCCC ACGGGGAGGCAGCGTCCCCGAGGCAGCAGCGGCAGCGGCGGCTCCTCT CCCCATGGCCCTGAGATCCACGTTACTCACCCGTGCTGGGCTCAGACCCG GGTGATAATATGGATCTCAGGGACCTGGGGACCCCGGCACCGGCAGGC CCCAAGGGGTGAGGTGAGCGGGCATTGGGACCTCCCCTCCCTGTACTC (SEQ ID NO: 269) |
| TIGIT + PD1 | miR17 + miR204 | TTAGCAGGAAAAAAGAGAACATCACCTTGTAAAACTGAAGATTGTGACC AGTCAGAATAATGTAGATCCACGTTACTCACCCTAGTGATATGTGCATCT AGGGTGTGTCATGTGGATGAAGCATTATGGTGACAGCTGCCTCGGGAAG CCAAGTTGGGCTTTAAAGTGCAGGGCCTGCTGATGTAGGAGGGTGGGG GTGGAGGCAAGCAGAGGACTTCCTGATCGCGTACCCATGGCTACAGTCT TTCTTCATGTGACTCGTGGACTTCAGGAATGGGTTCCAAGGATGAGAATA TATGAAGGATCCTGGAAGCTATTCCTGACGTTCAATTGTCATCACTGGCA TCTTTTTTGATCATTGCACCATCATCAAATGCATTGGGATAACCATGAC (SEQ ID NO: 270) |
| TIGIT + PD1 | miR17 + miR206 | TTAGCAGGAAAAAAGAGAACATCACCTTGTAAAACTGAAGATTGTGACC AGTCAGAATAATGTAGATCCACGTTACTCACCCTAGTGATATGTGCATCT AGGGTGTGTCATGTGGATGAAGCATTATGGTGACAGCTGCCTCGGGAAG CCAAGTTGGGCTTTAAAGTGCAGGGCCTGCTGATGTGATGCTACAAGTG GCCCACTTCTGAGATGCGGGCTGCTTCTGGATGACACTGCTTCCCGAGGC CTGTGGTTCTGTTATATCCATATATGGATTACTTTGCTATATAATATAATA GAACCACAGGTTTCGGCAAGTGCCTCCTCGCTGGCCCCAGGGTACCACCC GGAGCACAGGTTTGGTGACCTT (SEQ ID NO: 271) |
| TIGIT + PD1 | miR204 + miR206 | AGGAGGGTGGGGGTGGAGGCAAGCAGAGGACTTCCTGATCGCGTACCC ATGGCTACAGTCTTTCTTCATGTGACTCGTGGACAGATCCACGTTACTCAC CCCCTGAGAATATATGAAGGAGGGGTGAGAAGCGTGGATCCGTTCAATT GTCATCACTGGCATCTTTTTTGATCATTGCACCATCATCAAATGCATTGGG ATAACCATGACGATGCTACAAGTGGCCCACTTCTGAGATGCGGGCTGCTT CTGGATGACACTGCTTCCCGAGGCCTGTGGTTCTGTTATATCCATATATG GATTACTTTGCTATATAATATAATAGAACCACAGGTTTCGGCAAGTGCCT CCTCGCTGGCCCCAGGGTACCACCCGGAGCACAGGTTTGGTGACCTT (SEQ ID NO: 272) |
| TIGIT + PD1 | miR150 + miR204 | AGGGACTGGGCCCACGGGGAGGCAGCGTCCCCGAGGCAGCAGCGGCA GCGGCGGCTCCTCTCCCCATGGCCCTGAGATCCACGTTACTCACCCGTGC TGGGCTCAGACCCGGGTGATAATATGGATCTCAGGGACCTGGGGACCCC GGCACCGGCAGGCCCCAAGGGGTGAGGTGAGCGGGCATTGGGACCTCC CCTCCCTGTACTCAGGAGGGTGGGGGTGGAGGCAAGCAGAGGACTTCCT GATCGCGTACCCATGGCTACAGTCTTTCTTCATGTGACTCGTGGACTTCA GGAATGGGTTCCAAGGATGAGAATATATGAAGGATCCTGGAAGCTATTC CTGACGTTCAATTGTCATCACTGGCATCTTTTTTGATCATTGCACCATCAT CAAATGCATTGGGATAACCATGAC (SEQ ID NO: 273) |
| TIGIT + PD1 | miR150 + miR206 | AGGGACTGGGCCCACGGGGAGGCAGCGTCCCCGAGGCAGCAGCGGCA GCGGCGGCTCCTCTCCCCATGGCCCTGAGATCCACGTTACTCACCCGTGC TGGGCTCAGACCCGGGTGATAATATGGATCTCAGGGACCTGGGGACCCC GGCACCGGCAGGCCCCAAGGGGTGAGGTGAGCGGGCATTGGGACCTCC CCTCCCTGTACTCGATGCTACAAGTGGCCCACTTCTGAGATGCGGGCTGC TTCTGGATGACACTGCTTCCCGAGGCCTGTGGTTCTGTTATATCCATATAT GGATTACTTTGCTATATAATATAATAGAACCACAGGTTTCGGCAAGTGCC TCCTCGCTGGCCCCAGGGTACCACCCGGAGCACAGGTTTGGTGACCTT (SEQ ID NO: 274) |
| TIGIT + PD1 + PD1 | miR17 + miR204 + miR206 | TTAGCAGGAAAAAAGAGAACATCACCTTGTAAAACTGAAGATTGTGACC AGTCAGAATAATGTAGATCCACGTTACTCACCCTAGTGATATGTGCATCT AGGGTGTGTCATGTGGATGAAGCATTATGGTGACAGCTGCCTCGGGAAG CCAAGTTGGGCTTTAAAGTGCAGGGCCTGCTGATGTAGGAGGGTGGGG GTGGAGGCAAGCAGAGGACTTCCTGATCGCGTACCCATGGCTACAGTCT TTCTTCATGTGACTCGTGGACTTCAGGAATGGGTTCCAAGGATGAGAATA TATGAAGGATCCTGGAAGCTATTCCTGACGTTCAATTGTCATCACTGGCA TCTTTTTTGATCATTGCACCATCATCAAATGCATTGGGATAACCATGACGA |

-continued

Non-naturally occurring miRNA sequences (two or more pri-miRNAs)

| miRNA Target | miRNA backbone | DNA Sequence |
|---|---|---|
| | | TGCTACAAGTGGCCCACTTCTGAGATGCGGGCTGCTTCTGGATGACACTG<br>CTTCCCGAGGCCTGTGGTTCTGTTATATCCATATATGGATTACTTTGCTAT<br>ATAATATAATAGAACCACAGGTTTCGGCAAGTGCCTCCTCGCTGGCCCCA<br>GGGTACCACCCGGAGCACAGGTTTGGTGACCTT<br>(SEQ ID NO: 275) |
| TIGIT + PD1 + PD1 | miR17 + miR204 + miR206 extra spacing 1 | TTAGGATGAGTTGAGATCCCAGTGATCTTCTCGCTAAGAGTTTCCTGCCT<br>GGGCAAGGAGGAAATTAGCAGGAAAAAAGAGAACATCACCTTGTAAAA<br>CTGAAGATTGTGACCAGTCAGAATAATGTAGATCCACGTTACTCACCCTA<br>GTGATATGTGCATCTAGGGTGTGTCATGTGGATGAAGCATTATGGTGAC<br>AGCTGCCTCGGGAAGCCAAGTTGGGCTTTAAAGTGCAGGGCCTGCTGAT<br>GTAGGAGGGTGGGGGTGGAGGCAAGCAGAGGACTTCCTGATCGCGTAC<br>CCATGGCTACAGTCTTTCTTCATGTGACTCGTGGACTTCAGGAATGGGTT<br>CCAAGGATGAGAATATATGAAGGATCCTGGAAGCTATTCCTGACGTTCA<br>ATTGTCATCACTGGCATCTTTTTTGATCATTGCACCATCATCAAATGCATT<br>GGGATAACCATGACGATGCTACAAGTGGCCCACTTCTGAGATGCGGGCT<br>GCTTCTGGATGACACTGCTTCCCGAGGCCTGTGGTTCTGTTATATCCATAT<br>ATGGATTACTTTGCTATATAATATAATAGAACCACAGGTTTCGGCAAGTG<br>CCTCCTCGCTGGCCCCAGGGTACCACCCGGAGCACAGGTTTGGTGACCTT<br>CTTCCTCATCAGGGCTTTGTGCCAGCAAATGACTCCCTCACCAAGGAAGC<br>AAGAGCCTCTGAATCCCATCTGGGCTCTTCCTGAACACCCCTATCTCCCCC<br>TCT<br>(SEQ ID NO: 276) |
| TIGIT + PD1 + PD1 | miR17 + miR204 + miR206 extra spacing 2 | TTAGGGATTATGCTGAATTTGTATGGTTTATAGTTGTTAGAGTTTGAGGT<br>GTTAATTCTAATTATCTATTTCAAATTTTAGCAGGAAAAAAGAGAACATC<br>ACCTTGTAAAACTGAAGATTGTGACCAGTCAGAATAATGTAGATCCACGT<br>TACTCACCCTAGTGATATGTGCATCTAGGGTGTGTCATGTGGATGAAGCA<br>TTATGGTGACAGCTGCCTCGGGAAGCCAAGTTGGGCTTTAAAGTGCAGG<br>GCCTGCTGATGTAGGAGGGTGGGGGTGGAGGCAAGCAGAGGACTTCCT<br>GATCGCGTACCCATGGCTACAGTCTTTCTTCATGTGACTCGTGGACTTCA<br>GGAATGGGTTCCAAGGATGAGAATATATGAAGGATCCTGGAAGCTATTC<br>CTGACGTTCAATTGTCATCACTGGCATCTTTTTTGATCATTGCACCATCAT<br>CAAATGCATTGGGATAACCATGACGATGCTACAAGTGGCCCACTTCTGA<br>GATGCGGGCTGCTTCTGGATGACACTGCTTCCCGAGGCCTGTGGTTCTGT<br>TATATCCATATATGGATTACTTTGCTATATAATATAATAGAACCACAGGTT<br>TCGGCAAGTGCCTCCTCGCTGGCCCCAGGGTACCACCCGGAGCACAGGT<br>TTGGTGACCTTCTTCCTCATCAGGGCTTTGTGCCAGCAAATGACTCCCTCA<br>CCAAGGAAGCAAGAGCCTCTGAATCCCATCTGGGCTCTTCCTGAACACCC<br>CTATCTCCCCCTCT<br>(SEQ ID NO: 277) |
| PD1 + PD1 + TIGIT | miR204 + miR206 + miR17 | AGGAGGGTGGGGGTGGAGGCAAGCAGAGGACTTCCTGATCGCGTACCC<br>ATGGCTACAGTCTTTCTTCATGTGACTCGTGGACTTCAGGAATGGGTTCC<br>AAGGATGAGAATATATGAAGGATCCTGGAAGCTATTCCTGACGTTCAATT<br>GTCATCACTGGCATCTTTTTTGATCATTGCACCATCATCAAATGCATTGGG<br>ATAACCATGACGATGCTACAAGTGGCCCACTTCTGAGATGCGGGCTGCTT<br>CTGGATGACACTGCTTCCCGAGGCCTGTGGTTCTGTTATATCCATATATG<br>GATTACTTTGCTATATAATATAATAGAACCACAGGTTTCGGCAAGTGCCT<br>CCTCGCTGGCCCCAGGGTACCACCCGGAGCACAGGTTTGGTGACCTTTTA<br>GCAGGAAAAAAGAGAACATCACCTTGTAAAACTGAAGATTGTGACCAGT<br>CAGAATAATGTAGATCCACGTTACTCACCCTAGTGATATGTGCATCTAGG<br>GTGTGTCATGTGGATGAAGCATTATGGTGACAGCTGCCTCGGGAAGCCA<br>AGTTGGGCTTTAAAGTGCAGGGCCTGCTGATGT<br>(SEQ ID NO: 278) |
| PD1 + PD1 + TIGIT | miR204 + miR206 + miR17 extra spacing 1 | TTAGGATGAGTTGAGATCCCAGTGATCTTCTCGCTAAGAGTTTCCTGCCT<br>GGGCAAGGAGGAAAAGGAGGGTGGGGGTGGAGGCAAGCAGAGGACTT<br>CCTGATCGCGTACCCATGGCTACAGTCTTTCTTCATGTGACTCGTGGACTT<br>CAGGAATGGGTTCCAAGGATGAGAATATATGAAGGATCCTGGAAGCTAT<br>TCCTGACGTTCAATTGTCATCACTGGCATCTTTTTTGATCATTGCACCATC<br>ATCAAATGCATTGGGATAACCATGACGATGCTACAAGTGGCCCACTTCTG<br>AGATGCGGGCTGCTTCTGGATGACACTGCTTCCCGAGGCCTGTGGTTCTG<br>TTATATCCATATATGGATTACTTTGCTATATAATATAATAGAACCACAGGT<br>TTCGGCAAGTGCCTCCTCGCTGGCCCCAGGGTACCACCCGGAGCACAGG<br>TTTGGTGACCTTTTAGCAGGAAAAAAGAGAACATCACCTTGTAAAACTGA<br>AGATTGTGACCAGTCAGAATAATGTAGATCCACGTTACTCACCCTAGTGA<br>TATGTGCATCTAGGGTGTGTCATGTGGATGAAGCATTATGGTGACAGCT<br>GCCTCGGGAAGCCAAGTTGGGCTTTAAAGTGCAGGGCCTGCTGATGTCT<br>TCCTCATCAGGGCTTTGTGCCAGCAAATGACTCCCTCACCAAGGAAGCAAG<br>AGCCTCTGAATCCCATCTGGGCTCTTCCTGAACACCCCTATCTCCCCCTCT<br>(SEQ ID NO: 279) |

-continued

Non-naturally occurring miRNA sequences (two or more pri-miRNAs)

| miRNA Target | miRNA backbone | DNA Sequence |
|---|---|---|
| PD1 + PD1 + TIGIT | miR204 + miR206 + miR17 extra spacing 2 | TGGAGAGGAGGGTGGGGGTGGAGGCAAGCAGAGGACCTCCTGATCAT GTACCCATAGGACAGGGTGATGGAAAGGAGGGTGGGGGTGGAGGCAA GCAGAGGACTTCCTGATCGCGTACCCATGGCTACAGTCTTTCTTCATGTG ACTCGTGGACTTCAGGAATGGGTTCCAAGGATGAGAATATATGAAGGAT CCTGGAAGCTATTCCTGACGTTCAATTGTCATCACTGGCATCTTTTTTGAT CATTGCACCATCATCAAATGCATTGGGATAACCATGACGATGCTACAAGT GGCCCACTTCTGAGATGCGGGCTGCTTCTGGATGACACTGCTTCCCGAG GCCTGTGGTTCTGTTATATCCATATATGGATTACTTTGCTATATAATATAA TAGAACCACAGGTTTCGGCAAGTGCCTCCTCGCTGGCCCCAGGGTACCAC CCGGAGCACAGGTTTGGTGACCTTTTAGCAGGAAAAAAGAGAACATCAC CTTGTAAAACTGAAGATTGTGACCAGTCAGAATAATGTAGATCCACGTTA CTCACCCTAGTGATATGTGCATCTAGGGTGTGTCATGTGGATGAAGCATT ATGGTGACAGCTGCCTCGGGAAGCCAAGTTGGGCTTTAAAGTGCAGGGC CTGCTGATGTCTTCCTCATCAGGGCTTTGTGCCAGCAAATGACTCCCTCAC CAAGGAAGCAAGAGCCTCTGAATCCCATCTGGGCTCTTCCTGAACACCCC TATCTCCCCCTCT (SEQ ID NO: 280) |
| PD1 + CTLA4 | miR204 + miR26a | AGGAGGGTGGGGGTGGAGGCAAGCAGAGGACTTCCTGATCGCGTACCC ATGGCTACAGTCTTTCTTCATGTGACTCGTGGACTTCAGGAATGGGTTCC AAGGATGAGAATATATGAAGGATCCTGGAAGCTATTCCTGACGTTCAATT GTCATCACTGGCATCTTTTTTGATCATTGCACCATCATCAAATGCATTGGG ATAACCATGACTGAAGCCACAGGAGCCAAGAGCAGGAGGACCAAGGCC CTGGCGAAGGCCGTGGCCTCGAATATAGTCTTCTCCCTCGCTTGTGCAGG TCCCAATGGAGCGAGGGATAGGACTATACTCGGGGACGCGGGCCTGGA CGCCGGCATCCGGGCTCAGGACCCCCCTCTCTGCCAGAGGC (SEQ ID NO: 281) |
| PD1 + PD1 | miR204 + miR206 | AGGAGGGTGGGGGTGGAGGCAAGCAGAGGACTTCCTGATCGCGTACCC ATGGCTACAGTCTTTCTTCATGTGACTCGTGGACTTCAGGAATGGGTTCC AAGGATGAGAATATATGAAGGATCCTGGAAGCTATTCCTGACGTTCAATT GTCATCACTGGCATCTTTTTTGATCATTGCACCATCATCAAATGCATTGGG ATAACCATGACGATGCTACAAGTGGCCCACTTCTGAGATGCGGGCTGCTT CTGGATGACACTGCTTCCCGAGGCCTGTGGTTCTGTTATATCCATATATG GATTACTTTGCTATATAATATAATAGAACCACAGGTTTCGGCAAGTGCCT CCTCGCTGGCCCCAGGGTACCACCCGGAGCACAGGTTTGGTGACCTT (SEQ ID NO: 282) |
| PD1 + CTLA4 | miR206 + miR26a | GATGCTACAAGTGGCCCACTTCTGAGATGCGGGCTGCTTCTGGATGACA CTGCTTCCCGAGGCCTGTGGTTCTGTTATATCCATATATGGATTACTTTGC TATATAATATAATAGAACCACAGGTTTCGGCAAGTGCCTCCTCGCTGGCC CCAGGGTACCACCCGGAGCACAGGTTTGGTGACCTTTGAAGCCACAGGA GCCAAGAGCAGGAGGACCAAGGCCCTGGCGAAGGCCGTGGCCTCGAAT ATAGTCTTCTCCCTCGCTTGTGCAGGTCCCAATGGAGCGAGGGATAGGA CTATACTCGGGGACGCGGGCCTGGACGCCGGCATCCGGGCTCAGGACCC CCCTCTCTGCCAGAGGC (SEQ ID NO: 283) |
| PD1 + CTLA4 | miR206 + miR204 | GATGCTACAAGTGGCCCACTTCTGAGATGCGGGCTGCTTCTGGATGACA CTGCTTCCCGAGGCCTGTGGTTCTGTTATATCCATATATGGATTACTTTGC TATATAATATAATAGAACCACAGGTTTCGGCAAGTGCCTCCTCGCTGGCC CCAGGGTACCACCCGGAGCACAGGTTTGGTGACCTTAGGAGGGTGGGG GTGGAGGCAAGCAGAGGACTTCCTGATCGCGTACCCATGGCTACAGTCT TTCTTCATGTGACTCGTGGACAATATAGTCTTCTCCCTCGCTTGAGAATAT ATGAAGGAAGCAGGGACAGGACTATATTGTTCAATTGTCATCACTGGCA TCTTTTTTGATCATTGCACCATCATCAAATGCATTGGGATAACCATGAC (SEQ ID NO: 284) |
| TIGIT + CTLA4 | miR17 + miR26a | TTAGCAGGAAAAAAGAGAACATCACCTTGTAAAACTGAAGATTGTGACC AGTCAGAATAATGTAGATCCACGTTACTCACCCTAGTGATATGTGCATCT AGGGTGTGTCATGTGGATGAAGCATTATGGTGACAGCTGCCTCGGGAAG CCAAGTTGGGCTTTAAAGTGCAGGGCCTGCTGATGTTGAAGCCACAGGA GCCAAGAGCAGGAGGACCAAGGCCCTGGCGAAGGCCGTGGCCTCGAAT ATAGTCTTCTCCCTCGCTTGTGCAGGTCCCAATGGAGCGAGGGATAGGA CTATACTCGGGGACGCGGGCCTGGACGCCGGCATCCGGGCTCAGGACCC CCCTCTCTGCCAGAGGC (SEQ ID NO: 285) |
| TIGIT + CTLA4 | miR17 + miR204 | TTAGCAGGAAAAAAGAGAACATCACCTTGTAAAACTGAAGATTGTGACC AGTCAGAATAATGTAGATCCACGTTACTCACCCTAGTGATATGTGCATCT AGGGTGTGTCATGTGGATGAAGCATTATGGTGACAGCTGCCTCGGGAAG CCAAGTTGGGCTTTAAAGTGCAGGGCCTGCTGATGTAGGAGGGTGGGG GTGGAGGCAAGCAGAGGACTTCCTGATCGCGTACCCATGGCTACAGTCT |

-continued

| Non-naturally occurring miRNA sequences (two or more pri-miRNAs) | | |
|---|---|---|
| miRNA Target | miRNA backbone | DNA Sequence |
| | | TTCTTCATGTGACTCGTGGACAATATAGTCTTCTCCCTCGCTTGAGAATAT ATGAAGGAAGCAGGGACAGGACTATATTGTTCAATTGTCATCACTGGCA TCTTTTTTGATCATTGCACCATCATCAAATGCATTGGGATAACCATGAC (SEQ ID NO: 286) |
| TIGIT + PD1 | miR17 + miR204 | TTAGCAGGAAAAAAGAGAACATCACCTTGTAAAACTGAAGATTGTGACC AGTCAGAATAATGTAGATCCACGTTACTCACCCTAGTGATATGTGCATCT AGGGTGTGTCATGTGGATGAAGCATTATGGTGACAGCTGCCTCGGGAAG CCAAGTTGGGCTTTAAAGTGCAGGGCCTGCTGATGTAGGAGGGTGGGG GTGGAGGCAAGCAGAGGACTTCCTGATCGCGTACCCATGGCTACAGTCT TTCTTCATGTGACTCGTGGACTTCAGGAATGGGTTCCAAGGATGAGAATA TATGAAGGATCCTGGAAGCTATTCCTGACGTTCAATTGTCATCACTGGCA TCTTTTTTGATCATTGCACCATCATCAAATGCATTGGGATAACCATGAC (SEQ ID NO: 287) |
| TIGIT + PD1 | miR17 + 206 | TTAGCAGGAAAAAAGAGAACATCACCTTGTAAAACTGAAGATTGTGACC AGTCAGAATAATGTAGATCCACGTTACTCACCCTAGTGATATGTGCATCT AGGGTGTGTCATGTGGATGAAGCATTATGGTGACAGCTGCCTCGGGAAG CCAAGTTGGGCTTTAAAGTGCAGGGCCTGCTGATGTGATGCTACAAGTG GCCCACTTCTGAGATGCGGGCTGCTTCTGGATGACACTGCTTCCCGAGGC CTGTGGTTCTGTTATATCCATATATGGATTACTTTGCTATATAATATAATA GAACCACAGGTTTCGGCAAGTGCCTCCTCGCTGGCCCCAGGGTACCACCC GGAGCACAGGTTTGGTGACCTT (SEQ ID NO: 288) |
| TIGIT + CTLA4 | miR204 + miR26a | AGGAGGGTGGGGGTGGAGGCAAGCAGAGGACTTCCTGATCGCGTACCC ATGGCTACAGTCTTTCTTCATGTGACTCGTGGACAGATCCACGTTACTCAC CCCCTGAGAATATATGAAGGAGGGGTGAGAAGCGTGGATCCGTTCAATT GTCATCACTGGCATCTTTTTTGATCATTGCACCATCATCAAATGCATTGGG ATAACCATGACTGAAGCCACAGGAGCCAAGAGCAGGAGGACCAAGGCC CTGGCGAAGGCCGTGGCCTCGAATATAGTCTTCTCCCTCGCTTGTGCAGG TCCCAATGGAGCGAGGGATAGGACTATACTCGGGGACGCGGGCCTGGA CGCCGGCATCCGGGCTCAGGACCCCCCTCTCTGCCAGAGGC (SEQ ID NO: 289) |
| TIGIT + PD1 | miR204 + miR206 | AGGAGGGTGGGGGTGGAGGCAAGCAGAGGACTTCCTGATCGCGTACCC ATGGCTACAGTCTTTCTTCATGTGACTCGTGGACAGATCCACGTTACTCAC CCCCTGAGAATATATGAAGGAGGGGTGAGAAGCGTGGATCCGTTCAATT GTCATCACTGGCATCTTTTTTGATCATTGCACCATCATCAAATGCATTGGG ATAACCATGACGATGCTACAAGTGGCCCACTTCTGAGATGCGGGCTGCTT CTGGATGACACTGCTTCCCGAGGCCTGTGGTTCTGTTATATCCATATATG GATTACTTTGCTATATAATATAATAGAACCACAGGTTTCGGCAAGTGCCT CCTCGCTGGCCCCAGGGTACCACCCGGAGCACAGGTTTGGTGACCTT (SEQ ID NO: 290) |

Splice Donor and Splice Acceptor Site Sequences

| | |
|---|---|
| 5' side of intron (SEQ ID NO: 291) | AGGTAAGAGTCGATCG (SEQ ID NO: 291) |
| 3' side of intron (SEQ ID NO: 292) | ACGCGTTACTAACTGGTACCTCTTTTTTTTT TTGATATCCTGCAGGC (SEQ ID NO: 292) |

Additional miRNA Sequences

| Mature miRNA_Length (Sequence) | SEQ ID NO: |
|---|---|
| Guide PD1_204_21nt (TTCAGGAATGGGTTCCAAGGA) | 704 |
| Guide PD1_204_23nt (TTCAGGAATGGGTTCCAAGGATG) | 705 |
| Passenger PD1_204_21nt (TCCTGGAAGCTATTCCTGACG) | 706 |
| Passenger PD1_204_22nt (TCCTGGAAGCTATTCCTGACG T) | 707 |

-continued

| Mature miRNA_Length (Sequence) | SEQ ID NO: |
|---|---|
| Passenger PD1_204_23nt (TCCTGGAAGCTATTCCTGACG TT) | 708 |
| Guide PD1_206_21nt (TATAATATAATAGAACCACAG) | 709 |
| Guide PD1_206_23nt (TATAATATAATAGAACCACAGGA) | 710 |
| Passenger PD1_206_21nt (TGTGGTTCTGTTATATCCATA) | 711 |
| Passenger PD1_206_22nt (TGTGGTTCTGTTATATCCATA T) | 712 |
| Passenger PD1_206_23nt (TGTGGTTCTGTTATATCCATA TA) | 713 |

Exemplary Anti-CD33 VH and VL Sequences

| Name | SEQ ID NO | Amino Acid Sequence | SEQ ID NO | Nucleotide Sequence |
|---|---|---|---|---|
| hM195 VL | 293 | DIQMTQSPSSLSASVG DRVTITCRASESVDNY GISFMNWFQQKPGKA PKLLIYAASNQGSGVPS RFSGSGSGTDFTLTISSL QPDDFATYYCQQSKEV PWTFGQGTKVEIK | 301 | GACATTCAGATGACCCAGTCTCCGAGCTCTCTGTC CGCATCAGTAGGAGACAGGGTCACCATCACATGC AGAGCCAGCGAAAGTGTCGACAATTATGGCATTA GCTTTATGAACTGGTTCCAACAGAAACCCGGGAA GGCTCCTAAGCTTCTGATTTACGCTGCATCCAACC AAGGCTCCGGGGTACCCTCTCGCTTCTCAGGCAG TGGATCTGGGACAGACTTCACTCTCACCATTTCAT CTCTGCAGCCTGATGACTTCGCAACCTATTACTGT CAGCAAAGTAAGGAGGTTCCGTGGACGTTCGGTC AAGGGACCAAGGTGGAGATCAAA |
| hM195 VH | 294 | QVQLVQSGAEVKKPGS SVKVSCKASGYTFTDY NMHWVRQAPGQGLE WIGYIYPYNGGTGYNQ KFKSKATITADESTNTA YMELSSLRSEDTAVYYC ARGRPAMDYWGQGT LVTVSS | 302 | CAGGTTCAGCTGGTGCAGTCTGGAGCTGAGGTG AAGAAGCCTGGGAGCTCAGTGAAGGTTTCCTGCA AAGCTTCTGGCTACACCTTCACTGACTACAACATG CACTGGGTGAGGCAGGCTCCTGGCCAAGGCCTG GAATGGATTGGATATATTTATCCTTACAATGGTG GTACCGGCTACAACCAGAAGTTCAAGAGCAAGG CCACAATTACAGCAGACGAGAGTACTAACACAGC CTACATGGAACTCTCCAGCCTGAGGTCTGAGGAC ACTGCAGTCTATTACTGCGCAAGAGGGCGCCCCG CTATGGACTACTGGGGCCAAGGGACTCTGGTCAC TGTCTCTTCA |
| M2H12 VH | 295 | QVQLQQSGPELVRPGT FVKISCKASGYTFTNYDI NWVNQRPGQGLEWI GWIYPGDGSTKYNEKF KAKATLTADKSSSTAYL QLNNLTSENSAVYFCA SGYEDAMDYWGQGT SVTVSS | | |
| M2H12 VL | 296 | DIKMTQSPSSMYASLG ERVIINCKASQDINSYLS WFQQKPGKSPKTLIYR ANRLVDGVPSRFSGSG SGQDYSLTISSLEYEDM GIYYCLQYDEFPLTFGA GTKLELKR | | |
| DRB2 VH | 297 | EVKLQESGPELVKPGAS VKMSCKASGYKFTDYV VHWLKQKPGQGLEWI GYINPYNDGTKYNEKF KGKATLTSDKSSSTAY MEVSSLTSEDSAVYYC ARDYRYEVYGMDYWG QGTSVTVSS | | |
| DRB2 VL | 298 | DIVLTQSPTIMSASPGE RVTMTCTASSSVNYIH WYQQKSGDSPLRWIF DTSKVASGVPARFSGS GSGTSYSLTISTMEAED AATYYCQQWRSYPLTF GDGTRLELKRADAAPT VS | | |
| My9-6 VH | 299 | QVQLQQPGAEVVKPG ASVKMSCKASGYTFTS YYIHWIKQTPGQGLEW VGVIYPGNDDISYNQK FKGKATLTADKSSTTAY MQLSSLTSEDSAVYYC AREVRLRYFDVWGAG TTVTVSS | | |
| My9-6 VL | 300 | NIMLTQSPSSLAVSAG EKVTMSCKSSQSVFFSS SQKNYLAWYQQIPGQ SPKLLIYWASTRESGVP DRFTGSGSGTDFTLTIS SVQSEDLAIYYCHQYLS SRTFGGGTKLEIKR | | |

-continued

| Name | SEQ ID NO | Amino Acid Sequence | SEQ ID NO | Nucleotide Sequence |
|---|---|---|---|---|
| hM195 scFv | 303 | DIQMTQSPSSLSA SVGDRVTITCRAS ESVDNYGISFMN WFQQKPGKAPKL LIYAASNQGSGVP SRFSGSGSGTDFT LTISSLQPDDFATY YCQQSKEVPWTF GQGTKVEIKGGGG SGGGGSGGGGSQ VQLVQSGAEVKKP GSSVKVSCKASGY TFTDYNMHWVRQ APGQGLEWIGYIY PYNGGTGYNQKF KSKATITADESTNT AYMELSSLRSEDT AVYYCARGRPAM DYWGQGTLVTVSS | 304 | GACATTCAGATGACCCAGTCTCCGAGCTCTCTGTC CGCATCAGTAGGAGACAGGGTCACCATCACATGC AGAGCCAGCGAAAGTGTCGACAATTATGGCATTA GCTTTATGAACTGGTTCCAACAGAAACCCGGGAA GGCTCCTAAGCTTCTGATTTACGCTGCATCCAACC AAGGCTCCGGGGTACCCTCTCGCTTCTCAGGCAG TGGATCTGGGACAGACTTCACTCTCACCATTTCAT CTCTGCAGCCTGATGACTTCGCAACCTATTACTGT CAGCAAAGTAAGGAGGTTCCGTGGACGTTCGGTC AAGGGACCAAGGTGGAGATCAAAGGTGGCGGTG GCTCGGGCGGTGGTGGGTCGGGTGGCGGCGGAT CTCAGGTTCAGCTGGTGCAGTCTGGAGCTGAGGT GAAGAAGCCTGGGAGCTCAGTGAAGGTTTCCTGC AAAGCTTCTGGCTACACCTTCACTGACTACAACAT GCACTGGGTGAGGCAGGCTCCTGGCCAAGGCCT GGAATGGATTGGATATATTTATCCTTACAATGGT GGTACCGGCTACAACCAGAAGTTCAAGAGCAAG GCCACAATTACAGCAGACGAGAGTACTAACACAG CCTACATGGAACTCTCCAGCCTGAGGTCTGAGGA CACTGCAGTCTATTACTGCGCAAGAGGGCGCCCC GCTATGGACTACTGGGGCCAAGGGACTCTGGTCA CTGTCTCTTCA |

Exemplary Anti-MUC1 VH and VL Sequences

| Name | SEQ ID NO | Amino Acid Sequence |
|---|---|---|
| Anti-MUC1 VH1 | 305 | QVQLVQSGAEVKKPGSSVKVSCKASGYAFSNFWMNWVRQAPGQGLEWMGQI YPGDGDTNYNGKFKGRVTITADKSTSTAYMELSSLRSEDTAVYYCARSYYRSAWFA YWGQGTLVTVSS |
| Anti-MUC1 VH2 | 306 | QVQLVQSGAEVKKPGASVKVSCKASGYAFSNFWMNWVRQAPGQGLEWMGQI YPGDGDTNYNGKFKGRVTMTRDTSTSTVYMELSSLRSEDTAVYYCARSYYRSAWF AYWGQGTLVTVSS |
| Anti-MUC1 VH3 | 307 | QVQLVQSGAEVKKPGASVKVSCKASGYAFSNFWMNWVRQAPGQGLEWMGQI YPGDGDTNYNGKFKGRVTMTRDTSISTAYMELSRLRSDDTAVYYCARSYYRSAWF AYWGQGTLVTVSS |
| Anti-MUC1 VH4 | 308 | QVQLVQSGAEVKKPGATVKISCKVSGYAFSNFWMNWVQQAPGKGLEWMGQIY PGDGDTNYNGKFKGRVTITADTSTDTAYMELSSLRSEDTAVYYCARSYYRSAWFAY WGQGTLVTVSR |
| Anti-MUC1 VH5 | 309 | EVQLVQSGAEVKKPGESLKISCKGSGYAFSNFWMNWVRQMPGKGLEWMGQIY PGDGDTNYNGKFKGQVTISADKSISTAYLQWSSLKASDTAMYYCARSYYRSAWFA YWGQGTLVTVSL |
| Anti-MUC1 VL1 | 310 | EIVLTQSPDFQSVTPKEKVTITCRASQSIGTSIHWYQQKPDQSPKLLIKYASESISGVP SRFSGSGSGTDFTLTINSLEAEDAATYYCQQSNNWPLTFGQGTKVEIK |
| Anti-MUC1 VL2 | 311 | EIVMTQSPATLSVSPGERATLSCRASQSIGTSIHWYQQKPGQAPRLLIYYASESISGI PARFSGSGSGTEFTLTISSLQSEDFAVYYCQQSNNWPLTFGGGTKVEIK |
| Anti-MUC1 VL3 | 312 | EIVLTQSPATLSLSPGERATLSCRASQSIGTSIHWYQQKPGQAPRLLIYYASESISGIP ARFSGSGSGTDFTLTISSLEPEDFAVYYCQQSNNWPLTFGGGTKVEIK |
| Anti-MUC1 VL4 | 313 | AIQLTQSPSSLSASVGDRVTITCRASQSIGTSIHWYQQKPGKAPKLLIYYASESISGVP SRFSGSGSGTDFTLTISSLQPEDFATYYCQQSNNWPLTFGGGTKVEIK |
| Anti-MUC1 VL5 | 314 | DIVMTQSPSLLSASTGDRVTISCRASQSIGTSIHWYQQKPGKAPELLIYYASESISGV PSRFSGSGSGTDFTLTISCLQSEDFATYYCQQSNNWPLTFGQGTKVEIK |

Exemplary Anti-MUC16 Sequences

| Name | SEQ ID NO | Amino Acid Sequence | SEQ ID NO | Nucleotide Sequence |
|---|---|---|---|---|
| Anti-MUC16 VH1 | 315 | QVQLQESGPGLVKPS QTLSLTCTVSGYSIVSH YYWSWIRQHPGKGLE WIGYISSDGSNYYNPSL KSLVTISVDTSKNQFSL KLSSVTAADTAVYYCV RGVDYWGQGTMVTV SS | 316 | CAGGTGCAACTGCAGGAATCAGGTCCAGGCTTG GTCAAGCCATCGCAGACTCTTAGTCTGACATGCA CCGTGAGTGGCTATAGCATCGTGTCGCACTATTA TTGGTCTTGGATCAGGCAGCATCCAGGAAAGGG ACTGGAGTGGATCGGGTACATTAGCAGCGATGG GAGCAACTATTACAACCCATCTCTGAAGTCCCTGG TAACTATTAGCGTGGATACAAGCAAAAATCAGTT TTCATTAAAGCTCTCTTCAGTGACCGCAGCTGATA CCGCCGTCTATTATTGCGTGCGGGGGGTGGACTA CTGGGGTCAGGGCACCATGGTTACTGTGTCATCA |
| Anti-MUC16 VH2 | 317 | QVQLQESGPGLVKPSD TLSLTCAVSGYSIVSHY YWGWIRQPPGKGLE WIGYISSDGSNYYNPSL KSRVTMSVDTSKNQFS LKLSSVTAVDTAVYYCV RGVDYWGQGTMVTV SS | 318 | CAGGTACAGCTGCAGGAGAGTGGCCCTGGTTTA GTAAAGCCATCAGATACACTTTCACTTACCTGCGC CGTGTCTGGTTATTCTATCGTGAGCCACTATTACT GGGGATGGATCCGCCAGCCCCCTGGCAAAGGTCT TGAGTGGATTGGCTATATAAGTTCGGATGGCAGT AACTATTACAATCCTTCTCTGAAGAGCCGTGTCAC TATGAGCGTGGACACTAGCAAAAACCAGTTCAGC CTGAAGCTGTCCTCCGTCACCGCCGTAGACACCG CTGTCTACTATTGTGTTAGGGGGGTGGACTACTG GGGCCAAGGCACCATGGTCACGGTGAGCAGC |
| Anti-MUC16 VH3 | 319 | EVQLVESGGGLVQPG GSLRLSCAASGYSIVSH YYMSWVRQAPGKGLE WVSVISSDGSNYYADS VKGRFTISRDNSKNTLY LQMNSLRAEDTAVYYC VRGVDYWGQGTLVTV SS | 320 | |
| Anti-MUC16 VH4 | 321 | EVQLVESGGGLVQPG RSLRLSCAASGYSIVSH YYMHWVRQAPGKGL EWVSAISSDGSNEYAD SVEGRFTISRDNAKNSL YLQMNSLRAEDTAVYY CVRGVDYWGQGTLVT VSS | 322 | GAGGTGCAGCTCGTCGAGTCCGGAGGCGGTCTG GTGCAACCCGGCCGTTCTTTGCGGCTGAGTTGCG CTGCCAGTGGGTATAGCATCGTGAGTCACTATTA CATGCATTGGGTTCGTCAAGCCCCTGGCAAGGGA CTAGAGTGGGTGTCCGCCATCTCCTCAGACGGTA GTAATGAGTACGCGGACAGCGTAGAGGGTAGAT TCACCATTTCTCGGGACAATGCCAAAAATAGTCTA TACCTCCAAATGAATTCCCTTAGGGCCGAAGACA CTGCCGTGTACTACTGTGTTCGGGGCGTGGACTA CTGGGGGCAGGGGACATTGGTGACTGTGAGCTC A |
| Anti-MUC16 VH5 | 323 | QVQLQESGPGLVKPS QTLSLTCTVSGYSIVSH YYWSWIRQHPGKGLE WIGYISSDGSNEYNPSL KSLVTISVDTSKNQFSL KLSSVTAADTAVYFCV RGVDYWGQGTMVTV SS | 324 | CAGGTCCAACTGCAGGAATCTGGCCCCGGACTGG TTAAACCATCTCAGACACTCTCCCTGACCTGCACC GTGTCTGGATACAGCATCGTTTCTCATTATTACTG GTCATGGATTAGGCAGCATCCCGGAAAAGGGCTT GAATGGATTGGCTACATCTCCTCCGACGGCTCCA ATGAGTACAACCCATCACTTAAATCTCTGGTCACG ATAAGCGTAGACACATCTAAAAATCAGTTCTCATT AAAGCTCAGCTCTGTTACAGCTGCCGACACCGCT GTGTACTTCTGTGTGCGAGGGGTTGACTACTGGG GGCAGGGCACAATGGTGACAGTGTCTTCC |
| Anti-MUC16 VH6 | 325 | QVQLVQSGAEVKKPG SSVKVSCKASGYSIVSH YYISWVRQAPGQGLE WMGGISSDGSNNYA QKFQGRVTITADESTS TAYMELSSLRS EDTAVYYCVRGVDYW GQGTLVTVSS | 326 | CAGGTTCAACTGGTTCAGTCCGGAGCCGAGGTCA AAAAGCCTGGATCCTCTGTGAAGGTGTCATGTAA GGCTTCTGGCTACAGCATCGTCTCACATTATTACA TATCTTGGGTGCGACAGGCCCCCGGCCAGGGGCT CGAGTGGATGGGAGGTATTTCCTCCGACGGGAG TAACAATTACGCTCAGAAATTTCAGGGCCGGGTG ACCATTACCGCCGACGAAAGTACAAGCACCGCTT ATATGGAATTAAGCTCTTTAAGATCAGAGGACAC GGCTGTGTACTACTGTGTAAGGGGCGTGGATTAC TGGGGTCAGGGGACGCTCGTCACCGTCTCGAGC |
| Anti-MUC16 VH7 | 327 | QVQLQESGPGLVKPSE TLSLTCTVSGYSIVSHYY WSWIRQPPGKGLEWI GYISSDGSNNYNPSLKS RVTISVDTSKNQFSLKL SSVTAADTAVYYCVRG VDYWGQGTTVTVSS | 328 | CAGGTCCAGCTCCAGGAATCCGGCCCAGGGTTGG TGAAGCCTTCGGAGACCCTGTCTCTGACATGCAC AGTCAGCGGCTATAGTATCGTCTCCCACTATTATT GGTCTTGGATTCGGCAACCTCCAGGCAAGGGGTT AGAATGGATTGGATACATCTCAAGCGATGGTCC AATAACTACAACCCAAGTCTCAAAAGTAGAGTGA CTATCTCTGTGGATACCAGTAAAAACCAGTTTTCA CTCAAGTTGAGTTCCGTCACCGCCGCCGACACAG CCGTTTACTACTGTGTTCGGGGAGTGGACTACTG GGGCCAAGGTACCACGGTTACCGTGAGCAGC |

-continued

| Name | SEQ ID NO | Amino Acid Sequence | SEQ ID NO | Nucleotide Sequence |
|---|---|---|---|---|
| Anti-MUC16 VH8 | 648 | QVQLQESGPGLVKPSDTLSLTCAVSGYSIVSHYYWHWIRQPPGKGLEWMGYISSDGSNDFNPSLKTRITISRDTSKNQFSLKLSSVTAVDTAVYYCVRGVDYWGQGTLVTVSS | 649 | CAGGTGCAGCTGCAGGAGAGCGGCCCCGGCCTGGTGAAGCCCAGCGACACCCTGAGCCTGACCTGCGCCGTGAGCGGCTACAGCATCGTGAGCCACTACTACTGGCACTGGATCAGACAGCCCCCCGGCAAGGGCCTGGAGTGGATGGGCTACATCAGCAGCGACGGCAGCAACGACTTCAACCCCAGCCTGAAGACCAGAATCACCATCAGCAGAGACACCAGCAAGAACCAGTTCAGCCTGAAGCTGAGCAGCGTGACCGCCGTGGACACCGCCGTGTACTACTGCGTGAGAGGCGTGGACTACTGGGGCCAGGGCACCCTGGTGACCGTGAGCAGC |
| Anti-MUC16 VH9 | 650 | QVQLQESGPGLVKPSQTLSLTCAVYGYSIVSHYYWSWIRQPPGKGLEWIGEISSDGSNNYNPSLKSRVTISVDTSKNQFSLKLSSVTAADTAVYYCVRGVDYWGQGTLVTVSS | 651 | CAGGTGCAGCTGCAGGAGAGCGGCCCCGGCCTGGTGAAGCCCAGCCAGACCCTGAGCCTGACCTGCGCCGTGTACGGCTACAGCATCGTGAGCCACTACTACTGGAGCTGGATCAGACAGCCCCCCGGCAAGGGCCTGGAGTGGATCGGCGAGATCAGCAGCGACGGCAGCAACAACTACAACCCCAGCCTGAAGAGCAGAGTGACCATCAGCGTGGACACCAGCAAGAACCAGTTCAGCCTGAAGCTGAGCAGCGTGACCGCCGCCGACACCGCCGTGTACTACTGCGTGAGAGGCGTGGACTACTGGGGCCAGGGCACCCTGGTGACCGTGAGCAGC |
| Anti-MUC16 VH10 | 652 | QVQLQESGPGLVKPSETLSLTCAVSGYSIVSHYYWGWIRQPPGKGLEWIGSISSDGSNYYNPSLKSRVTISVDTSKNQFSLKLSSVTAADTAVYYCVRGVDYWGQGTLVTVSS | 653 | CAGGTGCAGCTGCAGGAGAGCGGCCCCGGCCTGGTGAAGCCCAGCGAGACCCTGAGCCTGACCTGCGCCGTGAGCGGCTACAGCATCGTGAGCCACTACTACTGGGGCTGGATCAGACAGCCCCCCGGCAAGGGCCTGGAGTGGATCGGCAGCATCAGCAGCGACGGCAGCAACTACTACAACCCCAGCCTGAAGAGCAGAGTGACCATCAGCGTGGACACCAGCAAGAACCAGTTCAGCCTGAAGCTGAGCAGCGTGACCGCCGCCGACACCGCCGTGTACTACTGCGTGAGAGGCGTGGACTACTGGGGCCAGGGCACCCTGGTGACCGTGAGCAGC |
| Anti-MUC16 VH11 | 654 | QVQLVESGGGVVQPGRSLRLSCAASGYSIVSHYYWNWVRQAPGKGLEWVAYISSDGSNEYNPSLKNRFTISRDNSKNTLYLQMNSLRAEDTAVYYCVRGVDYWGQGTTVTVSS | 655 | CAGGTGCAGCTGGTGGAGAGCGGCGGCGGCGTGGTGCAGCCCGGCAGAAGCCTGAGACTGAGCTGCGCCGCCAGCGGCTACAGCATCGTGAGCCACTACTACTGGAACTGGGTGAGACAGGCCCCCGGCAAGGGCCTGGAGTGGGTGGCCTACATCAGCAGCGACGGCAGCAACGAGTACAACCCCAGCCTGAAGAACAGATTCACCATCAGCAGAGACAACAGCAAGAACACCCTGTACCTGCAGATGAACAGCCTGAGAGCCGAGGACACCGCCGTGTACTACTGCGTGAGAGGCGTGGACTACTGGGGCCAGGGCACCACCGTGACCGTGAGCAGC |
| Anti-MUC16 VH12 | 656 | QVQLQESGPGLVKPSQTLSLTCTVSGYSIVSHYYWNWIRQHPGKGLEWIGYISSDGSNEYNPSLKNLVTISVDTSKNQFSLKLSSVTAADTAVYYCVRGVDYWGQGTMVTVSS | 657 | CAGGTGCAGCTGCAGGAGAGCGGCCCCGGCCTGGTGAAGCCCAGCCAGACCCTGAGCCTGACCTGCACCGTGAGCGGCTACAGCATCGTGAGCCACTACTACTGGAACTGGATCAGACAGCACCCCGGCAAGGGCCTGGAGTGGATCGGCTACATCAGCAGCGACGGCAGCAACGAGTACAACCCCAGCCTGAAGAACCTGGTGACCATCAGCGTGGACACCAGCAAGAACCAGTTCAGCCTGAAGCTGAGCAGCGTGACCGCCGCCGACACCGCCGTGTACTACTGCGTGAGAGGCGTGGACTACTGGGGCCAGGGCACCATGGTGACCGTGAGCAGC |
| Anti-MUC16 VH13 | 658 | QVQLQESGPGLVKPSDTLSLTCAVSGYSIVSHYYWNWIRQPPGKGLEWIGYISSDGSNEYNPSLKNRVTMSVDTSKNQFSLKLSSVTAVDTAVYYCVRGVDYWGQGTMVTVSS | 659 | CAGGTGCAGCTGCAGGAGAGCGGCCCCGGCCTGGTGAAGCCCAGCGACACCCTGAGCCTGACCTGCGCCGTGAGCGGCTACAGCATCGTGAGCCACTACTACTGGAACTGGATCAGACAGCCCCCCGGCAAGGGCCTGGAGTGGATCGGCTACATCAGCAGCGACGGCAGCAACGAGTACAACCCCAGCCTGAAGAACAGAGTGACCATGAGCGTGGACACCAGCAAGAACCAGTTCAGCCTGAAGCTGAGCAGCGTGACCGCCGTGGACACCGCCGTGTACTACTGCGTGAGAGGCGTGGACTACTGGGGCCAGGGCACCATGGTGACCGTGAGCAGC |

-continued

| Name | SEQ ID NO | Amino Acid Sequence | SEQ ID NO | Nucleotide Sequence |
|---|---|---|---|---|
| Anti-MUC16 VH14 | 660 | EVQLLESGGGLVQPGGSLRLSCAASGYSIVSHYYWNWVRQAPGKGLEWVSYISSDGSNEYNPSLKNRFTISRDNSKNTLYLQMNSLRAEDTAVYYCVRGVDYWGQGTLVTVSS | 661 | GAGGTGCAGCTGCTGGAGAGCGGCGGCGGCCTGGTGCAGCCCGGCGGCAGCCTGAGACTGAGCTGCGCCGCCAGCGGCTACAGCATCGTGAGCCACTACTACTGGAACTGGGTGAGACAGGCCCCCGGCAAGGGCCTGGAGTGGGTGAGCTACATCAGCAGCGACGGCAGCAACGAGTACAACCCCAGCCTGAAGAACAGATTCACCATCAGCAGAGACAACAGCAAGAACACCCTGTACCTGCAGATGAACAGCCTGAGAGCCGAGGACACCGCCGTGTACTACTGCGTGAGAGGCGTGGACTACTGGGGCCAGGGCACCCTGGTGACCGTGAGCAGC |
| Anti-MUC16 VH | 672 | VKLQESGGGFVKPGGSLKVSCAASGFTFSSYAMSWVRLSPEMRLEWVATISSAGGYIFYSDSVQGRFTISRDNAKNTLHLQMGSLRSGDTAMYYCARQGFGNYGDYYAMDYWGQGTTVTVSS | 673 | GTGAAGCTGCAAGAGTCCGGCGGAGGCTTTGTGAAGCCTGGCGGCTCTCTGAAAGTGTCCTGTGCCGCCAGCGGCTTCACCTTTAGCAGCTACGCCATGAGCTGGGTCCGACTGAGCCCTGAGATGAGACTGGAATGGGTCGCCACCATCAGTAGCGCAGGCGGCTACATCTTCTACAGCGACTCTGTGCAGGGCAGATTCACCATCAGCCGGGACAACGCCAAGAACACCCTGCACCTCCAGATGGGCAGTCTGAGAAGCGGCGATACCGCCATGTACTACTGCGCCAGACAAGGCTTCGGCAACTACGGCGACTACTATGCCATGGATTACTGGGGCCAGGGCACCACCGTGACAGTCTCTTCT |
| Anti-MUC16 VH | 674 | VKLEESGGGFVKPGGSLKISCAASGFTFRNYAMSWVRLSPEMRLEWVATISSAGGYIFYSDSVQGRFTISRDNAKNTHLQMGSLRSGDTAMYYCARQGFGNYGDYYAMDYWGQGTTVTVSS | 675 | GTGAAGCTGGAAGAGTCCGGCGGAGGCTTTGTGAAGCCTGGCGGAAGCCTGAAGATCAGCTGTGCCGCCAGCGGCTTCACCTTCAGAAACTACGCCATGAGCTGGGTCCGACTGAGCCCCGAGATGAGACTGGAATGGGTCGCCACAATCAGCAGCGCAGGCGGCTACATCTTCTACAGCGATAGCGTGCAGGGCAGATTCACCATCAGCCGGGACAACGCCAAGAACACCCTGCACCTCCAGATGGGCAGTCTGAGATCTGGCGACACCGCCATGTACTACTGGCCAGACAAGGCTTCGGCAACTACGGCGACTACTATGCCATGGATTACTGGGGCCAGGGCACCACCGTGACAGTCTCTTCT |
| Anti-MUC16 VH | 676 | DVQLLESGPGLVRPSQSLSLTCSVTGYSIVSHYYWNWIRQFPGNKLEWMGYISSDGSNEYNPSLKNRISISLDTSKNQFFLKFDFVTTADTATYFCVRGVDYWGQGTTLTVSS | 677 | GACGTGCAACTTCTGGAGAGCGGGCCAGGGCTAGTCAGGCCCTCCCAGTCGCTTTCACTGACTTGCAGTGTGACCGGTTACTCTATTGTGAGTCACTACTATTGGAACTGGATTCGGCAGTTCCCAGGCAACAAACTGGAATGGATGGGGTACATATCTTCCGATGGCTCGAATGAATATAACCCATCATTGAAAAATCGTATTTCCATCAGTCTGGATACGAGTAAAAACCAGTTTTTCCTCAAATTCGATTTCGTGACTACAGCAGATACTGCCACATACTTCTGTGTACGAGGTGTCGATTATTGGGGACAGGGCACAACGCTGACCGTAAGTTCT |
| Anti-MUC16 VH | 678 | DVQLQESGPGLVNPSQSLSLTCTVTGYSITNDYAWNWIRQFPGNKLEWMGYINYSGYTTYNPSLKSRISITRDTSKNQFFLHLNSVTTEDTATYYCARWDGGLTYWGQGTLVTVSA | 679 | GACGTTCAGCTGCAAGAGTCTGGCCCTGGCCTGGTCAATCCTAGCCAGAGCCTGAGCCTGACATGTACCGTGACCGGCTACAGCATCACCAACGACTACGCCTGGAACTGGATCAGACAGTTCCCCGGCAACAAGCTGGAATGGATGGGCTACATCAACTACAGCGGCTACACCACCTACAATCCCAGCCTGAAGTCCCGGATCTCCATCACCAGAGACACCAGCAAGAACCAGTTCTTCCTGCACCTGAACAGCGTGACCACCGAGGATACCGCCACCTACTACTGCGCTAGATGGGATGGCGGCCTGACATATTGGGGCCAGGGAACACTGGTCACCGTGTCTGCT |
| Anti-MUC16 VH | 680 | EVQLVESGGGLVQPGGSLRLSCAASGYSITNDYAWNWVRQAPGKGLEWVGYINYSGYTTYNPSLKSRFTISRDNSKNTLYLQMNSLRAEDTAVYYCARWDGGLTYWGQGTLVTVSS | 681 | GAGGTGCAGCTGGTGGAGAGCGGCGGCGGCCTGGTGCAGCCCGGCGGCAGCCTGAGGCTGAGCTGCGCCGCCAGCGGCTACAGCATCACCAACGACTACGCCTGGAACTGGGTGAGGCAGGCCCCCGGCAAGGGCCTGGAGTGGGTGGGCTACATCAACTACAGCGGCTACACCACCTACAACCCCAGCCTGAAGAGCAGGTTCACCATCAGCAGGGACAACAGCAAGAACACCCTGTACCTGCAGATGAACAGCCTGAGGGCCGAGGACACCGCCGTGTACTACTGCGCCAGGTGGGACGGCGGCCTGACCTACTGGGGCCAGGGCACCCTGGTGACCGTGAGCAGC |

-continued

| Name | SEQ ID NO | Amino Acid Sequence | SEQ ID NO | Nucleotide Sequence |
|---|---|---|---|---|
| Anti-MUC16 VH | 682 | EVQLVESGGGLVQPGGSLRLSCAASGYSITNDYAWNWVRQAPGKGLEWVGYINYSGYTTYNPSLKSRFTISRDNSKNTFYLQMNSLRAEDTAVYYCARWDGGLTYWGQGTLVTVSS | 683 | GAGGTGCAGCTGGTGGAGAGCGGCGGCGGCCTGGTGCAGCCCGGCGGCAGCCTGAGGCTGAGCTGCGCCGCCAGCGGCTACAGCATCACCAACGACTACGCCTGGAACTGGGTGAGGCAGGCCCCCGGCAAGGGCCTGGAGTGGGTGGGCTACATCAACTACAGCGGCTACACCACCTACAACCCCAGCCTGAAGAGCAGGTTCACCATCAGCAGGGACAACAGCAAGAACACCTTCTACCTGCAGATGAACAGCCTGAGGGCCGAGGACACCGCCGTGTACTACTGCGCCAGGTGGGACGGCGGCCTGACCTACTGGGGCCAGGGCACCCTGGTGACCGTGAGCAGC |
| Anti-MUC16 VH | 684 | EVQLQQSGAELVKPGASVKLSCTASGFNIKDTYMHWVKQRPEQGLEWIGRVDPANGNTKYDPKFQGKATLTADTSSNTAYLQLSSLTSEDTAVYFCVRDYYGHTYGFAFCDQGTTLTVSA | 685 | GAGGTTCAGCTGCAGCAGTCTGGCGCCGAACTTGTGAAACCTGGCGCCTCTGTGAAGCTGAGCTGTACCGCCAGCGGCTTCAACATCAAGGACACCTACATGCACTGGGTCAAGCAGAGGCCTGAGCAGGGCCTCGAATGGATCGGAAGAGTGGATCCCGCCAACGGCAACACCAAATACGACCCCAAGTTCCAGGGCAAAGCCACACTGACCGCCGACACCTCTAGCAACACAGCCTACCTGCAGCTGTCCAGCCTGACCTCTGAAGATACCGCCGTGTACTTCTGCGTGCGGGACTACTACGGCCATACCTACGGCTTCGCCTTCTGCGACCAAGGCACAACCCTGACAGTGTCTGCT |
| Anti-MUC16 VH | 686 | EVQLVESGGGLVQPGGSLRLSCAASGFNIKDTYMHWVRQAPGKGLEWVGRVDPANGNTKYDPKFQGRFTISADTSKNTAYLQMNSLRAEDTAVYYCVRDYYGHTYGFAFWGQGTLVTVSS | 687 | GAGGTGCAGCTGGTTGAATCTGGCGGAGGACTGGTTCAGCCTGGCGGATCTCTGAGACTGTCTTGTGCCGCCAGCGGCTTCAACATCAAGGACACCTACATGCACTGGGTCCGACAGGCCCCTGGCAAAGGACTTGAGTGGGTTGGAAGAGTGGACCCCGCCAACGGCAACACCAAATACGACCCCAAGTTCCAGGGCAGATTCACCATCAGCGCCGACACCAGCAAGAACACCGCCTACCTGCAGATGAACAGCCTGAGAGCCGAGGACACCGCCGTGTACTATTGCGTGCGGGATTACTACGGCCATACCTACGGCTTCGCCTTTTGGGGCCAGGGCACACTGGTTACCGTTAGCTCT |
| Anti-MUC16 VL1 | 329 | DIQMTQSPSSLSASVGDRVTITCQASRDINNFLNWYQQKPGKAPKLLIYRANNLETGVPSRFSGSGSGTDFTFTISSLQPEDIATYFCLQYGDLYTFGGGTKVEIK | 330 | GACATACAGATGACTCAGAGCCCCTCCTCACTCTCGGCATCAGTCGGCGACAGGGTCACAATTACCTGTCAGGCTTCTCGCGACATTAATAACTTCCTGAATTGGTATCAGCAAAAGCCCGGGAAGGCCCCTAAGCTGTTGATTTATAGAGCAAATAATCTCGAAACCGGCGTGCCCAGTAGGTTTAGCGGGTCCGGGAGCGGAACAGACTTCACATTCACCATTTCTAGTTTGCAGCCCGAAGACATTGCTACATATTTTTGCCTGCAGTACGGGGATCTCTACACTTTCGGGGGCGGAACAAAGGTTGAGATAAAA |
| Anti-MUC16 VL2 | 331 | DIQMTQSPSSLSASVGDRVTITCQASRDINNFLNWYQQKPGKAPKLLIYRANNLETGVPSRFSGSGSGTDFTFTISSLQPEDIATYYCLQYGDLYTFGGGTKVEIK | 332 | GATATTCAAATGACGCAGTCACCCTCATCGCTCTCTGCGTCAGTAGGGGATCGTGTCACGATAACCTGTCAAGCATCAAGGGACATCAACAACTTCCTCAACTGGTACCAACAGAAGCCTGGCAAGGCACCTAAACTCCTGATCTACCGGGCTAACAACCTAGAAACCGGGGTTCCGAGCCGATTCAGTGGGTCTGGAAGCGGGACAGACTTTACGTTCACTATTAGTTCGCTACAGCCCGAAGACATTGCGACATATTACTGTCTTCAGTATGGGGATTTGTATACCTTTGGGGGAGGCACCAAGGTAGAGATAAAG |
| Anti-MUC16 VL3 | 333 | DIQMTQSPSSLSASVGDRVTITCRASRDINNFLGWYQQKPGKAPKRLIYRANSLQSGVPSRFSGSGSGTEFTLTISSLQPEDFATYYCLQYGDLYTFGQGTKVEIK | 334 | GACATCCAGATGACTCAGAGCCCGTCTTCTCTATCCGCAAGTGTAGGCGATCGTGTCACCATCACATGCCGGGCTTCCCGGGATATCAACAACTTCCTTGGGTGGTATCAGCAGAAGCCCGGAAAAGCCCCCAAACGGCTCATCTACAGAGCGAATTCCCTGCAGTCAGGTGTCCCCAGTAGGTTCAGCGGATCAGGCTCGGGGACCGAATTCACTCTGACCATTAGCTCACTGCAGCCTGAGGATTTCGCTACTTACTATTGCCTGCAATACGGCGATCTGTACACTTTCGGGCAGGGCACCAAGGTGGAAATAAAA |

-continued

| Name | SEQ ID NO | Amino Acid Sequence | SEQ ID NO | Nucleotide Sequence |
|---|---|---|---|---|
| Anti-MUC16 VL4 | 335 | EIVLTQSPGTLSLSPGE RATLSCRASRDINNFLA WYQQKPGQAPRLLIYR ANSRATGIPDRFSGSG SGTDFTLTISRLEPEDF AVYYCLQYGDLYTFGQ GTKVEIK | 336 | GAAATCGTACTGACCCAGTCTCCCGGAACCCTGA GTCTCTCACCCGGCGAGCGCGCAACACTGTCGTG TAGGGCCAGTAGGGACATAAATAACTTCCTAGCC TGGTACCAACAAAAACCGGGTCAGGCTCCAAGAC TGTTGATCTATAGAGCTAACTCCAGGGCCACCGG CATCCCAGACCGATTCTCAGGCTCCGGATCTGGA ACCGACTTCACGCTCACCATTAGCCGACTAGAACC TGAGGACTTTGCTGTATACTATTGCCTGCAGTACG GCGACCTGTATACCTTTGGACAGGGTACCAAGGT CGAGATCAAG |
| Anti-MUC16 VL5 | 337 | EIVLTQSPATLSLSPGE RATLSCRASRDINNFLA WYQQKPGQAPRLLIYR ANNRATGIPARFSGSG PGTDFTLTISSLEPEDFA VYYCLQYGDLYTFGGG TKVEIK | 338 | GAGATCGTACTTACGCAGAGCCCAGCAACTCTGT CTCTGTCCCCCGGAGAACGGGCCACCCTGTCGTG CCGGGCCAGCCGTGATATTAATAATTTCCTGGCCT GGTATCAACAAAAACCGGGGCAGGCTCCTCGACT GTTGATCTACCGGGCCAACAATAGAGCAACTGGT ATCCCTGCTCGCTTCTCCGGCAGTGGGCCAGGTA CAGACTTCACCCTGACTATTTCGTCACTCGAACCA GAAGACTTTGCCGTGTATTATTGCTTACAATACGG GGATCTGTACACTTTCGGAGGAGGAACTAAGGTC GAAATTAAG |
| Anti-MUC16 VL6 | 339 | EIVLTQSPDFQSVTPKE KVTITCRASRDINNFLH WYQQKPDQSPKLLIKR ANQSFSGVPSRFSGSG SGTDFTLTINSLEAEDA ATYYCLQYGDLYTFGQ GTKVEIK | 340 | GAGATCGTGCTGACCCAGAGCCCCGACTTCCAGA GCGTGACCCCCAAGGAGAAGGTGACCATCACCTG CAGAGCCAGCAGAGACATCAACAACTTCCTGCAC TGGTACCAGCAGAAGCCCGACCAGAGCCCCAAG CTGCTGATCAAGAGAGCCAACCAGAGCTTCAGCG GCGTGCCCAGCAGATTCAGCGGCAGCGGCAGCG GCACCGACTTCACCCTGACCATCAACAGCCTGGA GGCCGAGGACGCCGCCACCTACTACTGCCTGCAG TACGGCGACCTGTACACCTTCGGCCAGGGCACCA AGGTGGAGATCAAG |
| Anti-MUC16 VL7 | 341 | DIQMTQSPSSLSASVG DRVTITCRASRDINNFL AWFQQKPGKAPKSLIY RANSLQSGVPSRFSGS GSGTDFTLTISSLQPED FATYYCLQYGDLYTFG GGTKVEIK | 342 | GACATCCAGATGACCCAGAGCCCCAGCAGCCTGA GCGCCAGCGTGGGCGACAGAGTGACCATCACCT GCAGAGCCAGCAGAGACATCAACAACTTCCTGGC CTGGTTCCAGCAGAAGCCCGGCAAGGCCCCCAAG AGCCTGATCTACAGAGCCAACAGCCTGCAGAGCG GCGTGCCCAGCAGATTCAGCGGCAGCGGCAGCG GCACCGACTTCACCCTGACCATCAGCAGCCTGCA GCCCGAGGACTTCGCCACCTACTACTGCCTGCAG TACGGCGACCTGTACACCTTCGGCGGCGGCACCA AGGTGGAGATCAAG |
| Anti-MUC16 VL8 | 662 | DIQMTQSPSSLSASVG DRVTITCRASRDINNFL AWYQQKPGKAPKLLL YRANRLESGVPSRFSG SGSGTDYTLTISSLQPE DFATYYCLQYGDLYTF GGGTKVEIK | 663 | GACATCCAGATGACCCAGAGCCCCAGCAGCCTGA GCGCCAGCGTGGGCGACAGAGTGACCATCACCT GCAGAGCCAGCAGAGACATCAACAACTTCCTGGC CTGGTACCAGCAGAAGCCCGGCAAGGCCCCCAA GCTGCTGCTGTACAGAGCCAACAGACTGGAGAG CGGCGTGCCCAGCAGATTCAGCGGCAGCGGCAG CGGCACCGACTACACCCTGACCATCAGCAGCCTG CAGCCCGAGGACTTCGCCACCTACTACTGCCTGC AGTACGGCGACCTGTACACCTTCGGCGGCGGCAC CAAGGTGGAGATCAAG |
| Anti-MUC16 VL9 | 664 | DIQMTQSPSSLSASVG DRVTITCKASRDINNFL SWYQQKPGKAPKLLIY RANRLVDGVPSRFSGS GSGTDFTFTISSLQPED IATYYCLQYGDLYTFGG GTKVEIK | 665 | GACATCCAGATGACCCAGAGCCCCAGCAGCCTGA GCGCCAGCGTGGGCGACAGAGTGACCATCACCT GCAAGGCCAGCAGAGACATCAACAACTTCCTGAG CTGGTACCAGCAGAAGCCCGGCAAGGCCCCCAA GCTGCTGATCTACAGAGCCAACAGACTGGTGGAC GGCGTGCCCAGCAGATTCAGCGGCAGCGGCAGC GGCACCGACTTCACCTTCACCATCAGCAGCCTGCA GCCCGAGGACATCGCCACCTACTACTGCCTGCAG TACGGCGACCTGTACACCTTCGGCGGCGGCACCA AGGTGGAGATCAAG |

-continued

| Name | SEQ ID NO | Amino Acid Sequence | SEQ ID NO | Nucleotide Sequence |
|---|---|---|---|---|
| Anti-<br>MUC16<br>VL10 | 666 | DIQMTQSPSSLSASVG<br>DRVTITCKASRDINNFL<br>SWYQQKPGKAPKLLIY<br>RANRLVDGVPSRFSGS<br>GSGTDFTLTISSLQPED<br>FATYYCLQYGDLYTFG<br>QGTKVEIK | 667 | GACATCCAGATGACCCAGAGCCCCAGCAGCCTGA<br>GCGCCAGCGTGGGCGACAGAGTGACCATCACCT<br>GCAAGGCCAGCAGAGACATCAACAACTTCCTGAG<br>CTGGTACCAGCAGAAGCCCGGCAAGGCCCCCAA<br>GCTGCTGATCTACAGAGCCAACAGACTGGTGGAC<br>GGCGTGCCCAGCAGATTCAGCGGCAGCGGCAGC<br>GGCACCGACTTCACCCTGACCATCAGCAGCCTGC<br>AGCCCGAGGACTTCGCCACCTACTACTGCCTGCA<br>GTACGGCGACCTGTACACCTTCGGCCAGGGCACC<br>AAGGTGGAGATCAAG |
| Anti-<br>MUC16<br>VL11 | 668 | EIVLTQSPGTLSLSPGE<br>RATLSCKASRDINNFLS<br>WYQQKPGQAPRLLIYR<br>ANRLVDGIPDRFSGSG<br>SGTDFTLTISRLEPEDF<br>AVYYCLQYGDLYTFGQ<br>GTKVEIK | 669 | GAGATCGTGCTGACCCAGAGCCCCGGCACCCTGA<br>GCCTGAGCCCCGGCGAGAGAGCCACCCTGAGCT<br>GCAAGGCCAGCAGAGACATCAACAACTTCCTGAG<br>CTGGTACCAGCAGAAGCCCGGCCAGGCCCCCAG<br>ACTGCTGATCTACAGAGCCAACAGACTGGTGGAC<br>GGCATCCCCGACAGATTCAGCGGCAGCGGCAGC<br>GGCACCGACTTCACCCTGACCATCAGCAGACTGG<br>AGCCCGAGGACTTCGCCGTGTACTACTGCCTGCA<br>GTACGGCGACCTGTACACCTTCGGCCAGGGCACC<br>AAGGTGGAGATCAAG |
| Anti-<br>MUC16<br>VL12 | 670 | EIVLTQSPATLSLSPGE<br>RATLSCKASRDINNFLS<br>WYQQKPGQAPRLLIYR<br>ANRLVDGIPARFSGSG<br>SGTDFTLTISSLEPEDFA<br>VYYCLQYGDLYTFGQG<br>TKVEIK | 671 | GAGATCGTGCTGACCCAGAGCCCCGCCACCCTGA<br>GCCTGAGCCCCGGCGAGAGAGCCACCCTGAGCT<br>GCAAGGCCAGCAGAGACATCAACAACTTCCTGAG<br>CTGGTACCAGCAGAAGCCCGGCCAGGCCCCCAG<br>ACTGCTGATCTACAGAGCCAACAGACTGGTGGAC<br>GGCATCCCCGCCAGATTCAGCGGCAGCGGCAGC<br>GGCACCGACTTCACCCTGACCATCAGCAGCCTGG<br>AGCCCGAGGACTTCGCCGTGTACTACTGCCTGCA<br>GTACGGCGACCTGTACACCTTCGGCCAGGGCACC<br>AAGGTGGAGATCAAG |
| Anti-<br>MUC16 VL | 688 | DIELTQSPSSLAVSAGE<br>KVTMSCKSSQSLLNSR<br>TRKNQLAWYQQKPG<br>QSPELLIYWASTRQSG<br>VPDRFTGSGSGTDFTL<br>TISSVQAEDLAVYYCQ<br>QSYNLLTFGPGTKLEV<br>KR | 689 | GACATCGAGCTGACACAGAGCCCATCTAGCCTG<br>GCTGTGTCTGCCGGCGAGAAAGTGACCATGAG<br>CTGCAAGAGCAGCCAGAGCCTGCTGAACAGCC<br>GGACCAGAAAGAATCAGCTGGCCTGGTATCAGC<br>AGAAGCCCGGCCAATCTCCTGAGCTGCTGATCT<br>ACTGGGCCAGCACAAGACAGAGCGGCGTGCC<br>CGATAGATTCACAGGATCTGGCAGCGGCACCG<br>ACTTCACCCTGACAATCAGTTCTGTGCAGGCCG<br>AGGACCTGGCCGTG<br>TACTACTGTCAGCAGAGCTACAACCTGCTGACCT<br>TCGGACCCGGCACCAAGCTGGAAGTGAAGAGA |
| Anti-<br>MUC16 VL | 690 | DIELTQSPSSLAVSAGE<br>KVTMSCKSSQSLLNSR<br>TRKNQLAWYQQKTG<br>QSPELLIYWASTRQSG<br>VPDRFTGSGSGTDFTL<br>TISSVQAEDLAVYYCQ<br>QSYNLLTFGPGTKLEIKR | 691 | GACATCGAGCTGACACAGAGCCCATCTAGCCTG<br>GCTGTGTCTGCCGGCGAGAAAGTGACCATGA<br>GCTGCAAGAGCAGCCAGAGCCTGCTGAACAGC<br>CGGACCAGAAAGAATCAGCTGGCCTGGTATCA<br>GCAGAAAACCGGACAGAGCCCCGAGCTGCTG<br>ATCTACTGGGCCAGCACAAGACAGAGCGGCGTG<br>CCCGATAGATTCACAGGATCTGGCAGCGGCACC<br>GACTTCACCCTGACAATCAGTTCTGTGCAGGCC<br>GAGGACCTGGCCGTGTACTACTGTCAGCAGAGC<br>TACAACCTGCTGACCTTCGGACCCGGCACCAAG<br>CTGGAAATCAAGAGA |
| Anti-<br>MUC16 VL | 692 | DIKMAQSPSSVNASL<br>GERVTITCKASRDINN<br>FLSWFHQKPGKSTL<br>IYRANRLVDGVPSRFS<br>GSGSGQDYSFTISSLEY<br>EDVGIYYCLQYGDLYTF<br>GGGTKLEIK | 693 | GACATCAAGATGGCTCAGTCCCCTTCTAGCGT<br>GAATGCTTCGCTAGGGGAGCGTGTGACCATCAC<br>ATGTAAAGCATCACGCGACATAAATAATTTCCTT<br>TCCTGGTTTCATCAGAAACCGGGCAAGTCGCCTA<br>AGACGCTGATTTACAGAGCAAATCGGTTGGTAG<br>ATGGAGTGCCAAGCAGATTCAGCGGGAGCGG<br>AAGTGGACAGGATTATAGCTTCACTATTTCATC<br>CCTGGAATACGAGGACGTAGGTATCTATTATTG<br>CCTCCAGTATGGCGATCTTTACACATTTGGTGGG<br>GGGACTAAGCTGGAGATTAAG |

-continued

| Name | SEQ ID NO | Amino Acid Sequence | SEQ ID NO | Nucleotide Sequence |
|---|---|---|---|---|
| Anti-MUC16 VL | 694 | DIQMTQSSSFLSVSLGGRVTITCKASDLIHNWLAWYQQKPGNAPRLLISGATSLETGVPSRFSGSGSGNDYTLSIASLQTEDAATYYCQQYWTTPFTFGSGTKLEIK | 695 | GACATCCAGATGACCCAGAGCAGCAGCTTCCTGAGCGTGTCCCTTGGCGGCAGAGTGACCATCACCTGTAAAGCCAGCGACCTGATCCACAACTGGCTGGCCTGGTATCAGCAGAAGCCTGGCAACGCTCCCAGACTGCTGATTAGCGGCGCCACCTCTCTGGAAACAGGCGTGCCAAGCAGATTTTCCGGCAGCGGCTCCGGCAACGACTACACACTGTCTATTGCCAGCCTGCAGACCGAGGATGCCGCCACCTATTACTGCCAGCAGTACTGGACCACACCTTTCACCTTTGGCAGCGGCACCAAGCTGGAAATCAAG |
| Anti-MUC16 VL | 696 | DIQMTQSPSSLSASVGDRVTITCKASDLIHNWLAWYQQKPGKAPKLLISGATSLETGVPSRFSGSGSGTDFTLTISSLQPEDFATYYCQQYWTTPFTFGQGTKVEIKR | 697 | GACATCCAGATGACCCAGAGCCCCAGCAGCCTGAGCGCCAGCGTGGGCGACAGGGTGACCATCACCTGCAAGGCCAGCGACCTGATCCACAACTGGCTGGCCTGGTACCAGCAGAAGCCCGGCAAGGCCCCCAAGCTGCTGATCAGCGGCGCCACCAGCCTGGAGACCGGCGTGCCCAGCAGGTTCAGCGGCAGCGGCAGCGGCACCGACTTCACCCTGACCATCAGCAGCCTGCAGCCCGAGGACTTCGCCACCTACTACTGCCAGCAGTACTGGACCACCCCCTTCACCTTCGGCCAGGGCACCAAGGTGGAGATCAAGAGG |
| Anti-MUC16 VL | 698 | DIVLTQSPAIMSASLGERVTMTCTASSSVSSSYLHWYQQKPGSSPKLWIYSTSNLASGVPGRFSGSGSGTSYSLTISSMEAEDAATYYCHQYHRSPYTFGGGTKVEIKR | 699 | GACATCGTGCTGACACAGAGCCCTGCCATCATGTCTGCCAGCCTCGGCGAGCGAGTGACCATGACATGTACAGCCAGCAGCAGCGTGTCCAGCAGCTACCTGCATTGGTATCAGCAGAAGCCCGGCAGCAGCCCCAAGCTGTGGATCTACAGCACAAGCAATCTGGCCAGCGGCGTGCCAGGCAGATTTTCTGGTTCTGGCAGCGGCACCAGCTACAGCCTGACAATCAGCAGCATGGAAGCCGAGGATGCCGCCACCTACTACTGCCACCAGTACCACAGAAGCCCCTACACCTTTGGCGGAGGCACCAAGGTGGAAATCAAGCGG |
| Anti-MUC16 VL | 700 | DIQMTQSPSSLSASVGDRVTITCTASSSVSSSYLHWYQQKPGKAPKLLIYSTSNLASGVPSRFSGSGSGTDFTLTISSLQPEDFATYYCHQYHRSPYTFGQGTKVEIKR | 701 | GACATCCAGATGACACAGAGCCCTAGCAGCCTGTCTGCCAGCGTGGGAGACAGAGTGACCATCACCTGTACAGCCAGCAGCAGCGTGTCCAGCAGCTACCTGCATTGGTATCAGCAGAAGCCCGGCAAGGCCCCTAAGCTGCTGATCTACAGCACCAGCAATCTGGCCAGCGGCGTGCCAAGCAGATTTTCTGGCTCTGGCAGCGGCACCGACTTCACCCTGACCATATCTAGCCTGCAGCCTGAGGACTTCGCCACCTACTACTGCCACCAGTACCACAGAAGCCCCTACACCTTTGGCCAGGGCACCAAGGTGGAAATCAAGCGG |
| Anti-MUC16 scFv | 343 | DIKMAQSPSSVNASLGERVTITCKASRDINNFLSWFHQKPGKSPKTLIYRANRLVDGVPSRFSGSGSGQDYSFTISSLEYEDVGIYYCLQYGDLYTFGGGTKLEIKGGGGSGGGGSGGGGSDVQLLESGPGLVRPSQSLSLTCSVTGYSIVSHYYWNWIRQFPGNKLEWMGYISSDGSNEYNPSLKNRISISLDTSKNQFFLKFDFVTTADTATYFCVRGVDYWGQGTTLTVSS | 344 | GACATCAAGATGGCTCAGTCCCCTTCTAGCGTGAATGCTTCGCTAGGGGAGCGTGTGACCATCACATGTAAAGCATCACGCGACATAAATAATTTCCTTTCCTGGTTTCATCAGAAACCGGGCAAGTCGCCTAAGACGCTGATTTACAGAGCAAATCGGTTGGTAGATGGAGTGCCAAGCAGATTCAGCGGGAGCGGAAGTGGACAGGATTATAGCTTCACTATTTCATCCCTGGAATACGAGGACGTAGGTATCTATTATTGCCTCCAGTATGGCGATCTTTACACATTTGGTGGGGGGACTAAGCTGGAGATTAAGGGCGGAGGCGGAAGCGGAGGCGGAGGCTCCGGCGGAGGCGGAAGCGACGTGCAACTTCTGGAGAGCGGGCCAGGGCTAGTCAGGCCCTCCCAGTCGCTTTCACTGACTTGCAGTGTGACCGGTTACTCTATTGTGAGTCACTACTATTGGAACTGGATTCGGCAGTTCCCAGGCAACAAACTGGAATGGATGGGGTACATATCTTCCGATGGCTCGAATGAATATAACCCATCATTGAAAAATCGTATTTCCATCAGTCTGGATACGAGTAAAAACCAGTTTTTCCTCAAATTCGATTTCGTGACTACAGCAGATACTGCCACATACTTCTGTGTACGAGGTGTCGATTATTGGGGACAGGGCACAACGCTGACCGTAAGTTCT |

Exemplary Anti-ROR1 Variable Heavy (VH) and Variable Light (VL) Sequences

| | | Amino acid sequence | | Nucleotide sequence |
|---|---|---|---|---|
| hROR1 VH_04 | 345 | EVQLVESGGGLVQPGGSLRLSCAA SGFTFSSYAMSWVRQAPGKGLEW VSAISRGGTTYYADSVKGRFTISRD NSKNTLYLQMNSLRAEDTAVYYCG RYDYDGYYAMDYWGQGTLVTVSS | 346 | GAGGTGCAGCTCGTGGAAT CCGGCGGTGGCCTGGTGCA GCCGGGCGGCAGTCTTCGA CTCTCCTGTGCGGCGTCAG GCTTTACGTTCAGTTCTTAT GCCATGAGCTGGGTGAGGC AAGCTCCCGGTAAGGGACT GGAGTGGGTCTCTGCTATC AGCCGGGGAGGTACGACCT ACTACGCTGACTCCGTAAAA GGAAGATTTACCATAAGTC GTGACAATTCCAAAAACACT CTATACTTACAGATGAACTC GCTCAGGGCCGAAGATACC GCAGTCTACTATTGTGGGA GATACGATTACGACGGCTA CTATGCTATGGATTATTGGG GTCAGGGTACGCTCGTGAC GGTGTCCTCC |
| hROR1 VL_04 | 347 | DIQMTQSPSSLSASVGDRVTITCQA SPDINSYLNWYQQKPGKAPKLLIYR ANNLETGVPSRFSGSGSGTDFTLTI SSLQPEDIATYYCLQYDEFPYTFGQ GTKLEIK | 348 | GATATTCAAATGACGCAAA GTCCCAGCAGCCTCTCCGCC TCCGTTGGAGACAGGGTGA CTATTACATGCCAAGCCAGC CCCGATATTAATAGCTACTT AAATTGGTATCAGCAGAAA CCTGGGAAGGCACCTAAAC TTCTCATCTACCGCGCTAAC AATCTGGAGACCGGCGTGC CGTCTAGATTTTCCGGCTCT GGATCAGGGACCGATTTTA CTCTGACAATTAGTTCCCTG CAACCCGAAGACATCGCCA CTTATTATTGCCTGCAATAT GATGAGTTTCCTTACACATT TGGTCAGGGAACTAAACTA GAGATTAAG |
| hROR1 VH_05 | 349 | EVQLVESGGGLVQPGGSLRLSCAA SGFTFSSYAMSWVRQAPGKGLEW VSSISRGGTTYYPDSVKGRFTISRDN SKNTLYLQMNSLRAEDTAVYYCGR YDYDGYYAMDYWGQGTLVTVSS | 350 | GAAGTGCAACTGGTCGAGT CTGGGGGCGGCCTTGTGCA ACCTGGAGGCAGCCTTCGA CTCAGTTGCGCCGCGTCTG GTTTTACCTTCTCCTCTTACG CGATGAGCTGGGTTCGCCA GGCCCCCGGCAAGGGACTT GAGTGGGTTAGTTCGATCT CCCGCGGAGGCACCACATA TTATCCTGACTCGGTTAAGG GACGCTTCACTATCTCTAGG GACAATTCAAAGAACACAC TGTATCTCCAAATGAACTCC TTGCGGGCCGAGGACACTG CTGTGTATTATTGCGGACG ATACGACTACGATGGGTAT TACGCCATGGATTACTGGG GGCAAGGTACACTGGTCAC TGTGAGTTCG |
| hROR1 VL_05 | 351 | DIQMTQSPSSLSASVGDRVTITCKA SPDINSYLSWYQQKPGKAPKLLIYR ANRLVDGVPSRFSGSGSGTDFTLTI SSLQPEDIATYYCLQYDEFPYTFGQ GTKLEIK | 352 | GATATTCAGATGACCCAGTC ACCTTCGAGTCTGAGCGCA TCCGTGGGCGACAGAGTGA CCATTACCTGTAAGGCCAGC CCGGACATTAACAGCTACCT ATCGTGGTATCAGCAAAAG CCTGGTAAGGCCCCTAAACT CCTTATCTACAGGGCTAATA GGTTGGTAGACGGGGTGCC TAGCCGGTTCTCTGGTTCCG GCAGCGGTACGGACTTTAC TCTGACCATAAGCTCTCTGC AACCAGAAGACATCGCAAC ATACTACTGTTTACAATACG ACGAATTTCCTTATACCTTT GGCCAGGGGACCAAGTTAG AGATCAAG |

-continued

| | | Amino acid sequence | | Nucleotide sequence |
|---|---|---|---|---|
| hROR1 VH_06 | 353 | EVQLVESGGGLVQPGGSLRLSCAA SGFTFSSYAIIWVRQAPGKGLEWV ARISRGGTTRYADSVKGRFTISADT SKETAYLQMNSLRAEDTAVYYCGR YDYDGYYAMDYWGQGTLVTVSS | 354 | GAGGTTCAGCTGGTCGAGT CCGGGGGAGGCTTAGTGCA GCCAGGAGGCAGTCTGCGG CTCTCTTGCGCTGCAAGTGG CTTCACATTCAGTTCATACG CAATCATCTGGGTTCGACA GGCTCCTGGTAAGGGCCTC GAATGGGTCGCAAGGATAT CACGAGGTGGAACCACTAG ATACGCAGACTCTGTTAAG GGCAGGTTCACAATTAGCG CGGATACCTCCAAGGAGAC TGCTTATTTACAGATGAACT CTCTGAGAGCCGAGGACAC TGCTGTTTACTACTGCGGCC GATACGATTACGACGGATA TTACGCAATGGATTACTGG GGCCAGGGCACGCTGGTGA CAGTTTCATCG |
| hROR1 VL_06 | 355 | DIQMTQSPSSLSASVGDRVTITCKA SPDINSYLSWYQQKPGKAPKLLIYR ANRLVDGVPSRFSGSGSGTDFTLTI SSLQPEDIATYYCLQYDEFPYTFGQ GTKLEIK | 356 | GATATCCAGATGACTCAGA GTCCCAGTAGCCTGTCGGC AAGCGTCGGAGATCGGGTC ACAATTACCTGCAAAGCTA GTCCTGATATTAATTCTTAC TTGTCCTGGTATCAGCAGA AGCCTGGTAAGGCCCCTAA GTTGCTCATCTATCGGGCTA ACCGGCTGGTGGACGGTGT TCCCTCTAGATTCTCAGGGA GTGGAAGCGGCACTGACTT CACCCTGACTATATCGAGCC TTCAGCCAGAGGACATTGC CACATACTACTGTCTGCAAT ATGATGAATTTCCATATACA TTCGGACAAGGTACAAAGT TAGAAATTAAG |
| hROR1 VH_07 | 357 | EVQLVESGGGLVQPGGSLRLSCAA SGFTFSSYAIIWVRQAPGKGLEWV ARISRGGTTRYADSVKGRFTISADT SKETAYLQMNSLRAEDTAVYYCGR YDYDGYYAMDYWGQGTLVTVSS | 358 | GAAGTCCAACTGGTGGAGT CTGGCGGGGGCTTGGTGCA GCCCGGTGGCTCCCTTAGG CTGTCTTGCGCTGCCAGCG GGTTCACATTCAGCTCCTAT GCGATTATATGGGTCCGAC AGGCACCCGGCAAGGGATT GGAGTGGGTGGCTCGCATC AGCAGAGGCGGCACTACTC GTTACGCCGACTCCGTGAA AGGCAGATTCACCATCAGT GCAGACACATCCAAGGAAA CCGCATATCTTCAGATGAAT AGCCTGCGAGCGGAGGATA CCGCCGTCTATTATTGCGGA CGCTATGATTACGACGGTT ATTATGCTATGGACTACTGG GGCCAGGGCACACTTGTGA CCGTCAGTAGC |
| hROR1 VL_07 | 359 | DIQMTQSPSSLSASVGDRVTITCRA SPDINSYVAWYQQKPGKAPKLLIYR ANFLESGVPSRFSGSRSGTDFTLTIS SLQPEDFATYYCLQYDEFPYTFGQG TKVEIK | 360 | GACATTCAAATGACGCAAA GCCCTAGTAGCTTGTCAGCT TCTGTGGGGGACCGTGTCA CAATCACTTGTCGGGCCTCT CCAGATATAAACTCCTACGT TGCTTGGTATCAGCAGAAG CCCGGAAAGGCTCCGAAAT TGTTGATTTATCGCGCTAAT TTCTTAGAGTCAGGAGTGC CCAGCCGGTTCTCAGGGTC TCGCTCTGGAACCGACTTCA CACTCACTATTTCTAGCCTA CAGCCTGAGGATTTTGCAA CTTACTACTGTCTACAGTAC GACGAGTTTCCGTACACTTT CGGACAGGGGACCAAGGT GGAGATCAAG |

-continued

| | | Amino acid sequence | | Nucleotide sequence |
|---|---|---|---|---|
| hROR1 VH_08 | 361 | QVQLVQSGGGLVKPGGSLRLSCAA SGFTFSSYAMSWVRQIPGKGLEW VSSISRGGTTYYPDSVKGRFTISRDN VKNTLYLQMSSLRAEDTAVYYCGR YDYDGYYAMDYWGQGTMVTVSS | 362 | CAAGTACAGCTCGTGCAGA GCGGCGGTGGCCTGGTGAA GCCAGGAGGTAGTCTTAGA CTGAGCTGTGCGGCTTCTG GTTTCACGTTCAGCAGTTAT GCTATGTCCTGGGTTAGGC AAATCCCCGGCAAAGGATT GGAGTGGGTTAGCAGTATC TCAAGGGGGGGAACCACAT ATTATCCTGACTCTGTCAAA GGACGGTTTACAATCAGCC GCGATAACGTTAAAAATAC CCTCTACCTCCAGATGTCTT CGCTCCGCGCTGAAGATAC AGCGGTTTACTACTGTGGC AGATACGACTACGACGGTT ATTACGCCATGGACTACTG GGGACAGGGAACTATGGTC ACAGTTAGCTCT |
| hROR1 VL_08 | 363 | DIKMTQSPSSLSASVGDRVTITCKA SPDINSYLSWYQQKPGKAPKTLIYR ANRLVDGVPSRFSGSGSGTDFTLTI SSLQYEDMAIYYCLQYDEFPYTFGD GTKVEIK | 364 | GACATCAAAATGACGCAGT CACCTAGTAGCCTCTCCGCC TCGGTTGGCGATCGGGTAA CCATTACCTGCAAAGCATCT CCAGACATAAATAGTTATCT TAGTTGGTATCAACAGAAA CCTGGCAAAGCTCCTAAGA CCCTCATCTACCGCGCTAAC CGCCTCGTGGATGGTGTTC CAAGTCGGTTCTCAGGAAG CGGCAGTGGCACAGACTTT ACACTGACAATTAGTTCCCT CCAGTATGAGGATATGGCC ATATATTACTGCCTTCAGTA TGATGAGTTTCCATACACAT TCGGAGACGGTACAAAGGT GGAGATCAAG |
| hROR1 VH_09 | 365 | QVSLRESGGGLVQPGRSLRLSCTAS GFTFSSYAMTWVRQAPGKGLEWV ASISRGGTTHFADSVKGRFTISRDN SNNTLYLQMDNVRDEDTAIYYCGR YDYDGYYAMDYWGRGTLVTVSS | 366 | CAAGTGAGCCTCCGGGAGA GTGGGGGCGGTCTGGTCCA ACCAGGACGGTCACTGCGG CTGTCATGCACTGCCAGCG GCTTCACATTTAGCTCTTAC GCCATGACTTGGGTCCGCC AAGCTCCCGGTAAGGGACT GGAGTGGGTGGCCAGCATT AGCAGGGGTGGTACAACCC ACTTCGCGGATTCAGTTAA GGGGAGATTCACTATCTCC AGGGATAATTCCAACAACA CGCTGTACCTTCAGATGGAT AACGTGAGAGACGAGGATA CCGCGATATACTACTGTGG CCGCTATGACTACGATGGTT ATTATGCTATGGATTACTGG GGGCGGGGCACCCTGGTG ACTGTGTCCTCG |
| hROR1 VL_09 | 367 | DIVMTQSPSSLSASVGDRVTITCRA SPDINSYLAWYQQKPGKAPKLLIYR ANSLQSGVPSRFSGSGSGTEFTLTIS SLQPEDFATYYCLQYDEFPYTFGQG TKLEMK | 368 | GATATCGTGATGACACAGT CACCTAGCTCCCTGAGCGCA AGCGTGGGGGATAGGGTT ACCATAACTTGCAGGGCCA GTCCCGACATCAATAGTTAT TTGGCCTGGTATCAACAGA AGCCTGGGAAGGCACCTAA GTTGCTTATTTATAGGGCTA ACTCGTTACAGAGCGGTGT GCCAAGTCGGTTCTCAGGC TCAGGGTCCGGGACCGAGT TCACCCTGACCATCAGTAGC TTGCAGCCAGAAGATTTTG CCACCTACTACTGTCTTCAA TACGATGAGTTTCCTTACAC TTTTGGACAGGGCACCAAA CTAGAGATGAAG |

-continued

| | | Amino acid sequence | | Nucleotide sequence |
|---|---|---|---|---|
| hROR1 VH_10 | 369 | QVQLVESGGGVVQPGRSLRLSCAA SGFTFSSYAMNWVRQAPAKGLEW VAIISRGGTQYYADSVKGRFTISRD NSKNTLYLQMNGLRAEDTAVYYCG RYDYDGYYAMDYWGQGTLVTVSS | 370 | CAGGTTCAACTGGTAGAAT CCGGCGGAGGTGTAGTGCA GCCTGGAAGGTCATTACGG TTAAGTTGCGCCGCCTCCG GGTTCACATTTAGCAGCTAT GCTATGAACTGGGTGCGCC AGGCCCCTGCGAAAGGACT CGAATGGGTTGCCATCATC AGCCGAGGAGGCACACAGT ATTATGCCGATTCTGTGAAG GGTCGTTTTACTATTTCCAG AGACAACAGTAAAAATACG CTGTACCTGCAAATGAACG GATTGAGGGCTGAGGATAC CGCCGTGTACTACTGTGGA CGCTACGACTATGATGGGT ACTACGCGATGGACTATTG GGGGCAAGGAACCCTTGTA ACCGTTAGTTCA |
| hROR1 VL_10 | 371 | EIVLTQSPDFQSVTPKEKVTITCRAS PDINSYLSWYQQKPDQSPKLLIKRA NQSFSGVPSRFSGSGSGTDFTLTIN SLEAEDAAAYYCLQYDEFPYTFGPG TKVDIK | 372 | GAGATCGTTTTGACACAGA GCCCCGATTTCCAGAGCGT CACGCCCAAGGAGAAGGTC ACCATCACCTGCCGAGCCA GCCCCGACATCAACAGTTAT CTTTCATGGTATCAACAGAA ACCTGATCAGAGCCCTAAG CTGCTGATTAAGCGCGCCA ACCAGAGCTTCTCAGGGGT TCCTTCACGGTTTTCCGGGT CAGGCAGCGGGACTGACTT CACGTTGACCATTAACTCTT TGGAGGCTGAGGATGCTGC TGCCTATTACTGCCTTCAGT ACGACGAGTTCCCCTATACA TTTGGTCCTGGAACAAAAG TGGATATAAAG |
| hROR1 VH_11 | 373 | QVQLVQSGAEVKKPGASVKVSCKA SGFTFSSYAMHWVRQAPGQGLE WMGNISRGGTTNYAEKFKNRVTM TRDTSISTAYMELSRLRSDDTAVYY CGRYDYDGYYAMDYWGQGTLVT VSS | 374 | CAGGTGCAGCTCGTCCAGA GCGGAGCCGAAGTGAAGA AGCCGGGAGCATCAGTGAA AGTTTCCTGCAAAGCAAGT GGCTTCACTTTCAGCAGTTA CGCGATGCACTGGGTGCGG CAGGCACCAGGTCAGGGAC TGGAATGGATGGGGAACAT CTCTCGCGGCGGAACAACC AATTACGCAGAGAAGTTTA AGAATCGCGTTACGATGAC CAGAGACACTTCTATTAGTA CAGCCTATATGGAGTTGTC GCGTCTGAGAAGCGACGAT ACCGCTGTCTACTATTGCGG CCGGTACGATTATGACGGC TACTATGCAATGGATTACTG GGGACAGGGCACACTTGTG ACAGTGTCTAGT |
| hROR1 VL_11 | 375 | DIVMTQSPLSLPVTPGEPASISCRSS PDINSYLEWYLQKPGQSPQLLIYRA NDRFSGVPDRFSGSGSGTDFTLKIS RVEAEDVGVYYCLQYDEFPYTFGQ GTKVEIK | 376 | GACATTGTGATGACTCAGT CTCCACTCAGCCTGCCTGTC ACGCCCGGCGAACCCGCTT CTATCTCTTGTAGGAGTAGC CCTGATATCAACAGCTACCT CGAATGGTATCTCCAGAAA CCTGGTCAGAGCCCCCAGC TCTTGATCTATAGAGCAAAC GACAGGTTCTCTGGCGTGC CTGATAGGTTTTCCGGTAGT GGCAGCGGAACCGACTTCA CACTTAAGATTTCAAGGGTC GAGGCCGAGGACGTGGGG GTGTATTACTGCTTACAGTA CGATGAGTTTCCGTATACAT TCGGGCAAGGCACAAAGGT GGAAATTAAG |

-continued

| | | Amino acid sequence | | Nucleotide sequence |
|---|---|---|---|---|
| hROR1 VH_12 | 377 | EVQLVESGGGLVQPGGSLRLSCTG SGFTFSSYAMHWLRQVPGEGLEW VSGISRGGTIDYADSVKGRFTISRD DAKKTLSLQMNSLRAEDTAVYYCG RYDYDGYYAMDYWGQGTMVTVSS | 378 | GAAGTGCAACTGGTCGAAA GTGGAGGGGGACTAGTGC AGCCCGGAGGGTCACTGAG GCTATCATGCACCGGCTCTG GTTTTACTTTTTCCAGCTAT GCCATGCACTGGCTCAGAC AGGTTCCGGGGGAAGGACT GGAGTGGGTTAGCGGAATC TCCAGAGGCGGAACTATTG ACTACGCAGACAGCGTGAA AGGTAGGTTTACCATCAGC AGGGACGATGCTAAAAAGA CCCTGTCACTTCAAATGAAT AGCCTGAGAGCTGAGGATA CGGCCGTGTATTACTGTGG ACGCTATGACTACGATGGA TATTACGCAATGGACTACTG GGGCCAGGGAACAATGGT GACCGTCTCAAGC |
| hROR1 VL_12 | 379 | EIVLTQSPATLSVSPGERATLSCRAS PDINSYLAWYQQKPGQAPRLLFSR ANNRATGIPARFTGSGSGTDFTLTI SSLEPEDFAIYYCLQYDEFPYTFGQG TKVEIK | 380 | GAGATCGTCCTGACCCAGA GCCCAGCTACTTTGTCAGTT TCGCCAGGCGAGCGGGCCA CACTGAGCTGTAGGGCTTC TCCTGATATCAATTCTTACC TGGCCTGGTATCAACAGAA ACCGGGACAGGCCCCTCGC CTGCTGTTCTCCCGCGCCAA CAATAGGGCGACTGGCATA CCAGCTCGGTTTACTGGGA GTGGGTCAGGCACTGATTT CACGCTTACAATCAGTAGCC TGGAGCCCGAAGACTTCGC CATCTACTACTGTTTACAAT ACGATGAGTTCCCCTATACC TTCGGCCAAGGGACCAAGG TGGAGATCAAG |
| hROR1 VH_13 | 381 | EVQLVESGGGVVQPGRSLRLSCAA SGFTFSSYAMSWVRQAPGKGLEW VASISRGGTQYYADSVKGRFTISRD NSKNTLYLQMNGLRAEDTAVYYCG RYDYDGYYAMDYWGQGTLVTVSS | 382 | GAAGTGCAGCTAGTAGAAA GTGGTGGTGGGGTCGTGCA GCCAGGCCGCTCGCTCAGG CTGTCTTGCGCTGCGAGTG GTTTCACATTCTCTTCATAC GCCATGAGCTGGGTGAGAC AGGCTCCCGGCAAGGGCCT CGAATGGGTCGCATCTATA AGCAGAGGCGGAACCCAGT ACTACGCTGACAGTGTGAA GGGTCGCTTTACAATCTCAC GGGACAACAGTAAAAACAC CCTCTATCTACAGATGAATG GCTTGCGAGCTGAAGACAC GGCTGTGTATTATTGCGGG CGCTATGACTATGATGGTTA CTACGCTATGGATTACTGG GGCCAGGGCACCCTGGTTA CTGTTTCATCA |
| hROR1 VL_13 | 383 | EIVLTQSPDFQSVTPKEKVTITCRAS PDINSYLPWYQQKPDQSPKLLIKRA NQSFSGVPSRFSGSGSGTDFTLTIN SLEAEDAAAYYCLQYDEFPYTFGPG TKVDIK | 384 | GAAATAGTCCTGACCCAGA GCCCAGACTTCCAGTCCGT GACCCCTAAGGAGAAGGTT ACTATCACTTGCAGGGCAA GCCCTGACATAAATTCATAC CTGCCATGGTATCAGCAGA AGCCAGACCAGTCGCCGAA GCTATTAATCAAACGCGCCA ACCAGTCTTTTAGCGGCGTA CCATCCCGATTCTCAGGTTC GGGGTCCGGGACCGATTTC ACACTCACGATAAACTCCCT TGAGGCAGAGGATGCAGC GGCTTACTACTGTTTACAGT ACGACGAGTTTCCATATACG TTCGGCCCCGGCACGAAGG TAGATATCAAG |

-continued

| | | Amino acid sequence | | Nucleotide sequence |
|---|---|---|---|---|
| hROR1 VH_14 | 385 | EVQLVESGGGLVQPGGSLRLSCAT SGFTFSSYAMSWMRQAPGKGLE WVASISRGGTTYYADSVKGRFTISV DKSKNTLYLQMNSLRAEDTAVYYC GRYDYDGYYAMDYWGQGTLVTVSS | 386 | GAAGTGCAGCTGGTGGAGT CTGGCGGCGGTCTGGTGCA GCCCGGCGGCTCTCTGCGC CTCTCCTGTGCCACCTCTGG TTTTACATTCTCCTCCTACGC TATGTCCTGGATGCGGCAA GCCCCCGGCAAGGGCCTAG AGTGGGTCGCCTCAATCAG CAGGGGCGGGACGACTTAT TATGCCGATTCAGTTAAGG GGAGATTCACAATTTCCGT GGATAAATCCAAGAATACC TTATACCTCCAGATGAACTC TCTGCGGGCCGAAGATACG GCCGTATATTATTGTGGGA GGTATGACTACGACGGATA TTACGCCATGGATTATTGG GGGCAGGGGACACTTGTTA CAGTGAGTTCC |
| hROR1 VL_14 | 387 | DIQMTQSPSSLSASVGDRVTITCKA SPDINSYLNWYQQKPGKAPKLLIYR ANRLVDGVPSRFSGSGSGTDYTLTI SSLQPEDFATYYCLQYDEFPYTFGA GTKVEIK | 388 | GATATACAGATGACACAGA GCCCTTCAAGTTTATCTGCA AGCGTCGGCGATCGTGTTA CAATAACTTGCAAGGCATCT CCCGACATCAATTCCTACCT CAACTGGTATCAGCAGAAG CCTGGGAAGGCTCCTAAGC TGCTTATTTACAGAGCAAAT CGCCTGGTGGACGGCGTGC CCAGTCGGTTTTCCGGGTCT GGGAGCGGAACGGATTACA CACTGACCATCTCAAGCCTG CAACCCGAAGACTTCGCTAC ATATTACTGCCTTCAGTATG ATGAGTTCCCATATACCTTC GGCGCTGGGACCAAGGTG GAGATAAAG |
| hROR1 VH_14-1 | 389 | EVQLVESGGGLVQPGGSLRLSCASS GFTFSSYAMSWRRQAPGKGLEWV AGISRGGTTSYADSVKGRFTISSDD SKNTLYLQMNSLRAEDTAVYYCGR YDYDGYYAMDYWGQGTLVTVSS | 390 | GAGGTCCAGCTCGTCGAAT CTGGCGGAGGTTTAGTGCA ACCAGGCGGGTCGCTCCGA TTAAGTTGTGCGTCCAGTG GCTTCACCTTCTCCAGCTAC GCCATGTCGTGGAGGCGAC AGGCTCCTGGCAAAGGCTT GGAGTGGGTTGCTGGTATC TCCCGAGGAGGCACCACTA GTTACGCTGACAGTGTAAA AGGACGTTTCACTATTTCCT CTGACGACAGCAAGAACAC ACTCTATCTGCAAATGAATA GTCTCCGTGCTGAGGACAC AGCCGTGTATTATTGCGGG CGGTATGATTACGACGGCT ACTACGCTATGGACTACTG GGGCCAGGGAACTCTGGTC ACTGTGAGCTCT |
| hROR1 VL 14-1 | 391 | DIQMTQSPSSLSASVGDRVTITCRA SPDINSYLSWYQQKPGKAPKLLIYR ANTLESGVPSRFSGSGSGTDFTLTIS SLQPEDFATYYCLQYDEFPYTFGQG TKIEIK | 392 | GATATACAGATGACTCAAA GTCCTAGCTCCTTGAGCGCC TCAGTGGGAGATCGGGTCA CTATAACTTGTAGAGCCTCA CCAGATATAAACTCCTATCT CTCTTGGTATCAGCAGAAG CCCGGCAAAGCACCAAAGC TCTTGATCTATAGAGCTAAT ACGCTAGAGAGCGGAGTGC CTTCACGGTTTTCTGGTTCC GGGAGCGGAACCGACTTTA CCCTTACAATTTCTAGCCTC CAGCCAGAGGACTTCGCAA CTTACTATTGTCTCCAGTAT GATGAATTTCCTTACACCTT CGGCCAAGGGACCAAGATC GAGATAAAG |

-continued

| | | Amino acid sequence | | Nucleotide sequence |
|---|---|---|---|---|
| hROR1 VH_14-2 | 393 | EVQLVESGGGLVQPGGSLRLSCASSGFTFSSYAMSWVRQAPGKGLEWVAGISRGGTTSYADSVKGRFTISADTSKNTLYLQMNSLRAEDTAVYYCGRYDYDGYYAMDYWGQGTLVTVSS | 394 | GAGGTGCAGCTCGTTGAGTCCGGTGGGGGGCTGGTGCAGCCTGGCGGGTCTCTCCGCCTCTCTTGTGCCTCCTCCGGCTTTACCTTCAGCAGCTATGCTATGTCATGGGTGCGGCAGGCACCAGGCAAAGGTCTGGAATGGGTCGCTGGGATCAGTAGAGGCGGCACAACCTCCTATGCCGACAGCGTTAAGGGGAGGTTCACAATCTCGGCTGATACAAGCAAGAACACTCTGTATCTCCAAATGAACAGTCTCCGGGCAGAGGACACCGCGGTCTATTACTGCGGCCGGTACGACTACGACGGGTACTACGCAATGGACTATTGGGGACAGGGAACTCTGGTTACTGTCAGCTCT |
| hROR1 VL_14-2 | 395 | DIQMTQSPSSLSASVGDRVTITCRASPDINSYLSWYQQKPGKAPKLLIYRANTLESGVPSRFSGSGSGTDFTLTISSLQPEDFATYYCLQYDEFPYTFGTGTKLEIK | 396 | GATATCCAGATGACTCAAAGCCCATCTTCTCTCAGCGCAAGCGTGGGTGACCGAGTGACCATCACCTGCCGGGCGTCTCCTGATATCAACTCATACCTGTCCTGGTATCAGCAGAAGCCCGGAAAGGCCCCTAAGCTGCTGATCTACCGCGCAAATACACTGGAGAGCGGGGTCCCAAGCAGATTCAGTGGGTCCGGCAGTGGTACGGACTTTACTCTGACCATCAGCTCCCTGCAACCGGAGGACTTTGCTACTTATTACTGTCTCCAGTACGACGAGTTCCCATACACTTTCGGAACAGGCACTAAGCTGGAGATCAAA |
| hROR1 VH_14-3 | 397 | EVQLVESGGGLVQPGGSLRLSCAASGFTFSSYAMSWVRQAPGKGLEWVASISRGGTTYYADSVKGRFTISRDNSKNTLYLQMNSLRAEDTAVYYCGRYDYDGYYAMDYWGQGTLVTVSS | 398 | GAGGTTCAACTTGTGGAATCCGGCGGCGGGTTAGTCCAGCCCGGCGGGAGCTTGCGGCTGTCCTGCGCCGCCTCTGGATTCACTTTTAGCTCCTATGCTATGTCTTGGGTAAGGCAGGCCCCTGGTAAAGGACTAGAGTGGGTGGCCTCGATCTCCCGTGGTGGCACTACATACTACGCCGACTCCGTTAAAGGCCGGTTTACCATCTCCCGTGACAACTCTAAAAATACTTTGTACCTGCAAATGAACTCCCTGCGGGCAGAAGACACAGCCGTGTACTATTGCGGGCGTTACGATTACGACGGATATTACGCAATGGACTACTGGGGCCAGGGCACACTGGTCACCGTGAGCAGC |
| hROR1 VL_14-3 | 399 | DIQMTQSPSSLSASVGDRVTITCKASPDINSYLNWYQQKPGKAPKLLIYRANRLVDGVPSRFSGSGSGTDFTLTISSLQPEDIATYYCLQYDEFPYTFGGGTKVEIK | 400 | GATATACAAATGACTCAGTCCCCTAGTAGCCTTAGTGCTAGTGTGGGAGACAGAGTGACCATCACCTGCAAAGCATCTCCTGATATCAATTCCTACCTTAACTGGTATCAACAGAAGCCTGGCAAAGCTCCAAAGCTCCTGATTTATCGCGCGAACAGATTGGTCGATGGGGTCCCTTCCAGATTCAGCGGCTCAGGGTCAGGGACCGATTTCACCCTCACAATTAGTTCACTTCAGCCCGAGGACATCGCCACGTATTATTGCCTTCAGTACGATGAGTTCCCTTACACCTTTGGCGGGGGAACTAAAGTCGAAATTAAG |

-continued

| | | Amino acid sequence | | Nucleotide sequence |
|---|---|---|---|---|
| hROR1 VH_14-4 | 401 | EVQLVESGGGLVQPGGSLRLSCAA SGFTFSSYAMSWVRQAPGKGLEW VASISRGGTTYYPDSVKGRFTISRD NVRNILYLQMSSLRSEDTAMYYCG RYDYDGYYAMDYWGQGTLVTVSS | 402 | GAAGTGCAGCTTGTGGAGT CAGGAGGAGGGCTAGTTCA GCCAGGCGGCTCTCTGAGA CTATCTTGTGCTGCCTCCGG CTTCACATTTAGCTCTTATG CAATGTCCTGGGTCCGCCA GGCCCCTGGTAAAGGCCTG GAATGGGTTGCTTCTATCTC TAGAGGCGGAACCACTTAC TACCCTGATTCAGTGAAGG GGAGATTCACAATTAGTAG GGACAACGTGCGGAACATC CTCTACCTACAGATGTCAAG TTTACGCAGTGAGGACACT GCGATGTATTACTGCGGTC GATACGATTATGATGGATA TTATGCAATGGATTATTGG GGCCAGGGCACTCTGGTCA CAGTATCTTCC |
| hROR1 VL_14-4 | 403 | DIQMTQSPSSLSASVGDRVTITCKA SPDINSYLNWYQQKPGKAPKLLIYR ANRLVDGVPSRFSGSGSGTDYTLTI SSLQPEDFATYYCLQYDEFPYTFGA GTKVEIK | 404 | GACATCCAGATGACCCAAT CACCATCGAGTCTTAGTGCA TCCGTTGGGGATAGAGTGA CAATCACTTGTAAGGCATCC CCGGACATCAACTCATATCT TAATTGGTATCAGCAAAAG CCGGGCAAGGCCCCTAAGC TCCTGATTTATAGGGCCAAC CGCCTTGTGGATGGAGTCC CCTCCCGCTTTAGTGGAAGC GGCTCTGGCACAGACTACA CCCTGACTATCAGCTCCTTG CAGCCTGAGGATTTTGCTAC CTACTACTGTCTTCAGTACG ATGAATTTCCATACACTTTC GGTGCTGGGACAAAAGTGG AGATCAAA |
| hROR1 VH_14-5 | 405 | EVQLVESGGGLVQPGGSLRLSCAT SGFTFSSYAMSWMRKAPGKGLEY VASISRGGTTYYADSVKGRFTISVDK SKNTLYLQMNSLRAEDTAVYYCGR YDYDGYYAMDYWGQGTLVTVSS | 406 | GAAGTCCAGCTGGTTGAGT CTGGCGGAGGCCTCGTGCA GCCCGGTGGTTCCTTGCGA CTGTCATGCGCTACCAGCG GGTTCACATTCAGCTCTTAT GCAATGTCCTGGATGCGGA AGGCACCGGGTAAGGGCCT GGAGTATGTGGCCTCAATC TCCCGAGGAGGCACCACAT ACTATGCCGATTCTGTGAAA GGCCGATTCACCATTTCTGT GGATAAGTCTAAAAACACT CTCTACCTCCAGATGAACTC CCTACGTGCCGAAGACACA GCCGTGTATTATTGCGGGC GATACGATTATGACGGTTA TTATGCGATGGATTACTGG GGTCAAGGCACACTGGTAA CAGTGTCTTCC |
| hROR1 VL_14-5 | 407 | DIQMTQSPSSLSASVGDRVTITCKA SPDINSYLNWYQQKPGKAPKLLIYR ANRLVDGVPSRFSGSGSGTDYTLTI SSLQPEDFATYYCLQYDEFPYTFGA GTKVEIK | 408 | GATATTCAGATGACACAATC ACCTAGCTCACTGTCAGCGA GCGTCGGTGACCGGGTTAC TATCACATGCAAAGCCTCAC CCGATATCAATTCATACCTT AACTGGTATCAACAAAAAC CAGGAAAGGCTCCAAAGCT GCTAATTTATCGGGCCAATC GGTTGGTGGATGGCGTCCC GTCGAGGTTTAGTGGCTCC GGGAGCGGGACAGACTAC ACTCTTACAATTTCTTCTCTC CAGCCAGAGGACTTCGCAA CCTACTACTGCTTGCAGTAC GATGAATTTCCATATACCTT CGGCGCAGGGACAAAAGT GGAAATCAAA |

-continued

| | | Amino acid sequence | | Nucleotide sequence |
|---|---|---|---|---|
| hROR1 VH_15 | 409 | EVQLVESGGGLVQPGGSLRLSCVTS GFTFSSYAMSWVRQAPGKGLEWV ASISRGGTTYYSDSVKGRFTISRDNS KNTLYLQMNSLRAEDTAVYYCGRY DYDGYYAMDYWGQGTLVTVSS | 410 | GAGGTGCAGCTTGTAGAAA GCGGGGGGGGCCTGGTGC AACCTGGCGGGTCCCTGCG GCTTAGTTGCGTTACGAGC GGATTTACATTTTCCAGTTA TGCCATGTCTTGGGTGAGA CAAGCCCCCGGTAAGGGTC TGGAGTGGGTGGCAAGCAT TAGCCGAGGCGGCACTACA TACTACAGTGATAGTGTGA AAGGCCGTTTCACAATCAGT AGAGATAATTCTAAAAACA CCCTGTACTTGCAGATGAAC AGCCTGCGCGCCGAGGATA CAGCCGTGTACTACTGTGG AAGATACGACTACGATGGA TATTATGCGATGGATTACTG GGGACAGGGAACCCTTGTC ACCGTTTCCTCT |
| hROR1 VL_15 | 411 | DIVLTQSPATLSLSPGERATLSCKAS PDINSYMNWYQQKPGQAPRLLISR ANRLVDGVPARFSGSGSGTDFTLTI SSLEPEDFAVYYCLQYDEFPYTFGQ GTKVEIK | 412 | GACATAGTGTTGACGCAGT CCCCTGCCACCCTGAGCCTG AGCCCCGGAGAGCGAGCAA CGTTAAGTTGCAAGGCCAG TCCAGATATTAACTCATACA TGAATTGGTATCAACAGAA ACCAGGCCAGGCTCCTAGA CTTCTCATATCTCGGGCAAA TCGACTGGTGGATGGAGTA CCCGCAAGATTCAGCGGCA GCGGCAGCGGAACGGATTT CACGCTCACCATCTCTTCCC TTGAGCCTGAGGACTTTGC AGTCTATTATTGCTTGCAGT ATGATGAGTTCCCCTACACA TTCGGGCAAGGCACAAAAG TGGAAATTAAG |
| hROR1 VH_16 | 413 | EVQLVESGGGLVQPGGSLRLSCAA SGFTFSSYAMSWVRQAPGKGLEW VASISRGGTTYYDPKFQDRATISAD NSKNTAYLQMNSLRAEDTAVYYCG RYDYDGYYAMDYWGQGTLVTVSS | 414 | GAGGTGCAGCTGGTGGAG AGCGGAGGGGGCCTTGTCC AACCAGGAGGTAGCCTCAG GCTGTCTTGCGCTGCCTCAG GATTTACTTTTTCATCCTAC GCAATGAGCTGGGTGCGGC AAGCCCCAGGGAAGGGATT AGAATGGGTTGCCAGCATT TCTAGGGGGGGGACGACCT ACTACGATCCGAAGTTTCAG GATCGCGCCACTATCTCAGC CGATAACTCCAAGAATACT GCCTACTTACAGATGAACA GCCTGCGGGCCGAAGACAC GGCCGTCTACTATTGCGGC CGATATGATTACGACGGCT ATTACGCCATGGATTACTG GGGGCAAGGGACTCTGGTC ACAGTGAGCTCT |
| hROR1 VL_16 | 415 | DIQMTQSPSSLSASVGDRVTITCKA SPDINSYLNWYQQKPGKAPKVLIYR ANRLVDGVPSRFSGSGSGTDYTLTI SSLQPEDFATYYCLQYDEFPYTFGQ GTKVEIK | 416 | GATATTCAGATGACCCAGTC GCCCAGCAGTCTCTCGGCCT CAGTGGGCGACCGGGTCAC TATCACTTGCAAAGCAAGTC CTGATATAAACTCCTATCTT AATTGGTATCAGCAGAAGC CCGGCAAGGCACCTAAGGT TCTGATATATCGCGCAAATC GGCTCGTGGATGGAGTACC CAGCCGATTTTCCGGCAGC GGCTCAGGCACTGACTACA CACTGACAATCAGCAGCTT GCAGCCTGAAGATTTCGCC ACATACTATTGTCTACAGTA CGACGAGTTCCCTTATACAT TCGGCCAGGGGACCAAGGT CGAGATCAAG |

-continued

| | | Amino acid sequence | | Nucleotide sequence |
|---|---|---|---|---|
| hROR1 VH_17 | 417 | EVQLVESGGGLVQPGGSLRLSCTG SGFTFSSYAMSWLRQVPGEGLEW VSSISRGGTTDYADSVKGRFTISRD DAKKTLSLQMNSLRAEDTAVYYCG RYDYDGYYAMDYWGQGTMVTVSS | 418 | GAGGTCCAACTCGTGGAGA GCGGAGGGGGGCTAGTGC AACCAGGTGGCTCCCTCCG CTTGTCCTGTACGGGCTCG GGGTTCACATTTTCATCCTA TGCCATGAGCTGGCTGAGA CAGGTGCCTGGCGAGGGCC TGGAATGGGTGTCTAGTAT CAGCAGAGGGGGTACAACT GATTACGCAGATTCCGTCAA GGGACGTTTTACCATCTCAA GAGACGATGCCAAGAAGAC ATTATCACTCCAAATGAACT CACTGAGGGCCGAGGACAC CGCTGTGTACTATTGTGGG AGATACGACTACGACGGAT ACTATGCCATGGACTATTG GGGACAAGGCACGATGGT GACGGTATCTAGC |
| hROR1 VL_17 | 419 | EIVLTQSPATLSVSPGERATLSCKAS PDINSYLAWYQQKPGQAPRLLFSR ANRLVDGIPARFTGSGSGTDFTLTIS SLEPEDFAIYYCLQYDEFPYTFGQGT KVEIK | 420 | GAGATAGTGCTAACCCAGT CTCCCGCAACCCTGTCTGTG TCCCCCGGAGAGCGCGCTA CTCTGAGCTGCAAAGCCAG CCCGGACATTAATTCCTACC TTGCCTGGTATCAGCAGAA GCCTGGACAGGCCCCAAGA TTGCTCTTTTCACGCGCCAA CCGCCTGGTAGATGGTATT CCAGCTAGGTTTACGGGCT CAGGCAGCGGAACAGACTT CACTCTCACTATTAGCTCAT TGGAGCCTGAGGACTTTGC AATTTACTATTGTCTTCAGT ACGACGAGTTCCCATATACT TTCGGCCAGGGCACAAAAG TAGAGATCAAG |
| hROR1 VH_18 | 421 | EVQLVESGGGLVQPGGSLRLSCSAS GFTFSSYAMSWVRQVPGKGLVWI SSISRGGTTYYADSVRGRFIISRDNA KNTLYLEMNNLRGEDTAVYYCARY DYDGYYAMDYWGQGTLVTVSS | 422 | GAGGTTCAACTCGTGGAGT CTGGAGGCGGGCTAGTGCA GCCTGGCGGCTCCCTGCGA CTGTCTTGCAGCGCATCAG GCTTTACATTCAGTTCTTAT GCCATGAGCTGGGTGAGGC AGGTGCCCGGCAAGGGTCT GGTGTGGATCAGCTCAATC TCCAGGGGCGGGACTACAT ATTACGCCGATTCGGTCAG GGGTCGTTTTATCATTAGCA GGGATAATGCCAAGAACAC CTTGTATTTGGAGATGAAC AACCTAAGAGGCGAAGACA CCGCTGTGTACTATTGTGCC CGTTACGACTACGATGGGT ACTACGCCATGGACTATTG GGGCCAGGGAACCTTGGTG ACTGTGTCAAGT |
| hROR1 VL_18 | 423 | DIQLTQSPDSLAVSLGERATINCKAS PDINSYLSWYQQRPGQPPRLLIHR ANRLVDGVPDRFSGSGFGTDFTLTI TSLQAEDVAIYYCLQYDEFPYTFGQ GTKLEIK | 424 | GACATACAGTTGACTCAGTC ACCGGATTCGCTGGCAGTT TCGCTGGGTGAGAGAGCAA CCATCAACTGCAAAGCATCT CCCGATATCAACTCTTATCT GTCTTGGTATCAGCAGCGT CCGGGACAACCCCCTAGGC TGCTTATTCACCGAGCCAAC AGGCTGGTGGACGGGGTG CCAGACCGCTTCTCGGGAT CAGGATTTGGAACCGATTTT ACCCTAACAATTACTAGTCT CCAAGCGGAAGACGTGGCG ATCTATTATTGTCTACAATA TGACGAGTTCCCCTACACCT TCGGCCAGGGCACGAAGTT GGAGATCAAG |

-continued

| | | Amino acid sequence | | Nucleotide sequence |
|---|---|---|---|---|
| hROR1 VH_19 | 425 | EVQLVESGGGLVQPGGSLRLSCAA SGFTFSSYAMSWVRQAPGKGLEW VASISRGGTTYYADSVKGRFTISADT SKNTAYLQMNSLRAEDTAVYYCAR YDYDGYYAMDYWGQGTLVTVSS | 426 | GAGGTCCAGCTCGTCGAAT CCGGTGGAGGGCTAGTTCA GCCAGGCGGCTCATTGCGT TTGTCTTGTGCCGCCTCCGG TTTCACATTCTCTTCTTACGC TATGTCCTGGGTCCGACAA GCCCCAGGAAAAGGCTTGG AATGGGTGGCCAGTATCAG TAGAGGTGGGACTACATAT TATGCCGACTCCGTGAAGG GCAGATTCACCATCTCAGCT GACACCAGTAAGAACACTG CCTACCTACAGATGAACAG CCTTCGGGCCGAGGACACC GCTGTGTATTACTGTGCCCG GTACGATTATGATGGATATT ATGCTATGGACTATTGGGG TCAGGGGACCTTGGTGACC GTCTCTAGC |
| hROR1 VL_19 | 427 | DIQMTQSPSSLSASVGDRVTITCKA SPDINSYLSWYQQKPGKAPKLLIYR ANRLVDGVPSRFSGSGSGTDFTLTI SSLQPEDFATYYCLQYDEFPYTFGQ GTKVEIK | 428 | GACATTCAGATGACTCAATC GCCGAGTTCTCTTAGCGCTT CTGTTGGGGACCGGGTGAC AATCACATGCAAGGCCTCTC CCGATATAAACTCCTATCTA AGCTGGTATCAGCAGAAGC CAGGGAAGGCCCCCAAGTT GTTAATCTATCGCGCCAACA GACTGGTGGATGGGGTGCC CTCTCGATTCTCCGGGAGTG GCAGTGGGACTGATTTTAC ACTGACCATTTCCTCATTGC AGCCCGAAGACTTCGCTAC CTATTACTGCTTGCAGTACG ATGAGTTCCCATATACATTC GGTCAGGGGACTAAAGTGG AGATAAAA |
| hROR1 VH_20 | 429 | EVQLLESGGGLVQPGGSLRLSCAAS GFTFSSYAMSWVRQAPGKGLEWV SSISRGGTTYYADSVKGRFTISRDNS KNTLYLQMNSLRAEDTAVYYCARY DYDGYYAMDYWGQGTLVTVSS | 430 | GAGGTACAGCTGCTGGAAT CTGGTGGGGGGCTGGTCCA GCCAGGGGGGTCACTACGA CTGAGCTGCGCTGCCTCCG GTTTTACATTCAGCAGCTAT GCAATGTCATGGGTCAGAC AGGCACCAGGTAAAGGCCT CGAATGGGTATCCTCCATCT CACGTGGTGGGACCACTTA CTATGCCGATAGTGTGAAG GGCAGGTTCACGATCTCAA GAGATAATTCAAAGAATAC ACTCTATCTACAAATGAACA GTTTAAGGGCCGAGGACAC CGCTGTTTACTATTGTGCCA GATATGACTACGACGGTTA TTATGCTATGGATTACTGGG GACAAGGAACGCTGGTAAC TGTTAGCTCT |
| hROR1 VL_20 | 431 | DIQMTQSPSSLSASVGDRVTITCKA SPDINSYLSWYQQKPGEAPKLLIYR ANRLVDGVPSRFSGSGSGTDFTLTI SSLQPEDFATYYCLQYDEFPYTFGQ GTKVEIK | 432 | GACATCCAAATGACCCAGT CGCCTTCCTCCTTGTCTGCA TCTGTCGGAGATCGGGTGA CGATCACTTGCAAAGCGAG TCCAGACATCAACTCATATC TGTCCTGGTATCAGCAGAA GCCGGGAGAGGCACCTAAG CTCCTGATCTACAGAGCAAA CAGATTAGTGGATGGTGTG CCCTCACGGTTTTCTGGCTC CGGGTCCGGCACCGATTTC ACCTTGACCATCTCATCCCT ACAGCCCGAGGATTTCGCT ACTTACTATTGCTTACAGTA TGATGAGTTTCCATACACCT TCGGTCAAGGCACCAAGGT TGAGATTAAG |

-continued

| | | Amino acid sequence | | Nucleotide sequence |
|---|---|---|---|---|
| hROR1 VH_21 | 433 | EVQLLETGGGLVKPGGSLRLSCAAS GFTFSSYAMSWIRQAPGKGLEWV ASISRGGTTYYGDSVKGRFTISRDH AKNSLYLQMNSLRVEDTAVYYCVR YDYDGYYAMDYWGLGTLVTVSS | 434 | GAAGTTCAACTGCTTGAGA CCGGAGGCGGCCTGGTAAA ACCTGGGGGCTCACTGAGG CTGAGTTGTGCCGCTTCTGG GTTCACCTTTTCATCCTATG CGATGTCATGGATACGGCA GGCTCCTGGGAAGGGGCTT GAGTGGGTTGCATCAATTT CACGAGGTGGGACAACTTA TTATGGGGATTCCGTTAAA GGTAGATTTACGATCTCTAG AGACCATGCCAAAAATTCTC TCTATCTCCAGATGAATAGT CTTAGGGTGGAGGACACCG CTGTGTACTACTGTGTCCGG TACGACTATGATGGGTACT ATGCTATGGACTATTGGGG GCTCGGCACTCTGGTCACT GTTAGCTCT |
| hROR1 VL_21 | 435 | AIRMTQSPSFLSASVGDRVTITCKA SPDINSYLSWYQQRPGKAPKLLIYR ANRLVDGVPSRFSGGGSGTDFTLTI SSLQPEDIATYYCLQYDEFPYTFGQ GTKLEIK | 436 | GCCATCCGCATGACACAATC TCCCTCCTTCCTTTCTGCCAG TGTCGGGGACAGAGTGACT ATCACATGCAAAGCCAGCC CAGATATTAATTCGTACCTG TCTTGGTATCAGCAGAGGC CCGGCAAGGCACCAAAGCT GTTGATATATCGGGCCAAC CGCTTAGTGGACGGTGTCC CCTCTCGATTCAGCGGAGG CGGTAGCGGGACGGACTTT ACACTGACCATCTCCAGTCT CCAACCCGAGGATATTGCC ACTTACTATTGTCTTCAGTA TGACGAGTTCCCCTACACAT TTGGACAGGGCACCAAGCT AGAAATTAAG |
| hROR1 VH_22 | 437 | EVQLVESGGGLVQPGGSLRLSCAA SGFTFSSYAMSWVRQAPGKGLEW VASISRGGTTYYAESLEGRFTISRDD SKNSLYLQMNSLKTEDTAVYYCARY DYDGYYAMDYWGQGTLVTVSS | 438 | GAGGTTCAGCTGGTGGAGT CTGGTGGGGGGCTCGTACA GCCGGGTGGCTCCCTAAGG CTGAGTTGCGCTGCCTCAG GCTTTACCTTCTCAAGCTAC GCGATGTCCTGGGTGAGAC AGGCCCCTGGCAAAGGACT GGAGTGGGTGGCAAGCATT AGCCGGGGCGGAACTACCT ATTACGCTGAGTCGTTAGA GGGGCGGTTTACTATCTCC AGAGACGATTCAAAGAACT CGTTATACTTGCAGATGAAC AGCCTCAAGACCGAGGACA CCGCCGTGTACTACTGCGCC CGGTACGACTATGACGGGT ACTATGCTATGGATTATTGG GGACAAGGCACCCTCGTGA CCGTCTCTAGC |
| hROR1 VL_22 | 439 | DIQMTQSPSSLSASVGDRVTITCKA SPDINSYLSWYQQKPGKAPKTLIYR ANRLVDGVPSRFSGSGSGTDFTLTI SSLQPEDFATYYCLQYDEFPYTFGQ GTKLEIK | 440 | GACATCCAGATGACACAGT CCCCTTCTTCACTTTCCGCTT CTGTGGGCGACAGGGTGAC GATCACGTGTAAGGCCTCG CCAGACATTAATTCGTACTT ATCGTGGTATCAGCAGAAA CCGGGTAAAGCTCCGAAGA CTCTGATCTATAGAGCAAAT AGGCTCGTAGACGGTGTCC CATCTAGATTTAGTGGGAG CGGCAGCGGAACCGACTTC ACTCTCACCATCTCATCCCT GCAACCGGAGGATTTCGCT ACTTACTATTGCTTGCAGTA TGACGAGTTTCCATATACGT TTGGTCAGGGAACCAAATT AGAGATCAAA |

-continued

| | | Amino acid sequence | | Nucleotide sequence |
|---|---|---|---|---|
| hROR1 VH_23 | 441 | QVTLRESGPALVKPTQTLTLTCAAS GFTFSSYAMSWIRQPPGKALEWLA SISRGGTTYYNPSLKDRLTISKDTSA NQVVLKVTNMDPADTATYYCARY DYDGYYAMDYWGQGTTVTVSS | 442 | CAGGTAACACTCCGAGAGA GTGGGCCAGCTCTCGTGAA GCCCACGCAGACTTTAACAC TAACGTGTGCGGCAAGCGG CTTTACATTTTCGAGCTACG CGATGAGCTGGATAAGGCA ACCTCCTGGGAAGGCGTTG GAGTGGTTGGCCTCAATTA GCCGGGGTGGCACCACTTA CTACAATCCTAGTCTTAAGG ACAGACTTACTATTTCAAAA GATACGTCCGCCAACCAGG TGGTACTGAAGGTCACAAA TATGGACCCAGCTGACACT GCTACTTACTACTGCGCCCG GTACGATTACGATGGTTACT ACGCTATGGATTACTGGGG TCAAGGAACCACAGTGACC GTCAGTTCA |
| hROR1 VL_23 | 443 | DIQMTQSPSTLSASVGDRVTITCKA SPDINSYLSWYQQKPGKAPKLLIYR ANRLVDGVPSRFSGSGSGTAFTLTI SSLQPDDFATYYCLQYDEFPYTFGG GTKVEIK | 444 | GATATCCAGATGACGCAGT CCCCTTCAACCCTCAGTGCC AGCGTTGGTGACCGGGTTA CTATCACCTGTAAGGCTAGT CCCGATATAAATTCCTATTT GTCTTGGTATCAGCAGAAG CCAGGCAAGGCTCCTAAGC TGCTCATCTACCGGGCTAAC AGGTTAGTTGACGGTGTGC CCTCCCGATTTTCCGGCAGT GGCAGCGGGACCGCTTTCA CTCTTACAATCTCATCTCTTC AACCGGACGACTTCGCTAC GTACTACTGCCTCCAATATG ATGAGTTTCCATACACATTC GGAGGAGGCACAAAAGTC GAAATCAAG |
| hROR1 VH_24 | 445 | EVQLVESGGGLVQPGGSLRLSCAA SGFTFSSYAMSWVRQAPGKGLEW VSAISRGGTTYYADSVKGRFTISADT SKETAYLQMNSLRAEDTAVYYCGR YDYDGYYAMDYWGQGTLVTVSS | 446 | GAAGTCCAGCTGGTGGAGT CCGGCGGAGGCTTGGTTCA GCCCGGAGGATCTTTGCGA CTGTCTTGCGCCGCCAGCG GTTTCACTTTCAGCAGCTAT GCCATGAGTTGGGTTAGAC AAGCTCCCGGCAAGGGGCT GGAATGGGTTAGTGCTATT AGCCGGGGAGGGACAACA TATTACGCTGACTCTGTCAA AGGCCGATTCACCATCTCTG CTGACACGAGCAAAGAAAC CGCCTACCTCCAAATGAACA GCCTGCGAGCTGAGGACAC TGCCGTCTACTATTGTGGTC GATATGATTATGATGGGTA CTATGCAATGGACTATTGG GGGCAGGGCACACTGGTGA CCGTGAGCTCT |
| hROR1 VL_24 | 447 | DIQMTQSPSSLSASVGDRVTITCKA SPDINSYLSWYQQKPGKAPKLLIYR ANRLVDGVPSRFSGSGSGTDFTLTI SSLQPEDIATYYCLQYDEFPYTFGQ GTKLEIK | 448 | GATATTCAGATGACGCAGA GTCCCTCCTCCCTATCTGCC TCTGTTGGAGATCGAGTCA CCATTACGTGTAAAGCGTCT CCCGATATCAACAGCTACCT CTCTTGGTATCAGCAGAAAC CAGGGAAGGCCCCCAAGCT GCTGATCTATAGAGCTAATC GCTTAGTGGATGGAGTGCC AAGCAGGTTCTCCGGGTCC GGCAGTGGAACCGATTTCA CCTTGACAATAAGTAGCTTG CAACCTGAGGATATTGCAA CATACTACTGTCTACAGTAC GACGAGTTCCCCTACACCTT CGGCCAAGGGACAAAGCTG GAGATTAAG |

-continued

| | | Amino acid sequence | | Nucleotide sequence |
|---|---|---|---|---|
| hROR1 VH_25 | 449 | EVQLVESGGGLVQPGGSLRLSCAA SGFTFSSYAMSWVRQAPGKGLEW VSAISRGGTTYYADSVKGRFTISRD NSKNTLYLQMNSLRAEDTAVYYCG RYDYDGYYAMDYWGQGTLVTVSS | 450 | GAAGTGCAGCTCGTGGAGA GCGGCGGCGGTCTGGTACA GCCAGGGGGGTCACTGCGT CTCTCATGTGCTGCGAGTG GCTTTACGTTCTCTTCCTAC GCTATGTCCTGGGTCAGGC AGGCACCGGGGAAGGGCTT AGAGTGGGTTAGTGCAATC TCTAGGGGCGGTACAACCT ACTATGCCGACTCTGTCAAG GGCAGGTTTACAATTTCAA GAGATAATTCTAAGAATACT CTTTACCTACAGATGAATAG CTTGCGGGCGGAAGACACA GCAGTCTATTATTGTGGCCG CTATGACTACGACGGATACT ATGCCATGGACTACTGGGG CCAAGGCACTTTGGTCACG GTGAGCTCT |
| hROR1 VL_25 | 451 | DIQMTQSPSSLSASVGDRVTITCKA SPDINSYLSWYQQKPGKAPKLLIYR ANRLVDGVPSRFSGSGSGTDFTLTI SSLQPEDIATYYCLQYDEFPYTFGQ GTKLEIK | 452 | GACATCCAGATGACCCAGA GCCCTAGTTCATTGTCTGCC AGTGTGGGGGATAGGGTC ACTATCACGTGTAAGGCTTC CCCTGACATCAATTCATACC TGTCATGGTATCAGCAGAA GCCTGGAAAAGCCCCTAAA CTGCTGATCTACCGCGCGA ATAGGCTTGTGGACGGCGT TCCAAGCCGCTTCTCTGGCT CTGGATCAGGGACCGACTT CACCCTCACGATCTCCAGCC TCCAACCCGAGGATATCGC CACCTATTATTGCCTTCAGT ACGATGAGTTCCCCTATACA TTCGGCCAGGGGACAAAGC TGGAAATCAAA |
| hROR1 VH_26 | 453 | EVQLVESGGGLVQPGGSLRLSCAA SGFTFSSYAMSWVRQAPGKGLEW VSAISRGGTTYYADSVKGRFTISADT SKETAYLQMNSLRAEDTAVYYCGR YDYDGYYAMDYWGQGTLVTVSS | 454 | GAGGTCCAGCTCGTCGAGT CGGGTGGGGGCTTGGTGCA ACCCGGTGGCAGTTTGCGC CTGAGCTGCGCCGCGAGCG GGTTCACTTTCAGTTCGTAT GCCATGAGTTGGGTGCGAC AAGCGCCCGGCAAAGGACT GGAGTGGGTGTCAGCCATT AGCCGGGGCGGTACTACCT ACTATGCGGACTCGGTCAA GGGAAGATTCACCATCAGC GCTGATACCAGTAAGGAAA CCGCTTATCTTCAGATGAAC TCCCTGCGTGCCGAGGATA CAGCAGTCTACTATTGCGG GCGCTACGATTATGACGGA TATTATGCCATGGATTACTG GGGGCAGGGCACTCTGGTC ACAGTCAGCTCT |
| hROR1 VL_26 | 455 | DIQMTQSPSSLSASVGDRVTITCQA SPDINSYLNWYQQKPGKAPKLLIYR ANNLETGVPSRFSGSGSGTDFTLTI SSLQPEDIATYYCLQYDEFPYTFGQ GTKLEIK | 456 | GATATTCAGATGACGCAGT CTCCCTCTTCCCTGAGCGCC TCCGTCGGCGATAGAGTTA CGATCACCTGTCAGGCCAG CCCAGATATCAACTCCTATC TGAATTGGTATCAGCAAAA GCCTGGGAAGGCTCCCAAG TTGCTGATCTACAGAGCCAA TAACTTAGAGACTGGCGTG CCGTCTCGGTTCAGCGGGT CCGGCAGTGGAACCGACTT TACACTGACCATTTCCAGCC TCCAACCTGAGGATATCGCC ACATATTATTGTCTCCAGTA TGACGAGTTCCCTTACACAT TTGGTCAAGGAACTAAACT GGAAATCAAA |

-continued

| | | Amino acid sequence | | Nucleotide sequence |
|---|---|---|---|---|
| hROR1 VH_27 | 457 | EVQLVESGGGLVQPGGSLRLSCAA SGFTFSSYAMSWVRQAPGKGLEW VSAISRGGTTYYADSVKGRFTISADT SKETAYLQMNSLRAEDTAVYYCGR YDYDGYYAMDYWGQGTLVTVSS | 458 | GAGGTGCAGCTGGTCGAAA GTGGAGGCGGACTCGTGCA GCCCGGCGGTAGTCTGCGA TTGAGCTGTGCCGCGTCCG GCTTTACTTTCTCATCTTACG CTATGAGTTGGGTCCGCCA GGCCCCAGGCAAAGGACTG GAGTGGGTATCAGCCATCA GTAGGGGGGGAACTACCTA TTACGCAGATTCTGTGAAG GGACGCTTCACCATCAGCG CGGACACTAGCAAGGAGAC TGCCTACCTGCAAATGAATA GTCTGAGAGCCGAGGATAC CGCCGTGTACTATTGTGGC AGGTATGACTACGATGGCT ATTATGCTATGGATTACTGG GGCCAGGGGACGTTAGTGA CAGTAAGCTCT |
| hROR1 VL_27 | 459 | DIQMTQSPSSLSASVGDRVTITCRA SPDINSYVAWYQQKPGKAPKLLIYR ANFLESGVPSRFSGSRSGTDFTLTIS SLQPEDFATYYCLQYDEFPYTFGQG TKVEIK | 460 | GATATTCAGATGACCCAATC CCCTTCTTCTCTGAGCGCTT CTGTGGGCGATAGAGTTAC AATAACCTGTCGGGCGTCC CCAGACATTAACTCTTATGT AGCATGGTATCAGCAAAAG CCTGGAAAGGCACCAAAGT TACTGATCTACCGGGCCAAT TTTCTGGAGTCGGGCGTGC CCTCACGATTTAGCGGTAG CAGATCAGGCACAGACTTT ACTCTGACCATTAGCTCTCT GCAACCCGAGGACTTCGCC ACCTACTACTGTTTGCAGTA TGACGAGTTTCCATACACTT TTGGTCAAGGAACCAAAGT CGAAATCAAA |
| hROR1 VH_28 | 461 | QIQLVQSGAEVKKPGASVKVSCAA SGFTFSSYAMSWVRQAPGKSFKW MGSISRGGTTYYSADFKGRFAITKD TSASTAYMELSSLRSEDTAVYYCAR YDYDGYYAMDYWGQGTLVTVSS | 462 | CAGATACAGCTGGTGCAGT CTGGTGCCGAGGTTAAAAA GCCCGGAGCCTCGGTTAAA GTGAGTTGTGCGGCAAGCG GATTCACGTTCAGTTCCTAC GCTATGTCCTGGGTGCGGC AGGCTCCTGGCAAGTCATTT AAGTGGATGGGGTCGATCT CACGGGGTGGAACCACCTA TTACTCTGCCGACTTCAAGG GGAGATTTGCGATTACAAA AGATACAAGCGCCTCTACG GCCTACATGGAGTTAAGTA GCCTTAGAAGCGAAGACAC GGCGGTGTACTACTGCGCC AGATATGACTATGACGGCT ACTACGCCATGGACTACTG GGGCCAGGGCACACTGGTT ACAGTCAGCTCT |
| hROR1 VL_28 | 463 | DIVMTQSPDSLAVSLGERATISCKA SPDINSYLSWYQQKPGQPPKLLIYR ANRLVDGVPDRFSGSGSRTDFTLTI SSLQAEDVAVYYCLQYDEFPYTFGQ GTKVEIK | 464 | GATATCGTGATGACACAAA GCCCAGACAGTCTGGCAGT GTCCCTCGGCGAGCGCGCT ACCATCTCATGCAAAGCTAG TCCCGACATCAATTCCTATC TGTCCTGGTATCAGCAAAA ACCAGGCCAACCCCCCAAG CTGCTTATCTATCGGGCTAA CCGATTAGTCGATGGGGTG CCAGATAGATTTTCAGGCTC TGGTTCCCGGACAGATTTTA CTCTCACGATCTCCTCACTA CAGGCAGAAGATGTTGCAG TGTATTACTGCCTGCAATAC GACGAGTTCCCCTACACCTT CGGCCAAGGCACGAAAGTG GAGATCAAG |

-continued

| | | Amino acid sequence | | Nucleotide sequence |
|---|---|---|---|---|
| hROR scFv | 465 | EVQLVESGGGLVQPGGSLRLSCAA SGFTFSSYAMSWVRQAPGKGLEW VSSISRGGTTYYPDSVKGRFTISRDN SKNTLYLQMNSLRAEDTAVYYCGR YDYDGYYAMDYWGQGTLVTVSSG GGGSGGGGSGGGGSDIQMTQSPS SLSASVGDRVTITCKASPDINSYLN WYQQKPGKAPKLLIYRANRLVDGV PSRFSGSGSGTDYTLTISSLQPEDFA TYYCLQYDEFPYTFGAGTKVEIK | 466 | GAAGTGCAACTGGTCGAGT CTGGGGGCGGCCTTGTGCA ACCTGGAGGCAGCCTTCGA CTCAGTTGCGCCGCGTCTG GTTTTACCTTCTCCTCTTACG CGATGAGCTGGGTTCGCCA GGCCCCCGGCAAGGGACTT GAGTGGGTTAGTTCGATCT CCCGCGGAGGCACCACATA TTATCCTGACTCGGTTAAGG GACGCTTCACTATCTCTAGG GACAATTCAAAGAACACAC TGTATCTCCAAATGAACTCC TTGCGGGCCGAGGACACTG CTGTGTATTATTGCGGACG ATACGACTACGATGGGTAT TACGCCATGGATTACTGGG GGCAAGGTACACTGGTCAC TGTGAGTTCG GGGGGCGGCGGAAGTGGT GGAGGGGGAAGTGGTGGA GGAGGAAGCGATATACAGA TGACACAGAGCCCTTCAAG TTTATCTGCAAGCGTCGGC GATCGTGTTACAATAACTTG CAAGGCATCTCCCGACATCA ATTCCTACCTCAACTGGTAT CAGCAGAAGCCTGGGAAG GCTCCTAAGCTGCTTATTTA CAGAGCAAATCGCCTGGTG GACGGCGTGCCCAGTCGGT TTTCCGGGTCTGGGAGCGG AACGGATTACACACTGACC ATCTCAAGCCTGCAACCCGA AGACTTCGCTACATATTACT GCCTTCAGTATGATGAGTTC CCATATACCTTCGGCGCTGG GACCAAGGTGGAGATAAAG |

Anti-ROR1 CDRs

| | | SEQ ID NO |
|---|---|---|
| IMGT Method | | |
| VH-CDR-1 | GFTFSSYA | 715 |
| VH-CDR-2 | ISRGGTT | 716 |
| VH-CDR-3 | GRYDYDGYYAMDY | 717 |
| Kabat Method | | |
| VH-CDR-1 | SYAMS | 718 |
| VH-CDR-2 | AISRGGTTYYADSVKG | 719 |
| VH-CDR-3 | YDYDGYYAMDY | 720 |

-continued

| | | SEQ ID NO |
|---|---|---|
| IMGT Method | | |
| VL-CDR-1 | PDINSY | 721 |
| VL-CDR-2 | RAN | 722 |
| VL-CDR-3 | LQYDEFPYT | 723 |
| Kabat Method | | |
| VL-CDR-1 | RASPDINSYLS | 724 |
| VL-CDR-2 | RANTLES | 725 |
| VL-CDR-3 | LQYDEFPYT | 723 |

Portions of ROR1-Specific Antigen Binding Domain

| | | |
|---|---|---|
| Portion of VH Domain | GFTFSSYAMSWVRQAPGKGLEWVSSISRGGTTYYPDSVKGRFT ISRDNSKNTLYLQMNSLRAEDTAVYYCGRYDYDGYYAMDY | SEQ ID NO: 726 |
| Portion of VL Domain | ASPDINSYLNWYQQKPGKAPKLLIYRANRLVDGVPSRFSGSGS GTDYTLTISSLQPEDFATYYCLQYDEFPYT | SEQ ID NO: 727 |
| Portion of VH Domain | SYAMSWVRQAPGKGLEWVSSISRGGTTYYPDSVKGRFTISRDN SKNTLYLQMNSLRAEDTAVYYCGRYDYDGYYAMDY | SEQ ID NO: 728 |
| Portion of VL Domain | PDINSYLNWYQQKPGKAPKLLIYRANRLVDGVPSRFSGSGSGT DYTLTISSLQPEDFATYYCLQYDEFPYT | SEQ ID NO: 729 |

Exemplary Spacer Sequences

| | | | | |
|---|---|---|---|---|
| CD8α hinge | 467 | KPTTTPAPRPPTPAPTIASQPLSLRP EACRPAAGGAVHTRGLDFACD | 468 | AAGCCCACCACCACCCCTGC CCCTAGACCTCCAACCCCAG CCCCTACAATCGCCAGCCAG CCCCTGAGCCTGAGGCCCG AAGCCTGTAGACCTGCCGC TGGCGGAGCCGTGCACACC AGAGGCCTGGATTTCGCCT GCGAC |
| CD8α hinge-homologous stalk extension region | 469 | KPTTTPAPRPPTPAPTIASQPLSLRP EASRPAAGGAVHTRGLDFASD | 470 | AAGCCTACCACCACCCCCGC ACCTCGTCCTCCAACCCCTG CACCTACGATTGCCAGTCAG CCTCTTTCACTGCGGCCTGA GGCCAGCAGACCAGCTGCC GGCGGTGCCGTCCATACAA GAGGACTGGACTTCGCGTC CGAT |
| CD8α hinge-homologous stalk extension region | 469 | KPTTTPAPRPPTPAPTIASQPLSLRP EASRPAAGGAVHTRGLDFASD | 471 | AAACCTACTACCACTCCAGC CCCAAGGCCCCCAACCCCA GCACCGACTATCGCATCACA GCCTTTGTCACTGCGTCCTG AAGCCAGCCGGCCAGCTGC AGGGGGGGCCGTCCACACA AGGGGACTCGACTTTGCGA GTGAT |
| CD8α hinge-homologous stalk extension region | 469 | KPTTTPAPRPPTPAPTIASQPLSLRP EASRPAAGGAVHTRGLDFASD | 472 | AAACCTACTACAACTCCTGC CCCCCGGCCTCCTACACCAG CTCCTACTATCGCCTCCCAG CCACTCAGTCTCAGACCCGA GGCTTCTAGGCCAGCGGCC GGAGGCGCGGTCCACACCC GCGGGCTGGACTTTGCATC CGAT |
| CD8α hinge and 2 CD8a-homologous stalk extension regions | 473 | KPTTTPAPRPPTPAPTIASOPLSLRP EASRPAAGGAVHTRGLDFASDKPT TTPAPRPPTPAPTIASQPLSLRPEAS RPAAGGAVHTRGLDFASDKPTTTP APRPPTPAPTIASQPLSLRPEACRPA AGGAVHTRGLDFACD | 474 | AAGCCTACCACCACCCCCGC ACCTCGTCCTCCAACCCCTG CACCTACGATTGCCAGTCAG CCTCTTTCACTGCGGCCTGA GGCCAGCAGACCAGCTGCC GGCGGTGCCGTCCATACAA GAGGACTGGACTTCGCGTC CGATAAACCTACTACCACTC CAGCCCCAAGGCCCCCAAC CCCAGCACCGACTATCGCAT CACAGCCTTTGTCACTGCGT CCTGAAGCCAGCCGGCCAG CTGCAGGGGGGGCCGTCCA CACAAGGGGACTCGACTTT GCGAGTGATAAGCCCACCA CCACCCCTGCCCCTAGACCT CCAACCCCAGCCCCTACAAT CGCCAGCCAGCCCCTGAGC CTGAGGCCCGAAGCCTGTA GACCTGCCGCTGGCGGAGC CGTGCACACCAGAGGCCTG GATTTCGCCTGCGAC |

Exemplary Transmembrane Domain Sequences

| | | | | |
|---|---|---|---|---|
| CD8a Trans-membrane Domain | 475 | IYIWAPLAGTCGVLLLSLVITLYCNH RN | 476 | ATCTACATCTGGGCCCCTCT GGCCGGCACCTGTGGCGTG CTGCTGCTGAGCCTGGTCAT CACCCTGTACTGCAACCACC GGAAT |
| CD28 Trans-membrane Domain | 477 | FWVLVVVGGVLACYSLLVTVAFIIF WVRSKRS | 478 | TTTTGGGTGCTGGTGGTGG TTGGTGGAGTCCTGGCTTG CTATAGCTTGCTAGTAACAG TGGCCTTTATTATTTTCTGG GTGAGGAGTAAGAGGAGC |

Exemplary Intracellular Signaling Domain Sequences

| | | | | |
|---|---|---|---|---|
| CD3ζ signaling domain | 479 | RVKFSRSADAPAYQQGQNQLYNEL NLGRREEYDVLDKRRGRDPEMGG KPRRKNPQEGLYNELQKDKMAEA YSEIGMKGERRRGKGHDGLYQGLS TATKDTYDALHMQALPPR | 480 | CGGGTGAAGTTCAGCCGGA GCGCCGACGCCCCTGCCTA CCAGCAGGGCCAGAACCAG CTGTACAACGAGCTGAACC TGGGCCGGAGGGAGGAGT ACGACGTGCTGGACAAGCG GAGAGGCCGGGACCCTGA GATGGGCGGCAAGCCCCG GAGAAAGAACCCTCAGGAG GGCCTGTATAACGAACTGC AGAAAGACAAGATGGCCGA GGCCTACAGCGAGATCGGC ATGAAGGGCGAGCGGCGG AGGGGCAAGGGCCACGAC GGCCTGTACCAGGGCCTGA GCACCGCCACCAAGGATAC CTACGACGCCCTGCACATGC AGGCCCTGCCCCCCAGA |
| CD28 co-stimulatory domain | 481 | RSKRSRGGHSDYMNMTPRRPGPT RKHYOPYAPPRDFAAYRS | 482 | AGGAGCAAGCGGAGCAGA GGCGGCCACAGCGACTACA TGAACATGACCCCCCGGAG GCCTGGCCCCACCCGGAAG CACTACCAGCCCTACGCCCC TCCCAGGGACTTCGCCGCCT ACCGGAGC |
| 4-1BB co-stimulatory domain | 483 | KRGRKKLLYIFKQPFMRPVQTTQEE DGCSCRFPEEEEGGCEL | 484 | AAGAGAGGCCGGAAGAAA CTGCTGTACATCTTCAAGCA GCCCTTCATGCGGCCCGTG CAGACCACCCAGGAAGAGG ACGGCTGCAGCTGCCGGTT CCCCGAGGAAGAGGAAGG CGGCTGCGAACTG |
| DNAX-activation protein 10 (DAP10) co-stimulatory domain | 485 | LCARPRRSPAQEDGKVYINMPGRG | 486 | CTGTGCGCACGCCCACGCC GCAGCCCCGCCCAAGAAGA TGGCAAAGTCTACATCAAC ATGCCAGGCAGGGGC |
| DNAX-activation protein 12 (DAP12) co-stimulatory | 487 | YFLGRLVPRGRGAAEAATRKQRITE TESPYQELQGQRSDVYSDLNTQRP YYK | 488 | TACTTCCTGGGCCGGCTGG TCCCTCGGGGGCGAGGGGC TGCGGAGGCAGCGACCCG GAAACAGCGTATCACTGAG ACCGAGTCGCCTTATCAGG AGCTCCAGGGTCAGAGGTC GGATGTCTACAGCGACCTC AACACACAGAGGCCGTATT ACAAA |

Exemplary Signal Peptide Sequences

| | | | | |
|---|---|---|---|---|
| GM-CSFRa signal peptide | 489 | MLLLVTSLLLCELPHPAFLLIP | 490 | ATGCTGCTGCTGGTGACCA GCCTGCTGCTGTGTGAGCT GCCCCACCCCGCCTTTCTGC TGATCCCC |
| Ig Kappa signal peptide | 491 | MRLPAQLLGLLMLWVPGSSG | 492 | ATGAGGCTCCCTGCTCAGCT CCTGGGGCTGCTAATGCTCT GGGTCCCAGGATCCAGTGG G |
| Immuno-globulin E signal peptide | 493 | MDWTWILFLVAAATRVHS | 494 | ATGGATTGGACCTGGATTCT GTTTCTGGTGGCCGCTGCCA CAAGAGTGCACAGC |
| CD8α signal peptide | 495 | MALPVTALLLPLALLLHAARP | 496 | ATGGCGCTGCCCGTGACCG CCTTGCTCCTGCCGCTGGCC TTGCTGCTCCACGCCGCCAG GCCG |
| Mouse Ig VH region 3 signal peptide | 497 | MGWSCIILFLVATATGVHS | 498 | ATGGGCTGGTCCTGCATCAT CCTGTTTCTGGTGGCTACCG CCACCGGCGTGCACAGC |

-continued

| | | | | |
|---|---|---|---|---|
| β2M signal peptide | 499 | MSRSVALAVLALLSLSGLEA | 500 | ATGTCTCGCTCCGTGGCCTT AGCTGTGCTCGCGCTACTCT |
| Azurocidin signal peptide | 501 | MTRLTVLALLAGLLASSRA | 502 | CTCTTTCTGGCCTGGAGGCT ATGACCCGGCTGACAGTCCT GGCCCTGCTGGCTGGTCTG |
| Human Serum Albumin signal peptide | 503 | MKWVTFISLLFLFSSAYS | 504 | CTGGCGTCCTCGAGGGCC ATGAAGTGGGTAACCTTTAT TTCCCTTCTTTTTCTCTTTAG CTCGGCTTATTCC |
| A2M receptor associated protein signal peptide | 505 | MGKNKLLHPSLVLLLLVLLPTDA | 506 | ATGGGGAAGAACAAACTCC TTCATCCAAGTCTGGTTCTT CTCCTCTTGGTCCTCCTGCCC ACAGACGCC |
| IGHV3-23 signal peptide | 507 | MEFGLSWLFLVAILKGVQC | 508 | ATGGAGTTTGGGCTGAGCT GGCTTTTTCTTGTGGCTATTT TAAAAGGTGTCCAGTGT |
| IGKV1-D33 (HuL1) signal peptide | 509 | MDMRVPAQLLGLLLLWLSGARC | 510 | ATGGACATGAGGGTCCCTG CTCAGCTCCTGGGGCTCCTG CTGCTCTGGCTCTCAGGTGC CAGATGT |
| IGHV3-33(L14F) (HuH7) signal peptide | 511 | MEFGLSWVFLVALFRGVQC | 512 | ATGGAGTTTGGGCTGAGCT GGGTTTTCCTCGTTGCTCTTT TTAGAGGTGTCCAGTGT |
| TVB2 (T21A) signal peptide | 513 | MGTSLLCWMALCLLGADHADA | 514 | ATGGGCACCAGCCTCCTCTG CTGGATGGCCCTGTGTCTCC TGGGGGCAGATCACGCAGA TGCT |
| CD52 signal peptide | 515 | MKRFLFLLLTISLLVMVQIQTGLS | 516 | ATGAAGCGCTTCCTCTTCCT CCTACTCACCATCAGCCTCC TGGTTATGGTACAGATACAA ACTGGACTCTCA |
| Low-affinity nerve growth factor receptor (LNGFR, TNFRSF16) signal peptide | 517 | MGAGATGRAMDGPRLLLLLLLGVS LGGA | 518 | ATGGGGGCAGGTGCCACCG GCCGCGCCATGGACGGGCC GCGCCTGCTGCTGTTGCTGC TTCTGGGGGTGTCCCTTGGA GGTGCC |

Exemplary Cytokine Sequences

| | | | | |
|---|---|---|---|---|
| IL-15 | 519 | NWVNVISDLKKIEDLIQSMHIDATL YTESDVHPSCKVTAMKCFLLELQVI SLESGDASIHDTVENLIILANNSLSS NGNVTESGCKECEELEEKNIKEFLQ SFVHIVQMFINTS | 520 | AACTGGGTGAATGTGATCA GCGACCTGAAGAAGATCGA GGATCTGATCCAGAGCATG CACATTGATGCCACCCTGTA CACAGAATCTGATGTGCAC CCTAGCTGTAAAGTGACCG CCATGAAGTGTTTTCTGCTG GAGCTGCAGGTGATTTCTCT GGAAAGCGGAGATGCCTCT ATCCACGACACAGTGGAGA ATCTGATCATCCTGGCCAAC AATAGCCTGAGCAGCAATG GCAATGTGACAGAGTCTGG CTGTAAGGAGTGTGAGGAG CTGGAGGAGAAGAACATCA AGGAGTTTCTGCAGAGCTT TGTGCACATCGTGCAGATG TTCATCAATACAAGC |
| IL-15Rα | 521 | ITCPPPMSVEHADIWVKSYSLYSRE RYICNSGFKRKAGTSSLTECVLNKA TNVAHWTTPSLKCIRDPALVHQRP APPSTVTTAGVTPQPESLSPSGKEP AASSPSSNNTAATTAAIVPGSQLM PSKSPSTGTTEISSHESSHGTPSQTT AKNWELTASASHQPPGVYPQGHS | 522 | ATTACATGCCCTCCTCCAAT GTCTGTGGAGCACGCCGAT ATTTGGGTGAAGTCCTACA GCCTGTACAGCAGAGAGAG ATACATCTGCAACAGCGGC TTTAAGAGAAAGGCCGGCA CCTCTTCTCTGACAGAGTGC |

-continued

| | | | | |
|---|---|---|---|---|
| | | DTTVAISTSTVLLCGLSAVSLLACYLK SRQTPPLASVEMEAMEALPVTWG TSSRDEDLENCSHHL | | GTGCTGAATAAGGCCACAA ATGTGGCCCACTGGACAAC ACCTAGCCTGAAGTGCATTA GAGATCCTGCCCTGGTCCA CCAGAGGCCTGCCCCTCCAT CTACAGTGACAACAGCCGG AGTGACACCTCAGCCTGAA TCTCTGAGCCCTTCTGGAAA AGAACCTGCCGCCAGCTCTC CTAGCTCTAATAATACCGCC GCCACAACAGCCGCCATTG TGCCTGGATCTCAGCTGAT GCCTAGCAAGTCTCCTAGCA CAGGCACAACAGAGATCAG CAGCCACGAATCTTCTCACG GAACACCTTCTCAGACCACC GCCAAGAATTGGGAGCTGA CAGCCTCTGCCTCTCACCAG CCTCCAGGAGTGTATCCTCA GGGCCACTCTGATACAACA GTGGCCATCAGCACATCTAC AGTGCTGCTGTGTGGACTG TCTGCCGTGTCTCTGCTGGC CTGTTACCTGAAGTCTAGAC AGACACCTCCTCTGGCCTCT GTGGAGATGGAGGCCATG GAAGCCCTGCCTGTGACAT GGGGAACAAGCAGCAGAG ATGAGGACCTGGAGAATTG TTCTCACCACCTG |
| mbIL15 | 523 | NWVNVISDLKKIEDLIQSMHIDATL YTESDVHPSCKVTAMKCFLLELQVI SLESGDASIHDTVENLIILANNSLSS NGNVTESGCKECEELEEKNIKEFLQ SFVHIVQMFINTSSGGGSGGGGSG GGGSGGGGSGGGSLQITCPPPMS VEHADIWVKSYSLYSRERYICNSGF KRKAGTSSLTECVLNKATNVAHWT TPSLKCIRDPALVHQRPAPPSTVTT AGVTPQPESLSPSGKEPAASSPSSN NTAATTAAIVPGSQLMPSKSPSTGT TEISSHESSHGTPSQTTAKNWELTA SASHQPPGVYPQGHSDTTVAISTST VLLCGLSAVSLLACYLKSRQTPPLAS VEMEAMEALPVTWGTSSRDEDLE NCSHHL | 524 | AACTGGGTGAATGTGATCA GCGACCTGAAGAAGATCGA GGATCTGATCCAGAGCATG CACATTGATGCCACCCTGTA CACAGAATCTGATGTGCAC CCTAGCTGTAAAGTGACCG CCATGAAGTGTTTTCTGCTG GAGCTGCAGGTGATTTCTCT GGAAAGCGGAGATGCCTCT ATCCACGACACAGTGGAGA ATCTGATCATCCTGGCCAAC AATAGCCTGAGCAGCAATG GCAATGTGACAGAGTCTGG CTGTAAGGAGTGTGAGGAG CTGGAGGAGAAGAACATCA AGGAGTTTCTGCAGAGCTT TGTGCACATCGTGCAGATG TTCATCAATACAAGCTCTGG CGGAGGATCTGGAGGAGG CGGATCTGGAGGAGGAGG CAGTGGAGGCGGAGGATCT GGCGGAGGATCTCTGCAGA TTACATGCCCTCCTCCAATG TCTGTGGAGCACGCCGATA TTTGGGTGAAGTCCTACAG CCTGTACAGCAGAGAGAGA TACATCTGCAACAGCGGCTT TAAGAGAAAGGCCGGCACC TCTTCTCTGACAGAGTGCGT GCTGAATAAGGCCACAAAT GTGGCCCACTGGACAACAC CTAGCCTGAAGTGCATTAG AGATCCTGCCCTGGTCCACC AGAGGCCTGCCCCTCCATCT ACAGTGACAACAGCCGGAG TGACACCTCAGCCTGAATCT CTGAGCCCTTCTGGAAAAG AACCTGCCGCCAGCTCTCCT AGCTCTAATAATACCGCCGC CACAACAGCCGCCATTGTG CCTGGATCTCAGCTGATGCC TAGCAAGTCTCCTAGCACA GGCACAACAGAGATCAGCA GCCACGAATCTTCTCACGGA ACACCTTCTCAGACCACCGC CAAGAATTGGGAGCTGACA GCCTCTGCCTCTCACCAGCC TCCAGGAGTGTATCCTCAG |

-continued

| | | | | |
|---|---|---|---|---|
| | | | | GGCCACTCTGATACAACAG<br>TGGCCATCAGCACATCTACA<br>GTGCTGCTGTGTGGACTGT<br>CTGCCGTGTCTCTGCTGGCC<br>TGTTACCTGAAGTCTAGACA<br>GACACCTCCTCTGGCCTCTG<br>TGGAGATGGAGGCCATGGA<br>AGCCCTGCCTGTGACATGG<br>GGAACAAGCAGCAGAGAT<br>GAGGACCTGGAGAATTGTT<br>CTCACCACCTG |
| mbIL15 + IgE signal Peptide | 525 | MDWTWILFLVAAATRVHSNWVN<br>VISDLKKIEDLIQSMHIDATLYTESD<br>VHPSCKVTAMKCFLLELQVISLESG<br>DASIHDTVENLIILANNSLSSNGNVT<br>ESGCKECEELEEKNIKEFLQSFVHIV<br>QMFINTSSGGGSGGGGSGGGGSG<br>GGGSGGGSLQITCPPPMSVEHADI<br>WVKSYSLYSRERYICNSGFKRKAGT<br>SSLTECVLNKATNVAHWTTPSLKCI<br>RDPALVHORPAPPSTVTTAGVTPQ<br>PESLSPSGKEPAASSPSSNNTAATT<br>AAIVPGSQLMPSKSPSTGTTEISSHE<br>SSHGTPSQTTAKNWELTASASHQP<br>PGVYPQGHSDTTVAISTSTVLLCGL<br>SAVSLLACYLKSRQTPPLASVEMEA<br>MEALPVTWGTSSRDEDLENCSHHL | 526 | ATGGATTGGACCTGGATTC<br>TGTTTCTGGTGGCCGCTGCC<br>ACAAGAGTGCACAGCAACT<br>GGGTGAATGTGATCAGCGA<br>CCTGAAGAAGATCGAGGAT<br>CTGATCCAGAGCATGCACA<br>TTGATGCCACCCTGTACACA<br>GAATCTGATGTGCACCCTA<br>GCTGTAAAGTGACCGCCAT<br>GAAGTGTTTTCTGCTGGAG<br>CTGCAGGTGATTTCTCTGGA<br>AAGCGGAGATGCCTCTATC<br>CACGACACAGTGGAGAATC<br>TGATCATCCTGGCCAACAAT<br>AGCCTGAGCAGCAATGGCA<br>ATGTGACAGAGTCTGGCTG<br>TAAGGAGTGTGAGGAGCTG<br>GAGGAGAAGAACATCAAG<br>GAGTTTCTGCAGAGCTTTGT<br>GCACATCGTGCAGATGTTC<br>ATCAATACAAGCTCTGGCG<br>GAGGATCTGGAGGAGGCG<br>GATCTGGAGGAGGAGGCA<br>GTGGAGGCGGAGGATCTG<br>GCGGAGGATCTCTGCAGAT<br>TACATGCCCTCCTCCAATGT<br>CTGTGGAGCACGCCGATAT<br>TTGGGTGAAGTCCTACAGC<br>CTGTACAGCAGAGAGAGAT<br>ACATCTGCAACAGCGGCTTT<br>AAGAGAAAGGCCGGCACCT<br>CTTCTCTGACAGAGTGCGT<br>GCTGAATAAGGCCACAAAT<br>GTGGCCCACTGGACAACAC<br>CTAGCCTGAAGTGCATTAG<br>AGATCCTGCCCTGGTCCACC<br>AGAGGCCTGCCCCTCCATCT<br>ACAGTGACAACAGCCGGAG<br>TGACACCTCAGCCTGAATCT<br>CTGAGCCCTTCTGGAAAAG<br>AACCTGCCGCCAGCTCTCCT<br>AGCTCTAATAATACCGCCGC<br>CACAACAGCCGCCATTGTG<br>CCTGGATCTCAGCTGATGCC<br>TAGCAAGTCTCCTAGCACA<br>GGCACAACAGAGATCAGCA<br>GCCACGAATCTTCTCACGGA<br>ACACCTTCTCAGACCACCGC<br>CAAGAATTGGGAGCTGACA<br>GCCTCTGCCTCTCACCAGCC<br>TCCAGGAGTGTATCCTCAG<br>GGCCACTCTGATACAACAG<br>TGGCCATCAGCACATCTACA<br>GTGCTGCTGTGTGGACTGT<br>CTGCCGTGTCTCTGCTGGCC<br>TGTTACCTGAAGTCTAGACA<br>GACACCTCCTCTGGCCTCTG<br>TGGAGATGGAGGCCATGGA<br>AGCCCTGCCTGTGACATGG<br>GGAACAAGCAGCAGAGAT<br>GAGGACCTGGAGAATTGTT<br>CTCACCACCTG |

Exemplary Linker Sequences

| Linker Name | SEQ ID NO | Amino Acids Sequence | SEQ ID NO | Polynucleotide Sequence |
|---|---|---|---|---|
| Whitlow Linker | 527 | GSTSGSGKPGSGEGSTKG | 528 | GGCAGCACCTCCGGCAGCGG CAAGCCTGGCAGCGGCGAGG GCAGCACCAAGGGC |
| Linker | 529 | SGGGSGGGGSGGGGSGGGGSGG GSLQ | 530 | TCTGGCGGAGGATCTGGAGG AGGCGGATCTGGAGGAGGAG GCAGTGGAGGCGGAGGATCT GGCGGAGGATCTCTGCAG |
| GSG linker | 531 | GSG | 532 | GGAAGCGGA |
| SGSG linker | 533 | SGSG | 534 | AGTGGCAGCGGC |
| (G4S)3 linker | 535 | GGGGSGGGGSGGGGS | 536 | GGTGGCGGTGGCTCGGGCGG TGGTGGGTCGGGTGGCGGCG GATCT |
| Furin cleavage site/Furinlink1 | 537 | RAKR | 538 | CGTGCAAAGCGT |
| Fmdv | 539 | RAKRAPVKQTLNFDLLKLAGDVESN PGP | 540 | AGAGCCAAGAGGGCACCGGT GAAACAGACTTTGAATTTTGA CCTTCTGAAGTTGGCAGGAGA CGTTGAGTCCAACCCTGGGCC C |
| Thosea asigna virus 2A region (T2A) | 541 | EGRGSLLTCGDVEENPGP | 542 | GAGGGCAGAGGAAGTCTGCT AACATGCGGTGACGTCGAGG AGAATCCTGGACCT |
| Furin-GSG-T2A | 543 | RAKRGSGEGRGSLLTCGDVEENPG P | 544 | AGAGCTAAGAGGGGAAGCGG AGAGGGCAGAGGAAGTCTGC TAACATGCGGTGACGTCGAGG AGAATCCTGGACCT |
| Furin-SGSG-T2A | 545 | RAKRSGSGEGRGSLLTCGDVEENP GP | 546 | AGGGCCAAGAGGAGTGGCAG CGGCGAGGGCAGAGGAAGTC TTCTAACATGCGGTGACGTGG AGGAGAATCCCGGCCCT |
| Porcine teschovirus-1 2A region (P2A) | 547 | ATNFSLLKQAGDVEENPGP | 548 | GCAACGAACTTCTCTCTCCTAA AACAGGCTGGTGATGTGGAG GAGAATCCTGGTCCA |
| GSG-P2A | 549 | GSGATNFSLLKQAGDVEENPGP | 550 | GGAAGCGGAGCTACTAACTTC AGCCTGCTGAAGCAGGCTGG AGACGTGGAGGAGAACCCTG GACCT |
| Equine rhinitis A virus 2A region (E2A) | 551 | QCTNYALLKLAGDVESNPGP | 552 | CAGTGTACTAATTATGCTCTCT TGAAATTGGCTGGAGATGTTG AGAGCAACCCTGGACCT |
| Foot-and-mouth disease virus 2A region (F2A) | 553 | VKQTLNFDLLKLAGDVESNPGP | 554 | GTCAAACAGACCCTAAACTTT GATCTGCTAAAACTGGCCGGG GATGTGGAAAGTAATCCCGGC CCC |
| FP2A | 555 | RAKRAPVKQGSGATNFSLLKQAGD VEENPGP | 556 | CGTGCAAAGCGTGCACCGGTG AAACAGGGAAGCGGAGCTAC TAACTTCAGCCTGCTGAAGCA GGCTGGAGACGTGGAGGAGA ACCCTGGACCT |
| Linker-GSG | 557 | APVKQGSG | 558 | GCACCGGTGAAACAGGGAAG CGGA |
| Linker | 559 | GGGGSGGGSGGGGSGGGGS | 560 | GGTGGCGGTGGCTCGGGCGG TGGTGGGTCGGGTGGCGGCG GATCTGGTGGCGGTGGCTCG |
| Linker | 561 | APVKQ | 562 | GCACCGGTGAAACAG |
| Linker | 563 | A(EAAAK)nA (n = 2-5) | 564 | |

Exemplary Cell Tag Sequences

| | SEQ ID NO | Amino Acid Sequence | SEQ ID NO | Polynucleotide Sequence |
|---|---|---|---|---|
| HER1 Domain III | 565 | RKVCNGIGIGEFKDSLSINATNIKHF KNCTSISGDLHILPVAFRGDSFTHTP PLDPQELD ILKTVKEITGFLLIQAWPENRTDLHA FENLEIIRGRTKQHGQFSLAVVSLNI TSLGLRSL KEISDGDVIISGNKNLCYANTINWK KLFGTSGQKTKIISNRGENSCKATG Q | 566 | CGCAAAGTGTGTAACGGAA TAGGTATTGGTGAATTTAA AGACTCACTCTCCATAAATG CTACGAATATTAAACACTTC AAAAACTGCACCTCCATCAG TGGCGATCTCCACATCCTGC CGGTGGCATTTAGGGGTGA CTCCTTCACACATACTCCTC CTCTGGATCCACAGGAACT GGATATTCTGAAAACCGTA AAGGAAATCACAGGGTTTT TGCTGATTCAGGCTTGGCCT GAAAACAGGACGGACCTCC ATGCCTTTGAGAACCTAGA AATCATACGCGGCAGGACC AAGCAACATGGTCAGTTTTC TCTTGCAGTCGTCAGCCTGA ACATAACATCCTTGGGATTA CGCTCCCTCAAGGAGATAA GTGATGGAGATGTGATAAT TTCAGGAAACAAAAATTTGT GCTATGCAAATACAATAAA CTGGAAAAAACTGTTTGGG ACCTCCGGTCAGAAAACCA AAATTATAAGCAACAGAGG TGAAAACAGCTGCAAGGCC ACAGGCCAG |
| HER1 truncated Domain IV | 567 | VCHALCSPEGCWGPEPRDCVS | 568 | GTCTGCCATGCCTTGTGCTC CCCCGAGGGCTGCTGGGGC CCGGAGCCCAGGGACTGCG TCTCT |
| HER1t | 569 | RKVCNGIGIGEFKDSLSINATNIKHF KNCTSISGDLHILPVAFRGDSFTHTP PLDPQELDILKTVKEITGFLLIQAWP ENRTDLHAFENLEIIRGRTKQHGQF SLAVVSLNITSLGLRSLKEISDGDVIIS GNKNLCYANTINWKKLFGTSGQKT KIISNRGENSCKATGQVCHALCSPE GCWGPEPRDCVSCRNVSRGRECV DKCNLLEGEPREFVENSECIQCHPE CLPQAMNITCTGRGPDNCIQCAHY IDGPHCVKTCPAGVMGENNTLVW KYADAGHVCHLCHPNCTYGCTGP GLEGCPTNGPKIPSIATGMVGALLL LLVVALGIGLFM | 570 | CGCAAAGTGTGTAACGGAA TAGGTATTGGTGAATTTAA AGACTCACTCTCCATAAATG CTACGAATATTAAACACTTC AAAAACTGCACCTCCATCAG TGGCGATCTCCACATCCTGC CGGTGGCATTTAGGGGTGA CTCCTTCACACATACTCCTC CTCTGGATCCACAGGAACT GGATATTCTGAAAACCGTA AAGGAAATCACAGGGTTTT TGCTGATTCAGGCTTGGCCT GAAAACAGGACGGACCTCC ATGCCTTTGAGAACCTAGA AATCATACGCGGCAGGACC AAGCAACATGGTCAGTTTTC TCTTGCAGTCGTCAGCCTGA ACATAACATCCTTGGGATTA CGCTCCCTCAAGGAGATAA GTGATGGAGATGTGATAAT TTCAGGAAACAAAAATTTGT GCTATGCAAATACAATAAA CTGGAAAAAACTGTTTGGG ACCTCCGGTCAGAAAACCA AAATTATAAGCAACAGAGG TGAAAACAGCTGCAAGGCC ACAGGCCAGGTCTGCCATG CCTTGTGCTCCCCCGAGGG CTGCTGGGGCCCGGAGCCC AGGGACTGCGTCTCTTGCC GGAATGTCAGCCGAGGCAG GGAATGCGTGGACAAGTGC AACCTTCTGGAGGGTGAGC CAAGGGAGTTTGTGGAGAA CTCTGAGTGCATACAGTGC CACCCAGAGTGCCTGCCTCA GGCCATGAACATCACCTGC ACAGGACGGGGACCAGAC AACTGTATCCAGTGTGCCCA CTACATTGACGGCCCCCACT GCGTCAAGACCTGCCCGGC AGGAGTCATGGGAGAAAAC AACACCCTGGTCTGGAAGT |

-continued

| | SEQ ID NO | Amino Acid Sequence | SEQ ID NO | Polynucleotide Sequence |
|---|---|---|---|---|
| | | | | ACGCAGACGCCGGCCATGT GTGCCACCTGTGCCATCCAA ACTGCACCTACGGATGCACT GGGCCAGGTCTTGAAGGCT GTCCAACGAATGGGCCTAA GATCCCGTCCATCGCCACTG GGATGGTGGGGCCCTCCT CTTGCTGCTGGTGGTGGCC CTGGGGATCGGCCTCTTCAT G |
| HER1t-1 | 571 | RKVCNGIGIGEFKDSLSINATNIKHF KNCTSISGDLHILPVAFRGDSFTHTP PLDPQELDILKTVKEITGFLLIQAWP ENRTDLHAFENLEIIRGRTKQHGQF SLAVVSLNITSLGLRSLKEISDGDVIIS GNKNLCYANTINWKKLFGTSGQKT KIISNRGENSCKATGQVCHALCSPE GCWGPEPRDCVSGGGGSGGGSG GGGSGGGGSFWVLVVVGGVLACY SLLVTVAFIIFWVRSKRS | 572 | CGCAAAGTGTGTAACGGAA TAGGTATTGGTGAATTTAA AGACTCACTCTCCATAAATG CTACGAATATTAAACACTTC AAAAACTGCACCTCCATCAG TGGCGATCTCCACATCCTGC CGGTGGCATTTAGGGGTGA CTCCTTCACACATACTCCTC CTCTGGATCCACAGGAACT GGATATTCTGAAAACCGTA AAGGAAATCACAGGGTTTT TGCTGATTCAGGCTTGGCCT GAAAACAGGACGGACCTCC ATGCCTTTGAGAACCTAGA AATCATACGCGGCAGGACC AAGCAACATGGTCAGTTTTC TCTTGCAGTCGTCAGCCTGA ACATAACATCCTTGGGATTA CGCTCCCTCAAGGAGATAA GTGATGGAGATGTGATAAT TTCAGGAAACAAAAATTTGT GCTATGCAAATACAATAAA CTGGAAAAAACTGTTTGGG ACCTCCGGTCAGAAAACCA AAATTATAAGCAACAGAGG TGAAAACAGCTGCAAGGCC ACAGGCCAGGTCTGCCATG CCTTGTGCTCCCCCGAGGG CTGCTGGGGCCCGGAGCCC AGGGACTGCGTCTCTGGTG GCGGTGGCTCGGGCGGTG GTGGGTCGGGTGGCGGCG GATCTGGTGGCGGTGGCTC GTTTTGGGTGCTGGTGGTG GTTGGTGGAGTCCTGGCTT GCTATAGCTTGCTAGTAACA GTGGCCTTTATTATTTTCTG GGTGAGGAGTAAGAGGAG CTAA |
| FL CD20 | 573 | MTTPRNSVNGTFPAEPMKGPIAM QSGPKPLFRRMSSLVGPTQSFFMR ESKTLGAVQIMNGLFHIALGGLLMI PAGIYAPICVTVWYPLWGGIMYIIS GSLLAATEKNSRKCLVKGKMIMNS LSLFAAISGMILSIMDILNIKISHFLK MESLNFIRAHTPYINIYNCEPANPSE KNSPSTQYCYSIQSLFLGILSVMLIFA FFQELVIAGIVENEWKRTCSRPKSNI VLLSAEEKKEQTIEIKEEVVGLTETSS QPKNEEDIEIIPIQEEEEEETETNFPE PPQDQESSPIENDSSP | 574 | ATGACAACACCCAGAAATT CAGTAAATGGGACTTTCCC GGCAGAGCCAATGAAAGGC CCTATTGCTATGCAATCTGG TCCAAAACCACTCTTCAGGA GGATGTCTTCACTGGTGGG CCCCACGCAAAGCTTCTTCA TGAGGGAATCTAAGACTTT GGGGGCTGTCCAGATTATG AATGGGCTCTTCCACATTGC CCTGGGGGGTCTTCTGATG ATCCCAGCAGGGATCTATG CACCCATCTGTGTGACTGTG TGGTACCCTCTCTGGGGAG GCATTATGTATATTATTTCC GGATCACTCCTGGCAGCAA CGGAGAAAAACTCCAGGAA GTGTTTGGTCAAAGGAAAA ATGATAATGAATTCATTGAG CCTCTTTGCTGCCATTTCTG GAATGATTCTTTCAATCATG GACATACTTAATATTAAAAT TTCCCATTTTTTAAAAATGG AGAGTCTGAATTTTATTAGA GCTCACACACCATATATTAA |

-continued

| | SEQ ID NO | Amino Acid Sequence | SEQ ID NO | Polynucleotide Sequence |
|---|---|---|---|---|
| | | | | CATATACAACTGTGAACCA GCTAATCCCTCTGAGAAAA ACTCCCCATCTACCCAATAC TGTTACAGCATACAATCTCT GTTCTTGGGCATTTTGTCAG TGATGCTGATCTTTGCCTTC TTCCAGGAACTTGTAATAGC TGGCATCGTTGAGAATGAA TGGAAAAGAACGTGCTCCA GACCCAAATCTAACATAGTT CTCCTGTCAGCAGAAGAAA AAAAAGAACAGACTATTGA AATAAAAGAAGAAGTGGTT GGGCTAACTGAAACATCTTC CCAACCAAAGAATGAAGAA GACATTGAAATTATTCCAAT CCAAGAAGAGGAAGAAGA AGAAACAGAGACGAACTTT CCAGAACCTCCCCAAGATCA GGAATCCTCACCAATAGAA AATGACAGCTCTCCT |
| CD20t-1 | 575 | MTTPRNSVNGTFPAEPMKGPIAM QSGPKPLFRRMSSLVGPTQSFFMR ESKTLGAVQIMNGLFHIALGGLLMI PAGIYAPICVTVWYPLWGGIMYIIS GSLLAATEKNSRKCLVKGKMIMNS LSLFAAISGMILSIMDILNIKISHFLK MESLNFIRAHTPYINIYNCEPANPSE KNSPSTQYCYSIQSLFLGILSVMLIFA FFQELVIAGIVENEWKRTCSRPKSNI VLLSAEEKKEQTIEIKEEVVGLTETSS QPKNEEDIE | 576 | ATGACCACACCACGGAACT CTGTGAATGGCACCTTCCCA GCAGAGCCAATGAAGGGAC CAATCGCAATGCAGAGCGG ACCCAAGCCTCTGTTTCGGA GAATGAGCTCCCTGGTGGG CCCAACCCAGTCCTTCTTTA TGAGAGAGTCTAAGACACT GGGCGCCGTGCAGATCATG AACGGACTGTTCCACATCGC CCTGGGAGGACTGCTGATG ATCCCAGCCGGCATCTACGC CCCTATCTGCGTGACCGTGT GGTACCCTCTGTGGGGCGG CATCATGTATATCATCTCCG GCTCTCTGCTGGCCGCCACA GAGAAGAACAGCAGGAAG TGTCTGGTGAAGGGCAAGA TGATCATGAATAGCCTGTCC CTGTTTGCCGCCATCTCTGG CATGATCCTGAGCATCATG GACATCCTGAACATCAAGA TCAGCCACTTCCTGAAGATG GAGAGCCTGAACTTCATCA GAGCCCACACCCCTTACATC AACATCTATAATTGCGAGCC TGCCAACCCATCCGAGAAG AATTCTCCAAGCACACAGTA CTGTTATTCCATCCAGTCTC TGTTCCTGGGCATCCTGTCT GTGATGCTGATCTTTGCCTT CTTTCAGGAGCTGGTCATC GCCGGCATCGTGGAGAACG AGTGGAAGAGGACCTGCAG CCGCCCCAAGTCCAATATCG TGCTGCTGTCCGCCGAGGA GAAGAAGGAGCAGACAATC GAGATCAAGGAGGAGGTG GTGGGCCTGACCGAGACAT CTAGCCAGCCTAAGAATGA GGAGGATATCGAG |

Exemplary Vector Sequences

| | | |
|---|---|---|
| Human EF1A1 Promoter | 577 | GCCGCAATAAAATATCTTTA TTTTCATTACATCTGTGTGTT GGTTTTTTGTGTGAATCGTA ACTAACATACGCTCTCCATC AAAACAAAACGAAACAAAA CAAACTAGCAAAATAGGCT GTCCCCAGTGCAAGTGCAG |

| | | |
|---|---|---|
| | | GTGCCAGAACATTTCTCTAT<br>CGAAGGATCTGCGATCGCT<br>CCGGTGCCCGTCAGTGGGC<br>AGAGCGCACATCGCCCACA<br>GTCCCCGAGAAGTTGGGGG<br>GAGGGGTCGGCAATTGAAC<br>CGGTGCCTAGAGAAGGTGG<br>CGCGGGGTAAACTGGGAAA<br>GTGATGTCGTGTACTGGCTC<br>CGCCTTTTTCCCGAGGGTGG<br>GGGAGAACCGTATATAAGT<br>GCAGTAGTCGCCGTGAACG<br>TTCTTTTTCGCAACGGGTTT<br>GCCGCCAGAACACAG |
| Human CMV immediate Early Promoter | 578 | GTGATGCGGTTTTGGCAGT<br>ACATCAATGGGCGTGGATA<br>GCGGTTTGACTCACGGGGA<br>TTTCCAAGTCTCCACCCCATT<br>GACGTCAATGGGAGTTTGT<br>TTTGGCACCAAAATCAACGG<br>GACTTTCCAAAATGTCGTAA<br>CAACTCCGCCCCATTGACGC<br>AAATGGGCGGTAGGCGTGT<br>ACGGTGGGAGGTCTATATA<br>AGCAGAGCTC |
| ColE1 ORI | 579 | TGTGAGCAAAAGGCCAGCA<br>AAAGGCCAGGAACCGTAAA<br>AAGGCCGCGTTGCTGGCGT<br>TTTTCCATAGGCTCCGCCCC<br>CCTGACGAGCATCACAAAA<br>ATCGACGCTCAAGTCAGAG<br>GTGGCGAAACCCGACAGGA<br>CTATAAAGATACCAGGCGTT<br>TCCCCCTGGAAGCTCCCTCG<br>TGCGCTCTCCTGTTCCGACC<br>CTGCCGCTTACCGGATACCT<br>GTCCGCCTTTCTCCCTTCGG<br>GAAGCGTGGCGCTTTCTCAT<br>AGCTCACGCTGTAGGTATCT<br>CAGTTCGGTGTAGGTCGTTC<br>GCTCCAAGCTGGGCTGTGT<br>GCACGAACCCCCCGTTCAGC<br>CCGACCGCTGCGCCTTATCC<br>GGTAACTATCGTCTTGAGTC<br>CAACCCGGTAAGACACGAC<br>TTATCGCCACTGGCAGCAGC<br>CACTGGTAACAGGATTAGC<br>AGAGCGAGGTATGTAGGCG<br>GTGCTACAGAGTTCTTGAA<br>GTGGTGGCCTAACTACGGC<br>TACACTAGAAGAACAGTATT<br>TGGTATCTGCGCTCTGCTGA<br>AGCCAGTTACCTTCGGAAAA<br>AGAGTTGGTAGCTCTTGATC<br>CGG CAAACAAACCACCG CT<br>GGTAGCGGTGGTTTTTTTGT<br>TTGCAAGCAGCAGATTACG<br>CGCAGAAAAAAAGGATCTC<br>AAGAAGATCCTTTGATCTTT<br>TCTACGGGG |
| Left Transposon Repeat Region | 580 | CTACAGTTGA<br>AGTCGGAAGT<br>TTACATACAC TTAAGTTGGA<br>GTCATTAAAA CTCGTTTTTC<br>AACTACTCCA CAAATTTCTT<br>GTTAACAAAC<br>AATAGTTTTG<br>GCAAGTCAGT<br>TAGGACATCT ACTTTGTGCA<br>TGACACAAGT CATTTTTCCA<br>ACAATTGTTT<br>ACAGACAGAT TATTTCACTT<br>ATAATTCACT GTATCACAAT<br>TCCAGTGGGT<br>CAGAAGTTTA<br>CATACACTAA |

-continued

| | | |
|---|---|---|
| | | GTTGACTGTG CCTTTAAACA GCTTGGAAAA TTCCAGAAAA TGATGTCATG GCTTTAG |
| Right Transposon Repeat Region | 581 | GTGGAAGGCT ACTCGAAATG TTTGACCCAA GTTAAACAAT TTAAAGGCAA TGCTACCAAA TACTAATTGA GTGTATGTTA ACTTCTGACC CACTGGGAAT GTGATGAAAG AAATAAAAGC TGAAATGAAT CATTCTCTCT ACTATTATTC TGATATTTCA CATTCTTAAA ATAAAGTGGT GATCCTAACT GACCTTAAGA CAGGGAATCT TTACTCGGAT TAAATGTCAG GAATTGTGAA AAAGTGAGTT TAAATGTATT TGGCTAAGGT GTATGTAAAC TTCCGACTTC AACTGTAGG |

Exemplary Control Sequences

| miRNA Target | SEQ ID NO | miRNA backbone | DNA sequence of Pri-miRNA |
|---|---|---|---|
| Scrambled control 2 | 582 | miR206, shorter arms | GATGCTACAAGTGGCCCACTTCTGAGATGCGGGCTGCTTCT GGATGACACTGCTTCCCGAGGCATTTCGCCCTATCTGCAAGT ACTATGGATTACTTTGCTAGTGGTGTAGATAGGGTGAAATG TTTCGGCAAGTGCCTCCTCGCTGGCCCCAGGGTACCACCCGG AGCACAGGTTTGGTGACCTT |
| neg. ctl *c.elegans* cel-miR-67 | 583 | miR150 | AGGGACTGGGCCCACGGGGAGGCAGCGTCCCCGAGGCAGC AGCGGCAGCGGCGGCTCCTCTCCCCATGGCCCTGTCACAACC TCCTAGAAAGAGTACTGGGCTCAGACCCTCTTTCAGGCCGTT GTGACAGGGACCTGGGGACCCCGGCACCGGCAGGCCCCAA GGGGTGAGGTGAGCGGGCATTGGGACCTCCCCTCCCTGTAC TC |
| neg. ctl *c.elegans* cel-miR-67 | 584 | miR204 | AGGAGGGTGGGGGTGGAGGCAAGCAGAGGACTTCCTGATC GCGTACCCATGGCTACAGTCTTTCTTCATGTGACTCGTGGAC TTGTACTACACAAAAGTACTGTGAGAATATATGAAGGACAG GCTTTAGTGTAGTATGCGTTCAATTGTCATCACTGGCATCTTT TTTGATCATTGCACCATCATCAAATGCATTGGGATAACCATG AC |
| 210 bp stuffer | 585 | — | GGTAAGTCATGACTCCCTACAATGGACATGATCATAGTAGGT ACTATAAGGCACCTAGCTATACCCTCCTATAGAGAGTTTGAG TCTATTGTAGCAAGTCTTTCTTTTAGGGCCTAGGACTCTTCCC ACTCTCTTCCATCGCCTAAGCTCTAACTCTTCCTTGTAGTAGA AATAAGTCACTTCTAAGGCTGGGACCCTCCTAGACCCTAA |
| Scrambled control 1 | 586 | miR206 | TTAGGATGAGTTGAGATCCCAGTGATCTTCTCGCTAAGAGTT TCCTGCCTGGGCAAGGAGGAAAGATGCTACAAGTGGCCCAC TTCTGAGATGCGGGCTGCTTCTGGATGACACTGCTTCCCGAG GCATTTCGCCCTATCTGCAAGTACTATGGATTACTTTGCTAGT GGTGTAGATAGGGTGAAATGTTTCGGCAAGTGCCTCCTCGC TGGCCCCAGGGTACCACCCGGAGCACAGGTTTGGTGACCTT CTTCCTCATCAGGGCTTTGTGCCAGCAAATGACTCCCTCACC AAGGAAGCAAGAGCCTCTGAATCCCATCTGGGCTCTTCCTGA ACACCCCTATCTCCCCCTCT |

TABLE 14

| Additional Sequences | | | | |
|---|---|---|---|---|
| Name | SEQ ID NO | Amino Acid Sequence | SEQ ID NO | Nucleotide Sequence |
| CAR Sequences | | | | |
| Human ROR1 | 587 | PLLALLAALLLAARGAAAQETELSVS<br>AELVPTSSWNISSELNKDSYLTLDEP<br>MNNITTSLGQTAELHCKVSGNPPP<br>TIRWFKNDAPVVQEPRRLSFRSTIY<br>GSRLRIRNLDTTDTGYFQCVATNG<br>KEVVSSTGVLFVKFGPPPTASPGYS<br>DEYEEDGFCQPYRGIACARFIGNRT<br>VYMESLHMQGEIENQITAAFTMIG<br>TSSHLSDKCSQFAIPSLCHYAFPYCD<br>ETSSVPKPRDLCRDECEILENVLCQT<br>EYIFARSNPMILMRLKLPNCEDLPQ<br>PESPEAANCIRIGIPMADPINKNHK<br>CYNSTGVDYRGTVSVTKSGRQCQP<br>WNSQYPHTHTFTALRFPELNGGHS<br>YCRNPGNQKEAPWCFTLDENFKS<br>DLCDIPACDSKDSKEKNKMEILYILV<br>PSVAIPLAIALLFFFICVCRNNQKSSS<br>APVQRQPKHVRGQNVEMSMLNA<br>YKPKSKAKELPLSAVRFMEELGECA<br>FGKIYKGHLYLPGMDHAQLVAIKTL<br>KDYNNPQQWTEFQQEASLMAEL<br>HHPNIVCLLGAVTQEQPVCMLFEYI<br>NQGDLHEFLIMRSPHSDVGCSSDE<br>DGTVKSSLDHGDFLHIAIQIAAGME<br>YLSSHFFVHKDLAARNILIGEQLHVK<br>ISDLGLSREIYSADYYRVQSKSLLPIR<br>WMPPEAIMYGKFSSDSDIWSFGV<br>VLWEIFSFGLQPYYGFSNQEVIEMV<br>RKRQLLPCSEDCPPRMYSLMTECW<br>NEIPSRRPRFKDIHVRLRSWEGLSS<br>HTSSTTPSGGNATTQTTSLSASPVS<br>NLSNPRYPNYMFPSQGITPQGQIA<br>GFIGPPIPQNQRFIPINGYPIPPGYA<br>AFPAAHYQPTGPPRVIQHCPPPKS<br>RSPSSASGSTSTGHVTSLPSSGSNQ<br>EANIPLLPHMSIPNHPGGMGITVF<br>GNKSQKPYKIDSKQASLLGDANIHG<br>HTESMISAEL | 588 | ATGCACCGGCCGCGCCGCC<br>GCGGGACGCGCCCGCCGCT<br>CCTGGCGCTGCTGGCCGCG<br>CTGCTGCTGGCCGCACGCG<br>GGGCTGCTGCCCAAGAAAC<br>AGAGCTGTCAGTCAGTGCT<br>GAATTAGTGCCTACCTCATC<br>ATGGAACATCTCAAGTGAA<br>CTCAACAAAGATTCTTACCT<br>GACCCTCGATGAACCAATG<br>AATAACATCACCACGTCTCT<br>GGGCCAGACAGCAGAACTG<br>CACTGCAAAGTCTCTGGGA<br>ATCCACCTCCCACCATCCGC<br>TGGTTCAAAAATGATGCTCC<br>TGTGGTCCAGGAGCCCCGG<br>AGGCTCTCCTTTCGGTCCAC<br>CATCTATGGCTCTCGGCTGC<br>GGATTAGAAACCTCGACAC<br>CACAGACACAGGCTACTTCC<br>AGTGCGTGGCAACAAACGG<br>CAAGGAGGTGGTTTCTTCC<br>ACTGGAGTCTTGTTTGTCAA<br>GTTTGGCCCCCCTCCCACTG<br>CAAGTCCAGGATACTCAGA<br>TGAGTATGAAGAAGATGGA<br>TTCTGTCAGCCATACAGAG<br>GGATTGCATGTGCAAGATT<br>TATTGGCAACCGCACCGTCT<br>ATATGGAGTCTTTGCACATG<br>CAAGGGGAAATAGAAAATC<br>AGATCACAGCTGCCTTCACT<br>ATGATTGGCACTTCCAGTCA<br>CTTATCTGATAAGTGTTCTC<br>AGTTCGCCATTCCTTCCCTG<br>TGCCACTATGCCTTCCCGTA<br>CTGCGATGAAACTTCATCCG<br>TCCCAAAGCCCCGTGACTTG<br>TGTCGCGATGAATGTGAAA<br>TCCTGGAGAATGTCCTGTGT<br>CAAACAGAGTACATTTTTGC<br>AAGATCAAATCCCATGATTC<br>TGATGAGGCTGAAACTGCC<br>AAACTGTGAAGATCTCCCCC<br>AGCCAGAGAGCCCAGAAGC<br>TGCGAACTGTATCCGGATT<br>GGAATTCCCATGGCAGATC<br>CTATAAATAAAAATCACAA<br>GTGTTATAACAGCACAGGT<br>GTGGACTACCGGGGGACCG<br>TCAGTGTGACCAAATCAGG<br>GCGCCAGTGCCAGCCATGG<br>AATTCCCAGTATCCCCACAC<br>ACACACTTTCACCGCCCTTC<br>GTTTCCCAGAGCTGAATGG<br>AGGCCATTCCTACTGCCGCA<br>ACCCAGGGAATCAAAAGGA<br>AGCTCCCTGGTGCTTCACCT<br>TGGATGAAAACTTTAAGTCT<br>GATCTGTGTGACATCCCAG<br>CGTGCGATTCAAAGGATTC<br>CAAGGAGAAGAATAAAATG<br>GAAATCCTGTACATACTAGT<br>GCCAAGTGTGGCCATTCCC<br>CTGGCCATTGCTTTACTCTT<br>CTTCTTCATTTGCGTCTGTC<br>GGAATAACCAGAAGTCATC<br>GTCGGCACCAGTCCAGAGG<br>CAACCAAAACACGTCAGAG<br>GTCAAAATGTAGAGATGTC<br>AATGCTGAATGCATATAAA<br>CCCAAGAGCAAGGCTAAAG<br>AGCTACCTCTTTCTGCTGTA |

TABLE 14-continued

| Additional Sequences | | | | |
|---|---|---|---|---|
| Name | SEQ ID NO | Amino Acid Sequence | SEQ ID NO | Nucleotide Sequence |
| | | | | CGCTTTATGGAAGAATTGG |
| | | | | GTGAGTGTGCCTTTGGAAA |
| | | | | AATCTATAAAGGCCATCTCT |
| | | | | ATCTCCCAGGCATGGACCAT |
| | | | | GCTCAGCTGGTTGCTATCAA |
| | | | | GACCTTGAAAGACTATAAC |
| | | | | AACCCCCAGCAATGGACGG |
| | | | | AATTTCAACAAGAAGCCTCC |
| | | | | CTAATGGCAGAACTGCACC |
| | | | | ACCCCAATATTGTCTGCCTT |
| | | | | CTAGGTGCCGTCACTCAGG |
| | | | | AACAACCTGTGTGCATGCTT |
| | | | | TTTGAGTATATTAATCAGGG |
| | | | | GGATCTCCATGAGTTCCTCA |
| | | | | TCATGAGATCCCCACACTCT |
| | | | | GATGTTGGCTGCAGCAGTG |
| | | | | ATGAAGATGGGACTGTGAA |
| | | | | ATCCAGCCTGGACCACGGA |
| | | | | GATTTTCTGCACATTGCAAT |
| | | | | TCAGATTGCAGCTGGCATG |
| | | | | GAATACCTGTCTAGTCACTT |
| | | | | CTTTGTCCACAAGGACCTTG |
| | | | | CAGCTCGCAATATTTTAATC |
| | | | | GGAGAGCAACTTCATGTAA |
| | | | | AGATTTCAGACTTGGGGCT |
| | | | | TTCCAGAGAAATTTACTCCG |
| | | | | CTGATTACTACAGGGTCCA |
| | | | | GAGTAAGTCCTTGCTGCCC |
| | | | | ATTCGCTGGATGCCCCCTGA |
| | | | | AGCCATCATGTATGGCAAA |
| | | | | TTCTCTTCTGATTCAGATAT |
| | | | | CTGGTCCTTTGGGGTTGTCT |
| | | | | TGTGGGAGATTTTCAGTTTT |
| | | | | GGACTCCAGCCATATTATG |
| | | | | GATTCAGTAACCAGGAAGT |
| | | | | GATTGAGATGGTGAGAAAA |
| | | | | CGGCAGCTCTTACCATGCTC |
| | | | | TGAAGACTGCCCACCCAGA |
| | | | | ATGTACAGCCTCATGACAG |
| | | | | AGTGCTGGAATGAGATTCC |
| | | | | TTCTAGGAGACCAAGATTTA |
| | | | | AAGATATTCACGTCCGGCTT |
| | | | | CGGTCCTGGGAGGGACTCT |
| | | | | CAAGTCACACAAGCTCTACT |
| | | | | ACTCCTTCAGGGGGAAATG |
| | | | | CCACCACACAGACAACCTCC |
| | | | | CTCAGTGCCAGCCCAGTGA |
| | | | | GTAATCTCAGTAACCCCAGA |
| | | | | TATCCTAATTACATGTTCCC |
| | | | | GAGCCAGGGTATTACACCA |
| | | | | CAGGGCCAGATTGCTGGTT |
| | | | | TCATTGGCCCGCCAATACCT |
| | | | | CAGAACCAGCGATTCATTCC |
| | | | | CATCAATGGATACCCAATAC |
| | | | | CTCCTGGATATGCAGCGTTT |
| | | | | CCAGCTGCCCACTACCAGCC |
| | | | | AACAGGTCCTCCCAGAGTG |
| | | | | ATTCAGCACTGCCCACCTCC |
| | | | | CAAGAGTCGGTCCCCAAGC |
| | | | | AGTGCCAGTGGGTCGACTA |
| | | | | GCACTGGCCATGTGACTAG |
| | | | | CTTGCCCTCATCAGGATCCA |
| | | | | ATCAGGAAGCAAATATTCCT |
| | | | | TTACTACCACACATGTCAAT |
| | | | | TCCAAATCATCCTGGTGGAA |
| | | | | TGGGTATCACCGTTTTTGGC |
| | | | | AACAAATCTCAAAAACCCTA |
| | | | | CAAAATTGACTCAAAGCAA |
| | | | | GCATCTTTACTAGGAGACG |
| | | | | CCAATATTCATGGACACACC |
| | | | | GAATCTATGATTTCTGCAGA |
| | | | | ACTG |

TABLE 14-continued

| Additional Sequences | | | | |
|---|---|---|---|---|
| Name | SEQ ID NO | Amino Acid Sequence | SEQ ID NO | Nucleotide Sequence |
| Human ROR1 (1-437) | 589 | MHRPRRRGTRPPLLALLAALLLAAR<br>GAAAQETELSVSAELVPTSSWNISS<br>ELNKDSYLTLDEPMNNITTSLGQTA<br>ELHCKVSGNPPPTIRWFKNDAPVV<br>QEPRRLSFRSTIYGSRLRIRNLDTTD<br>TGYFQCVATNGKEVVSSTGVLFVK<br>FGPPPTASPGYSDEYEEDGFCQPYR<br>GIACARFIGNRTVYMESLHMQGEI<br>ENQITAAFTMIGTSSHLSDKCSQFA<br>IPSLCHYAFPYCDETSSVPKPRDLCR<br>DECEILENVLCQTEYIFARSNPMIL<br>MRLKLPNCEDLPQPESPEAANCIRI<br>GIPMADPINKNHKCYNSTGVDYRG<br>TVSVTKSGRQCQPWNSQYPHTHT<br>FTALRFPELNGGHSYCRNPGNQKE<br>APWCFTLDENFKSDLCDIPACDSKD<br>SKEKNKMEILYILVPSVAIPLAIALLF<br>FFICVCRNNQKSSSA | 590 | ATGCACCGGCCGCGCCGCC<br>GCGGGACGCGCCCGCCGCT<br>CCTGGCGCTGCTGGCCGCG<br>CTGCTGCTGGCCGCACGCG<br>GGGCTGCTGCCCAAGAAAC<br>AGAGCTGTCAGTCAGTGCT<br>GAATTAGTGCCTACCTCATC<br>ATGGAACATCTCAAGTGAA<br>CTCAACAAAGATTCTTACCT<br>GACCCTCGATGAACCAATG<br>AATAACATCACCACGTCTCT<br>GGGCCAGACAGCAGAACTG<br>CACTGCAAAGTCTCTGGGA<br>ATCCACCTCCCACCATCCGC<br>TGGTTCAAAAATGATGCTCC<br>TGTGGTCCAGGAGCCCCGG<br>AGGCTCTCCTTTCGGTCCAC<br>CATCTATGGCTCTCGGCTGC<br>GGATTAGAAACCTCGACAC<br>CACAGACACAGGCTACTTCC<br>AGTGCGTGGCAACAAACGG<br>CAAGGAGGTGGTTTCTTCC<br>ACTGGAGTCTTGTTTGTCAA<br>GTTTGGCCCCCCTCCCACTG<br>CAAGTCCAGGATACTCAGA<br>TGAGTATGAAGAAGATGGA<br>TTCTGTCAGCCATACAGAG<br>GGATTGCATGTGCAAGATT<br>TATTGGCAACCGCACCGTCT<br>ATATGGAGTCTTTGCACATG<br>CAAGGGGAAATAGAAAATC<br>AGATCACAGCTGCCTTCACT<br>ATGATTGGCACTTCCAGTCA<br>CTTATCTGATAAGTGTTCTC<br>AGTTCGCCATTCCTTCCCTG<br>TGCCACTATGCCTTCCCGTA<br>CTGCGATGAAACTTCATCCG<br>TCCCAAAGCCCCGTGACTTG<br>TGTCGCGATGAATGTGAAA<br>TCCTGGAGAATGTCCTGTGT<br>CAAACAGAGTACATTTTTGC<br>AAGATCAAATCCCATGATTC<br>TGATGAGGCTGAAACTGCC<br>AAACTGTGAAGATCTCCCCC<br>AGCCAGAGAGCCCAGAAGC<br>TGCGAACTGTATCCGGATT<br>GGAATTCCCATGGCAGATC<br>CTATAAATAAAAATCACAA<br>GTGTTATAACAGCACAGGT<br>GTGGACTACCGGGGGACCG<br>TCAGTGTGACCAAATCAGG<br>GCGCCAGTGCCAGCCATGG<br>AATTCCCAGTATCCCCACAC<br>ACACACTTTCACCGCCCTTC<br>GTTTCCCAGAGCTGAATGG<br>AGGCCATTCCTACTGCCGCA<br>ACCCAGGGAATCAAAAGGA<br>AGCTCCCTGGTGCTTCACCT<br>TGGATGAAAACTTTAAGTCT<br>GATCTGTGTGACATCCCAG<br>CGTGCGATTCAAAGGATTC<br>CAAGGAGAAGAATAAAATG<br>GAAATCCTGTACATACTAGT<br>GCCAAGTGTGGCCATTCCC<br>CTGGCCATTGCTTTACTCTT<br>CTTCTTCATTTGCGTCTGTC<br>GGAATAACCAGAAGTCATC<br>GTCGGCA |

TABLE 14-continued

| Additional Sequences | | | | |
|---|---|---|---|---|
| Name | SEQ ID NO | Amino Acid Sequence | SEQ ID NO | Nucleotide Sequence |
| Murine ROR1 (VL-VH). IgG4 Fc-CD28m-Z | 591 | DIKMTQSPSSMYASLGERVTITCKA SPDINSYLSWFQQKPGKSPKTLIYR ANRLVDGVPSRFSGGGSGQDYSLT INSLEYEDMGIYYCLQYDEFPYTFG GGTKLEMKGSTSGSGKPGSGEGST KGEVKLVESGGGLVKPGGSLKLSCA ASGFTFSSYAMSWVRQIPEKRLEW VASISRGGTTYYPDSVKGRFTISRD NVRNILYLQMSSLRSEDTAMYYCG RYDYDGYYAMDYWGQGTSVTVSS ESKYGPPCPPCPAPEFEGGPSVFLF PPKPKDTLMISRTPEVTCVVVDVSQ EDPEVQFNWYVDGVEVHNAKTKP REEQFQSTYRVVSVLTVLHQDWLN GKEYKCKVSNKGLPSSIEKTISKAKG QPREPQVYTLPPSQEEMTKNQVSL TCLVKGFYPSDIAVEWESNGQPEN NYKTTPPVLDSDGSFFLYSRLTVDKS QKSLSLSLGKMFWVLVVVGGVLAC YSLLVTVAFIIFWVRSKRSRGGHSD YMNMTPRRPGPTRKHYQPYAPPR DFAAYRSRVKFSRSADAPAYQQGQ NCILYNELNLGRREEYDVLDKRRGR DPEMGGKPRRKNPQEGLYNELQK DKMAEAYSEIGMKGERRRGKGHD GLYQGLSTATKDTYDALHMQALPP R | 592 | GACATCAAGATGACCCAGA GCCCCAGCTCTATGTACGCC AGCCTGGGCGAGCGCGTGA CCATCACATGCAAGGCCAG CCCCGACATCAACAGCTACC TGTCCTGGTTCCAGCAGAA GCCCGGCAAGAGCCCCAAG ACCCTGATCTACCGGGCCA ACCGGCTGGTGGACGGCGT GCCAAGCAGATTTTCCGGC GGAGGCAGCGGCCAGGAC TACAGCCTGACCATCAACA GCCTGGAATACGAGGACAT GGGCATCTACTACTGCCTGC AGTACGACGAGTTCCCCTAC ACCTTCGGAGGCGGCACCA AGCTGGAAATGAAGGGCA GCACCTCCGGCAGCGGCAA GCCTGGCAGCGGCGAGGG CAGCACCAAGGGCGAAGTG AAGCTGGTGGAAAGCGGC GGAGGCCTGGTGAAACCTG CTGCGCCGCCAGCGGCTTC ACCTTCAGCAGCTACGCCAT GAGCTGGGTCCGACAGATC CCCGAGAAGCGGCTGGAAT GGGTGGCCAGCATCAGCAG GGGCGGCACCACCTACTAC CCCGACAGCGTGAAGGGCC GGTTCACCATCAGCCGGGA CAACGTGCGGAACATCCTG TACCTGCAGATGAGCAGCC TGCGGAGCGAGGACACCGC CATGTACTACTGCGGCAGA TACGACTACGACGGCTACT ACGCCATGGATTACTGGGG CCAGGGCACCAGCGTGACC GTGTCTAGCGAGAGCAAGT ACGGCCCTCCCTGCCCCCCT TGCCCTGCCCCCGAGTTCGA GGGCGGACCCAGCGTGTTC CTGTTCCCCCCCAAGCCCAA GGACACCCTGATGATCAGC CGGACCCCCGAGGTGACCT GTGTGGTGGTGGACGTGTC CCAGGAGGACCCCGAGGTC CAGTTCAACTGGTACGTGG ACGGCGTGGAGGTGCACAA CGCCAAGACCAAGCCCCGG GAGGAGCAGTTCCAGAGCA CCTACCGGGTGGTGTCCGT GCTGACCGTGCTGCACCAG GACTGGCTGAACGGCAAGG AATACAAGTGTAAGGTGTC CAACAAGGGCCTGCCCAGC AGCATCGAGAAAACCATCA GCAAGGCCAAGGGCCAGCC TCGGGAGCCCCAGGTGTAC ACCCTGCCCCCTAGCCAAGA GGAGATGACCAAGAATCAG GTGTCCCTGACCTGCCTGGT GAAGGGCTTCTACCCCAGC GACATCGCCGTGGAGTGGG AGAGCAACGGCCAGCCCGA GAACAACTACAAGACCACC CCCCCTGTGCTGGACAGCG ACGGCAGCTTCTTCCTGTAC AGCAGGCTGACCGTGGACA AGAGCCGGTGGCAGGAGG GCAACGTCTTTAGCTGCTCC GTGATGCACGAGGCCCTGC ACAACCACTACACCCAGAA GAGCCTGTCCCTGAGCCTG GGCAAGATGTTCTGGGTGC |

TABLE 14-continued

| Additional Sequences | | | | |
|---|---|---|---|---|
| Name | SEQ ID NO | Amino Acid Sequence | SEQ ID NO | Nucleotide Sequence |
| | | | | TGGTCGTGGTGGGTGGCGT GCTGGCCTGCTACAGCCTG CTGGTGACAGTGGCCTTCA TCATCTTTTGGGTGAGGAG CAAGCGGAGCAGAGGCGG CCACAGCGACTACATGAAC ATGACCCCCCGGAGGCCTG GCCCCACCCGGAAGCACTA CCAGCCCTACGCCCCTCCCA GGGACTTCGCCGCCTACCG GAGCCGGGTGAAGTTCAGC CGGAGCGCCGACGCCCCTG CCTACCAGCAGGGCCAGAA CCAGCTGTACAACGAGCTG AACCTGGGCCGGAGGGAG GAGTACGACGTGCTGGACA AGCGGAGAGGCCGGGACC CTGAGATGGGCGGCAAGCC CCGGAGAAAGAACCCTCAG GAGGGCCTGTATAACGAAC TGCAGAAAGACAAGATGGC CGAGGCCTACAGCGAGATC GGCATGAAGGGCGAGCGG CGGAGGGGCAAGGGCCAC GACGGCCTGTACCAGGGCC TGAGCACCGCCACCAAGGA TACCTACGACGCCCTGCACA TGCAGGCCCTGCCCCCCAG A |
| Murine ROR1 (VL-VH). IgG4 Fcm-CD28m-Z | 593 | DIKMTQSPSSMYASLGERVTITCKA SPDINSYLSWFQQKPGKSPKTLIYR ANRLVDGVPSRFSGGGSGQDYSLT INSLEYEDMGIYYCLQYDEFPYTFG GGTKLEMKGSTSGSGKPGSGEGST KGEVKLVESGGGLVKPGGSLKLSCA ASGFTFSSYAMSWVRQIPEKRLEW VASISRGGTTYYPDSVKGRFTISRD NVRNILYLQMSSLRSEDTAMYYCG RYDYDGYYAMDYWGQGTSVTVSS QGTSVTVSSESKYGPPCPPCPAPEF LGGPSVFLFPPKPKDTLMISRTPEVT CVVVDVSQEDPEVQFNWYVDGVE VHNAKTKPREEQFNSTYRVVSVLT VLHQDWLNGKEYKCKVSNKGLPSS IEKTISKAKGQPREPQVYTLPPSQEE MTKNQVSLTCLVKGFYPSDIAVEW ESNGQPENNYKTTPPVLDSDGSFFL YSRLTVDKSRWQEGNVFSCSVMH EALHNHYTQKSLSLSLGKMFWVLV VVGGVLACYSLLVTVAFIIFWVRSK RSRGGHSDYMNMTPRRPGPTRKH YQPYAPPRDFAAYRSRVKFSRSAD APAYQQGQNQLYNELNLGRREEY DVLDKRRGRDPEMGGKPRRKNPQ EGLYNELQKDKMAEAYSEIGMKGE RRRGKGHDGLYQGLSTATKDTYDA LHMQALPPR | 594 | GACATCAAGATGACCCAGA GCCCCAGCTCTATGTACGCC AGCCTGGGCGAGCGCGTGA CCATCACATGCAAGGCCAG CCCCGACATCAACAGCTACC TGTCCTGGTTCCAGCAGAA GCCCGGCAAGAGCCCCAAG ACCCTGATCTACCGGGCCA ACCGGCTGGTGGACGGCGT GCCAAGCAGATTTTCCGGC GGAGGCAGCGGCCAGGAC TACAGCCTGACCATCAACA GCCTGGAATACGAGGACAT GGGCATCTACTACTGCCTGC AGTACGACGAGTTCCCCTAC ACCTTCGGAGGCGGCACCA AGCTGGAAATGAAGGGCA GCACCAGCGGCAGCGGCAA GCCTGGAAGCGGCGAGGG CTCCACCAAGGGCGAAGTG AAGCTGGTGGAAAGCGGC GGAGGCCTGGTGAAACCTG GCGGCAGCCTGAAGCTGAG CTGCGCCGCCAGCGGCTTC ACCTTCAGCAGCTACGCCAT GAGCTGGGTCCGACAGATC CCCGAGAAGCGGCTGGAAT GGGTGGCCAGCATCAGCAG GGGCGGCACCACCTACTAC CCCGACAGCGTGAAGGGCC GGTTCACCATCAGCCGGGA CAACGTGCGGAACATCCTG TACCTGCAGATGAGCAGCC TGCGGAGCGAGGACACCGC CATGTACTACTGCGGCAGA TACGACTACGACGGCTACT ACGCCATGGATTACTGGGG CCAGGGCACCAGCGTGACC GTGTCTAGCCAGGGAACCT CCGTGACAGTGTCCAGCGA GTCCAAATATGGTCCCCCAT GCCCACCATGCCCAGCACCT GAGTTCCTGGGGGGACCAT CAGTCTTCCTGTTCCCCCCA AAACCCAAGGACACTCTCAT |

TABLE 14-continued

Additional Sequences

| Name | SEQ ID NO | Amino Acid Sequence | SEQ ID NO | Nucleotide Sequence |
| --- | --- | --- | --- | --- |
| | | | | GATCTCCCGGACCCCTGAG GTCACGTGCGTGGTGGTGG ACGTGAGCCAGGAAGACCC CGAGGTCCAGTTCAACTGG TACGTGGATGGCGTGGAGG TGCATAATGCCAAGACAAA GCCCCGGGAGGAGCAGTTC AATAGCACCTACCGGGTGG TGTCCGTGCTGACCGTGCT GCACCAGGACTGGCTGAAC GGCAAGGAATACAAGTGTA AGGTGTCCAACAAGGGCCT GCCCAGCAGCATCGAGAAA ACCATCAGCAAGGCCAAGG GCCAGCCTCGGGAGCCCCA GGTGTACACCCTGCCCCCTA GCCAAGAGGAGATGACCAA GAATCAGGTGTCCCTGACC TGCCTGGTGAAGGGCTTCT ACCCCAGCGACATCGCCGT GGAGTGGGAGAGCAACGG CCAGCCCGAGAACAACTAC AAGACCACCCCCCCTGTGCT GGACAGCGACGGCAGCTTC TTCCTGTACAGCAGGCTGA CCGTGGACAAGAGCCGGTG GCAGGAGGGCAACGTCTTT AGCTGCTCCGTGATGCACG AGGCCCTGCACAACCACTA CACCCAGAAGAGCCTGTCC CTGAGCCTGGGCAAGATGT TCTGGGTGCTGGTCGTGGT GGGTGGCGTGCTGGCCTGC TACAGCCTGCTGGTGACAG TGGCCTTCATCATCTTTTGG GTGAGGAGCAAGCGGAGC AGAGGCGGCCACAGCGACT ACATGAACATGACCCCCCG GAGGCCTGGCCCCACCCGG AAGCACTACCAGCCCTACG CCCCTCCCAGGGACTTCGCC GCCTACCGGAGCCGGGTGA AGTTCAGCCGGAGCGCCGA CGCCCCTGCCTACCAGCAG GGCCAGAACCAGCTGTACA ACGAGCTGAACCTGGGCCG GAGGGAGGAGTACGACGT GCTGGACAAGCGGAGAGG CCGGGACCCTGAGATGGGC GGCAAGCCCCGGAGAAAG AACCCTCAGGAGGGCCTGT ATAACGAACTGCAGAAAGA CAAGATGGCCGAGGCCTAC AGCGAGATCGGCATGAAGG GCGAGCGGCGGAGGGGCA AGGGCCACGACGGCCTGTA CCAGGGCCTGAGCACCGCC ACCAAGGATACCTACGACG CCCTGCACATGCAGGCCCT GCCCCCCAGA |
| Murine ROR1 (VL-VH). CD8α. CD28z | 595 | DIKMTQSPSSMYASLGERVTITCKA SPDINSYLSWFQQKPGKSPKTLIYR ANRLVDGVPSRFSGGGSGQDYSLT INSLEYEDMGIYYCLQYDEFPYTFG GGTKLEMKGSTSGSGKPGSGEGST KGEVKLVESGGGLVKPGGSLKLSCA ASGFTFSSYAMSWVRQIPEKRLEW VASISRGGTTYYPDSVKGRFTISRD NVRNILYLQMSSLRSEDTAMYYCG RYDYDGYYAMDYWGQGTSVTVSS KPTTTPAPRPPTPAPTIASQPLSLRP EACRPAAGGAVHTRGLDFACDIYI WAPLAGTCGVLLLSLVITLYCNHRN RSKRSRGGHSDYMNMTPRRPGPT | 596 | GACATCAAGATGACCCAGA GCCCCAGCTCTATGTACGCC AGCCTGGGCGAGCGCGTGA CCATCACATGCAAGGCCAG CCCCGACATCAACAGCTACC TGTCCTGGTTCCAGCAGAA GCCCGGCAAGAGCCCCAAG ACCCTGATCTACCGGGCCA ACCGGCTGGTGGACGGCGT GCCAAGCAGATTTTCCGGC GGAGGCAGCGGCCAGGAC TACAGCCTGACCATCAACA GCCTGGAATACGAGGACAT GGGCATCTACTACTGCCTGC |

TABLE 14-continued

| Additional Sequences | | | | |
|---|---|---|---|---|
| Name | SEQ ID NO | Amino Acid Sequence | SEQ ID NO | Nucleotide Sequence |
| | | RKHYQPYAPPRDFAAYRSRVKFSRS ADAPAYQQGQNQLYNELNLGRRE EYDVLDKRRGRDPEMGGKPRRKN PQEGLYNELQKDKMAEAYSEIGMK GERRRGKGHDGLYQGLSTATKDTY DALHMQALPPR | | AGTACGACGAGTTCCCCTAC ACCTTCGGAGGCGGCACCA AGCTGGAAATGAAGGGCA GCACCTCCGGCAGCGGCAA GCCTGGCAGCGGCGAGGG CAGCACCAAGGGCGAAGTG AAGCTGGTGGAAAGCGGC GGAGGCCTGGTGAAACCTG GCGGCAGCCTGAAGCTGAG CTGCGCCGCCAGCGGCTTC ACCTTCAGCAGCTACGCCAT GAGCTGGGTCCGACAGATC CCCGAGAAGCGGCTGGAAT GGGTGGCCAGCATCAGCAG GGGCGGCACCACCTACTAC CCCGACAGCGTGAAGGGCC GGTTCACCATCAGCCGGGA CAACGTGCGGAACATCCTG TACCTGCAGATGAGCAGCC TGCGGAGCGAGGACACCGC CATGTACTACTGCGGCAGA TACGACTACGACGGCTACT ACGCCATGGATTACTGGGG CCAGGGCACCAGCGTGACC GTGTCTAGCAAGCCCACCA CCACCCCTGCCCCTAGACCT CCAACCCCAGCCCCTACAAT CGCCAGCCAGCCCCTGAGC CTGAGGCCCGAAGCCTGTA GACCTGCCGCTGGCGGAGC CGTGCACACCAGAGGCCTG GATTTCGCCTGCGACATCTA CATCTGGGCCCCTCTGGCC GGCACCTGTGGCGTGCTGC TGCTGAGCCTGGTCATCACC CTGTACTGCAACCACCGGA ATAGGAGCAAGCGGAGCA GAGGCGGCCACAGCGACTA CATGAACATGACCCCCCGG AGGCCTGGCCCCACCCGGA AGCACTACCAGCCCTACGCC CCTCCCAGGGACTTCGCCG CCTACCGGAGCCGGGTGAA GTTCAGCCGGAGCGCCGAC GCCCCTGCCTACCAGCAGG GCCAGAACCAGCTGTACAA CGAGCTGAACCTGGGCCGG AGGGAGGAGTACGACGTG CTGGACAAGCGGAGAGGCC GGGACCCTGAGATGGGCG GCAAGCCCCGGAGAAAGAA CCCTCAGGAGGGCCTGTAT AACGAACTGCAGAAAGACA AGATGGCCGAGGCCTACAG CGAGATCGGCATGAAGGGC GAGCGGCGGAGGGGCAAG GGCCACGACGGCCTGTACC AGGGCCTGAGCACCGCCAC CAAGGATACCTACGACGCC CTGCACATGCAGGCCCTGC CCCCCAGA |
| Murine ROR1 (VL-VH). CD8α(2x). CD28z | 597 | DIKMTQSPSSMYASLGERVTITCKA SPDINSYLSWFQQKPGKSPKTLIYR ANRLVDGVPSRFSGGGSGQDYSLT INSLEYEDMGIYYCLQYDEFPYTFG GGTKLEMKGSTSGSGKPGSGEGST KGEVKLVESGGGLVKPGGSLKLSCA ASGFTFSSYAMSWVRQIPEKRLEW VASISRGGTTYYPDSVKGRFTISRD NVRNILYLQMSSLRSEDTAMYYCG RYDYDGYYAMDYWGQGTSVTVSS KPTTTPAPRPPTPAPTIASQPLSLRP EASRPAAGGAVHTRGLDFASDKPT TTPAPRPPTPAPTIASQPLSLRPEAC | 598 | GACATCAAGATGACCCAGA GCCCCAGCTCTATGTACGCC AGCCTGGGCGAGCGCGTGA CCATCACATGCAAGGCCAG CCCCGACATCAACAGCTACC TGTCCTGGTTCCAGCAGAA GCCCGGCAAGAGCCCCAAG ACCCTGATCTACCGGGCCA ACCGGCTGGTGGACGGCGT GCCAAGCAGATTTTCCGGC GGAGGCAGCGGCCAGGAC TACAGCCTGACCATCAACA GCCTGGAATACGAGGACAT |

TABLE 14-continued

| Additional Sequences | | | | |
|---|---|---|---|---|
| Name | SEQ ID NO | Amino Acid Sequence | SEQ ID NO | Nucleotide Sequence |
| | | RPAAGGAVHTRGLDFACDIYIWAP LAGTCGVLLLSLVITLYCNHRNRSKR SRGGHSDYMNMTPRRPGPTRKHY QPYAPPRDFAAYRSRVKFSRSADA PAYQQGQNQLYNELNLGRREEYD VLDKRRGRDPEMGGKPRRKNPQE GLYNELQKDKMAEAYSEIGMKGER RRGKGHDGLYQGLSTATKDTYDAL HMQALPPR | | GGGCATCTACTACTGCCTGC AGTACGACGAGTTCCCCTAC ACCTTCGGAGGCGGCACCA AGCTGGAAATGAAGGGCA GCACCTCCGGCAGCGGCAA GCCTGGCAGCGGCGAGGG CAGCACCAAGGGCGAAGTG AAGCTGGTGGAAAGCGGC GGAGGCCTGGTGAAACCTG GCGGCAGCCTGAAGCTGAG CTGCGCCGCCAGCGGCTTC ACCTTCAGCAGCTACGCCAT GAGCTGGGTCCGACAGATC CCCGAGAAGCGGCTGGAAT GGGTGGCCAGCATCAGCAG GGGCGGCACCACCTACTAC CCCGACAGCGTGAAGGGCC GGTTCACCATCAGCCGGGA CAACGTGCGGAACATCCTG TACCTGCAGATGAGCAGCC TGCGGAGCGAGGACACCGC CATGTACTACTGCGGCAGA TACGACTACGACGGCTACT ACGCCATGGATTACTGGGG CCAGGGCACCAGCGTGACC GTGTCTAGCAAACCTACTAC AACTCCTGCCCCCCGGCCTC CTACACCAGCTCCTACTATC GCCTCCCAGCCACTCAGTCT CAGACCCGAGGCTTCTAGG CCAGCGGCCGGAGGCGCG GTCCACACCCGCGGGCTGG ACTTTGCATCCGATAAGCCC ACCACCACCCCTGCCCCTAG ACCTCCAACCCCAGCCCCTA CAATCGCCAGCCAGCCCCT GAGCCTGAGGCCCGAAGCC TGTAGACCTGCCGCTGGCG GAGCCGTGCACACCAGAGG CCTGGATTTCGCCTGCGACA TCTACATCTGGGCCCCTCTG GCCGGCACCTGTGGCGTGC TGCTGCTGAGCCTGGTCATC ACCCTGTACTGCAACCACCG GAATAGGAGCAAGCGGAG CAGAGGCGGCCACAGCGAC TACATGAACATGACCCCCCG GAGGCCTGGCCCCACCCGG AAGCACTACCAGCCCTACG CCCCTCCCAGGGACTTCGCC GCCTACCGGAGCCGGGTGA AGTTCAGCCGGAGCGCCGA CGCCCCTGCCTACCAGCAG GGCCAGAACCAGCTGTACA ACGAGCTGAACCTGGGCCG GAGGGAGGAGTACGACGT GCTGGACAAGCGGAGAGG CCGGGACCCTGAGATGGGC GGCAAGCCCCGGAGAAAG AACCCTCAGGAGGGCCTGT ATAACGAACTGCAGAAAGA CAAGATGGCCGAGGCCTAC AGCGAGATCGGCATGAAGG GCGAGCGGCGGAGGGGCA AGGGCCACGACGGCCTGTA CCAGGGCCTGAGCACCGCC ACCAAGGATACCTACGACG CCCTGCACATGCAGGCCCT GCCCCCCAGA |

TABLE 14-continued

| Additional Sequences | | | | |
|---|---|---|---|---|
| Name | SEQ ID NO | Amino Acid Sequence | SEQ ID NO | Nucleotide Sequence |
| Murine ROR1 (VL-VH). CD8a(3x). CD28z | 599 | DIKMTQSPSSMYASLGERVTITCKA SPDINSYLSWFQQKPGKSPKTLIYR ANRLVDGVPSRFSGGGSGQDYSLT INSLEYEDMGIYYCLQYDEFPYTFG GGTKLEMKGSTSGSGKPGSGEGST KGEVKLVESGGGLVKPGGSLKLSCA ASGFTFSSYAMSWVRQIPEKRLEW VASISRGGTTYYPDSVKGRFTISRD NVRNILYLQMSSLRSEDTAMYYCG RYDYDGYYAMDYWGQGTSVTVSS KPTTTPAPRPPTPAPTIASQPLSLRP EASRPAAGGAVHTRGLDFASDKPT TTPAPRPPTPAPTIASQPLSLRPEAS RPAAGGAVHTRGLDFASDKPTTTP APRPPTPAPTIASQPLSLRPEACRPA AGGAVHTRGLDFACDIYIWAPLAG TCGVLLLSLVITLYCNHRNRSKRSRG GHSDYMNMTPRRPGPTRKHYQPY APPRDFAAYRSRVKFSRSADAPAY QQGQNQLYNELNLGRREEYDVLD KRRGRDPEMGGKPRRKNPQEGLY NELQKDKMAEAYSEIGMKGERRR GKGHDGLYQGLSTATKDTYDALH MQALPPR | 600 | GACATCAAGATGACCCAGA GCCCCAGCTCTATGTACGCC AGCCTGGGCGAGCGCGTGA CCATCACATGCAAGGCCAG CCCCGACATCAACAGCTACC TGTCCTGGTTCCAGCAGAA GCCCGGCAAGAGCCCCAAG ACCCTGATCTACCGGGCCA ACCGGCTGGTGGACGGCGT GCCAAGCAGATTTTCCGGC GGAGGCAGCGGCCAGGAC TACAGCCTGACCATCAACA GCCTGGAATACGAGGACAT GGGCATCTACTACTGCCTGC AGTACGACGAGTTCCCCTAC ACCTTCGGAGGCGGCACCA AGCTGGAAATGAAGGGCA GCACCTCCGGCAGCGGCAA GCCTGGCAGCGGCGAGGG CAGCACCAAGGGCGAAGTG AAGCTGGTGGAAAGCGGC GGAGGCCTGGTGAAACCTG GCGGCAGCCTGAAGCTGAG CTGCGCCGCCAGCGGCTTC ACCTTCAGCAGCTACGCCAT GAGCTGGGTCCGACAGATC CCCGAGAAGCGGCTGGAAT GGGTGGCCAGCATCAGCAG GGGCGGCACCACCTACTAC CCCGACAGCGTGAAGGGCC GGTTCACCATCAGCCGGGA CAACGTGCGGAACATCCTG TACCTGCAGATGAGCAGCC TGCGGAGCGAGGACACCGC CATGTACTACTGCGGCAGA TACGACTACGACGGCTACT ACGCCATGGATTACTGGGG CCAGGGCACCAGCGTGACC GTGTCTAGCAAGCCTACCAC CACCCCCGCACCTCGTCCTC CAACCCCTGCACCTACGATT GCCAGTCAGCCTCTTTCACT GCGGCCTGAGGCCAGCAGA CCAGCTGCCGGCGGTGCCG TCCATACAAGAGGACTGGA CTTCGCGTCCGATAAACCTA CTACCACTCCAGCCCCAAGG CCCCCAACCCCAGCACCGAC TATCGCATCACAGCCTTTGT CACTGCGTCCTGAAGCCAG CCGGCCAGCTGCAGGGGG GGCCGTCCACACAAGGGGA CTCGACTTTGCGAGTGATA AGCCCACCACCACCCCTGCC CCTAGACCTCCAACCCCAGC CCCTACAATCGCCAGCCAGC CCCTGAGCCTGAGGCCCGA AGCCTGTAGACCTGCCGCT GGCGGAGCCGTGCACACCA GAGGCCTGGATTTCGCCTG CGACATCTACATCTGGGCCC CTCTGGCCGGCACCTGTGG CGTGCTGCTGCTGAGCCTG GTCATCACCCTGTACTGCAA CCACCGGAATAGGAGCAAG CGGAGCAGAGGCGGCCAC AGCGACTACATGAACATGA CCCCCCGGAGGCCTGGCCC CACCCGGAAGCACTACCAG CCCTACGCCCCTCCCAGGGA CTTCGCCGCCTACCGGAGC CGGGTGAAGTTCAGCCGGA GCGCCGACGCCCCTGCCTA CCAGCAGGGCCAGAACCAG |

TABLE 14-continued

| Additional Sequences | | | | |
|---|---|---|---|---|
| Name | SEQ ID NO | Amino Acid Sequence | SEQ ID NO | Nucleotide Sequence |
| | | | | CTGTACAACGAGCTGAACC TGGGCCGGAGGGAGGAGT ACGACGTGCTGGACAAGCG GAGAGGCCGGGACCCTGA GATGGGCGGCAAGCCCCG GAGAAAGAACCCTCAGGAG GGCCTGTATAACGAACTGC AGAAAGACAAGATGGCCGA GGCCTACAGCGAGATCGGC ATGAAGGGCGAGCGGCGG AGGGGCAAGGGCCACGAC GGCCTGTACCAGGGCCTGA GCACCGCCACCAAGGATAC CTACGACGCCCTGCACATGC AGGCCCTGCCCCCCAGA |
| Murine ROR1 (VL-VH). CD8a(4x). CD28z | 601 | DIKMTQSPSSMYASLGERVTITCKA SPDINSYLSWFQQKPGKSPKTLIYR ANRLVDGVPSRFSGGGSGQDYSLT INSLEYEDMGIYYCLQYDEFPYTFG GGTKLEMKGSTSGSGKPGSGEGST KGEVKLVESGGGLVKPGGSLKLSCA ASGFTFSSYAMSWVRQIPEKRLEW VASISRGGTTYYPDSVKGRFTISRD NVRNILYLQMSSLRSEDTAMYYCG RYDYDGYYAMDYWGQGTSVTVSS KPTTTPAPRPPTPAPTIASQPLSLRP EASRPAAGGAVHTRGLDFASDKPT TTPAPRPPTPAPTIASQPLSLRPEAS RPAAGGAVHTRGLDFASDKPTTTP APRPPTPAPTIASQPLSLRPEASRPA AGGAVHTRGLDFASDKPTTTPAPR PPTPAPTIASQPLSLRPEACRPAAG GAVHTRGLDFACDIYIWAPLAGTC GVLLLSLVITLYCNHRNRSKRSRGG HSDYMNMTPRRPGPTRKHYQPYA PPRDFAAYRSRVKFSRSADAPAYQ QGQNQLYNELNLGRREEYDVLDKR RGRDPEMGGKPRRKNPQEGLYNE LQKDKMAEAYSEIGMKGERRRGK GHDGLYQGLSTATKDTYDALHMQ ALPPR | 602 | GACATCAAGATGACCCAGA GCCCCAGCTCTATGTACGCC AGCCTGGGCGAGCGCGTGA CCATCACATGCAAGGCCAG CCCCGACATCAACAGCTACC TGTCCTGGTTCCAGCAGAA GCCCGGCAAGAGCCCCAAG ACCCTGATCTACCGGGCCA ACCGGCTGGTGGACGGCGT GCCAAGCAGATTTTCCGGC GGAGGCAGCGGCCAGGAC TACAGCCTGACCATCAACA GCCTGGAATACGAGGACAT GGGCATCTACTACTGCCTGC AGTACGACGAGTTCCCCTAC ACCTTCGGAGGCGGCACCA AGCTGGAAATGAAGGGCA GCACCTCCGGCAGCGGCAA GCCTGGCAGCGGCGAGGG CAGCACCAAGGGCGAAGTG AAGCTGGTGGAAAGCGGC GGAGGCCTGGTGAAACCTG GCGGCAGCCTGAAGCTGAG CTGCGCCGCCAGCGGCTTC ACCTTCAGCAGCTACGCCAT GAGCTGGGTCCGACAGATC CCCGAGAAGCGGCTGGAAT GGGTGGCCAGCATCAGCAG GGGCGGCACCACCTACTAC CCCGACAGCGTGAAGGGCC GGTTCACCATCAGCCGGGA CAACGTGCGGAACATCCTG TACCTGCAGATGAGCAGCC TGCGGAGCGAGGACACCGC CATGTACTACTGCGGCAGA TACGACTACGACGGCTACT ACGCCATGGATTACTGGGG CCAGGGCACCAGCGTGACC GTGTCTAGCAAGCCTACCAC CACCCCCGCACCTCGTCCTC CAACCCCTGCACCTACGATT GCCAGTCAGCCTCTTTCACT GCGGCCTGAGGCCAGCAGA CCAGCTGCCGGCGGTGCCG TCCATACAAGAGGACTGGA CTTCGCGTCCGATAAACCTA CTACCACTCCAGCCCCAAGG CCCCCAACCCCAGCACCGAC TATCGCATCACAGCCTTTGT CACTGCGTCCTGAAGCCAG CCGGCCAGCTGCAGGGGG GGCCGTCCACACAAGGGGA CTCGACTTTGCGAGTGATA AACCTACTACAACTCCTGCC CCCCGGCCTCCTACACCAGC TCCTACTATCGCCTCCCAGC CACTCAGTCTCAGACCCGA GGCTTCTAGGCCAGCGGCC GGAGGCGCGGTCCACACCC |

TABLE 14-continued

| Additional Sequences | | | | |
|---|---|---|---|---|
| Name | SEQ ID NO | Amino Acid Sequence | SEQ ID NO | Nucleotide Sequence |
| | | | | GCGGGCTGGACTTTGCATC CGATAAGCCCACCACCACCC CTGCCCCTAGACCTCCAACC CCAGCCCCTACAATCGCCAG CCAGCCCCTGAGCCTGAGG CCCGAAGCCTGTAGACCTG CCGCTGGCGGAGCCGTGCA CACCAGAGGCCTGGATTTC GCCTGCGACATCTACATCTG GGCCCCTCTGGCCGGCACC TGTGGCGTGCTGCTGCTGA GCCTGGTCATCACCCTGTAC TGCAACCACCGGAATAGGA GCAAGCGGAGCAGAGGCG GCCACAGCGACTACATGAA CATGACCCCCCGGAGGCCT GGCCCCACCCGGAAGCACT ACCAGCCCTACGCCCCTCCC AGGGACTTCGCCGCCTACC GGAGCCGGGTGAAGTTCAG CCGGAGCGCCGACGCCCCT GCCTACCAGCAGGGCCAGA ACCAGCTGTACAACGAGCT GAACCTGGGCCGGAGGGA GGAGTACGACGTGCTGGAC AAGCGGAGAGGCCGGGAC CCTGAGATGGGCGGCAAGC CCCGGAGAAAGAACCCTCA GGAGGGCCTGTATAACGAA CTGCAGAAAGACAAGATGG CCGAGGCCTACAGCGAGAT CGGCATGAAGGGCGAGCG GCGGAGGGGCAAGGGCCA CGACGGCCTGTACCAGGGC CTGAGCACCGCCACCAAGG ATACCTACGACGCCCTGCAC ATGCAGGCCCTGCCCCCCA GA |
| Murine ROR1 (VL-VH). LNGFR ECD. CD8TM. CD28z | 603 | DIKMTQSPSSMYASLGERVTITCKA SPDINSYLSWFQQKPGKSPKTLIYR ANRLVDGVPSRFSGGGSGQDYSLT INSLEYEDMGIYYCLQYDEFPYTFG GGTKLEMKGSTSGSGKPGSGEGST KGEVKLVESGGGLVKPGGSLKLSCA ASGFTFSSYAMSWVRQIPEKRLEW VASISRGGTTYYPDSVKGRFTISRD NVRNILYLQMSSLRSEDTAMYYCG RYDYDGYYAMDYWGQGTSVTVSS KEACPTGLYTHSGECCKACNLGEG VAQPCGANQTVCEPCLDSVTFSDV VSATEPCKPCTECVGLQSMSAPCV EADDAVCRCAYGYYQDETTGRCEA CRVCEAGSGLVFSCQDKCINTVCEE CPDGTYSDEANHVDPCLPCTVCED TERQLRECTRWADAECEEIPGRWI TRSTPPEGSDSTAPSTQEPEAPPEQ DLIASTVAGVVTTVMGSSQPVVTR GTTDNIYIWAPLAGTCGVLLLSLVIT LYCNHRNRSKRSRGGHSDYMNMT PRRPGPTRKHYQPYAPPRDFAAYR SRVKFSRSADAPAYQQGQNQLYN ELNLGRREEYDVLDKRRGRDPEMG GKPRRKNPQEGLYNELQKDKMAE AYSEIGMKGERRRGKGHDGLYQGL STATKDTYDALHMQALPPR | 604 | GACATCAAGATGACCCAGA GCCCCAGCTCTATGTACGCC AGCCTGGGCGAGCGCGTGA CCATCACATGCAAGGCCAG CCCCGACATCAACAGCTACC TGTCCTGGTTCCAGCAGAA GCCCGGCAAGAGCCCCAAG ACCCTGATCTACCGGGCCA ACCGGCTGGTGGACGGCGT GCCAAGCAGATTTTCCGGC GGAGGCAGCGGCCAGGAC TACAGCCTGACCATCAACA GCCTGGAATACGAGGACAT GGGCATCTACTACTGCCTGC AGTACGACGAGTTCCCCTAC ACCTTCGGAGGCGGCACCA AGCTGGAAATGAAGGGCA GCACCTCCGGCAGCGGCAA GCCTGGCAGCGGCGAGGG CAGCACCAAGGGCGAAGTG AAGCTGGTGGAAAGCGGC GGAGGCCTGGTGAAACCTG GCGGCAGCCTGAAGCTGAG CTGCGCCGCCAGCGGCTTC ACCTTCAGCAGCTACGCCAT GAGCTGGGTCCGACAGATC CCCGAGAAGCGGCTGGAAT GGGTGGCCAGCATCAGCAG GGGCGGCACCACCTACTAC CCCGACAGCGTGAAGGGCC GGTTCACCATCAGCCGGGA CAACGTGCGGAACATCCTG TACCTGCAGATGAGCAGCC TGCGGAGCGAGGACACCGC CATGTACTACTGCGGCAGA TACGACTACGACGGCTACT |

TABLE 14-continued

| Additional Sequences | | | | |
|---|---|---|---|---|
| Name | SEQ ID NO | Amino Acid Sequence | SEQ ID NO | Nucleotide Sequence |
| | | | | ACGCCATGGATTACTGGGG CCAGGGCACCAGCGTGACC GTGTCTAGCAAGGAGGCAT GCCCCACAGGCCTGTACAC ACACAGCGGTGAGTGCTGC AAAGCCTGCAACCTGGGCG AGGGTGTGGCCCAGCCTTG TGGAGCCAACCAGACCGTG TGTGAGCCCTGCCTGGACA GCGTGACGTTCTCCGACGT GGTGAGCGCGACCGAGCC GTGCAAGCCGTGCACCGAG TGCGTGGGGCTCCAGAGCA TGTCGGCGCCGTGCGTGGA GGCCGACGACGCCGTGTGC CGCTGCGCCTACGGCTACT ACCAGGATGAGACGACTGG GCGCTGCGAGGCGTGCCGC GTGTGCGAGGCGGGCTCG GGCCTCGTGTTCTCCTGCCA GGACAAGCAGAACACCGTG TGCGAGGAGTGCCCCGACG GCACGTATTCCGACGAGGC CAACCACGTGGACCCGTGC CTGCCCTGCACCGTGTGCG AGGACACCGAGCGCCAGCT CCGCGAGTGCACACGCTGG GCCGACGCCGAGTGCGAG GAGATCCCTGGCCGTTGGA TTACACGGTCCACACCCCCA GAGGGCTCGGACAGCACAG CCCCCAGCACCCAGGAGCC TGAGGCACCTCCAGAACAA GACCTCATAGCCAGCACGG TGGCAGGTGTGGTGACCAC AGTGATGGGCAGCTCCCAG CCCGTGGTGACCCGAGGCA CCACCGACAACATCTACATC TGGGCCCCTCTGGCCGGCA CCTGTGGCGTGCTGCTGCT GAGCCTGGTCATCACCCTGT ACTGCAACCACCGGAATAG GAGCAAGCGGAGCAGAGG CGGCCACAGCGACTACATG AACATGACCCCCCGGAGGC CTGGCCCCACCCGGAAGCA CTACCAGCCCTACGCCCCTC CCAGGGACTTCGCCGCCTA CCGGAGCCGGGTGAAGTTC AGCCGGAGCGCCGACGCCC CTGCCTACCAGCAGGGCCA GAACCAGCTGTACAACGAG CTGAACCTGGGCCGGAGGG AGGAGTACGACGTGCTGGA CAAGCGGAGAGGCCGGGA CCCTGAGATGGGCGGCAAG CCCCGGAGAAAGAACCCTC AGGAGGGCCTGTATAACGA ACTGCAGAAAGACAAGATG GCCGAGGCCTACAGCGAGA TCGGCATGAAGGGCGAGCG GCGGAGGGGCAAGGGCCA CGACGGCCTGTACCAGGGC CTGAGCACCGCCACCAAGG ATACCTACGACGCCCTGCAC ATGCAGGCCCTGCCCCCCA GA |

TABLE 14-continued

| Additional Sequences | | | | |
|---|---|---|---|---|
| Name | SEQ ID NO | Amino Acid Sequence | SEQ ID NO | Nucleotide Sequence |
| Murine ROR1 (VH-VL). CD8a(3x). 41BBz | 605 | EVKLVESGGGLVKPGGSLKLSCAAS GFTFSSYAMSWVRQIPEKRLEWVA SISRGGTTYYPDSVKGRFTISRDNVR NILYLQMSSLRSEDTAMYYCGRYD YDGYYAMDYWGQGTSVTVSSGST SGSGKPGSGEGSTKGDIKMTQSPS SMYASLGERVTITCKASPDINSYLS WFQQKPGKSPKTLIYRANRLVDGV PSRFSGGGSGQDYSLTINSLEYEDM GIYYCLQYDEFPYTFGGGTKLEMKK PTTTPAPRPPTPAPTIASQPLSLRPE ASRPAAGGAVHTRGLDFASDKPTT TPAPRPPTPAPTIASQPLSLRPEASR PAAGGAVHTRGLDFASDKPTTTPA PRPPTPAPTIASQPLSLRPEACRPAA GGAVHTRGLDFACDIYIWAPLAGT CGVLLLSLVITLYCNHRNKRGRKKLL YIFKQPFMRPVQTTQEEDGCSCRF PEEEEGGCELRVKFSRSADAPAYQ QGQNQLYNELNLGRREEYDVLDKR RGRDPEMGGKPRRKNPQEGLYNE LQKDKMAEAYSEIGMKGERRRGK GHDGLYQGLSTATKDTYDALHMQ ALPPR | 606 | GAAGTGAAGCTGGTGGAAA GCGGCGGAGGCCTGGTGA AACCTGGCGGCAGCCTGAA GCTGAGCTGCGCCGCCAGC GGCTTCACCTTCAGCAGCTA CGCCATGAGCTGGGTCCGA CAGATCCCCGAGAAGCGGC TGGAATGGGTGGCCAGCAT CAGCAGGGGCGGCACCACC TACTACCCCGACAGCGTGA AGGGCCGGTTCACCATCAG CCGGGACAACGTGCGGAAC ATCCTGTACCTGCAGATGA GCAGCCTGCGGAGCGAGG ACACCGCCATGTACTACTGC GGCAGATACGACTACGACG GCTACTACGCCATGGATTAC TGGGGCCAGGGCACCAGC GTGACCGTGTCTAGCGGCA GCACCTCCGGCAGCGGCAA GCCTGGCAGCGGCGAGGG CAGCACCAAGGGCGACATC AAGATGACCCAGAGCCCCA GCTCTATGTACGCCAGCCTG GGCGAGCGCGTGACCATCA CATGCAAGGCCAGCCCCGA CATCAACAGCTACCTGTCCT GGTTCCAGCAGAAGCCCGG CAAGAGCCCCAAGACCCTG ATCTACCGGGCCAACCGGC TGGTGGACGGCGTGCCAAG CAGATTTTCCGGCGGAGGC AGCGGCCAGGACTACAGCC TGACCATCAACAGCCTGGA ATACGAGGACATGGGCATC TACTACTGCCTGCAGTACGA CGAGTTCCCCTACACCTTCG GAGGCGGCACCAAGCTGGA AATGAAGAAGCCTACCACC ACCCCCGCACCTCGTCCTCC AACCCCTGCACCTACGATTG CCAGTCAGCCTCTTTCACTG CGGCCTGAGGCCAGCAGAC CAGCTGCCGGCGGTGCCGT CCATACAAGAGGACTGGAC TTCGCGTCCGATAAACCTAC TACCACTCCAGCCCCAAGGC CCCCAACCCCAGCACCGACT ATCGCATCACAGCCTTTGTC ACTGCGTCCTGAAGCCAGC CGGCCAGCTGCAGGGGGG GCCGTCCACACAAGGGGAC TCGACTTTGCGAGTGATAA GCCCACCACCACCCCTGCCC CTAGACCTCCAACCCCAGCC CCTACAATCGCCAGCCAGCC CCTGAGCCTGAGGCCCGAA GCCTGTAGACCTGCCGCTG GCGGAGCCGTGCACACCAG AGGCCTGGATTTCGCCTGC GACATCTACATCTGGGCCCC TCTGGCCGGCACCTGTGGC GTGCTGCTGCTGAGCCTGG TCATCACCCTGTACTGCAAC CACCGGAATAAGAGAGGCC GGAAGAAACTGCTGTACAT CTTCAAGCAGCCCTTCATGC GGCCCGTGCAGACCACCCA GGAAGAGGACGGCTGCAG CTGCCGGTTCCCCGAGGAA GAGGAAGGCGGCTGCGAA CTGCGGGTGAAGTTCAGCC GGAGCGCCGACGCCCCTGC CTACCAGCAGGGCCAGAAC |

TABLE 14-continued

| Additional Sequences | | | | |
|---|---|---|---|---|
| Name | SEQ ID NO | Amino Acid Sequence | SEQ ID NO | Nucleotide Sequence |
| | | | | CAGCTGTACAACGAGCTGA ACCTGGGCCGGAGGGAGG AGTACGACGTGCTGGACAA GCGGAGAGGCCGGGACCC TGAGATGGGCGGCAAGCCC CGGAGAAAGAACCCTCAGG AGGGCCTGTATAACGAACT GCAGAAAGACAAGATGGCC GAGGCCTACAGCGAGATCG GCATGAAGGGCGAGCGGC GGAGGGGCAAGGGCCACG ACGGCCTGTACCAGGGCCT GAGCACCGCCACCAAGGAT ACCTACGACGCCCTGCACAT GCAGGCCCTGCCCCCCAGA |
| Murine ROR1 (VH-VL). IgG4 Fcm. CD8aTM. 41BBz | 607 | EVKLVESGGGLVKPGGSLKLSCAAS GFTFSSYAMSWVRQIPEKRLEWVA SISRGGTTYYPDSVKGRFTISRDNVR NILYLQMSSLRSEDTAMYYCGRYD YDGYYAMDYWGQGTSVTVSSGST SGSGKPGSGEGSTKGDIKMTQSPS SMYASLGERVTITCKASPDINSYLS WFQQKPGKSPKTLIYRANRLVDGV PSRFSGGGSGQDYSLTINSLEYEDM GIYYCLQYDEFPYTFGGGTKLEMKE SKYGPPCPPCPAPEFEGGPSVFLFP PKPKDTLMISRTPEVTCVVVDVSQE DPEVQFNWYVDGVEVHNAKTKPR EEQFQSTYRVVSVLTVLHQDWLNG KEYKCKVSNKGLPSSIEKTISKAKGQ PREPQVYTLPPSQEEMTKNQVSLT CLVKGFYPSDIAVEWESNGQPENN YKTTPPVLDSDGSFFLYSRLTVDKSR WQEGNVFSCSVMHEALHNHYTQ KSLSLSLGKMIYIWAPLAGTCGVLLL SLVITLYCNHRNKRGRKKLLYIFKQP FMRPVQTTQEEDGCSCRFPEEEEG GCELRVKFSRSADAPAYQQGQNQ LYNELNLGRREEYDVLDKRRGRDPE MGGKPRRKNPQEGLYNELQKDK MAEAYSEIGMKGERRRGKGHDGL YQGLSTATKDTYDALHMQALPPR | 608 | GAAGTGAAGCTGGTGGAAA GCGGCGGAGGCCTGGTGA AACCTGGCGGCAGCCTGAA GCTGAGCTGCGCCGCCAGC GGCTTCACCTTCAGCAGCTA CGCCATGAGCTGGGTCCGA CAGATCCCCGAGAAGCGGC TGGAATGGGTGGCCAGCAT CAGCAGGGGCGGCACCACC TACTACCCCGACAGCGTGA AGGGCCGGTTCACCATCAG CCGGGACAACGTGCGGAAC ATCCTGTACCTGCAGATGA GCAGCCTGCGGAGCGAGG ACACCGCCATGTACTACTGC GGCAGATACGACTACGACG GCTACTACGCCATGGATTAC TGGGGCCAGGGCACCAGC GTGACCGTGTCTAGCGGCA GCACCTCCGGCAGCGGCAA GCCTGGCAGCGGCGAGGG CAGCACCAAGGGCGACATC AAGATGACCCAGAGCCCCA GCTCTATGTACGCCAGCCTG GGCGAGCGCGTGACCATCA CATGCAAGGCCAGCCCCGA CATCAACAGCTACCTGTCCT GGTTCCAGCAGAAGCCCGG CAAGAGCCCCAAGACCCTG ATCTACCGGGCCAACCGGC TGGTGGACGGCGTGCCAAG CAGATTTTCCGGCGGAGGC AGCGGCCAGGACTACAGCC TGACCATCAACAGCCTGGA ATACGAGGACATGGGCATC TACTACTGCCTGCAGTACGA CGAGTTCCCCTACACCTTCG GAGGCGGCACCAAGCTGGA AATGAAGGAGAGCAAGTAC GGCCCTCCCTGCCCCCCTTG CCCTGCCCCCGAGTTCGAG GGCGGACCCAGCGTGTTCC TGTTCCCCCCCAAGCCCAAG GACACCCTGATGATCAGCC GGACCCCCGAGGTGACCTG TGTGGTGGTGGACGTGTCC CAGGAGGACCCCGAGGTCC AGTTCAACTGGTACGTGGA CGGCGTGGAGGTGCACAAC GCCAAGACCAAGCCCCGGG AGGAGCAGTTCCAGAGCAC CTACCGGGTGGTGTCCGTG CTGACCGTGCTGCACCAGG ACTGGCTGAACGGCAAGGA ATACAAGTGTAAGGTGTCC AACAAGGGCCTGCCCAGCA GCATCGAGAAAACCATCAG CAAGGCCAAGGGCCAGCCT CGGGAGCCCCAGGTGTACA |

TABLE 14-continued

| Additional Sequences | | | | |
|---|---|---|---|---|
| Name | SEQ ID NO | Amino Acid Sequence | SEQ ID NO | Nucleotide Sequence |
| | | | | CCCTGCCCCCTAGCCAAGA GGAGATGACCAAGAATCAG GTGTCCCTGACCTGCCTGGT GAAGGGCTTCTACCCCAGC GACATCGCCGTGGAGTGGG AGAGCAACGGCCAGCCCGA GAACAACTACAAGACCACC CCCCCTGTGCTGGACAGCG ACGGCAGCTTCTTCCTGTAC AGCAGGCTGACCGTGGACA AGAGCCGGTGGCAGGAGG GCAACGTCTTTAGCTGCTCC GTGATGCACGAGGCCCTGC ACAACCACTACACCCAGAA GAGCCTGTCCCTGAGCCTG GGCAAGATGATCTACATCT GGGCCCCTCTGGCCGGCAC CTGTGGCGTGCTGCTGCTG AGCCTGGTCATCACCCTGTA CTGCAACCACCGGAATAAG AGAGGCCGGAAGAAACTGC TGTACATCTTCAAGCAGCCC TTCATGCGGCCCGTGCAGA CCACCCAGGAAGAGGACGG CTGCAGCTGCCGGTTCCCC GAGGAAGAGGAAGGCGGC TGCGAACTGCGGGTGAAGT TCAGCCGGAGCGCCGACGC CCCTGCCTACCAGCAGGGC CAGAACCAGCTGTACAACG AGCTGAACCTGGGCCGGAG GGAGGAGTACGACGTGCTG GACAAGCGGAGAGGCCGG GACCCTGAGATGGGCGGCA AGCCCCGGAGAAAGAACCC TCAGGAGGGCCTGTATAAC GAACTGCAGAAAGACAAGA TGGCCGAGGCCTACAGCGA GATCGGCATGAAGGGCGA GCGGCGGAGGGGCAAGGG CCACGACGGCCTGTACCAG GGCCTGAGCACCGCCACCA AGGATACCTACGACGCCCT GCACATGCAGGCCCTGCCC CCCAGA |
| Murine ROR1_v2 VL | 609 | DVQITQSPSSLYASLGERVTITCKAS PDINSYLSWFQQKPGKSPKTLIYRA NRLVDGVPSRFSGGGSGQDYSLTI NSLEYEDMGIYYCLQYDEFPYTFGG GTKLEMK | 610 | GACGTGCAGATCACCCAGA GCCCCAGCAGCCTGTATGC CAGCCTGGGCGAGAGAGTG ACCATTACCTGCAAGGCCA GCCCCGACATCAACAGCTA CCTGAGCTGGTTCCAGCAG AAGCCCGGCAAGAGCCCCA AGACCCTGATCTACCGGGC CAACAGACTGGTGGATGGC GTGCCCAGCAGATTCAGCG GCGGAGGCTCTGGCCAGGA CTACAGCCTGACCATCAACT CCCTGGAATACGAGGACAT GGGCATCTACTACTGCCTGC AGTACGACGAGTTCCCCTAC ACCTTCGGAGGCGGCACCA AGCTGGAAATGAAG |
| Murine ROR1_v2 VH | 611 | EVKLVESGGGLVKPGGSLKLSCAAS GFTFSSYAMSWVRQIPEKRLEWVA SISRGGTTYYPDSVKGRFTISRDNVR NILYLQMSSLRSEDTAMYYCGRYD YDGYYAMDYWGQGTSVTVSS | 612 | GAAGTGAAGCTGGTGGAAT CTGGCGGCGGACTCGTGAA GCCTGGCGGCTCTCTGAAG CTGTCTTGTGCCGCCAGCG GCTTCACCTTCAGCAGCTAC GCCATGAGCTGGGTGCGGC AGATCCCCGAGAAGCGGCT GGAATGGGTGGCCAGCATC AGCAGAGGCGGAACCACCT ACTACCCCGACTCTGTGAAG GGCCGGTTCACCATCAGCC |

TABLE 14-continued

| Additional Sequences | | | | |
|---|---|---|---|---|
| Name | SEQ ID NO | Amino Acid Sequence | SEQ ID NO | Nucleotide Sequence |
| | | | | GGGACAACGTGCGGAACAT CCTGTACCTGCAGATGAGC AGCCTGCGGAGCGAGGACA CCGCCATGTACTACTGTGGC AGATACGACTACGACGGCT ACTATGCCATGGATTACTG GGGCCAGGGCACCAGCGT GACCGTGTCATCT |
| Murine ROR1_v2 (VL-VH). CD8a(3x). CD28z | 613 | DVQITQSPSSLYASLGERVTITCKAS PDINSYLSWFQQKPGKSPKTLIYRA NRLVDGVPSRFSGGGSGQDYSLTI NSLEYEDMGIYYCLQYDEFPYTFGG GTKLEMKGSTSGSGKPGSGEGSTK GEVKLVESGGGLVKPGGSLKLSCAA SGFTFSSYAMSWVRQIPEKRLEWV ASISRGGTTYYPDSVKGRFTISRDN VRNILYLQMSSLRSEDTAMYYCGR YDYDGYYAMDYWGQGTSVTVSSK PTTTPAPRPPTPAPTIASQPLSLRPE ASRPAAGGAVHTRGLDFASDKPTT TPAPRPPTPAPTIASQPLSLRPEASR PAAGGAVHTRGLDFASDKPTTTPA PRPPTPAPTIASQPLSLRPEACRPAA GGAVHTRGLDFACDIYIWAPLAGT CGVLLLSLVITLYCNHRNRSKRSRG GHSDYMNMTPRRPGPTRKHYQPY APPRDFAAYRSRVKFSRSADAPAY QQGQNQLYNELNLGRREEYDVLD KRRGRDPEMGGKPRRKNPQEGLY NELQKDKMAEAYSEIGMKGERRR GKGHDGLYQGLSTATKDTYDALH MQALPPR | 614 | GACGTGCAGATCACCCAGA GCCCCAGCAGCCTGTATGC CAGCCTGGGCGAGAGAGTG ACCATTACCTGCAAGGCCA GCCCCGACATCAACAGCTA CCTGAGCTGGTTCCAGCAG AAGCCCGGCAAGAGCCCCA AGACCCTGATCTACCGGGC CAACAGACTGGTGGATGGC GTGCCCAGCAGATTCAGCG GCGGAGGCTCTGGCCAGGA CTACAGCCTGACCATCAACT CCCTGGAATACGAGGACAT GGGCATCTACTACTGCCTGC AGTACGACGAGTTCCCCTAC ACCTTCGGAGGCGGCACCA AGCTGGAAATGAAGGGCA GCACAAGCGGCAGCGGCAA GCCTGGATCTGGCGAGGGA AGCACCAAGGGCGAAGTGA AGCTGGTGGAATCTGGCGG CGGACTCGTGAAGCCTGGC GGCTCTCTGAAGCTGTCTTG TGCCGCCAGCGGCTTCACCT TCAGCAGCTACGCCATGAG CTGGGTGCGGCAGATCCCC GAGAAGCGGCTGGAATGG GTGGCCAGCATCAGCAGAG GCGGAACCACCTACTACCCC GACTCTGTGAAGGGCCGGT TCACCATCAGCCGGGACAA CGTGCGGAACATCCTGTAC CTGCAGATGAGCAGCCTGC GGAGCGAGGACACCGCCAT GTACTACTGTGGCAGATAC GACTACGACGGCTACTATG CCATGGATTACTGGGGCCA GGGCACCAGCGTGACCGTG TCATCTAAGCCTACCACCAC CCCCGCACCTCGTCCTCCAA CCCCTGCACCTACGATTGCC AGTCAGCCTCTTTCACTGCG GCCTGAGGCCAGCAGACCA GCTGCCGGCGGTGCCGTCC ATACAAGAGGACTGGACTT CGCGTCCGATAAACCTACTA CCACTCCAGCCCCAAGGCCC CCAACCCCAGCACCGACTAT CGCATCACAGCCTTTGTCAC TGCGTCCTGAAGCCAGCCG GCCAGCTGCAGGGGGGGC CGTCCACACAAGGGGACTC GACTTTGCGAGTGATAAGC CCACCACCACCCCTGCCCCT AGACCTCCAACCCCAGCCCC TACAATCGCCAGCCAGCCCC TGAGCCTGAGGCCCGAAGC CTGTAGACCTGCCGCTGGC GGAGCCGTGCACACCAGAG GCCTGGATTTCGCCTGCGA CATCTACATCTGGGCCCCTC TGGCCGGCACCTGTGGCGT GCTGCTGCTGAGCCTGGTC ATCACCCTGTACTGCAACCA CCGGAATAGGAGCAAGCG GAGCAGAGGCGGCCACAG |

TABLE 14-continued

Additional Sequences

| Name | SEQ ID NO | Amino Acid Sequence | SEQ ID NO | Nucleotide Sequence |
|---|---|---|---|---|
| | | | | CGACTACATGAACATGACC CCCCGGAGGCCTGGCCCCA CCCGGAAGCACTACCAGCC CTACGCCCCTCCCAGGGACT TCGCCGCCTACCGGAGCCG GGTGAAGTTCAGCCGGAGC GCCGACGCCCCTGCCTACCA GCAGGGCCAGAACCAGCTG TACAACGAGCTGAACCTGG GCCGGAGGGAGGAGTACG ACGTGCTGGACAAGCGGAG AGGCCGGGACCCTGAGATG GGCGGCAAGCCCCGGAGA AAGAACCCTCAGGAGGGCC TGTATAACGAACTGCAGAA AGACAAGATGGCCGAGGCC TACAGCGAGATCGGCATGA AGGGCGAGCGGCGGAGGG GCAAGGGCCACGACGGCCT GTACCAGGGCCTGAGCACC GCCACCAAGGATACCTACG ACGCCCTGCACATGCAGGC CCTGCCCCCCAGA |
| hROR1 (VH-VL)_ 14. CD8a(3x). CD28z | 615 | EVQLVESGGGLVQPGGSLRLSCAT SGFTFSSYAMSWMRQAPGKGLE WVASISRGGTTYYADSVKGRFTISV DKSKNTLYLQMNSLRAEDTAVYYC GRYDYDGYYAMDYWGQGTLVTVS SGGGGSGGGGSGGGGSDIQMTQ SPSSLSASVGDRVTITCKASPDINSY LNWYQQKPGKAPKLLIYRANRLVD GVPSRFSGSGSGTDYTLTISSLQPED FATYYCLQYDEFPYTFGAGTKVEIKK PTTTPAPRPPTPAPTIASQPLSLRPE ASRPAAGGAVHTRGLDFASDKPTT TPAPRPPTPAPTIASQPLSLRPEASR PAAGGAVHTRGLDFASDKPTTTPA PRPPTPAPTIASQPLSLRPEACRPAA GGAVHTRGLDFACDIYIWAPLAGT CGVLLLSLVITLYCNHRNRSKRSRG GHSDYMNMTPRRPGPTRKHYQPY APPRDFAAYRSRVKFSRSADAPAY QQGQNQLYNELNLGRREEYDVLD KRRGRDPEMGGKPRRKNPQEGLY NELQKDKMAEAYSEIGMKGERRR GKGHDGLYQGLSTATKDTYDALH MQALPPR | 616 | GAAGTGCAGCTGGTGGAGT CTGGCGGCGGTCTGGTGCA GCCCGGCGGCTCTCTGCGC CTCTCCTGTGCCACCTCTGG TTTTACATTCTCCTCCTACGC TATGTCCTGGATGCGGCAA GCCCCCGGCAAGGGCCTAG AGTGGGTCGCCTCAATCAG CAGGGGCGGGACGACTTAT TATGCCGATTCAGTTAAGG GGAGATTCACAATTTCCGT GGATAAATCCAAGAATACC TTATACCTCCAGATGAACTC TCTGCGGGCCGAAGATACG GCCGTATATTATTGTGGGA GGTATGACTACGACGGATA TTACGCCATGGATTATTGG GGGCAGGGGACACTTGTTA CAGTGAGTTCCGGTGGTGG GGGGTCTGGAGGCGGGGG CAGTGGAGGCGGAGGGTC TGATATACAGATGACACAG AGCCCTTCAAGTTTATCTGC AAGCGTCGGCGATCGTGTT ACAATAACTTGCAAGGCAT CTCCCGACATCAATTCCTAC CTCAACTGGTATCAGCAGA AGCCTGGGAAGGCTCCTAA GCTGCTTATTTACAGAGCAA ATCGCCTGGTGGACGGCGT GCCCAGTCGGTTTTCCGGG TCTGGGAGCGGAACGGATT ACACACTGACCATCTCAAGC CTGCAACCCGAAGACTTCG CTACATATTACTGCCTTCAG TATGATGAGTTCCCATATAC CTTCGGCGCTGGGACCAAG GTGGAGATAAAGAAGCCTA CCACCACCCCCGCACCTCGT CCTCCAACCCCTGCACCTAC GATTGCCAGTCAGCCTCTTT CACTGCGGCCTGAGGCCAG CAGACCAGCTGCCGGCGGT GCCGTCCATACAAGAGGAC TGGACTTCGCGTCCGATAA ACCTACTACCACTCCAGCCC CAAGGCCCCCAACCCCAGC ACCGACTATCGCATCACAGC CTTTGTCACTGCGTCCTGAA GCCAGCCGGCCAGCTGCAG GGGGGGCCGTCCACACAAG |

TABLE 14-continued

| Additional Sequences | | | | |
|---|---|---|---|---|
| Name | SEQ ID NO | Amino Acid Sequence | SEQ ID NO | Nucleotide Sequence |
| | | | | GGGACTCGACTTTGCGAGT<br>GATAAGCCCACCACCACCCC<br>TGCCCCTAGACCTCCAACCC<br>CAGCCCCTACAATCGCCAGC<br>CAGCCCCTGAGCCTGAGGC<br>CCGAAGCCTGTAGACCTGC<br>CGCTGGCGGAGCCGTGCAC<br>ACCAGAGGCCTGGATTTCG<br>CCTGCGACATCTACATCTGG<br>GCCCCTCTGGCCGGCACCT<br>GTGGCGTGCTGCTGCTGAG<br>CCTGGTCATCACCCTGTACT<br>GCAACCACCGGAATAGGAG<br>CAAGCGGAGCAGAGGCGG<br>CCACAGCGACTACATGAAC<br>ATGACCCCCCGGAGGCCTG<br>GCCCCACCCGGAAGCACTA<br>CCAGCCCTACGCCCCTCCCA<br>GGGACTTCGCCGCCTACCG<br>GAGCCGGGTGAAGTTCAGC<br>CGGAGCGCCGACGCCCCTG<br>CCTACCAGCAGGGCCAGAA<br>CCAGCTGTACAACGAGCTG<br>AACCTGGGCCGGAGGGAG<br>GAGTACGACGTGCTGGACA<br>AGCGGAGAGGCCGGGACC<br>CTGAGATGGGCGGCAAGCC<br>CCGGAGAAAGAACCCTCAG<br>GAGGGCCTGTATAACGAAC<br>TGCAGAAAGACAAGATGGC<br>CGAGGCCTACAGCGAGATC<br>GGCATGAAGGGCGAGCGG<br>CGGAGGGGCAAGGGCCAC<br>GACGGCCTGTACCAGGGCC<br>TGAGCACCGCCACCAAGGA<br>TACCTACGACGCCCTGCACA<br>TGCAGGCCCTGCCCCCCAG<br>A |
| hROR1<br>(VL-VH)_<br>05.<br>CD8a(3x).<br>CD28z | 617 | DIQMTQSPSSLSASVGDRVTITCKA<br>SPDINSYLSWYQQKPGKAPKLLIYR<br>ANRLVDGVPSRFSGSGSGTDFTLTI<br>SSLQPEDIATYYCLQYDEFPYTFGQ<br>GTKLEIKGGGGSGGGGSGGGGSEV<br>QLVESGGGLVQPGGSLRLSCAASG<br>FTFSSYAMSWVRQAPGKGLEWVS<br>SISRGGTTYYPDSVKGRFTISRDNSK<br>NTLYLQMNSLRAEDTAVYYCGRYD<br>TAGCCGGTTCTCTGGTTCCG<br>YDGYYAMDYWGQGTLVTVSSKPT<br>TTPAPRPPTPAPTIASQPLSLRPEAS<br>RPAAGGAVHTRGLDFASDKPTTTP<br>APRPPTPAPTIASQPLSLRPEASRPA<br>AGGAVHTRGLDFASDKPTTTPAPR<br>PPTPAPTIASQPLSLRPEACRPAAG<br>GAVHTRGLDFACDIYIWAPLAGTC<br>GVLLLSLVITLYCNHRNRSKRSRGG<br>HSDYMNMTPRRPGPTRKHYQPYA<br>PPRDFAAYRSRVKFSRSADAPAYQ<br>QGQNQLYNELNLGRREEYDVLDKR<br>RGRDPEMGGKPRRKNPQEGLYNE<br>LQKDKMAEAYSEIGMKGERRRGK<br>GHDGLYQGLSTATKDTYDALHMQ<br>ALPPR | 618 | GATATTCAGATGACCCAGTC<br>ACCTTCGAGTCTGAGCGCA<br>TCCGTGGGCGACAGAGTGA<br>CCATTACCTGTAAGGCCAGC<br>CCGGACATTAACAGCTACCT<br>ATCGTGGTATCAGCAAAAG<br>CCTGGTAAGGCCCCTAAACT<br>CCTTATCTACAGGGCTAATA<br>GGTTGGTAGACGGGGTGCC<br>GCAGCGGTACGGACTTTAC<br>TCTGACCATAAGCTCTCTGC<br>AACCAGAAGACATCGCAAC<br>ATACTACTGTTTACAATACG<br>ACGAATTTCCTTATACCTTT<br>GGCCAGGGGACCAAGTTAG<br>AGATCAAGGGGGGCGGCG<br>GAAGTGGTGGAGGGGGAA<br>GTGGTGGAGGAGGAAGCG<br>AAGTGCAACTGGTCGAGTC<br>TGGGGGCGGCCTTGTGCAA<br>CCTGGAGGCAGCCTTCGAC<br>TCAGTTGCGCCGCGTCTGG<br>TTTTACCTTCTCCTCTTACGC<br>GATGAGCTGGGTTCGCCAG<br>GCCCCCGGCAAGGGACTTG<br>AGTGGGTTAGTTCGATCTCC<br>CGCGGAGGCACCACATATT<br>ATCCTGACTCGGTTAAGGG<br>ACGCTTCACTATCTCTAGGG<br>ACAATTCAAAGAACACACT<br>GTATCTCCAAATGAACTCCT<br>TGCGGGCCGAGGACACTGC<br>TGTGTATTATTGCGGACGAT<br>ACGACTACGATGGGTATTA<br>CGCCATGGATTACTGGGGG<br>CAAGGTACACTGGTCACTG |

TABLE 14-continued

| Additional Sequences | | | | |
|---|---|---|---|---|
| Name | SEQ ID NO | Amino Acid Sequence | SEQ ID NO | Nucleotide Sequence |
| | | | | TGAGTTCGAAGCCTACCACC ACCCCCGCACCTCGTCCTCC AACCCCTGCACCTACGATTG CCAGTCAGCCTCTTTCACTG CGGCCTGAGGCCAGCAGAC CAGCTGCCGGCGGTGCCGT CCATACAAGAGGACTGGAC TTCGCGTCCGATAAACCTAC TACCACTCCAGCCCCAAGGC CCCCAACCCCAGCACCGACT ATCGCATCACAGCCTTTGTC ACTGCGTCCTGAAGCCAGC CGGCCAGCTGCAGGGGGG GCCGTCCACACAAGGGGAC TCGACTTTGCGAGTGATAA GCCCACCACCACCCCTGCCC CTAGACCTCCAACCCCAGCC CCTACAATCGCCAGCCAGCC CCTGAGCCTGAGGCCCGAA GCCTGTAGACCTGCCGCTG GCGGAGCCGTGCACACCAG AGGCCTGGATTTCGCCTGC GACATCTACATCTGGGCCCC TCTGGCCGGCACCTGTGGC GTGCTGCTGCTGAGCCTGG TCATCACCCTGTACTGCAAC CACCGGAATAGGAGCAAGC GGAGCAGAGGCGGCCACA GCGACTACATGAACATGAC CCCCCGGAGGCCTGGCCCC ACCCGGAAGCACTACCAGC CCTACGCCCCTCCCAGGGAC TTCGCCGCCTACCGGAGCC GGGTGAAGTTCAGCCGGAG CGCCGACGCCCCTGCCTACC AGCAGGGCCAGAACCAGCT GTACAACGAGCTGAACCTG GGCCGGAGGGAGGAGTAC GACGTGCTGGACAAGCGGA GAGGCCGGGACCCTGAGAT GGGCGGCAAGCCCCGGAG AAAGAACCCTCAGGAGGGC CTGTATAACGAACTGCAGA AAGACAAGATGGCCGAGGC CTACAGCGAGATCGGCATG AAGGGCGAGCGGCGGAGG GGCAAGGGCCACGACGGCC TGTACCAGGGCCTGAGCAC CGCCACCAAGGATACCTAC GACGCCCTGCACATGCAGG CCCTGCCCCCCAGATGA |
| hROR1 (VH-VL)_ 14-3. CD8a(3x). CD28z | 619 | EVQLVESGGGLVQPGGSLRLSCAA SGFTFSSYAMSWVRQAPGKGLEW VASISRGGTTYYADSVKGRFTISRD NSKNTLYLQMNSLRAEDTAVYYCG RYDYDGYYAMDYWGQGTLVTVSS GGGGSGGGGSGGGGSDIQMTQS PSSLSASVGDRVTITCKASPDINSYL NWYQQKPGKAPKLLIYRANRLVDG VPSRFSGSGSGTDFTLTISSLQPEDI ATYYCLQYDEFPYTFGGGTKVEIKK PTTTPAPRPPTPAPTIASQPLSLRPE ASRPAAGGAVHTRGLDFASDKPTT TPAPRPPTPAPTIASQPLSLRPEASR PAAGGAVHTRGLDFASDKPTTTPA | 620 | GAGGTTCAACTTGTGGAAT CCGGCGGCGGGTTAGTCCA GCCCGGCGGGAGCTTGCGG CTGTCCTGCGCCGCCTCTGG ATTCACTTTTAGCTCCTATG CTATGTCTTGGGTAAGGCA GGCCCCTGGTAAAGGACTA GAGTGGGTGGCCTCGATCT CCCGTGGTGGCACTACATA CTACGCCGACTCCGTTAAAG GCCGGTTTACCATCTCCCGT GACAACTCTAAAAATACTTT GTACCTGCAAATGAACTCCC TGCGGGCAGAAGACACAGC |

TABLE 14-continued

| Additional Sequences | | | | |
|---|---|---|---|---|
| Name | SEQ ID NO | Amino Acid Sequence | SEQ ID NO | Nucleotide Sequence |
| | | PRPPTPAPTIASQPLSLRPEACRPAAGGAVHTRGLDFACDIYIWAPLAGTCGVLLLSLVITLYCNHRNRSKRSRGGHSDYMNMTPRRPGPTRKHYQPYAPPRDFAAYRSRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | | CGTGTACTATTGCGGGCGTTACGATTACGACGGATATTACGCAATGGACTACTGGGGCCAGGGCACACTGGTCACCGTGAGCAGCGGGGGCGGAGGAAGTGGAGGAGGCGGTAGTGGTGGGGGAGGAAGCGATATACAAATGACTCAGTCCCCTAGTAGCCTTAGTGCTAGTGTGGGAGACAGAGTGACCATCACCTGCAAAGCATCTCCTGATATCAATTCCTACCTTAACTGGTATCAACAGAAGCCTGGCAAAGCTCCAAAGCTCCTGATTTATCGCGCGAACAGATTGGTCGATGGGGTCCCTTCCAGATTCAGCGGCTCAGGGTCAGGGACCGATTTCACCCTCACAATTAGTTCACTTCAGCCCGAGGACATCGCCACGTATTATTGCCTTCAGTACGATGAGTTCCCTTACACCTTTGGCGGGGGAACTAAAGTCGAAATTAAGAAGCCTACCACCACCCCCGCACCTCGTCCTCCAACCCCTGCACCTACGATTGCCAGTCAGCCTCTTTCACTGCGGCCTGAGGCCAGCAGACCAGCTGCCGGCGGTGCCGTCCATACAAGAGGACTGGACTTCGCGTCCGATAAACCTACTACCACTCCAGCCCCAAGGCCCCCAACCCCAGCACCGACTATCGCATCACAGCCTTTGTCACTGCGTCCTGAAGCCAGCCGGCCAGCTGCAGGGGGGGCCGTCCACACAAGGGGACTCGACTTTGCGAGTGATAAGCCCACCACCACCCCTGCCCCTAGACCTCCAACCCCAGCCCCTACAATCGCCAGCCAGCCCCTGAGCCTGAGGCCCGAAGCCTGTAGACCTGCCGCTGGCGGAGCCGTGCACACCAGAGGCCTGGATTTCGCCTGCGACATCTACATCTGGGCCCCTCTGGCCGGCACCTGTGGCGTGCTGCTGCTGAGCCTGGTCATCACCCTGTACTGCAACCACCGGAATAGGAGCAAGCGGAGCAGAGGCGGCCACAGCGACTACATGAACATGACCCCCCGGAGGCCTGGCCCCACCCGGAAGCACTACCAGCCCTACGCCCCTCCCAGGGACTTCGCCGCCTACCGGAGCCGGGTGAAGTTCAGCCGGAGCGCCGACGCCCCTGCCTACCAGCAGGGCCAGAACCAGCTGTACAACGAGCTGAACCTGGGCCGGAGGGAGGAGTACGACGTGCTGGACAAGCGGAGAGGCCGGGACCCTGAGATGGGCGGCAAGCCCCGGAGAAAGAACCCTCAGGAGGGCCTGTATAACGAACTGCAGAAAGACAAGATGGCCGAGGCCTACAGCGAGATCGGCATGAAGGGCGAGCGGCGGAGGGGCAAGGGCCACGACGGCCTGTACCAGGGCCTGAGCACCGCCACCAAGGATACCTACGACGCCCTGCACATGCAGGCCCTGCCCCCCAGA |

TABLE 14-continued

| Additional Sequences | | | | |
|---|---|---|---|---|
| Name | SEQ ID NO | Amino Acid Sequence | SEQ ID NO | Nucleotide Sequence |
| hROR1 (VH-VL)_ 14-4. CD8a(3x). CD28z | 621 | EVQLVESGGGLVQPGGSLRLSCAASGFTFSSYAMSWVRQAPGKGLEWVASISRGGTTYYPDSVKGRFTISRDNVRNILYLQMSSLRSEDTAMYYCGRYDYDGYYAMDYWGQGTLVTVSSGGGGSGGGGSGGGGSDIQMTQSPSSLSASVGDRVTITCKASPDINSYLNWYQQKPGKAPKLLIYRANRLVDGVPSRFSGSGSGTDYTLTISSLQPEDFATYYCLQYDEFPYTFGAGTKVEIKKPTTTPAPRPPTPAPTIASQPLSLRPEASRPAAGGAVHTRGLDFASDKPTTTPAPRPPTPAPTIASQPLSLRPEASRPAAGGAVHTRGLDFASDKPTTTPAPRPPTPAPTIASQPLSLRPEACRPAAGGAVHTRGLDFACDIYIWAPLAGTCGVLLLSLVITLYCNHRNRSKRSRGGHSDYMNMTPRRPGPTRKHYQPYAPPRDFAAYRSRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | 622 | GAAGTGCAGCTTGTGGAGTCAGGAGGAGGGCTAGTTCAGCCAGGCGGCTCTCTGAGACTATCTTGTGCTGCCTCCGGCTTCACATTTAGCTCTTATGCAATGTCCTGGGTCCGCCAGGCCCCTGGTAAAGGCCTGGAATGGGTTGCTTCTATCTCTAGAGGCGGAACCACTTACTACCCTGATTCAGTGAAGGGGAGATTCACAATTAGTAGGGACAACGTGCGGAACATCCTCTACCTACAGATGTCAAGTTTACGCAGTGAGGACACTGCGATGTATTACTGCGGTCGATACGATTATGATGGATATTATGCAATGGATTATTGGGGCCAGGGCACTCTGGTCACAGTATCTTCCGGCGGCGGTGGTTCTGGCGGTGGTGGAAGCGGAGGGGGGGGGTCCGACATCCAGATGACCCAATCACCATCGAGTCTTAGTGCATCCGTTGGGGATAGAGTGACAATCACTTGTAAGGCATCCCCGGACATCAACTCATATCTTAATTGGTATCAGCAAAAGCCGGGCAAGGCCCCTAAGCTCCTGATTTATAGGGCCAACCGCCTTGTGGATGGAGTCCCCTCCCGCTTTAGTGGAAGCGGCTCTGGCACAGACTACACCCTGACTATCAGCTCCTTGCAGCCTGAGGATTTTGCTACCTACTACTGTCTTCAGTACGATGAATTTCCATACACTTTCGGTGCTGGGACAAAAGTGGAGATCAAAAAGCCTACCACCACCCCCGCACCTCGTCCTCCAACCCCTGCACCTACGATTGCCAGTCAGCCTCTTTCACTGCGGCCTGAGGCCAGCAGACCAGCTGCCGGCGGTGCCGTCCATACAAGAGGACTGGACTTCGCGTCCGATAAACCTACTACCACTCCAGCCCCAAGGCCCCCAACCCCAGCACCGACTATCGCATCACAGCCTTTGTCACTGCGTCCTGAAGCCAGCCGGCCAGCTGCAGGGGGGGCCGTCCACACAAGGGGACTCGACTTTGCGAGTGATAAGCCCACCACCACCCCTGCCCCTAGACCTCCAACCCCAGCCCCTACAATCGCCAGCCAGCCCCTGAGCCTGAGGCCCGAAGCCTGTAGACCTGCCGCTGGCGGAGCCGTGCACACCAGAGGCCTGGATTTCGCCTGCGACATCTACATCTGGGCCCCTCTGGCCGGCACCTGTGGCGTGCTGCTGCTGAGCCTGGTCATCACCCTGTACTGCAACCACCGGAATAGGAGCAAGCGGAGCAGAGGCGGCCACAGCGACTACATGAACATGACCCCCCGGAGGCCTGGCCCCACCCGGAAGCACTACCAGCCCTACGCCCCTCCCAGGGACTTCGCCGCCTACCGGAGCCGGGTGAAGTTCAGCCGGAGCGCCGACGCCCCTGCCTACCAGCAGGGCCAGAACCAGCTGTACAACGAGCTGAACCTGGGCCGGAGGGAGGAGT |

TABLE 14-continued

Additional Sequences

| Name | SEQ ID NO | Amino Acid Sequence | SEQ ID NO | Nucleotide Sequence |
|---|---|---|---|---|
| | | | | ACGACGTGCTGGACAAGCG GAGAGGCCGGGACCCTGA GATGGGCGGCAAGCCCCG GAGAAAGAACCCTCAGGAG GGCCTGTATAACGAACTGC AGAAAGACAAGATGGCCGA GGCCTACAGCGAGATCGGC ATGAAGGGCGAGCGGCGG AGGGGCAAGGGCCACGAC GGCCTGTACCAGGGCCTGA GCACCGCCACCAAGGATAC CTACGACGCCCTGCACATGC AGGCCCTGCCCCCCAGA |
| hROR1 (VH_5-VL_14). CD8a(3x). CD28z | 623 | EVQLVESGGGLVQPGGSLRLSCAA SGFTFSSYAMSWVRQAPGKGLEW VSSISRGGTTYYPDSVKGRFTISRDN SKNTLYLQMNSLRAEDTAVYYCGR YDYDGYYAMDYWGQGTLVTVSSG GGGSGGGGSGGGGSDIQMTQSPS SLSASVGDRVTITCKASPDINSYLN WYQQKPGKAPKLLIYRANRLVDGV PSRFSGSGSGTDYTLTISSLQPEDFA TYYCLQYDEFPYTFGAGTKVEIKKPT TTPAPRPPTPAPTIASQPLSLRPEAS RPAAGGAVHTRGLDFASDKPTTTP APRPPTPAPTIASQPLSLRPEASRPA AGGAVHTRGLDFASDKPTTTPAPR PPTPAPTIASQPLSLRPEACRPAAG GAVHTRGLDFACDIYIWAPLAGTC GVLLLSLVITLYCNHRNRSKRSRGG HSDYMNMTPRRPGPTRKHYQPYA PPRDFAAYRSRVKFSRSADAPAYQ QGQNQLYNELNLGRREEYDVLDKR RGRDPEMGGKPRRKNPQEGLYNE LQKDKMAEAYSEIGMKGERRRGK GHDGLYQGLSTATKDTYDALHMQ ALPPR | 624 | GAAGTGCAACTGGTCGAGT CTGGGGGCGGCCTTGTGCA ACCTGGAGGCAGCCTTCGA CTCAGTTGCGCCGCGTCTG GTTTTACCTTCTCCTCTTACG CGATGAGCTGGGTTCGCCA GGCCCCCGGCAAGGGACTT GAGTGGGTTAGTTCGATCT CCCGCGGAGGCACCACATA TTATCCTGACTCGGTTAAGG GACGCTTCACTATCTCTAGG GACAATTCAAAGAACACAC TGTATCTCCAAATGAACTCC TTGCGGGCCGAGGACACTG CTGTGTATTATTGCGGACG ATACGACTACGATGGGTAT TACGCCATGGATTACTGGG GGCAAGGTACACTGGTCAC TGTGAGTTCGGGGGGCGGC GGAAGTGGTGGAGGGGGA AGTGGTGGAGGAGGAAGC GATATACAGATGACACAGA GCCCTTCAAGTTTATCTGCA AGCGTCGGCGATCGTGTTA CAATAACTTGCAAGGCATCT CCCGACATCAATTCCTACCT CAACTGGTATCAGCAGAAG CCTGGGAAGGCTCCTAAGC TGCTTATTTACAGAGCAAAT CGCCTGGTGGACGGCGTGC CCAGTCGGTTTTCCGGGTCT GGGAGCGGAACGGATTACA CACTGACCATCTCAAGCCTG CAACCCGAAGACTTCGCTAC ATATTACTGCCTTCAGTATG ATGAGTTCCCATATACCTTC GGCGCTGGGACCAAGGTG GAGATAAAGAAGCCTACCA CCACCCCCGCACCTCGTCCT CCAACCCCTGCACCTACGAT TGCCAGTCAGCCTCTTTCAC TGCGGCCTGAGGCCAGCAG ACCAGCTGCCGGCGGTGCC GTCCATACAAGAGGACTGG ACTTCGCGTCCGATAAACCT ACTACCACTCCAGCCCCAAG GCCCCCAACCCCAGCACCG ACTATCGCATCACAGCCTTT GTCACTGCGTCCTGAAGCC AGCCGGCCAGCTGCAGGG GGGGCCGTCCACACAAGGG GACTCGACTTTGCGAGTGA TAAGCCCACCACCACCCCTG CCCCTAGACCTCCAACCCCA GCCCCTACAATCGCCAGCCA GCCCCTGAGCCTGAGGCCC GAAGCCTGTAGACCTGCCG CTGGCGGAGCCGTGCACAC CAGAGGCCTGGATTTCGCC TGCGACATCTACATCTGGG CCCCTCTGGCCGGCACCTGT |

TABLE 14-continued

| Additional Sequences | | | | |
|---|---|---|---|---|
| Name | SEQ ID NO | Amino Acid Sequence | SEQ ID NO | Nucleotide Sequence |
| | | | | GGCGTGCTGCTGCTGAGCC TGGTCATCACCCTGTACTGC AACCACCGGAATAGGAGCA AGCGGAGCAGAGGCGGCC ACAGCGACTACATGAACAT GACCCCCCGGAGGCCTGGC CCCACCCGGAAGCACTACC AGCCCTACGCCCCTCCCAGG GACTTCGCCGCCTACCGGA GCCGGGTGAAGTTCAGCCG GAGCGCCGACGCCCCTGCC TACCAGCAGGGCCAGAACC AGCTGTACAACGAGCTGAA CCTGGGCCGGAGGGAGGA GTACGACGTGCTGGACAAG CGGAGAGGCCGGGACCCT GAGATGGGCGGCAAGCCCC GGAGAAAGAACCCTCAGGA GGGCCTGTATAACGAACTG CAGAAAGACAAGATGGCCG AGGCCTACAGCGAGATCGG CATGAAGGGCGAGCGGCG GAGGGGCAAGGGCCACGA CGGCCTGTACCAGGGCCTG AGCACCGCCACCAAGGATA CCTACGACGCCCTGCACATG CAGGCCCTGCCCCCCAGA |
| hROR1 (VH_5-VL_16). CD8a(3x). CD28z | 625 | EVQLVESGGGLVQPGGSLRLSCAA SGFTFSSYAMSWVRQAPGKGLEW VSSISRGGTTYYPDSVKGRFTISRDN SKNTLYLQMNSLRAEDTAVYYCGR YDYDGYYAMDYWGQGTLVTVSSG GGGSGGGGSGGGGSDIQMTQSPS SLSASVGDRVTITCKASPDINSYLN WYQQKPGKAPKVLIYRANRLVDG VPSRFSGSGSGTDYTLTISSLQPEDF ATYYCLQYDEFPYTFGQGTKVEIKK PTTTPAPRPPTPAPTIASQPLSLRPE ASRPAAGGAVHTRGLDFASDKPTT TPAPRPPTPAPTIASQPLSLRPEASR PAAGGAVHTRGLDFASDKPTTTPA PRPPTPAPTIASQPLSLRPEACRPAA GGAVHTRGLDFACDIYIWAPLAGT CGVLLLSLVITLYCNHRNRSKRSRG GHSDYMNMTPRRPGPTRKHYQPY APPRDFAAYRSRVKFSRSADAPAY QQGQNQLYNELNLGRREEYDVLD KRRGRDPEMGGKPRRKNPQEGLY NELQKDKMAEAYSEIGMKGERRR GKGHDGLYQGLSTATKDTYDALH MQALPPR | 626 | GAAGTGCAACTGGTCGAGT CTGGGGGCGGCCTTGTGCA ACCTGGAGGCAGCCTTCGA CTCAGTTGCGCCGCGTCTG GTTTTACCTTCTCCTCTTACG CGATGAGCTGGGTTCGCCA GGCCCCCGGCAAGGGACTT GAGTGGGTTAGTTCGATCT CCCGCGGAGGCACCACATA TTATCCTGACTCGGTTAAGG GACGCTTCACTATCTCTAGG GACAATTCAAAGAACACAC TGTATCTCCAAATGAACTCC TTGCGGGCCGAGGACACTG CTGTGTATTATTGCGGACG ATACGACTACGATGGGTAT TACGCCATGGATTACTGGG GGCAAGGTACACTGGTCAC TGTGAGTTCGGGGGGCGGC GGAAGTGGTGGAGGGGGA AGTGGTGGAGGAGGAAGC GATATTCAGATGACCCAGTC GCCCAGCAGTCTCTCGGCCT CAGTGGGCGACCGGGTCAC TATCACTTGCAAAGCAAGTC CTGATATAAACTCCTATCTT AATTGGTATCAGCAGAAGC CCGGCAAGGCACCTAAGGT TCTGATATATCGCGCAAATC GGCTCGTGGATGGAGTACC CAGCCGATTTTCCGGCAGC GGCTCAGGCACTGACTACA CACTGACAATCAGCAGCTT GCAGCCTGAAGATTTCGCC ACATACTATTGTCTACAGTA CGACGAGTTCCCTTATACAT TCGGCCAGGGGACCAAGGT CGAGATCAAGAAGCCTACC ACCACCCCCGCACCTCGTCC TCCAACCCCTGCACCTACGA TTGCCAGTCAGCCTCTTTCA CTGCGGCCTGAGGCCAGCA GACCAGCTGCCGGCGGTGC CGTCCATACAAGAGGACTG GACTTCGCGTCCGATAAACC TACTACCACTCCAGCCCCAA GGCCCCCAACCCCAGCACC |

TABLE 14-continued

| Additional Sequences | | | | |
|---|---|---|---|---|
| Name | SEQ ID NO | Amino Acid Sequence | SEQ ID NO | Nucleotide Sequence |
| | | | | GACTATCGCATCACAGCCTT TGTCACTGCGTCCTGAAGCC AGCCGGCCAGCTGCAGGG GGGGCCGTCCACACAAGGG GACTCGACTTTGCGAGTGA TAAGCCCACCACCACCCCTG CCCCTAGACCTCCAACCCCA GCCCCTACAATCGCCAGCCA GCCCCTGAGCCTGAGGCCC GAAGCCTGTAGACCTGCCG CTGGCGGAGCCGTGCACAC CAGAGGCCTGGATTTCGCC TGCGACATCTACATCTGGG CCCCTCTGGCCGGCACCTGT GGCGTGCTGCTGCTGAGCC TGGTCATCACCCTGTACTGC AACCACCGGAATAGGAGCA AGCGGAGCAGAGGCGGCC ACAGCGACTACATGAACAT GACCCCCCGGAGGCCTGGC CCCACCCGGAAGCACTACC AGCCCTACGCCCCTCCCAGG GACTTCGCCGCCTACCGGA GCCGGGTGAAGTTCAGCCG GAGCGCCGACGCCCCTGCC TACCAGCAGGGCCAGAACC AGCTGTACAACGAGCTGAA CCTGGGCCGGAGGGAGGA GTACGACGTGCTGGACAAG CGGAGAGGCCGGGACCCT GAGATGGGCGGCAAGCCCC GGAGAAAGAACCCTCAGGA GGGCCTGTATAACGAACTG CAGAAAGACAAGATGGCCG AGGCCTACAGCGAGATCGG CATGAAGGGCGAGCGGCG GAGGGGCAAGGGCCACGA CGGCCTGTACCAGGGCCTG AGCACCGCCACCAAGGATA CCTACGACGCCCTGCACATG CAGGCCCTGCCCCCCAGA |
| hROR1 (VH_18-VL_04). CD8a(3x). CD28z | 627 | EVQLVESGGGLVQPGGSLRLSCSAS GFTFSSYAMSWVRQVPGKGLVWI SSISRGGTTYYADSVRGRFIISRDNA KNTLYLEMNNLRGEDTAVYYCARY DYDGYYAMDYWGQGTLVTVSSG GGGSGGGGSGGGGSDIQMTQSPS SLSASVGDRVTITCQASPDINSYLN WYQQKPGKAPKLLIYRANNLETGV PSRFSGSGSGTDFTLTISSLQPEDIA TYYCLQYDEFPYTFGQGTKLEIKKPT TTPAPRPPTPAPTIASQPLSLRPEAS RPAAGGAVHTRGLDFASDKPTTTP APRPPTPAPTIASQPLSLRPEASRPA AGGAVHTRGLDFASDKPTTTPAPR PPTPAPTIASQPLSLRPEACRPAAG GAVHTRGLDFACDIYIWAPLAGTC GVLLLSLVITLYCNHRNRSKRSRGG HSDYMNMTPRRPGPTRKHYQPYA PPRDFAAYRSRVKFSRSADAPAYQ QGQNQLYNELNLGRREEYDVLDKR RGRDPEMGGKPRRKNPQEGLYNE LQKDKMAEAYSEIGMKGERRRGK GHDGLYQGLSTATKDTYDALHMQ ALPPR | 628 | GAGGTTCAACTCGTGGAGT CTGGAGGCGGGCTAGTGCA GCCTGGCGGCTCCCTGCGA CTGTCTTGCAGCGCATCAG GCTTTACATTCAGTTCTTAT GCCATGAGCTGGGTGAGGC AGGTGCCCGGCAAGGGTCT GGTGTGGATCAGCTCAATC TCCAGGGGCGGGACTACAT ATTACGCCGATTCGGTCAG GGGTCGTTTTATCATTAGCA GGGATAATGCCAAGAACAC CTTGTATTTGGAGATGAAC AACCTAAGAGGCGAAGACA CCGCTGTGTACTATTGTGCC CGTTACGACTACGATGGGT ACTACGCCATGGACTATTG GGGCCAGGGAACCTTGGTG ACTGTGTCAAGTGGCGGGG GCGGCAGCGGAGGCGGTG GCAGCGGAGGCGGCGGTT CTGATATTCAAATGACGCAA AGTCCCAGCAGCCTCTCCGC CTCCGTTGGAGACAGGGTG ACTATTACATGCCAAGCCAG CCCCGATATTAATAGCTACT TAAATTGGTATCAGCAGAA ACCTGGGAAGGCACCTAAA CTTCTCATCTACCGCGCTAA CAATCTGGAGACCGGCGTG CCGTCTAGATTTTCCGGCTC TGGATCAGGGACCGATTTT ACTCTGACAATTAGTTCCCT |

TABLE 14-continued

| Additional Sequences | | | | |
|---|---|---|---|---|
| Name | SEQ ID NO | Amino Acid Sequence | SEQ ID NO | Nucleotide Sequence |
| | | | | GCAACCCGAAGACATCGCC<br>ACTTATTATTGCCTGCAATA<br>TGATGAGTTTCCTTACACAT<br>TTGGTCAGGGAACTAAACT<br>AGAGATTAAGAAGCCTACC<br>ACCACCCCCGCACCTCGTCC<br>TCCAACCCCTGCACCTACGA<br>TTGCCAGTCAGCCTCTTTCA<br>CTGCGGCCTGAGGCCAGCA<br>GACCAGCTGCCGGCGGTGC<br>CGTCCATACAAGAGGACTG<br>GACTTCGCGTCCGATAAACC<br>TACTACCACTCCAGCCCCAA<br>GGCCCCCAACCCCAGCACC<br>GACTATCGCATCACAGCCTT<br>TGTCACTGCGTCCTGAAGCC<br>AGCCGGCCAGCTGCAGGG<br>GGGGCCGTCCACACAAGGG<br>GACTCGACTTTGCGAGTGA<br>TAAGCCCACCACCACCCCTG<br>CCCCTAGACCTCCAACCCCA<br>GCCCCTACAATCGCCAGCCA<br>GCCCCTGAGCCTGAGGCCC<br>GAAGCCTGTAGACCTGCCG<br>CTGGCGGAGCCGTGCACAC<br>CAGAGGCCTGGATTTCGCC<br>TGCGACATCTACATCTGGG<br>CCCCTCTGGCCGGCACCTGT<br>GGCGTGCTGCTGCTGAGCC<br>TGGTCATCACCCTGTACTGC<br>AACCACCGGAATAGGAGCA<br>AGCGGAGCAGAGGCGGCC<br>ACAGCGACTACATGAACAT<br>GACCCCCCGGAGGCCTGGC<br>CCCACCCGGAAGCACTACC<br>AGCCCTACGCCCCTCCCAGG<br>GACTTCGCCGCCTACCGGA<br>GCCGGGTGAAGTTCAGCCG<br>GAGCGCCGACGCCCCTGCC<br>TACCAGCAGGGCCAGAACC<br>AGCTGTACAACGAGCTGAA<br>CCTGGGCCGGAGGGAGGA<br>GTACGACGTGCTGGACAAG<br>CGGAGAGGCCGGGACCCT<br>GAGATGGGCGGCAAGCCCC<br>GGAGAAAGAACCCTCAGGA<br>GGGCCTGTATAACGAACTG<br>CAGAAAGACAAGATGGCCG<br>AGGCCTACAGCGAGATCGG<br>CATGAAGGGCGAGCGGCG<br>GAGGGGCAAGGGCCACGA<br>CGGCCTGTACCAGGGCCTG<br>AGCACCGCCACCAAGGATA<br>CCTACGACGCCCTGCACATG<br>CAGGCCCTGCCCCCCAGA<br>GAGGTTCAACTCGTGGAGT<br>CTGGAGGCGGGCTAGTGCA<br>GCCTGGCGGCTCCCTGCGA<br>CTGTCTTGCAGCGCATCAG<br>GCTTTACATTCAGTTCTTAT<br>GCCATGAGCTGGGTGAGGC<br>AGGTGCCCGGCAAGGGTCT<br>GGTGTGGATCAGCTCAATC<br>TCCAGGGGCGGGACTACAT |

TABLE 14-continued

| Additional Sequences | | | | |
|---|---|---|---|---|
| Name | SEQ ID NO | Amino Acid Sequence | SEQ ID NO | Nucleotide Sequence |
| hROR1 (VH_18-VL_14). CD8a(3x). CD28z | 629 | EVQLVESGGGLVQPGGSLRLSCSAS GFTFSSYAMSWVRQVPGKGLVWI SSISRGGTTYYADSVRGRFIISRDNA KNTLYLEMNNLRGEDTAVYYCARY DYDGYYAMDYWGQGTLVTVSSG GGGSGGGGSGGGGSDIQMTQSPS SLSASVGDRVTITCKASPDINSYLN WYQQKPGKAPKLLIYRANRLVDGV PSRFSGSGSGTDYTLTISSLQPEDFA TYYCLQYDEFPYTFGAGTKVEIKKPT TTPAPRPPTPAPTIASQPLSLRPEAS RPAAGGAVHTRGLDFASDKPTTTP APRPPTPAPTIASQPLSLRPEASRPA AGGAVHTRGLDFASDKPTTTPAPR PPTPAPTIASQPLSLRPEACRPAAG GAVHTRGLDFACDIYIWAPLAGTC GVLLLSLVITLYCNHRNRSKRSRGG HSDYMNMTPRRPGPTRKHYQPYA PPRDFAAYRSRVKFSRSADAPAYQ QGQNQLYNELNLGRREEYDVLDKR RGRDPEMGGKPRRKNPQEGLYNE LQKDKMAEAYSEIGMKGERRRGK GHDGLYQGLSTATKDTYDALHMQ ALPPR | 630 | ATTACGCCGATTCGGTCAG GGGTCGTTTTATCATTAGCA GGGATAATGCCAAGAACAC CTTGTATTTGGAGATGAAC AACCTAAGAGGCGAAGACA CCGCTGTGTACTATTGTGCC CGTTACGACTACGATGGGT ACTACGCCATGGACTATTG GGGCCAGGGAACCTTGGTG ACTGTGTCAAGTGGCGGGG GCGGCAGCGGAGGCGGTG GCAGCGGAGGCGGCGGTT CTGATATACAGATGACACA GAGCCCTTCAAGTTTATCTG CAAGCGTCGGCGATCGTGT TACAATAACTTGCAAGGCAT CTCCCGACATCAATTCCTAC CTCAACTGGTATCAGCAGA AGCCTGGGAAGGCTCCTAA GCTGCTTATTTACAGAGCAA ATCGCCTGGTGGACGGCGT GCCCAGTCGGTTTTCCGGG TCTGGGAGCGGAACGGATT ACACACTGACCATCTCAAGC CTGCAACCCGAAGACTTCG CTACATATTACTGCCTTCAG TATGATGAGTTCCCATATAC CTTCGGCGCTGGGACCAAG GTGGAGATAAAGAAGCCTA CCACCACCCCCGCACCTCGT CCTCCAACCCCTGCACCTAC GATTGCCAGTCAGCCTCTTT CACTGCGGCCTGAGGCCAG CAGACCAGCTGCCGGCGGT GCCGTCCATACAAGAGGAC TGGACTTCGCGTCCGATAA ACCTACTACCACTCCAGCCC CAAGGCCCCCAACCCCAGC ACCGACTATCGCATCACAGC CTTTGTCACTGCGTCCTGAA GCCAGCCGGCCAGCTGCAG GGGGGGCCGTCCACACAAG GGGACTCGACTTTGCGAGT GATAAGCCCACCACCACCCC TGCCCCTAGACCTCCAACCC CAGCCCCTACAATCGCCAGC CAGCCCCTGAGCCTGAGGC CCGAAGCCTGTAGACCTGC CGCTGGCGGAGCCGTGCAC ACCAGAGGCCTGGATTTCG CCTGCGACATCTACATCTGG GCCCCTCTGGCCGGCACCT GTGGCGTGCTGCTGCTGAG CCTGGTCATCACCCTGTACT GCAACCACCGGAATAGGAG CAAGCGGAGCAGAGGCGG CCACAGCGACTACATGAAC ATGACCCCCCGGAGGCCTG GCCCCACCCGGAAGCACTA CCAGCCCTACGCCCCTCCCA GGGACTTCGCCGCCTACCG GAGCCGGGTGAAGTTCAGC CGGAGCGCCGACGCCCCTG CCTACCAGCAGGGCCAGAA CCAGCTGTACAACGAGCTG AACCTGGGCCGGAGGGAG GAGTACGACGTGCTGGACA AGCGGAGAGGCCGGGACC CTGAGATGGGCGGCAAGCC CCGGAGAAAGAACCCTCAG GAGGGCCTGTATAACGAAC TGCAGAAAGACAAGATGGC CGAGGCCTACAGCGAGATC GGCATGAAGGGCGAGCGG |

TABLE 14-continued

| Name | SEQ ID NO | Amino Acid Sequence | SEQ ID NO | Nucleotide Sequence |
|---|---|---|---|---|
| Additional Sequences | | | | |
| | | | | CGGAGGGGCAAGGGCCAC GACGGCCTGTACCAGGGCC TGAGCACCGCCACCAAGGA TACCTACGACGCCCTGCACA TGCAGGCCCTGCCCCCCAG A |
| IgG4-Fc 12 amino acid hinge region | 631 | ESKYGPPCPPCP | | |
| RTS-COMPONENTS | | | | |
| VP16 activation domain | 632 | GPKKKRKVAPPTDVSLGDELHLDG EDVAMAHADALDDFDLDMLGDG DSPGPGFTPHDSAPYGALDMADF EFEQMFTDALGIDEYGG | 633 | GGCCCCAAGAAGAAAAGG AAGGTGGCCCCCCCCACCG ACGTGAGCCTGGGCGACGA GCTGCACCTGGACGGCGAG GACGTGGCCATGGCCCACG CCGACGCCCTGGACGACTT CGACCTGGACATGCTGGGC GACGGCGACAGCCCCGGCC CCGGCTTCACCCCCCACGAC AGCGCCCCCTACGGCGCCC TGGACATGGCCGACTTCGA GTTCGAGCAGATGTTCACC GACGCCCTGGGCATCGACG AGTACGGCGGC |
| Retinoid x receptor (RxR) | 634 | EMPVDRILEAELAVEQKSDQGVEG PGGTGGSGSSPNDPVTNICQAADK QLFTLVEWAKRIPHFSSLPLDDQVIL LRAGWNELLIASFSHRSIDVRDGILL ATGLHVHRNSAHSAGVGAIFDRVL TELVSKMRDMRMDKTELGCLRAII LFNPEVRGLKSAQEVELLREKVYAA LEEYTRTTHPDEPGRFAKLLLRLPSL RSIGLKCLEHLFFFRLIGDVPIDTFLM EMLESPSDS | 635 | GAGATGCCCGTGGACAGGA TTCTGGAGGCCGAACTCGC CGTGGAGCAGAAAAGCGAC CAGGGCGTGGAGGGCCCC GGCGGAACCGGCGGCAGC GGCAGCAGCCCCAACGACC CCGTGACCAACATCTGCCA GGCCGCCGACAAGCAGCTG TTCACCCTGGTGGAGTGGG CCAAGAGGATTCCCCACTTC AGCAGCCTGCCCCTGGACG ACCAGGTGATCCTGCTGAG GGCCGGATGGAACGAGCTG CTGATCGCCAGCTTCAGCCA CAGGAGCATCGACGTGAGG GACGGCATCCTGCTGGCCA CCGGCCTGCACGTCCATAG GAACAGCGCCCACAGCGCC GGAGTGGGCGCCATCTTCG ACAGGGTGCTGACCGAGCT GGTGAGCAAGATGAGGGA CATGAGGATGGACAAGACC GAGCTGGGCTGCCTGAGGG CCATCATCCTGTTCAACCCC GAGGTGAGGGGCCTGAAA AGCGCCCAGGAGGTGGAG CTGCTGAGGGAGAAGGTGT ACGCCGCCCTGGAGGAGTA CACCAGGACCACCCACCCC GACGAGCCCGGCAGATTCG CCAAGCTGCTGCTGAGGCT GCCCAGCCTGAGGAGCATC GGCCTGAAGTGCCTGGAGC ACCTGTTCTTCTTCAGGCTG ATCGGCGACGTGCCCATCG ACACCTTCCTGATGGAGAT GCTGGAGAGCCCCAGCGAC AGC |
| VP16-linker-RxR | 636 | GPKKKRKVAPPTDVSLGDELHLDG EDVAMAHADALDDFDLDMLGDG DSPGPGFTPHDSAPYGALDMADF EFEQMFTDALGIDEYGGEFEMPVD RILEAELAVEQKSDQGVEGPGGTG GSGSSPNDPVTNICQAADKQLFTL VEWAKRIPHFSSLPLDDQVILLRAG WNELLIASFSHRSIDVRDGILLATGL | 637 | GGCCCCAAGAAGAAAAGG AAGGTGGCCCCCCCCACCG ACGTGAGCCTGGGCGACGA GCTGCACCTGGACGGCGAG GACGTGGCCATGGCCCACG CCGACGCCCTGGACGACTT CGACCTGGACATGCTGGGC GACGGCGACAGCCCCGGCC |

TABLE 14-continued

| Additional Sequences | | | | |
|---|---|---|---|---|
| Name | SEQ ID NO | Amino Acid Sequence | SEQ ID NO | Nucleotide Sequence |
| | | HVHRNSAHSAGVGAIFDRVLTELV SKMRDMRMDKTELGCLRAIILFNP EVRGLKSAQEVELLREKVYAALEEY TRTTHPDEPGRFAKLLLRLPSLRSIG LKCLEHLFFFRLIGDVPIDTFLMEML ESPSDS | | CCGGCTTCACCCCCCACGAC AGCGCCCCCTACGGCGCCC TGGACATGGCCGACTTCGA GTTCGAGCAGATGTTCACC GACGCCCTGGGCATCGACG AGTACGGCGGCGAATTCGA GATGCCCGTGGACAGGATT CTGGAGGCCGAACTCGCCG TGGAGCAGAAAAGCGACCA GGGCGTGGAGGGCCCCGG CGGAACCGGCGGCAGCGG CAGCAGCCCCAACGACCCC GTGACCAACATCTGCCAGG CCGCCGACAAGCAGCTGTT CACCCTGGTGGAGTGGGCC AAGAGGATTCCCCACTTCA GCAGCCTGCCCCTGGACGA CCAGGTGATCCTGCTGAGG GCCGGATGGAACGAGCTGC TGATCGCCAGCTTCAGCCAC AGGAGCATCGACGTGAGG GACGGCATCCTGCTGGCCA CCGGCCTGCACGTCCATAG GAACAGCGCCCACAGCGCC GGAGTGGGCGCCATCTTCG ACAGGGTGCTGACCGAGCT GGTGAGCAAGATGAGGGA CATGAGGATGGACAAGACC GAGCTGGGCTGCCTGAGGG CCATCATCCTGTTCAACCCC GAGGTGAGGGGCCTGAAA AGCGCCCAGGAGGTGGAG CTGCTGAGGGAGAAGGTGT ACGCCGCCCTGGAGGAGTA CACCAGGACCACCCACCCC GACGAGCCCGGCAGATTCG CCAAGCTGCTGCTGAGGCT GCCCAGCCTGAGGAGCATC GGCCTGAAGTGCCTGGAGC ACCTGTTCTTCTTCAGGCTG ATCGGCGACGTGCCCATCG ACACCTTCCTGATGGAGAT GCTGGAGAGCCCCAGCGAC AGC |
| GAL4 DNA Binding Domain | 638 | MKLLSSIEQACDICRLKKLKCSKEKP KCAKCLKNNWECRYSPKTKRSPLTR AHLTEVESRLERLEQLFLLIFPREDLD MILKMDSLQDIKALLTGLFVQDNV NKDAVTDRLASVETDMPLTLRQHR ISATSSSEESSNKGQRQLTVSPEF | 639 | ATGAAGCTGCTGAGCAGCA TCGAGCAGGCTTGCGACAT CTGCAGGCTGAAGAAGCTG AAGTGCAGCAAGGAGAAG CCCAAGTGCGCCAAGTGCC TGAAGAACAACTGGGAGTG CAGATACAGCCCCAAGACC AAGAGGAGCCCCCTGACCA GGGCCCACCTGACCGAGGT GGAGAGCAGGCTGGAGAG GCTGGAGCAGCTGTTCCTG CTGATCTTCCCCAGGGAGG ACCTGGACATGATCCTGAA GATGGACAGCCTGCAAGAC ATCAAGGCCCTGCTGACCG GCCTGTTCGTGCAGGACAA CGTGAACAAGGACGCCGTG ACCGACAGGCTGGCCAGCG TGGAGACCGACATGCCCCT GACCCTGAGGCAGCACAGG ATCAGCGCCACCAGCAGCA GCGAGGAGAGCAGCAACA AGGGCCAGAGGCAGCTGAC CGTGAGCCCCGAGTTT |

TABLE 14-continued

| Additional Sequences | | | | |
|---|---|---|---|---|
| Name | SEQ ID NO | Amino Acid Sequence | SEQ ID NO | Nucleotide Sequence |
| Ecdysone Receptor Ligand Binding Domain-VY variant (EcR) | 640 | IRPECVVPETQCAMKRKEKKAQKE<br>KDKLPVSTTTVDDHMPPIMQCEPP<br>PPEAARIHEVVPRFLSDKLLVTNRQ<br>KNIPQLTANQQFLIARLIWYQDGYE<br>QPSDEDLKRITQTWQQADDENEE<br>SDTPFRQITEMTILTVQLIVEFAKGL<br>PGFAKISQPDQITLLKACSSEVMML<br>RVARRYDAASDSILFANNQAYTRD<br>NYRKAGMAEVIEDLLHFCRCMYS<br>MALDNIHYALLTAVVIFSDRPGLEQ<br>PQLVEEIQRYYLNTLRIYILNQLSGS<br>ARSSVIYGKILSILSELRTLGMQNSN<br>MCISLKLKNRKLPPFLEEIWDVAD<br>MSHTQPPPILESPTNL | 641 | ATCAGGCCCGAGTGCGTGG<br>TGCCCGAGACCCAGTGCGC<br>CATGAAAAGGAAGGAGAA<br>GAAGGCCCAGAAGGAGAA<br>GGACAAGCTGCCCGTGAGC<br>ACCACCACCGTCGATGACC<br>ACATGCCCCCCATCATGCAG<br>TGCGAGCCCCCCCCCCCGA<br>GGCCGCCAGGATTCACGAG<br>GTCGTGCCCAGGTTCCTGA<br>GCGACAAGCTGCTGGTGAC<br>CAACAGGCAGAAGAACATC<br>CCCCAGCTGACCGCCAACC<br>AGCAGTTCCTGATCGCCAG<br>GCTGATCTGGTATCAGGAC<br>GGCTACGAGCAGCCCAGCG<br>ACGAGGACCTGAAAAGGAT<br>CACCCAGACCTGGCAGCAG<br>GCCGACGACGAGAACGAG<br>GAGAGCGACACCCCCTTCA<br>GGCAGATCACCGAGATGAC<br>CATCCTGACCGTGCAGCTG<br>ATCGTGGAGTTCGCCAAGG<br>GCCTGCCCGGATTCGCCAA<br>GATCAGCCAGCCCGACCAG<br>ATCACCCTGCTGAAGGCTT<br>GCAGCAGCGAGGTGATGAT<br>GCTGAGGGTGGCCAGGAG<br>GTACGACGCCGCCAGCGAC<br>AGCATCCTGTTCGCCAACAA<br>CCAGGCTTACACCAGGGAC<br>AACTACAGGAAGGCTGGCA<br>TGGCCGAGGTGATCGAGGA<br>CCTCCTGCACTTCTGCAGAT<br>GTATGTACAGCATGGCCCT<br>GGACAACATCCACTACGCC<br>CTGCTGACCGCCGTGGTGA<br>TCTTCAGCGACAGGCCCGG<br>CCTGGAGCAGCCCCAGCTG<br>GTGGAGGAGATCCAGAGGT<br>ACTACCTGAACACCCTGAG<br>GATCTACATCCTGAACCAGC<br>TGAGCGGCAGCGCCAGGA<br>GCAGCGTGATCTACGGCAA<br>GATCCTGAGCATCCTGAGC<br>GAGCTGAGGACCCTGGGAA<br>TGCAGAACAGCAATATGTG<br>TATCAGCCTGAAGCTGAAG<br>AACAGGAAGCTGCCCCCCT<br>TCCTGGAGGAGATTTGGGA<br>CGTGGCCGACATGAGCCAC<br>ACCCAGCCCCCCCCCATCCT<br>GGAGAGCCCCACCAACCTG |
| Ecdysone Receptor Ligand Binding Domain_VY variant (EcR) | 642 | RPECVVPETQCAMKRKEKKAQKEK<br>DKLPVSTTTVDDHMPPIMQCEPPP<br>PEAARIHEVVPRFLSDKLLVTNRQK<br>NIPQLTANQQFLIARLIWYQDGYE<br>QPSDEDLKRITQTWQQADDENEE<br>SDTPFRQITEMTILTVQLIVEFAKGL<br>PGFAKISQPDQITLLKACSSEVMML<br>RVARRYDAASDSILFANNQAYTRD<br>NYRKAGMAEVIEDLLHFCRCMYS<br>MALDNIHYALLTAVVIFSDRPGLEQ<br>PQLVEEIQRYYLNTLRIYILNQLSGS<br>ARSSVIYGKILSILSELRTLGMQNSN<br>MCISLKLKNRKLPPFLEEIWDVAD<br>MSHTQPPPILESPTNL | 643 | CGGCCTGAGTGCGTAGTAC<br>CCGAGACTCAGTGCGCCAT<br>GAAGCGGAAAGAGAAGAA<br>AGCACAGAAGGAGAAGGA<br>CAAACTGCCTGTCAGCACG<br>ACGACGGTGGACGACCACA<br>TGCCGCCCATTATGCAGTGT<br>GAACCTCCACCTCCTGAAGC<br>AGCAAGGATTCACGAAGTG<br>GTCCCAAGGTTTCTCTCCGA<br>CAAGCTGTTGGTGACAAAC<br>CGGCAGAAAAACATCCCCC<br>AGTTGACAGCCAACCAGCA<br>GTTCCTTATCGCCAGGCTCA<br>TCTGGTACCAGGACGGGTA<br>CGAGCAGCCTTCTGATGAA<br>GATTTGAAGAGGATTACGC<br>AGACGTGGCAGCAAGCGG<br>ACGATGAAAACGAAGAGTC<br>GGACACTCCCTTCCGCCAGA |

TABLE 14-continued

| Additional Sequences | | | | |
|---|---|---|---|---|
| Name | SEQ ID NO | Amino Acid Sequence | SEQ ID NO | Nucleotide Sequence |
| | | | | TCACAGAGATGACTATCCTC ACGGTCCAACTTATCGTGG AGTTCGCGAAGGGATTGCC AGGGTTCGCCAAGATCTCG CAGCCTGATCAAATTACGCT GCTTAAGGCTTGCTCAAGT GAGGTAATGATGCTCCGAG TCGCGCGACGATACGATGC GGCCTCAGACAGTATTCTGT TCGCGAACAACCAAGCGTA CACTCGCGACAACTACCGC AAGGCTGGCATGGCCGAGG TCATCGAGGATCTACTGCAC TTCTGCCGGTGCATGTACTC TATGGCGTTGGACAACATC CATTACGCGCTGCTCACGG CTGTCGTCATCTTTTCTGAC CGGCCAGGGTTGGAGCAGC CGCAACTGGTGGAAGAGAT CCAGCGGTACTACCTGAAT ACGCTCCGCATCTATATCCT GAACCAGCTGAGCGGGTCG GCGCGTTCGTCCGTCATATA CGGCAAGATCCTCTCAATCC TCTCTGAGCTACGCACGCTC GGCATGCAAAACTCCAACA TGTGCATCTCCCTCAAGCTC AAGAACAGAAAGCTGCCGC CTTTCCTCGAGGAGATCTG GGATGTGGCGGACATGTCG CACACCCAACCGCCGCCTAT CCTCGAGTCCCCCACGAATC TCTAG |
| GAL4-Linker-EcR | 644 | MKLLSSIEQACDICRLKKLKCSKEKP KCAKCLKNNWECRYSPKTKRSPLTR AHLTEVESRLERLEQLFLLIFPREDLD MILKMDSLQDIKALLTGLFVQDNV NKDAVTDRLASVETDMPLTLRQHR ISATSSSEESSNKGQRQLTVSPEFPG IRPECVVPETQCAMKRKEKKAQKE KDKLPVSTTTVDDHMPPIMQCEPP PPEAARIHEVVPRFLSDKLLVTNRQ KNIPQLTANQQFLIARLIWYQDGYE QPSDEDLKRITQTWQQADDENEE SDTPFRQITEMTILTVQLIVEFAKGL PGFAKISQPDQITLLKACSSEVMML RVARRYDAASDSILFANNQAYTRD NYRKAGMAEVIEDLLHFCRCMYS MALDNIHYALLTAVVIFSDRPGLEQ PQLVEEIQRYYLNTLRIYILNQLSGS ARSSVIYGKILSILSELRTLGMQNSN MCISLKLKNRKLPPFLEEIWDVAD MSHTQPPPILESPTNL | 645 | ATGAAGCTACTGTCTTCTAT CGAACAAGCATGCGATATT TGCCGACTTAAAAAGCTCA AGTGCTCCAAAGAAAAACC GAAGTGCGCCAAGTGTCTG AAGAACAACTGGGAGTGTC GCTACTCTCCCAAAACCAAA AGGTCTCCGCTGACTAGGG CACATCTGACAGAAGTGGA ATCAAGGCTAGAAAGACTG GAACAGCTATTTCTACTGAT TTTTCCTCGAGAAGACCTTG ACATGATTTTGAAAATGGAT TCTTTACAGGATATAAAAGC ATTGTTAACAGGATTATTTG TACAAGATAATGTGAATAA AGATGCCGTCACAGATAGA TTGGCTTCAGTGGAGACTG ATATGCCTCTAACATTGAGA CAGCATAGAATAAGTGCGA CATCATCATCGGAAGAGAG TAGTAACAAAGGTCAAAGA CAGTTGACTGTATCGCCGG AATTCCCGGGGATCCGGCC TGAGTGCGTAGTACCCGAG ACTCAGTGCGCCATGAAGC GGAAAGAGAAGAAAGCAC AGAAGGAGAAGGACAAAC TGCCTGTCAGCACGACGAC GGTGGACGACCACATGCCG CCCATTATGCAGTGTGAACC TCCACCTCCTGAAGCAGCAA GGATTCACGAAGTGGTCCC AAGGTTTCTCTCCGACAAGC TGTTGGTGACAAACCGGCA GAAAAACATCCCCCAGTTG ACAGCCAACCAGCAGTTCCT TATCGCCAGGCTCATCTGGT ACCAGGACGGGTACGAGCA GCCTTCTGATGAAGATTTGA AGAGGATTACGCAGACGTG |

TABLE 14-continued

Additional Sequences

| Name | SEQ ID NO | Amino Acid Sequence | SEQ ID NO | Nucleotide Sequence |
|---|---|---|---|---|
| | | | | GCAGCAAGCGGACGATGAA AACGAAGAGTCGGACACTC CCTTCCGCCAGATCACAGA GATGACTATCCTCACGGTCC AACTTATCGTGGAGTTCGC GAAGGGATTGCCAGGGTTC GCCAAGATCTCGCAGCCTG ATCAAATTACGCTGCTTAAG GCTTGCTCAAGTGAGGTAA TGATGCTCCGAGTCGCGCG ACGATACGATGCGGCCTCA GACAGTATTCTGTTCGCGA ACAACCAAGCGTACACTCG CGACAACTACCGCAAGGCT GGCATGGCCGAGGTCATCG AGGATCTACTGCACTTCTGC CGGTGCATGTACTCTATGG CGTTGGACAACATCCATTAC GCGCTGCTCACGGCTGTCG TCATCTTTTCTGACCGGCCA GGGTTGGAGCAGCCGCAAC TGGTGGAAGAGATCCAGCG GTACTACCTGAATACGCTCC GCATCTATATCCTGAACCAG CTGAGCGGGTCGGCGCGTT CGTCCGTCATATACGGCAA GATCCTCTCAATCCTCTCTG AGCTACGCACGCTCGGCAT GCAAAACTCCAACATGTGC ATCTCCCTCAAGCTCAAGAA CAGAAAGCTGCCGCCTTTCC TCGAGGAGATCTGGGATGT GGCGGACATGTCGCACACC CAACCGCCGCCTATCCTCGA GTCCCCCACGAATCTCTAG |
| GAL4-Linker-EcR | 646 | MKLLSSIEQACDICRLKKLKCSKEKP KCAKCLKNNWECRYSPKTKRSPLTR AHLTEVESRLERLEQLFLLIFPREDLD MILKMDSLQDIKALLTGLFVQDNV NKDAVTDRLASVETDMPLTLRQHR ISATSSSEESSNKGQRQLTVSPEFPG RPECVVPETQCAMKRKEKKAQKEK DKLPVSTTTVDDHMPPIMQCEPPP PEAARIHEVVPRFLSDKLLVTNRQK NIPQLTANQQFLIARLIWYQDGYE QPSDEDLKRITQTWQQADDENEE SDTPFRQITEMTILTVQLIVEFAKGL PGFAKISQPDQITLLKACSSEVMML RVARRYDAASDSILFANNQAYTRD NYRKAGMAEVIEDLLHFCRCMYS MALDNIHYALLTAVVIFSDRPGLEQ PQLVEEIQRYYLNTLRIYILNQLSGS ARSSVIYGKILSILSELRTLGMQNSN MCISLKLKNRKLPPFLEEIWDVAD MSHTQPPPILESPTNL | 647 | ATGAAGCTGCTGAGCAGCA TCGAGCAGGCTTGCGACAT CTGCAGGCTGAAGAAGCTG AAGTGCAGCAAGGAGAAG CCCAAGTGCGCCAAGTGCC TGAAGAACAACTGGGAGTG CAGATACAGCCCCAAGACC AAGAGGAGCCCCCTGACCA GGGCCCACCTGACCGAGGT GGAGAGCAGGCTGGAGAG GCTGGAGCAGCTGTTCCTG CTGATCTTCCCCAGGGAGG ACCTGGACATGATCCTGAA GATGGACAGCCTGCAAGAC ATCAAGGCCCTGCTGACCG GCCTGTTCGTGCAGGACAA CGTGAACAAGGACGCCGTG ACCGACAGGCTGGCCAGCG TGGAGACCGACATGCCCCT GACCCTGAGGCAGCACAGG ATCAGCGCCACCAGCAGCA GCGAGGAGAGCAGCAACA AGGGCCAGAGGCAGCTGAC CGTGAGCCCCGAGTTTCCC GGGCGGCCTGAGTGCGTAG TACCCGAGACTCAGTGCGC CATGAAGCGGAAAGAGAA GAAAGCACAGAAGGAGAA GGACAAACTGCCTGTCAGC ACGACGACGGTGGACGACC ACATGCCGCCCATTATGCAG TGTGAACCTCCACCTCCTGA AGCAGCAAGGATTCACGAA GTGGTCCCAAGGTTTCTCTC CGACAAGCTGTTGGTGACA AACCGGCAGAAAAACATCC CCCAGTTGACAGCCAACCA GCAGTTCCTTATCGCCAGGC TCATCTGGTACCAGGACGG |

TABLE 14-continued

| Additional Sequences | | | | |
|---|---|---|---|---|
| Name | SEQ ID NO | Amino Acid Sequence | SEQ ID NO | Nucleotide Sequence |
| | | | | GTACGAGCAGCCTTCTGAT GAAGATTTGAAGAGGATTA CGCAGACGTGGCAGCAAGC GGACGATGAAAACGAAGA GTCGGACACTCCCTTCCGCC AGATCACAGAGATGACTAT CCTCACGGTCCAACTTATCG TGGAGTTCGCGAAGGGATT GCCAGGGTTCGCCAAGATC TCGCAGCCTGATCAAATTAC GCTGCTTAAGGCTTGCTCAA GTGAGGTAATGATGCTCCG AGTCGCGCGACGATACGAT GCGGCCTCAGACAGTATTC TGTTCGCGAACAACCAAGC GTACACTCGCGACAACTACC GCAAGGCTGGCATGGCCGA GGTCATCGAGGATCTACTG CACTTCTGCCGGTGCATGTA CTCTATGGCGTTGGACAAC ATCCATTACGCGCTGCTCAC GGCTGTCGTCATCTTTTCTG ACCGGCCAGGGTTGGAGCA GCCGCAACTGGTGGAAGAG ATCCAGCGGTACTACCTGA ATACGCTCCGCATCTATATC CTGAACCAGCTGAGCGGGT CGGCGCGTTCGTCCGTCAT ATACGGCAAGATCCTCTCAA TCCTCTCTGAGCTACGCACG CTCGGCATGCAAAACTCCA ACATGTGCATCTCCCTCAAG CTCAAGAACAGAAAGCTGC CGCCTTTCCTCGAGGAGATC TGGGATGTGGCGGACATGT CGCACACCCAACCGCCGCCT ATCCTCGAGTCCCCCACGAA TCTCTAG |
| EMCV IRES | | | 702 | CCCCCTCTCCCTCCCCCCCCC CTAACGTTACTGGCCGAAG CCGCTTGGAATAAGGCCGG TGTGCGTTTGTCTATATGTT ATTTTCCACCATATTGCCGT CTTTTGGCAATGTGAGGGC CCGGAAACCTGGCCCTGTC TTCTTGACGAGCATTCCTAG GGGTCTTTCCCCTCTCGCCA AAGGAATGCAAGGTCTGTT GAATGTCGTGAAGGAAGCA GTTCCTCTGGAAGCTTCTTG AAGACAAACAACGTCTGTA GCGACCCTTTGCAGGCAGC GGAACCCCCCACCTGGCGA CAGGTGCCTCTGCGGCCAA AAGCCACGTGTATAAGATA CACCTGCAAAGGCGGCACA ACCCCAGTGCCACGTTGTG AGTTGGATAGTTGTGGAAA GAGTCAAATGGCTCTCCTCA AGCGTATTCAACAAGGGGC TGAAGGATGCCCAGAAGGT ACCCCATTGTATGGGATCTG ATCTGGGGCCTCGGTGCAC ATGCTTTACATGTGTTTAGT CGAGGTTAAAAAACGTCTA GGCCCCCCGAACCACGGGG ACGTGGTTTTCCTTTGAAAA ACACGATC |
| 2xRbm3 IRES | | | 703 | ACTAGTTTTATAATTTCTTCT TCCAGAATTTCTGACATTTT ATAATTTCTTCTTCCAGAAG ACTCACAACCTC |

The invention claimed is:

1. A non-naturally occurring polynucleotide comprising:

(a) a first nucleic acid sequence comprising SEQ ID NO: 179;

(b) a second nucleic acid sequence comprising SEQ ID NO: 180; and (c) a third nucleic acid sequence encoding a chimeric antigen receptor (CAR), the CAR comprising:

(i) a variable light chain (VL) domain comprising the amino acid sequence set forth in SEQ ID NO: 387, (ii) a variable heavy chain (VH) domain comprising the amino acid sequence set forth in SEQ ID NO: 349.

2. The polynucleotide of claim 1, further encoding a cytokine.

3. The polynucleotide of claim 1, further encoding a fusion protein comprising: (a) a polypeptide comprising the amino acid sequence set forth in SEQ ID NO: 519; and (b) a polypeptide comprising the amino acid sequence set forth in SEQ ID NO: 521.

4. The polynucleotide of claim 1, further encoding a cell tag.

5. The polynucleotide of claim 4, wherein the cell tag comprises: (a) a truncated HER1; and (b) a CD28 transmembrane domain.

6. The polynucleotide of claim 1, wherein the first and second nucleic acid sequences are contained within the polynucleotide sequence set forth in SEQ ID NO: 267.

7. The polynucleotide of claim 1, wherein the CAR comprises the amino acid sequence set forth in SEQ ID NO: 465.

8. The polynucleotide of claim 1, wherein the CAR comprises the amino acid sequence set forth in SEQ ID NO: 623.

9. A vector comprising the polynucleotide of claim 1.

10. The vector of claim 9, further comprising a Sleeping Beauty transposon.

11. An in vitro modified immune effector cell comprising the polynucleotide of claim 1.

12. A composition comprising the polynucleotide of claim 1.

13. A kit comprising the polynucleotide of claim 1.

* * * * *